(12) United States Patent
Geierstanger et al.

(10) Patent No.: US 10,280,139 B2
(45) Date of Patent: May 7, 2019

(54) CYTOTOXIC PEPTIDES AND CONJUGATES THEREOF

(71) Applicant: NOVARTIS AG, Basel (CH)

(72) Inventors: Bernhard Hubert Geierstanger, Solana Beach, CA (US); Jan Grunewald, San Diego, CA (US); Weijia Ou, San Diego, CA (US); Shifeng Pan, San Diego, CA (US); Tetsuo Uno, San Diego, CA (US); Yongqin Wan, San Diego, CA (US); Xing Wang, San Diego, CA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 15/822,930

(22) Filed: Nov. 27, 2017

(65) Prior Publication Data
US 2018/0155281 A1 Jun. 7, 2018

Related U.S. Application Data

(62) Division of application No. 15/317,532, filed as application No. PCT/IB2015/054400 on Jun. 11, 2015, now Pat. No. 9,884,817.

(60) Provisional application No. 62/011,961, filed on Jun. 13, 2014.

(51) Int. Cl.
| C07D 207/09 | (2006.01) |
| C07K 5/02 | (2006.01) |
| A61K 47/68 | (2017.01) |
| C07D 401/12 | (2006.01) |
| C07D 403/12 | (2006.01) |
| C07D 403/14 | (2006.01) |
| C07D 413/12 | (2006.01) |
| C07K 16/32 | (2006.01) |

(52) U.S. Cl.
CPC ........ *C07D 207/09* (2013.01); *A61K 47/6803* (2017.08); *A61K 47/6849* (2017.08); *A61K 47/6851* (2017.08); *A61K 47/6855* (2017.08); *C07D 401/12* (2013.01); *C07D 403/12* (2013.01); *C07D 403/14* (2013.01); *C07D 413/12* (2013.01); *C07K 5/0205* (2013.01); *C07K 16/32* (2013.01)

(58) Field of Classification Search
CPC .................... C07D 207/09; A61K 47/6851
See application file for complete search history.

(56) References Cited

U.S. PATENT DOCUMENTS

| 5,654,399 A | 8/1997 | Sakakibara et al. |
| 5,767,237 A | 6/1998 | Sakakibara et al. |
| 5,840,699 A | 11/1998 | Sakakibara et al. |
| 6,004,934 A | 12/1999 | Sakakibara et al. |
| 6,124,431 A | 9/2000 | Sakakibara et al. |
| 7,498,298 B2 | 3/2009 | Doronina et al. |
| 7,745,394 B2 | 6/2010 | Doronina et al. |
| 7,749,504 B2 | 7/2010 | Cairns et al. |
| 7,750,116 B1 | 7/2010 | Doronina et al. |
| 7,803,915 B2 | 9/2010 | Cairns et al. |
| 7,964,566 B2 | 6/2011 | Doronina et al. |
| 7,964,567 B2 | 6/2011 | Doronina et al. |
| 7,968,687 B2 | 6/2011 | McDonagh et al. |
| 7,994,135 B2 | 8/2011 | Doronina et al. |
| 8,242,252 B2 | 8/2012 | McDonagh et al. |
| 8,512,707 B2 | 8/2013 | Doronina et al. |
| 8,557,780 B2 | 10/2013 | Doronina et al. |
| 8,609,105 B2 | 12/2013 | Senter et al. |
| 8,703,714 B2 | 4/2014 | Doronina et al. |
| 8,828,401 B2 | 9/2014 | Doroski et al. |
| 8,987,209 B2 | 3/2015 | Lerchen et al. |
| 8,992,932 B2 | 3/2015 | Lerchen et al. |
| 9,029,406 B2 | 5/2015 | Lerchen et al. |
| 9,073,993 B2 | 7/2015 | McDonagh et al. |
| 9,109,035 B2 | 8/2015 | Liang et al. |
| 9,138,486 B2 | 9/2015 | Doroski et al. |

(Continued)

FOREIGN PATENT DOCUMENTS

| WO | 2007103288 | 9/2007 |
| WO | 2013072813 | 5/2013 |

(Continued)

*Primary Examiner* — Golam M Shameem

(74) *Attorney, Agent, or Firm* — Daniel E. Raymond; Genomics Institute of the Novartis Research Foundation

(57) ABSTRACT

Disclosed herein are novel compounds of formula (I) as described herein:

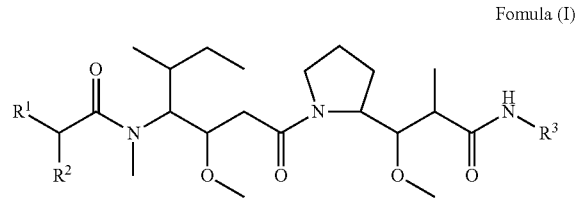

Formula (I)

and the use of such peptides in making immunoconjugates (i.e Antibody Drug Conjugates) Also described herein are immunoconjugates (i.e Antibody Drug Conjugates) comprising such novel compound linked to an antigen binding moiety, such as an antibody; where such immunoconjugates are useful for treating cell proliferative disorders. The invention further provides pharmaceutical compositions comprising these immunoconjugates, compositions comprising the immunoconjugates with a therapeutic co-agent, and methods to use these immunoconjugates and compositions for treating cell proliferation disorders.

20 Claims, 10 Drawing Sheets

Specification includes a Sequence Listing.

(56) References Cited

U.S. PATENT DOCUMENTS

| | | |
|---|---|---|
| 9,249,186 B2 | 2/2016 | Doroski et al. |
| 9,272,052 B2 | 3/2016 | Lewis et al. |
| 9,463,252 B2 | 10/2016 | Senter et al. |
| 9,545,449 B2 | 1/2017 | Krantz |
| 9,884,817 B2 * | 2/2018 | Geierstanger ...... A61K 47/6803 |
| 9,988,420 B2 * | 6/2018 | Geierstanger ........ C07K 5/0205 |
| 2007/0160617 A1 | 7/2007 | Ma et al. |
| 2008/0300192 A1 | 12/2008 | Doronina et al. |
| 2008/0305044 A1 | 12/2008 | McDonagh et al. |
| 2009/0068178 A1 | 3/2009 | Crowley et al. |
| 2011/0070243 A1 | 3/2011 | Crowley et al. |
| 2013/0189287 A1 | 7/2013 | Bregeon et al. |
| 2015/0314007 A1 | 11/2015 | Satomaa et al. |
| 2016/0052966 A1 | 2/2016 | Miao et al. |

FOREIGN PATENT DOCUMENTS

| | | |
|---|---|---|
| WO | 2013184514 | 12/2013 |
| WO | 2015095301 | 6/2015 |

\* cited by examiner

SEQUENCE LISTING

<160> NUMBER OF SEQ ID NOS: 49

<210> SEQ ID NO 1
<211> LENGTH: 450
<212> TYPE: PRT
<213> ORGANISM: Artificial Sequence
<220> FEATURE:
<223> OTHER INFORMATION: anti-Her2 heavy chain wild-type

<400> SEQUENCE: 1

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
```

```
                    355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: anti-Her2 light chain wild-type

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 331
<212> TYPE: PRT
<213> ORGANISM: Artificial Sequence
<220> FEATURE:
<223> OTHER INFORMATION: constant region of the heavy chain wild-type of
``` antibody 20507 and anti-Her2)

<400> SEQUENCE: 3

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330
```

<210> SEQ ID NO 4
<211> LENGTH: 108
<212> TYPE: PRT
<213> ORGANISM: Artificial Sequence
<220> FEATURE:
<223> OTHER INFORMATION: constant region of the light chain wild-type of antibody 20507 and of anti-Her2

<400> SEQUENCE: 4

Lys Arg Thr Val Ala Ala Pro Ser Val Phe Ile Phe Pro Pro Ser Asp

```
                1               5                   10                  15
            Glu Gln Leu Lys Ser Gly Thr Ala Ser Val Val Cys Leu Leu Asn Asn
                            20                  25                  30

Phe Tyr Pro Arg Glu Ala Lys Val Gln Trp Lys Val Asp Asn Ala Leu
                            35                  40                  45

Gln Ser Gly Asn Ser Gln Glu Ser Val Thr Glu Gln Asp Ser Lys Asp
                            50                  55                  60

Ser Thr Tyr Ser Leu Ser Ser Thr Leu Thr Leu Ser Lys Ala Asp Tyr
             65                  70                  75                  80

Glu Lys His Lys Val Tyr Ala Cys Glu Val Thr His Gln Gly Leu Ser
                            85                  90                  95

Ser Pro Val Thr Lys Ser Phe Asn Arg Gly Glu Cys
                            100                 105

<210> SEQ ID NO 5
<211> LENGTH: 108
<212> TYPE: PRT
<213> ORGANISM: Artificial Sequence
<220> FEATURE:
<223> OTHER INFORMATION: constant region of the mutant light chain of
      anti-Her2 LC-S159C and antibody 20507 LC-S159C

<400> SEQUENCE: 5

Lys Arg Thr Val Ala Ala Pro Ser Val Phe Ile Phe Pro Pro Ser Asp
 1               5                   10                  15

Glu Gln Leu Lys Ser Gly Thr Ala Ser Val Val Cys Leu Leu Asn Asn
                20                  25                  30

Phe Tyr Pro Arg Glu Ala Lys Val Gln Trp Lys Val Asp Asn Ala Leu
                35                  40                  45

Gln Ser Gly Asn Cys Gln Glu Ser Val Thr Glu Gln Asp Ser Lys Asp
                50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
                100                 105

<210> SEQ ID NO 6
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-E152C

<400> SEQUENCE: 6

Ser Ala Ser Thr Lys Gly Pro Ser Val Phe Pro Leu Ala Pro Ser Ser
 1               5                   10                  15

Lys Ser Thr Ser Gly Gly Thr Ala Ala Leu Gly Cys Leu Val Lys Asp
                20                  25                  30

Tyr Phe Pro Cys Pro Val Thr Val Ser Trp Asn Ser Gly Ala Leu Thr
                35                  40                  45

Ser Gly Val His Thr Phe Pro Ala Val Leu Gln Ser Ser Gly Leu Tyr
                50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
```

```
                85                  90                  95
Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 7
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-S375C

<400> SEQUENCE: 7

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110
```

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 8
<211> LENGTH: 108
<212> TYPE: PRT
<213> ORGANISM: Artificial Sequence
<220> FEATURE:
<223> OTHER INFORMATION: constant region of the mutant light chain of
      antibody 20507 LC-K107C

<400> SEQUENCE: 8

Cys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 9
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-K360C

<400> SEQUENCE: 9

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Cys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 10
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-E152C-S375C and of anti-Her2 HC-E152C-S375C

<400> SEQUENCE: 10

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
        210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
        290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 11
<211> LENGTH: 343
<212> TYPE: PRT
<213> ORGANISM: Artificial Sequence
<220> FEATURE:
<223> OTHER INFORMATION: constant region of the mutant heavy chain of
      HC-ins388-A1 in anti-Her2 and antibody 20507

<400> SEQUENCE: 11

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp

```
                 20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
 50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
            130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Gly Asp Ser Leu Asp Met Leu Glu Trp Ser Leu Met Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 12
<211> LENGTH: 12
<212> TYPE: PRT
<213> ORGANISM: Artificial Sequence
<220> FEATURE:
<223> OTHER INFORMATION: A1 tag

<400> SEQUENCE: 12

Gly Asp Ser Leu Asp Met Leu Glu Trp Ser Leu Met
1               5                   10

<210> SEQ ID NO 13
<211> LENGTH: 24
<212> TYPE: PRT
```

```
<213> ORGANISM: Artificial Sequence
<220> FEATURE:
<223> OTHER INFORMATION: signal sequence

<400> SEQUENCE: 13

Met Lys Thr Phe Ile Leu Leu Leu Trp Val Leu Leu Leu Trp Val Ile
1               5                   10                  15

Phe Leu Leu Pro Gly Ala Thr Ala
            20

<210> SEQ ID NO 14
<211> LENGTH: 342
<212> TYPE: PRT
<213> ORGANISM: Artificial Sequence
<220> FEATURE:
<223> OTHER INFORMATION: constant region of the mutant heavy chain of
      anti-Her2 HC-ins388-ybbR

<400> SEQUENCE: 14

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asp Ser Leu Glu Phe Ile Ala Ser Lys Leu Ala Asn Asn Tyr Lys Thr
        275                 280                 285

Thr Pro Pro Val Leu Asp Ser Asp Gly Ser Phe Phe Leu Tyr Ser Lys
    290                 295                 300
```

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
            325                 330                 335

Ser Leu Ser Pro Gly Lys
            340

<210> SEQ ID NO 15
<211> LENGTH: 342
<212> TYPE: PRT
<213> ORGANISM: Artificial Sequence
<220> FEATURE:
<223> OTHER INFORMATION: constant region of the mutant heavy chain of
      anti-Her2 HC-ins388-ybbR-S390C

<400> SEQUENCE: 15

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asp Cys Leu Glu Phe Ile Ala Ser Lys Leu Ala Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys

```
                                305                 310                 315                 320
                    Ser Val Met His Glu Ala Leu His Asn His Tyr Thr Gln Lys Ser Leu
                                    325                 330                 335

Ser Leu Ser Pro Gly Lys
                                    340

<210> SEQ ID NO 16
<211> LENGTH: 335
<212> TYPE: PRT
<213> ORGANISM: Artificial Sequence
<220> FEATURE:
<223> OTHER INFORMATION: constant region of the mutant heavy chain of
      anti-Her2 HC-S119G-T120D-K121S-G122L-P123D-ins123-MLEW

<400> SEQUENCE: 16

Ser Ala Gly Asp Ser Leu Asp Met Leu Glu Trp Ser Val Phe Pro Leu
1               5                   10                  15

Ala Pro Ser Ser Lys Ser Thr Ser Gly Gly Thr Ala Ala Leu Gly Cys
                20                  25                  30

Leu Val Lys Asp Tyr Phe Pro Glu Pro Val Thr Val Ser Trp Asn Ser
            35                  40                  45

Gly Ala Leu Thr Ser Gly Val His Thr Phe Pro Ala Val Leu Gln Ser
        50                  55                  60

Ser Gly Leu Tyr Ser Leu Ser Ser Val Val Thr Val Pro Ser Ser Ser
65                  70                  75                  80

Leu Gly Thr Gln Thr Tyr Ile Cys Asn Val Asn His Lys Pro Ser Asn
                85                  90                  95

Thr Lys Val Asp Lys Lys Val Glu Pro Lys Ser Cys Asp Lys Thr His
                100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
        130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
        210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
        290                 295                 300

Trp Gln Gln Gly Asn Val Phe Ser Cys Ser Val Met His Glu Ala Leu
305                 310                 315                 320
```

```
His Asn His Tyr Thr Gln Lys Ser Leu Ser Leu Ser Pro Gly Lys
                325                 330                 335

<210> SEQ ID NO 17
<211> LENGTH: 331
<212> TYPE: PRT
<213> ORGANISM: Artificial Sequence
<220> FEATURE:
<223> OTHER INFORMATION: constant region of the mutant heavy chain of
      anti-Her2HC-P189G-S190D-S192L-L193S-G194W-T195L

<400> SEQUENCE: 17

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Gly Asp Ser Leu Ser Trp Leu Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 18
```

```
<211> LENGTH: 331
<212> TYPE: PRT
<213> ORGANISM: Artificial Sequence
<220> FEATURE:
<223> OTHER INFORMATION: constant region of the mutant heavy chain of
      anti-Her2 HC-S190D-S192L-L193S-G194W-T195L

<400> SEQUENCE: 18
```

| | | | | | | | | | | | | | | | |
|---|---|---|---|---|---|---|---|---|---|---|---|---|---|---|---|
| Ser | Ala | Ser | Thr | Lys | Gly | Pro | Ser | Val | Phe | Pro | Leu | Ala | Pro | Ser | Ser |
| 1 | | | | 5 | | | | | 10 | | | | | 15 | |
| Lys | Ser | Thr | Ser | Gly | Gly | Thr | Ala | Ala | Leu | Gly | Cys | Leu | Val | Lys | Asp |
| | | | 20 | | | | | 25 | | | | | 30 | | |
| Tyr | Phe | Pro | Glu | Pro | Val | Thr | Val | Ser | Trp | Asn | Ser | Gly | Ala | Leu | Thr |
| | | 35 | | | | | 40 | | | | | 45 | | | |
| Ser | Gly | Val | His | Thr | Phe | Pro | Ala | Val | Leu | Gln | Ser | Ser | Gly | Leu | Tyr |
| 50 | | | | | 55 | | | | | 60 | | | | | |
| Ser | Leu | Ser | Ser | Val | Val | Thr | Val | Pro | Asp | Ser | Leu | Ser | Trp | Leu | Gln |
| 65 | | | | | 70 | | | | | 75 | | | | | 80 |
| Thr | Tyr | Ile | Cys | Asn | Val | Asn | His | Lys | Pro | Ser | Asn | Thr | Lys | Val | Asp |
| | | | | 85 | | | | | 90 | | | | | 95 | |
| Lys | Lys | Val | Glu | Pro | Lys | Ser | Cys | Asp | Lys | Thr | His | Thr | Cys | Pro | Pro |
| | | | 100 | | | | | 105 | | | | | 110 | | |
| Cys | Pro | Ala | Pro | Glu | Leu | Leu | Gly | Gly | Pro | Ser | Val | Phe | Leu | Phe | Pro |
| | | 115 | | | | | 120 | | | | | 125 | | | |
| Pro | Lys | Pro | Lys | Asp | Thr | Leu | Met | Ile | Ser | Arg | Thr | Pro | Glu | Val | Thr |
| 130 | | | | | 135 | | | | | 140 | | | | | |
| Cys | Val | Val | Val | Asp | Val | Ser | His | Glu | Asp | Pro | Glu | Val | Lys | Phe | Asn |
| 145 | | | | | 150 | | | | | 155 | | | | | 160 |
| Trp | Tyr | Val | Asp | Gly | Val | Glu | Val | His | Asn | Ala | Lys | Thr | Lys | Pro | Arg |
| | | | | 165 | | | | | 170 | | | | | 175 | |
| Glu | Glu | Gln | Tyr | Asn | Ser | Thr | Tyr | Arg | Val | Val | Ser | Val | Leu | Thr | Val |
| | | | 180 | | | | | 185 | | | | | 190 | | |
| Leu | His | Gln | Asp | Trp | Leu | Asn | Gly | Lys | Glu | Tyr | Lys | Cys | Lys | Val | Ser |
| | | | | 195 | | | | | 200 | | | | | 205 | |
| Asn | Lys | Ala | Leu | Pro | Ala | Pro | Ile | Glu | Lys | Thr | Ile | Ser | Lys | Ala | Lys |
| 210 | | | | | 215 | | | | | 220 | | | | | |
| Gly | Gln | Pro | Arg | Glu | Pro | Gln | Val | Tyr | Thr | Leu | Pro | Pro | Ser | Arg | Glu |
| 225 | | | | | 230 | | | | | 235 | | | | | 240 |
| Glu | Met | Thr | Lys | Asn | Gln | Val | Ser | Leu | Thr | Cys | Leu | Val | Lys | Gly | Phe |
| | | | | 245 | | | | | 250 | | | | | 255 | |
| Tyr | Pro | Ser | Asp | Ile | Ala | Val | Glu | Trp | Glu | Ser | Asn | Gly | Gln | Pro | Glu |
| | | | 260 | | | | | 265 | | | | | 270 | | |
| Asn | Asn | Tyr | Lys | Thr | Thr | Pro | Pro | Val | Leu | Asp | Ser | Asp | Gly | Ser | Phe |
| | | | 275 | | | | | 280 | | | | | 285 | | |
| Phe | Leu | Tyr | Ser | Lys | Leu | Thr | Val | Asp | Lys | Ser | Arg | Trp | Gln | Gln | Gly |
| | 290 | | | | | 295 | | | | | 300 | | | | |
| Asn | Val | Phe | Ser | Cys | Ser | Val | Met | His | Glu | Ala | Leu | His | Asn | His | Tyr |
| 305 | | | | | 310 | | | | | 315 | | | | | 320 |
| Thr | Gln | Lys | Ser | Leu | Ser | Leu | Ser | Pro | Gly | Lys | | | | | |
| | | | | 325 | | | | | 330 | | | | | | |

```
<210> SEQ ID NO 19
<211> LENGTH: 332
<212> TYPE: PRT
<213> ORGANISM: Artificial Sequence
<220> FEATURE:
<223> OTHER INFORMATION: constant region of the mutant heavy chain of
``` anti-Her2 HC-ins388-C

<400> SEQUENCE: 19

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Cys Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 20
<211> LENGTH: 11
<212> TYPE: PRT
<213> ORGANISM: Artificial Sequence
<220> FEATURE:
<223> OTHER INFORMATION: ybbR tag

<400> SEQUENCE: 20

Asp Ser Leu Glu Phe Ile Ala Ser Lys Leu Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: ybbR-S2C

<400> SEQUENCE: 21

Asp Cys Leu Glu Phe Ile Ala Ser Lys Leu Ala
1               5                   10

<210> SEQ ID NO 22
<211> LENGTH: 9
<212> TYPE: PRT
<213> ORGANISM: Artificial Sequence
<220> FEATURE:
<223> OTHER INFORMATION: A1-3aa

<400> SEQUENCE: 22

Gly Asp Ser Leu Asp Met Leu Glu Trp
1               5

<210> SEQ ID NO 23
<211> LENGTH: 7
<212> TYPE: PRT
<213> ORGANISM: Artificial Sequence
<220> FEATURE:
<223> OTHER INFORMATION: S6-5aa

<400> SEQUENCE: 23

Gly Asp Ser Leu Ser Trp Leu
1               5

<210> SEQ ID NO 24
<211> LENGTH: 6
<212> TYPE: PRT
<213> ORGANISM: Artificial Sequence
<220> FEATURE:
<223> OTHER INFORMATION: S6-6aa

<400> SEQUENCE: 24

Asp Ser Leu Ser Trp Leu
1               5

<210> SEQ ID NO 25
<211> LENGTH: 132
<212> TYPE: PRT
<213> ORGANISM: Artificial Sequence
<220> FEATURE:
<223> OTHER INFORMATION: E. coli AcpS R26L-C119S

<400> SEQUENCE: 25

Met Ala Ile Leu Gly Leu Gly Thr Asp Ile Val Glu Ile Ala Arg Ile
1               5                   10                  15

Glu Ala Val Ile Ala Arg Ser Gly Asp Leu Leu Ala Arg Arg Val Leu
            20                  25                  30

Ser Asp Asn Glu Trp Ala Ile Trp Lys Thr His His Gln Pro Val Arg
        35                  40                  45

Phe Leu Ala Lys Arg Phe Ala Val Lys Glu Ala Ala Ala Lys Ala Phe
    50                  55                  60

Gly Thr Gly Ile Arg Asn Gly Leu Ala Phe Asn Gln Phe Glu Val Phe
65                  70                  75                  80

Asn Asp Glu Leu Gly Lys Pro Arg Leu Arg Leu Trp Gly Glu Ala Leu

```
                85                  90                  95
Lys Leu Ala Glu Lys Leu Gly Val Ala Asn Met His Val Thr Leu Ala
            100                 105                 110

Asp Glu Arg His Tyr Ala Ser Ala Thr Val Ile Ile Glu Ser His His
        115                 120                 125

His His His His
    130

<210> SEQ ID NO 26
<211> LENGTH: 41
<212> TYPE: DNA
<213> ORGANISM: Artificial Sequence
<220> FEATURE:
<223> OTHER INFORMATION: LC-S159C: Sense

<400> SEQUENCE: 26
agcggcaact gtcaggagag cgtcaccgag caggacagca a                41

<210> SEQ ID NO 27
<211> LENGTH: 40
<212> TYPE: DNA
<213> ORGANISM: Artificial Sequence
<220> FEATURE:
<223> OTHER INFORMATION: LC-S159C: Anti-sense

<400> SEQUENCE: 27
ctctcctgac agttgccgct ctgcagggcg ttgtccacct                 40

<210> SEQ ID NO 28
<211> LENGTH: 39
<212> TYPE: DNA
<213> ORGANISM: Artificial Sequence
<220> FEATURE:
<223> OTHER INFORMATION: HC-E152C : Sense

<400> SEQUENCE: 28
tacttcccct gtcccgtgac cgtgtcctgg aacagcgga                  39

<210> SEQ ID NO 29
<211> LENGTH: 38
<212> TYPE: DNA
<213> ORGANISM: Artificial Sequence
<220> FEATURE:
<223> OTHER INFORMATION: HC-E152C : Anti-sense

<400> SEQUENCE: 29
ggtcacggga cagggaagt agtccttcac caggcagc                    38

<210> SEQ ID NO 30
<211> LENGTH: 40
<212> TYPE: DNA
<213> ORGANISM: Artificial Sequence
<220> FEATURE:
<223> OTHER INFORMATION: HC-S375C: Sense

<400> SEQUENCE: 30
ttctacccct gcgacatcgc cgtggagtgg gagagcaacg                 40

<210> SEQ ID NO 31
<211> LENGTH: 41
<212> TYPE: DNA
<213> ORGANISM: Artificial Sequence
<220> FEATURE:
<223> OTHER INFORMATION: HC-S375C: Anti-sense
```

<400> SEQUENCE: 31
ggcgatgtcg cagggtaga agcccttcac cagacaggtc a                 41

<210> SEQ ID NO 32
<211> LENGTH: 39
<212> TYPE: DNA
<213> ORGANISM: Artificial Sequence
<220> FEATURE:
<223> OTHER INFORMATION: HC-K360C: Sense

<400> SEQUENCE: 32
agctgacctg caaccaggtg tccctgacct gtctggtga                   39

<210> SEQ ID NO 33
<211> LENGTH: 40
<212> TYPE: DNA
<213> ORGANISM: Artificial Sequence
<220> FEATURE:
<223> OTHER INFORMATION: HC-K360C: Anti-sense

<400> SEQUENCE: 33
cacctggttg caggtcagct cgtcccggga tggaggcagg                  40

<210> SEQ ID NO 34
<211> LENGTH: 40
<212> TYPE: DNA
<213> ORGANISM: Artificial Sequence
<220> FEATURE:
<223> OTHER INFORMATION: LC-K107C: Sense

<400> SEQUENCE: 34
gtggagatct gtcgaacggt ggccgctccc agcgtgttca                  40

<210> SEQ ID NO 35
<211> LENGTH: 39
<212> TYPE: DNA
<213> ORGANISM: Artificial Sequence
<220> FEATURE:
<223> OTHER INFORMATION: LC-K107C: Anti-sense

<400> SEQUENCE: 35
accgttcgac agatctccac cttggtaccc tgtccgaac                   39

<210> SEQ ID NO 36
<211> LENGTH: 39
<212> TYPE: DNA
<213> ORGANISM: Artificial Sequence
<220> FEATURE:
<223> OTHER INFORMATION: HC-ins388-C: Sense

<400> SEQUENCE: 36
cccgagtgta acaactacaa gaccacacct ccagtgctg                   39

<210> SEQ ID NO 37
<211> LENGTH: 39
<212> TYPE: DNA
<213> ORGANISM: Artificial Sequence
<220> FEATURE:
<223> OTHER INFORMATION: HC-ins388-C: Anti-sense

<400> SEQUENCE: 37
gttgttacac tcgggctggc cgttgctctc ccactccac                   39

<210> SEQ ID NO 38
<211> LENGTH: 52

```
<212> TYPE: DNA
<213> ORGANISM: Artificial Sequence
<220> FEATURE:
<223> OTHER INFORMATION: HC-ins388-A1: Sense

<400> SEQUENCE: 38
ctggacatgc tggagtggag cctgatgaac aactacaaga ccacacctcc ag        52

<210> SEQ ID NO 39
<211> LENGTH: 46
<212> TYPE: DNA
<213> ORGANISM: Artificial Sequence
<220> FEATURE:
<223> OTHER INFORMATION: HC-ins388-A1: Anti-sense

<400> SEQUENCE: 39
ccactccagc atgtccaggc tgtcgccctc gggctggccg ttgctc                46

<210> SEQ ID NO 40
<211> LENGTH: 52
<212> TYPE: DNA
<213> ORGANISM: Artificial Sequence
<220> FEATURE:
<223> OTHER INFORMATION: HC-ins388-ybbR: Sense

<400> SEQUENCE: 40
ctggagttca tcgccagcaa gctggccaac aactacaaga ccacacctcc ag        52

<210> SEQ ID NO 41
<211> LENGTH: 46
<212> TYPE: DNA
<213> ORGANISM: Artificial Sequence
<220> FEATURE:
<223> OTHER INFORMATION: HC-ins388-ybbR: Anti-sense

<400> SEQUENCE: 41
cttgctggcg atgaactcca ggctgtcctc gggctggccg ttgctc                46

<210> SEQ ID NO 42
<211> LENGTH: 44
<212> TYPE: DNA
<213> ORGANISM: Artificial Sequence
<220> FEATURE:
<223> OTHER INFORMATION: anti-Her2 HC-S119G-T120D-K121S-G122L-P123D-
     ins123-MLEW: Sense

<400> SEQUENCE: 42
tggacatgct ggagtggagc gtgttccccc tggcccccag cagc                  44

<210> SEQ ID NO 43
<211> LENGTH: 50
<212> TYPE: DNA
<213> ORGANISM: Artificial Sequence
<220> FEATURE:
<223> OTHER INFORMATION: anti-Her2 HC-S119G-T120D-K121S-G122L-P123D-
     ins123-MLEW:
        Anti-sense

<400> SEQUENCE: 43
ctccagcatg tccaggctgt cgccagccga ggagacggtg accagggttc            50

<210> SEQ ID NO 44
<211> LENGTH: 44
<212> TYPE: DNA
<213> ORGANISM: Artificial Sequence
<220> FEATURE:
<223> OTHER INFORMATION: anti-Her2 HC-P189G-S190D- S192L-L193S-G194W-
```

```
                 T195L: Sense

<400> SEQUENCE: 44
gcgacagcct gagctggctg cagacctaca tctgcaacgt gaac          44

<210> SEQ ID NO 45
<211> LENGTH: 42
<212> TYPE: DNA
<213> ORGANISM: Artificial Sequence
<220> FEATURE:
<223> OTHER INFORMATION: anti-Her2 HC-P189G-S190D- S192L-L193S-G194W-
      T195L: Anti-sense

<400> SEQUENCE: 45
cagccagctc aggctgtcgc ccactgtcac cacgctggac ag            42

<210> SEQ ID NO 46
<211> LENGTH: 40
<212> TYPE: DNA
<213> ORGANISM: Artificial Sequence
<220> FEATURE:
<223> OTHER INFORMATION: anti-Her2 HC-S190D- S192L-L193S-G194W-T195L:
      Sense

<400> SEQUENCE: 46
gacagtgccc gacagcctga gctggctgca gacctacatc               40

<210> SEQ ID NO 47
<211> LENGTH: 39
<212> TYPE: DNA
<213> ORGANISM: Artificial Sequence
<220> FEATURE:
<223> OTHER INFORMATION: anti-Her2 HC-S190D- S192L-L193S-G194W-T195L

<400> SEQUENCE: 47
gctgtcgggc actgtcacca cgctggacag gctgtacag                39

<210> SEQ ID NO 48
<211> LENGTH: 26
<212> TYPE: DNA
<213> ORGANISM: Artificial Sequence
<220> FEATURE:
<223> OTHER INFORMATION: HC-ins388-ybbR-S390C: Sense

<400> SEQUENCE: 48
cagcccgagg actgcctgga gttcat                              26

<210> SEQ ID NO 49
<211> LENGTH: 27
<212> TYPE: DNA
<213> ORGANISM: Artificial Sequence
<220> FEATURE:
<223> OTHER INFORMATION: HC-ins388-ybbR-S390C: Anti-sense

<400> SEQUENCE: 49
atgaactcca ggcagtcctc gggctgg                             27
```

CYTOTOXIC PEPTIDES AND CONJUGATES THEREOF

CROSS-REFERENCE TO RELATED APPLICATIONS

This application is a divisional application of U.S. patent application Ser. No. 15/317,532 filed 9 Dec. 2016, which was a 371 U.S. national phase application of international application number PCT/162015/05440 filed 11 Jun. 2015, which application claims the benefit of priority under 35 U.S.C. § 119(e) to U.S. Provisional Patent Application No. 62/011,961, filed 13 Jun. 2014, the disclosures of which are incorporated herein by reference in their entirety and for all purposes.

FIELD OF THE INVENTION

The invention provides compounds that are anti-mitotic cytotoxic peptides, and are useful to treat cellular proliferative disorders. The invention also includes conjugates that comprise such compounds linked to an antigen-binding moiety, and pharmaceutical compositions containing these conjugates. Also included are methods of using these compounds and conjugates to treat cell proliferation disorders, including cancers.

BACKGROUND

The use of antibody-drug conjugates (ADCs) for the targeted delivery of cell proliferation inhibitors and/or cytotoxic agents to specific cells has been the focus of significant research. Antibody-Drug Conjugate, Methods in Molecular Biology, Vol. 1045, Editor L. Ducry, Humana Press (2013). ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed.

Many antibodies that recognize and selectively bind to targeted cells, like cancer cells, have been disclosed for use in ADCs, and many methods for attaching payload (drug) compounds such as cytotoxins to antibodies have also been described. In spite of the extensive work on ADCs, though, only a few classes of cell proliferation inhibitors have been used extensively as ADC payloads. Even though the first ADC approved for use in humans in the U.S. was launched in 2000 (and later withdrawn from the market), a decade later only a few chemical classes of drug compounds (maytansinoids, auristatins, calicheamycins and duocarmycins) had reached clinical trials as payloads for ADCs. *Antibody-Drug Conjugates: the Next Generation of Moving Parts*, A. Lash, *Start-Up*, December 2011, 1-6. Given the widely acknowledged value of ADCs as therapeutics, particularly for treating cancer, there thus remains a need for compounds with improved properties for use as payloads in ADCs.

SUMMARY OF THE INVENTION

The invention provided herein includes compounds and methods of using such compounds as the drug component of an antibody-drug conjugate (ADC). The present invention includes novel compounds and the use of such novel compounds as payloads for ADCs. The invention further includes methods and intermediates useful for incorporating such novel compounds into ADCs, and methods to use the novel compounds and conjugates to treat cell proliferation disorders. Such compounds are anti-mitotic agents that inhibit cell division by blocking the polymerization of tubulin and thereby blocking nuclear migration and nuclear and cellular division.

In one aspect of the invention are compounds, or stereoisomer thereof, and tautomers, hydrates and pharmaceutically acceptable salts thereof, having the structure of Formula (I)

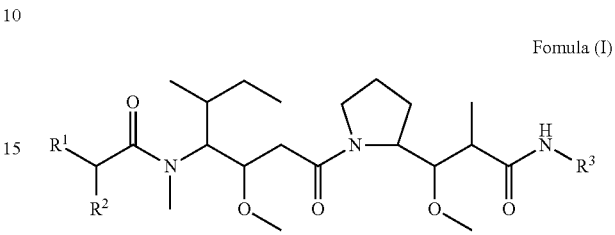

Formula (I)

wherein:
$R^1$ is —N=$CR^4R^5$, —N=$R^{19}$, —N=$CR^5$ $R^{20}$, —N=$CR^5NR^{12}(CH_2)_mN(R^{12})C(O)OR^{12}$, —N=$CR^5NR^{12}(CH_2)_mN(R^{12})_2$, —NHC(=$NR^6$)$R^4$, —NHC(=O)$R^4$, —NHC(=O)$R^{20}$, —$NHR^8$, —$NHLR^{11}$, —$NHR^{21}$, —N=$CR^5R^{10}$, —N=$R^{22}$, —N=$CR^5R^{23}$ or —NHC(=O)$R^{23}$ ;

$R^2$ is —$C_1$-$C_6$alkyl;

$R^3$ is

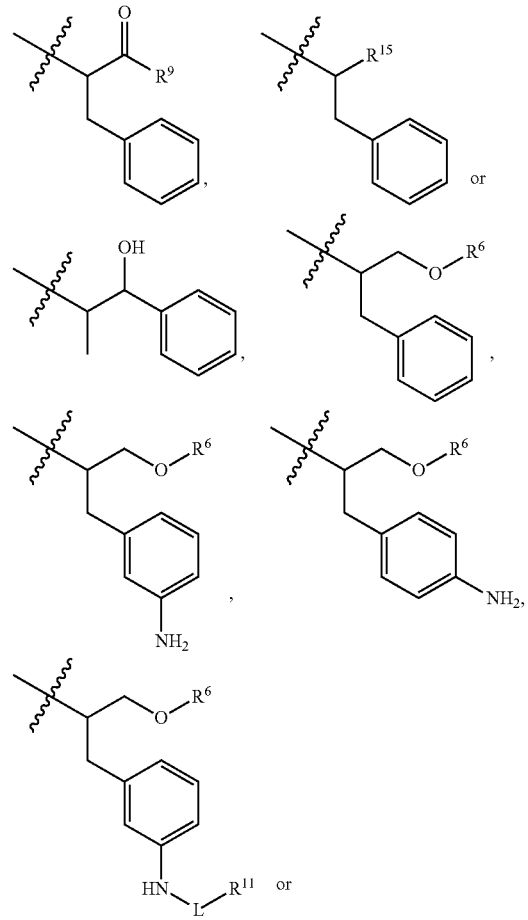

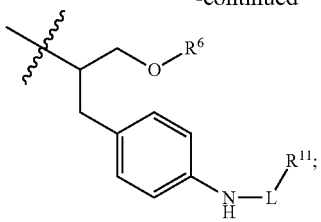

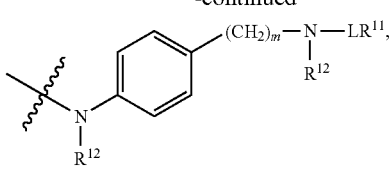

R[4] is —N(R[6])[2] or —NR[6]R[7];
R[5] is N(R[6])[2];
each R[6] is independently selected from H and —C[1]-C[6]alkyl;
R[7] is —(CH[2])[m]N(R[12])[2], —(CH[2])[m]N(R[12])C(=O)OR[12] or an unsubstituted C[3]-C[8]cycloalkyl;
or R[7] is a C[3]-C[8]cycloalkyl substituted with 1-3 substituents independently selected from C[1]-C[6]alkyl, oxo, —C(=O)R[18], —(CH[2])[m]OH, —C(=O)(CH[2])[m]OH, —C(=O)((CH[2])[m]O)[n]R[12], —((CH[2])[m]O)[n]R[12] or a C[1]-C[6]alkyl which is optionally substituted with 1 to 5 hydroxyl;
R[8] is an unsubstituted C-linked 5-6 membered heteroaryl having 1-2 N heteroatoms;
or R[8] is a C-linked 5-6 membered heteroaryl having 1-2 N heteroatoms which is substituted with 1-3 substituents independently selected from C[1]-C[6]alkyl, C[1]-C[6]haloalkyl, halogen, C[1]-C[6]alkoxy, —OH, —CN, —NO[2], —C(=O)OR[6], —C(=O)N(R[6])[2], —C(=O)NR[6](CH[2])[m]N(R[6])C(O)OR[6] and —C(=O)NR[6](CH[2])[m]N(R[6])[2];
R[9] is —OH, C[1]-C[6]alkoxy, —NHS(O)[2](CH[2])[m]N[3], —NHS(=O)[2]LR[11], —NHLR[11], —NHS(O)[2](CH[2])[m]NH[2], —N(R[12])[2], —R[16], —NR[12](CH[2])[m]N(R[12])[2], —NR[12](CH[2])[m]R[16], -LR[11], —NHS(O)[2]R[18],

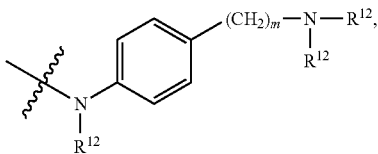

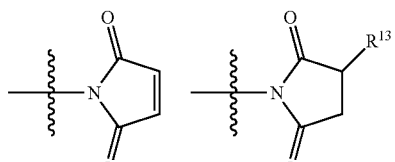

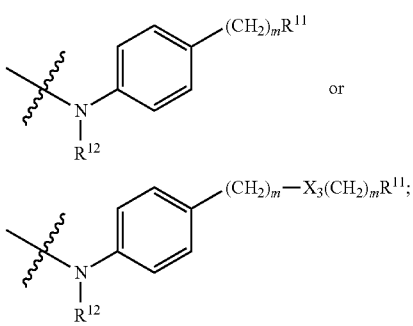

R[10] is LR[11] or

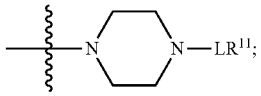

R[11] is

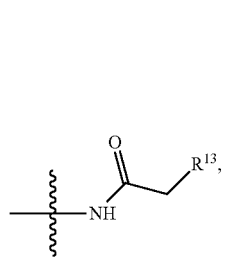

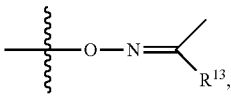

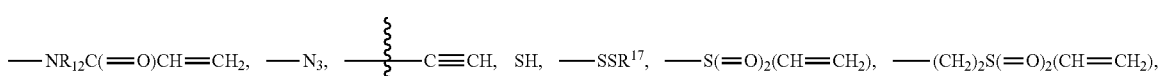

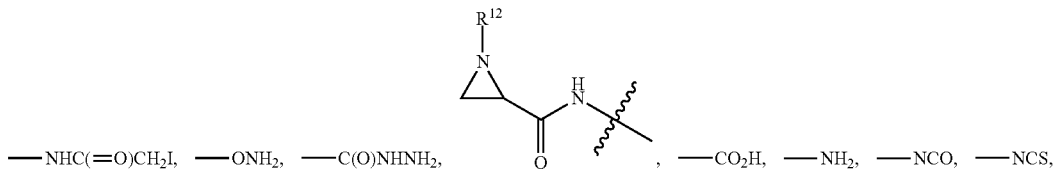

-continued
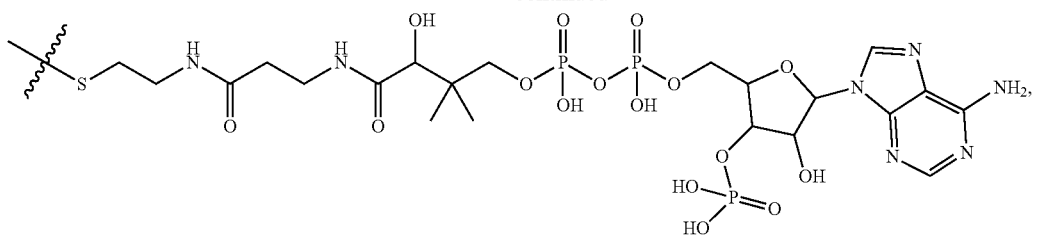
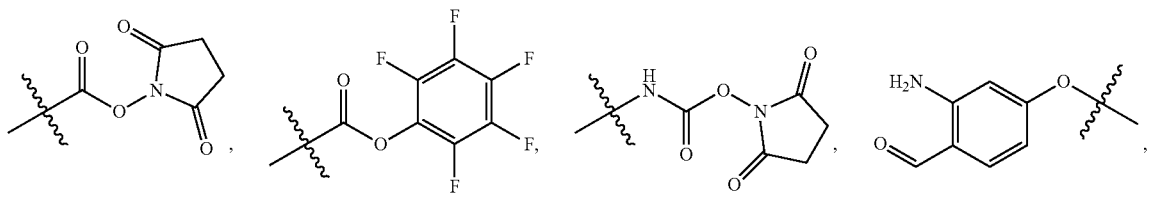
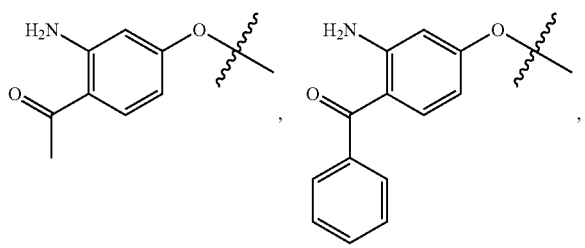
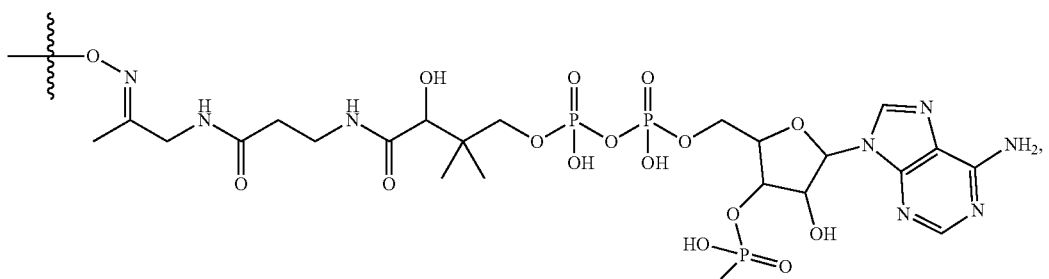
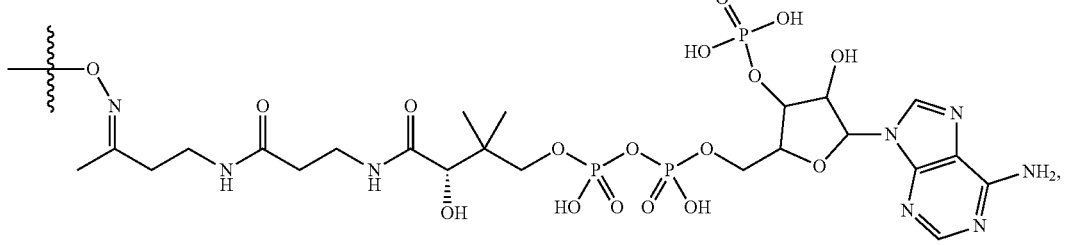
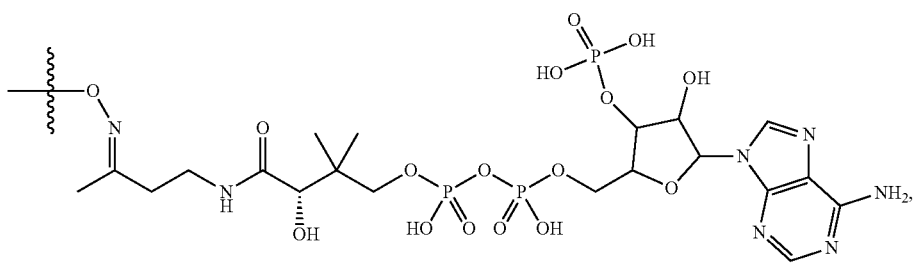

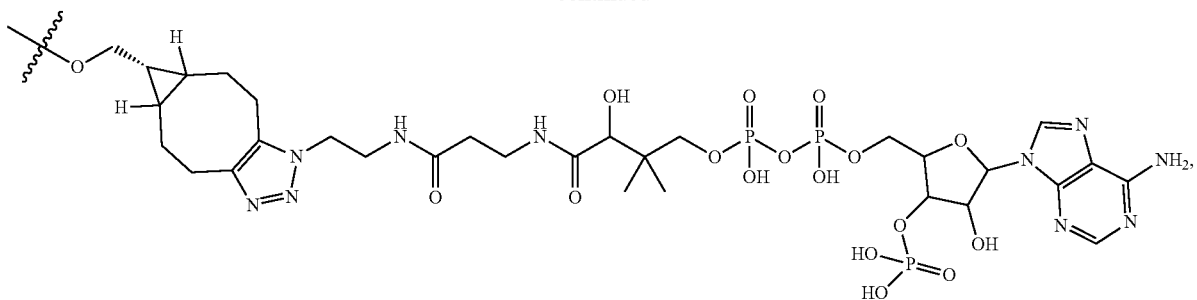
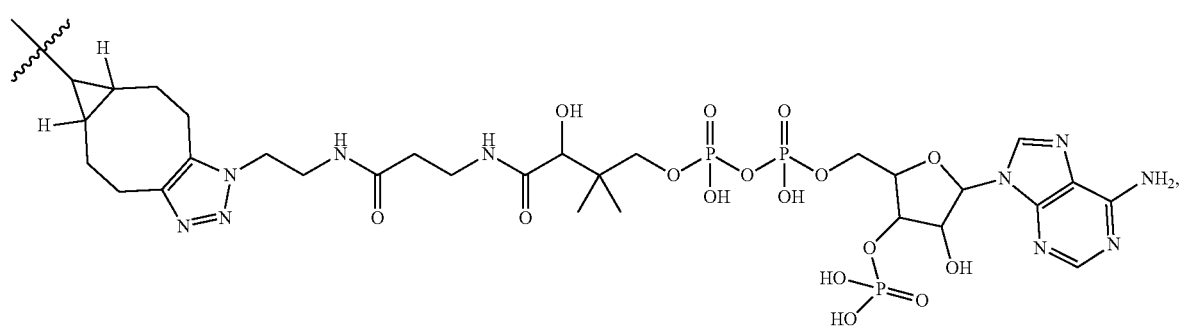
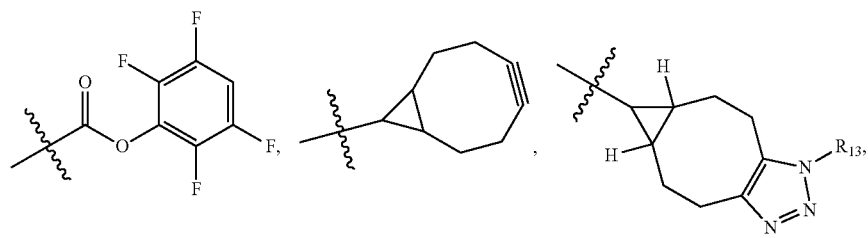
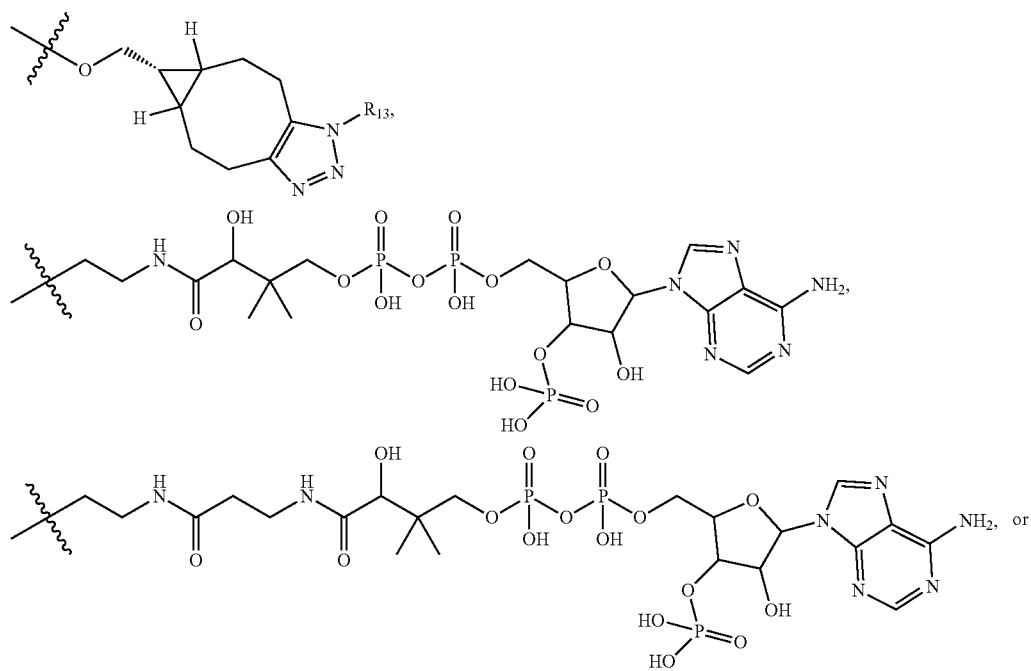

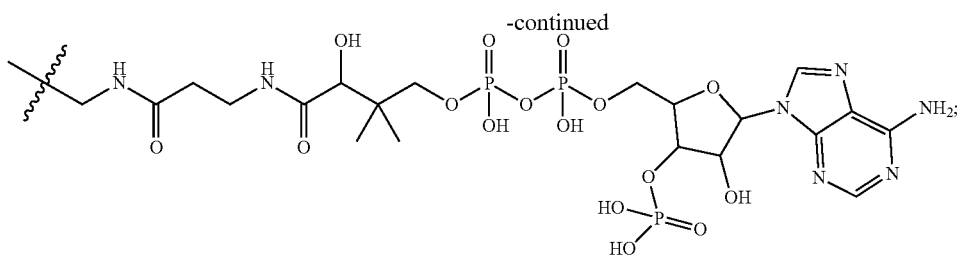
each $R^{12}$ is independently selected from H and $C_1$-$C_6$alkyl;
$R^{13}$ is —S(CH_2)_nCHR^{14}NHC(=O)R^{12},
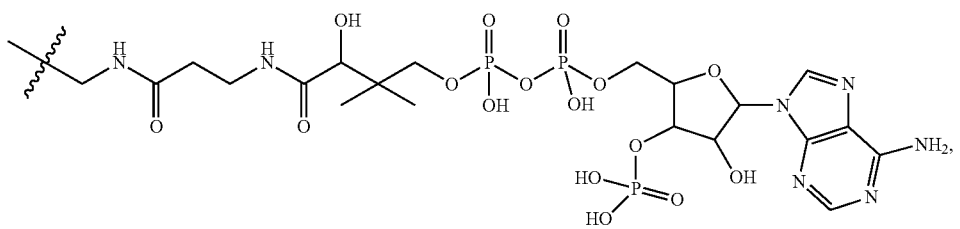
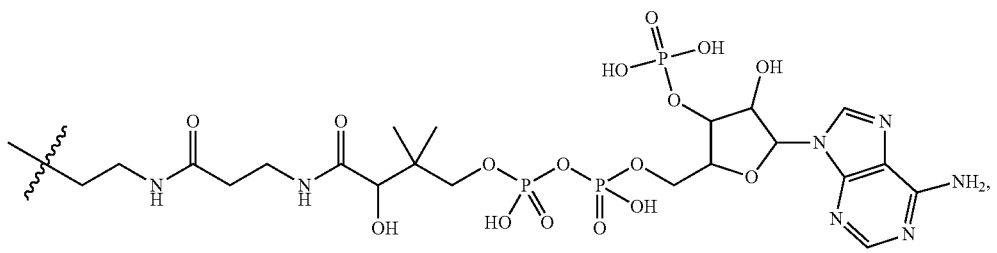
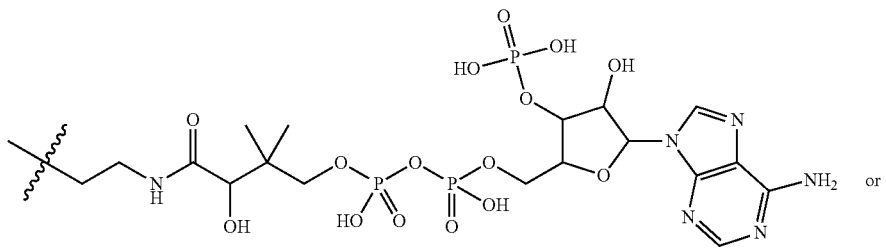 or
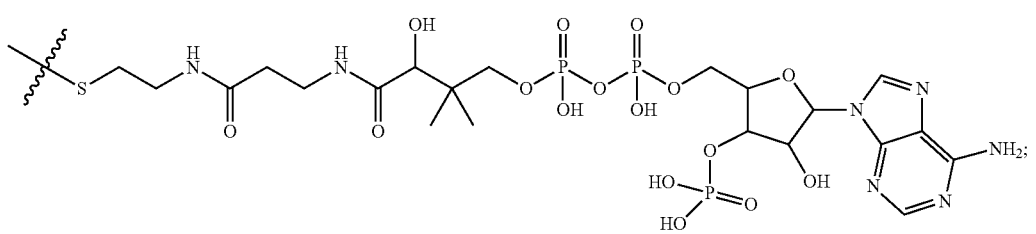

$R^{14}$ is $R^{12}$ or —C(=O)OR$^{12}$;
$R^{15}$ is tetrazolyl, —CN, —C(=O)OR$^{12}$,

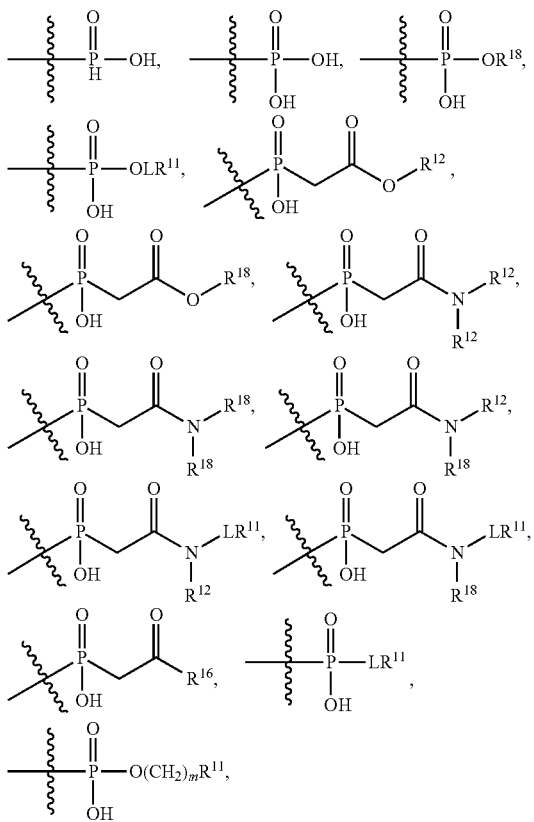

-LR$^{11}$ or —X$_4$LR$^{11}$;

each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;

$R^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;

$R^{17}$ is 2-pyridyl or 4-pyridyl;

each $R^{18}$ is independently selected from a C$_1$-C$_6$alkyl, a C$_1$-C$_6$alkyl which is substituted with azido and a C$_1$-C$_6$alkyl which is substituted with 1 to 5 hydroxyl;

$R^{19}$ is an unsubstituted C-linked 5-6 membered heterocycloalkyl having 1-2 heteroatoms independently selected from N and O;

or $R^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;

$R^{20}$ is an unsubstituted N-linked 5-6 membered heterocycloalkyl having 1-2 heteroatoms independently selected from N, O and S;

or $R^{20}$ is an N-linked 5-6 membered heterocycloalkyl having 1-2 heteroatoms independently selected from N, O and S, which is substituted with 1-3 substituents independently selected from C$_1$-C$_6$alkyl, —C(=O)OR$^{12}$, —C(=O)(CH$_2$)$_m$N$_3$, C$_1$-C$_6$haloalkyl, halogen, oxo, —OH and C$_1$-C$_6$alkoxy;

$R^{21}$ is a C-linked 5-6 membered heteroaryl having 1-2 N heteroatoms which is substituted with LR$^{11}$ and 0-2 substituents independently selected from C$_1$-C$_6$alkyl, C$_1$-C$_6$haloalkyl, halogen, —CN, NO$_2$, —C(=O)OR$^6$, —C(=O)N(R$^6$)$_2$ and C$_1$-C$_6$alkoxy;

$R^{22}$ is a C-linked 5-6 membered heterocycloalkyl having 1-2 heteroatoms independently selected from N, O and S which is substituted with LR$^{11}$ and 0-2 substituents independently selected from C$_1$-C$_6$alkyl, C$_1$-C$_6$haloalkyl, halogen and C$_1$-C$_6$alkoxy;

$R^{23}$ is an N-linked 5-6 membered heterocycloalkyl having 1-2 heteroatoms independently selected from N and O which is substituted with LR$^{11}$ and 0-2 substituents independently selected from C$_1$-C$_6$alkyl, C$_1$-C$_6$haloalkyl, halogen and C$_1$-C$_6$alkoxy;

X$_3$ is

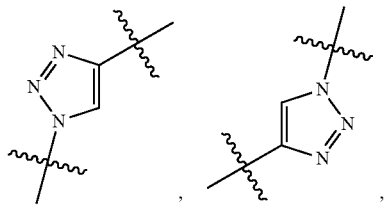

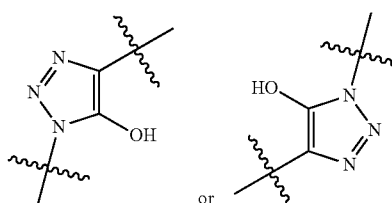

X$_4$ is 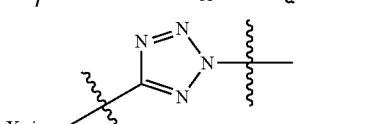 or

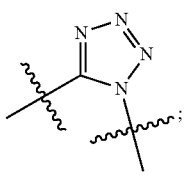;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18, or a tautomer, a hydrate, or a pharmaceutically acceptable salt thereof.

In an embodiment of this aforementioned aspect, $R^1$ is —N=CR$^4$R$^5$, —N=R$^{19}$, —N=CR$^5$R$^{20}$, —N=CR$^5$NR$^{12}$(CH$_2$)$_m$N(R$^{12}$)C(O)OR$^{12}$, —N=CR$^5$NR$^{12}$(CH$_2$)$_m$N(R$^{12}$)$_2$, —NHC(=NR$^6$)R$^4$, —NHC(=O)R$^4$, —NHC(=O)R$^{20}$, —NHR$^8$, —NHLR$^{11}$, —NHR$^{21}$, —N=CR$^5$R$^{10}$, —N=R$^{22}$, —N=CR$^5$R$^{23}$ or —NHC(=O)R$^{23}$;

$R^2$ is —C$_1$-C$_6$alkyl;

R³ is

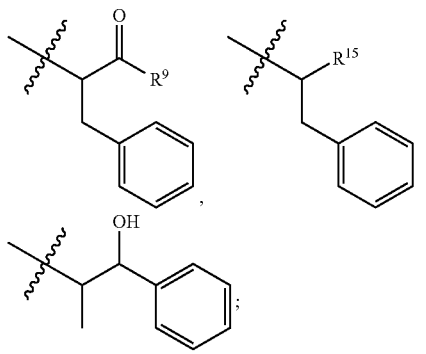

R⁴ is —N(R⁶)₂ or —NR⁶R⁷;
R⁵ is N(R⁶)₂;
each R⁶ is independently selected from H and —C₁-C₆alkyl;
R⁷ is —(CH₂)$_m$N(R¹²)₂, —(CH₂)$_m$N(R¹²)C(=O)OR¹² or an unsubstituted C₃-C₈cycloalkyl;
or R⁷ is a C₃-C₈cycloalkyl substituted with 1-3 substituents independently selected from C₁-C₆alkyl, oxo, —C(=O)R¹⁸, —(CH₂)$_m$OH, —C(=O)(CH₂)$_m$OH, —C(=O)((CH₂)$_m$O)$_n$R¹², —((CH₂)$_m$O)$_n$R¹² or a C₁-C₆alkyl which is optionally substituted with 1 to 5 hydroxyl;
R⁸ is an unsubstituted C-linked 5-6 membered heteroaryl having 1-2 N heteroatoms;
or R⁸ is a C-linked 5-6 membered heteroaryl having 1-2 N heteroatoms which is substituted with 1-3 substituents independently selected from C₁-C₆alkyl, C₁-C₆haloalkyl, halogen, C₁-C₆alkoxy, —OH, —CN, —NO₂, —C(=O)OR⁶, —C(=O)N(R⁶)₂, —C(=O)NR⁶(CH₂)$_m$N(R⁶)C(O)OR⁶ and —C(=O)NR⁶(CH₂)$_m$N(R⁶)₂;
R⁹ is —OH, C₁-C₆alkoxy, —NHS(O)₂(CH₂)$_m$N₃, —N(R¹²)₂, —R¹⁶, —NR¹²(CH₂)$_m$N(R¹²)₂, —NR¹²(CH₂)$_m$R¹⁶, -LR¹¹, —NHS(O)₂R¹⁸, —NHS(=O)₂LR¹¹,

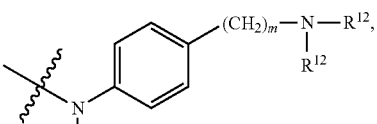

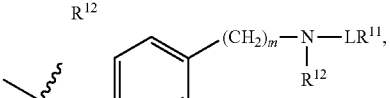

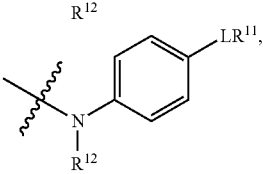

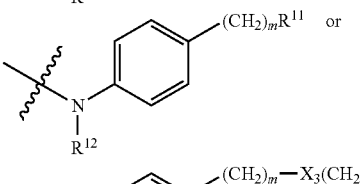

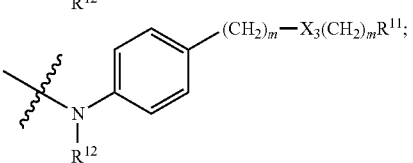

R¹⁰ is LR¹¹ or

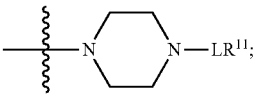

R¹¹ is

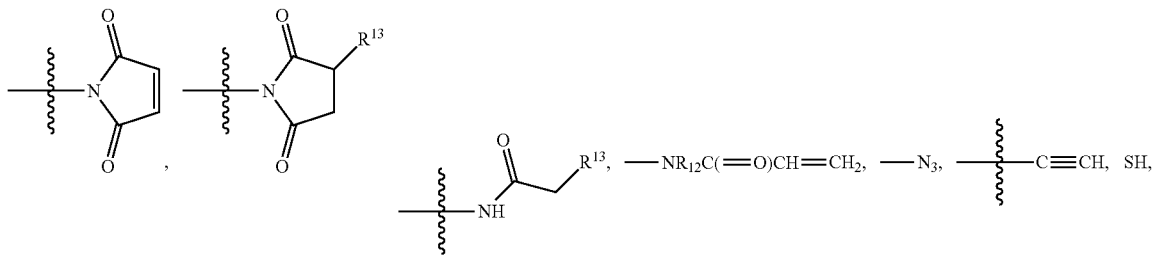

—SSR¹⁷, —S(=O)₂(CH=CH₂), —(CH₂)₂S(=O)₂(CH=CH₂), —NR¹²S(=O)₂(CH=CH₂), —NR¹²C(=O)CH₂R¹³,

—NR¹²C(=O)CH₂Br, —NR¹²C(=O)CH₂I, —NHC(=O)CH₂Br, —NHC(=O)CH₂I, —ONH₂, —C(O)NHNH₂,

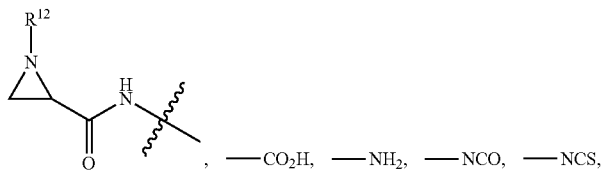

, —CO₂H, —NH₂, —NCO, —NCS,

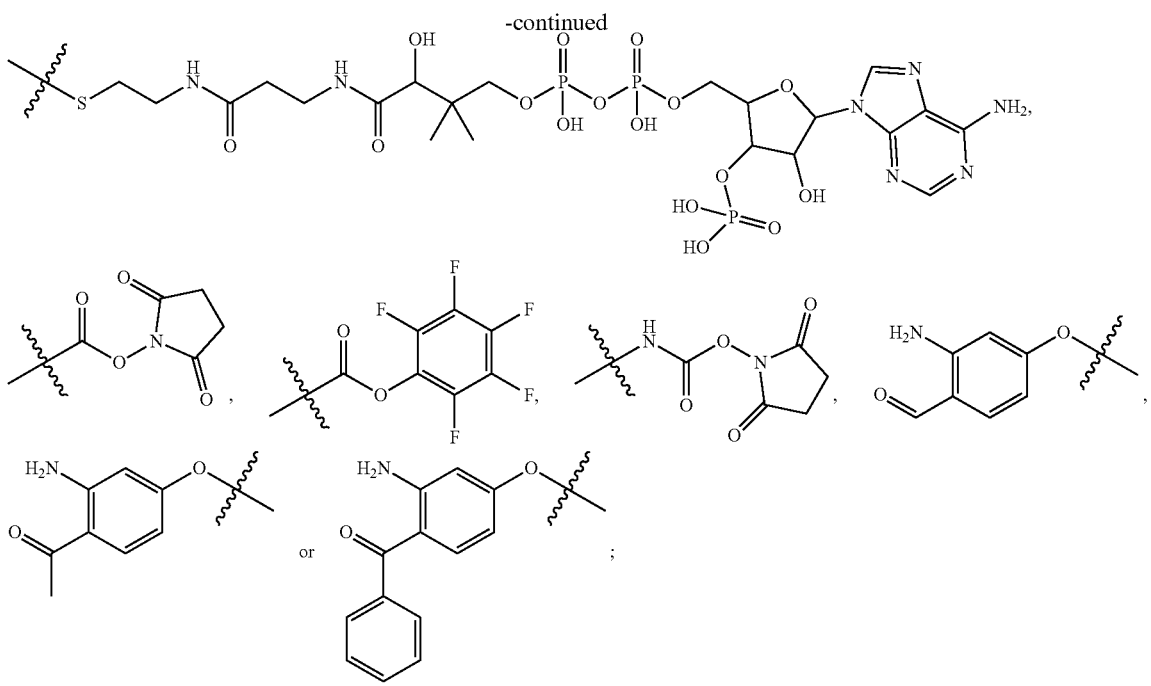

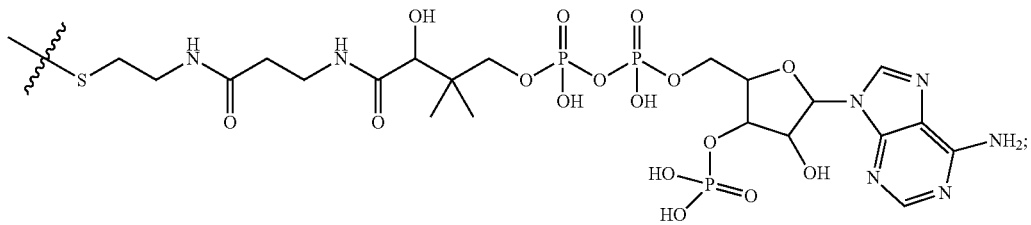

each $R^{12}$ is independently selected from H and $C_1$-$C_6$alkyl;
$R^{13}$ is —S(CH$_2$)$_n$CHR$^{14}$NHC(=O)R$^{12}$ or

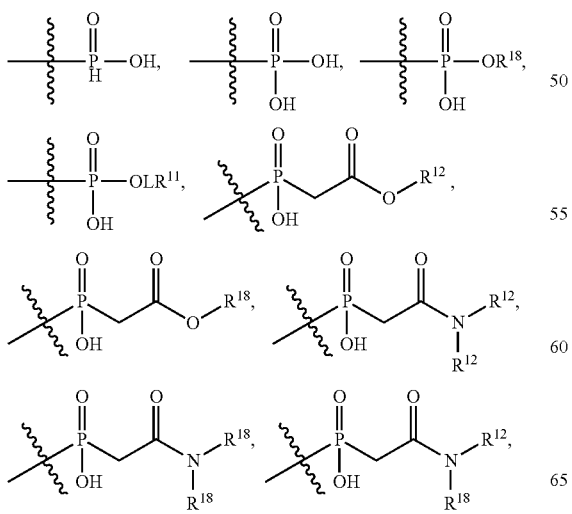

$R^{14}$ is $R^{12}$ or —C(=O)OR$^{12}$;
$R^{15}$ is tetrazolyl, —CN, —C(=O)OR$^{12}$,

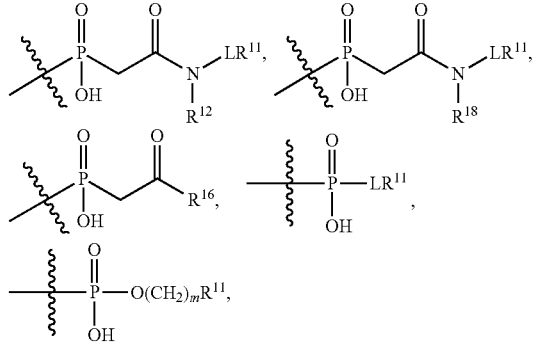

-LR$^{11}$ or —X$_4$LR$^{11}$;
$R^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;
$R^{17}$ is 2-pyridyl or 4-pyridyl;
each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

$R^{19}$ is an unsubstituted C-linked 5-6 membered heterocycloalkyl having 1-2 heteroatoms independently selected from N and O;

or $R^{19}$ is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;

$R^{20}$ is an unsubstituted N-linked 5-6 membered heterocycloalkyl having 1-2 heteroatoms independently selected from N, O and S;

or $R^{20}$ is an N-linked 5-6 membered heterocycloalkyl having 1-2 heteroatoms independently selected from N, O and S, which is substituted with 1-2 substituents independently selected from $C_1$-$C_6$alkyl, —C(=O)OR$^{12}$, —C(=O)(CH$_2$)$_m$N$_3$, $C_1$-$C_6$haloalkyl, halogen, oxo, —OH and $C_1$-$C_6$alkoxy;

$R^{21}$ is a C-linked 5-6 membered heteroaryl having 1-2 N heteroatoms which is substituted with LR$^{11}$ and 0-2 substituents independently selected from $C_1$-$C_6$alkyl, $C_1$-$C_6$haloalkyl, halogen, —CN, NO$_2$, —C(=O)OR$^6$, —C(=O)N(R$^6$)$_2$ and $C_1$-$C_6$alkoxy;

$R^{22}$ is a C-linked 5-6 membered heterocycloalkyl having 1-2 heteroatoms independently selected from N, O and S which is substituted with LR$^{11}$ and 0-2 substituents independently selected from $C_1$-$C_6$alkyl, $C_1$-$C_6$haloalkyl, halogen and $C_1$-$C_6$alkoxy;

$R^{23}$ is an N-linked 5-6 membered heterocycloalkyl having 1-2 heteroatoms independently selected from N and O which is substituted with LR$^{11}$ and 0-2 substituents independently selected from $C_1$-$C_6$alkyl, $C_1$-$C_6$haloalkyl, halogen and $C_1$-$C_6$alkoxy;

$X_3$ is

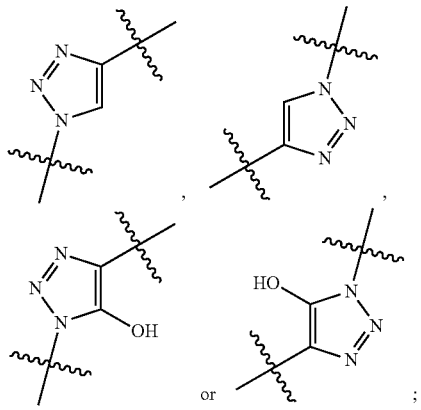

$X_4$ is

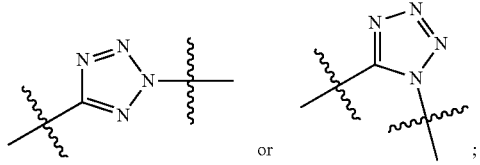

each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In certain embodiments of this aspect of the compounds having the structure of Formula (I), $R^1$ is —N=CR$^4$R$^5$, —N=R$^{19}$, —N=CR$^5$ R$^{20}$, —N=CR$^5$NR$^{12}$(CH$_2$)$_m$N(R$^{12}$)C(O)OR$^{12}$, —N=CR$^5$NR$^{12}$(CH$_2$)$_m$N(R$^{12}$)$_2$, —NHC(=NR$^6$)R$^4$, —NHC(=O)R$^4$, —NHC(=O)R$^{20}$ or —NHR$^8$;

$R^2$ is —C$_1$-C$_6$alkyl;

$R^3$ is

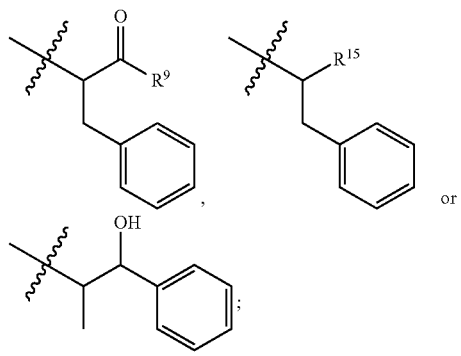

$R^4$ is —N(R$^6$)$_2$ or —NR$^6$R$^7$;
$R^5$ is N(R$^6$)$_2$;
each $R^6$ is independently selected from H and —C$_1$-C$_6$alkyl;
$R^7$ is —(CH$_2$)$_m$N(R$^{12}$)$_2$, —(CH$_2$)$_m$N(R$^{12}$)C(=O)OR$^{12}$ or an unsubstituted C$_3$-C$_8$cycloalkyl;

or $R^7$ is a C$_3$-C$_8$cycloalkyl substituted with 1-3 substituents independently selected from C$_1$-C$_6$alkyl, oxo, —C(=O)R$^{18}$, —(CH$_2$)$_m$OH, —C(=O)(CH$_2$)$_m$OH, —C(=O)((CH$_2$)$_m$O)$_n$R$^{12}$, —((CH$_2$)$_m$O)$_n$R$^{12}$ or a C$_1$-C$_6$alkyl which is optionally substituted with 1 to 5 hydroxyl;

$R^8$ is an unsubstituted C-linked 5-6 membered heteroaryl having 1-2 N heteroatoms;

or $R^8$ is a C-linked 5-6 membered heteroaryl which is substituted with 1-3 substituents independently selected from C$_1$-C$_6$alkyl, C$_1$-C$_6$haloalkyl, halogen, C$_1$-C$_6$alkoxy, —OH, —CN, —NO$_2$, —C(=O)OR$^6$, —C(=O)N(R$^6$)$_2$, —C(=O)NR$^6$(CH$_2$)$_m$N(R$^6$)C(O)OR$^6$ and —C(=O)NR$^6$(CH$_2$)$_m$N(R$^6$)$_2$;

$R^9$ is —OH, C$_1$-C$_6$alkoxy, —N(R$^{12}$)$_2$, —R$^{16}$, —NR$^{12}$(CH$_2$)$_m$ N(R$^{12}$)$_2$, —NR$^{12}$(CH$_2$)$_m$R$^{16}$, —NHS(O)$_2$R$^{18}$, or

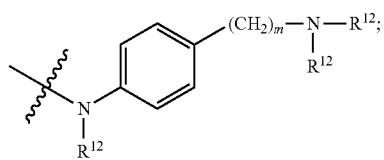

each R$^{12}$ is independently selected from H and C$_1$-C$_6$alkyl;
R$^{14}$ is R$^{12}$ or C(=O)OR$^{12}$;
R$^{15}$ is tetrazolyl, —CN, —C(=O)OR$^{12}$,

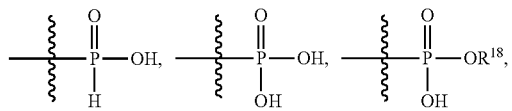

-continued

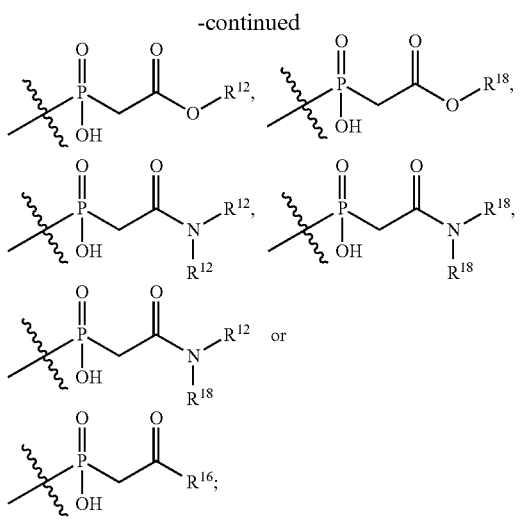

- $R^{16}$ is an N-linked 4-8 membered heterocycloalkyl containing 1-2 heteroatoms independently selected from N, O, S, S(=O) and S(=O)$_2$;
- $R^{17}$ is 2-pyridyl or 4-pyridyl;
- each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;
- $R^{19}$ is an unsubstituted C-linked 5-6 membered heterocycloalkyl having 1-2 heteroatoms independently selected from N and O;
- or $R^{19}$ is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;
- $R^{20}$ is an unsubstituted N-linked 5-6 membered heterocycloalkyl having 1-2 heteroatoms independently selected from N, O and S;
- or $R^{20}$ is an N-linked 5-6 membered heterocycloalkyl having 1-2 heteroatoms independently selected from N, O and S, which is substituted with 1-2 substituents independently selected from $C_1$-$C_6$alkyl, —C(=O)O$R^{12}$, —C(=O)(CH$_2$)$_m$N$_3$, $C_1$-$C_6$haloalkyl, halogen, oxo, —OH and $C_1$-$C_6$alkoxy;
- each m is independently selected from 1, 2, 3, 4, 5, 6, 7, 8, 9 and 10, and
- each n is independently selected from 1, 2, 3, 4, 5, 6, 7, 8, 9, 10, 11, 12, 13, 14, 15, 16, 17 and 18.

In certain embodiments of this aspect of the compounds having the structure of Formula (I), are compounds having the structure of Formula (Ia):

(Formula (Ia))

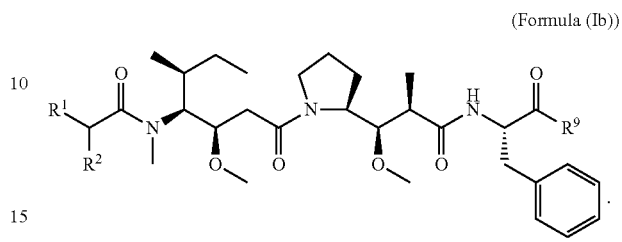

In other embodiments of the aspect of the compounds having the structure of Formula (I) or Formula (Ia), are compounds having the structure of Formula (Ib):

(Formula (Ib))

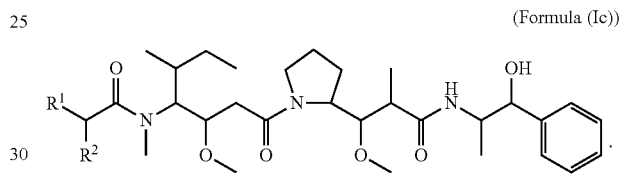

In certain embodiments of the aspect of the compounds having the structure of Formula (I), are compounds having the structure of Formula (Ic):

(Formula (Ic))

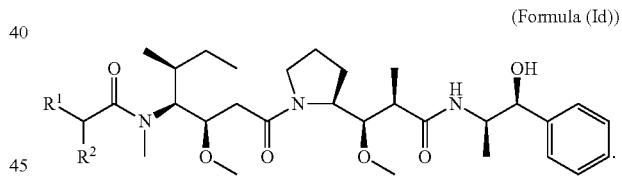

In other embodiments of the aspect of the compounds having the structure of Formula (I) or Formula (Ic), are compounds having the structure of Formula (Id):

(Formula (Id))

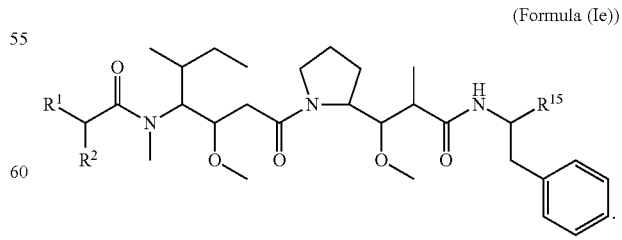

In certain embodiments of the aspect of the compounds having the structure of Formula (I), are compounds having the structure of Formula (Ie):

(Formula (Ie))

In other embodiments of the aspect of the compounds having the structure of Formula (I) or Formula (Ie), are compounds having the structure of Formula (If):

(Formula (If))

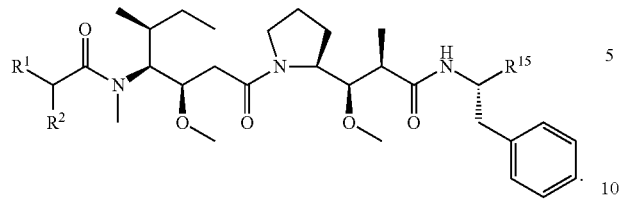

The present invention provides immunoconjugates, also referred to herein as ADCs, containing compounds of Formula (I) linked to an antigen binding moiety, such as an antibody or antibody fragment. These conjugates comprising a compound of Formula (I) are useful to treat cell proliferation disorders, particularly when the comound is linked to an antibody that recognizes cancer cells and thus promotes delivery of the compound to a cell targeted for attack. The immunoconjugates are especially useful for treating certain cancers as further detailed herein. Data provided herein demonstrate that these immunoconjugates are effective inhibitors of cell proliferation; without being bound by theory, it is believed their activity is due to inhibition of the polymerization of tubulin in cells.

In one aspect of the immunoconjugates of the invention include immunoconjugates of Formula (II):

(Formula (II))

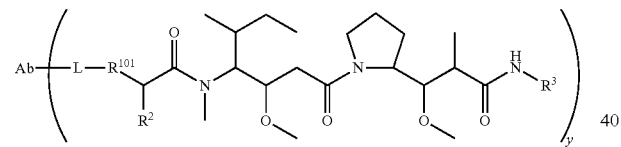

wherein:
Ab represents an antigen binding moiety;
L is selected from -$L_1L_2L_3L_4L_5L_6$-, -$L_6L_5L_4L_3L_2L_1$-, -$L_1L_2L_3L_4L_5$-, -$L_5L_4L_3L_2L_1$-, -$L_1L_2L_3L_4$-, -$L_4L_3L_2L_1$-, -$L_1L_2L_3$-, -$L_3L_2L_1$-, -$L_1L_2$-, -$L_2L_1$- and -$L_1$, wherein -$L_1$, $L_2$, $L_3$, $L_4$, $L_5$, and $L_6$ are as defined herein;
y is an integer from 1 to 16;
$R_{101}$ is

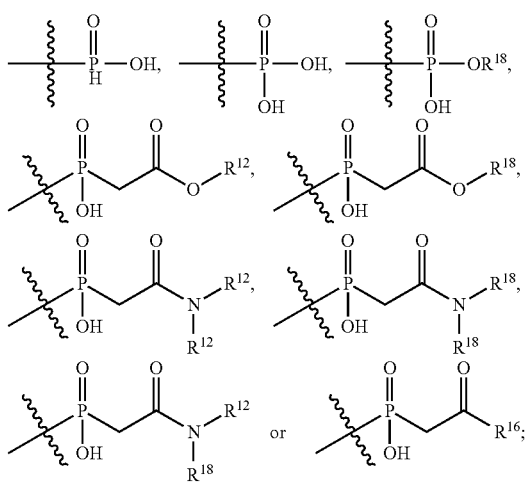

where the * denotes the point of attachment to L;
$R^2$ is —$C_1$-$C_6$alkyl;

$R^3$ is

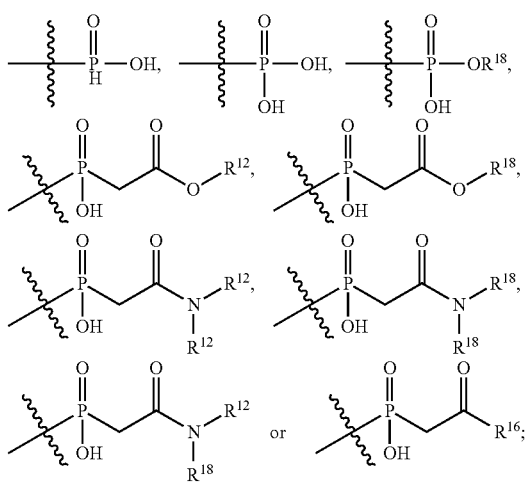

$R^5$ is $N(R^6)_2$;
each $R^6$ is independently selected from H and —$C_1$-$C_6$alkyl;
$R^9$ is —OH, $C_1$-$C_6$alkoxy, —$N(R^{12})_2$, —$R^{16}$, —$NR^{12}(CH_2)_m N(R^{12})_2$, —$NR^{12}(CH_2)_m R^{16}$, —$NHS(O)_2R^{18}$ or

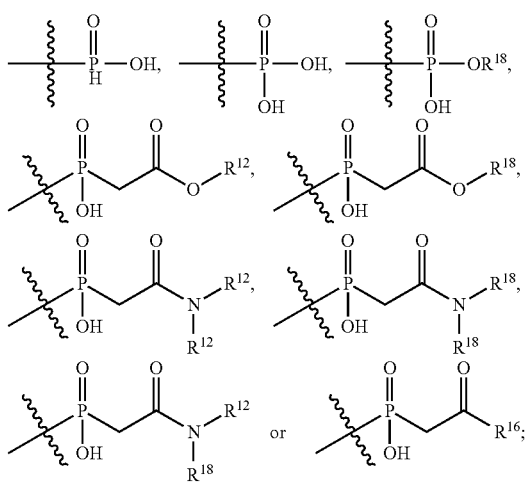

each $R^{12}$ is independently selected from H and $C_1$-$C_6$alkyl;
$R^{15}$ is tetrazolyl,

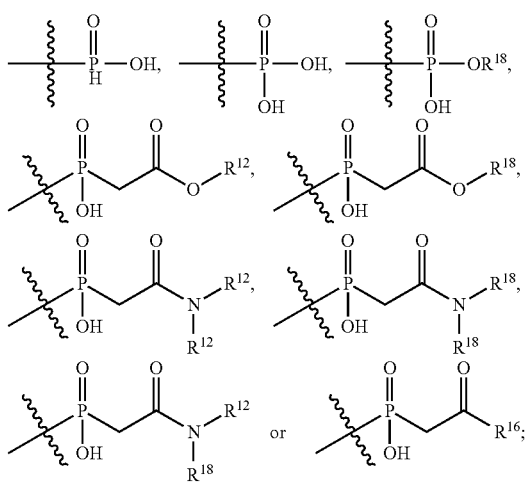

$R^{16}$ is an N-linked 4-8 membered heterocycloalkyl containing 1-2 heteroatoms independently selected from N, O, S, S(=O) and S(=O)$_2$, which is unsubstitituted or substituted with -L$R^{11}$ each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

$R^{110}$ is a bond or

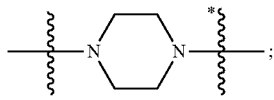

$R^{121}$ is a C-linked 5-6 membered heteroarylene having 1-2 N heteroatoms which is substituted with 0-2 substituents independently selected from $C_1$-$C_6$alkyl, $C_1$-$C_6$haloalkyl, halogen, —CN, NO$_2$, —C(=O)O$R^6$, —C(=O)N($R^6$)$_2$ and $C_1$-$C_6$alkoxy;

$R^{122}$ is a C-linked 5-6 membered heterocycloalkylene having 1-2 heteroatoms independently selected from N, O and S which is substituted with 0-2 substituents independently selected from $C_1$-$C_6$alkyl, $C_1$-$C_6$haloalkyl, halogen and $C_1$-$C_6$alkoxy;

$R^{123}$ is an N-linked 5-6 membered heterocycloalkylene having 1-2 heteroatoms independently selected from N and O which is substituted with 0-2 substituents independently selected from $C_1$-$C_6$alkyl, $C_1$-$C_6$haloalkyl, halogen and $C_1$-$C_6$alkoxy;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In one embodiment of the immunoconjugates of Formula (II):

Ab represents an antigen binding moiety;

L is selected from -$L_1L_2L_3L_4L_5L_6$-, -$L_6L_5L_4L_3L_2L_1$-, -$L_1L_2L_3L_4L_5$-, -$L_5L_4L_3L_2L_1$-, -$L_1L_2L_3L_4$-, -$L_4L_3L_2L_1$-, -$L_1L_2L_3$-, -$L_3L_2L_1$-, -$L_1L_2$-, -$L_2L_1$- and -$L_1$, wherein -$L_1$, $L_2$, $L_3$, $L_4$, $L_5$, and $L_6$ are as defined herein;

y is an integer from 1 to 16;

$R^{101}$ is

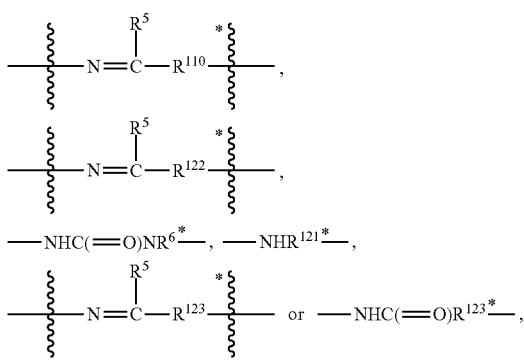

where the * denotes the point of attachment to L;

$R^2$ is —$C_1$-$C_6$alkyl;

$R^3$ is

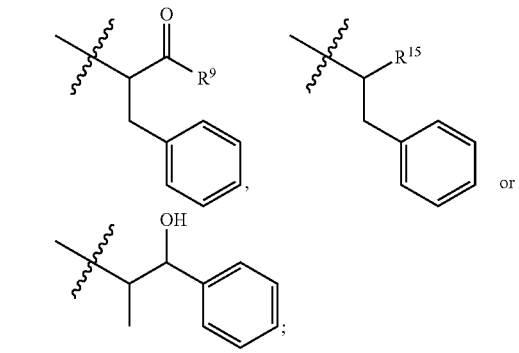

$R^5$ is N($R^6$)$_2$;
each $R^6$ is independently selected from H and —$C_1$-$C_6$alkyl;
$R^9$ is —OH, $C_1$-$C_6$alkoxy, —N($R^{12}$)$_2$, —$R^{16}$, —N$R^{12}$(CH$_2$)$_m$N($R^{12}$)$_2$, —N$R^{12}$(CH$_2$)$_m$$R^{16}$, —NHS(O)$_2$$R^{18}$ or

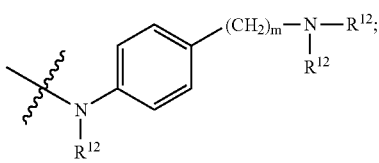

each $R^{12}$ is independently selected from H and $C_1$-$C_6$alkyl;
$R^{15}$ is tetrazolyl,

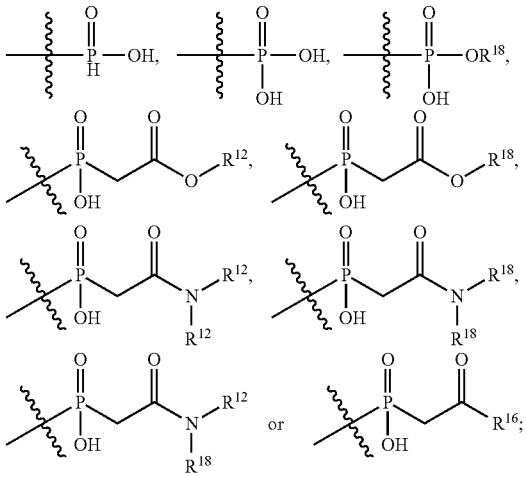

$R^{16}$ is an N-linked 4-8 membered heterocycloalkyl containing 1-2 heteroatoms independently selected from N, O, S, S(=O) and S(=O)$_2$, which is unsubstitituted or substituted with -L$R^{11}$ each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

$R^{110}$ is a bond or

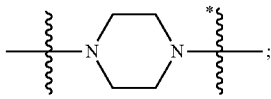

R$^{121}$ is a C-linked 5-6 membered heteroarylene having 1-2 N heteroatoms which is substituted with 0-2 substituents independently selected from C$_1$-C$_6$alkyl, C$_1$-C$_6$haloalkyl, halogen, —CN, NO$_2$, —C(=O)OR$^6$, —C(=O)N(R$^6$)$_2$ and C$_1$-C$_6$alkoxy;

R$^{122}$ is a C-linked 5-6 membered heterocycloalkylene having 1-2 heteroatoms independently selected from N, O and S which is substituted with 0-2 substituents independently selected from C$_1$-C$_6$alkyl, C$_1$-C$_6$haloalkyl, halogen and C$_1$-C$_6$alkoxy;

R$^{123}$ is an N-linked 5-6 membered heterocycloalkylene having 1-2 heteroatoms independently selected from N and O which is substituted with 0-2 substituents independently selected from C$_1$-C$_6$alkyl, C$_1$-C$_6$haloalkyl, halogen and C$_1$-C$_6$alkoxy;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In another aspect of the immunoconjugates of the invention are immunoconjugates having the structure of Formula (III):

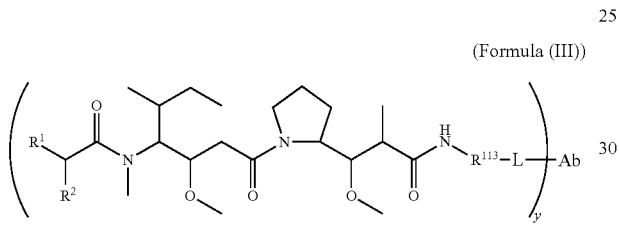

(Formula (III))

wherein:
Ab represents an antigen binding moiety;
L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, L$_1$L$_2$-, -L$_2$L$_1$- and -L$_1$, wherein -L$_1$, L$_2$, L$_3$, L$_4$, L$_5$, and L$_6$ are as defined herein;
y is an integer from 1 to 16;
R$^1$ is —N=CR$^4$R$^5$, —N=R$^{19}$, —N=CR$^5$R$^{20}$, —NHC(=NR$^6$)R$^4$, —NHC(=O)R$^4$, —NHC(=O)R$^{20}$ or —NHR$^8$;
R$^2$ is —C$_1$-C$_6$alkyl;
R$^4$ is —N(R$^6$)$_2$ or —NR$^6$R$^7$;
R$^5$ is N(R$^6$)$_2$;
each R$^6$ is independently selected from H and —C$_1$-C$_6$alkyl;
R$^7$ is an unsubstituted C$_3$-C$_8$cycloalkyl;
or R$^7$ is a C$_3$-C$_8$cycloalkyl substituted with 1-3 substituents independently selected from C$_1$-C$_6$alkyl, oxo, —C(=O)R$^{18}$, —(CH$_2$)$_m$OH, —C(=O)(CH$_2$)$_m$OH, —C(=O)((CH$_2$)$_m$O)$_n$R$^{12}$, —((CH$_2$)$_m$O)$_n$R$^{12}$ or a C$_1$-C$_6$alkyl which is optionally substituted with 1 to 5 hydroxyl;
R$^8$ is an unsubstituted C-linked 5-6 membered heteroaryl having 1-2 N heteroatoms;
or R$^8$ is a C-linked 5-6 membered heteroaryl having 1-2 N heteroatoms which is substituted with 1-3 substituents independently selected from C$_1$-C$_6$alkyl, C$_1$-C$_6$haloalkyl, halogen, —OH, —N(R$^6$)$_2$, —CN, —NO$_2$, —C(=O)OR$^6$ and C$_1$-C$_6$alkoxy;
each R$^{12}$ is independently selected from H and C$_1$-C$_6$alkyl;
R$^{19}$ is an unsubstituted C-linked 5-6 membered heterocycloalkyl having 1-2 heteroatoms independently selected from N and O;
or R$^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;

R$^{20}$ is an unsubstituted N-linked 5-6 membered heterocycloalkyl having 1-2 heteroatoms independently selected from N, O and S;

or R$^{20}$ is an N-linked 5-6 membered heterocycloalkyl having 1-2 heteroatoms independently selected from N, O and S, which is substituted with 1-3 substituents independently selected from C$_1$-C$_6$alkyl, C$_1$-C$_6$haloalkyl, halogen, —C(=O)OR$^{12}$, oxo, —OH and C$_1$-C$_6$alkoxy;

R$^{113}$ is

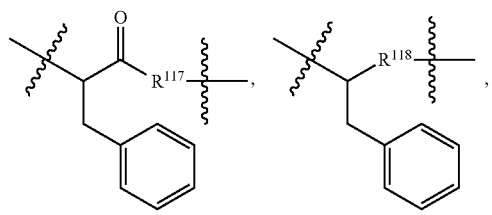

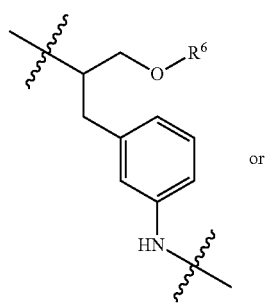

or

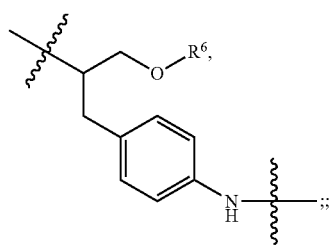

R$^{117}$ is a bond, —NH—, —NHS(=O)$_2$—, —NHS(=O)$_2$(CH$_2$)$_m$X$_3$(CH$_2$)$_m$—, -, —NHS(=O)$_2$(CH$_2$)$_m$NHC(=O)—, —NHS(=O)$_2$(CH$_2$)$_m$NHC(=O)O(CH$_2$)$_m$—,

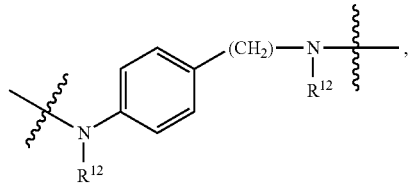

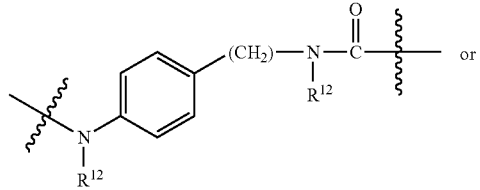

or

-continued

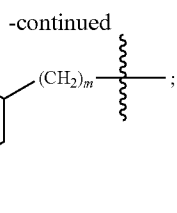

$R^{118}$ is a bond, tetrazolyl,

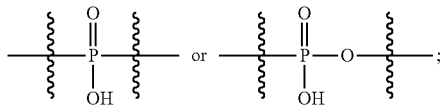

$R_{26}$ is

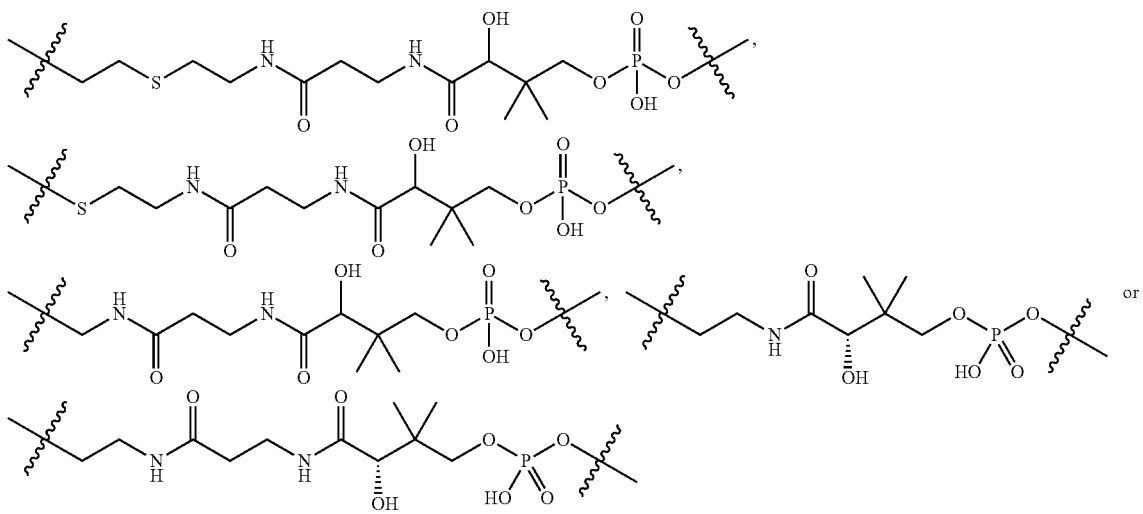

each m is independently selected from 1, 2, 3, 4, 5, 6, 7, 8, 9 and 10,
and
each n is independently selected from 1, 2, 3, 4, 5, 6, 7, 8, 9, 10, 11, 12, 13, 14, 15, 16, 17 and 18.

In an embodiment of the immunoconjugates of Formula (III):
Ab represents an antigen binding moiety;
L is selected from $-L_1L_2L_3L_4L_5L_6-$, $-L_6L_5L_4L_3L_2L_1-$, $-L_1L_2L_3L_4L_5-$, $-L_5L_4L_3L_2L_1-$, $-L_1L_2L_3L_4-$, $-L_4L_3L_2L_1-$, $-L_1L_2L_3-$, $-L_3L_2L_1-$, $-L_1L_2-$, $-L_2L_1-$ and $-L_1$, wherein $-L_1$, $L_2$, $L_3$, $L_4$, $L_5$, and $L_6$ are as defined herein;
y is an integer from 1 to 16;
$R^1$ is $-N=CR^4R^5$, $-N=R^{19}$, $-N=CR^5R^{20}$, $-NHC(=NR^6)R^4$, $-NHC(=O)R^4$, $-NHC(=O)R^{20}$ or $-NHR^8$;
$R^2$ is $-C_1-C_6$alkyl;
$R^4$ is $-N(R^6)_2$ or $-NR^6R^7$;
$R^5$ is $N(R^6)_2$;
each $R^6$ is independently selected from H and $-C_1-C_6$alkyl;
$R^7$ is an unsubstituted $C_3-C_8$cycloalkyl;
or $R^7$ is a $C_3-C_8$cycloalkyl substituted with 1-3 substituents independently selected from $C_1-C_6$alkyl, oxo, $-C(=O)R^{18}$, $-(CH_2)_m OH$, $-C(=O)(CH_2)_m OH$, $-C(=O)((CH_2)_m O)_n R^{12}$, $-((CH_2)_m O)_n R^{12}$ or a $C_1-C_6$alkyl which is optionally substituted with 1 to 5 hydroxyl;

$R^8$ is an unsubstituted C-linked 5-6 membered heteroaryl having 1-2 N heteroatoms;
or $R^8$ is a C-linked 5-6 membered heteroaryl having 1-2 N heteroatoms which is substituted with 1-3 substituents independently selected from $C_1-C_6$alkyl, $C_1-C_6$haloalkyl, halogen, $-OH$, $-N(R^6)_2$, $-CN$, $-NO_2$, $-C(=O)OR^6$ and $C_1-C_6$alkoxy;
each $R^{12}$ is independently selected from H and $C_1-C_6$alkyl;
$R^{19}$ is an unsubstituted C-linked 5-6 membered heterocycloalkyl having 1-2 heteroatoms independently selected from N and O;
or $R^{19}$ is a C-linked 5-6 membered heterocycloalkyl having 1-2 heteroatoms independently selected from N and O which is substituted with 1-3 substituents independently selected from $C_1-C_6$alkyl, $C_1-C_6$haloalkyl, halogen and $C_1-C_6$alkoxy;

$R^{20}$ is an unsubstituted N-linked 5-6 membered heterocycloalkyl having 1-2 heteroatoms independently selected from N, O and S;
or $R^{20}$ is an N-linked 5-6 membered heterocycloalkyl having 1-2 heteroatoms independently selected from N, O and S, which is substituted with 1-2 substituents independently selected from $C_1-C_6$alkyl, $C_1-C_6$haloalkyl, halogen, $-C(=O)OR^{12}$, oxo, $-OH$ and $C_1-C_6$alkoxy;
$R^{113}$ is

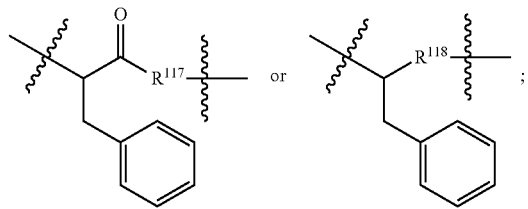

$R^{117}$ is a bond, —NH—, —NHS(=O)$_2$—,

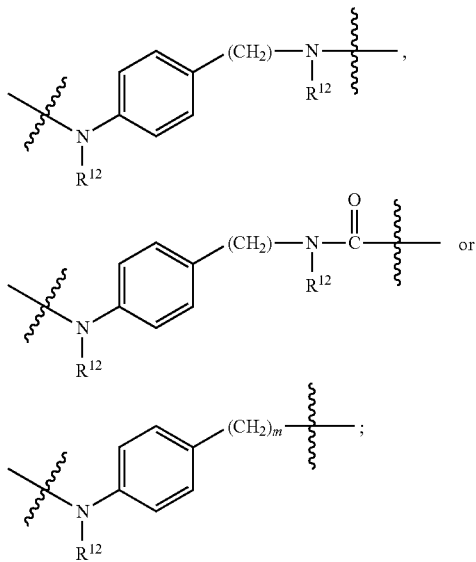

$R^{118}$ is a bond, tetrazolyl,

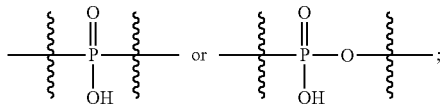

each m is independently selected from 1, 2, 3, 4, 5, 6, 7, 8, 9 and 10,
and
each n is independently selected from 1, 2, 3, 4, 5, 6, 7, 8, 9, 10, 11, 12, 13, 14, 15, 16, 17 and 18.

The invention provides methods for making such ADCs using compounds of Formula (I) as the payload (drug) to be delivered. Such compounds are anti-mitotic cytotoxic peptides wherein the N-terminus or C-teminus has been modified to have a reactive functional group, and optionally one or more linker components, to facilitate connecting the compound either directly or indirectly to the antibody or antigen binding fragment, for instance the above described second and third aspects of the compounds of Formula (I). In addition, the invention provides methods to use these ADCs to treat cell proliferation disorders.

In another aspect, the invention provides pharmaceutical compositions comprising an immunoconjugate of Formula (II) or Formula (III), or subformulae thereof, admixed with at least one pharmaceutically acceptable carrier or excipient, optionally admixed with two or more pharmaceutically acceptable carriers or excipients, and methods to use these compositions to treat cell proliferation disorders.

In another aspect, the invention provides a method to treat a condition characterized by excessive or undesired cell proliferation, which comprises administering to a subject in need of such treatment an effective amount of an immunoconjugate of Formula (II) or Formula (III). The subject for treatment can be a mammal, and is preferably a human. Conditions treatable by the immunoconjugates and methods described herein include various forms of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. Other cell proliferation disorders that can be treated with these methods and compositions include diabetic retinopathy, liver and lung fibrosis, Sjogren's syndrome, and lupus erythematous.

The invention includes compositions of Formulas (I)-(III) and the subformulae thereof as described herein, and all stereoisomers (including diastereoisomers and enantiomers), tautomers, and isotopically enriched versions thereof (including deuterium substitutions) as well as pharmaceutically acceptable salts of these compounds. The present invention also comprises polymorphs of Formula (I) (or sub-formulas thereof) and salts, particularly pharmaceutically acceptable salts, thereof.

DETAILED DESCRIPTION

Figure 1A:
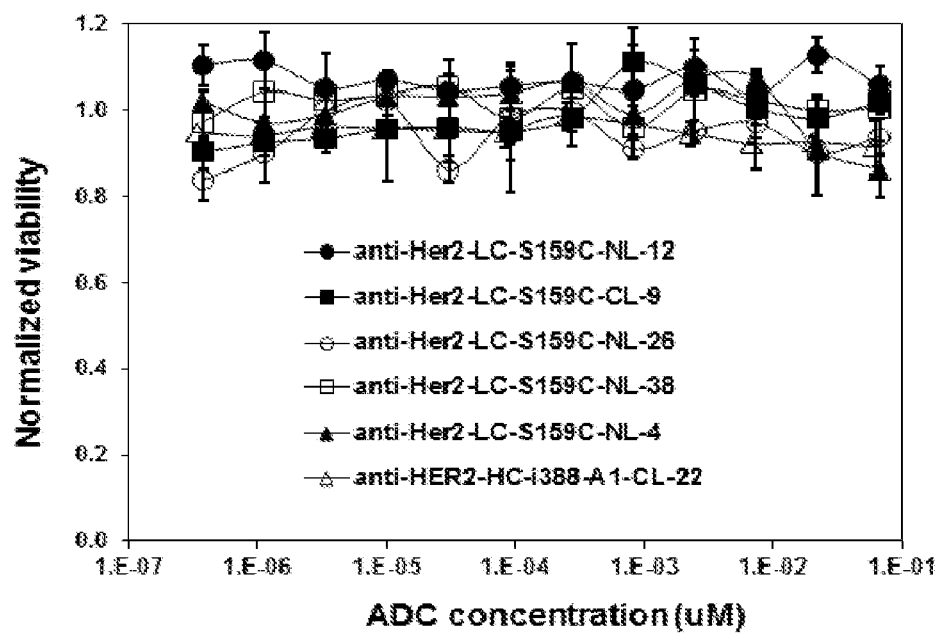
FIG. 1A-1D: In vitro cell proliferation assays of anti-Her2 ADCs: (A) MDA-MB-231 clone 40 cells, (B) MDA-MB-231 clone 16 cells, (C) HCC1954 cells, and (D) JimT-1 cells.
Figure 1B:
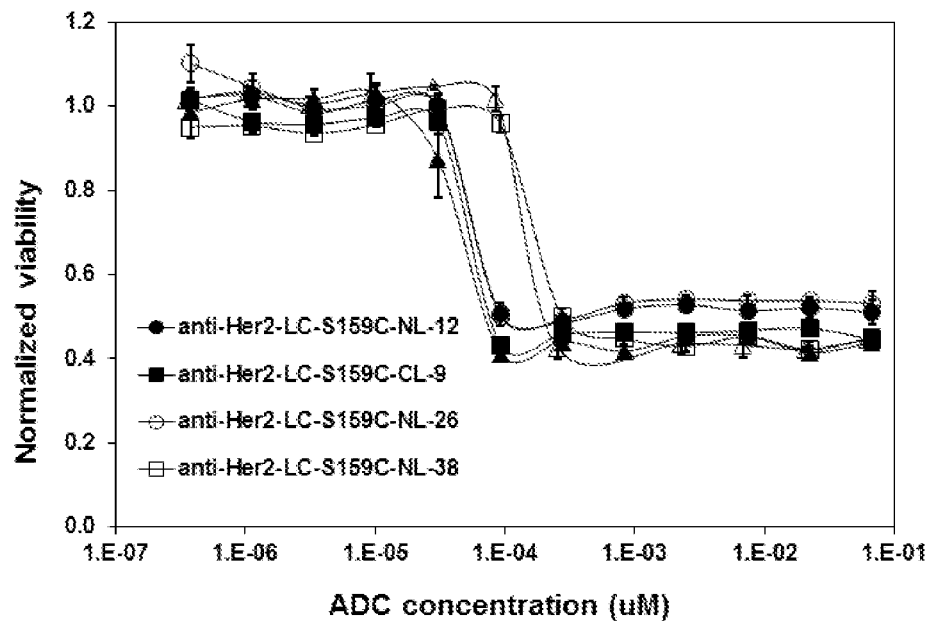
Figure 1C:
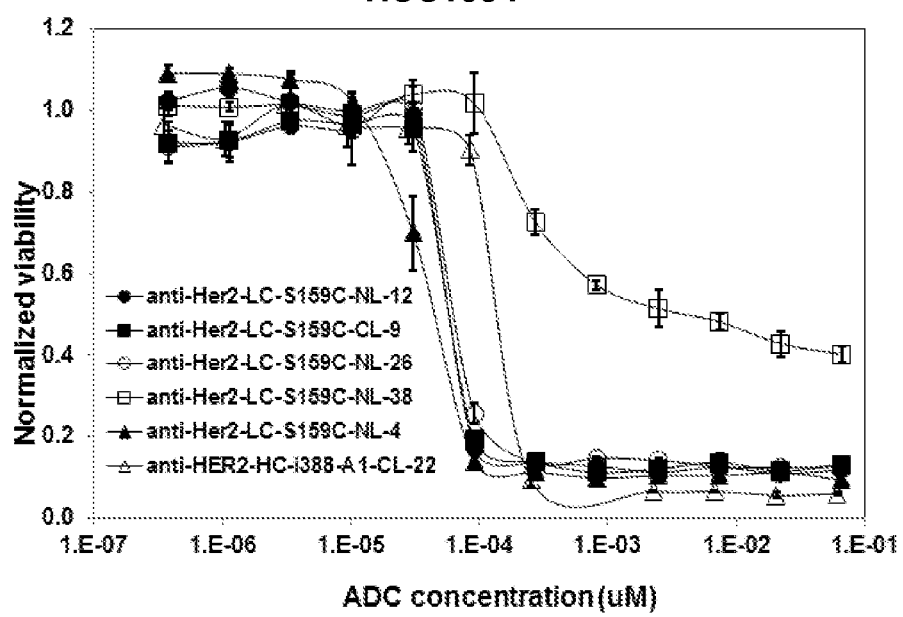
Figure 1D:
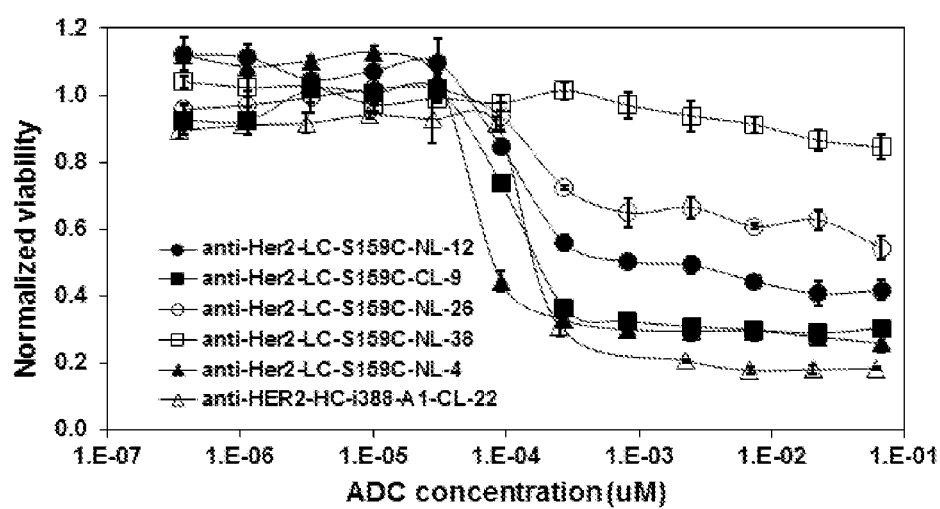
Figure 2A:
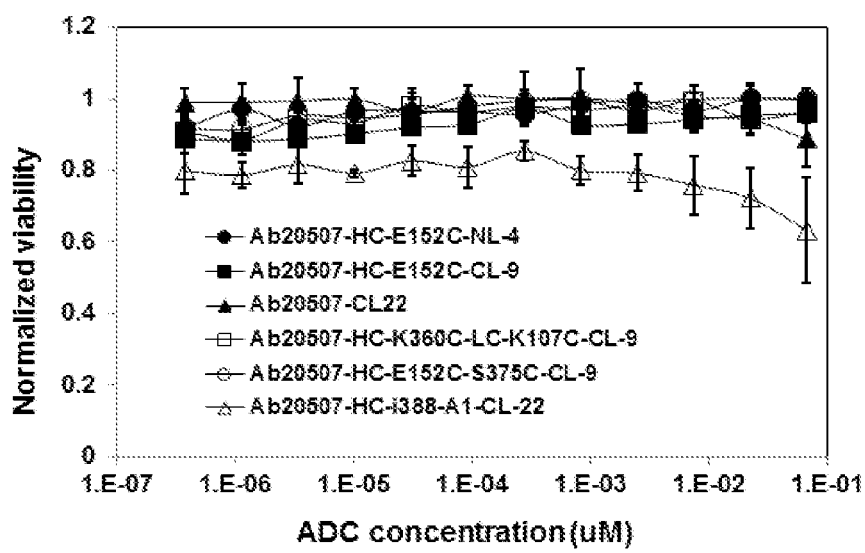
FIG. 2A-2D: In vitro cell proliferation assays of antibody 20507 ADCs: (A) Jurkat cells, (B) NCI-H526 cells, (C) KU812 cells, and (D) CMK11-5 cells.
Figure 2B:
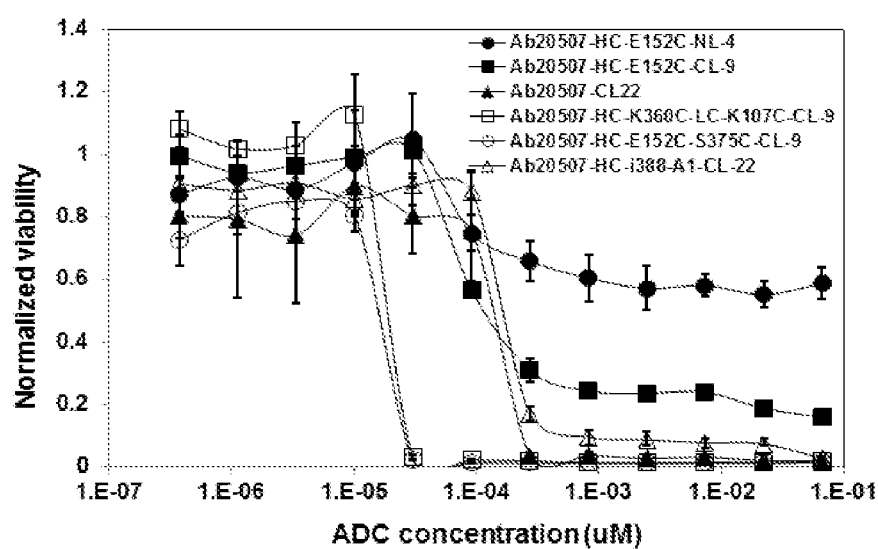
Figure 2C:
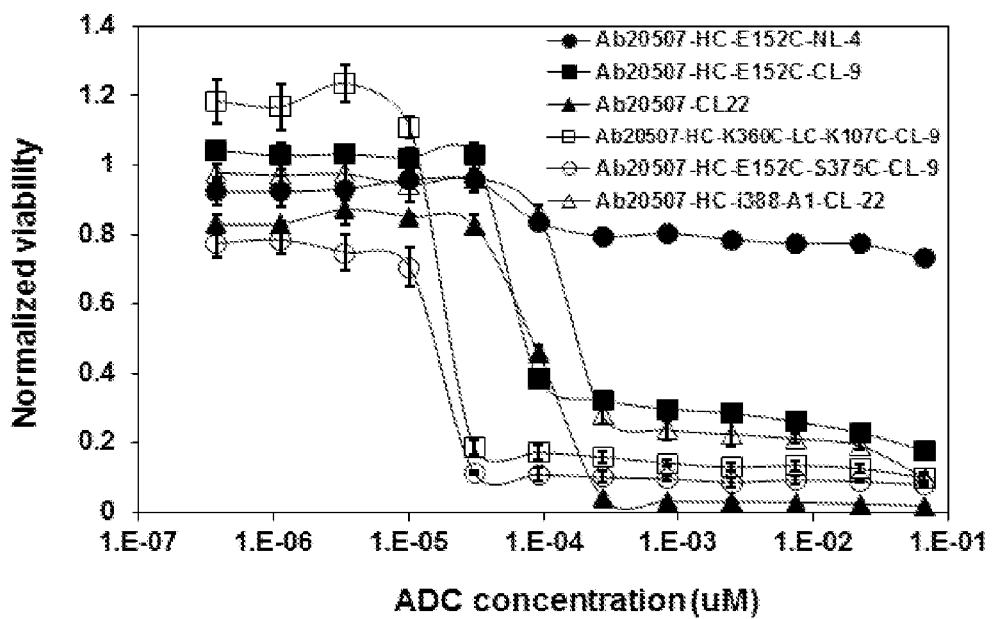
Figure 2D:
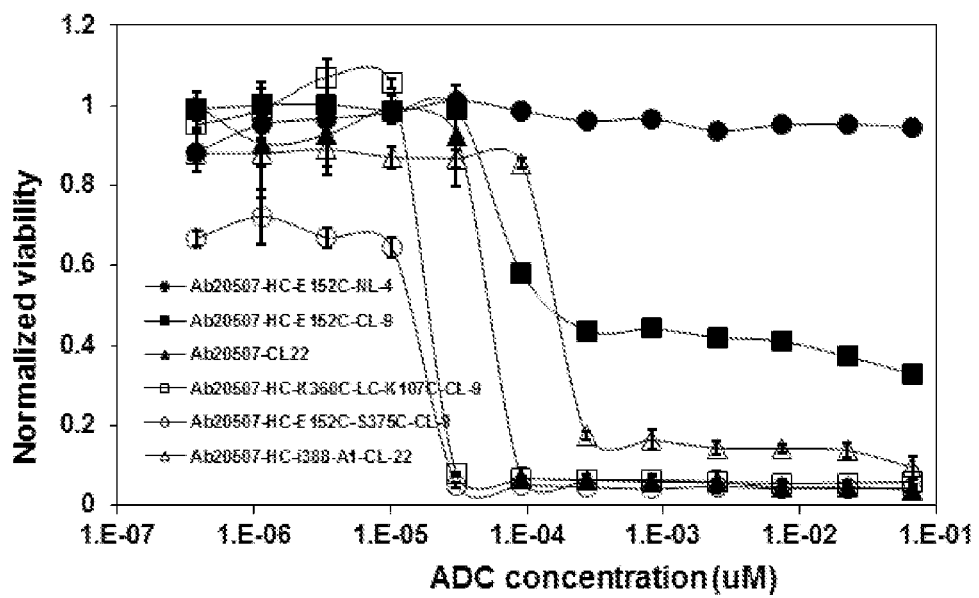

The following definitions apply unless otherwise expressly provided.

The term "amino acid" refers to canonical, synthetic, and unnatural amino acids, as well as amino acid analogs and amino acid mimetics that function in a manner similar to the canonical amino acids. Canonical amino acids are proteinogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, as well as selenocysteine, pyrrolysine and pyrroline-carboxy-lysine. Amino acid analogs refer to compounds that have the same basic chemical structure as a canonical amino acid, i.e., an a-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a canonical amino acid.

The term "antigen binding moiety" as used herein refers to a moiety capable of binding specifically to an antigen, and includes but is not limited to antibodies and antigen binding fragments.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "specifically binds" or "selectively binds," when used in the context of describing the interaction between an antigen (e.g., a protein or a glycan) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses modified variants thereof.

The term "immunoconjugate" or "antibody-drug-conjugate" as used herein refers to the linkage of an antigen binding moiety such as an antibody or an antigen binding fragment thereof with a compound of Formula (I). The linkage can be covalent bonds, or non-covalent interactions, and can include chelation. Various linkers, known in the art, can be employed in order to form the immunoconjugate.

The term "cytotoxic peptide", "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein, refers to a chemical moiety that is or can be conjugated to an antibody or antigen binding fragment to form an immunoconjugate, and can include any moiety that is useful to attach to the antibody or antigen binding fragment. For example, "drug moiety" or "payload" includes, but is not limited to, the compounds described herein. The immunoconjugates of the invention comprise one or more compounds described herein as a payload, but may also include one or more other payloads. Other payloads include, for example, a drug moiety or payload can be an anti-cancer agent, an anti-inflammatory agent, an antifungal agent, an antibacterial agent, an anti-parasitic agent, an anti-viral agent, or an anesthetic agent. In certain embodiments a drug moiety is selected from an Eg5 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include calicheamycins such as gamma-calicheamycin; and maytansinoids such as DM1, DM3 and DM4. Methods for attaching each of these to a linker compatible with the antibodies and method of the invention are known in the art. See, e.g., Singh et al., (2009) Therapeutic Antibodies: Methods and Protocols, vol. 525, 445-457.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to at least partially alleviate, inhibit, prevent and/or ameliorate a condition, or a disorder or a disease.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In certain embodiments, the modified immunoconjugates of the invention are described according to a "drug-to-antibody" ratio of, e.g., 1, 2, 3, 4, 5, 6, 7, or 8, or 12 or 16; this ratio corresponds to "y" in Formula (II) and Formula (III). While this ratio has an integer value for a specific conjugate molecule, it is understood that an average value is typically used to describe a sample containing many molecules, due to some degree of inhomogeneity within a sample of an immunoconjugate. The average loading for a sample of an immunoconjugate is referred to herein as the "drug to antibody ratio," or DAR. In some embodiments, the DAR is between about 1 to about 16, and typically is about 1, 2, 3, 4, 5, 6, 7, or 8. In some embodiments, at least 50% of a sample by weight is compound having the average DAR plus or minus 2, and preferably at least 50% of the sample is a product that contains the average DAR plus or minus 1.5. Preferred embodiments include immunoconjugates wherein the DAR is about 2 to about 8, e.g., about 2, about 3, about 4, about 5, about 6, about 7, or about 8. In these embodiments, a DAR of "about q" means the measured value for DAR is within ±20% of q, or preferably within ±10% of q.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms, unless otherwise stated, e.g., where a specific isomer is identified. Optically active (R)- and (S)-isomers may be prepared using chiral synthons or chiral reagents, or resolved using conventional techniques. If the compound contains a double bond, the substituent may be E or Z configuration. If the compound contains a di-substituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. "Substantially pure" or "substantially free of other isomers" as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of Formula (I) of the present invention, including salts, hydrates and solvates thereof, may inherently or by design form polymorphs.

The term "thiol-maleimide" as used herein refers to a group formed by reaction of a thiol with maleimide, having this general formula

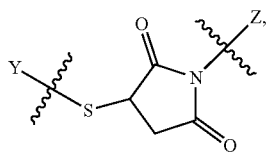

where Y and Z are groups to be connected via the thiol-maleimide linkage and can comprise linker components, antibodies or payloads.

"Cleavable" as used herein refers to a linker or linker component that connects two moieties by covalent connections, but breaks down to sever the covalent connection between the moieties under physiologically relevant conditions, typically a cleavable linker is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linker or linker component attached to the payload, or it may release the payload without any residual part or component of the linker.

"Pcl" as used herein refers to pyrroline carboxy lysine, e.g.,

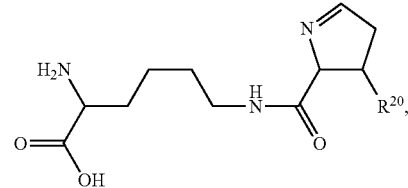

where $R^{20}$ is H, which has the following formula when incorporated into a peptide:

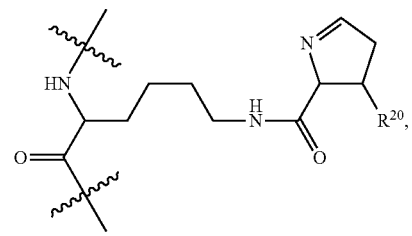

The corresponding compound wherein $R^{20}$ is methyl is pyrrolysine.

"Non-cleavable" as used herein refers to a linker or linker component that is not especially susceptible to breaking down under physiological conditions, e.g., it is at least as stable as the antibody or antigen binding fragment portion of the immunoconjugate.

Such linkers are sometimes referred to as "stable", meaning they are sufficiently resistant to degradation to keep the payload connected to the antigen binding moiety Ab until Ab is itself at least partially degraded, i.e., the degradation of Ab precedes cleavage of the linker in vivo. Degradation of the antibody portion of an ADC having a stable or non-cleavable linker may leave some or all of the linker, and one or more amino acid groups from an antibody, attached to the payload or drug moiety that is delivered in vivo.

The terms "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl", as used herein, refer to a fully saturated branched or straight chain hydrocarbon containing 1-3 carbon atoms, 2-3 carbon atoms, 1-4 carbon atoms, 1-5 carbon atoms, 1-6 carbon atoms or 2-6 carbon atoms, respectively. Non-limiting examples of "$C_1$-$C_3$alkyl" groups include methyl, ethyl, n-propyl and isopropyl. Non-limiting examples of "$C_2$-$C_3$alkyl" groups include ethyl, n-propyl and isopropyl. Non-limiting examples of "$C_1$-$C_4$alkyl" groups include methyl, ethyl, n-propyl, isopropyl, n-butyl, isobutyl, sec-butyl and tert-butyl. Non-limiting examples of "$C_1$-$C_5$alkyl" groups include methyl, ethyl, n-propyl, isopropyl, n-butyl, isobutyl, sec-butyl, tert-butyl, n-pentyl and isopentyl. Non-limiting examples of "$C_1$-$C_6$alkyl" groups include methyl, ethyl, n-propyl, isopropyl, n-butyl, isobutyl, sec-butyl, tert-butyl, n-pentyl, isopentyl and hexyl. Non-limiting examples of "$C_2$-$C_6$alkyl" groups include ethyl, n-propyl, isopropyl, n-butyl, isobutyl, sec-butyl, tert-butyl, n-pentyl, isopentyl and hexyl.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

The terms "$C_1$-$C_3$alkoxy", "$C_2$-$C_3$alkoxy", "$C_1$-$C_4$alkoxy", "$C_1$-$C_5$alkoxy", "$C_1$-$C_6$alkoxy" and "$C_2$-$C_6$alkoxy", as used herein, refer to the groups —O—$C_1$-$C_3$alkyl, —O—$C_2$-$C_3$alkyl, —O—$C_1$-$C_4$alkyl, —O—$C_1$-$C_5$alkyl, —O—$C_1$-$C_6$alkyl and O—$C_2$-$C_6$alkyl, respectively, wherein the groups "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl" are as defined herein. Non-limiting examples of "$C_1$-$C_3$alkoxy" groups include methoxy, ethoxy, n-propoxy and isopropoxy. Non-limiting examples of "$C_2$-$C_3$alkoxy" groups include ethoxy, n-propoxy and isopropoxy. Non-limiting examples of "$C_1$-$C_4$alkoxy" groups include methoxy, ethoxy, n-propoxy, isopropoxy, n-butoxy, isobutoxy, sec-butoxy and tert-butoxy. Non-limiting examples of "$C_1$-$C_5$alkoxy" groups include methoxy, ethoxy, n-propoxy, isopropoxy, n-butoxy, isobutoxy, sec-butoxy, tert-butoxy, n-pentyloxy and isopentyloxy. Non-limiting examples of "$C_1$-$C_6$alkoxy" groups include methoxy, ethoxy, n-propoxy, isopropoxy, n-butoxy, isobutoxy, sec-butoxy, tert-butoxy, n-pentyloxy, isopentyloxy and hexyloxy. Non-limiting examples of "$C_2$-$C_6$alkoxy" groups include ethoxy, n-propoxy, isopropoxy, n-butoxy, isobutoxy, sec-butoxy, tert-butoxy, n-pentyloxy, isopentyloxy and hexyloxy.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "heteroatoms" refers to nitrogen (N), oxygen (O) or sulfur (S) atoms, in particular nitrogen or oxygen, unless otherwise provided.

The term "4-8 membered heterocycloalkyl," as used herein refers to a saturated 4-8 membered monocyclic hydrocarbon ring structure wherein one to two of the ring carbons of the hydrocarbon ring structure are replaced by one to two NR groups, wherein R is hydrogen, a bond, an $R^5$ group as defined herein or an $R^7$ group as defined herein. Non-limiting examples of 4-8 membered heterocycloalkyl groups, as used herein, include azetadinyl, azetadin-1-yl, azetadin-2-yl, azetadin-3-yl, pyrrolidinyl, pyrrolidin-1-yl, pyrrolidin-2-yl, pyrrolidin-3-yl, pyrrolidin-4-yl, pyrrolidin-5-yl, piperidinyl, piperidin-1-yl, piperidin-2-yl, piperidin-3-yl, piperidin-4-yl, piperidin-5-yl, piperidin-6-yl, piperazinyl, piperazin-1-yl, piperazin-2-yl, piperazin-3-yl, piperazin-4-yl, piperazin-5-yl, piperazin-6-yl, azepanyl, azepan-1-yl, azepan-2-yl, azepan-3-yl, azepan-4-yl, azepan-5-yl, azepan-6-yl, and azepan-7-yl.

The term "6 membered heterocycloalkyl," as used herein refers to a saturated 6 membered monocyclic hydrocarbon ring structure wherein one to two of the ring carbons of the hydrocarbon ring structure are replaced by one to two NR groups, wherein R is hydrogen, a bond, an $R^5$ group as defined herein or an $R^7$ group as defined herein. Non-limiting examples of 6 membered heterocycloalkyl groups, as used herein, include piperidinyl, piperidin-1-yl, piperidin-2-yl, piperidin-3-yl, piperidin-4-yl, piperidin-5-yl, piperidin-6-yl, piperazinyl, piperazin-1-yl, piperazin-2-yl, piperazin-3-yl, piperazin-4-yl, piperazin-5-yl and piperazin-6-yl.

The term "4-8 membered heterocycloalkylene," as used herein refers to a divalent radical derived from a 4-8 membered heterocycloalkyl group.

The term "6 membered heterocycloalkylene," as used herein refers to a divalent radical derived from a 6 membered heterocycloalkyl group.

The term "heteroaryl," as used herein, refers to a 5-6 membered heteroaromatic monocyclic ring having 1 to 4 heteroatoms independently selected from nitrogen, oxygen and sulfur. Non-limiting examples of such heteroaryl groups, as used herein, include 2- or 3-furyl; 1-, 2-, 4-, or 5-imidazolyl; 3-, 4-, or 5-isothiazolyl; 3-, 4-, or 5-isoxazolyl; 2-, 4-, or 5-oxazolyl; 4- or 5-1,2,3-oxadiazolyl; 2- or 3-pyrazinyl; 1-, 3-, 4-, or 5-pyrazolyl; 3-, 4-, 5- or 6-pyridazinyl; 2-, 3-, or 4-pyridyl; 2-, 4-, 5- or 6-pyrimidinyl; 1-, 2- or 3-pyrrolyl; 1- or 5-tetrazolyl; 2- or 5-1,3,4-thiadiazolyl; 2-, 4-, or 5-thiazolyl; 2- or 3-thienyl; 2-, 4- or 6-1,3,5-triazinyl; 1-, 3- or 5-1,2,4-triazolyl; and 1-, 4- or 5-1,2,3-triazolyl. Preferred embodiments of a heteroaryl used herein are 5-6 membered heteroaromatic monocyclic ring having 1-2 N heteroatoms. In certain embodiments, non-limiting examples of heteroaryl groups, as used herein, include 2- or 3-pyrazinyl; 3-, 4-, 5- or 6-pyridazinyl; 2-, 3-, or 4-pyridyl; and 2-, 4-, 5- or 6-pyrimidinyl.

The term "heteroarylene," as used herein, refers to a divalent radical derived from a heteroaryl group.

The immunoconjugate naming convention used herein is antibody-Compound Number, where Compound Number refers to the compound of Formula (I) used for conjugation to the particular antibody. By way of example, anti-Her2-LC-S159C-CL-12 describes antibody anti-Her2-LC-S159C conjugated to Compound CL-12. By way of Example anti-Her2-HC-ins388-A1-CoA-1-CL-22 describes antibody anti-Her2-HC-ins388 tagged with an A1 peptide which is coupled to CoA analog (CoA-1) and then conjugated to Compound CL-22.

Linkers

The compounds provided herein for use as ADC payloads can be attached to a linker, L, or directly to an antigen binding moiety. Suitable linkers for use in such ADCs are well known in the art, and can be used in the conjugates of the invention. The linker, L, can be attached to the antigen binding moiety at any suitable available position on the antigen binding moiety: typically, L is attached to an available amino nitrogen atom (i.e., a primary or secondary amine, rather than an amide) or a hydroxylic oxygen atom, or to an available sulfhydryl, such as on a cysteine. The compounds provided herein are anti-mitotic cytotoxic peptides and the attachment of the linker, L, to the compound can be at the N-terminus or at the C-terminus. A wide variety of linkers for use in ADCs are known (see, e.g., Lash, *Antibody-Drug Conjugates: the Next Generation of Moving Parts, Start-Up,* December 2011, 1-6), and can be used in conjugates within the scope of the invention.

The linker, L, in Formula (I), Formula (II) and Formula (III) is a linking moiety comprising one or more linker components $L_1$, $L_2$, $L_3$, $L_4$, $L_5$, $L_6$, etc. In certain embodiments a linker component can represent a bond connecting the groups flanking it together. In certain embodiments, L is -*$L_1L_2L_3L_4L_5L_6$-, where the * denotes the site of attachment to the compound of the invention. In certain embodiments a linker component can represent a bond connecting the groups flanking it together. In certain embodiments, L is -*$L_1L_2L_3L_4L_5$-, where the * denotes the site of attachment to the compound of the invention. In certain embodiments a linker component can represent a bond connecting the groups flanking it together. In certain embodiments, L is -*$L_1L_2L_3L_4$-, where the * denotes the site of attachment to the compound of the invention. In certain embodiments a linker component can represent a bond connecting the groups flanking it together. In certain embodiments, L is -*$L_1L_2L_3$-, where the * denotes the site of attachment to the compound of the invention. In a preferred embodiment L is -*$L_1L_2$-, where the * denotes the site of attachment to the compound of the invention. In certain embodiment L is -$L_1$-. Some preferred linkers and linker components are depicted herein.

The linker, L, in Formula (I), Formula (II) and Formula (III) may be divalent, meaning it can used to link only one payload per linker to an antigen binding moiety, or it can be trivalent an is able to link two payloads per linker to an antigen binding moiety, or it can be polyvalent. Trivalent, tetravalent, and polyvalent linkers can be used to increase the loading of a payload (drug) on an antigen binding moiety (e.g. an antibody), thereby increasing the drug to antibody ratio (DAR) without requiring additional sites on the antibody for attaching multiple linkers. Examples of such linkers given in Bioconjugate Chem., 1999 March-April; 10(2): 279-88; U.S. Pat. No. 6,638,499; Clin Cancer Res Oct. 15, 2004 10; 7063; and WO2012/113847A1.

A linker, L, for use in the compounds of Formula (I) and the immunoconjugates of Formula (II) and Formula (III) can be cleavable or non-cleavable. Cleavable linkers, such as those containing a hydrazone, a disulfide, the dipeptide Val-Cit, and ones containing a glucuronidase-cleavable p-aminobenzyloxycarbonyl moiety, are well known in the art, and can be used. See, e.g., Ducry, et al., *Bioconjugate Chem.*, vol. 21, 5-13 (2010). For the immunoconjugates of comprising a cleavable linker, the linker is substantially stable in vivo until the immunoconjugate binds to or enters a cell, at which point either intracellular enzymes or intracellular chemical conditions (pH, reduction capacity) cleave the linker to free the compound.

Alternatively, non-cleavable linkers can be used in compounds of Formula (I) and the immunoconjugates of Formula (II) and Formula (III). Non-cleavable linkers lack structural components designed to degrade in cells, and thus their structures can vary substantially. See, e.g., Ducry, et al., *Bioconjugate Chem.*, vol. 21, 5-13 (2010). These immunoconjugates are believed to enter a targeted cell and undergo proteolytic degradation of the antibody rather than linker decomposition; thus at least a portion, or all, of the linker and even some of the antibody or antibody fragment may remain attached to the payload.

The linker, L, in the compounds of Formula (I) and the immunoconjugates of Formula (II) and Formula (III) typically commonly contain two or more linker components, which may be selected for convenience in assembly of the conjugate, or they may be selected to impact properties of the conjugate. Suitable linker components for forming linker, L, are known in the art, as are methods for constructing the linker L. Linker components can include the groups commonly used to attach a group to an amino acid, spacers such as alkylene groups and ethylene oxide oligomers, amino acids and short peptides up to about 4 amino acids in length; a bond; and carbonyl, carbamate, carbonate, urea, ester and amide linkages, and the like. Linker components can comprise thiol-maleimide groups, thioethers, amides, and esters; groups that are easily cleaved in vivo under conditions found in, on or around targeted cells, such as disulfides, hydrazones, dipeptides like Val-Cit, substituted benzyloxycarbonyl groups, and the like; spacers to orient the payload in a suitable position relative to the antigen binding moiety, such as phenyl, heteroaryl, cycloalkyl or heterocyclyl rings, and alkylene chains; and/or pharmacokinetic property-enhancing groups, such as alkylene substituted with one or more polar groups (carboxy, sulfonate, hydroxyl, amine, amino acid, saccharide), and alkylene chains containing one or more —NH— or —O— in place of methylene group(s), such as glycol ethers (—$CH_2CH_2O$—)$_p$ where p is 1-10, which may enhance solubility or reduce intermolecular aggregation, for example.

In addition, linker components can comprise chemical moieties that are readily formed by reaction between two reactive groups. Non-limiting examples of such chemical moieties are given in Table 1.

TABLE 1

| Reactive Group 1 | Reactive Group 2 | Chemical Moiety |
|---|---|---|
| a thiol | a thiol | —S—S— |
| a thiol | a maleimide | (succinimide-thioether structure) |
| a thiol | a haloacetamide | (acetamide-thioether structure) |

TABLE 1-continued
| Reactive Group 1 | Reactive Group 2 | Chemical Moiety |
| --- | --- | --- |
| an azide | an alkyne | 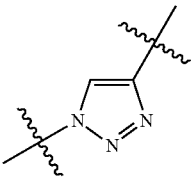 |
| an azide | a triaryl phosphine | 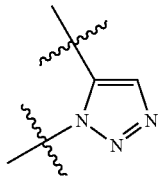 |
| an azide | a cyclooctene | 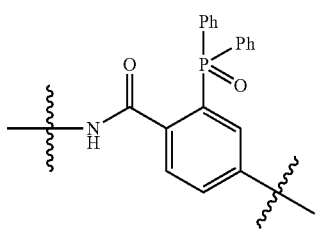 |
| an azide | an oxanorbornadiene | 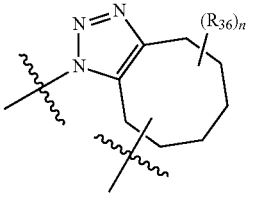 |
| a triaryl phosphine | an azide | 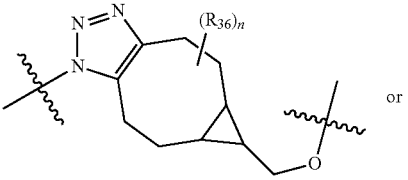 |

TABLE 1-continued
| Reactive Group 1 | Reactive Group 2 | Chemical Moiety |
| --- | --- | --- |
| an oxanobornadiene | an azide | 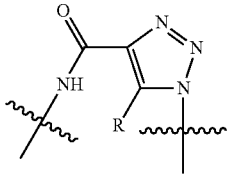 |
| an alkyne | an azide | 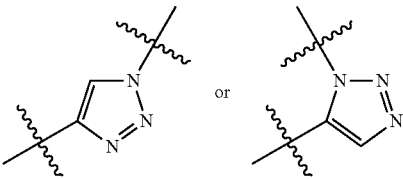 |
| a cyclooctyne | azide | 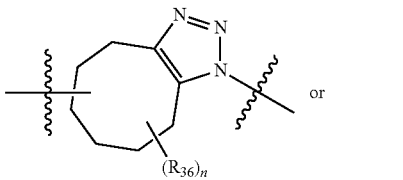 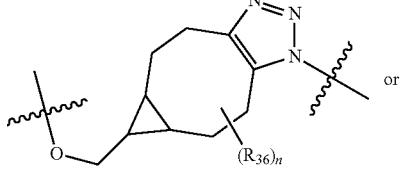 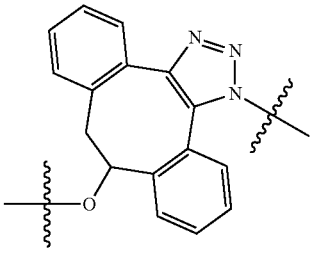 |
| a cyclooctyne | a diaryl tetrazine | 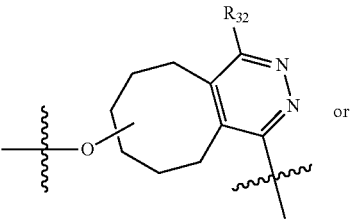 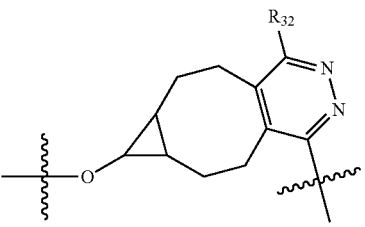 |

TABLE 1-continued
| Reactive Group 1 | Reactive Group 2 | Chemical Moiety |
|---|---|---|
| a diaryl tetrazine | a cyclooctene | 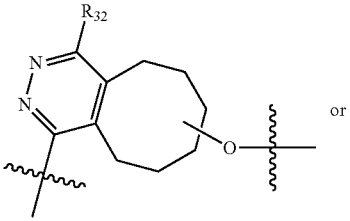 or 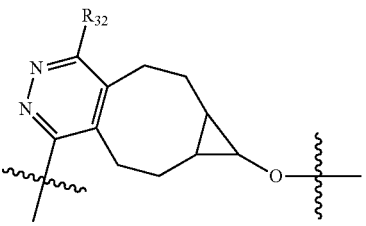 |
| a monoaryl tetrazine | a norbornene | 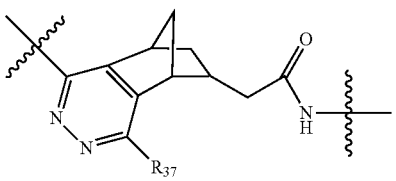 |
| a norbornene | a monoaryl tetrazine | 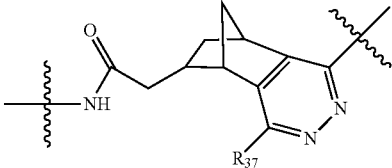 |
| an aldehyde | a hydroxylamine | 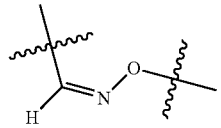 |
| an aldehyde | a hydrazine | 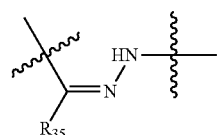 |
| an aldehyde | NH$_2$—NH—C(=O)— | 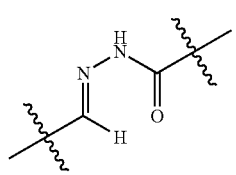 |
| a ketone | a hydroxylamine | 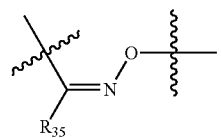 |

TABLE 1-continued

| Reactive Group 1 | Reactive Group 2 | Chemical Moiety |
|---|---|---|
| a ketone | a hydrazine | (structure) |
| a ketone | $NH_2-NH-C(=O)-$ | (structure) |
| a hydroxylamine | an aldehyde | (structure) |
| a hydroxylamine | a ketone | (structure) |
| a hydrazine | an aldehyde | (structure) |
| a hydrazine | a ketone | (structure) |
| $NH_2-NH-C(=O)-$ | an aldehyde | (structure) |
| $NH_2-NH-C(=O)-$ | a ketone | (structure) |
| a haloacetamide | a thiol | (structure) |

TABLE 1-continued

| Reactive Group 1 | Reactive Group 2 | Chemical Moiety |
| --- | --- | --- |
| a maleimide | a thiol | |
| a vinyl sulfone | a thiol | |
| a thiol | a vinyl sulfone | |
| an aziridine | a thiol | (two alternatives) |
| a thiol | an aziridine | (two alternatives) |
| (dithioketone) | hydroxylamine | |
| (ketone) | hydroxylamine | |

TABLE 1-continued

| Reactive Group 1 | Reactive Group 2 | Chemical Moiety |
|---|---|---|
| 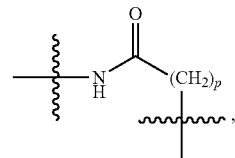 | | | where: $R^{32}$ in Table 1 is H, $C_{1-4}$ alkyl, phenyl, pyrimidine or pyridine; $R^{35}$ in Table 1 is H, $C_{1-6}$alkyl, phenyl or $C_{1-4}$alkyl substituted with 1 to 3 —OH groups; each $R^{36}$ in Table 1 is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH; $R^{37}$ in Table 1 is independently selected from H, phenyl and pyridine.

In some embodiments, a linker component of linker, L, of immunoconjugates of Formula (II) and Formula (III) is a group formed upon reaction of a reactive functional group with one of the amino acid side chains commonly used for conjugation, e.g., the thiol of cysteine, or the free —$NH_2$ of lysine, or a Pcl or Pyl group engineered into an antibody. See e.g., Ou, et al., *PNAS* 108(26), 10437-42 (2011). Linker components formed by reaction with a cysteine residue of the antigen binding moiety include, but are not limited to

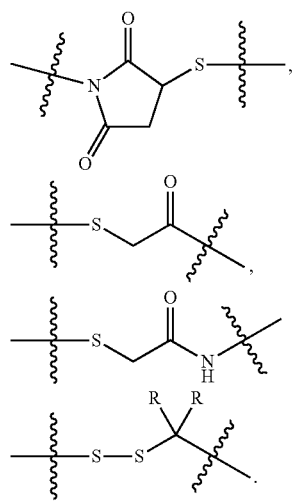

Linker components formed by reaction with the —$NH_2$ of a lysine residue of the antigen binding moiety, where each p is 1-10, and each R is independently H or $C_{1-4}$ alkyl (preferably methyl) include, but are not limited to,

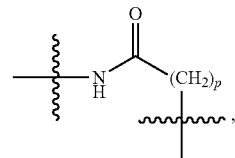

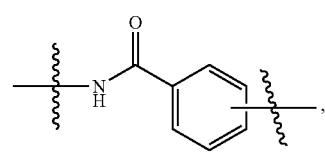

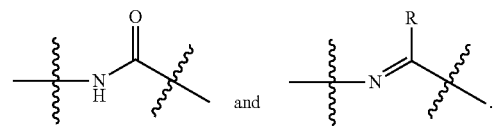

Linker components formed by reaction with a Pcl or Pyl group include, but are not limited to,

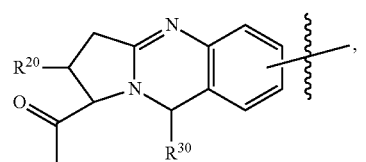

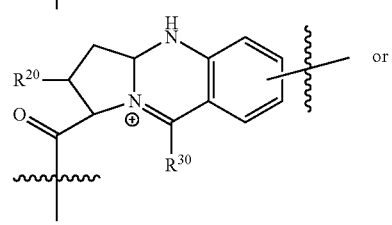

-continued

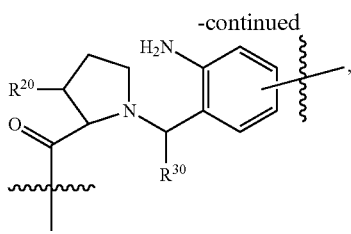

wherein $R^{20}$ is H or Me, and $R^{30}$ is H, Me or Phenyl, for linking, where the acyl group shown attaches to the lysine portion of a Pcl or Pyl in an engineered antibody.

In some embodiments, a linker component of linker, L, of immunoconjugates of Formula (II) and Formula (III) is

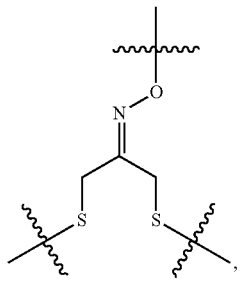

which is formed upon reaction of

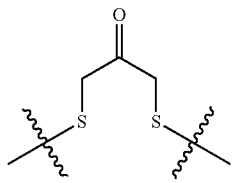

and a compound of Formula (I) which contains an hydroxylamine. In some embodiments, a linker component of linker, L, of immunoconjugates of Formula (II) and Formula (III) is

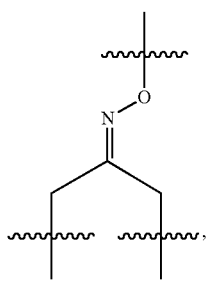

which is formed upon reaction of

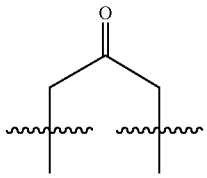

and a compound of Formula (I) which contains an hydroxylamine.

In some embodiments, a linker component of linker, L, of immunoconjugates of Formula (II) and Formula (III) include, for example, alkylene groups —$(CH_2)_n$— (where n is typically 1-10 or 1-6), ethylene glycol units (—$CH_2CH_2O$—)$_n$ (where n is 1-20, typically 1-10 or 1-6), —O—, —S—, carbonyl —C(=O)—), amides C(=O)—NH— or —NH—C(=O)—, esters —C(=O)—O— or —O—C(=O)—, ring systems having two available points of attachment such as a divalent ring selected from phenyl (including 1,2- 1,3- and 1,4-di-substituted phenyls), $C_{5-6}$ heteroaryl, $C_{3-8}$ cycloalkyl including 1,1-disubstituted cyclopropyl, cyclobutyl, cyclopentyl or cyclohexyl, and 1,4-disubstituted cyclohexyl, and $C_{4-8}$ heterocyclyl rings, and specific examples depicted below; amino acids —NH—CHR*—C=O— or C(=O)—CHR*—NH—, or groups derived from amino acids that attach to N of an adjacent structure (e.g., to a maleimide nitrogen) having the formula [N]—CHR*—C(=O)— where R* is the side chain of a known amino acid (frequently one of the canonical amino acids, e.g., trp, ala, asp, lys, gly, and the like, but also including e.g. norvaline, norleucine, homoserine, homocysteine, phenylglycine, citrulline, and other commonly named alpha-amino acids), polypeptides of known amino acids (e.g., dipeptides, tripeptides, tetrapeptides, etc.), thiol-maleimide linkages (from addition of —SH to maleimide), —S—$CR_2$— and other thiol ethers such as —S—$CR_2$—C(=O)— or —C(=O)—$CR_2$—S— where R is independently at each occurrence H or $C_{1-4}$ alkyl, —$CH_2$—C(=O)—, and disulfides (—S—S—), as well as combinations of any of these with other linker components described below, e.g., a bond, a non-enzymatically cleavable linker, a non-cleavable linker, an enzymatically cleavable linker, a photo-stable linker, a photo-cleavable linker or a linker that comprises a self-immolative spacer.

In certain embodiments, Linker, L, of compounds of Formula (I) and immunoconjugates of Formula (II) and Formula (III) is -*$L_1L_2L_3L_4L_5L_6$-, where the * denotes the site of attachment to the compound of the invention. In certain embodiments, Linker, L, of compounds of Formula (I) and immunoconjugates of Formula (II) and Formula (III) is -*$L_1L_2L_3L_4L_5$-, where the * denotes the site of attachment to the compound of the invention. In certain embodiments, Linker, L, of compounds of Formula (I) and immunoconjugates of Formula (II) and Formula (III) is -*$L_1L_2L_3L_4$-, where the * denotes the site of attachment to the compound of the invention. In certain embodiments, Linker, L, of compounds of Formula (I) and immunoconjugates of Formula (II) and Formula (III) is -*$L_1L_2L_3$-, where the * denotes the site of attachment to the compound of the invention. In a preferred embodiment Linker, L, of compounds of Formula (I) and immunoconjugates of Formula (II) and Formula (III) is -*$L_1L_2$-, where the * denotes the site of attachment to the compound of the invention. In certain embodiments Linker, L, of compounds of Formula (I) is -$L_1$-.

Linker component $L_1$ of compounds of Formula (I) and immunoconjugates of Formula (II) and Formula (III) is selected from —$(CH_2)_m$—, —$C(=O)(CH_2)_m$—, —$NR^{12}C(=O)(CH_2)_m$—, —$C(=O)X_1X_2C(=O)(CH_2)_m$—, —$C(=O)X_1X_2C(=O)(CH_2)_mNR^{12}C(=O)(CH_2)_m$—, —$C(=O)X_1X_2C(=O)(CH_2)_mX_3(CH_2)_m$—, —$C(=O)X_1X_2C(=O)((CH_2)_mO)_n(CH_2)_m$—, —$C(=O)X_1X_2C(=O)((CH_2)_mO)_n(CH_2)_mNR^{12}C(=O)(CH_2)_m$—, —$C(=O)X_1X_2C(=O)((CH_2)_mO)_n(CH_2)_mNR^{12}C(=O)(CH_2)_mX_3(CH_2)_m$—, —$C(=O)X_1X_2C(=O)((CH_2)_mO)_n(CH_2)_mX_3(CH_2)_m$—, —$C(=O)X_1X_2C(=O)(CH_2)_mNR^{12}C(=O)((CH_2)_mO)_n(CH_2)_m$—, —$C(=O)X_1X_2C(=O)(CH_2)_mNR^{12}C(=O)((CH_2)_mO)_n(CH_2)_mX_3(CH_2)_m$—, —$C(=O)X_1X_2(CH_2)_mX_3(CH_2)_m$—, —$C(=O)X_1X_2((CH_2)_mO)_n(CH_2)_m$—, —$C(=O)X_1X_2((CH_2)_mO)_n(CH_2)_mNR^{12}C(=O)(CH_2)_m$—, —$C(=O)X_1X_2((CH_2)_mO)_n(CH_2)_mNR^{12}C(=O)(CH_2)_mX_3(CH_2)_m$—, —$C(=O)X_1X_2((CH_2)_mO)_n(CH_2)_mX_3(CH_2)_m$—, —$C(=O)X_1X_2(CH_2)_mNR^{12}((CH_2)_mO)_n(CH_2)_m$—, —$C(=O)X_1X_2C(=O)(CH_2)_mNR^{12}((CH_2)_mO)_n(CH_2)_mX_3(CH_2)_m$—, —$(CH_2)_mNR^{12}C(=O)(CH_2)_m$—, —$C(=O)((CH_2)_mO)_n(CH_2)_m$—, —$(CH_2)_mS(=O)_2((CH_2)_mO)_n(CH_2)_m$—, —$C(=O)(CH_2)_mNR^{12}(CH_2)_m$—, —$C(=O)NR^{12}(CH_2)_m$—, —$C(=O)NR^{12}(CH_2)_mX_3(CH_2)_m$—, —$C(=O)NR^{12}(CH_2)_mNR^{12}C(=O)X_1X_2C(=O)(CH_2)_m$—, —$C(=O)X_1C(=O)NR^{12}(CH_2)_mNR^{12}C(=O)(CH_2)_m$—, —$C(=O)X_1C(=O)NR^{12}(CH_2)_mX_3(CH_2)_m$—, —$C(=O)NR^{12}(CH_2)_mNR^{12}C(=O)(CH_2)_m$—, —$C(=O)NR^{12}(CH_2)_mNR^{12}C(=O)(CH_2)_mX_3(CH_2)_m$—,

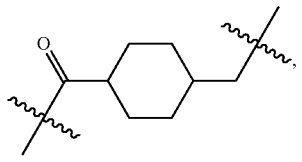

—$(CH_2)_mC(=O)NR^{12}(CH_2)_mNR^{12}C(=O)(CH_2)_m$—, —$(CH_2)_mC(=O)$—, —$C(=O)(CH_2)_mNR^{12}(CH_2)_mC(=O)X_2X_1C(=O)$—, —$(CH_2)_mX_3(CH_2)_mC(=O)X_2X_1C(=O)$—, —$(CH_2)_mC(=O)NR^{12}(CH_2)_m$—, —$(CH_2)_mC(=O)NR^{12}(CH_2)_mX_3(CH_2)_m$—, —$(CH_2)_mX_3(CH_2)_mNR^{12}C(=O)(CH_2)_m$—, —$(CH_2)_mC(=O)NR^{12}(CH_2)_mX_3$—, —$X_3(CH_2)_mNR^{12}C(=O)(CH_2)_m$—, —$(CH_2)_mX_3(CH_2)_mC(=O)NR^{12}(CH_2)_m$—, —$(CH_2)_mNR^{12}C(=O)(CH_2)_mX_3(CH_2)_m$—, —$(CH_2)_mO)_n(CH_2)_mNR^{12}C(=O)(CH_2)_m$—, —$(CH_2)_mC(=O)NR^{12}(CH_2)_m(OCH_2)_m)_n$—, —$((C(R^{12})_2)_mOC(=O)NR^{12}(CH_2)_mO(CH_2)_m$—, —$(CH_2)_m(O(CH_2)_m)_nNR^{12}C(=O)O(C(R^{12})_2)_m$—, —$(CH_2)_m(O(CH_2)_m)_nC(=O)$—, —$(CH_2)_m(O(CH_2)_m)_nS(=O)_2(CH_2)_m$—, —$(CH_2)_mNR^{12}(CH_2)_nC(=O)$—, —$(CH_2)_mO(CH_2)_mNR^{12}C(=O)O((C(R^{12})_2)_m$—, —$(CH_2)_mNR^{12}C(=O)$—, —$(CH_2)_mC(=O)X_2X_1C(=O)NR^{12}(CH_2)_mNR^{12}C(=O)$—, —$(CH_2)_mC(=O)NR^{12}(CH_2)_mNR^{12}C(=O)X_1$—, —$(CH_2)_mC(=O)NR^{12}(CH_2)_mNR^{12}C(=O)$—,

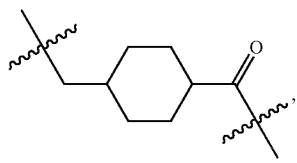

—$((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_mC(=O)$—, —$C(=O)(CH_2)_mX_3(CH_2)_m$—, —$(CH_2)_mC(=O)NR^{12}(CH_2)_mO)_n(CH_2)_mX_3$—, —$X_3(CH_2)_m(O(CH_2)_m)_nNR^{12}C(=O)(CH_2)_m$—, —$(CH_2)_mC(=O)NR^{12}(CH_2)_mO)_n(CH_2)_mX_3(CH_2)_m$—, —$(CH_2)_mX_3(CH_2)_mC(=O)NR^{12}(CH_2)_mO)_n(CH_2)_mX_3(CH_2)_m$—, —$(CH_2)_mX_3(CH_2)_m(O(CH_2)_m)_nC(=O)$—, —$C(=O)((CH_2)_mO)_n(CH_2)_mX_3(CH_2)_m$—, —$(CH_2)_mC(=O)NR^{12}(CH_2)_mC(=O)$—, —$C(=O)(CH_2)_mNR^{12}C(=O)(CH_2)_m$—, —$(CH_2)_mC(=O)NR^{12}(CH_2)_m(O(CH_2)_m)_nC(=O)$—, —$C(=O)((CH_2)_mO)_n(CH_2)_mNR^{12}C(=O)(CH_2)_m$—, —$(CH_2)_mC(=O)NR^{12}(CH_2)_mC(=O)NR^{12}(CH_2)_m$—, —$(CH_2)_mNR^{12}C(=O)(CH_2)_mNR^{12}C(=O)(CH_2)_m$—, —$C(=O)NR^{12}(CH_2)_mNR^{12}C(=O)$—, —$(CH_2)_mS(CH_2)_m$—, —$NR^{12}C(=O)(CH_2)_m$—, —$NR^{12}C(=O)(CH_2)_mX_3(CH_2)_m$—, —$(CH_2)_mX_3(CH_2)_mC(=O)NR^{12}$—, —$(CH_2)_mC(=O)NR^{12}$—, —$(CH_2)_mNR^{12}(CH_2)_m$—, —$(CH_2)_mX_3(CH_2)_m$—, —$(CH_2)_mX_3$—, —$X_3(CH_2)_m$—, —$((CH_2)_mO)_n(CH_2)_mX_3(CH_2)_m$—, —$(CH_2)_mX_3(CH_2)_m(O(CH_2)_m)_n$—, —$NR^{12}(CH_2)_m$—, —$NR^{12}C(R^{12})_2(CH_2)_m$—, —$(CH_2)_mC(R^{12})_2NR^{12}$—, —$(CH_2)_mC(=O)NR^{12}(CH_2)_mNR^{12}$—, —$(CH_2)_mC(=O)NR^{12}(CH_2)_mNR^{12}C(=O)NR^{12}$—, —$(CH_2)_mC(=O)NR^{12}(CH_2)_mNR^{12}C(=O)$—, —$(CH_2)_mC(=O)X_2X_1C(=O)$—, —$NR^{12}(CH_2)_mNR^{12}C(=O)(CH_2)_m$—, —$NR^{12}C(R^{12})_2(CH_2)_mNR^{12}C(=O)(CH_2)_m$—, —$(CH_2)_mC(=O)NR^{12}(CH_2)_mC(R^{12})_2NR^{12}$—, —$NR^{12}(CH_2)_mX_3(CH_2)_m$—, —$NR^{12}C(R^{12})_2(CH_2)_mX_3(CH_2)_m$—, —$(CH_2)_mX_3(CH_2)_mC(R^{12})_2NR^{12}$—, —$NR^{12}C(R^{12})_2(CH_2)_mOC(=O)NR^{12}(CH_2)_m$—, —$(CH_2)_mNR^{12}C(=O)O(CH_2)_m$—, —$(CH_2)_mNR^{12}C(=O)O(CH_2)_mC(R^{12})_2NR^{12}$—, —$NR^{12}C(R^{12})_2(CH_2)_mOC(=O)NR^{12}(CH_2)_mX_3(CH_2)_m$—, —$(CH_2)_mX_3(CH_2)_mNR^{12}C(=O)O(CH_2)_mC(R^{12})_2NR^{12}$—, —$NR^{12}C(R^{12})_2(CH_2)_mOC(=O)NR^{12}((CH_2)_mO)_n(CH_2)_m$—, —$(CH_2)_m(O(CH_2)_m)_nNR^{12}C(=O)O(CH_2)_mC(R^{12})_2NR^{12}$—, —$NR^{12}C(R^{12})_2(CH_2)_mOC(=O)NR^{12}((CH_2)_mO)_n(CH_2)_mX_3(CH_2)_m$—, —$(CH_2)_mX_3(CH_2)_m(O(CH_2)_m)_nNR^{12}C(=O)O(CH_2)_mC(R^{12})_2NR^{12}$—, —$(CH_2)_mX_3(CH_2)_mNR^{12}$—, —$NR^{12}((CH_2)_mO)_n(CH_2)_mX_3(CH_2)_m$—, —$(CH_2)_mX_3(CH_2)_m(O(CH_2)_m)_nNR^{12}$—, —$(CH_2)_mNR^{12}$—, —$NR^{12}((CH_2)_mO)_n(CH_2)_m$—, —$NR^{12}((CH_2)_mO)_n(CH_2)_mNR^{12}C(=O)(CH_2)_m$—, —$(CH_2)_mC(=O)NR^{12}(CH_2)_m(O(CH_2)_m)_nNR^{12}$—, —$(CH_2)_m(O(CH_2)_m)_nNR^{12}$—, —$(C(R_{12})_2)_m$—, —$(CH_2CH_2O)_n$—, —$(OCH_2CH_2)_n$—, —$(CH_2)_mO(CH_2)_m$—, —$S(=O)_2(CH_2)_m$—, —$(CH_2)_mS(=O)_2$—, —$S(=O)_2(CH_2)_mNR^{12}C(=O)(CH_2)_m$—, —$(CH_2)_mC(=O)NR^{12}(CH_2)_mS(=O)_2$—, —$S(=O)_2(CH_2)_mX_3(CH_2)_m$—, —$(CH_2)_mX_3(CH_2)_mS(=O)_2$—, —$(CH_2)_mX_2X_1C(=O)$—, —$C(=O)X_1X_2(CH_2)_m$—, —$(CH_2)_m(O(CH_2)_m)_nC(=O)X_2X_1C(=O)$—, —$C(=O)X_1X_2C(=O)((CH_2)_mO)_n(CH_2)_m$—, —$(CH_2)_m(O(CH_2)_m)_nX_2X_1C(=O)$—, —$(CH_2)_mX_3(CH_2)_mX_2X_1C(=O)$—, —$C(=O)X_1X_2(CH_2)_mX_3(CH_2)_m$—, —$(CH_2)_mX_3(CH_2)_m(O(CH_2)_m)_nX_2X_1C(=O)$—, —$(CH_2)_mX_3(CH_2)_mC(=O)NR^{12}(CH_2)_mNR^{12}C(=O)$—, —$(CH_2)_mX_3(CH_2)_mC(=O)NR^{12}(CH_2)_mC(=O)$—, —$C(=O)(CH_2)_mNR^{12}C(=O)(CH_2)_mX_3(CH_2)_m$—, —$(CH_2)_mX_3(CH_2)_mC(=O)NR^{12}(CH_2)_m(O(CH_2)_m)_nC(=O)$—, —$C(=O)((CH_2)_mO)_n(CH_2)_mNR^{12}C(=O)(CH_2)_mX_3(CH_2)_m$—, —$(CH_2)_mNR^{12}C(=O)X_1X_2C(=O)(CH_2)_m$—, —$(CH_2)_mC(=O)X_2X_1C(=O)NR^{12}(CH_2)_m$—, —$X_4X_1X_2C(=O)(CH_2)_m$—, —$(CH_2)_mC(=O)X_2X_1X_4$—, —$X_1C(=O)(CH_2)_mNR^{12}C(=O)(CH_2)_m$—, —$(CH_2)_mC(=O)NR^{12}(CH_2)_mC(=O)X_1$—, —$C(=O)CHR^{aa}NR^{12}$—, —$NR^{12}CHR^{aa}C(=O)$—, —$C(=O)NR^{12}$—, —$C(=O)O$—, —$S$—, —$SCH_2(C=O)NR^{12}$—, —$NR^{12}C(=O)CH_2S$—, —$S(=O)_2CH_2CH_2S$—, —$SCH_2CH_2S(=O)_2$—, —$(CH_2)_2S(=O)_2CH_2CH_2S$—, —$SCH_2CH_2S(=O)_2CH_2CH_2$—, —$NR^{12}C(=S)$—,

—(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$— and —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—, —NHS(=O)$_2$(CH$_2$)$_m$X$_3$(CH$_2$)$_m$—, —S(=O)$_2$(CH$_2$)$_m$X$_3$(CH$_2$)$_m$—, —(CH$_2$)$_m$X3(CH$_2$)m—, —NHS(=O)$_2$(CH$_2$)$_m$NHC(=O)—, —S(=O)$_2$(CH$_2$)$_m$NHC(=O)—, —(CH$_2$)$_m$NHC(=O)—, —NHS(=O)$_2$(CH$_2$)$_m$NHC(=O)O(CH$_2$)$_m$—, —S(=O)$_2$(CH$_2$)$_m$NHC(=O)O(CH$_2$)$_m$—, —(CH$_2$)$_m$NHC(=O)O(CH$_2$)$_m$— and L$_1$ is selected from the groups shown in Table 2 below:

TABLE 2

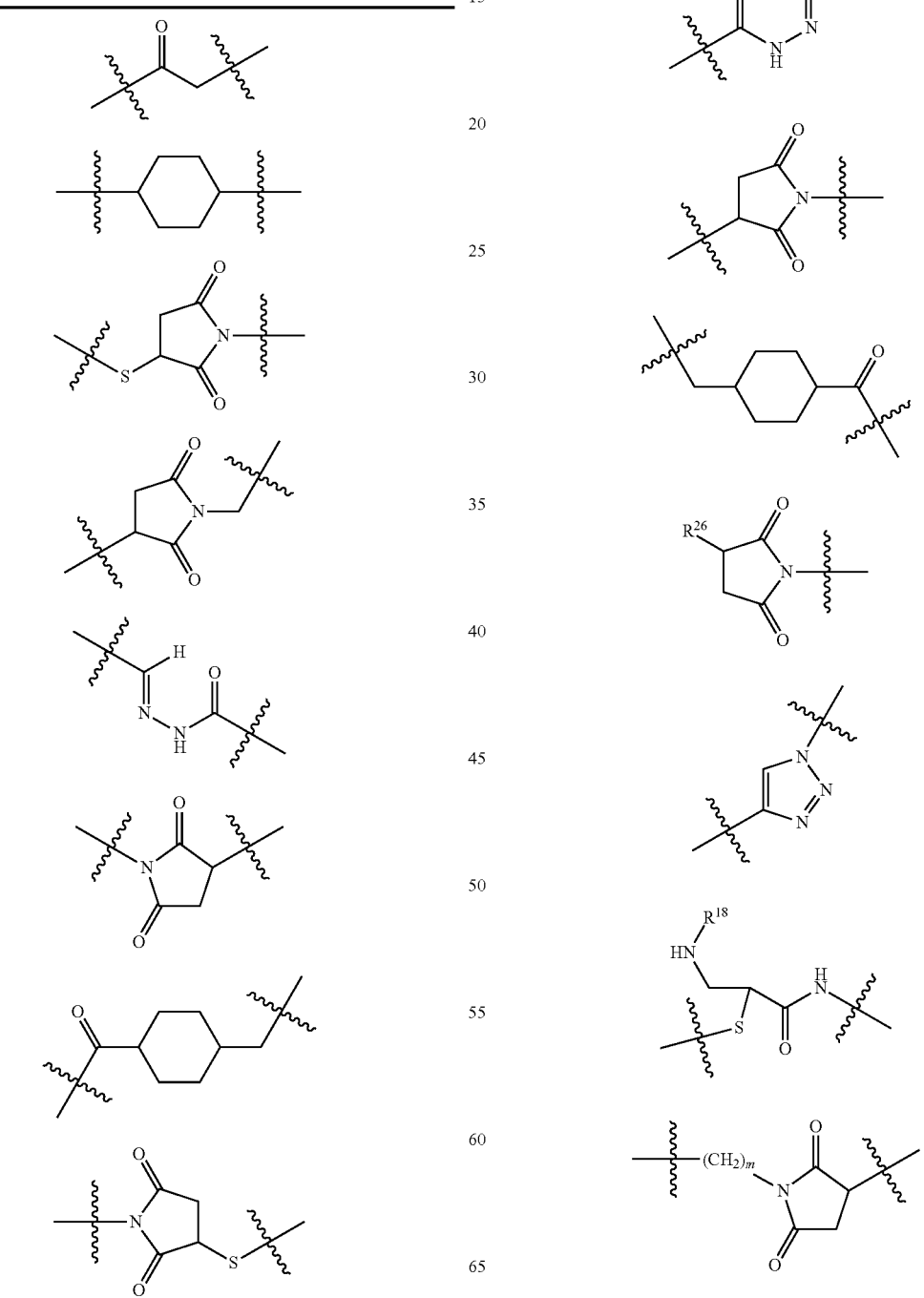

TABLE 2-continued
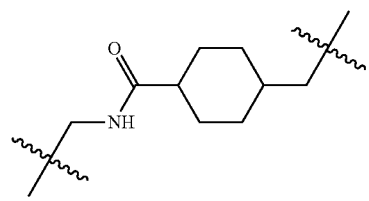
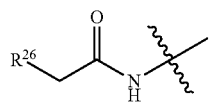
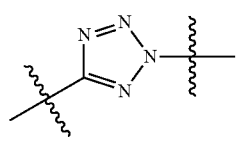
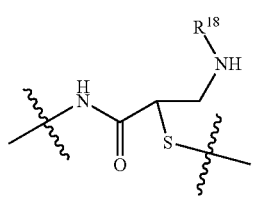
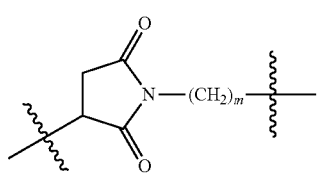
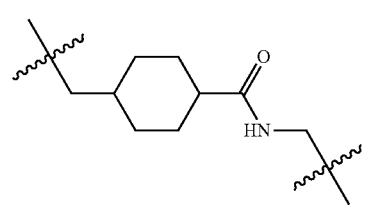
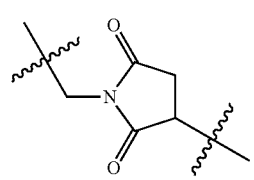
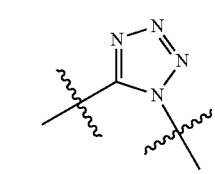
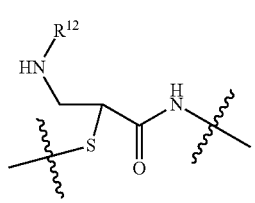
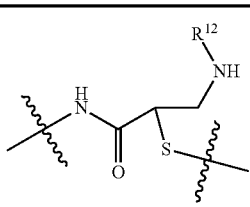
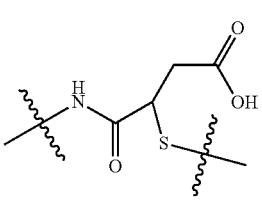
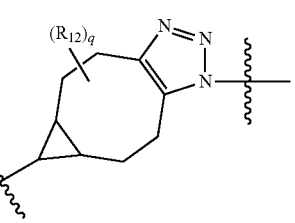
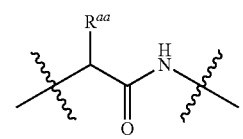
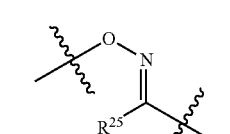
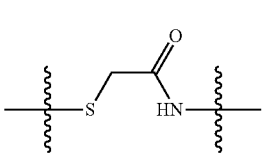
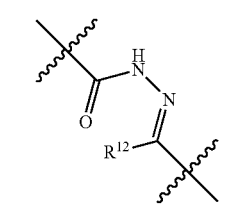
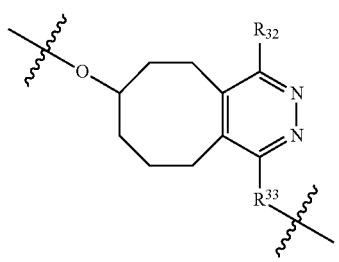

TABLE 2-continued
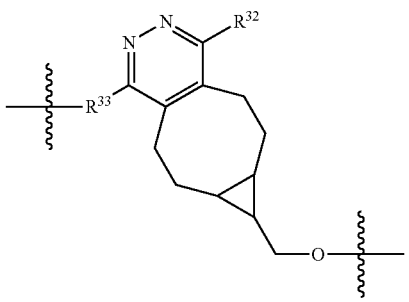
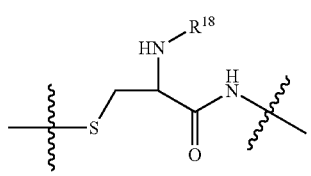
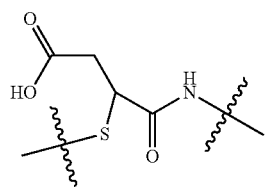
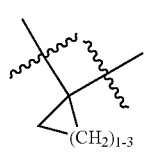
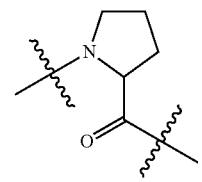
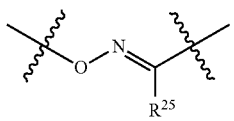
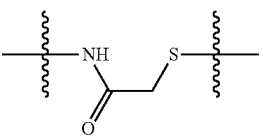
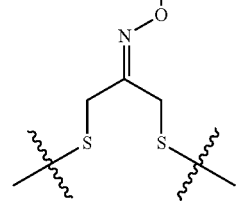
TABLE 2-continued
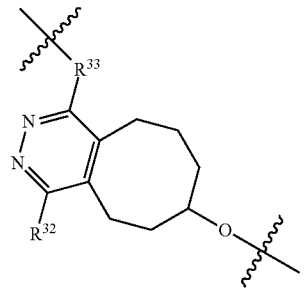
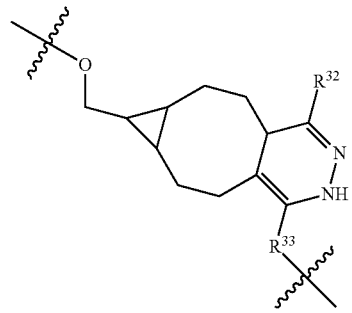
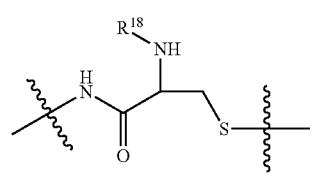
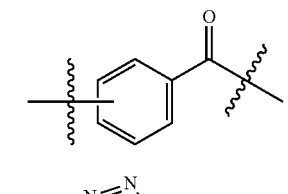
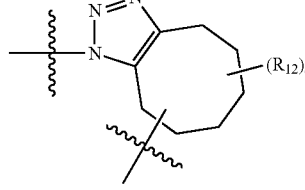
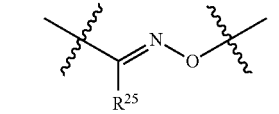
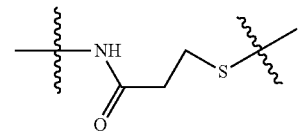

TABLE 2-continued
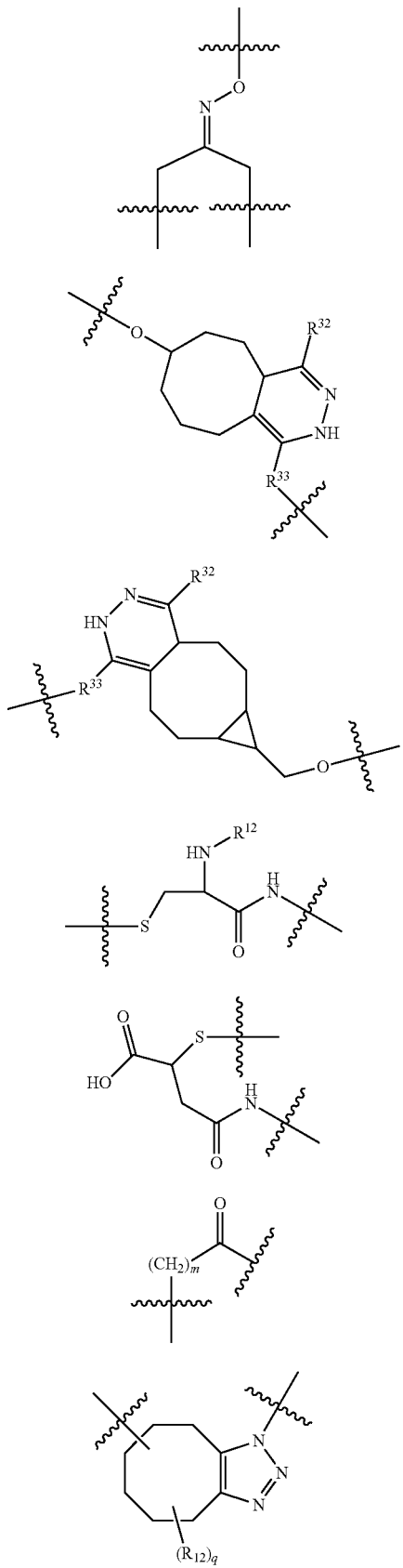
TABLE 2-continued
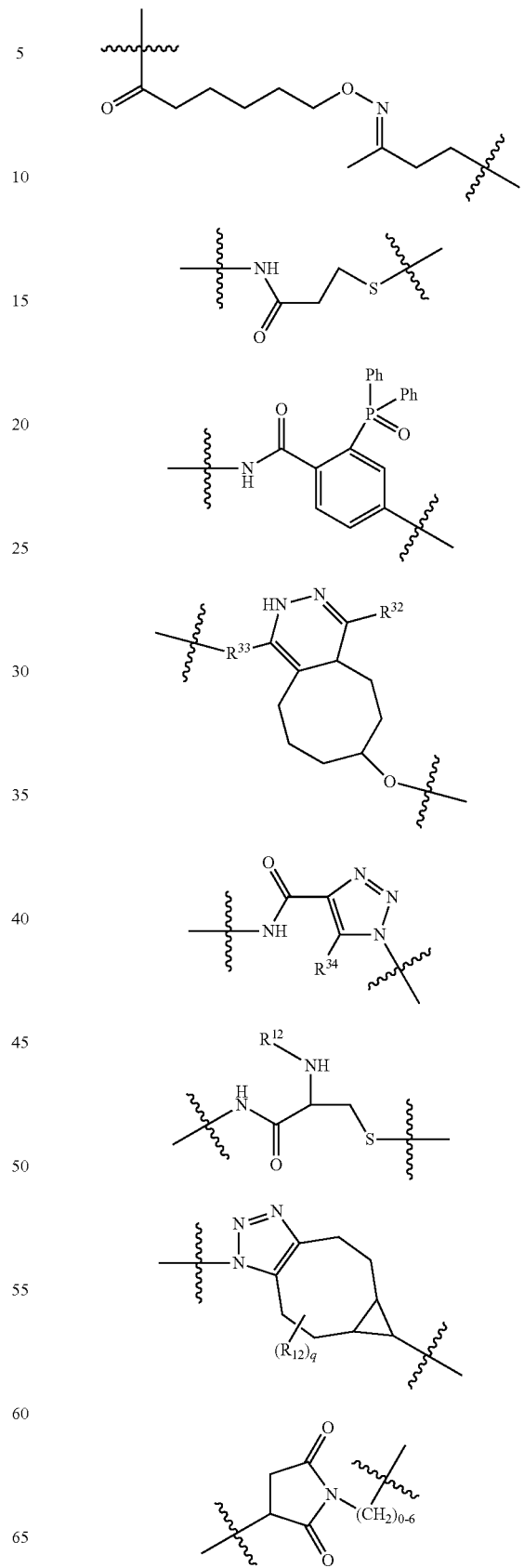

TABLE 2-continued
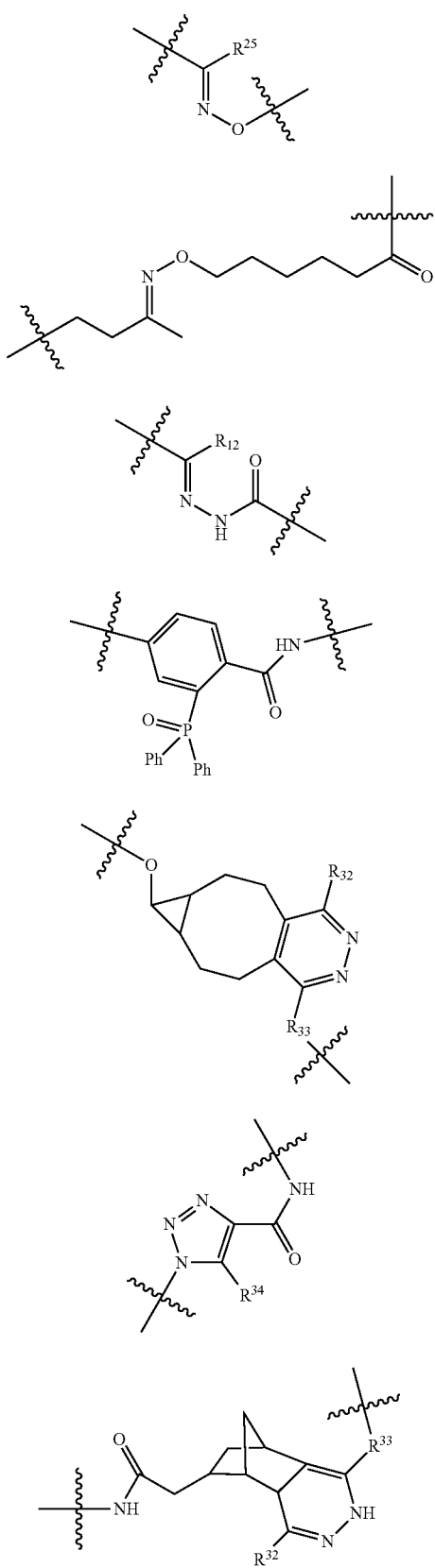
TABLE 2-continued
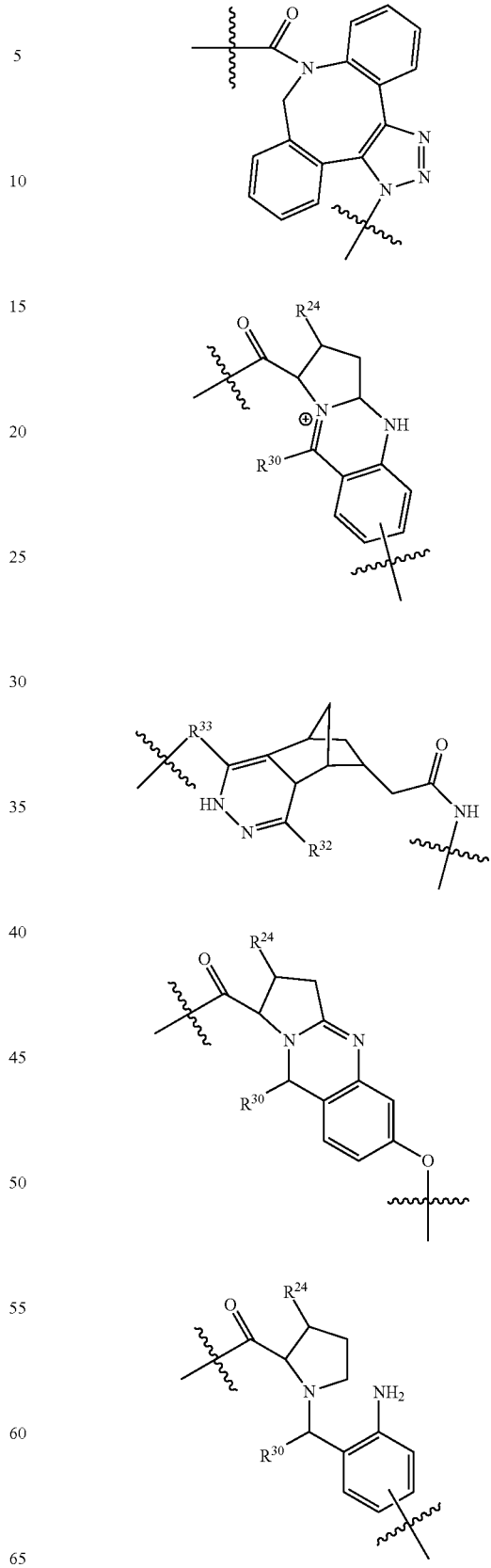

TABLE 2-continued
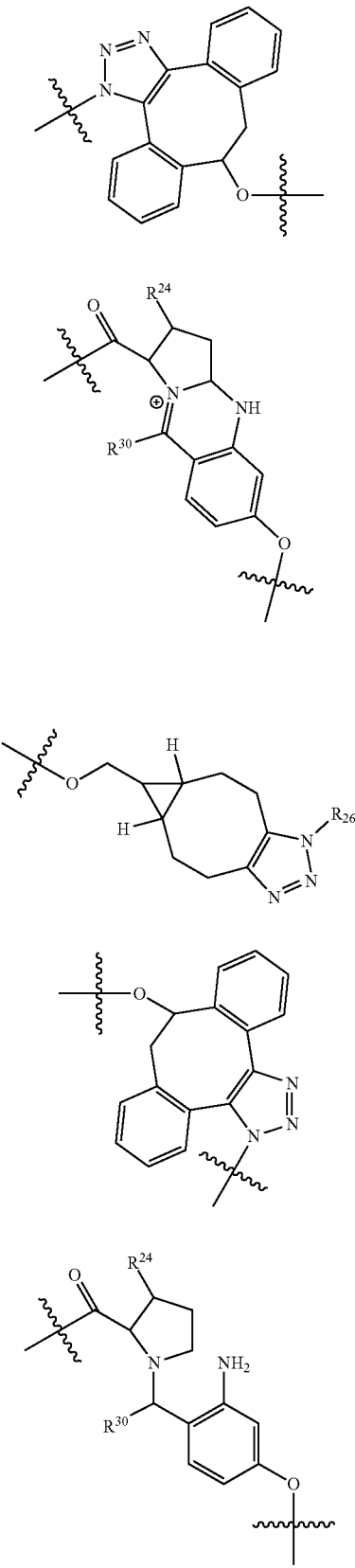
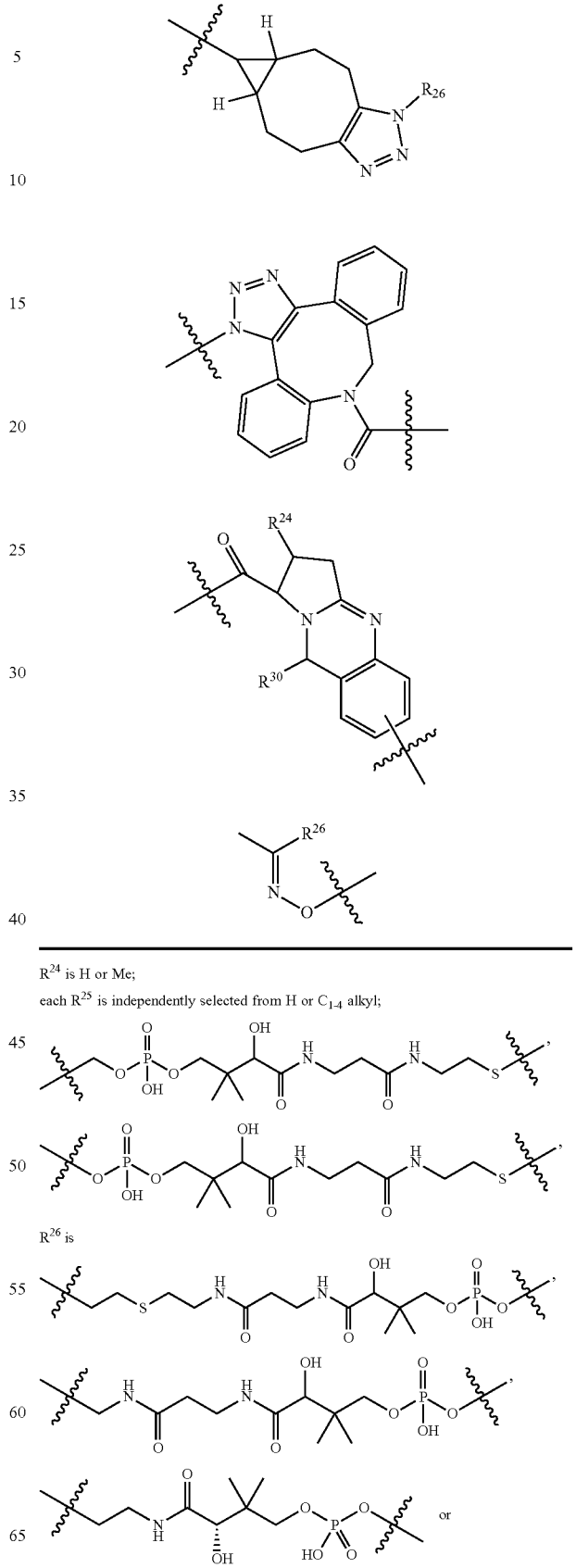
R²⁴ is H or Me;
each R²⁵ is independently selected from H or C₁₋₄ alkyl;
R²⁶ is

TABLE 2-continued

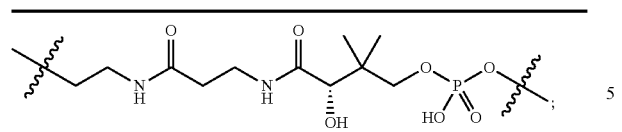

$R^{aa}$ is H or a side chain of an amino acid selected from alanine, tryptophan, tyrosine, phenylalanine, leucine, isoleucine, valine, asparagine, glutamic acid, glutamine, aspatic acid, histidine, arginine, lysine, cysteine, methionine, serine, threonine, citrulline, ornithing, phenylglycine and t-butylglycine;
$R^{30}$ is H, —CH$_3$ or phenyl;
$R^{32}$ is independently selected from H, C$_{1-4}$ alkyl, phenyl, pyrimidine and pyridine;

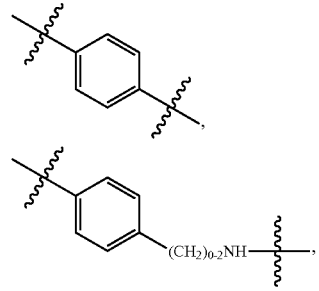

$R^{33}$ is independently selected from

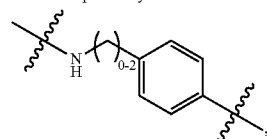

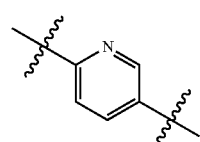

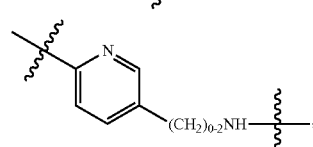

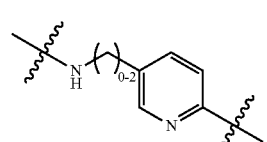

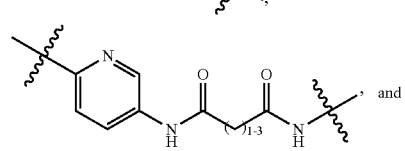

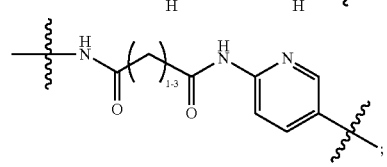

$R^{34}$ is independently selected from H, C$_{1-4}$ alkyl, and C$_{1-6}$ haloalkyl.

and wherein:
$X_1$ is self immolative spacer selected from

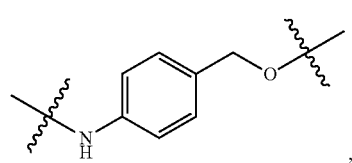

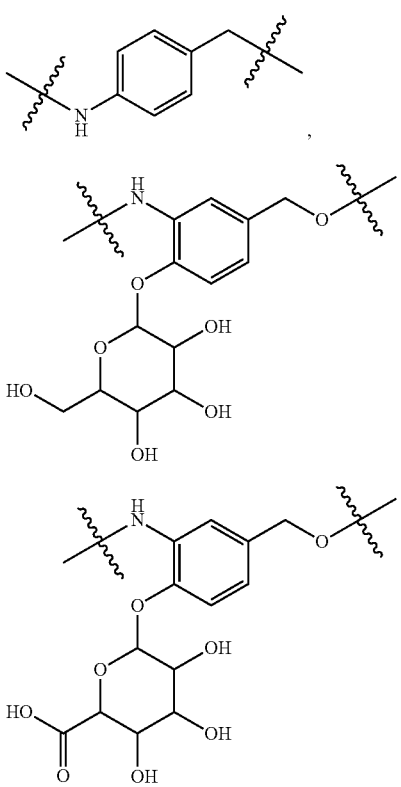

or $X_2$ is dipeptide selected from

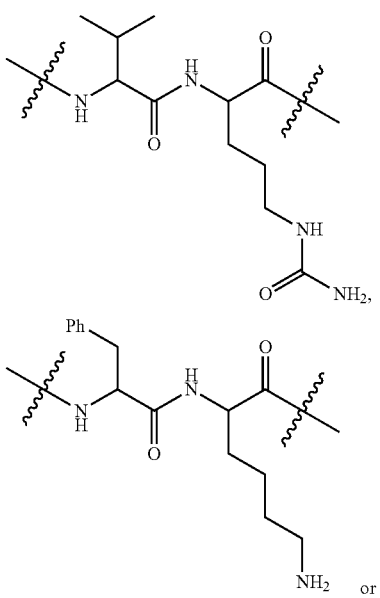

or

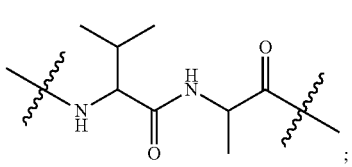

$X_3$ is

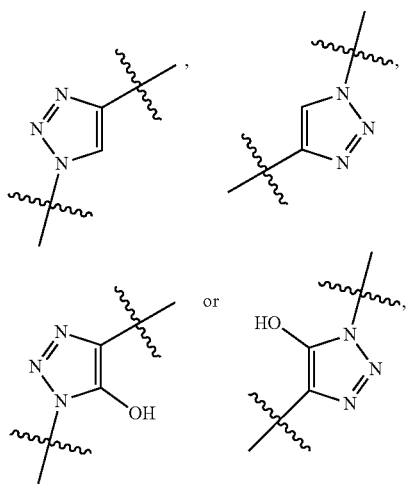

and
$X_4$ is

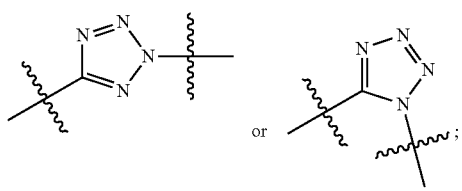

each m is independently selected from 1, 2, 3, 4, 5, 6, 7, 8, 9 and 10, and
each n is independently selected from 1, 2, 3, 4, 5, 6, 7, 8, 9, 10, 11, 12, 13, 14, 15, 16, 17 and 18.

Linker components $L_2$, $L_3$, $L_4$, $L_5$, and $L_6$ of compounds of Formula (I) and immunoconjugates of Formula (II) and Formula (III) are each independently selected from a bond and $L_1$.

Cytotoxic peptides

The compounds of the invention are anti-mitotic cytotoxic peptides, and such compounds, or stereoisomer thereof, and tautomers, hydrates and pharmaceutically acceptable salts thereof, are compounds having the structure of Formula (I)

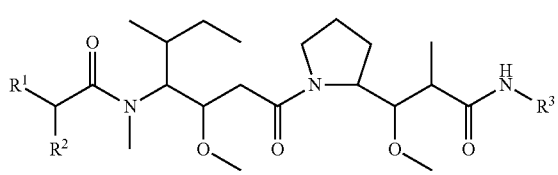

Formula (I)

wherein:
$R^1$ is $N=CR^4R^5$, $-N=R^{19}$, $-N=CR^5 R^{20}$, $-N=CR^5NR^{12}(CH_2)_mN(R^{12})C(O)OR^{12}$, $-N=CR^5NR^{12}(CH_2)N(R^{12})_2$, $-NHC(=NR^6)R^4$, $-NHC(=O)R^4$, $-NHC(=O)R^{20}$, $-NHR^8$, $-NHLR^{11}$, $-NHR^{21}$, $-N=CR^5R^{10}$, $-N=R^{22}$, $-N=CR^5R^{23}$ or $-NHC(=O)R^{23}$;
$R^2$ is $-C_1$-$C_6$alkyl;

$R^3$ is

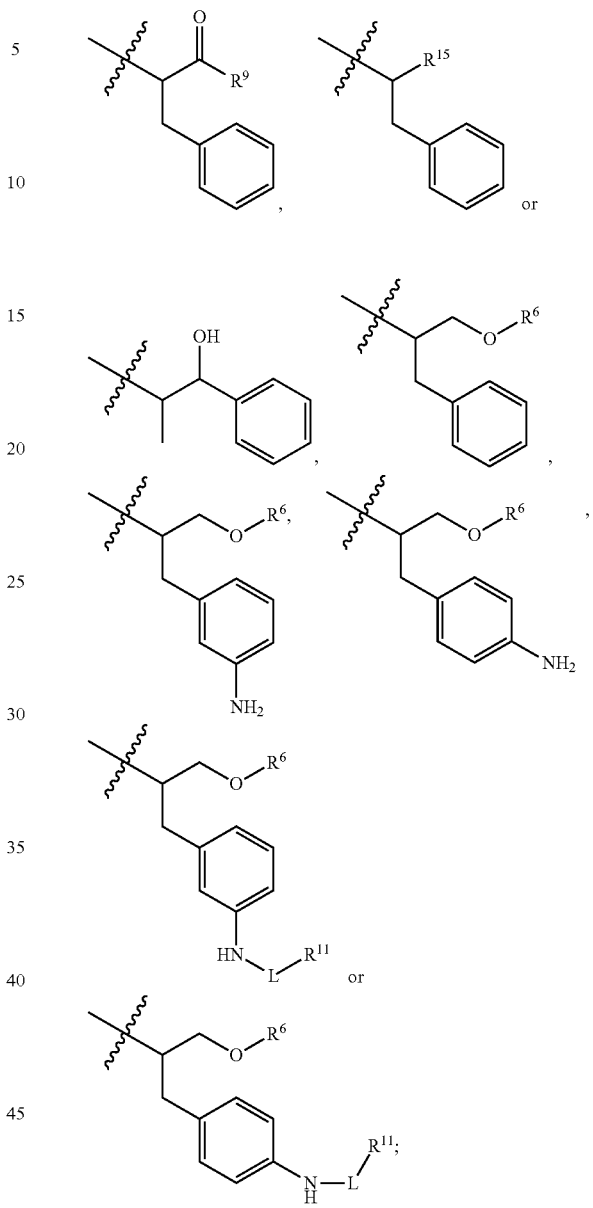

$R^4$ is $-N(R^6)_2$ or $-NR^6R^7$;
$R^5$ is $N(R^6)_2$;
each $R^6$ is independently selected from H and $-C_1$-$C_6$alkyl;
$R^7$ is $-(CH_2)_mN(R^{12})_2$, $-(CH_2)_mN(R^{12})C(=O)OR^{12}$ or an unsubstituted $C_3$-$C_8$cycloalkyl;
or $R^7$ is a $C_3$-$C_8$cycloalkyl substituted with 1-3 substituents independently selected from $C_1$-$C_6$alkyl, oxo, $-C(=O)R^{18}$, $-(CH_2)_mOH$, $-C(=O)(CH_2)_mOH$, $-C(=O)((CH_2)_mO)_nR^{12}$, $-((CH_2)_mO)_nR^{12}$ or a $C_1$-$C_6$alkyl which is optionally substituted with 1 to 5 hydroxyl;
$R^8$ is an unsubstituted C-linked 5-6 membered heteroaryl having 1-2 N heteroatoms;
or $R^8$ is a C-linked 5-6 membered heteroaryl having 1-2 N heteroatoms which is substituted with 1-3 substituents independently selected from $C_1$-$C_6$alkyl, $C_1$-$C_6$haloalkyl, halogen, $C_1$-$C_6$alkoxy, $-OH$, $-CN$, $-NO_2$, $-C(=O)OR^6$, $-C(=O)N(R^6)_2$, $-C(=O)NR^6(CH_2)_mN(R^6C(O)OR^6$ and $-C(=O)NR^6(CH_2)_mN(R^6_2)$;

$R^9$ is —OH, $C_1$-$C_6$alkoxy, —NHS(O)$_2$(CH$_2$)$_m$N$_3$, —NHS(=O)$_2$LR$^{11}$, —NHLR$^{11}$, —NHS(O)$_2$(CH$_2$)$_m$NH$_2$, —N(R$^{12}$)$_2$, —R$^{16}$, —NR$^{12}$(CH$_2$)$_m$N(R$^{12}$)$_2$, —NR$^{12}$(CH$_2$)$_m$R$^{16}$, -LR$^{11}$, —NHS(O)$_2$R$^{18}$, —NHS(=O)$_2$LR$^{11}$,
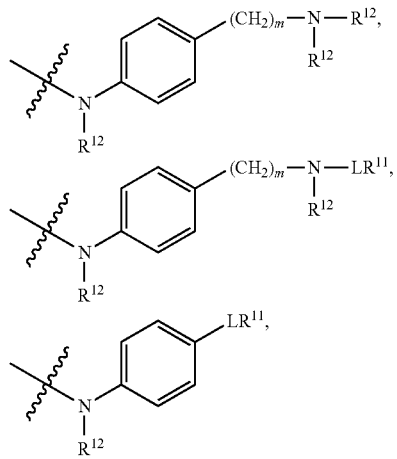
-continued
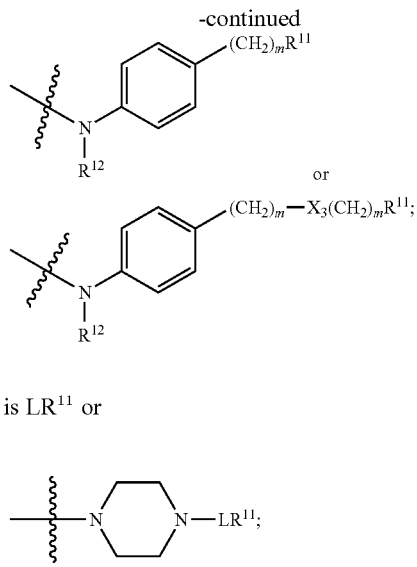
$R^{10}$ is LR$^{11}$ or
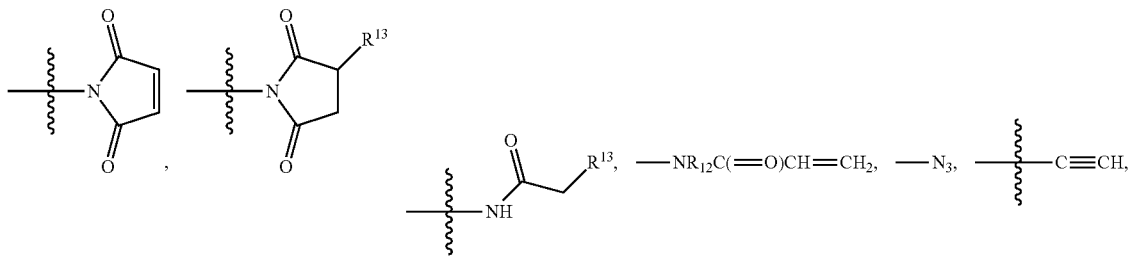;
$R^{11}$ is is
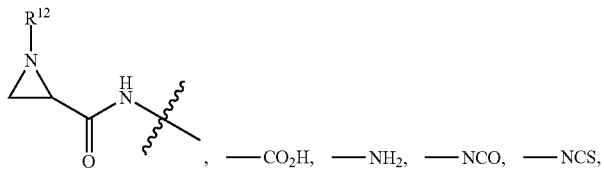
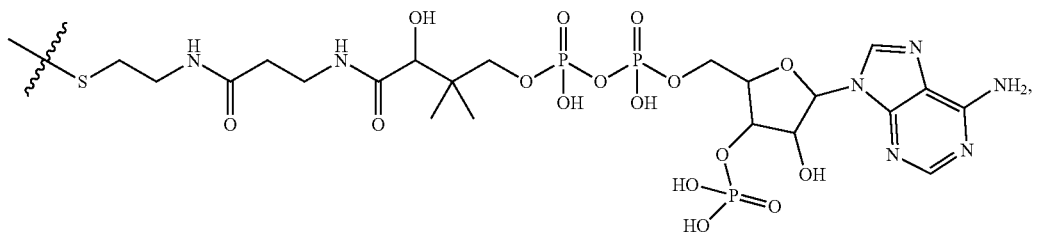
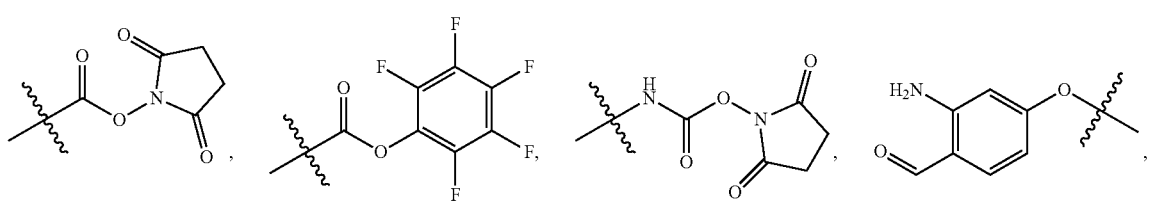

-continued
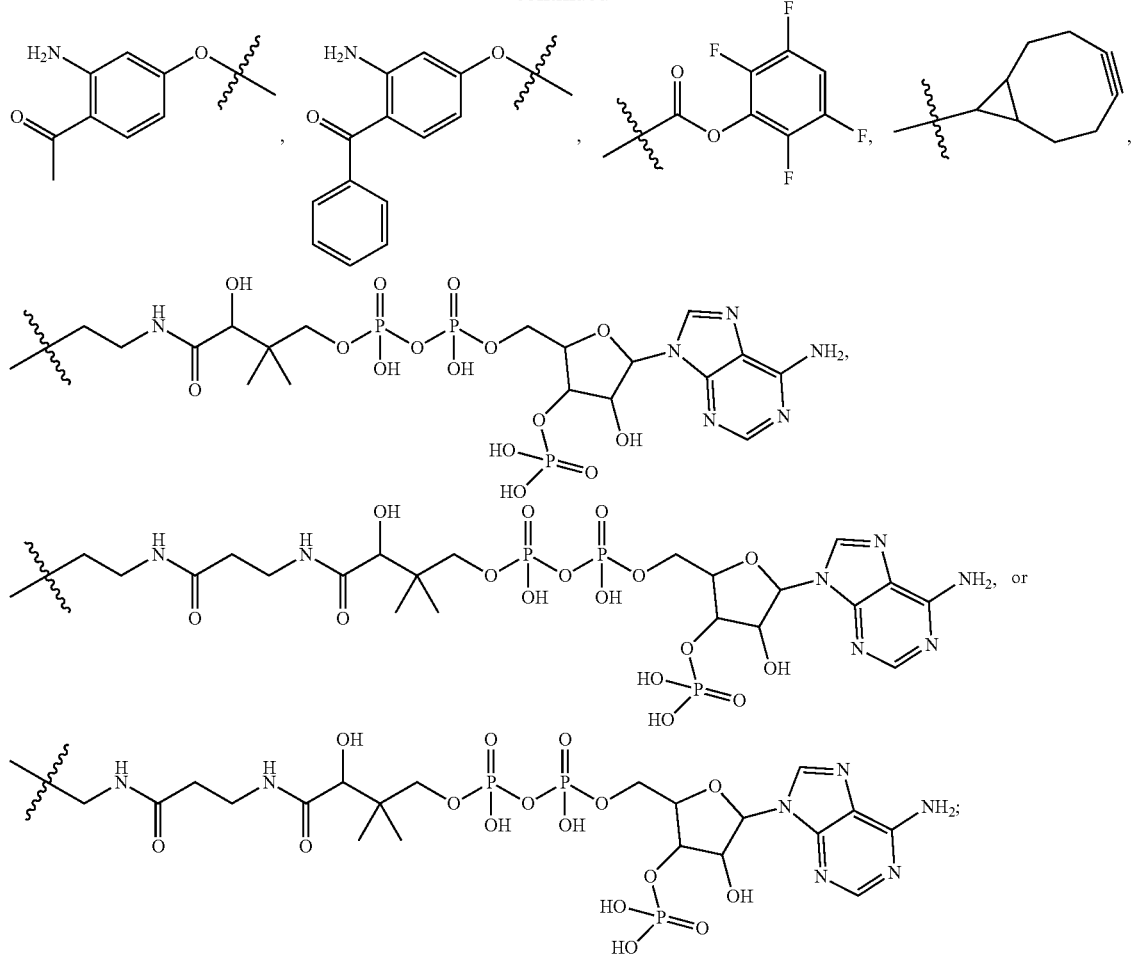
each $R^{12}$ is independently selected from H and $C_1$-$C_6$alkyl;
$R^{13}$ is $S(CH_2)_n CHR^{14} NHC(=O)R^{12}$ or
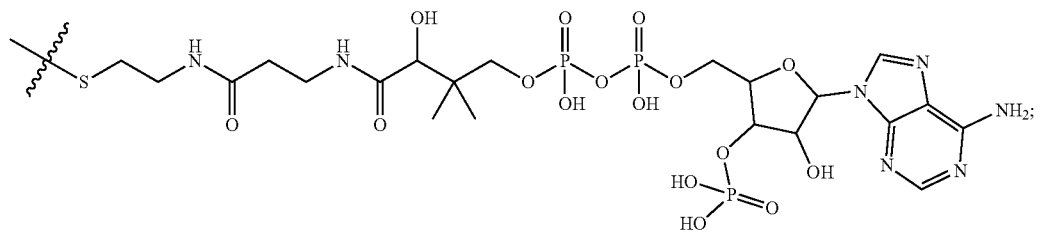
$R^{14}$ is $R^{12}$ or $C(=O)OR^{12}$;
$R^{15}$ is tetrazolyl, —CN, —$C(=O)OR^{12}$,
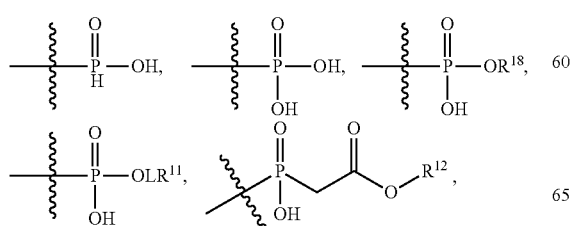
-continued
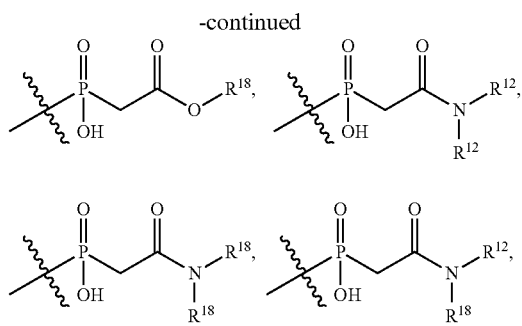

-continued

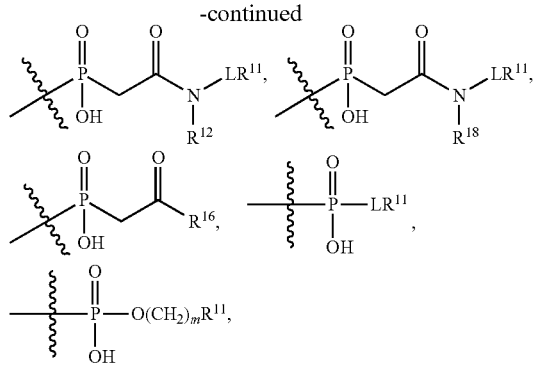

-LR$^{11}$ or —X$_4$LR$^{11}$;

R$^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;

R$^{17}$ is 2-pyridyl or 4-pyridyl;

each R$^{18}$ is independently selected from a C$_1$-C$_6$alkyl, a C$_1$-C$_6$alkyl which is substituted with azido and a C$_1$-C$_6$alkyl which is substituted with 1 to 5 hydroxyl;

R$^{19}$ is an unsubstituted C-linked 5-6 membered heterocycloalkyl having 1-2 heteroatoms independently selected from N and O;

or R$^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;

R$^{20}$ is an unsubstituted N-linked 5-6 membered heterocycloalkyl having 1-2 heteroatoms independently selected from N, O and S;

or R$^{20}$ is an N-linked 5-6 membered heterocycloalkyl having 1-2 heteroatoms independently selected from N, O and S, which is substituted with 1-3 substituents independently selected from C$_1$-C$_6$alkyl, —C(=O)OR$^{12}$, —C(=O)(CH$_2$)$_m$N$_3$, C$_1$-C$_6$haloalkyl, halogen, oxo, —OH and C$_1$-C$_6$alkoxy;

R$^{21}$ is a C-linked 5-6 membered heteroaryl having 1-2 N heteroatoms which is substituted with LR$^{11}$ and 0-2 substituents independently selected from C$_1$-C$_6$alkyl, C$_1$-C$_6$haloalkyl, halogen, —CN, NO$_2$, —C(=O)OR$^6$, —C(=O)N(R$^6$)$_2$ and C$_1$-C$_6$alkoxy;

R$^{22}$ is a C-linked 5-6 membered heterocycloalkyl having 1-2 heteroatoms independently selected from N, O and S which is substituted with LR$^{11}$ and 0-2 substituents independently selected from C$_1$-C$_6$alkyl, C$_1$-C$_6$haloalkyl, halogen and C$_1$-C$_6$alkoxy;

R$^{23}$ is an N-linked 5-6 membered heterocycloalkyl having 1-2 heteroatoms independently selected from N and O which is substituted with LR$^{11}$ and 0-2 substituents independently selected from C$_1$-C$_6$alkyl, C$_1$-C$_6$haloalkyl, halogen and C$_1$-C$_6$alkoxy;

X$_3$ is

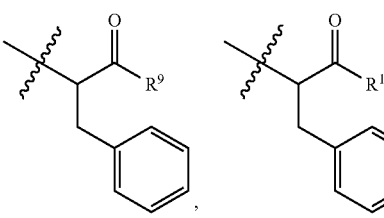

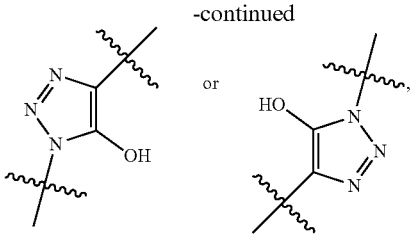

X$_4$ is

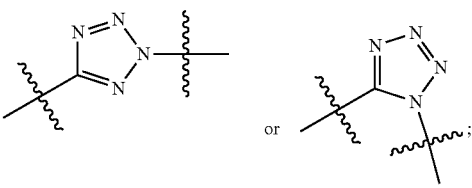

each L is a linker independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18.

In one aspect of the invention are compounds, or stereoisomer thereof, and pharmaceutically acceptable salts thereof, having the structure of Formula (I)

(Formula (I))

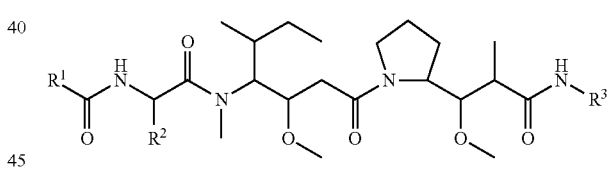

wherein:

R$^1$ is —N=CR$^4$R$^5$, —N=R$^{19}$, —N=CR$^5$ R$^{20}$, —N=CR$^5$NR$^{12}$(CH$_2$)$_m$N(R$^{12}$)C(O)OR$^{12}$, —N=CR$^5$NR$^{12}$(CH$_2$)$_m$N(R$^{12}$)$_2$, —NHC(=NR$^6$)R$^4$, —NHC(=O)R$^4$, —NHC(=O)R$^{20}$, —NHR$^8$, —NHLR$^{11}$, —NHR$^{21}$, —N=CR$^5$R$^{10}$, —N=R$^{22}$, —N=CR$^5$R$^{23}$ or —NHC(=O)R$^{23}$;

R$^2$ is —C$_1$-C$_6$alkyl;

R$^3$ is

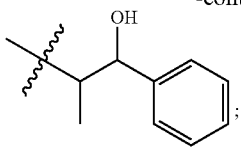

$R^4$ is —N($R^6$)$_2$ or —N$R^6R^7$;
$R^5$ is N($R^6$)$_2$;
each $R^6$ is independently selected from H and —$C_1$-$C_6$alkyl;
$R^7$ is —(CH$_2$)$_m$N($R^{12}$)$_2$, —(CH$_2$)$_m$N($R^{12}$)C(=O)O$R^{12}$ or an unsubstituted $C_3$-$C_8$cycloalkyl;
or $R^7$ is a $C_3$-$C_8$cycloalkyl substituted with 1-3 substituents independently selected from $C_1$-$C_6$alkyl, oxo, —C(=O)$R^{18}$, —(CH$_2$)$_m$OH, —C(=O)(CH$_2$)$_m$OH, —C(=O)((CH$_2$)$_m$O)$_n$$R^{12}$, —((CH$_2$)$_m$O)$_n$$R^{12}$ or a $C_1$-$C_6$alkyl which is optionally substituted with 1 to 5 hydroxyl;
$R^8$ is an unsubstituted C-linked 5-6 membered heteroaryl having 1-2 N heteroatoms;
or $R^8$ is a C-linked 5-6 membered heteroaryl having 1-2 N heteroatoms which is substituted with 1-3 substituents independently selected from $C_1$-$C_6$alkyl, $C_1$-$C_6$haloalkyl, halogen, $C_1$-$C_6$alkoxy, —OH, —CN, —NO$_2$, —C(=O)O$R^6$, —C(=O)N($R^6$)$_2$, —C(=O)N$R^6$(CH$_2$)$_m$N($R^6$)C(O)O$R^6$ and —C(=O)N$R^6$(CH$_2$)$_m$N($R^6_2$);
$R^9$ is —OH, $C_1$-$C_6$alkoxy, —NHS(O)$_2$(CH$_2$)$_m$N$_3$, —NHS(O)$_2$(CH$_2$)$_m$NH$_2$, —N($R^{12}$)$_2$, -$R^{16}$, —N$R^{12}$(CH$_2$)$_m$N($R^{12}$)$_2$, —N$R^{12}$(CH$_2$)$_m$$R^{16}$, -$LR^{11}$, —NHS(O)$_2$$R^{18}$, —NHS(=O)$_2$$LR^{11}$,

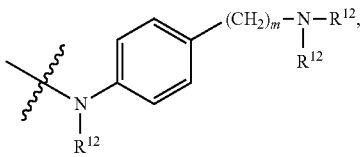

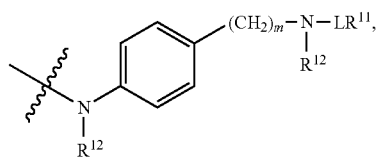

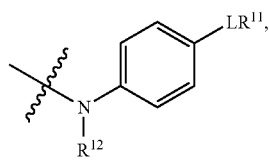

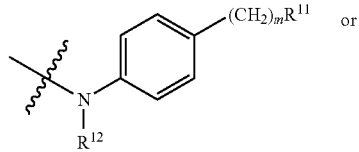

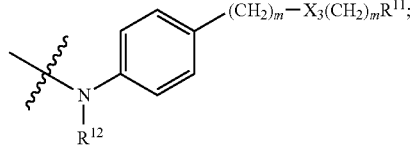

$R^{10}$ is $LR^{11}$ or

$R^{11}$ is

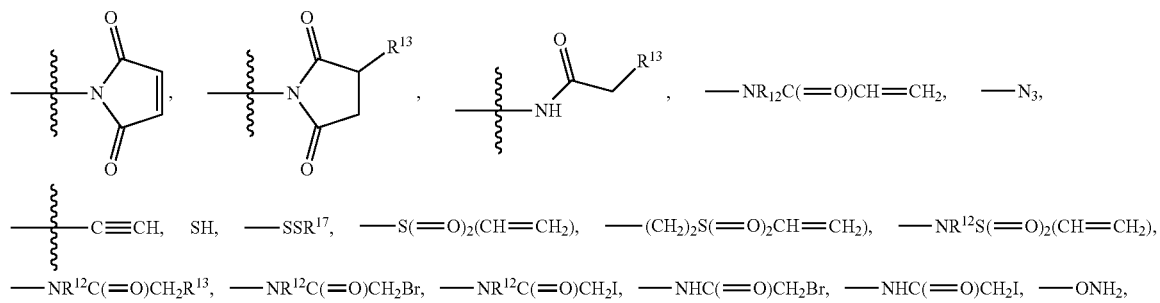

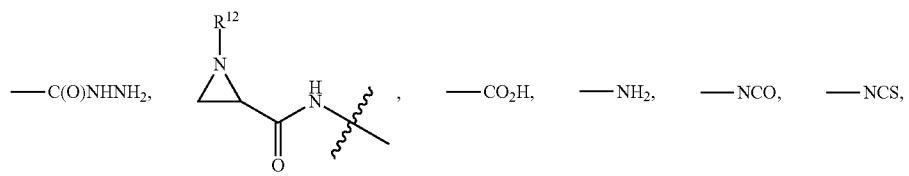

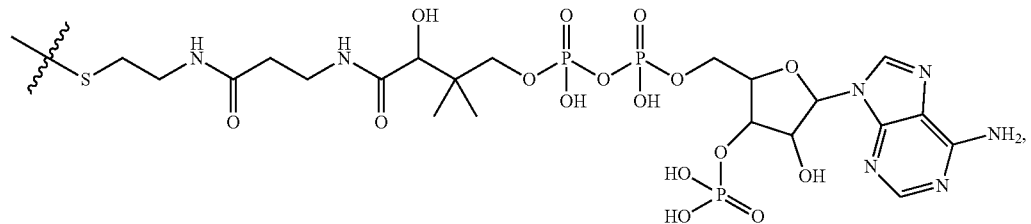

-continued

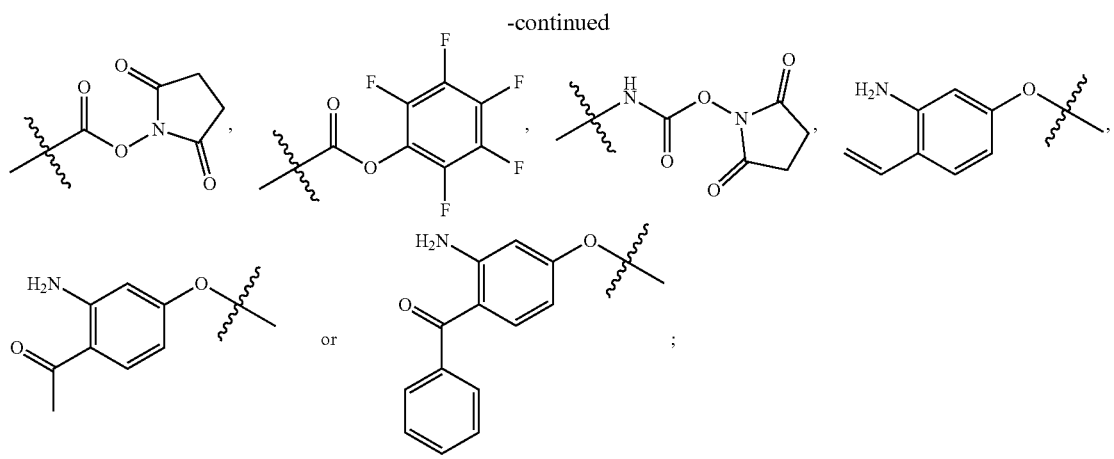

each R$^{12}$ is independently selected from H and C$_1$-C$_6$alkyl;
R$^{13}$ is —S(CH$_2$)$_n$CHR$^{14}$NHC(=O)R$^{12}$ or

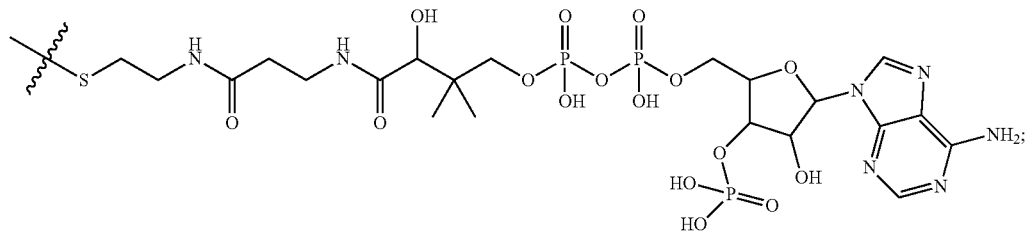

R$^{14}$ is R$^{12}$ or —C(=O)OR$^{12}$;
R$^{15}$ is tetrazolyl, —CN, —C(=O)OR$^{12}$,

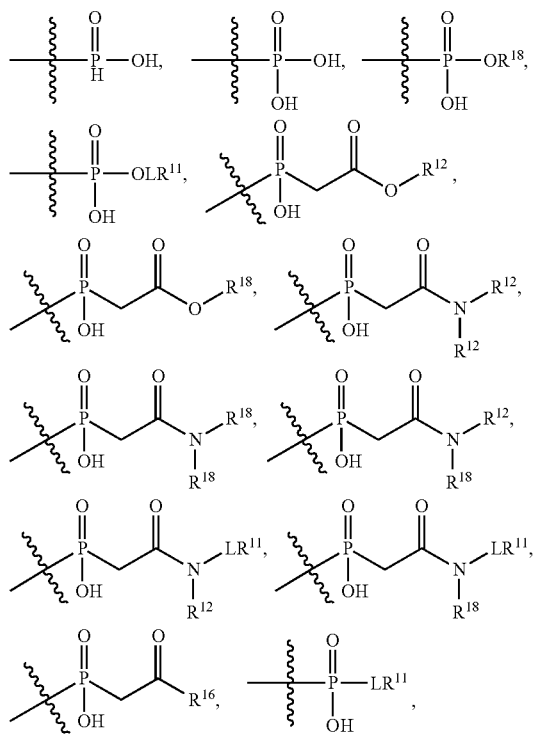

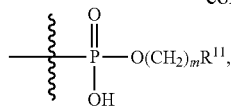

-LR$^{11}$ or X$_4$LR$^{11}$;

R$^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;

R$^{17}$ is 2-pyridyl or 4-pyridyl;

each R$^{18}$ is independently selected from a C$_1$-C$_6$alkyl, a C$_1$-C$_6$alkyl which is substituted with azido and a C$_1$-C$_6$alkyl which is substituted with 1 to 5 hydroxyl;

R$^{19}$ is an unsubstituted C-linked 5-6 membered heterocycloalkyl having 1-2 heteroatoms independently selected from N and O;

or R$^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;

R$^{20}$ s an unsubstituted N-linked 5-6 membered heterocycloalkyl having 1-2 heteroatoms independently selected from N, O and S;

or R$^{20}$ is an N-linked 5-6 membered heterocycloalkyl having 1-2 heteroatoms independently selected from N, O and S, which is substituted with 1-2 substituents independently selected from C$_1$-C$_6$alkyl, —C(=O)OR$^{12}$, —C(=O)(CH$_2$)$_m$N$_3$, C$_1$-C$_6$haloalkyl, halogen, oxo, —OH and C$_1$-C$_6$alkoxy;

$R^{21}$ is a C-linked 5-6 membered heteroaryl having 1-2 N heteroatoms which is substituted with $LR^{11}$ and 0-2 substituents independently selected from $C_1$-$C_6$alkyl, $C_1$-$C_6$haloalkyl, halogen, —CN, $NO_2$, —C(=O)$OR^6$, —C(=O)N($R^6$)$_2$ and $C_1$-$C_6$alkoxy;

$R^{22}$ is a C-linked 5-6 membered heterocycloalkyl having 1-2 heteroatoms independently selected from N, O and S which is substituted with $LR^{11}$ and 0-2 substituents independently selected from $C_1$-$C_6$alkyl, $C_1$-$C_6$haloalkyl, halogen and $C_1$-$C_6$alkoxy;

$R^{23}$ is an N-linked 5-6 membered heterocycloalkyl having 1-2 heteroatoms independently selected from N and O which is substituted with $LR^{11}$ and 0-2 substituents independently selected from $C_1$-$C_6$alkyl, $C_1$-$C_6$haloalkyl, halogen and $C_1$-$C_6$alkoxy;

$X_3$ is

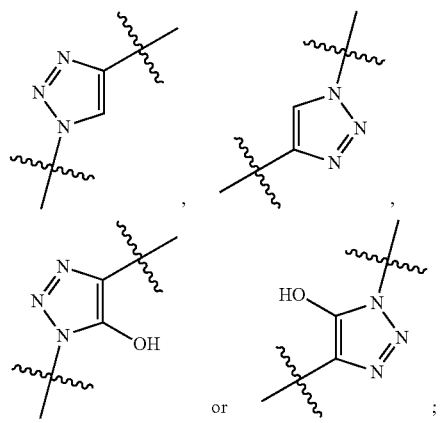

$X_4$ is

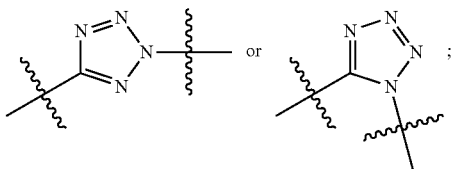

each L is a linker independently selected from $-L_1L_2L_3L_4L_5L_6$-, $-L_6L_5L_4L_3L_2L_1$-, $-L_1L_2L_3L_4L_5$-, $-L_5L_4L_3L_2L_1$-, $-L_1L_2L_3L_4$-, $-L_4L_3L_2L_1$-, $-L_1L_2L_3$-, $-L_3L_2L_1$-, $-L_1L_2$-, $-L_2L_1$- and $-L_1$, wherein $-L_1$, $L_2$, $L_3$, $L_4$, $L_5$, and $L_6$ are as defined herein;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18.

Synthetic Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis*, Thieme, Volume 21). Further, the compounds of the present invention can be produced by organic synthesis methods known to one of ordinary skill in the art in view of the following examples.

Illustrative examples of synthetic approaches to the compound of Formula (I), and subformulae thereof, are provided in the following general Schemes 1-25. In the following schemes $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and L are as defined herein. Although the general schemes may show specific reagents used for various synthetic steps, it is understood that other known reagents can be used to accomplish such synthetic steps.

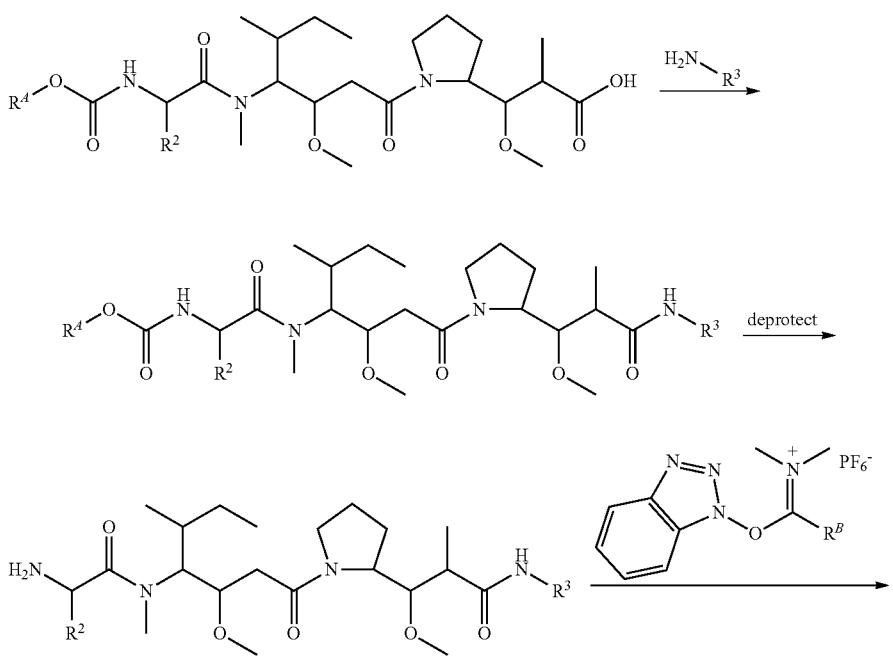

Scheme 1

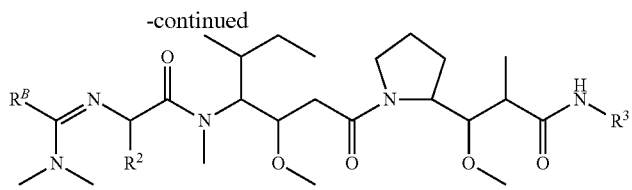

In Scheme 1, $R^3$ is coupled to a short peptide via amide bond formation followed by a deprotection step with subsequent coupling of $R^B$ via imine bond formation.

In Scheme 1, by way of example, $R^A$ can be t-butyl, fluorenyl or benzyl. In Scheme 1, by way of example, $R^B$ can be —$R^4$, —$R^{20}$, —$NR^{12}(CH_2)_mN(R^{12})C(O)OR^{12}$, —$NR^{12}(CH_2)_mN(R^{12})_2$, —$R^{10}$, —$R^{22}$, —$R^{19}$ or —$R^{23}$, each of which are as defined herein.

Scheme 2

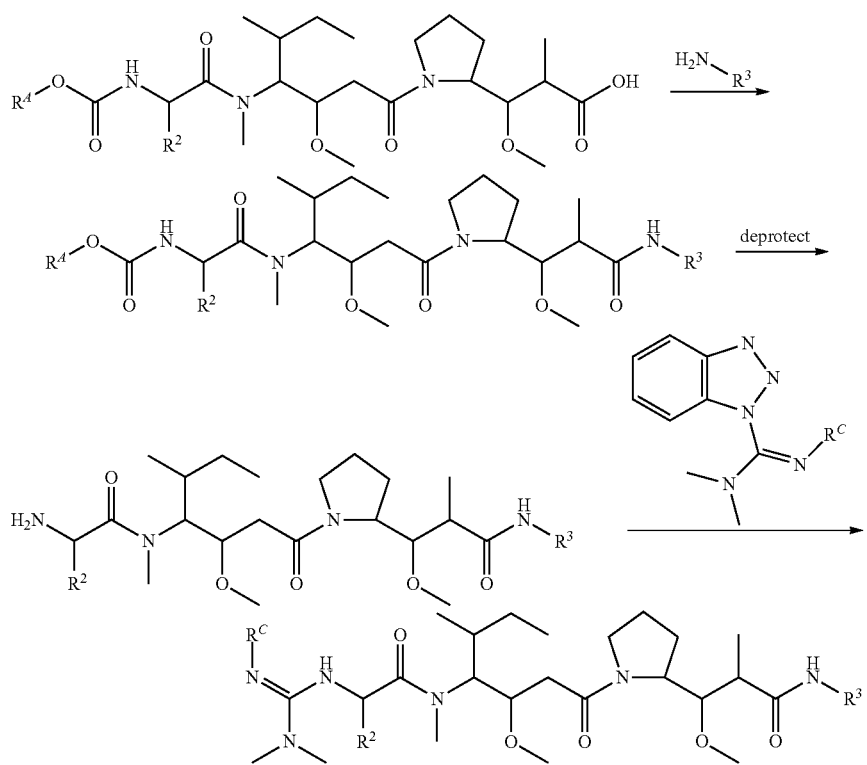

In Scheme 2, $R^3$ is coupled to a short peptide via amide bond formation followed by a deprotection step with subsequent coupling of $R^B$ via imine bond formation.

In Scheme 2, by way of example, $R^A$ can be t-butyl, fluorenyl or benzyl and $R^C$ can be H or —$R^6$.

Scheme 3

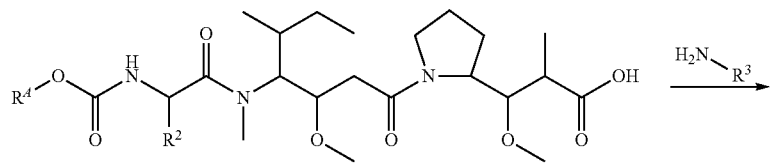

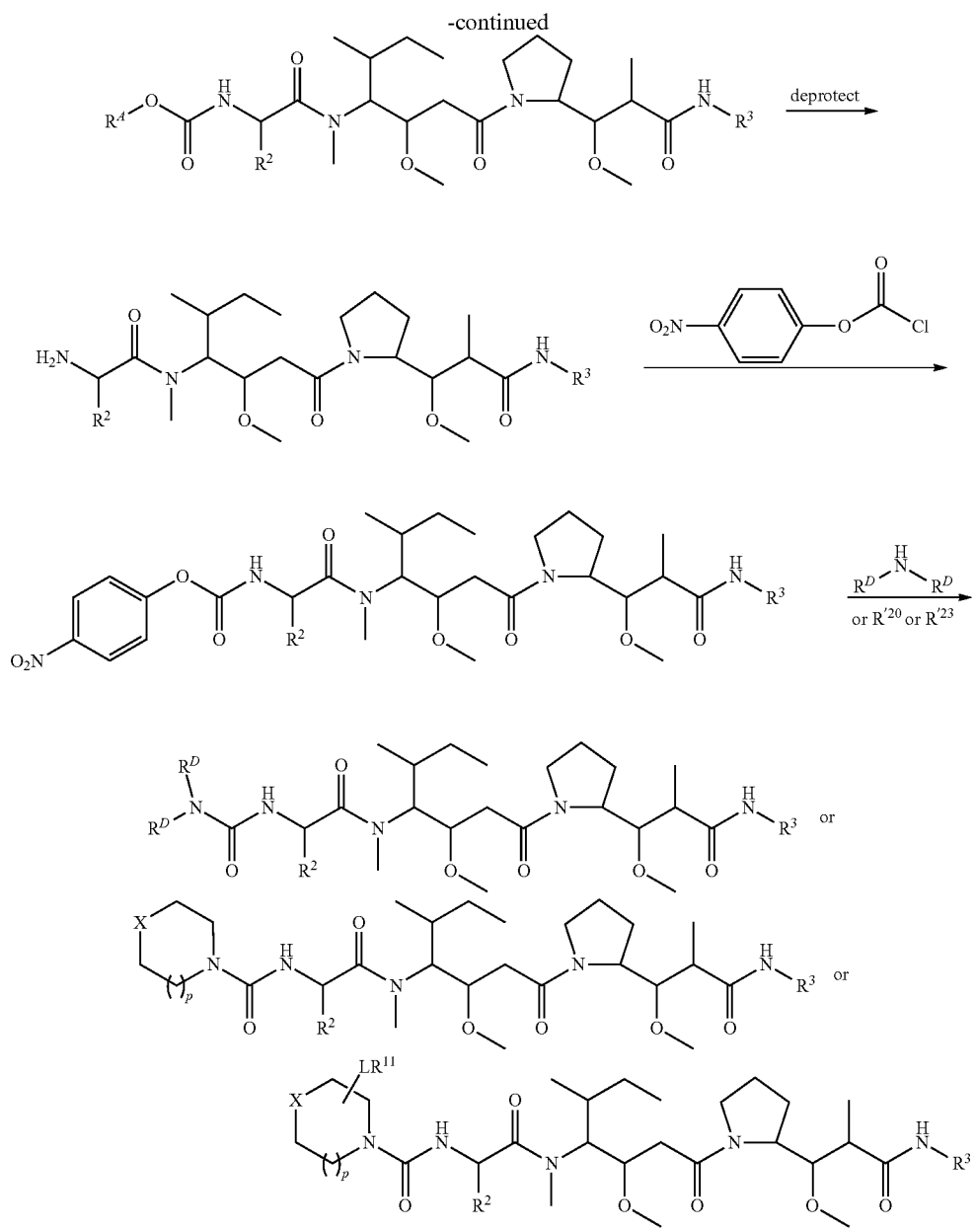

In Scheme 3, $R^3$ is coupled to a short peptide via amide bond formation followed by a deprotection step with subsequent coupling of —N($R^D$)$_2$ via amide bond formation.

In Scheme 3, by way of example, $R^A$ can be t-butyl, fluorenyl or benzyl, and each $R^D$ can independently be —$R^6$ or —$R^7$. In Scheme 3, by way of example, $R^{20}$ can be

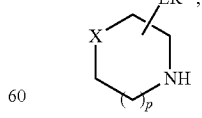

where X is —NC(=O)O$R^{12}$, NH, O or S and p is 1 or 2, $R'^{20}$ can be unsubstituted or substituted with 1-2 substituents independently selected from $C_1$-$C_6$alkyl, —C(=O)O$R^{12}$, —C(=O)(CH$_2$)$_m$N$_3$, $C_1$-$C_6$haloalkyl, halogen, oxo, —OH and $C_1$-$C_6$alkoxy. In Scheme 3, by way of example, $R'^{23}$ can be where X is —NC(=O)O$R^{12}$, NH, O or S and p is 1 or 2, $R'^{23}$ can be unsubstituted or substituted with 0-2 substituents independently selected from $C_1$-$C_6$alkyl, $C_1$-$C_6$haloalkyl, halogen and $C_1$-$C_6$alkoxy.

Scheme 4

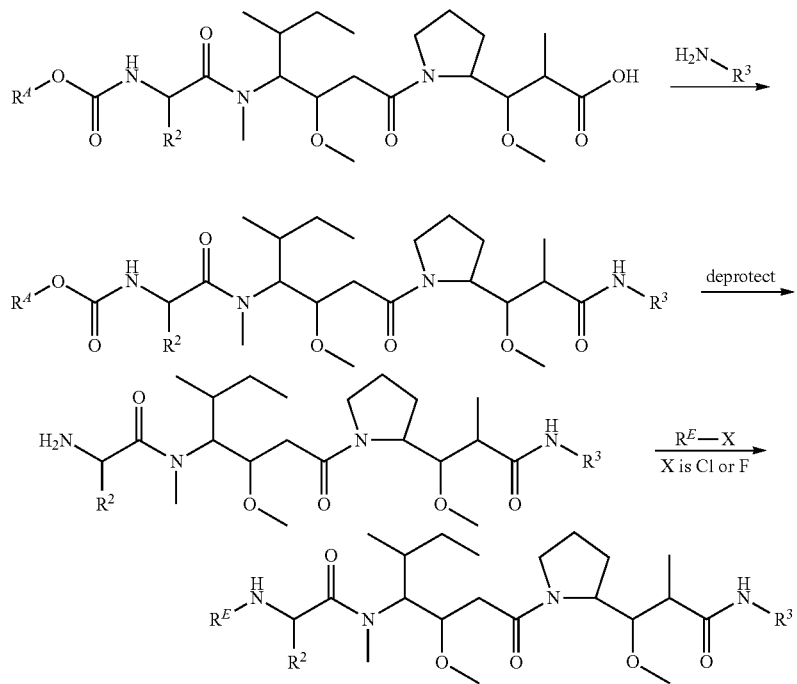

In Scheme 4, $R^3$ is coupled to a short peptide via amide bond formation followed by a deprotection step with subsequent coupling of $R^E$ via amine bond formation.

In Scheme 1, by way of example, $R^A$ can be t-butyl, fluorenyl or benzyl, and $R^E$ can be —$R^8$, $LR^{11}$ or —$R^{21}$.

Scheme 5

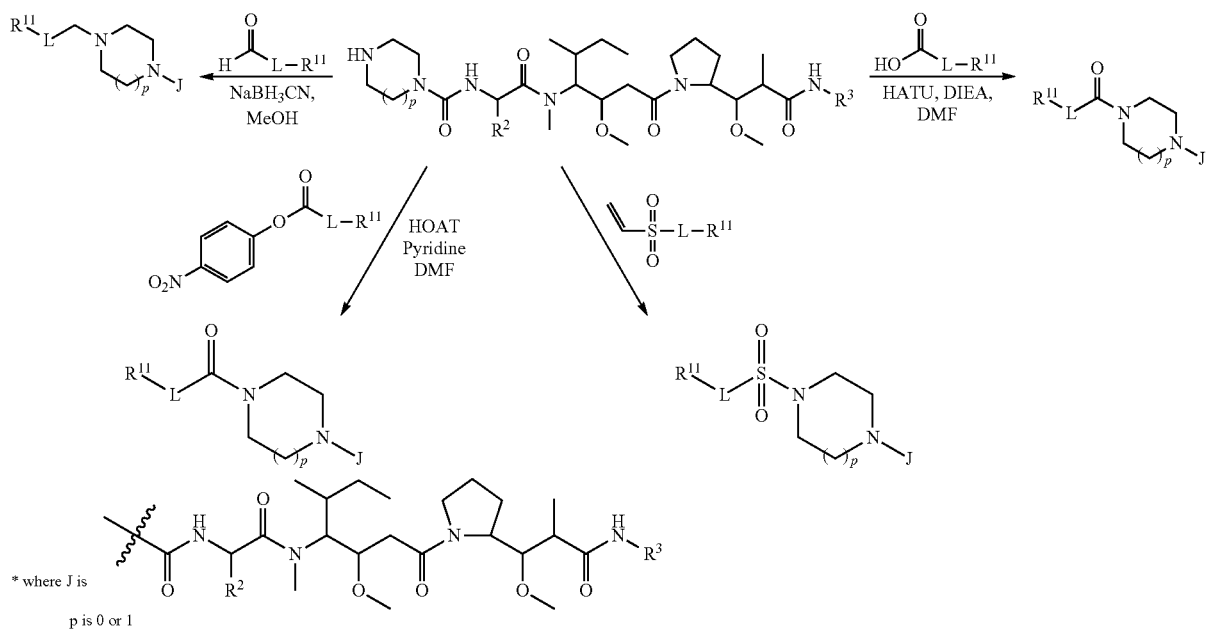

Scheme 5 illustrates further modification of the N-terminal end of certain compounds of Formula (I).

Scheme 6
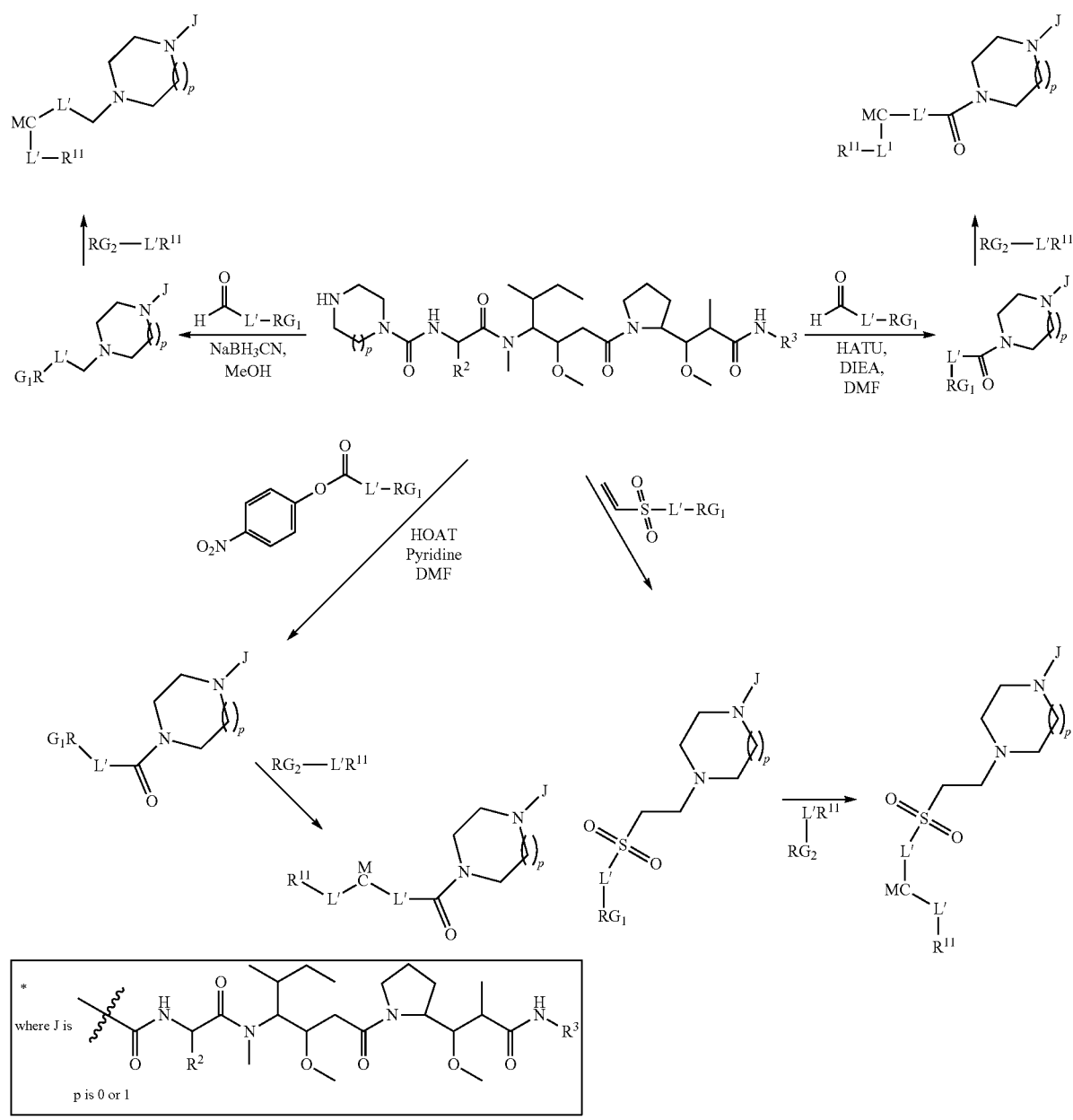
Scheme 6 illustrates further modification of the N-terminal end of certain compounds of Formula (I), where $RG_1$ and $RG_2$ are reactive groups, and CM is the chemical moiety resulting from reaction between $RG_1$ and $RG_2$, such as those given in Table 1, and L' is one or more linker components. Other illustrative examples are shown in the scheme 7.

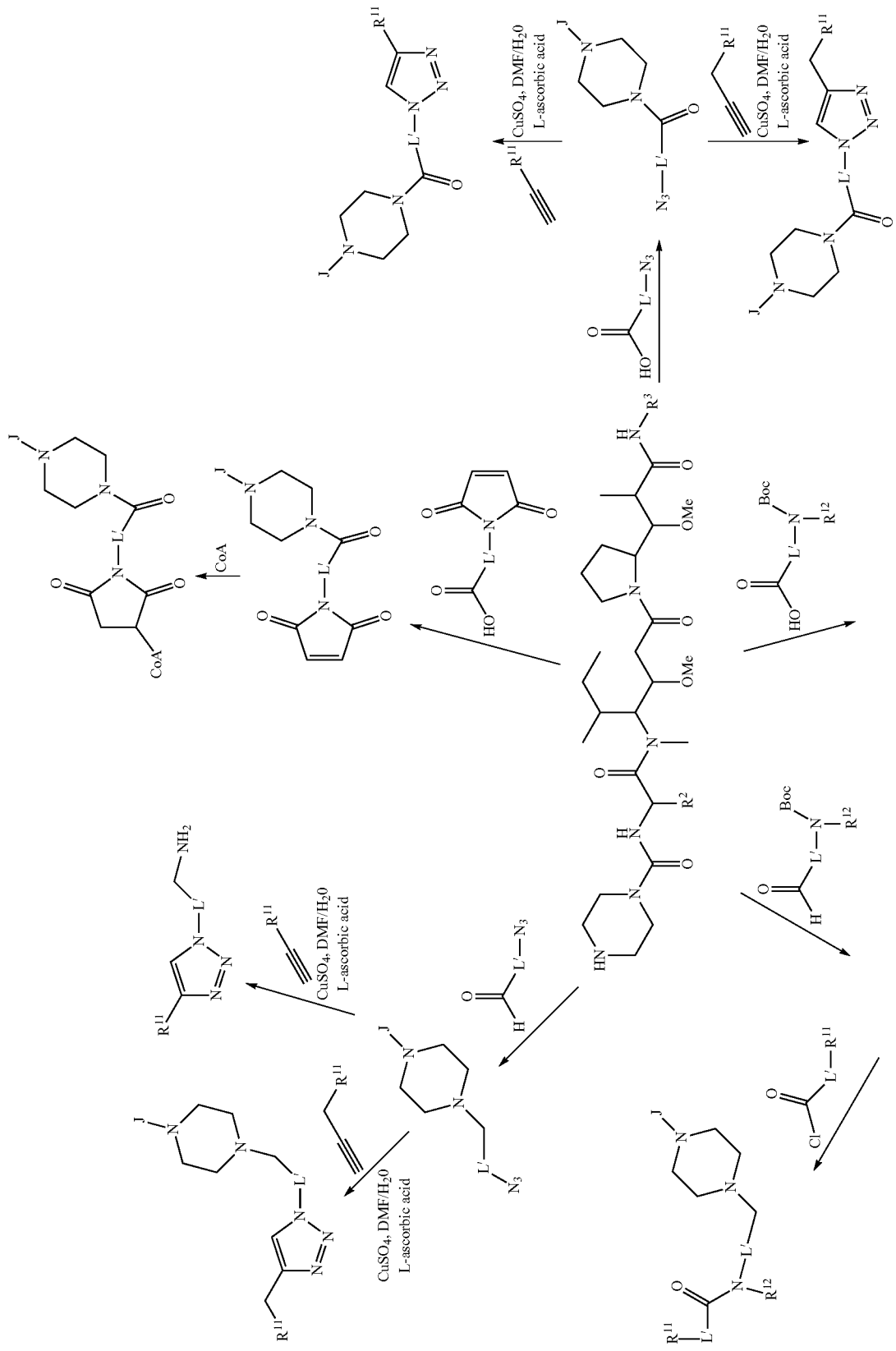
Scheme 7

-continued
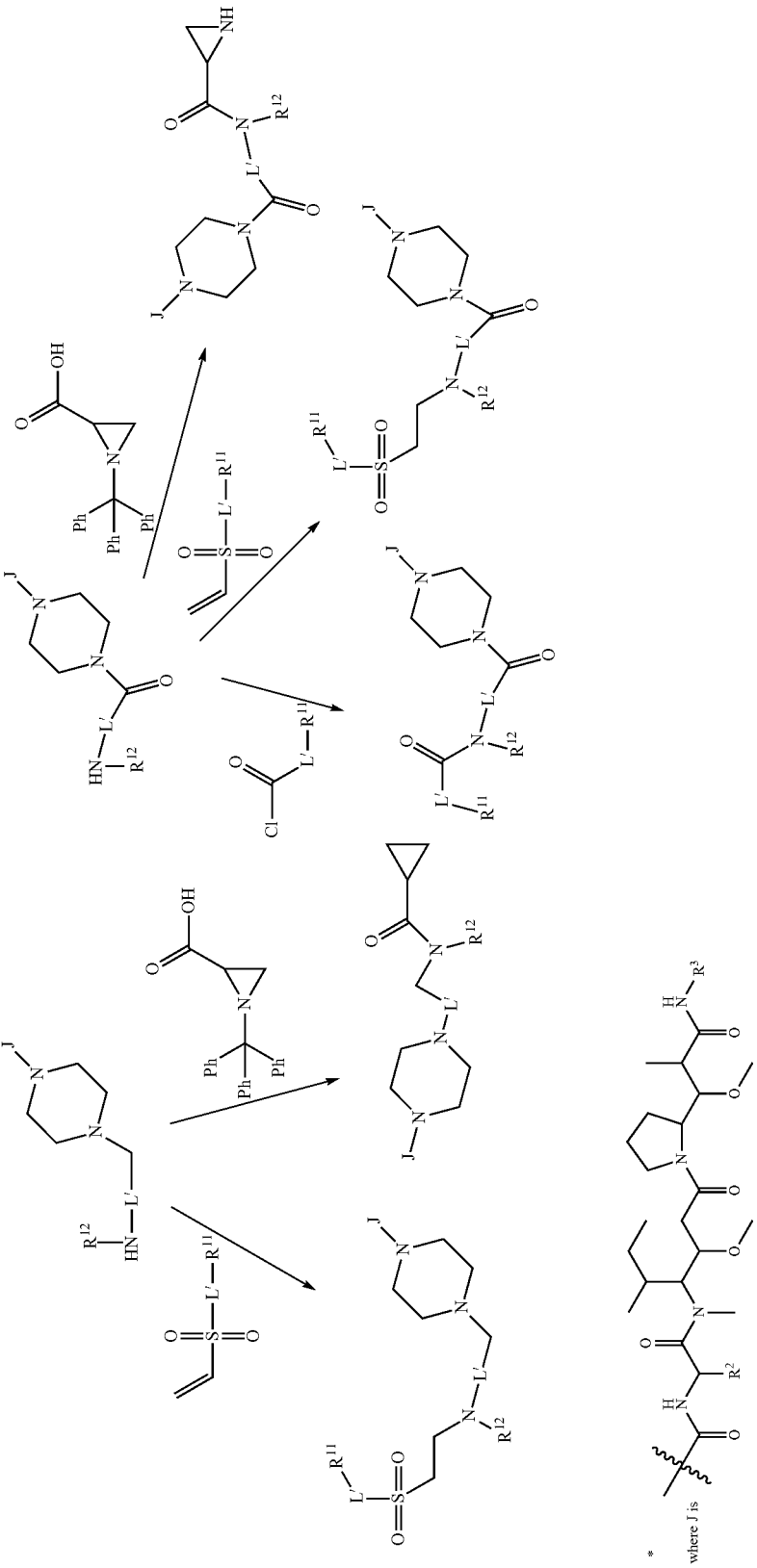
where J is 
L' is one or more linker components

Scheme 8
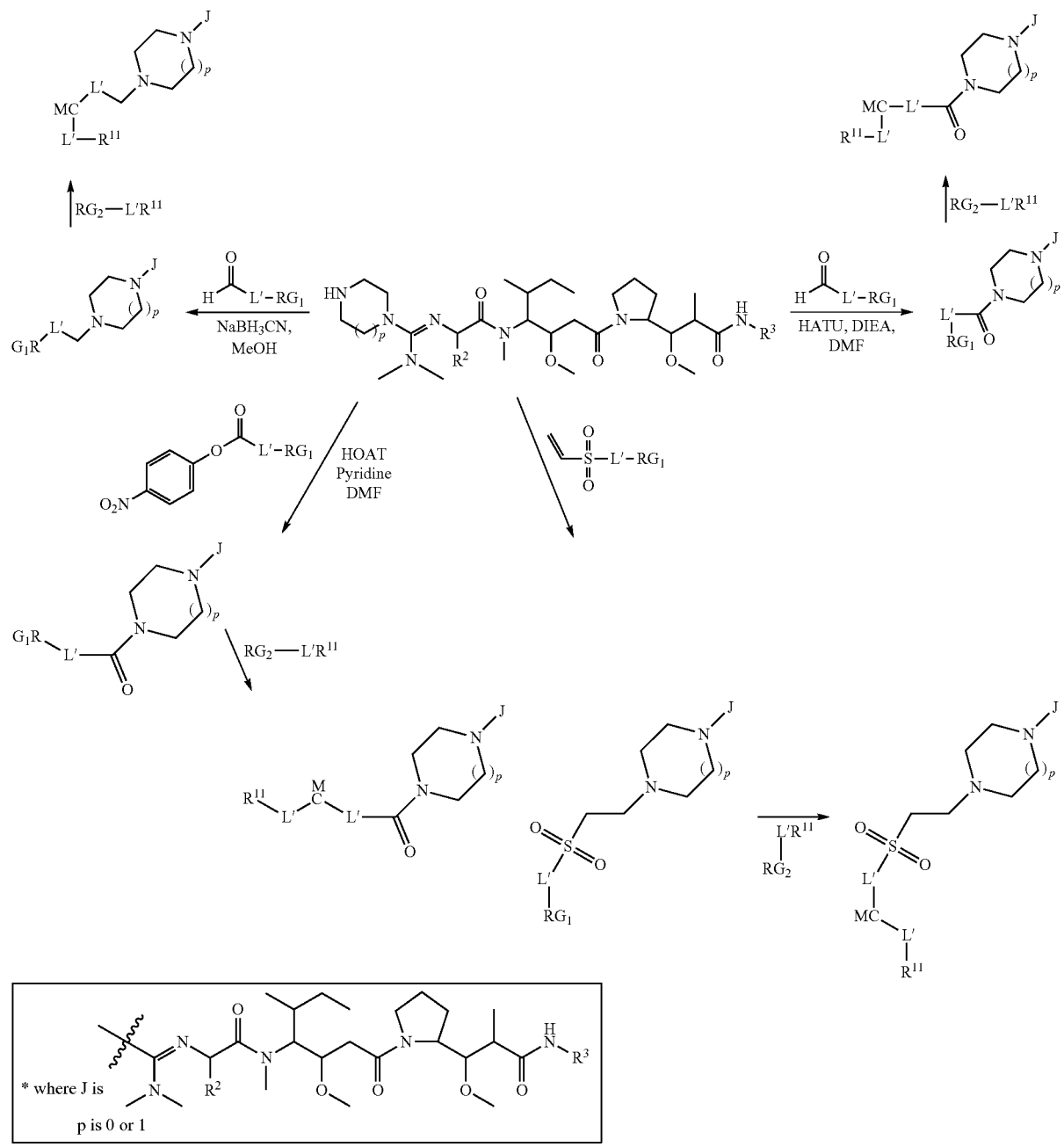
Scheme 8 illustrates further modification of the N-terminal end of certain compounds of Formula (I), where $RG_1$ and $RG_2$ are reactive groups, and CM is the chemical moiety resulting from reaction between $RG_1$ and $RG_2$, such as those given in Table 1, and L' is one or more linker components. Other illustrative examples are shown in the scheme 9

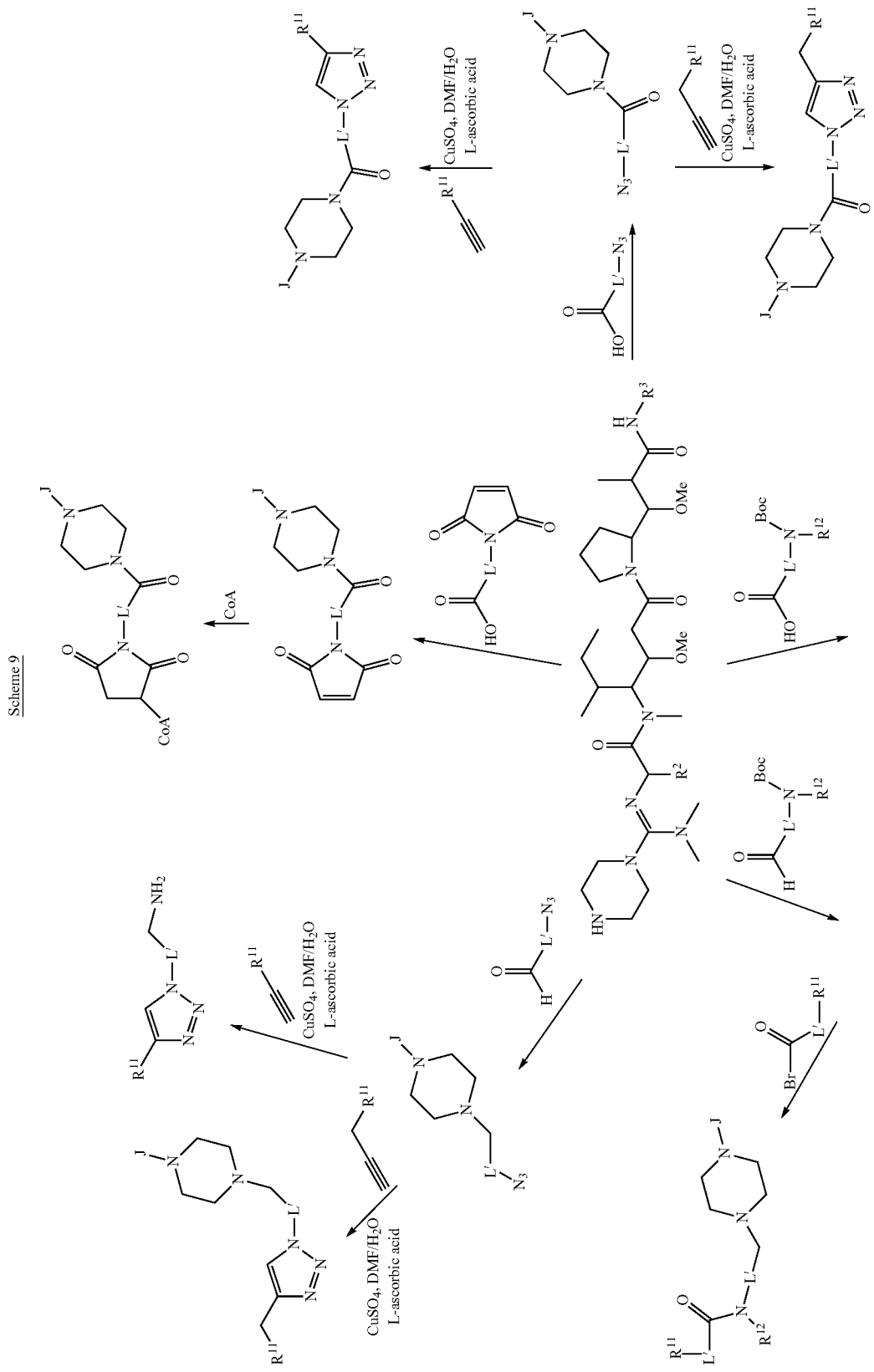

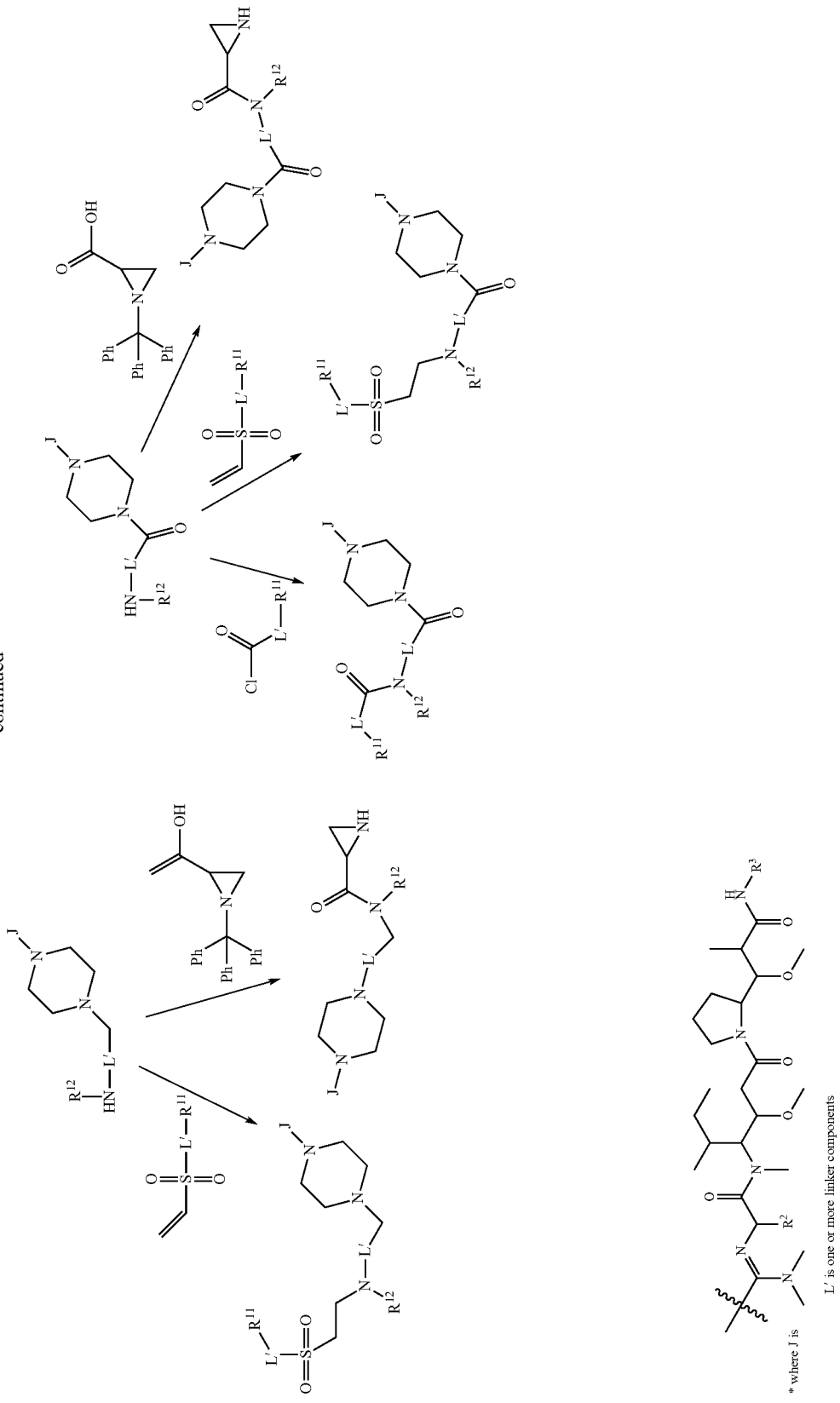

Scheme 10
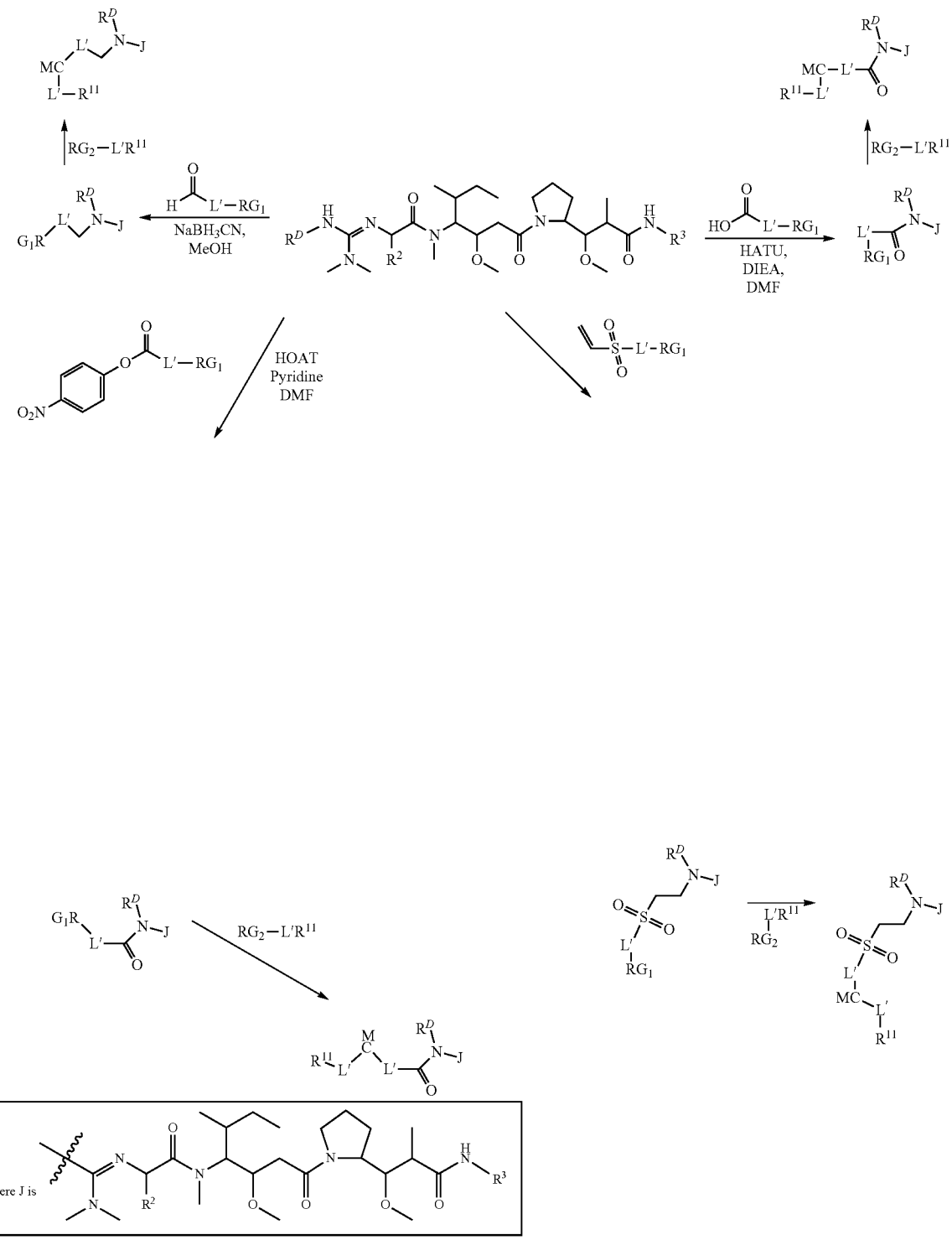
Scheme 10 illustrates further modification of the N-terminal end of certain compounds of Formula (I), where $RG_1$ and $RG_2$ are reactive groups, and CM is the chemical moiety resulting from reaction between $RG_1$ and $RG_2$, such as those given in Table 1, and L' is one or more linker components. Other illustrative examples are shown in the scheme 11.

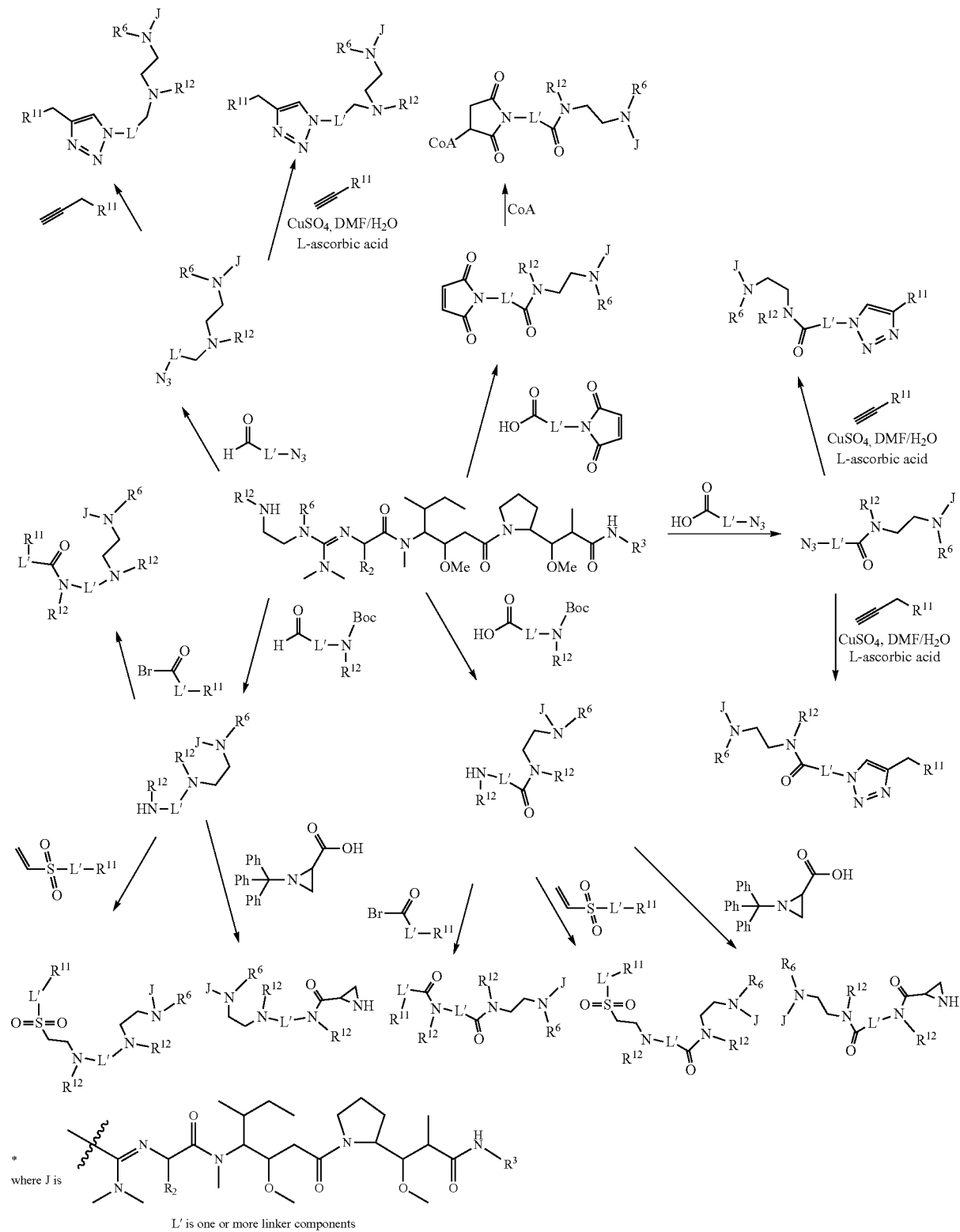
Scheme 11

Scheme 12
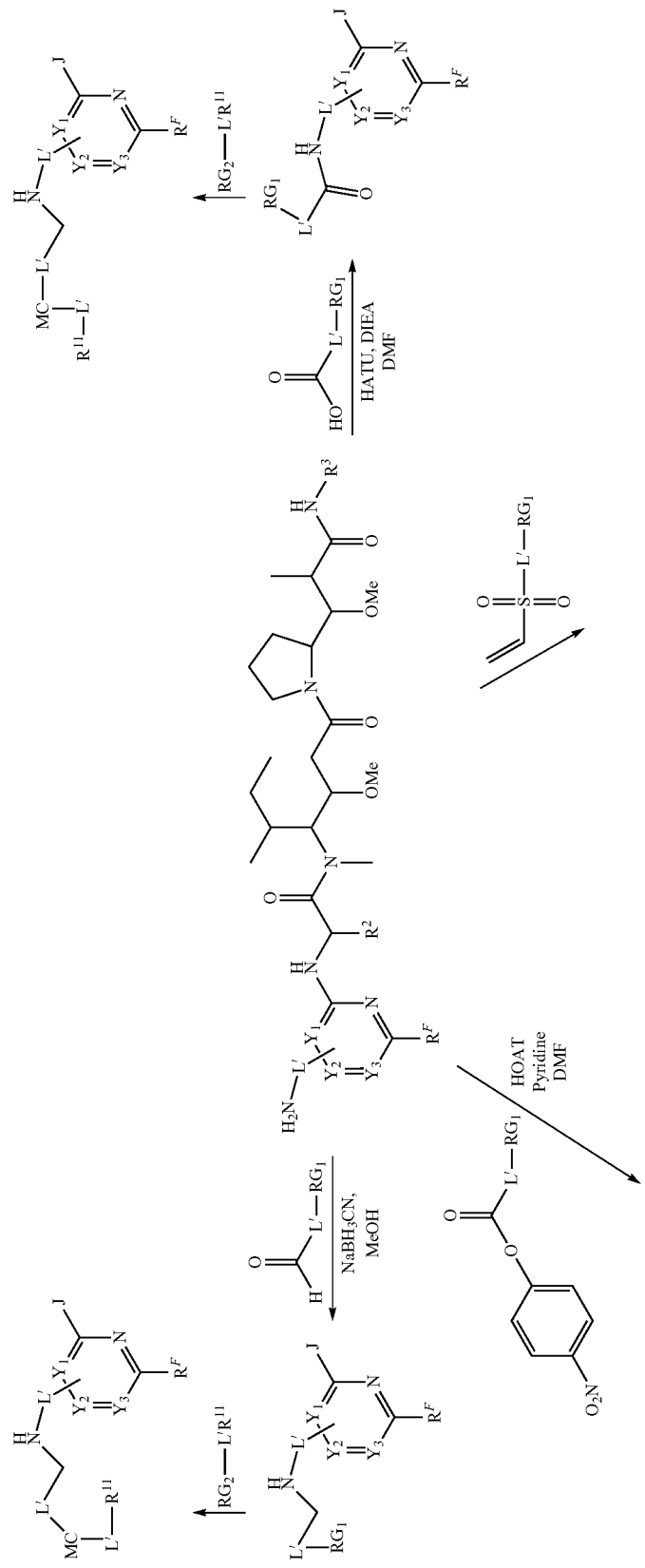

-continued
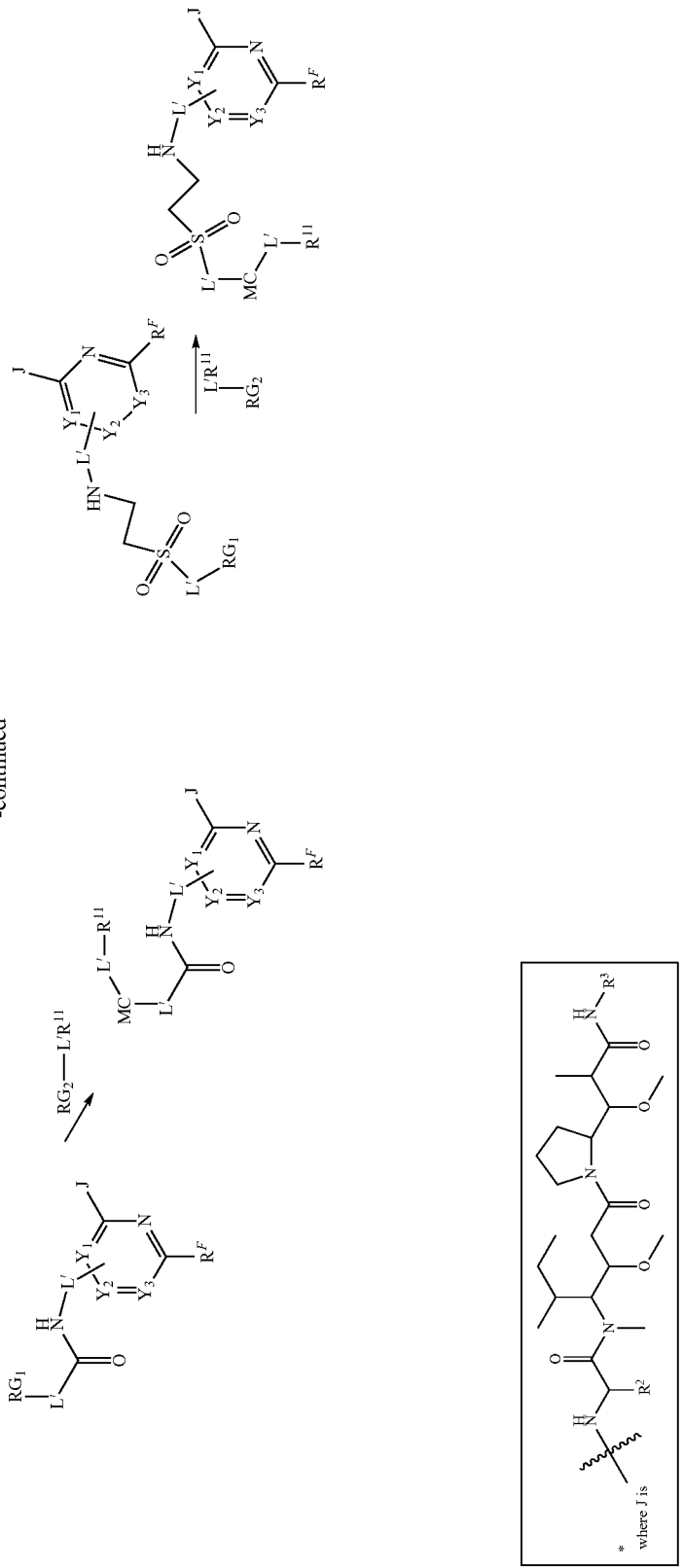

Scheme 12 illustrates further modification of the N-terminal end of certain compounds of Formula (I), where $RG_1$ and $RG_2$ are reactive groups, and CM is the chemical moiety resulting from reaction between $RG_1$ and $RG_2$, such as those given in Table 1, and L' is one or more linker components. Other illustrative examples are shown in the scheme 13.

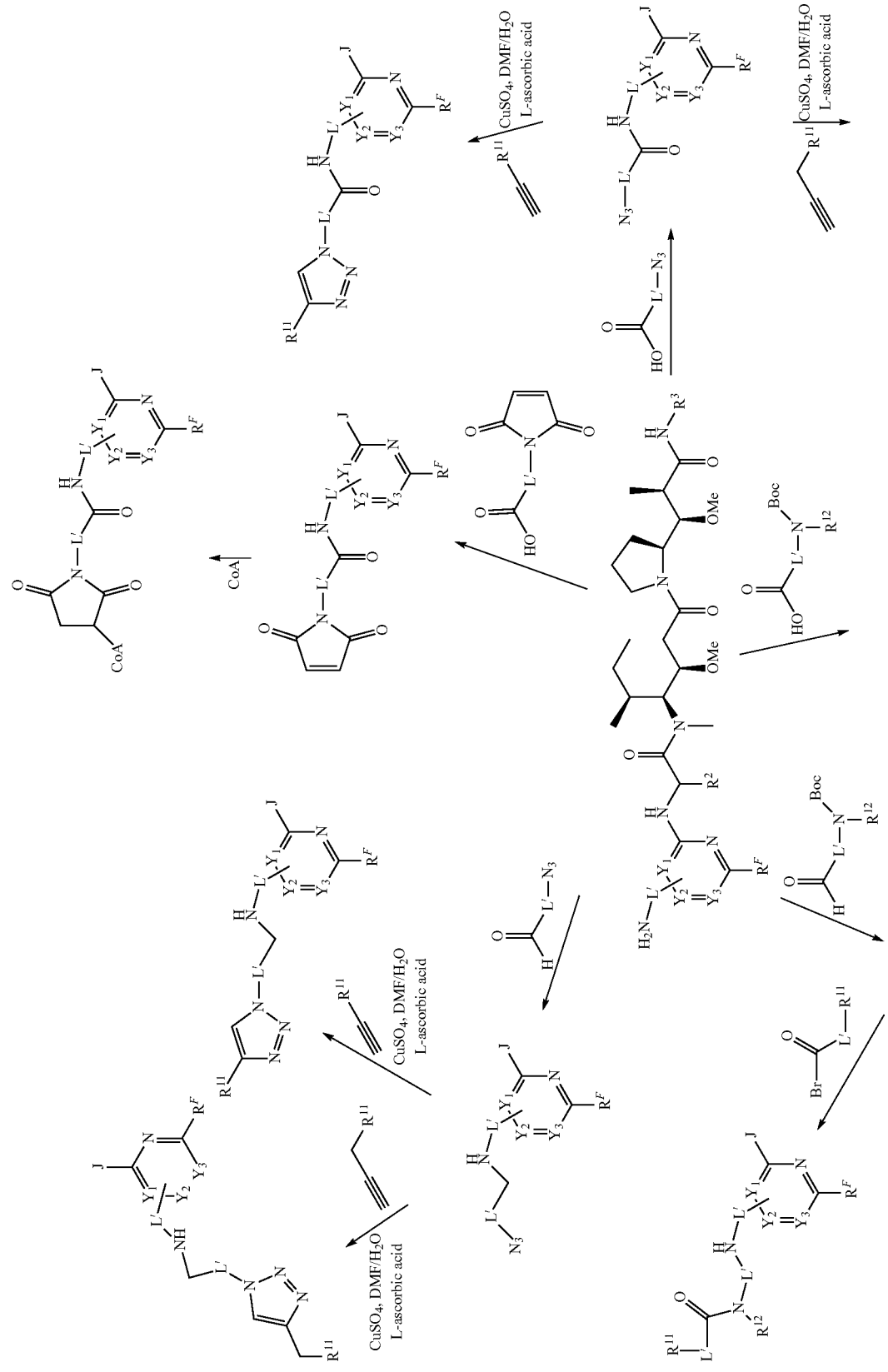
Scheme 13

-continued
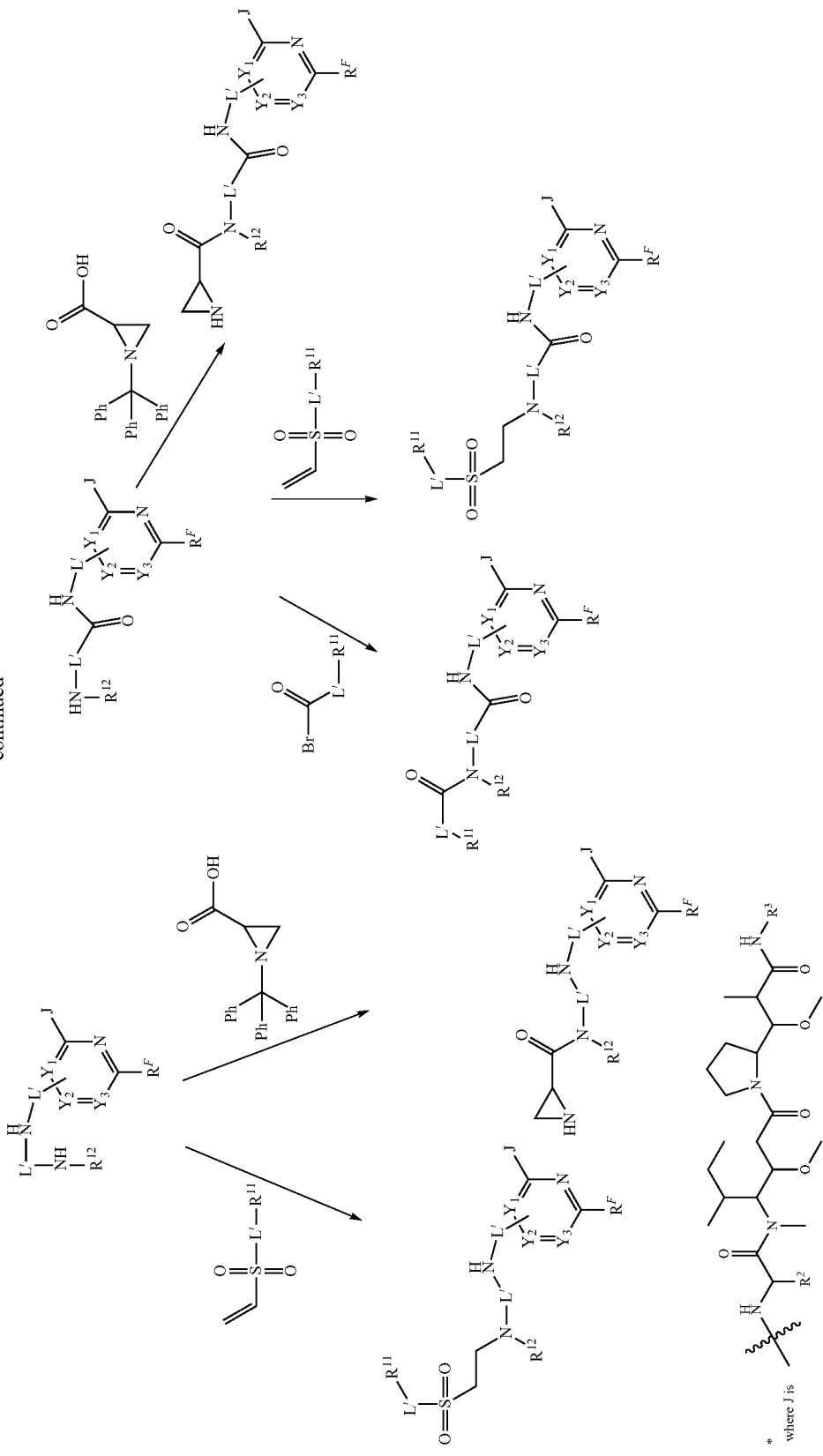

In Scheme 13 $Y_1$, $Y_2$ and $Y_3$ are each independently C*, N or $CR^F$, where the * indicates the point of attachement of the -L'NH$_2$ group and $R^F$ is $C_1$-$C_6$alkyl, $C_1$-$C_6$haloalkyl, halogen, —CN, NO$_2$, —C(=O)OR$^6$, —C(=O)N(R$^6$)$_2$ or $C_1$-$C_6$alkoxy. Only one of $Y_1$, $Y_2$ and $Y_3$ can be N and only one of $Y_1$, $Y_2$ and $Y_3$ can be C*.

Another synthetic approach for compounds of Formula (I), and sub formulae thereof is shown below in Scheme 14.

Scheme 14

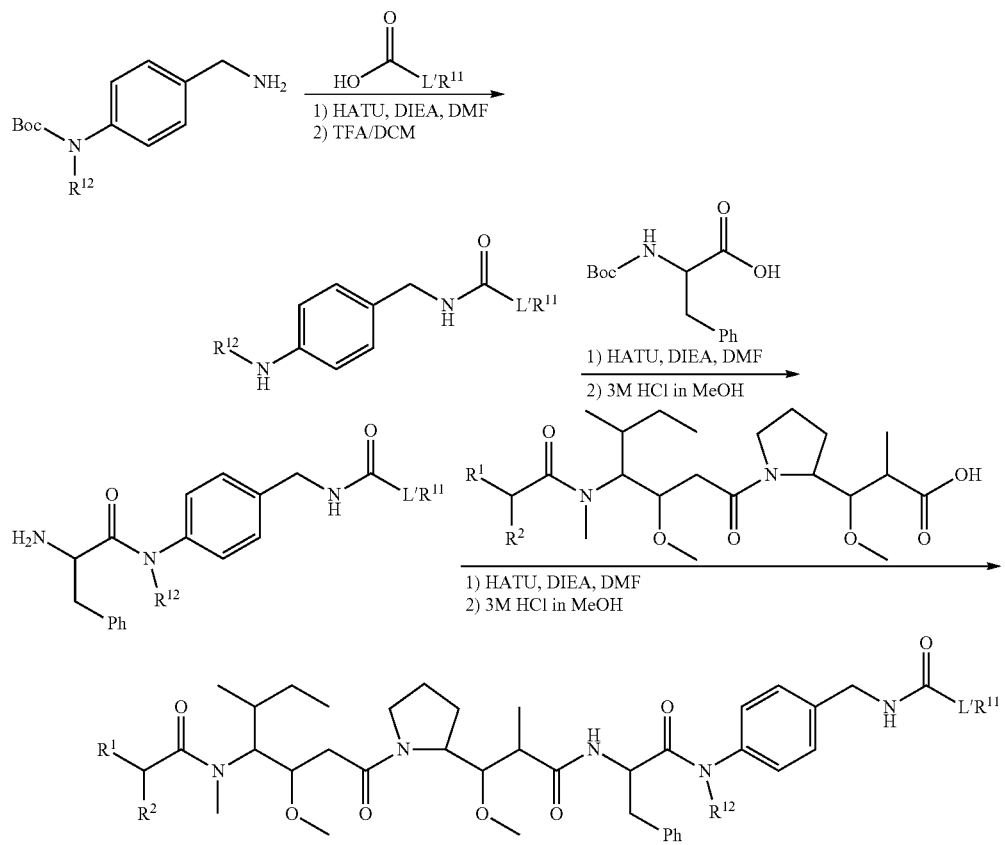

Another synthetic approach for compounds of Formula (I), and sub formulae thereof is shown below in Scheme 15.

Scheme 15

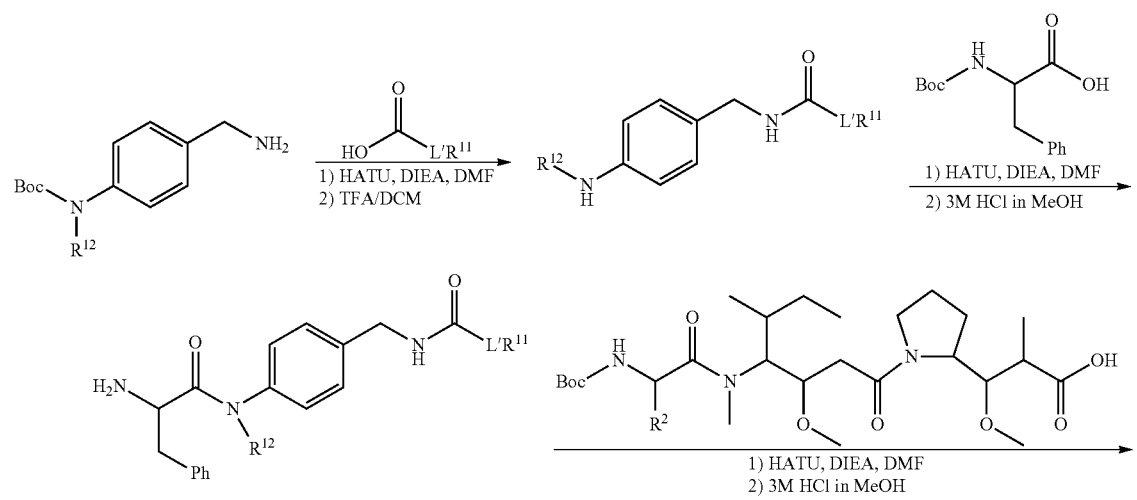

-continued

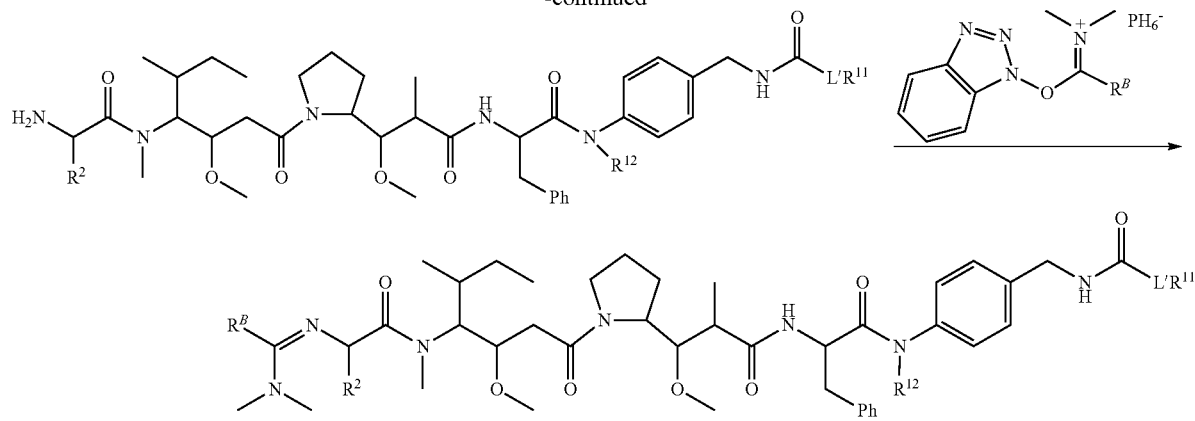

In Scheme 15, by way of example, $R^B$ can be $-R^4$, $-R^{20}$, $-NR^{12}(CH_2)_m N(R^{12})C(O)OR^{12}$, $-NR^{12}(CH_2)_m N(R^{12})_2$, $-R^{22}$ or $-R^{19}$, each of which are as defined herein.

Another synthetic approach for compounds of Formula (I), and sub formulae thereof is shown below in Scheme 16.

Scheme 16

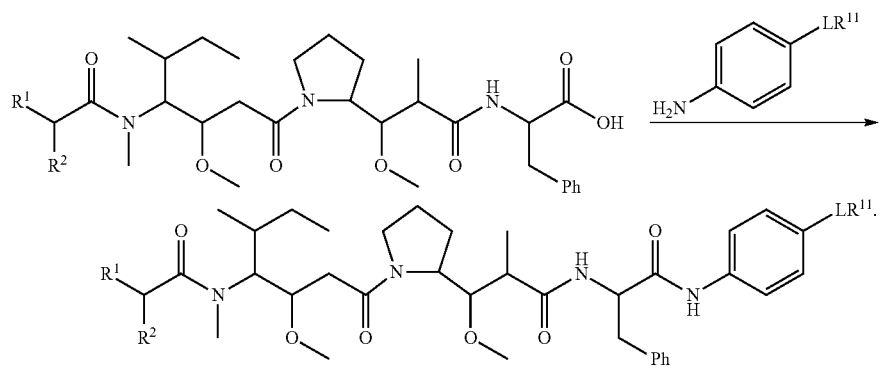

Another synthetic approach for compounds of Formula (I), and sub formulae thereof is shown below in Scheme 17.

Scheme 17

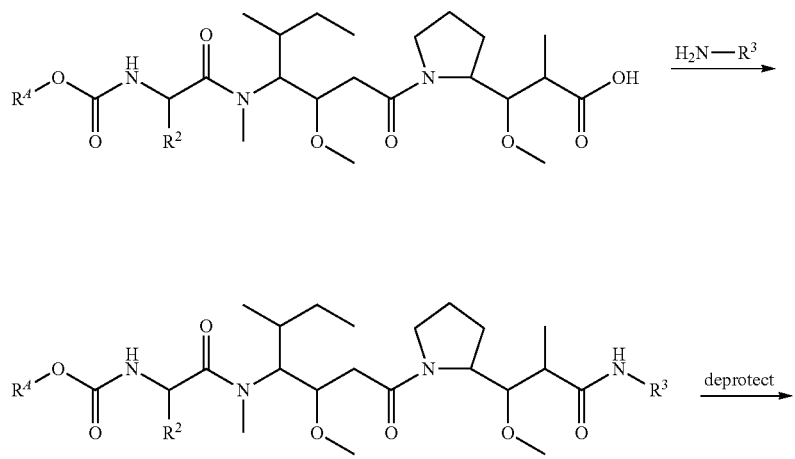

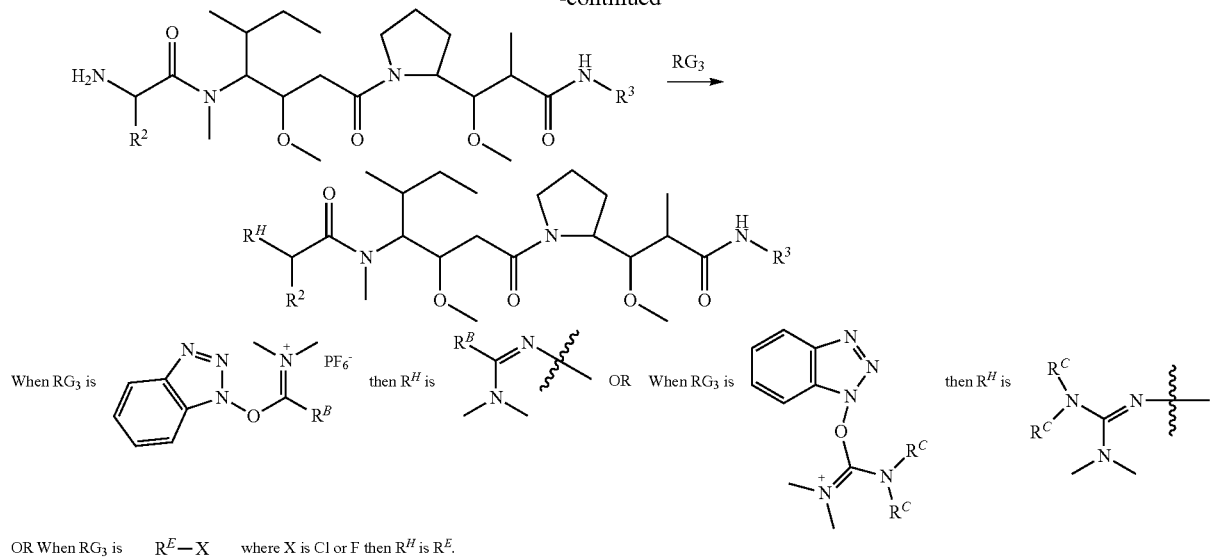
In Scheme 17, by way of example, $R^B$ can be —$R^4$, —$R^{20}$, —$NR^{12}(CH_2)_mN(R^{12})C(O)OR^{12}$, —$NR^{12}(CH_2)_m N(R^{12})_2$, —$R^{22}$ or —$R^{19}$, each of which are as defined herein. In Scheme 17, by way of example, $R^C$ can be H or —$R^6$, and $R^E$ can be —$R^8$.
Another synthetic approach for compounds of Formula (I), and sub formulae thereof is shown below in Scheme 18.
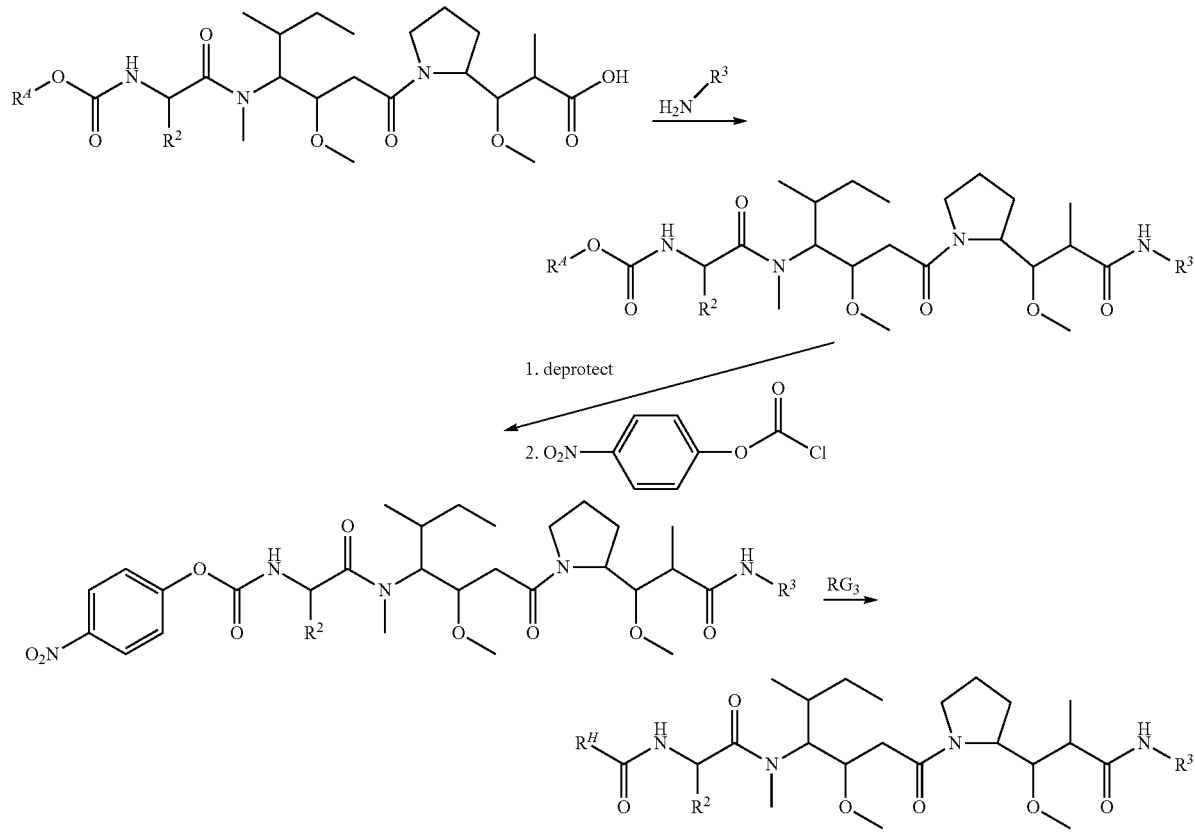

When RG₃ is 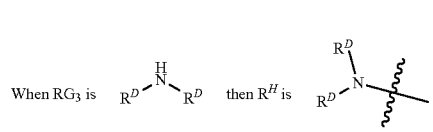 then R^H is 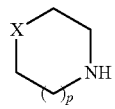 OR When RG₃ is 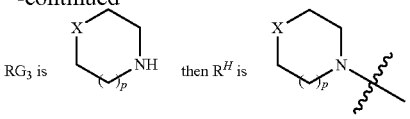 then R^H is In Scheme 18, $R^A$ can be t-butyl, fluorenyl or benzyl, and each $R^D$ can independently be —$R^6$ or —$R^7$. In Scheme 21, by way of example, X is —NC(=O)OR$^{12}$, NH, O or S and p is 1 or 2, and can be unsubstituted or substituted with 1-2 substituents independently selected from $C_1$-$C_6$alkyl, —C(=O)OR$^{12}$, —C(=O)(CH$_2$)$_m$N$_3$, $C_1$-$C_6$haloalkyl, halogen, oxo, —OH and $C_1$-$C_6$alkoxy.

Another synthetic approach for compounds of Formula (I), and sub formulae thereof is shown below in Scheme 19.

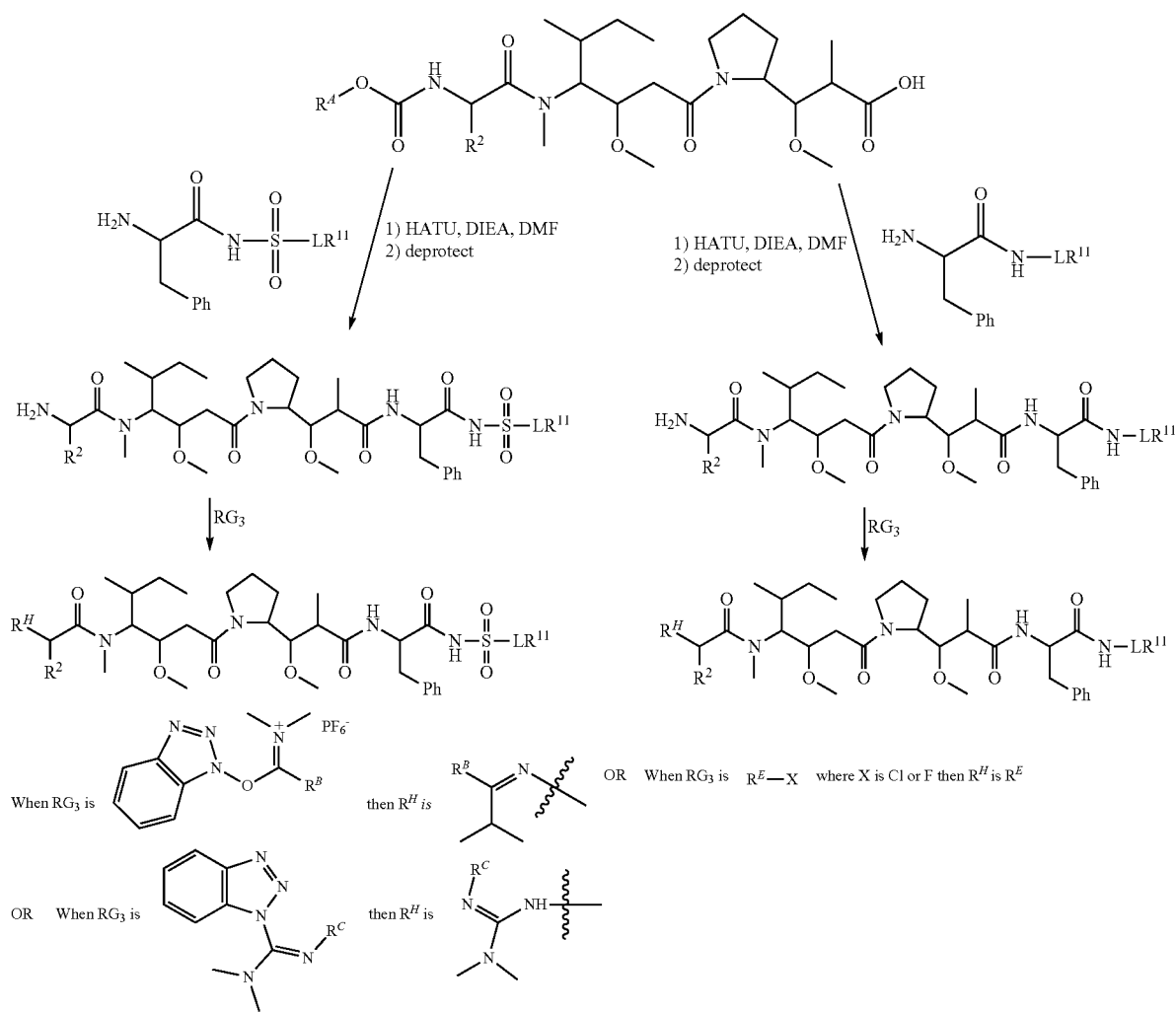

In Scheme 19, by way of example, $R^B$ can be —$R^4$, —$R^{20}$, —$NR^{12}(CH_2)_mN(R^{12})C(O)OR^{12}$, —$NR^{12}(CH_2)_mN(R^{12})_2$, —$R^{22}$ or —$R^{19}$, each of which are as defined herein. In Scheme 19, by way of example, $R^C$ can be H or —$R^6$, and $R^E$ can be —$R^8$.

Another synthetic approach for compounds of Formula (I), and sub formulae thereof is shown below in Scheme 20.

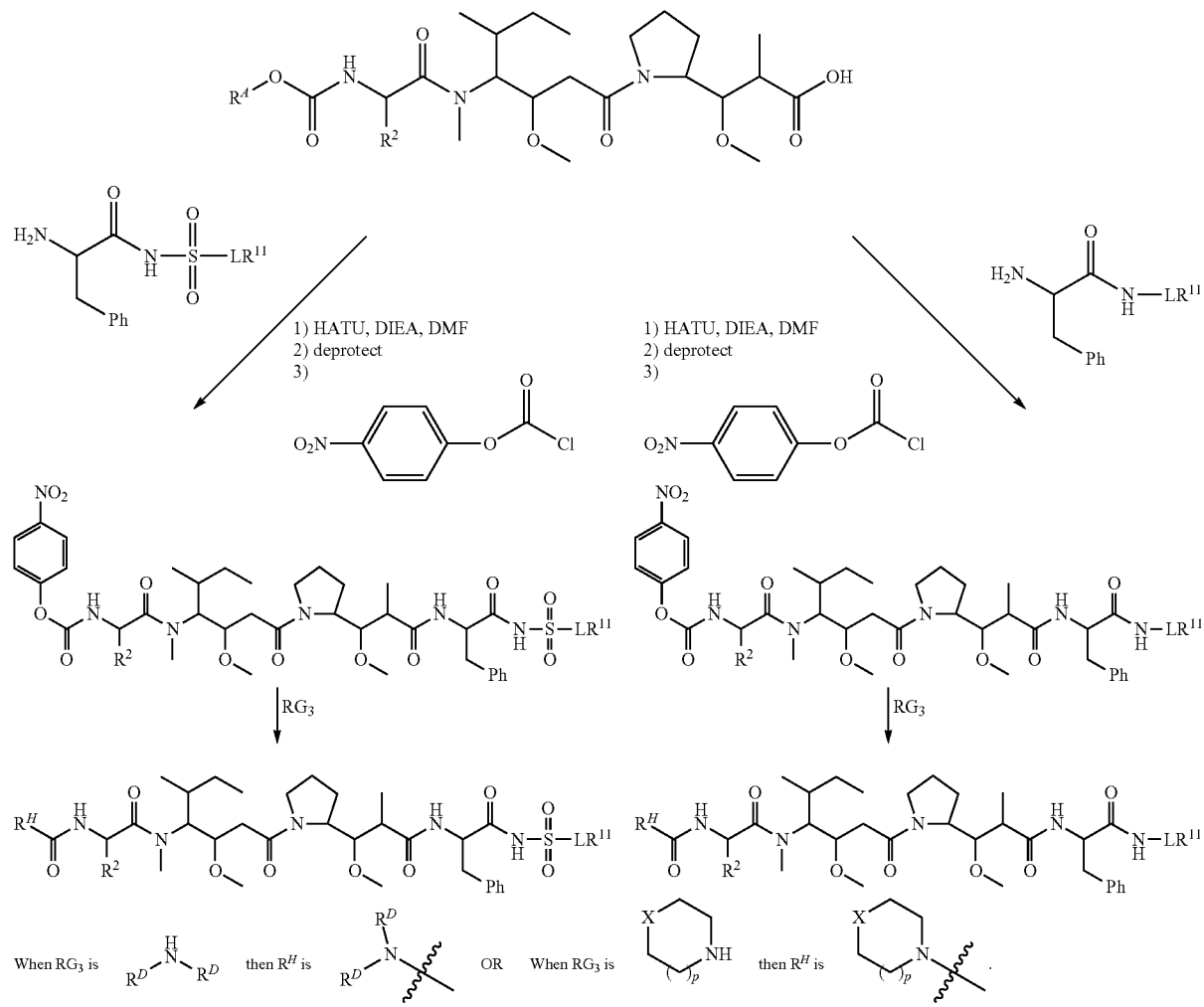

In Scheme 20, by way of example, X is —$NC(=O)OR^{12}$, NH, O or S and p is 1 or 2, and

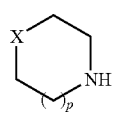

can be unsubstituted or substituted with 1-2 substituents independently selected from $C_1$-$C_6$alkyl, —$C(=O)OR^{12}$, —$C(=O)(CH_2)_mN_3$, $C_1$-$C_6$haloalkyl, halogen, oxo, —OH and $C_1$-$C_6$alkoxy.

Another synthetic approach for compounds of Formula (I), and sub formulae thereof is shown below in Scheme 21.

Scheme 21
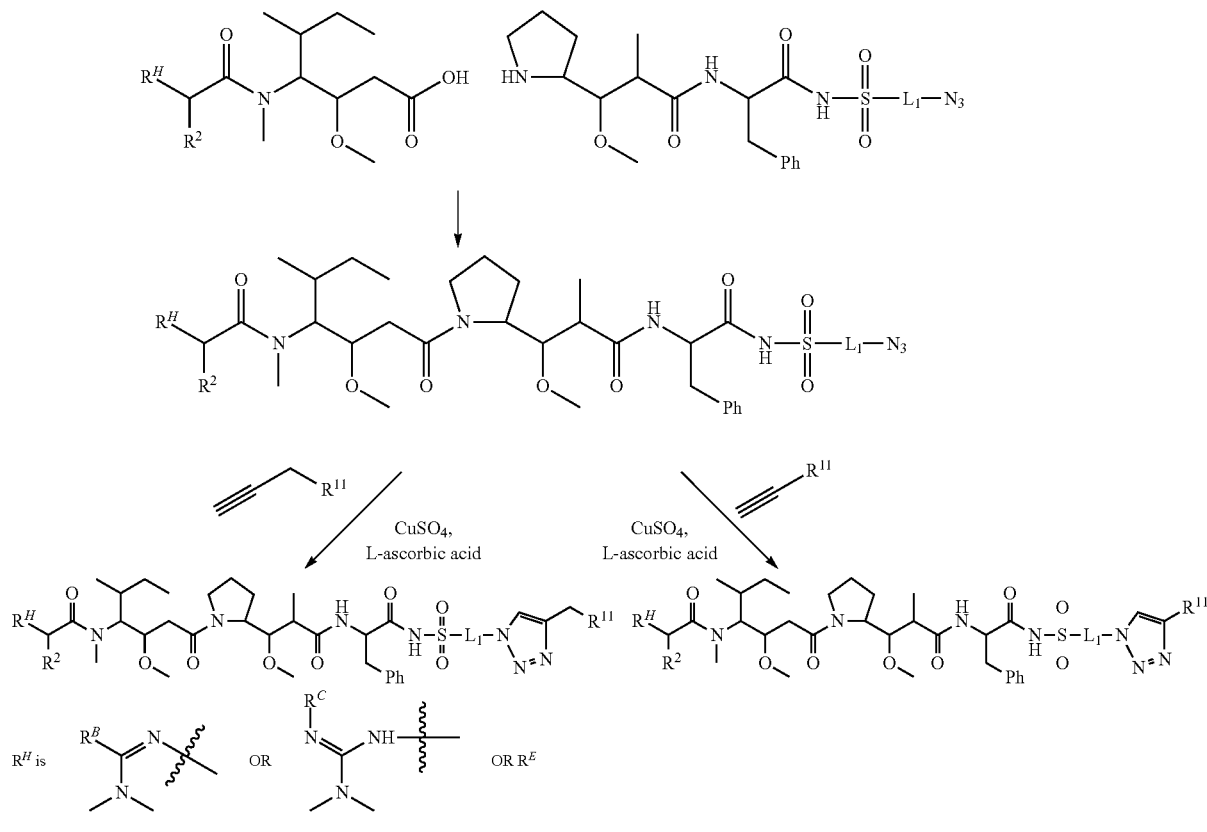
In Scheme 21, by way of example, $R^B$ can be —$R^4$, —$R^{20}$, —$NR^{12}(CH_2)_mN(R^{12})C(O)OR^{12}$, —$NR^{12}(CH_2)_mN(R^{12})_2$, —$R^{22}$ or —$R^{19}$, each of which are as defined herein. In Scheme 21, by way of example, $R^C$ can be H or —$R^6$, and $R^E$ can be —$R^8$.
Another synthetic approach for compounds of Formula (I), and sub formulae thereof is shown below in Scheme 22.
Scheme 22
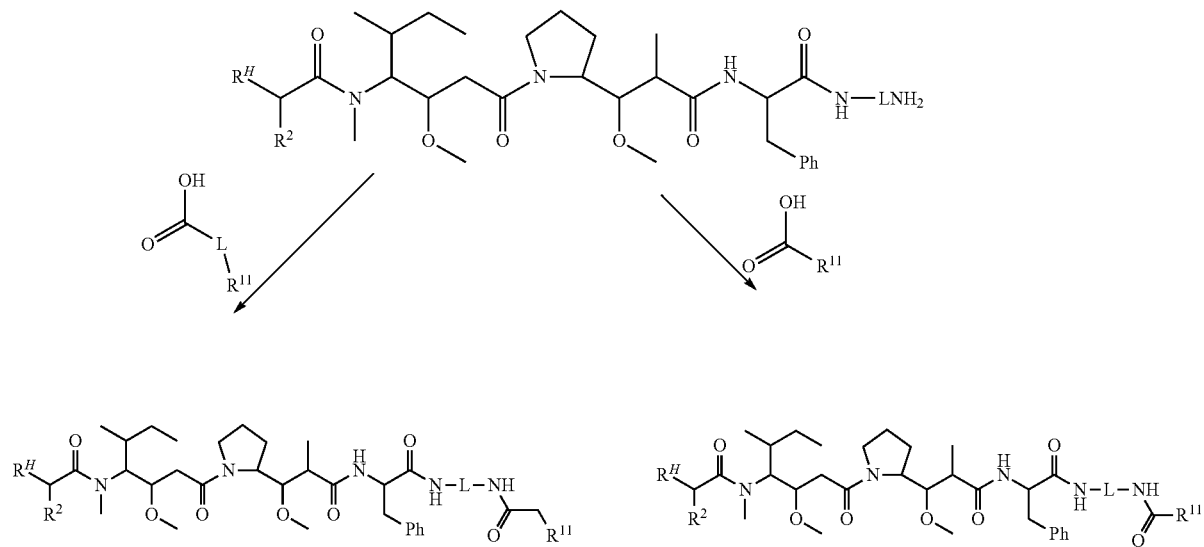

-continued

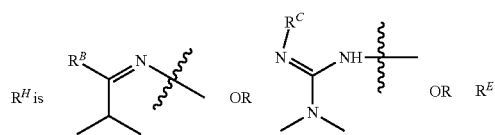

$R^H$ is

In Scheme 22, by way of example, $R^B$ can be —$R^4$, —$R^{20}$, —$NR^{12}(CH_2)_mN(R^{12})C(O)OR^{12}$, —$NR^{12}(CH_2)_mN(R^{12})_2$, —$R^{22}$ or —$R^{19}$, each of which are as defined herein. In Scheme 22, by way of example, $R^C$ can be H or —$R^6$, and $R^E$ can be —$R^8$.

Another synthetic approach for compounds of Formula (I), and sub formulae thereof is shown below in Scheme 23.

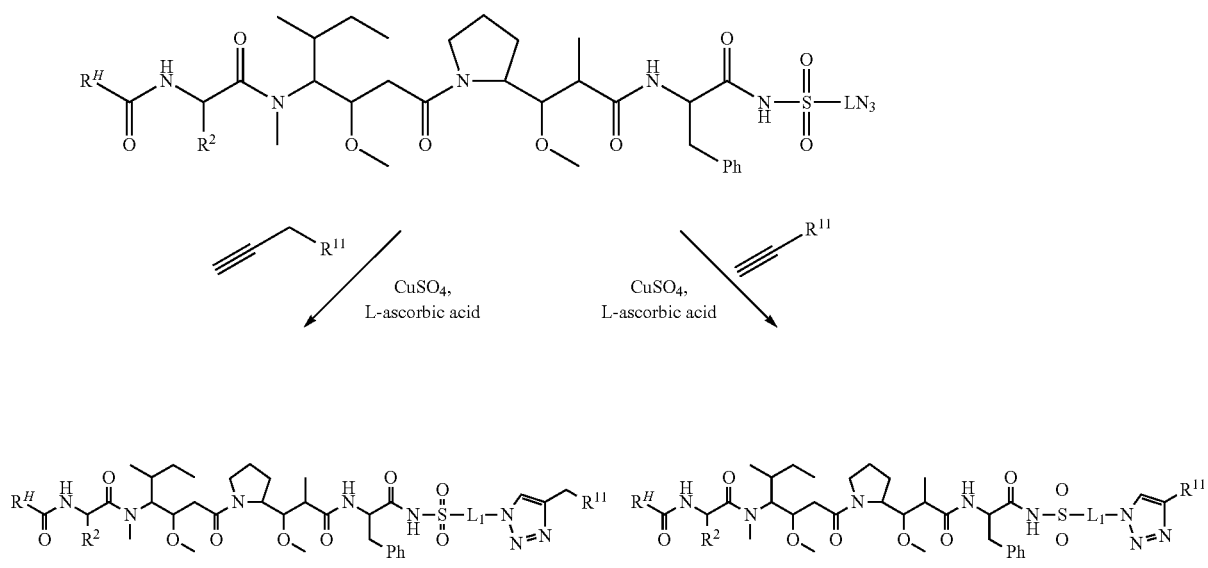

Scheme 23

In Scheme 23, by way of example, X is —$NC(=O)OR^{12}$, NH, O or S and p is 1 or 2, and

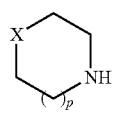

can be unsubstituted or substituted with 1-2 substituents independently selected from $C_1$-$C_6$alkyl, —$C(=O)OR^{12}$, —$C(=O)(CH_2)_mN_3$, $C_1$-$C_6$haloalkyl, halogen, oxo, —OH and $C_1$-$C_6$alkoxy.

Anther synthetic approach for compounds of Formula (I), and sub formulae thereof is shown below in Scheme 24.

Scheme 24

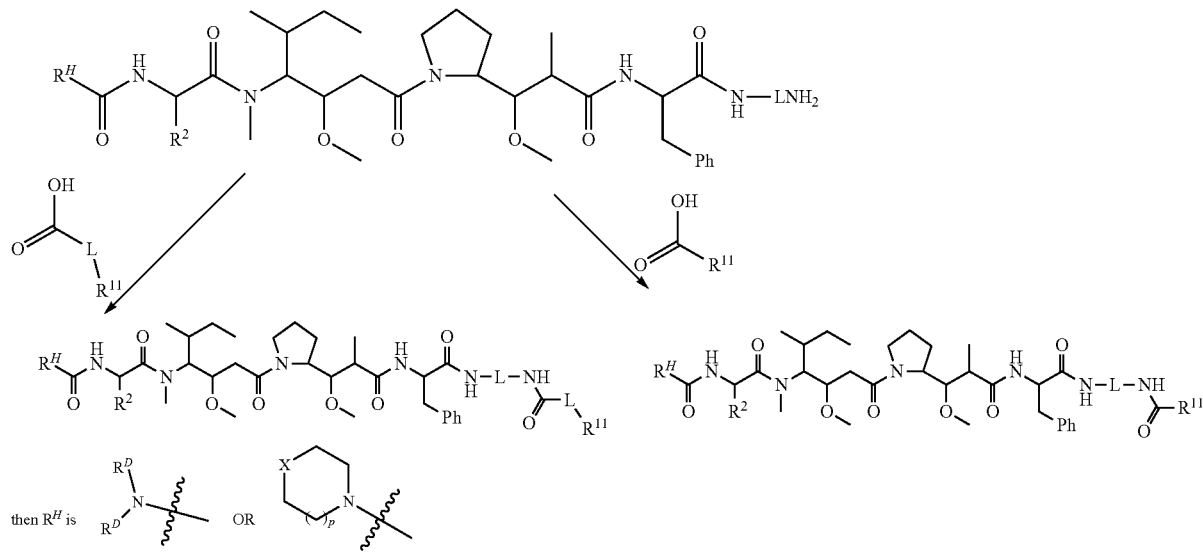

Scheme 24, by way of example, X is —NC(=O)OR$^{12}$, NH, O or S and p is 1 or 2, and

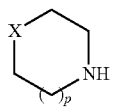

can be unsubstituted or substituted with 1-2 substituents independently selected from $C_1$-$C_6$alkyl, —C(=O)OR$^{12}$, —C(=O)(CH$_2$)$_m$N$_3$, $C_1$-$C_6$haloalkyl, halogen, oxo, —OH and $C_1$-$C_6$alkoxy.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The following examples are intended to illustrate the invention and are not to be construed as being limitations thereon. Temperatures are given in degrees Celsius. Room temperature (rt) is 20 to 21° C. If not mentioned otherwise, all evaporations are performed under reduced pressure, typically between about 15 mm Hg and 100 mm Hg (=20-133 mbar). Abbreviations used are those conventional in the art. All reactions were carried out under nitrogen using commercial grade anhydrous solvents without any further distillation. Reagents were used as commercial grade without further purification. Thin layer chromatography was carried out using TLC silica gel plates. Column chromatography was carried out using an ISCO Combiflash Rf system, using flash grade prepacked Redisep® columns.

Preparative HPLC was performed on Waters Autopurification system using the following conditions: Column Sunfire C18 30×100 mm, 5µ, gradient elution with CH$_3$CN in water+0.05% TFA-CH$_3$CN at 30 ml/min.

After chromatography purification fractions containing desired product of appropreate purity were combined and concentrated to obtain desired products.

Analytical Methods

Unless otherwise indicated, the following HPLC and HPLC/MS methods were used in the preparation of Intermediates and Examples.

LC/MS analysis was performed on an Agilent 1200 sl/6140 system.

Column: Waters Acquity HSS T3 C18, 50×2.0, 1.8 um

Mobile Phase: A) H$_2$O+0.05% TFA; B: acetonitrile+ 0.035% TFA

Pump Method:

| Time | A % | B % | Flow (mL/min) |
|------|-----|-----|---------------|
| 0    | 90  | 10  | 0.9 |
| 1.35 | 0   | 100 | 0.9 |
| 1.36 | 0   | 100 | 0.9 |
| 1.95 | 0   | 100 | 0.9 |
| 1.96 | 90  | 10  | 0.9 |
| 2.0  | 90  | 10  | 0.9 |

Detection: UV Diode Array at 190 nm 400 nm

MS Scan: 200-1350 amu

ELSD: 60° C.

MS Parameters:

| Polarity | Positive |
|----------|----------|
| Drying Gas | 12 |
| Nebulizer Pressure | 50 |
| Drying Gas Temperature | 350 |
| Capillary Voltage | 3000 |

Synthetic Procedure for Intermediates

Synthesis of Lithium (E)-6-(((1-ethoxyethylidene)amino)oxy)hexanoate (I-1)

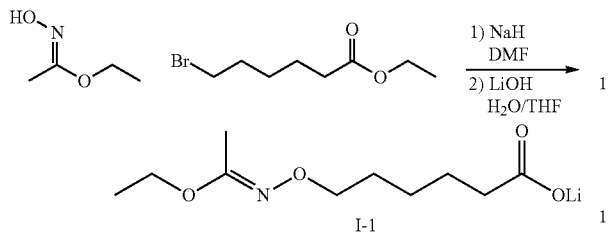

In a 500 mL flask were combined ethyl N-hydroxyacetimidate (6.18 g, 59.9 mmol), ethyl 6-bromohexanoate (8.9 mL, 50 mmol) and N,N-dimethylformamide (DMF, 100 mL). NaH (60% in mineral oil, 2.20 g, 55 mmol) was added to the flask in several portions with stirring at 20° C. and the reaction was stirred at 20° C. for 18 h. The reaction mixture was poured into 200 mL of saturated aq NH4Cl with 150 mL ice, and stirred until ice melted. The mixture was extracted with EtOAc (125 mL×3). The combined organic layers was successively washed with 100 mL each of 10% aq citric acid, water, saturated aq NaHCO3, and saturated aq NaCl, dryed over MgSO4, filtered and concentrated, affording 12.6 g of reddish oil as crude product. The crude oil was distilled using a Buchi glass oven at less than 1 mbar. Ethyl 6-(((1-ethoxyethylidene)amino)oxy)hexanoate was obtained as a colorless oil. MS (ESI+) calc 246.2, found 246.1 (M+1). $^1$H NMR (400 MHz, CDCl$_3$): δ 4.121 (q, 2H, J=4.7 Hz), 4.004 (q, 2H, J=4.7 Hz), 3.881 (t, 2H, J=4.4 Hz), 2.303 (t, 2H, J=5.0 Hz), 1.920 (s, 3H), 1.686-1.616 (m, 4H), 1.418-1.366 (m, 2H), 1.266 (t, 3H, J=4.8 Hz), 1.249 (t, 3H, J=4.8 Hz). Ethyl 6-(((1-ethoxyethylidene)amino)oxy)hexanoate (2.457 g, 10.0 mmol) was charged in a 100 mL round bottom flask, and dissolved in THF (30 mL). Aqeous LiOH (1.0 M, 10.0 mL) was added to the reaction, and the reaciton was stirred at 20° C. for 16 h. An additonal 2.5 mL of 1M aq LiOH was added to the reaction and the reaction was stirred at 50° C. for 13 h. LCMS anlysis indicated completion of the reaction. THF was removed by evaporation, and the remaining mixture was lyophilized, affording Lithium (E)-6-(((1-ethoxyethylidene)amino)oxy)hexanoate (I-1) as a white solid. MS (ESI+) calc 218.1, found 218.1 (M+1, H form). $^1$H NMR (400 MHz, MeOH-d4): δ 3.980 (q, 2H, J=7.2 Hz), 3.861 (t, 2H, J=6.6 Hz), 2.161 (t, 2H, J=7.6 Hz), 1.883 (s, 3H), 1.665-1.588 (m, 4H), 1.431-1.370 (m, 2H), 1.250 (t, 3H, J=7.0 Hz). $^{13}$C NMR (100 MHz, MeOH-d4): δ 182.976, 163.331, 74.495, 63.180, 39.324, 29.972, 27.737, 27.394, 14.779, 13.646.

Synthesis of 1-(2-(2-Aminoethoxy)ethyl)-1H-pyrrole-2,5-dione (I-2)

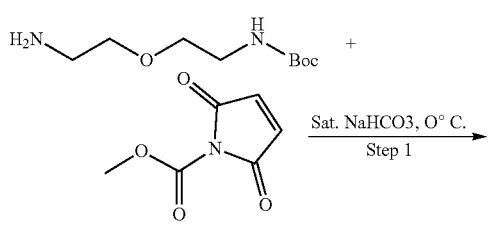

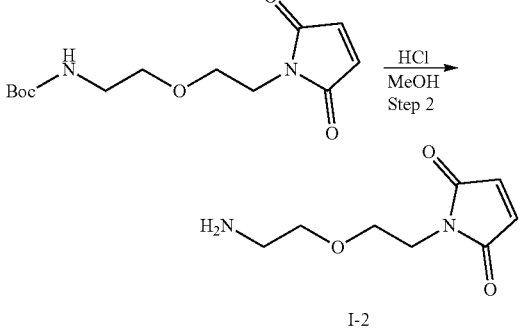

Step 1: t-Butyl (2-(2-aminoethoxy)ethyl)carbamate (204 mg, 1 mmol) was dissolved in saturated aq. NaHCO$_3$ (10 mL). The solution was cooled to 0° C. Methyl-2,5-dioxo-2,5-dihydro-1H-pyrrole-1-carboxylate (155 mg, 1.0 mmol) was then added. The reaction was stirred for 1.5 h at 0° C. The pH was adjusted to 1-2 with 2M HCl, and the mixture was extracted with EtOAc (3×20 mL). The combined organic phases was washed with brine, dried over MgSO$_4$, filtered, and concentrated. The residue was purified by ISCO using a 0-4% gradient of MeOH in DCM to obtain tert-butyl (2-(2-(2,5-dioxo-2,5-dihydro-1 H-pyrrol-1-yl)ethoxy)ethyl)carbamate. $^1$H NMR (400 MHz, CD$_3$OD): δ 6.82 (s, 2H), 3.68 (t, J=5.4 Hz, 2H), 3.59 (t, J=5.4 Hz, 2H), 3.46 (t, J=5.6 Hz, 2H), 3.18-3.14 (m, 2H), 1.43 (s, 9H). MS m/z 185.1(M+1-Boc). Retention time 0.918 min.

Step 2: t-Butyl (2-(2-(2,5-dioxo-2,5-dihydro-1H-pyrrol-1-yl)ethoxy)ethyl)carbamate (162 mg, 0.57 mmol) was dissolved in methanolic HCl (3 M, 2 mL). Solvent was slowly removed by evaporation. The residual solvent was further removed under high vacuum to afford 1-(2-(2-aminoethoxy)ethyl)-1H-pyrrole-2,5-dione (I-2). MS m/z185.1(M+1). Retention time 0.307 min.

Synthesis of Cbz-Val-Dil-OtBu: ((3R,4S,5S)-tert-butyl 4-((S)-2-(((benzyloxy)carbonyl)amino)-N,3-dimethylbutanamido)-3-methoxy-5-methylheptanoate) (I-3)

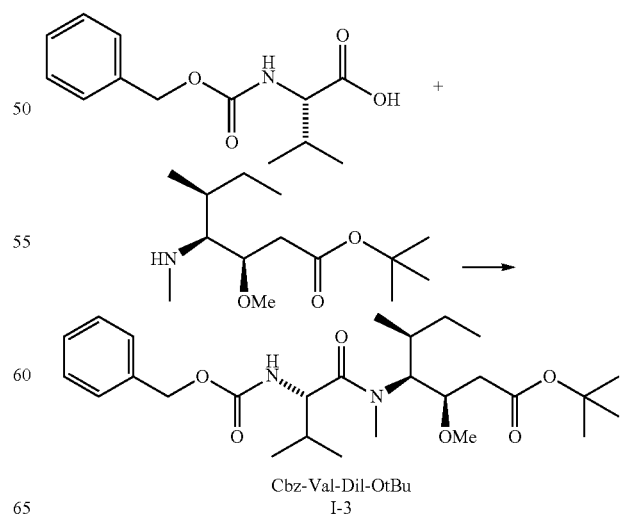

Cbz-Val-Dil-OtBu
I-3

Cbz-Val—OH (Bachem, 3.682 g, 14.7 mmol) and H-Dil-OtBu ((3R,4S,5S)-tert-butyl 3-methoxy-5-methyl-4-(methylamino)heptanoate)(Small Molecules Inc., 3.006 g, 9.75 mmol) were placed in a 200 mL flask, and dissolved in DMF (60 mL). DIEA (8.0 mL, 46 mmol) was added. A solution of 1-[bis(dimethylamino)methylene]-1H-1,2,3-triazolo[4,5-b]pyridinium 3-oxid hexafluorophosphate (HATU, 5.56 g, 14.6 mmol) in DMF (30 mL) was added dropwise to the flask over 3 min with stirring at 20° C. The reaction was stirred at 20° C. for 2 days. The reaction mixture was diluted with EtOAc (200 mL) and washed successively with 100 mL each of 5% aq citric acid, water and saturated aq NaCl. The combined aq phases was extracted with 100 mL EtOAC and combined with the first organic phase. The combined organic phases was dryed and concentrated. The resudue was purified by ISCO using a 220 g silica gel column with a gradient of 10-20% EtOAc in hexanes, affording Cbz-Val-Dil-OtBu (I-3) as a viscous oil. MS (ESI+) m/z 493.4 (M+1). Retention time 1.494 min.

Synthesis of Val-Dil-OtBu: ((3R,4S,5S)-tert-butyl 4-((S)-2-amino-N,3-dimethylbutanamido)-3-methoxy-5-methylheptanoate) (I-4)

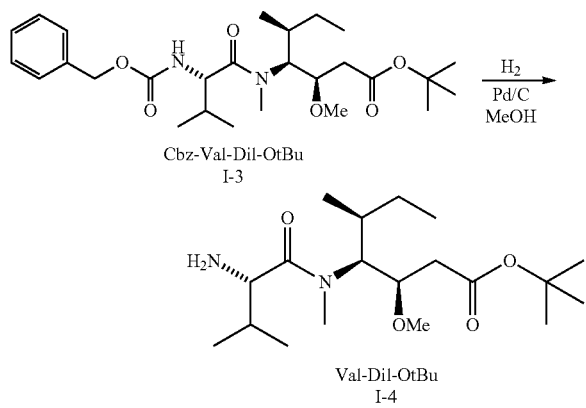

Cbz-Val-Dil-OtBu (I-3) (1.076 g, 2.16 mmol), Pd on activated carbon (5% Pd, 98 mg) and MeOH (50 mL) were combined in a 200 mL flask equipped with a magnetic stirrer bar. The reaction atmosphere was replaced with H₂, and the reaction was vigorously stirred at 20° C. for 1 h. The reaction mixture was filtered through a Celite pad to remove the spent catalyst. The filtrate was concentrated, affording H-Val-Dil-OtBu (I-4) as a slightly yellow viscous oil. MS (ESI+) m/z 359.3 (M+1). Retention time 0.979 min.

Synthesis of (3R,4S,5S)-tert-butyl 4-((S)-2-((bis(dimethylamino)methylene)amino)-N,3-dimethylbutanamido)-3-methoxy-5-methylheqtanoate (I-5)

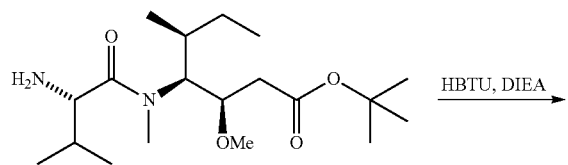

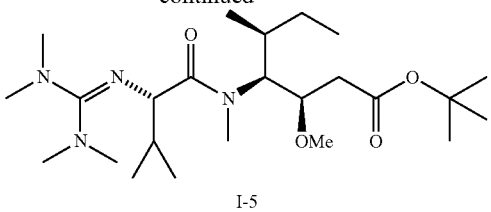

(3R,4S,5S)-tert-butyl 4-((S)-2-amino-N,3-dimethylbutanamido)-3-methoxy-5-methylheptanoate (360 mg, 0.994 mmol) was dissolved in DMSO (5.0 mL) and HBTU (526 mg, 1.383 mmol) was added. The reaction was stirred at 20° C. for 17 h. DIEA (0.174 mL) was added to the reaction and the raction was stirred at 20° C. for 1 h. The reaction was stirred at 20° C. for 17 h. DI EA (0.174 mL) was added to the reaction and the raction was stirred at 20° C. for 1 h. The reaction mixture was purified by ISCO using a 50 g C18 column with a gradient of acetonitrile in water, affording (3R,4S,5S)-tert-butyl 4-((S)-2-((bis(dimethylamino)methylene)amino)-N,3-dimethylbutanamido)-3-methoxy-5-methylheptanoate (I-5) as a white solid. MS (ESI+) calc 457.4, found 457.4 (M+1). Retention time 1.089 min.

Synthesis of (3R,4S,5S)-4-((S)-2-((Bis(dimethylamino)methylene)amino)-N,3-dimethylbutanamido)-3-methoxy-5-methylheptanoic acid (I-6)

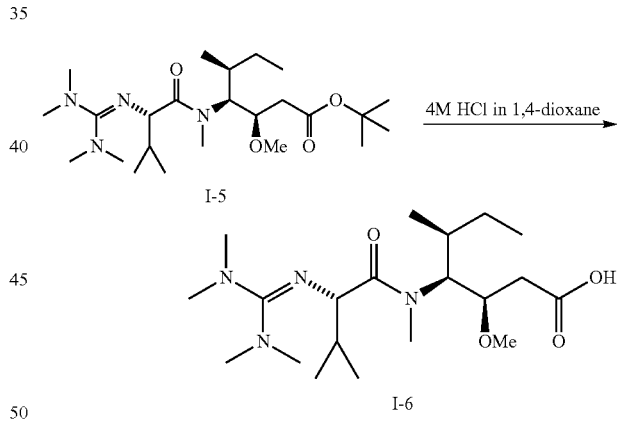

(3R,4S,5S)-tert-butyl 4-((S)-2-((bis(dimethylamino)methylene)amino)-N,3-dimethylbutanamido)-3-methoxy-5-methylheptanoate TFA salt (I-5) (292 mg, 0.511 mmol) was dissolved in 4M HCl in 1,4-dioxane (10 mL), and the resulting solution was let stand at rt for 20 h. The solution was concentrated. The residue was taken up in acetonitrile and water, and lyophilized, affording very viscous yellow oil. The F-NMR suggested this material contained TFA. To remove TFA the oil was dissolved in acetonitle (10 mL) and treated with 6N hydrochloric acid (10 mL). The solvents were removed under reduced pressure, affording (3R,4S,5S)-4-((S)-2-((Bis(dimethylamino)methylene)amino)-N,3-dimethylbutanamido)-3-methoxy-5-methylheptanoic acid (I-6). MS m/z calc 401.3, found 401.3. Retention time 0.760 min.

Synthesis of Cbz-Val-Dil-OH: ((3R,4S,5S)-4-((S)-2((benzyloxy)carbonyl)amino)-N,3-dimethylbutanamido)-3-methoxy-5-methylheptanoic acid) (I-7)

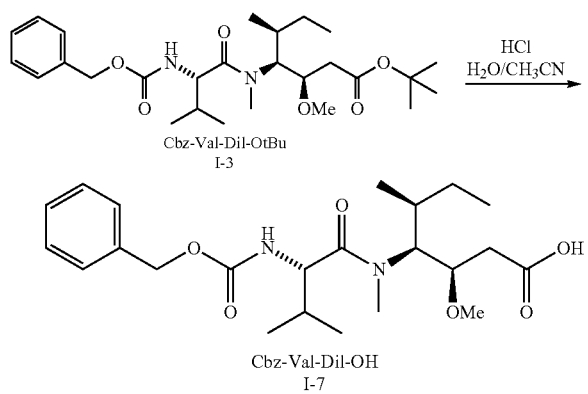

Cbz-Val-Dil-Dil-OtBu (I-3) (0.371 g, 0.745 mmol) was dissoved in acetonitrile (3.0 mL) and 1 N hydrochloric acid (2.0 mL) was added. The reaction was stirred at 40° C. for 1 hour and at rt for 17 h. Most acetonitrile was removed by evaporation under reduced pressure to remove excess HCl. White precipitates formed. The mixture was diluted with 15 mL acetonitrile and 10 mL water. The resulting solution was frozen and lyophilized, affording Cbz-Val-Dil-OH (I-7) as a white solid. MS (ESI+) m/z 437.2 (M+1). Retention time 1.145 min.

Synthesis of Boc-Dap-OMe: ((S)-tert-butyl 2-((1R,2R)-1,3-dimethoxy-2-methyl-3-oxopropyl)pyrrolidine-1-carboxylate) (I-8)

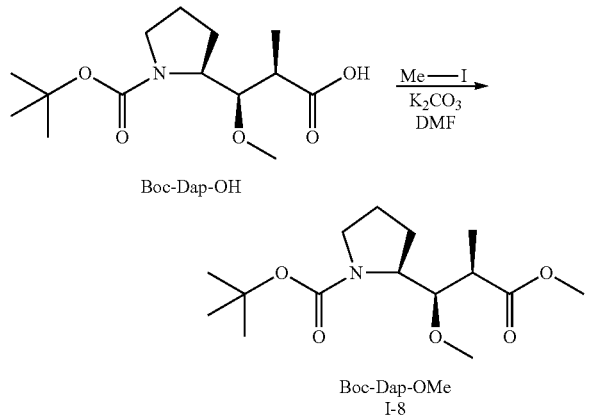

Boc-Dap-OH (Small Molecules Inc., 3.11 g, 10.8 mmol), K2CO3 (2.99 g, 21.6 mmol), iodomethane (2.95 g) and acetone (55 mL) were combined. The reaction was stirred at 20° C. for 2 h. An additonal methyliodide (2.28 g) was added to the reaction and the reaction was stirred at 40° C. for 3 h. The reaction mixture was concentrated. The residue was partitioned between 200 mL EtOAc and 100 mL H2O. The organic layer was separated, washed with 50 mL saturated aq NaCl, dried over MgSO4, filtered and concentrated, affording Boc-Dap-OMe (I-8) as a yellow oil. MS (ESI+) m/z calc 324.2, found 324.2 (M+23). Retention time 1.245 min.

Synthesis of Dap-OMe: ((2R,3R)-methyl 3-methoxy-2-methyl-3-((S)-pyrrolidin-2-yl)propanoate) (I-9)

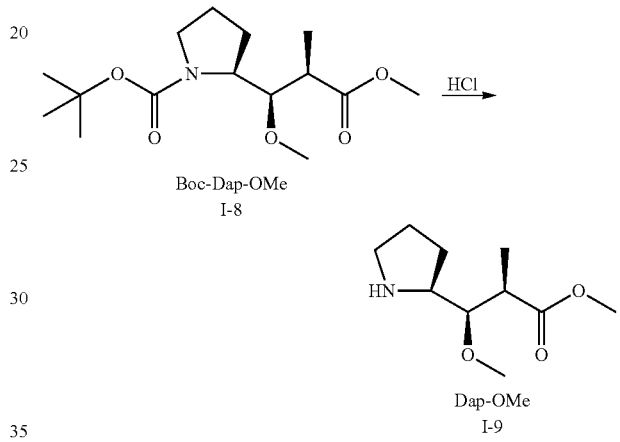

Boc-Dap-OMe (3.107 g, 10.3 mmol) was combined with HCl in diethyl ether (2 M, 10 mL) and concentrated. This operation was repeated. The reaction was complete after the 7$^{th}$ treatment. HCl salt of Dap-OMe (I-9) was obtained as a white solid after being concentrated. MS (ESI+) m/z calc 202.1, found 202.2 (M+1). Retention time 0.486 min. $^1$H NMR (400 MHz, CDCl$_3$): δ 4.065-4.041 (m, 1H), 3.732 (br.s, 1H), 3.706 (s, 3H), 3.615 (s, 3H), 3.368 (br.s, 1H), 3.314 (br.s, 1H), 2.795 (q, 1H, J=6.8 Hz), 2.085-1.900 (m, 4H), 1.287 (d, 3H, J=7.2 Hz).

Synthesis of (2R,3R)-Methyl 3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanoate (I-10)

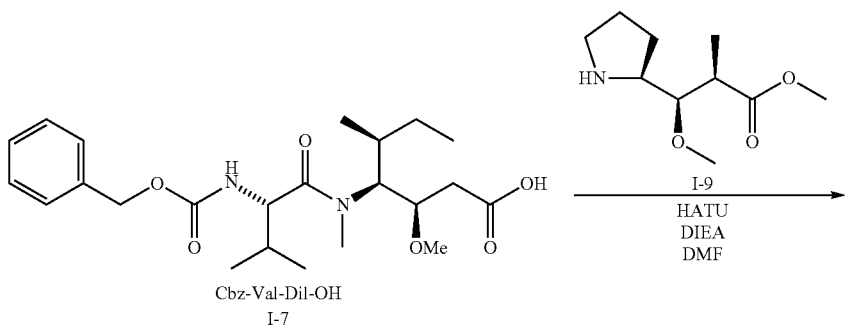

-continued

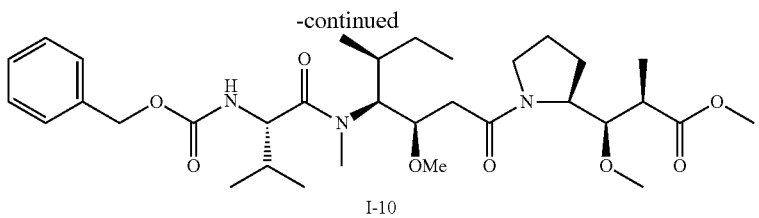

I-10

Cbz-Val-Dil-OH (I-7) (208 mg, 0.875 mmol), HATU (281 mg, 0.739 mmol) and DMF (7.5 mL) were combined in a 40 mL glass vial. DIEA (0.256 mL) was added and the reaction was shaken at 21° C. for 50 min. (2R,3R)-Methyl 3-methoxy-2-methyl-3-((S)-pyrrolidin-2-yl)propanoate (I-9) (208 mg, 0.875 mmol) was added to the reaction, followed by additional DIEA (0.256 mL). The reaction was shaken at 21° C. for 3 h. The reaction mixture was diluted with EtOAc (60 mL), and washed successively with 5% aq citric acid, H$_2$O, and saturated aq NaCl, dryed over MgSO$_4$, filtered and concentrated. The residue was purified by ISCO using a 150 g C18 column with a 20-80% gradient of acetonitrile in H$_2$O, affording (2R,3R)-methyl 3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanoate (1-10) as a yellow glassy material. MS (ESI+) m/z Calc 620.4, found 620.5 (M+1). Retention time 1.391 min.

Synthesis of (2R,3R)-3-((S)-1-((3R,4S,5S)-4-((S)-2-((Bis(dimethylamino)methylene)amino)-N,3-dimethylbutanamido)-3-methoxy-5-methylheptanoyl)pyrrolidin-2-4-3-methoxy-2-methylpropanoic acid (i-11)

(i-11)

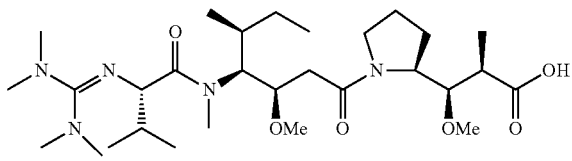

Step 1: To (2R,3R)-methyl 3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanoate (i-10) (200 mg, 0.32 mmol) in MeOH (5 ml) was added Pd/C (10% wet, 68.7 mg), and the reaction mixture was stirred for 2 h at rt under H$_2$ atmosphere, and then filtered and concentrated to obtain (2R,3R)-methyl 3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanoate,

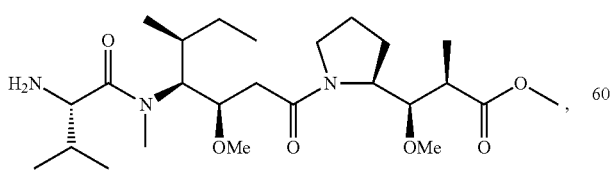

MS m/z 486.4 (M+1). Retention time 0.883 min.
Step 2: DIEA (0.27 m, 1.54 mmol) and HATU (141 mg, 0.37 mmol) were added to (2R,3R)-methyl 3-((S)-1-((3R,4S, 5S)-4-((S)-2-amino-N,3-dimethylbutanamido)-3-methoxy-5-methylheptanoyl)pyrrolidin-2-yl)-3-methoxy-2-methylpropanoate (150 mg, 0.31 mmol) in DMF (4 ml). The reaction mixture was stirred for 2 h at rt and then purified by preparative HPLC (20-70% acetonitrile-H$_2$O containing 0.05% TFA) to obtain (2R,3R)-methyl 3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoate,

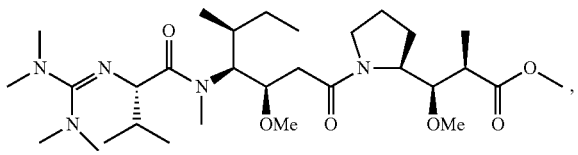

as a TFA salt. MS m/z 584.4 (M+1). Retention time 1.027 min.

Step 3: (2R,3R)-Methyl 3-((S)-1-((3R,4S,5S)-4-((S)-2-((bis (dimethylamino)methylene)amino)-N,3-dimethylbutanamido)-3-methoxy-5-methylheptanoyl)pyrrolidin-2-yl)-3-methoxy-2-methylpropanoate (133 mg, 228 □mol) in ACN (2.5 ml) and water (1.6 ml) was treated first with 1N aqueous NaOH (0.68 ml) at rt for 2 h followed by additional 1.02 mL of 1N aqueous NaOH for 3 h at the same temperature. The pH of the reaction was adjusted to 5~6 using 1N hydrochloric acid and lyophilized. The residue was purified using reverse phase ISCO (20-70% ACN in H2O) to obtain (2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoic acid (i-11). MS m/z 570.4 (M+1). Retention time 1.028 min.

Synthesis of (R)-2,4-dihydroxy-3,3-dimethyl-N-(3-oxo-3-((2-oxopropyl)amino) propyl)butanamide (i-12)

(i-12)

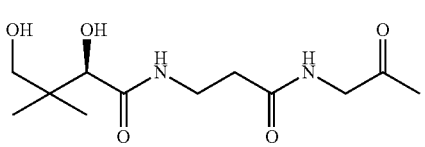

Step 1: Panthotheic acid (50 mg, 0.23 mmol) was dissolved in DMF (5 mL) and diphenylphosphoryl azide (98 µL, 0.46 mmol) and 2-(2-methyl-1,3-dioxolan-2-yl)ethanamine (40 mg, 0.34 mmol) were added. The reaction mixture was cooled to 0° C. and triethylamine (79 μL, 0.57 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over $Na_2SO_4$ and filtered. The filtrate was concentrated in vacuo and the residue was purified by HPLC and lyopylized to give (R)-2,4-dihydroxy-3,3-dimethyl-N-(3-(((2-methyl-1,3-dioxolan-2-yl)methyl)amino)-3-oxopropyl)butanamide. MS (m+1)=319.2, Retention time: 0.466 min Step 2: (R)-2,4-dihydroxy-3,3-dimethyl-N-(3-(((2-methyl-1,3-dioxolan-2-yl)methyl)amino)-3-oxopropyl)butanamide (46 mg, 0.14 mmol) was dissolved in THF (5 mL) and 3N HCl solution (3 mL) and stirred at rt for 4 h. After cooling to 0° C., the reaction mixture was neutralized with 1N NaOH solution and concentrated half volumn in vacuo. The reaction mixture was purified by ISCO RP-C18 and lyophilized to give (R)-2,4-dihydroxy-3,3-dimethyl-N-(3-oxo-3-((2-oxopropyl)amino)propyl)butanamide (i-12). MS (m+1)=275.2, Retention time: 0.337 min, 1H-NMR (MeOD, 400 MHz) δ 3.99 (s, 2H), 3.84 (s, 1H), 3.42~4.47 (m, 2H), 3.42 (d, 1H, J=11.2 Hz), 3.34 (d, 1H, J=11.2 Hz), 2.45 (t, 2H, J=6.8 Hz), 2.10 (s, 3H), 0.87 (s, 6H).

Synthesis of (R)-N-(3-((2-azidoethyl)amino)-3-oxopropyl)-2,4-dihydroxy-3,3-dimethylbutanamide (i-13)

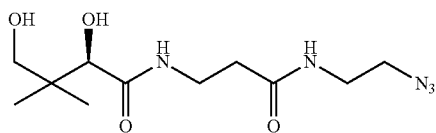

(i-13)

Panthotheic acid (50 mg, 0.23 mmol) was dissolved in DMF (5 mL) and diphenylphosphoryl azide (98 μL, 0.46 mmol) and 2-azidoethanamine (30 mg, 0.34 mmol) were added. The reaction mixture was cooled to 0° C. and triethylamine (79 μL, 0.57 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over $Na_2SO_4$ and filtered. The filtrate was concentrated in vacuo and the residue was purified by HPLC and lyopylized to give (R)-N-(3-((2-azidoethyl)amino)-3-oxopropyl)-2,4-dihydroxy-3,3-dimethylbutanamide (i-13). MS (m+1)=288.2, Retention time: 0.504 min, 1H-NMR (MeOD, 400 MHz) δ 3.84 (s, 1H), 3.41~4.47 (m, 3H), 3.31~3.35 (m, 5H), 2.40 (t, 2H, J=6.8 Hz), 0.87 (s, 6H).

Synthesis of (R)-2,4-dihydroxy-3,3-dimethyl-N-(3-oxo-3-((3-oxobutyl)amino)propyl) butanamide (i-14)

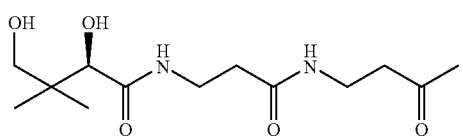

(i-14)

Step 1: Panthotheic acid hemicalcium salt (100 mg, 0.390 mmol) was dissolved in $CH_3CN$ (10 mL) and exchanged to panthotheic acid using sulfuric acid resin. Panthotheic acid (10 mg, 0.046 mmol) was dissolved in DMF (2 mL) and diphenylphosphoryl azide (20 μL, 0.091 mmol) and 2-(2-methyl-1,3-dioxolan-2-yl)ethanamine (7 mg, 0.005 mmol) were added. The reaction mixture was cooled to 0° C. and triethylamine (16 μL, 0.114 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over $Na_2SO_4$ and filtered. The filtrate was concentrated in vacuo and the residue was purified by HPLC and lyopylized to give (R)-2,4-dihydroxy-3,3-dimethyl-N-(3-((2-(2-methyl-1,3-dioxolan-2-yl)ethyl)amino)-3-oxopropyl)butanamide. MS (m+1)=333.2, Retention time: 0.512 min Step 2: (R)-2,4-dihydroxy-3,3-dimethyl-N-(3-((2-(2-methyl-1,3-dioxolan-2-yl)ethyl)amino)-3-oxopropyl)butanamide (6 mg, 0.02 mmol) was dissolved in THF (2 mL) and 3N HCl solution (1 mL) and stirred at rt for 4 h. After cooling to 0° C., the reaction mixture was neutralized with 1N NaOH solution and concentrated to half volumn in vacuo. The reaction mixture was purified by ISCO RP-$C_{18}$ and lyophilized to give (R)-2,4-dihydroxy-3,3-dimethyl-N-(3-oxo-3-((3-0xobutyl)amino)propyl) butanamide (i-14). MS (m+1)=289.2, Retention time: 0.362 min, 1H-NMR (MeOD, 400 MHz) δ 3.83 (s, 1H), 3.37~4.45 (m, 3H), 3.34 (d, 2H, J=7.2 Hz), 3.32 (d, 1H, J=3.2 Hz), 2.65 (t, 2H, J=6.4 Hz), 2.34 (t, 2H, J=6.8 Hz), 2.10 (s, 3H), 0.87 (s, 6H).

Synthesis of 2,4-dihydroxy-3,3-dimethyl-N-(3-oxobutyl)butanamide (i-15)

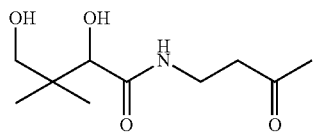

(i-15)

Step 1: Lithium aluminum hydride (583 mg, 15 mmol) was dissolved in THF (100 mL) and cooled to 0° C. A solution of (±)-pantolactone (1 g, 8 mmol) in THF (50 mL) was added at 0° C. and stirred at rt for 4 h. To the reaction mixture was added anhydrous sodium sulfate slowly, followed by EtOAc (50 mL). The reaction mixture was filtered over a short celite pad and the filtrate was concentrated. The residue was purified by ISCO (5% to 20% of MeOH in $CH_2CL_2$) to give 3,3-dimethylbutane-1,2,4-triol. 1H-NMR (CDCl$_3$, 400 MHz) δ 3.71~3.74 (m, 1H), 3.65 (dd, 1H, J=4.8 and 7.6 Hz), 3.57 (dd, 1H, J=2.4 and 4.8 Hz), 3.54 (d, 1H, J=7.2 Hz), 3.48 (d, 1H, J=7.2 Hz), 0.95 (s, 3H), 0.93 (s, 3H).

Step 2: 3,3-dimethylbutane-1,2,4-triol (570 mg, 4 mmol) and 1-(dimethoxymethyl)-4-methoxybenzene (1.16 g, 6 mmol) were dissolved in $CH_2Cl_2$ (50 mL) and (7,7-dimethyl-2-oxobicyclo[2.2.1]heptan -1-yl) methanesulfonic acid (99 mg, 0.4 mmol) was added. The reaction mixture was stirred at rt for 2 h and triethylamine (0.29 mL, 2 mmol) was added. After concentration, the residue was purified by ISCO (0% to 30% of EtOAc in n-Hexane) to give 2-(4-methoxyphenyl)-5,5-dimethyl-1,3-dioxan-4-yl)methanol. 1H-NMR (CDCl$_3$, 400 MHz) δ 7.44 (d, 2H, J=6.0 Hz), 6.91 (d, 2H, J=6.0 Hz), 5.47 (s, 1H), 3.90 (s, 1H), 3.81 (s, 3H), 3.59~3.70 (m, 5H), 1.14 (s, 3H), 0.84 (s, 3H).

Step 3: DMSO (0.27 mL, 4 mmol) was dissolved in anhydrous CH$_2$Cl$_2$ (20 mL) and oxalyl chloride (0.25 mL, 3 mmol) was added at −78° C. The reaction mixture was stirred for 15 min at −78° C. and a solution of 2-(4-methoxyphenyl)-5,5-dimethyl-1,3-dioxan-4-yl)methanol (485 mg, 2 mmol) in anhydrous CH$_2$Cl$_2$ (1 mL) was added slowly. The reaction mixture was stirred at −78° C. for 30 min and triethylamine (1.34 mL, 10 mmol) was added. The reaction mixture was allowed to warm up to rt and stirred for 1 h. The reaction mixture was partitioned between water (50 mL) and CH$_2$Cl$_2$ (100 mL), and the organic layer was washed with sat. NaHCO$_3$ (50 mL) and brine (50 mL), dried over Na$_2$SO$_4$, filtered and concentrated. The residue was purified by ISCO (20% to 50% of EtOAc in n-Hexane) to give 2-(4-methoxyphenyl)-5,5-dimethyl-1,3-dioxane-4-carbaldehyde. MS (m+1)=251.2, Retention time: 1.105 min.

Step 4: 2-(4-methoxyphenyl)-5,5-dimethyl-1,3-dioxane-4-carbaldehyde (289 mg, 1 mmol) was dissolved in acetone/CH$_2$Cl$_2$ (3:1, 20 mL) and freshly prepared solution of NaH$_2$PO$_4$.H$_2$O (1593 mg, 12 mmol) and NaCl$_2$O (528 mg, 6 mmol) in water (5 mL) was added at rt. The reaction mixture was stirred for 30 min at rt and concentrated. The residue was purified by ISCO (C18) to give 2-(4-methoxyphenyl)-5,5-dimethyl-1,3-dioxane-4-carboxylic acid. MS (m+1)=267.2, Retention time: 0.957 min.

Step 5: 2-(4-methoxyphenyl)-5,5-dimethyl-1,3-dioxane-4-carboxylic acid (40 mg, 0.2 mmol) was dissolved in DMF (3 mL) and HATU (39 mg, 0.2 mmol) and DIEA (0.05 mL, 0.3 mmol) were added. The reaction mixture was stirred for 10 min at rt and 2-(2-methyl-1,3-dioxolan-2-yl)ethanamine (40 mg, 0.3 mmol) was added. The reaction mixture was stirred at rt for 1 h and purified by preparative HPLC to give 2-(4-methoxyphenyl)-5,5-dimethyl-N-(2-(2-methyl-1,3-dioxolan-2-ypethyl)-1,3-dioxane-4-carboxamide. MS (m+1)=380.2, Retention time: 1.102 min, 1H-NMR (CDCl$_3$, 400 MHz) δ 7.44 (d, 2H, J=5.6 Hz), 7.33 (bs, 1H), 6.90 (d, 2H, J=5.2 Hz), 5.46 (s, 1H), 4.08 (s, 1H), 3.82~3.88 (m, 2H), 3.81 (s, 3H), 3.75 (m, 1H), 3.68 (dd, 2H, J=7.6 and 16.0 Hz),3.38 (m, 2H), 1.86 (m, 4H), 1.31 (s, 3H), 1.11(s, 3H), 1.09 (s, 3H).

Step 5: 2-(4-methoxyphenyl)-5,5-dimethyl-N-(2-(2-methyl-1,3-dioxolan-2-ypethyl)-1,3-dioxane-4-carboxamide (10 mg, 0.03 mmol) was dissolved in 3M HCl in MeOH (1 mL) and water (0.1 mL) was added. The reaction mixture was concentrated in vacuo and purified by ISCO (C18) to give 2,4-dihydroxy-3,3-dimethyl-N-(3-oxobutyl)butanamide (i-15). MS (m+1)=218.2, Retention time: =0.400 min, 1H-NMR (MeOD-d$_4$, 400 MHz) δ 3.84 (s, 1H), 3.31~3.44 (m, 4H), 2.70 (t, 2H, J=4.0 Hz), 2.12 (s, 3H), 0.88 (s, 3H).

Synthetic Procedure for Non-Linked Peptides

EXAMPLE 1

Synthesis of (S)-Methyl-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoate (FP-1) and (S)-2-((2R,3R)-3-((S)-1-((3R,4S,5S)-4-((S)-2-((Bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoic acid (FP-22)

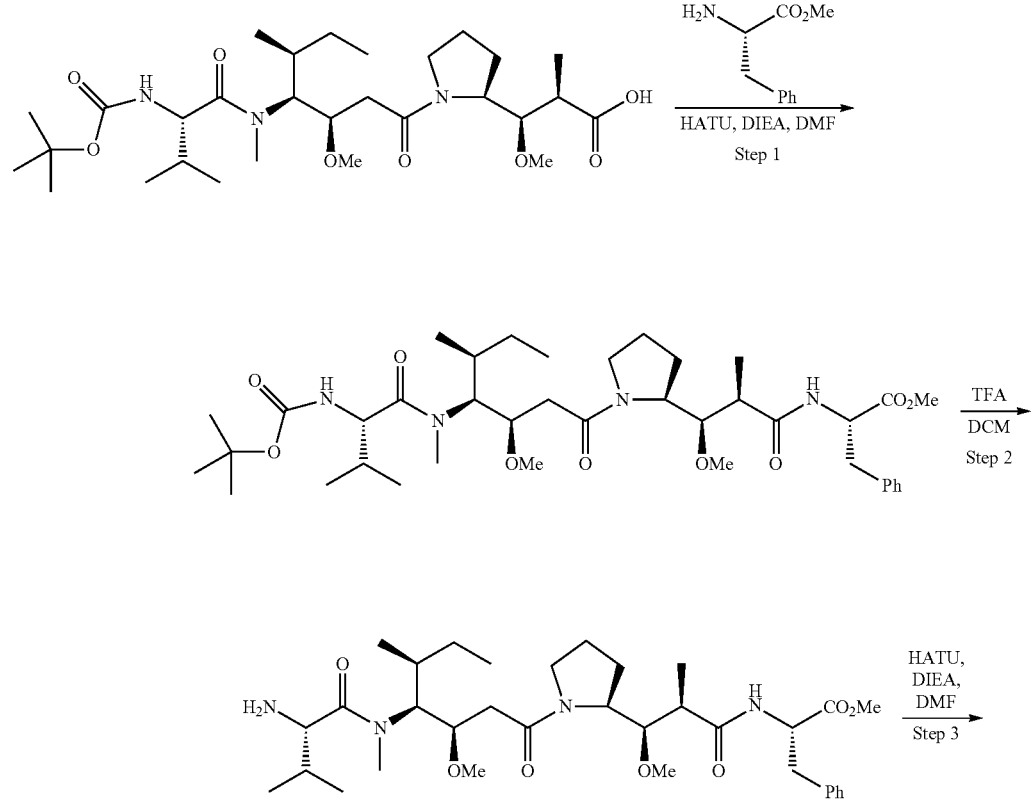

-continued

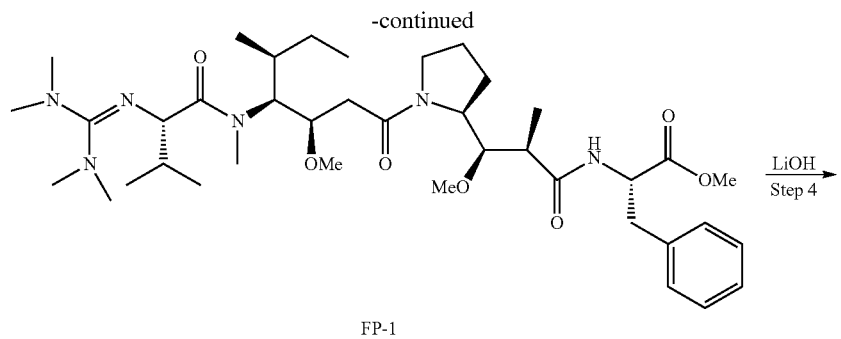

FP-1

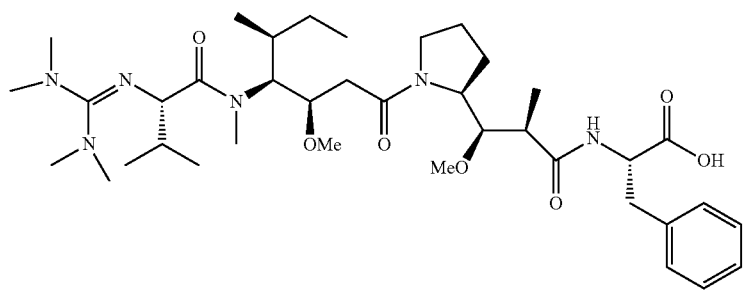

FP-22

Step 1: To a solution of Boc-Val-Dil-Dap-OH (1.00 g, 1.75 mmol) in DMF (20.0 mL) at 0° C. were added DIEA (0.677 g, 5.25 mmol) and HATU (0.731 g, 1.93 mmol). The resulting solution was stirred for 5 min and added to a solution of L-phenylalanine methyl ester HCl salt (0.377 g, 1.75 mmol) and DIEA (0.226 g, 1.75 mmol) in DMF (5.0 mL) at 0° C. The reaction was warmed to rt and stirred for an additional 30 min, and the reaction mixture was concentrated. The residue was purified by ISCO using a C18 column with a 20-90% gradient of acetonitrile in water to obtain BocVal-Dil-Dap-PheOMe, MS m/z 733.4 (M+1). Retention time 1.47 min.

Step 2: HCl (4N in 1,4-dioxane, 16 mL) was added to a solution of BocVal-Dil-Dap-PheOMe (0.683 g, 0.932 mmol) obtained in Step 1 in methanol (20 mL). The reaction mixture was stirred at rt for 7 h and concentrated. The residue was dissolved in dioxane and lyophilized to obtain Val-Dil-Dap-PheOMe HCl salt, MS m/z 633.4 (M+1). Retention time 0.96 min.

Step 3: To a solution of Val-Dil-Dap-PheOMe (4.2 mg, 0.0067 mmol) were added DMF (1 mL) and DIEA (4.3 mg, 0.033 mmol), followed by HATU (2.6 mg, 0.0067 mmol). The reaction was stirred at rt for 1 hr. The crude was purified by preparative HPLC with a 20-50% gradient to give (S)-Methyl-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoate (FP-1) as a TFA salt. MS m/z 731.4 (M+1). Retention time 1.122 min.

Step 4: To a solution of (S)-methyl-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoate TFA salt (FP-1) (10.2 mg, 0.012 mmol) in MeOH-H2O (2:1, 3 mL) was added LiOH (20 mg, 0.84 mmol). The reaction was stirred at rt for 18 h and the crude material was purified by preparative HPLC with a 20-45% gradient to obtain (S)-2-((2R,3R)-3-((S)-1-((3R,4S,5S)-4-((S)-2-((Bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoic acid (FP-22). MS m/z 717.5 (M+1). Retention time 1.008 min.

EXAMPLE 2

Synthesis of (S)-methyl-2-((2R,3R)-3-((S)-1-((3R,4S,5S)-4-((S)-2-(3,3-dimethylguanidino)-N,3-dimethylbutanamido)-3-methoxy-5-methylheptanoyl)pyrrolidin-2-yl)-3-methoxy-2-methylpropanamido)-3-phenylpropanoate (FP-2)

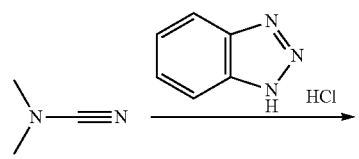

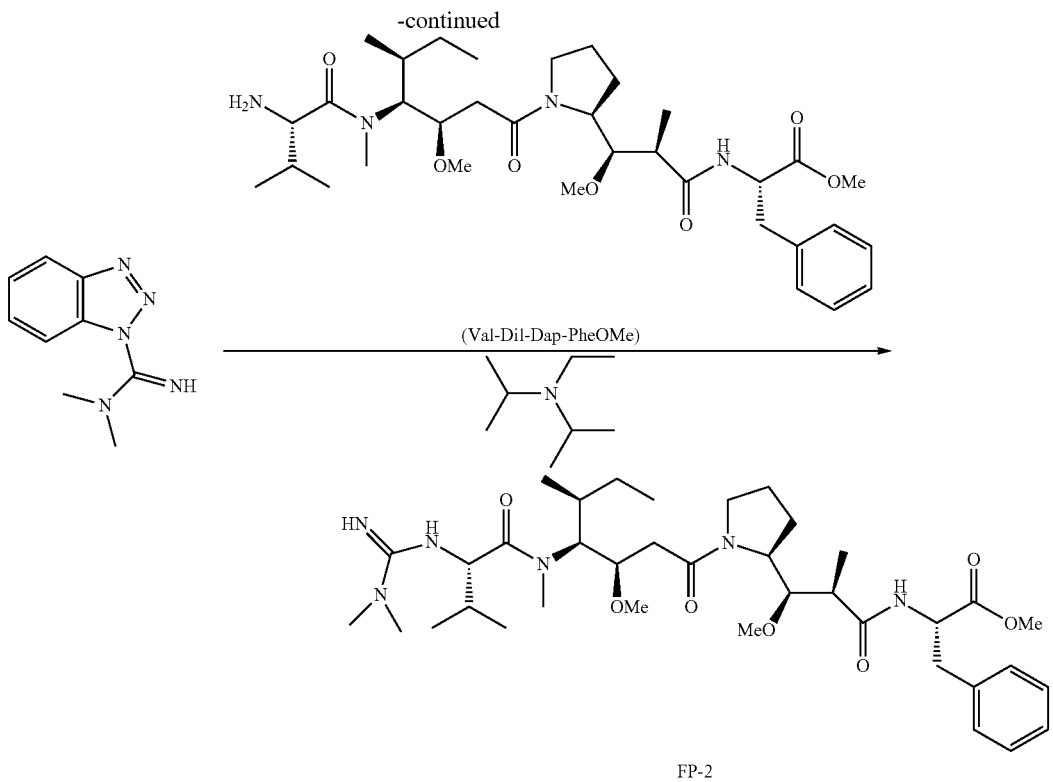

(Val-Dil-Dap-PheOMe)

FP-2

To a 25 ml round-bottom flask were added benzotriazole (1.19 g, 9.99 mmol) and 6 N HCl in 2-propanol (3 mL). A homogenous solution resulted within 5 min, but later white solids precipitated. The solvent was then removed by evaporation to obtain benzotriazole HCl salt (1.55 g, 9.96 mmol). To this benzotriazole HCl salt was added N,N-dimethylcyanamide (0.84 g, 12 mmol). The reaction was heated at 80° C. for 30 min. The reaction turned clear first and then solid started to form. The crystals were collected to obtain N,N-dimethyl-1H-benzo[d][1,2,3]triazole-1-carboximidamide.

To a solution of (S)-methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate (Val-Dil-Dap-PheOMe) (5.0 mg, 0.0067 mmol) in acetonitrile (1 mL) was added DIEA (0.023 mL, 0.13 mmol) and N,N-dimethyl-1H-benzo[d][1,2,3]triazole-1-carboximidamide (0.015 g, 0.067 mmol). The mixture was sonicated for 30 sec, sealed and heated at 60° C. for 20 h. LCMS showed the conversion was about 50%. The crude was purified by preparative HPLC with a 20-70% gradient to obtain (S)-methyl-2-((2R,3R)-3-((S)-1-((3R,4S,5S)-4-((S)-2-(3,3-dimethylguanidino)-N,3-dimethylbutanamido)-3-methoxy-5-methylheptanoyl)pyrrolidin-2-yl)-3-methoxy-2-methylpropanamido)-3-phenylpropanoate (FP-2) as a TFA salt. MS m/z 703.4 (M+1). Retention time 1.256 min.

EXAMPLE 3

Synthesis of (S)-2-((bis(dimethylamino)methylene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (FP-3)

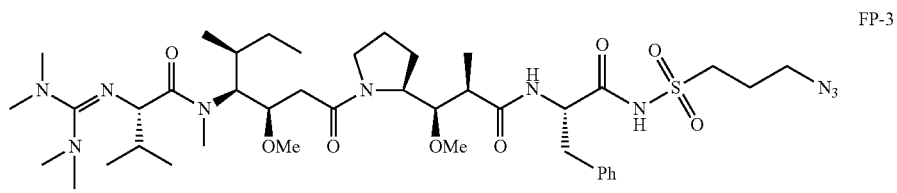

FP-3

Step 1: To a stirred solution of sodium azide (3.5 g, 54 mmol) in water (25 ml) was added a solution of 1,3-propane sultone (6.1 g, 50 mmol) in acetone (25 ml). The reaction mixture was stirred at rt for 24 h, and concentrated. The resulting solid was suspended in diethyl ether (100 ml) and stirred at reflux for 1 h. The suspension was cooled to rt. The solid was collected by filtration, washed with acetone and diethyl ether, and dried under vacuum, affording of 3-azido-1-propanesulfonic acid. MS m/z 188.1 (M+23). $^1$H NMR (400 MHz, CD$_3$OD): δ 3.47 (t, J=6.8 Hz, 2H), 2.87 (t, J=7.6 Hz, 2H), 2.07-2.00 (m, 2H).

Step 2: 3-Azido-1-propanesulfonic acid (2.07 g, 13 mmol) was suspended in toluene. PCl$_5$ (2.61 g, 13 mmol) was added. The mixture was heated at reflux for 3 h. The reaction was cooled to rt. Insolble matters were removed by filtratio, and washed with DCM. The combined filtrate was concentrated to give 3-azidopropane-1-sulfonyl chloride as a yellow-brown oil, which was used in the next step without further purification.

Step 3: NH₄OH (28%, 5 mL) was cooled to 0° C. 3-azidopropane-1-sulfonyl chloride (1.75 g, 9.53 mmol) was added. After 10 min, the reaction was warmed to rt, and then was stirred for 3 hours at rt. The two phases became homogeneous. The reaction mixture was extracted with EtOAc three times. The combined organic phases was washed with brine, dried over MgSO₄, and concentrated on a rotary evporater followed by high vacuum for 18 h to give 3-azidopropane-1-sulfonamide. MS m/z 187.1 (M+23). $^{1}$H NMR (400 MHz, CDCl₃): δ 4.83 (s, 2H), 3.51 (t, J=6.4 Hz, 2H), 3.23 (t, J=7.6 Hz, 2H), 2.17-2.10 (m, 2H).

Step 4: (S)-2-((tert-Butoxycarbonyl)amino)-3-phenylpropanoic acid (100 mg, 0.38 mmol) was dissolved in DMF (4 mL). DIEA (0.395 mL, 2.26 mmol) and HATU (358 mg, 0.94 mmol) were added. After 15 min, 3-azidopropane-1-sulfonamide (186 mg, 1.13 mmol) was added. The reaction was stirred for 2 h. LCMS indicated a completion of the reaction. The reaction mixture was purified by preparative HPLC using a 10-90% gradient. to obtain (S)-tert-butyl (1-(3-azidopropylsulfonamido)-1-oxo-3-phenylpropan-2-yl)carbamate. MS m/z 312.1 (M+1-Boc). Retention time 1.15 min. The product thus obtained (72.4 mg. 0.176 mmol) was dissolved in methanolic HCl (3 M, 5 mL). The solvent was removed by evapolation. The residue was lyophilized from acetonitrile and H₂O to give (S)-2-amino-N-((3-azidopropyl)sulfonyl)-3-phenylpropanamide as a pinkish yellowish solid. MS m/z 312.1 (M+1) $^{1}$H NMR (400 MHz, CD₃OD): δ 7.42-7.31 (m, 5H), 4.16-4.13 (m, 1H), 3.51-3.47 (m, 4H), 3.32-3.26 (m, 1H), 3.13-3.08 (m, 1H), 2.00-1.94 (m, 2H).

Step 5: To Boc-Val-Dil-Dap-OH (195 mg, 0.3 4mmol) in DMF (4mL) were added DIEA (132 mg, 1.02 mmol) and HATU(108 mg, 0.28 mmol). It was stirred 15 min at rt. (S)-2-amino-N-((3-azidopropyl)sulfonyl)-3-phenylpropanamide (59.2 mg, 0.17 mmol) was added. The reaction was stirred for 2 h at rt. The crude material was purified by prepative HPLC to afford the desired product (95 mg, 65% yield, MS m/z 865.4 (M+1), Retention time 1.43 minutes). The product was dissolved in 3M HCl in MeOH (3 mL). Solvents were removed by evapolation. The residue was lyophilized from acetonitle-water to obtained (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane,

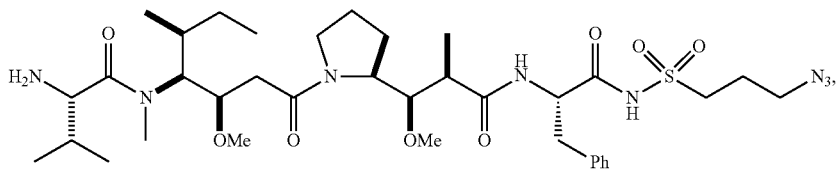

as HCl salt, MS m/z 765.4 (M+1), retention time 1.04 min.

Step 6: To (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane HCl salt (20 mg, 0.025 mmol) in DMF (2 mL) were added DIEA (0.024 mL, 0.14 mmol) and HATU (21.6 mg, 0.057 mmol). The reaction was stirred at rt for 2 h. LCMS indicated completion of the reaction. The crude was purified by preparative HPLC using a 10-90% gradient to obtain (S)-2-((bis(dimethylamino)methylene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (FP-3) as a TFA salt. MS m/z 863.5 (M+1). Retention time 1.169 min.

EXAMPLE 4

Synthesis of (S)-methyl-2-((2R,3R)-3-((S)-1-((3R,4S,5S)-4-((S)-2-(3,3-dimethylureido)-N,3-dimethylbutanamido)-3-methoxy-5-methylheptanoyl)pyrrolidin-2-yl)-3-methoxy-2-methylpropanamido)-3-phenylpropanoate (FP-4)

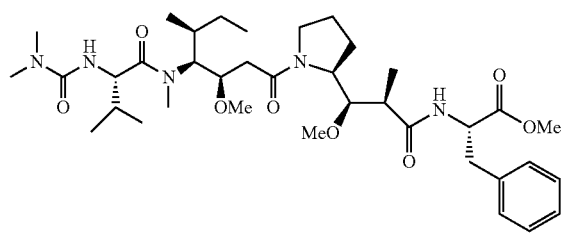

FP-4

Val-Dil-Dap-PheOMe (4.2 mg, 0.0067 mmol) was dissolved in THF-DMF (1:1, 1.6 ml) and 4-nitrophenyl chloroformate (20 mg, 0.099 mmol) was added, followed by DIEA (20 mg, 0.17 mmol). After stirred at rt for 1 h, the reaction mixture was concentrated and purified by ISCO using a C18 column with a 30%-70% gradient of acetonitrile in H₂O to obtain (S)-methyl-2-((2R,3R)-3-((S)-1-((3R,4S,5S)-4-((S)-N,3-dimethyl-2-(((4-nitrophenoxy)carbonyl)amino)butanamido)-3-methoxy-5-methylheptanoyl)pyrrolidin-2-yl)-3-methoxy-2-methylpropanamido)-3-phenylpropanoate. MS m/z 798.5 (M+1). Retention time 1.481 min. The nitrophenylcarbamate thus obtained was dissolved in THF-DMF (1:1, 1.6 mL) and dimethylamine HCl salt (0.010 mg, 0.12 mmol) was added, followed by DIEA (0.027 mL, 0.16 mmol). The reaction was stirred at rt for 72 h and then concentrated. The crude was purified by preparative HPLC using a 0-55% gradient to obtain (S)-methyl-2-((2R,3R)-3-((S)-1-((3R,4S,5S)-4-((S)-2-(3,3-dimethylureido)-N,3-dimethylbutanamido)-3-methoxy-5-methylheptanoyl)pyrrolidin-2-yl)-3-methoxy-2- methylpropanamido)-3-phenylpropanoate (FP-4). MS m/z 704.4 (M+1). Retention time 1.251 min.

EXAMPLE 5

Synthesis of (S)-methyl-2-((2R,3R)-3-((S)-1-((3R, 4S,5S)-4-((S)-2-(3,3-diisopropylureido)-N,3-dimethylbutanamido)-3-methoxy-5-methylheptanoyl)pyrrolidin-2-yl)-3-methoxy-2-methylpropanamido)-3-phenylpropanoate (FP-5)

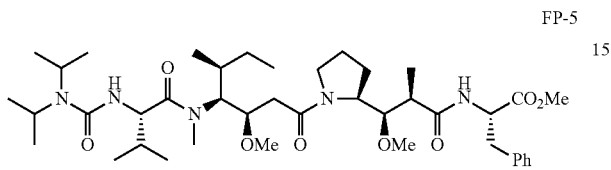

FP-5

(S)-Methyl-2-((2R,3R)-3-((S)-1-((3R,4S,5S)-4-((S)-2-(3,3-diisopropylureido)-N,3-dimethylbutanamido)-3-methoxy-5-methylheptanoyl)pyrrolidin-2-yl)-3-methoxy-2-methylpropanamido)-3-phenylpropanoate (FP-5) was synthesized using the same method as described for compound FP-4, except by using diisopropylamine (10 mg, 0.099 mmol) in place of dimethylamine. MS m/z 760.5 (M+1). Retention time 1.481 min.

EXAMPLE 6

Synthesis of (S)-methyl-2-((2R,3R)-3-((S)-1-((3R, 4S,5S)-4-((S)-2-(3-ethyl-3-isopropylureido)-N,3-dimethylbutanamido)-3-methoxy-5-methylheptanoyl)pyrrolidin-2-yl)-3-methoxy-2-methylpropanamido)-3-phenylpropanoate (FP-6)

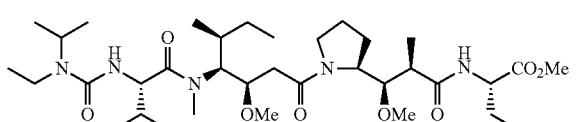

FP-6

(S)-Methyl-2-((2R,3R)-3-((S)-1-((3R,4S,5S)-4-((S)-2-(3-ethyl-3-isopropylureido)-N,3-dimethylbutanamido)-3-methoxy-5-methylheptanoyl)pyrrolidin-2-yl)-3-methoxy-2-methylpropanamido)-3-phenylpropanoate (FP-6) was synthesized using the same method as described for compound FP-4, except using ethylisopropylamine (10 mg, 0.099 mmol) in place of dimethylamine. MS m/z 746.5 (M+1). Retention time 1.412 min.

EXAMPLE 7

(S)-Methyl-2-((2R,3R)-3-((S)-1-((3R,4S,5S)-4-((S)-2-(3-(1-(hydroxymethyl)cyclobutyl)ureido)-N,3-dimethylbutanamido)-3-methoxy-5-methylheptanoyl)pyrrolidin-2-yl)-3-methoxy-2-methylpropanamido)-3-phenylpropanoate (FP-7)

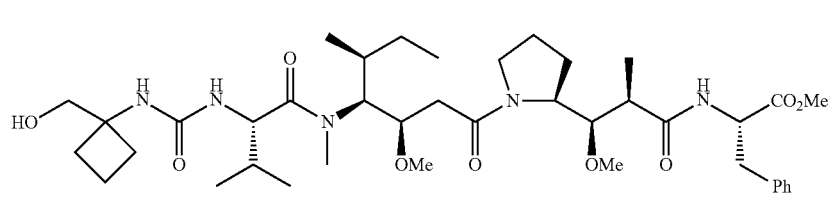

FP-7

(S)-Methyl-2-((2R,3R)-3-((S)-1-((3R,4S,5S)-4-((S)-2-(3-(1-(hydroxymethyl)cyclobutyl)ureido)-N,3-dimethylbutanamido)-3-methoxy-5-methylheptanoyl)pyrrolidin-2-yl)-3-methoxy-2-methylpropanamido)-3-phenylpropanoate (FP-7) was synthesized using the same method as described for compound FP-4, except using (1-aminocyclobutyl)methanol (10 mg, 0.099 mmol) in place of dimethylamine. MS m/z 760.5 (M+1). Retention time 1.224 min.

EXAMPLE 8

Synthesis of (S)-methyl-2-((2R,3R)-3-((S)-1-((3R, 4S,5S)-4-((S)-N,3-dimethyl-2-((4-methylpyrimidin-2-yl)amino)butanamido)-3-methoxy-5-methylheptanoyl)pyrrolidin-2-yl)-3-methoxy-2-methylpropanamido)-3-phenylpropanoate (FP-8)

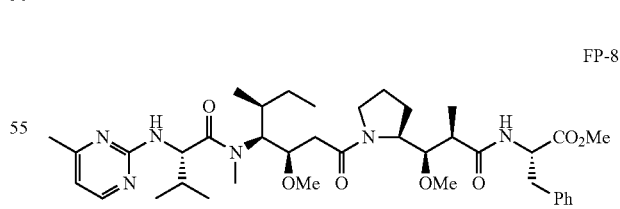

FP-8

To a solution of Val-Dil-Dap-PheOMe TFA salt (5.0 mg, 0.0067 mmol) in 2-propanol (2 ml) in a 4 oz. vial were added 2-chloro-4-methylpyrimidine (2.6 mg, 0.020 mmol) and DIEA (4.3 mg, 0.033 mmol). The vial was sealed and heated at 100° C. for 4 days. The crude was purified by preparative HPLC using a 20-50% gradient to obtain (S)-methyl-2-((2R, 3R)-3-((S)-1-((3R,4S,5S)-4-((S)-N,3-dimethyl-2-((4-methylpyrimidin-2-yl)amino)butanamido)-3-methoxy-5-methylheptanoyl)pyrrolidin-2-yl)-3-methoxy-2-methylpropanamido)-3-phenylpropanoate (FP-8) as a TFA salt MS m/z 725.4 (M+1). Retention time 1.177 min.

EXAMPLE 9

Synthesis of (S)-methyl-2-((2R,3R)-3-((S)-1-((3R,4S,5S)-4-((S)-N,3-dimethyl-2-((4-(trifluoromethyl)pyrimidin-2-yl)amino)butanamido)-3-methoxy-5-methylheptanoyl)pyrrolidin-2-yl)-3-methoxy-2-methylpropanamido)-3-phenylpropanoate (FP-9)

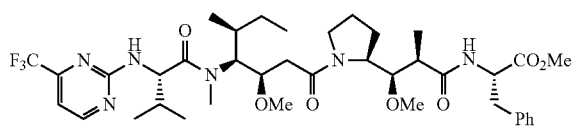

FP-9

(S)-Methyl-2-((2R,3R)-3-((S)-1-((3R,4S,5S)-4-((S)-N,3-dimethyl-2-((4-(trifluoromethyl)pyrimidin-2-yl)amino)butanamido)-3-methoxy-5-methylheptanoyl)pyrrolidin-2-yl)-3-methoxy-2-methylpropanamido)-3-phenylpropanoate (FP-9) was synthesized using the same method as described for compound FP-8, except using 2-chloro-4-(trifluoromethyl)pyrimidine (3.7 mg, 0.020 mmol) in place of 2-chloro-4-methylpyrimidine. The reaction was heated at 90° C. for 18 h. MS m/z 779.3 (M+1). Retention time 1.481 min.

EXAMPLE 10

Synthesis of (S)-methyl-2-((2R,3R)-3-((S)-1-((3R,4S,5S)-4-((S)-2-((3-chloro-5-(trifluoromethyl)pyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-10)

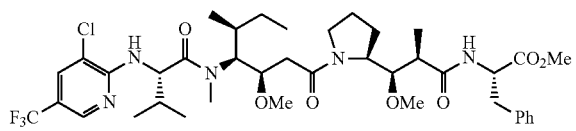

FP-10

(S)-Methyl-2-((2R,3R)-3-((S)-1-((3R,4S,5S)-4-((S)-2-((3-chloro-5-(trifluoromethyl)pyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-10) was synthesized using the same method as described for compound FP-8, except using 3-chloro-2-fluoro-5-(trifluoromethyl)pyridine (1.3 mg, 0.0067 mmol) in place of 2-chloro-4-methylpyrimidine. The reaction was heated at 90° C. for 18 h. MS m/z 812.3 (M+1). Retention time 1.638 min.

EXAMPLE 11

Synthesis of (S)-methyl-2-((2R,3R)-3-((S)-1-((3R,4S,5S)-4-((S)-2-((5-bromo-3-fluoropyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-11)

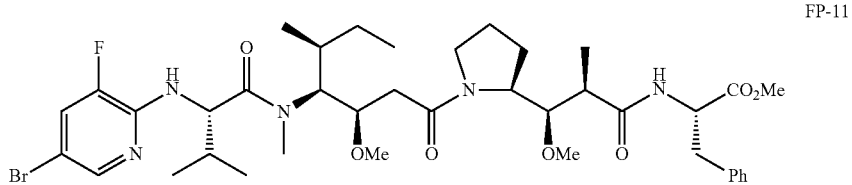

FP-11

(S)-Methyl-2-((2R,3R)-3-((S)-1-((3R,4S,5S)-4-((S)-2-((5-bromo-3-fluoropyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-11) was synthesized using the same method as described for compound FP-8, except using 5-bromo-2,3-difluoropyridine (1.3 mg, 0.0067 mmol) in place of 2-chloro-4-methylpyrimidine. The reaction was heated at 100° C. for 96 h. MS m/z 806.3 (M+1). Retention time 1.592 min.

EXAMPLE 12

Synthesis of (S)-methyl-2-((2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanamido)-3-phenylpropanoate (FP-12)

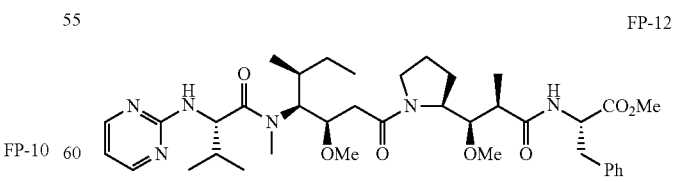

FP-12

(S)-Methyl-2-((2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanamido)-3-phenylpropanoate (FP-12) This compound was synthesized using the same method as described for compound FP-8, by using 2-chloropyrimidine (7.7 mg, 0.067 mmol) in place of 2-chloro-4-methylpyrimidine. The reaction was heated at 120° C. for 48 h. MS m/z 711.4 (M+1). Retention time 1.221 min.

EXAMPLE 13

Synthesis of (S)-methyl-2-((2R,3R)-3-((S)-1-((3R, 4S,5S)-4-((S)-2-((4-ethylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-13)

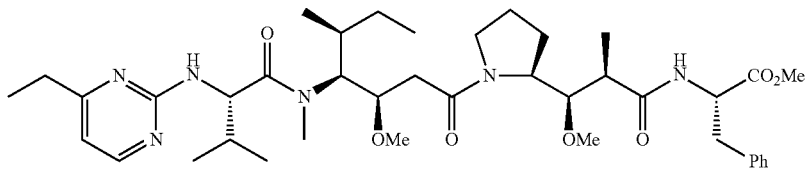

FP-13

(S)-Methyl-2-((2R,3R)-3-((S)-1-((3R,4S,5S)-4-((S)-2-((4-ethylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-13) was synthesized using the same method as described for compound FP-8, by using 2-chloro-4-ethylpyrimidine (9.6 mg, 0.067 mmol) in place of 2-chloro-4-methylpyrimidine. The reaction was heated at 120° C. for 48 h. MS m/z 739.4 (M+1). Retention time 1.221 min.

EXAMPLE 14

Synthesis of (S)-methyl-2-((2R,3R)-3-((S)-1-((3R, 4S,5S)-4-((S)-N,3-dimethyl-2-((6-methylpyrimidin-4-yl)amino)butanamido)-3-methoxy-5-methylheptanoyl)pyrrolidin-2-yl)-3-methoxy-2-methylpropanamido)-3-phenylpropanoate (FP-14)

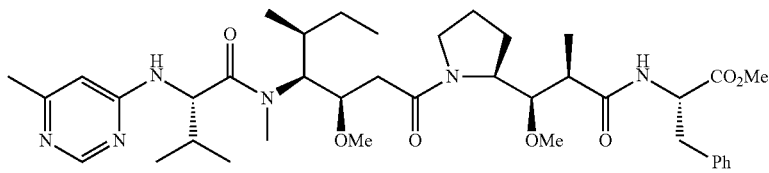

FP-14

(S)-Methyl-2-((2R,3R)-3-((S)-1-((3R,4S,5S)-4-((S)-N,3-dimethyl-2-((6-methylpyrimidin-4-yl)amino)butanamido)-3-methoxy-5-methylheptanoyl)pyrrolidin-2-yl)-3-methoxy-2-methylpropanamido)-3-phenylpropanoate (FP-14) was synthesized using the same method as described for compound FP-8, except using 4-chloro-6-methylpyrimidine (8.6 mg, 0.067 mmol) in place of 2-chloro-4-methylpyrimidine. The reaction was heated at 160° C. for 6 h. MS m/z 725.4 (M+1). Retention time 1.068 min.

EXAMPLE 15

Synthesis of (S)-methyl-2-((2R,3R)-3-((S)-1-((3R,4S,5S)-4-((S)-2-((4,6-dimethylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-15)

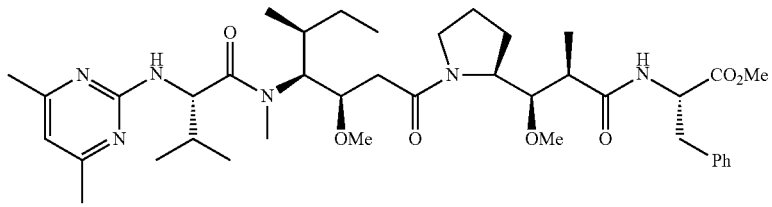

FP-15

(S)-Methyl-2-((2R,3R)-3-((S)-1-((3R,4S,5S)-4-((S)-2-((4,6-dimethylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-15) was synthesized using the same method as described for compound FP-8, except using 2-chloro-4,6-dimethylpyrimidine (9.6 mg, 0.067 mmol) in place of 2-chloro-4-methylpyrimidine. The reaction was heated at 120° C. for 48 h. MS m/z 739.3 (M+1). Retention time 1.164 min.

EXAMPLE 16

Synthesis of (S)-methyl-2-((2R,3R)-3-((S)-1-((3R,4S,5S)-4-((S)-2-((6-fluoropyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-16)

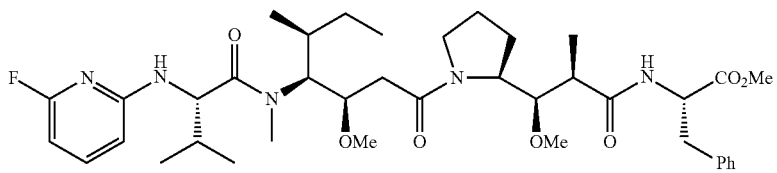

FP-16

(S)-Methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate TFA salt (5.0 mg, 0.0067 mmol), 2,6-difluoropyridine (7.7 mg, 0.067 mmol), K$_2$CO$_3$ (10 mg, 0.072 mmol), DIEA (8.7 mg, 0.067 mmol) and DMSO (1 mL) were combined and heated in a sealed vial at 160° C. for 24 h. The crude was purified by reverse phase HPLC using a 20-50% gradient to obtain (S)-methyl 2-((2R,3R)-3-((S)-1-((3R,4S,5S)-4-((S)-2-((6-fluoropyridin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-16). MS m/z 728.4 (M+1). Retention time 1.457 min.

EXAMPLE 17

Synthesis of (S)-methyl-2-((2R,3R)-3-((S)-1-((3R,4S,5S)-4-((S)-2-((4-isopropylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-17)

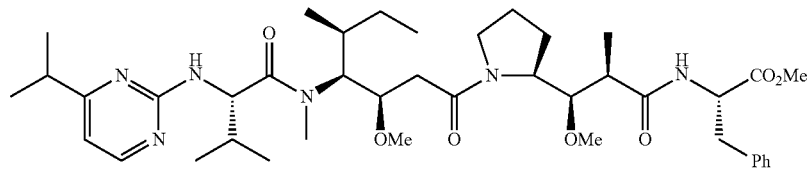

FP-17

S)-Methyl-2-((2R,3R)-3-((S)-1-((3R,4S,5S)-4-((S)-2-((4-isopropylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (FP-17) was synthesized using the same method as described for compound FP-8, except using 2-chloro-4-isopropylpyrimidine (10.5 mg, 0.067 mmol) in place of 2-chloro-4-methylpyrimidine. The reaction was heated at 155° C. for 10 h. MS m/z 753.4 (M+1). Retention time 1.266 min.

EXAMPLE 18

Synthesis of (S)-methyl-2-((2R,3R)-3-((S)-1-((3R,4S,5S)-4-((S)-N,3-dimethyl-2-(pyrazin-2-ylamino)butanamido)-3-methoxy-5-methylheptanoyl)pyrrolidin-2-yl)-3-methoxy-2-methylpropanamido)-3-phenylpropanoate (FP-18)

FP-18

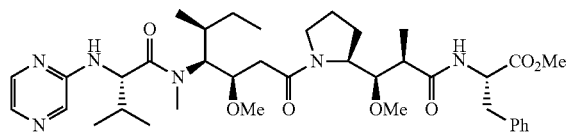

(S)-Methyl-2-((2R,3R)-3-((S)-1-((3R,4S,5S)-4-((S)-N,3-dimethyl-2-(pyrazin-2-ylamino)butanamido)-3-methoxy-5-methylheptanoyl)pyrrolidin-2-yl)-3-methoxy-2-methylpropanamido)-3-phenylpropanoate (FP-18) was synthesized using the same method as described for compound FP-16, except using 2-chloropyrazine (7.7 mg, 0.067 mmol) in place of 2,6-difluoropyridine. The reaction was heated at 130° C. for 10 h. MS m/z 711.4 (M+1). Retention time 1.295 min.

EXAMPLE 19

Synthesis of (S)-methyl-2-((2R,3R)-3-methoxy-3-((S)-1-((3R,4S,5S)-3-methoxy-4-((S)-2-((4-methoxypyrimidin-2-yl)amino)-N,3-dimethylbutanamido)-5-methylheptanoyl)pyrrolidin-2-yl)-2-methylpropanamido)-3-phenylpropanoate (FP-19)

FP-19

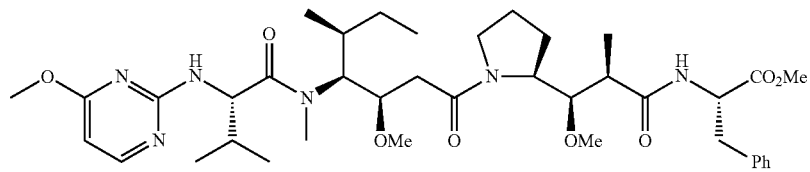

(S)-Methyl-2-((2R,3R)-3-methoxy-3-((S)-1-((3R,4S,5S)-3-methoxy-4-((S)-2-((4-methoxypyrimidin-2-yl)amino)-N,3-dimethylbutanamido)-5-methylheptanoyl)pyrrolidin-2-yl)-2-methylpropanamido)-3-phenylpropanoate (FP-19) was synthesized using the same method as described for compound FP-8, except using 2-chloro-4-methoxypyrimidine (20 mg, 0.14 mmol) in place of 2-chloro-4-methylpyrimidine. The reaction was heated at 155° C. for 4 h. MS m/z 741.5 (M+1). Retention time 1.135 min.

EXAMPLE 20

Synthesis of (S)-tert-butyl-2-((2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanamido)-3-phenylpropanoate (FP-20)

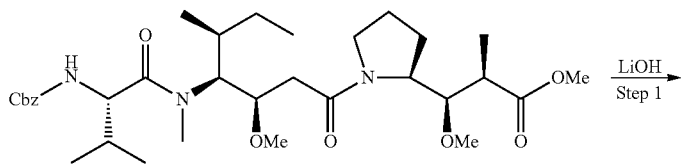

-continued

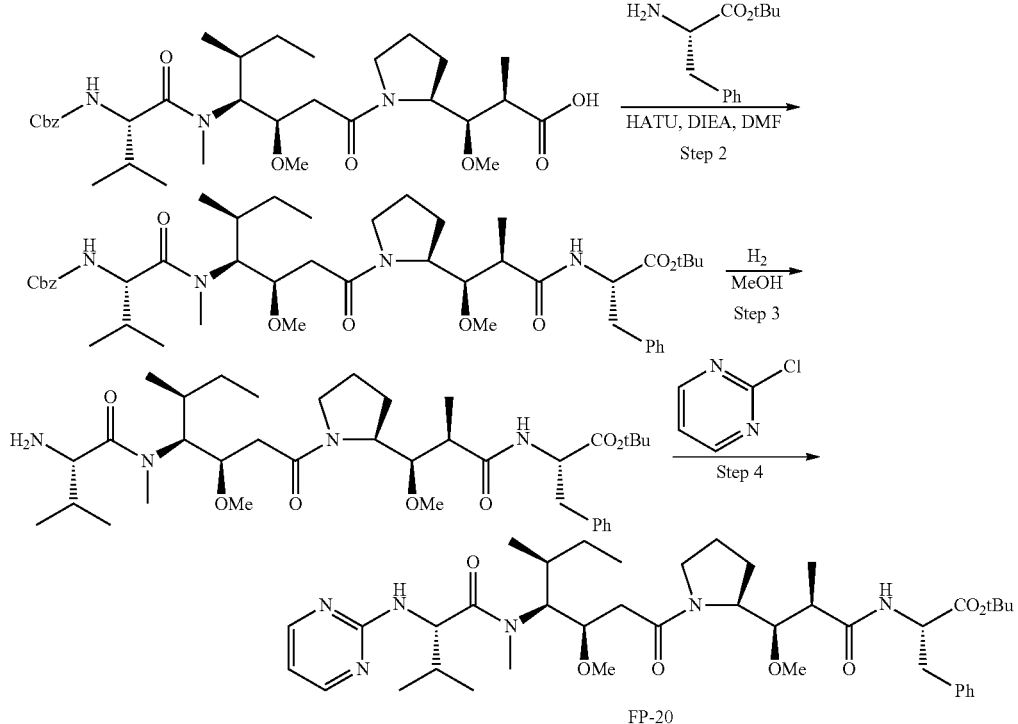

FP-20

Step 1: LiOH (240 mg, 10.0 mmol) was added to Cbz-Val-Dil-Dap-OMe (516 mg, 0.833 mmol) in MeOH—H₂O (5:1, 12 ml). The reaction was stirred at 40° C. for 18 h. The reaction mixture was concentrated, dissolved in 10 mL water and acidified with 1 N aq HCl. The mixture was extracted with ethyl acetate (10 mL×3). The organic layers were combined, dried over Na₂SO₄, filtered and concentrated to obtain Cbz-Val-Dil-Dap—OH MS m/z 606.3 (M+1). Retention time 1.423 min.

Step 2: To Cbz-Val-Dil-Dap—OH (30 mg, 0.050 mmol) in DMF (1.0 mL) at rt were added DIEA (19 mg, 0.15 mmol) and HATU (18.8 mg, 0.050 mmol). The resulting solution was stirred for 5 min and added to a solution of L-phenylalanine tert-butyl ester (11 mg, 0.050 mmol). The reaction was stirred at rt for 18 h. The reaction mixture was purified by preparative HPLC using a 30-90% gradient to obtain Cbz-Val-Dil-Dap-PheOtBu, MS m/z 809.1 (M+1). Retention time 1.595 min.

Step 3: To BocVal-Dil-Dap-PheOtBu (10.2 mg, 0.013 mmol) obtained in step 2 in methanol (2 mL) was added 10% Pd on carbon (10 mg). The reaction was stirred at rt for 1 h under H₂. The catalyst was removed by filtration, and the filtrate was concentrated to give Val-Dil-Dap-PheOtBu. MS m/z 675.1 (M+1). Retention time 1.247 min.

Step 4: To a microwave reaction tube were added Val-Dil-Dap-PheOtBu (4.5 mg, 0.0067 mmol), 2-chloropyrimidine (8.7 mg, 0.076 mmol), DIEA (0.0088 ml, 0.050 mmol) and sec-BuOH (2.0 ml). The tube was sealed and heated at 130° C. for 18 h. The reaction mixture was concentrated and purified by preparative HPLC using a 30-60% to obtain (5)-tert-butyl 2-((2R,3R)-3-((S)-1-((3R, 4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanamido)-3-phenylpropanoate (FP-20) as a TFA salt. MS m/z 753.4 (M+1). Retention time 1.410 min.

EXAMPLE 21

Synthesis of (S)-N-((3R,4S,5S)-1-((S)-2-((1R,2R)-3-(((S)-1-cyano-2-phenylethyl)amino)-1-methoxy-2-methyl-3-oxopropyl)pyrrolidin-1-yl)-3-methoxy-5-methyl-1-oxoheptan-4-yl)-N,3-dimethyl-2-(pyrimidin-2-ylamino)butanamide (FP-21)

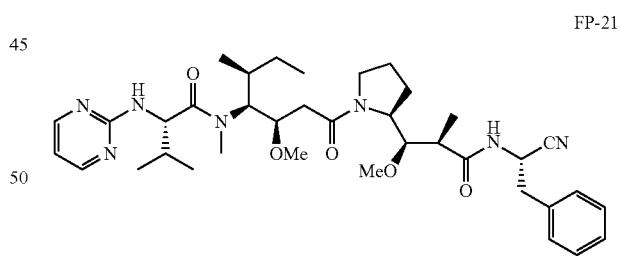

FP-21

Step 1: To Cbz-Val-Dil-Dap—OH (30 mg, 0.050 mmol) in DMF (1.0 mL) were added DIEA (6.4 mg, 0.05 mmol) and HATU (18.8 mg, 0.050 mmol) at rt. The resulting solution was stirred for 5 min and added to a solution of (S)-2-amino-3-phenylpropanenitrile (13 mg, 0.050 mmol). The reaction mixture was stirred at rt for 18 h and purified by preparative HPLC using a 30-75% gradient to obtain benzyl ((S)-1-(((3R,4S,5S)-1-((S)-2-((1R,2R)-3-(((S)-1-cyano-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate, MS m/z 734.1 (M+1). Retention time 1.469 min.

Step 2: To the product obtained in Step 1 (28.2 mg, 0.038 mmol) in methanol (2 mL) was added 10% Pd on carbon (10 mg). The reaction was stirred at rt for 1 h under H₂. The catalyst was removed by filtration, and the filtrate was concentrated to give (S)-2-amino-N-((3R,4S,5S)-1-((S)-2-((1R,2R)-3-(((S)-1-cyano-2-phenylethyl)amino)-1-methoxy-2-methyl-3-oxopropyl)pyrrolidin-1-yl)-3-methoxy-5-methyl-1-oxoheptan-4-yl)-N,3-dimethylbutanamide. MS m/z 600.1 (M+1). Retention time 1.119 min.

Step 3: To a microwave reaction tube were added (S)-2-amino-N-((3R,4S,5S)-1-((S)-2-((1R,2R)-3-(((S)-1-cyano-2-phenylethyl)amino)-1-methoxy-2-methyl-3-oxopropyl)pyrrolidin-1-yl)-3-methoxy-5-methyl-1-oxoheptan-4-yl)-N,3-dimethylbutanamide obtained from step 2 (4.5 mg, 0.0075 mmol), 2-chloropyrimidine (8.7 mg, 0.076 mmol), DIEA (0.0022 ml, 0.013 mmol) and sec-BuOH (2.0 mL). The reaction tube was sealed and heated at 130° C. for 18 h. The reaction mixture was concentrated and purified by preparative HPLC using a 20-60% gradient to obtain (S)-N-((3R,4S,5S)-1-((S)-2-((1R,2R)-3-(((S)-1-Cyano-2-phenylethyl)amino)-1-methoxy-2-methyl-3-oxopropyl)pyrrolidin-1-yl)-3-methoxy-5-methyl-1-oxoheptan-4-yl)-N,3-dimethyl-2-(pyrimidin-2-ylamino)butanamide (FP-21) as a TFA salt. MS m/z 678.4 (M+1). Retention time 1.272 min.

EXAMPLE 22

Synthesis of (S)-N-((3R,4S,5S)-1-((S)-2-((3R,4R,7S)-16-amino-7-benzyl-4,9,12-trimethyl-5,8,13-trioxo-2-oxa-6,9,12-triazahexadecan-3-yl)pyrrolidin-1-yl)-3-methoxy-5-methyl-1-oxoheptan-4-yl)-2-((bis(dimethylamino)methylene)amino)-N,3-dimethylbutanamide (FP-23)

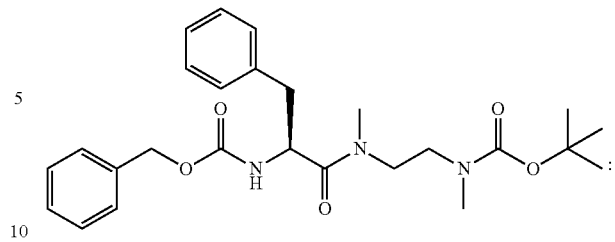

MS m/z 470.2 (M+1). Retention time 1.313 min.

Step 2: To (S)-t-butyl (2-(2-(((benzyloxy)carbonyl)amino)-N-methyl-3-phenylpropanamido)ethyl)(methyl)carbamate (104.5 mg, 0.223 mmol) in MeOH (5 ml) was added Pd/C (47.4 mg, 10% wet). The reaction vessel was filled with H₂. The reaction was stirred for 2 h at rt. The reaction mixture was filtered, concentrated to give ((S)-t-butyl (2-(2-amino-N-methyl-3-phenylpropanamido)ethyl)(methyl)carbamate),

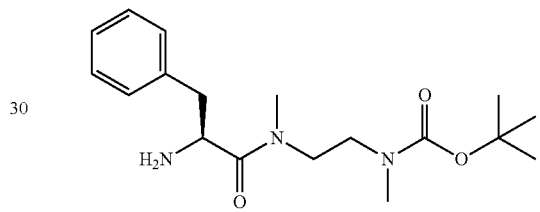

as a colorless oil. MS m/z 336.2 (M+1). Retention time 0.851 minutes.

Step 3: DIEA (65 gl) and HATU (31.2 mg, 0.082 mmol) were added to (2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoic acid (i-11) (61.2 mg, 89 gmol) in DMF (2 ml). After being stirred for 15 min, (S)-tert-butyl (2-(2-amino-N-methyl-3-phenylpropanamido)ethyl)(methyl)carbamate (25 mg, 75 gmol) in DMF

FP-23

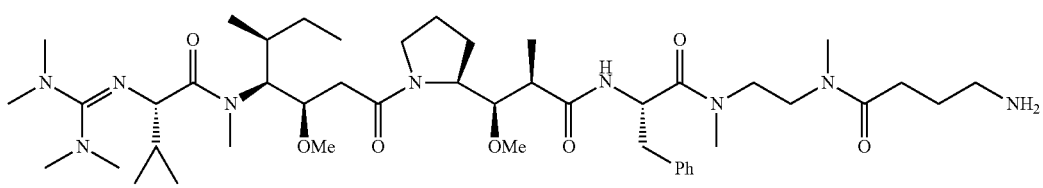

Step 1: To Cbz-Phe-OH (114 mg, 0.382 mmol) in DMF (4 ml) were added DIEA (278 µl, 1.59 mmol) and HATU (133 mg, 0.351 mmol). The resulting mixture was stirred for 15 min at rt and then t-butyl methyl(2-(methylamino)ethyl)carbamate (60 mg, 0.32 mmol) was added. The reaction was stirred for 2 h at rt. Preparative HPLC purification (20-70% acetonitrile-H20 containing 0.05% TFA) afforded ((S)-tert-butyl (2-(2-(((benzyloxy)carbonyl)amino)-N-methyl-3-phenylpropanamido)ethyl)(methyl)carbamate), (1.5 ml) was added. The reaction was stirred at rt for 2 h. Preparative HPLC purification (30-50% acetonitrile-H₂O containing 0.05% TFA) afforded t-butyl (2-((S)-2-((2R,3R)-3-((S)-1-((3R,4S,5S)-4-((S)-2-((bis(dimethylam ino)methylene)amino)-N,3-dimethylbutanamido)-3-methoxy-5-methylheptanoyl)pyrrolidin-2-yl)-3-methoxy-2-methylpropanamido)-N-methyl-3-phenylpropanamido)ethyl)(methyl)carbamate,

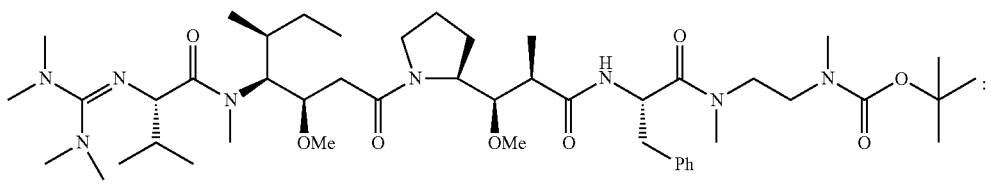

MS m/z 887.6 (M+1). Retention time 1.167 min. The product (37.8 mg, 38 μmol) in DCM (2 ml) was treated with TFA (0.4 ml) at 0° C. for 30 min and then at rt for 2 h. Removal of the solvent by evaporation gave (S)-N-((3R,4S,5S)-1-((S)-2-((7S,10R,11R)-7-benzyl-5,10-dimethyl-6,9-dioxo-12-oxa-2,5,8-triazatridecan-11-yl)pyrrolidin-1-yl)-3-methoxy-5-methyl-1-oxoheptan-4-yl)-2-((bis(dimethylamino)methylene)amino)-N,3-dimethylbutanamide,

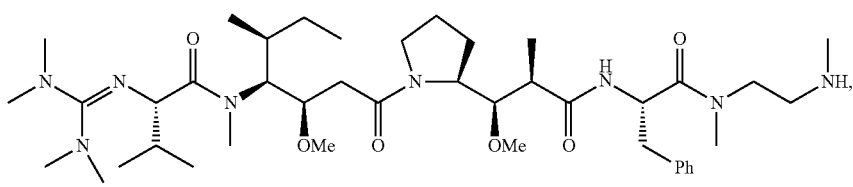

as TFA salt. MS m/z 787.6 (M+1). Retention time 0.891 min.
Step 4: To 4-((t-butoxycarbonyl)amino)butanoic acid (7.9 mg, 39 μmol) in DMF (2 ml) was added DIEA (25.2 mg, 195 gmol) and then HATU (14.8 mg, 39 μgmol). The reaction mixture was stirred at rt for 5 min and then added to (S)-N-((3R,4S,5S)-1-((S)-2-((7S,10R,11R)-7-benzyl-5,10-dimethyl-6,9-dioxo-12-oxa-2,5,8-triazatridecan-11-yl)pyrrolidin-1-yl)-3-methoxy-5-methyl-1-oxoheptan-4-yl)-2-((bis(dimethylamino)methylene)amino)-N,3-dimethylbutanamide TFA salt (39.6 mg, 39 μmol) in DMF (1 ml). The reaction mixture was stirred at rt for 1 h, then concentrated, and purified by preparative HPLC (20-60% acetonitrile-H$_2$O containing 0.05% TFA) to obtain tert-butyl ((3R,4R,7S)-7-benzyl-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-4,9,12-trimethyl-5,8,13-trioxo-2-oxa-6,9,12-triazahexadecan-16-yl)carbamate,

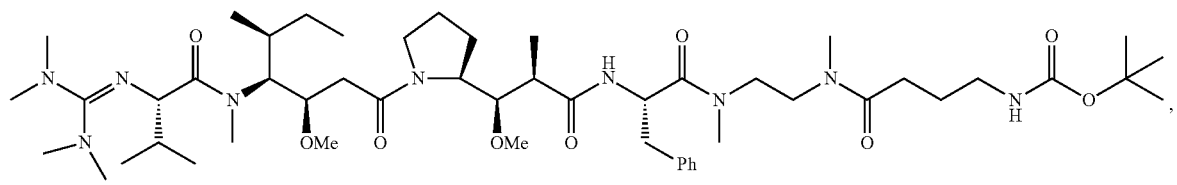

as TFA salt. MS m/z 972.7 (M+1). Retention time 1.106 min. This product (42.4 mg, 39 μmol) in DCM (3 ml) was treated with TFA (1 ml) at rt for 4 h and then concentrated. The crude was purified by preparative HPLC (10-40% acetonitrile-H$_2$O containing 0.05% TFA) to obtain (S)-N-((3R,4S,5S)-1-((S)-2-((3R,4R,7S)-16-Amino-7-benzyl-4,9,12-trimethyl-5,8,13-trioxo-2-oxa-6,9,12-triazahexadecan-3-yl)pyrrolidin-1-yl)-3-methoxy-5-methyl-1-oxoheptan-4-yl)-2-((bis(dimethylamino)methylene)amino)-N,3-dimethylbutanamide (FP-23) as TFA salt. MS m/z 872.7 (M+1). Retention time 0.874 min.

EXAMPLE 23

Synthesis of N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-4-methylpiperazine-1-carboxamide (FP-24)

FP-24

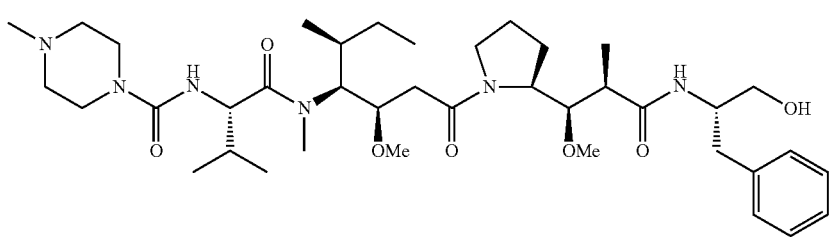

Step 1: 4-nitrophenyl carbonochloridate (20 mg, 10 μmol) and DIEA (25 mg, 190 μmol) were added to 1-methylpiperazine (10 mg, 10 μmol) in DMF (1 ml) and THF (1 ml). The resulting mixture was stirred for 10 min and then Val-Dil-Dap-OH,

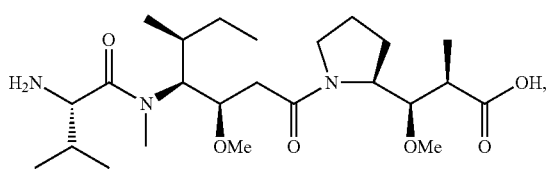

(30 mg, 64 μmol) was added. The reaction mixture was stirred at 40° C. for 16 h, then concentrated and purified by preparative HPLC (10-30% acetonitrile-H₂O containing 0.05% TFA) to obtain (2R,3R)-3-((S)-1-((3R,4S,5S)-4-((S)-N,3-dimethyl-2-(4-methylpiperazine-1-carboxamido)butanamido)-3-methoxy-5-methylheptanoyl)pyrrolidin-2-yl)-3-methoxy-2-methylpropanoic acid,

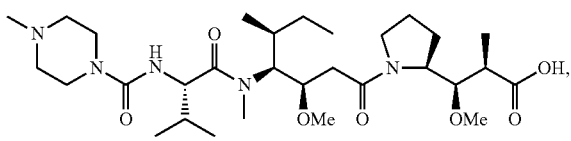

as TFA salt. MS m/z 598.4 (M+1). Retention time 0.874 min.
Step 2: DIEA (8 mg, 6 μmol) and HATU (3.9 mg, 10 μmol) were added to the product obtained in step 1 (7.4 mg, 10 μmol) in DMF (1 ml) and stirred at rt for 5 min. (S)-2-amino-3-phenylpropan-1-ol (1.6 mg, 10 μmol) was then added and the reaction mixture was stirred at rt for 1 h and then purified by preparative HPLC (10-40% acetonitrile-H₂O containing 0.05% TFA to obtain compound (FP-24) as TFA salt. MS m/z 731.5 (M+1). Retention time 0.925 min.

EXAMPLE 24

Synthesis of N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)morpholine-4-carboxamide (FP-25)

FP-25

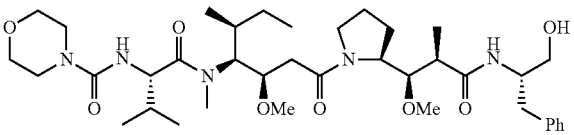

Step 1: 4-nitrophenyl carbonochloridate (8.3 mg, 41 μmol) and DIEA (16 mg, 120 μmol) were added to Val-Dil-Dap-OMe,

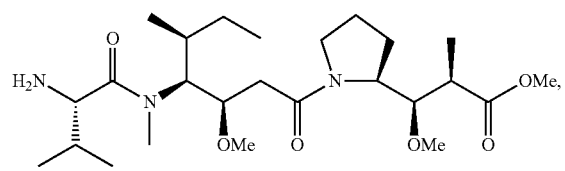

(20 mg, 41 μmol) in DMF (1 ml) and THF (1 ml) and stirred for 10 min. Morpholine (3.6 mg, 41 μmol) was then added and the reaction mixture was stirred at rt for 1 h, then concentrated and purified by preparative HPLC (25-60% acetonitrile-H₂O containing 0.05% TFA) to obtain (2R,3R)-methyl 3-((S)-1-((3R,4S,5S)-4-((S)-N,3-dimethyl-2-(morpholine-4-carboxamido)butanamido)-3-methoxy-5-methylheptanoyl)pyrrolidin-2-yl)-3-methoxy-2-methylpropanoate,

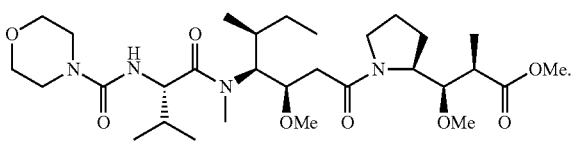

MS m/z 599.4 (M+1). Retention time 1.164 min.

Step 2: The urea obtained in step 1 (24 mg, 41 μmol) was dissolved in MeOH-H₂O (2:1 3ml) and treated with LiOH (20 mg, 0.84 mmol) at rt for 2 days. The reaction mixture was then concentrated and HOAc (40 μl) was added. The crude was purified by preparative HPLC (20-45% acetonitrile-H₂O containing 0.05% TFA) to obtain (2R, 3R)-3-((S)-1-((3R, 4S, 5S)-4-((S)-N, 3-dimethyl-2-(morpholine-4-carboxamido) butanamido)-3-methoxy-5-methylheptanoyl) pyrrolidin-2-yl)-3-methoxy-2-methylpropanoic acid,

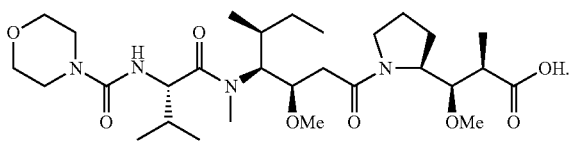

MS m/z 585.4 (M+1). Retention time 1.036 min.

Step 3: DIEA (2.8 mg, 21 μmol) and HATU (3.2 mg, 84 μmol) were added to the acid obtained in step 2 (5.0 mg, 8.4 μmol) and then stirred at rt for 5 min. S)-2-amino-3-phenylpropan-1-ol (1.3 mg, 8.4 μmol) was then added and the mixture was stirred at rt for 16 h. The crude was then purified by preparative HPLC (10-70% acetonitrile-H₂O containing 0.05% TFA) to obtain compound (FP-25). MS m/z 718.5 (M+1). Retention time 1.097 min.

EXAMPLE 25

Synthesis of (S)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-methylmorpholine-4-carboxamide (FP-26)

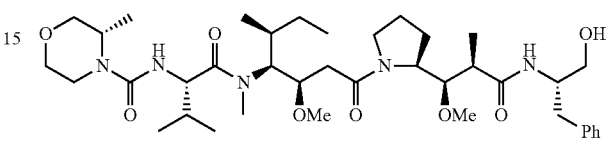

Compound (FP-26) (MS m/z 732.5 (M+1); Retention time 1.136 min.) was prepared using the method described in Example 24 except (S)-3-methylmorpholine was used in step 1 rather than morpholine.

EXAMPLE 26

Synthesis of (2S,6R)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,6-dimethylmorpholine-4-carboxamide (FP-27)

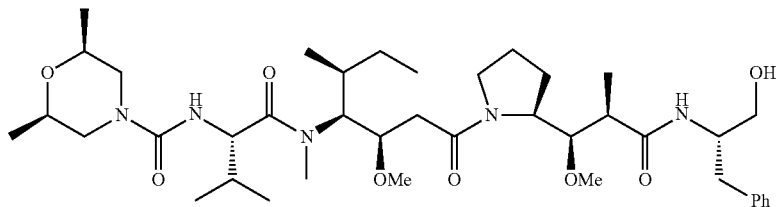

Compound (FP-27) (MS m/z 746.5 (M+1); Retention time 1.193 min.) was prepared using the method described in Example 24 except (2R,6S)-2,6-dimethylmorpholine was used in step 1 rather than morpholine.

EXAMPLE 27

Synthesis of (R)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methylmorpholine-4-carboxamide (FP-28)

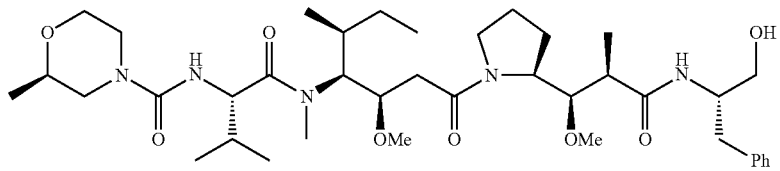

Compound (FP-28) (MS m/z 732.5 (M+1); Retention time 1.143 min.) was prepared using the method described in Example 24 except (R)-2-methylmorpholine HCl salt was used in step 1 rather than morpholine.

EXAMPLE 28

Synthesis of (S)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methylmorpholine-4-carboxamide (FP-29)

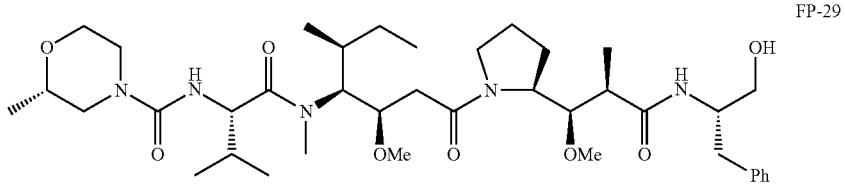

FP-29

Compound (FP-29) (MS m/z 732.5 (M+1); Retention time 1.144 min.) was prepared using the method described in Example 24 except (S)-2-methylmorpholine HCl salt was used in step 1 rather than morpholine.

EXAMPLE 29

Synthesis of (R)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-methylmorpholine-4-carboxamide (FP-30)

FP-30

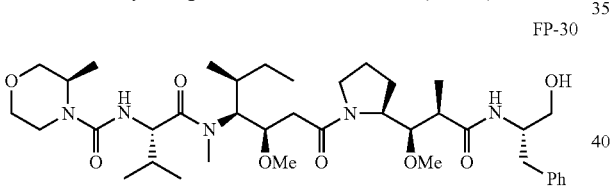

Compound (FP-30) (MS m/z 732.5 (M+1); Retention time 1.145 min.) was prepared using the method described in Example 24 except (R)-3-methylmorpholine HCl salt was used in step 1 rather than morpholine.

EXAMPLE 30

Synthesis of (2S,6S)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,6-dimethylmorpholine-4-carboxamide (FP-31)

FP-31

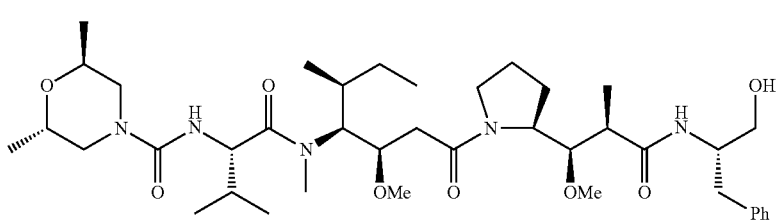

Compound (FP-31) (MS m/z 746.5 (M+1); Retention time 1.179 min.) was prepared using the method described in Example 24 except (2S,6S)-2,6-dimethylmorpholine was used in step 1 rather than morpholine.

EXAMPLE 31

Synthesis of N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-oxopiperazine-1-carboxamide (FP-32)

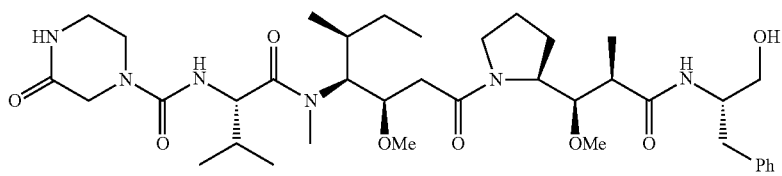

FP-32

Compound (FP-32) (MS m/z 731.5 (M+1); Retention time 1.129 min.) was prepared using the method described in Example 24 except piperazin-2-one was used in step 1 rather than morpholine.

EXAMPLE 32

Synthesis of N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,2-dimethyl-3-oxopiperazine-1-carboxamide (FP-33)

FP-33

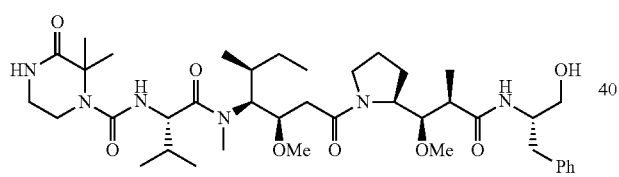

Compound (FP-33) (MS m/z 759.5 (M+1); Retention time 1.084 min.) was prepared using the method described in Example 24 except 3,3-dimethylpiperazin-2-one was used in step 1 rather than morpholine.

EXAMPLE 33

Synthesis of (S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,4-dimethylpiperazine-1-carboxamide (FP-34)

FP-34

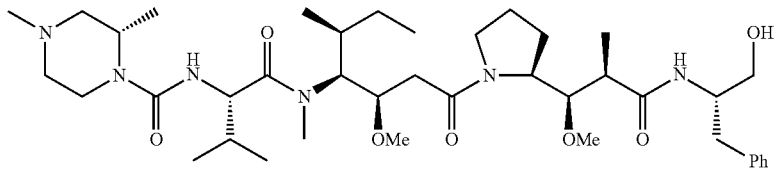

Compound (FP-34) (MS m/z 745.6 (M+1); Retention time 0.946 min.) was prepared using the method described in Example 24 except (S)-1,3-dimethylpiperazine was used in step 1 rather than morpholine.

EXAMPLE 34

Synthesis of (2R,6S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,6-dimethylpiperazine-1-carboxamide (FP-35)

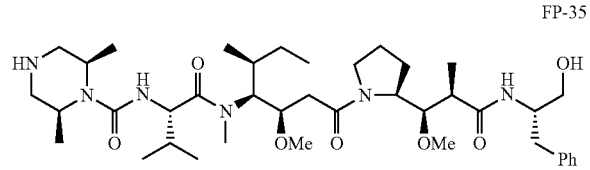

FP-35

Compound (FP-35) (MS m/z 745.6 (M+1); Retention time 0.946 min.) was prepared using the method described in Example 24 except (3S,5R)-tert-butyl 3,5-dimethylpiperazine-1-carboxylate was used in step 1 rather than morpholine and the boc protecting group was removed from the final intermediate by treatment with 5% HCl in 1:1 acetonitrile-water mixture (4 ml) and stirred for 48 h to afford the title compound as an HCl salt.

EXAMPLE 35

N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,2-dimethylpiperazine-1-carboxamide (FP-36)

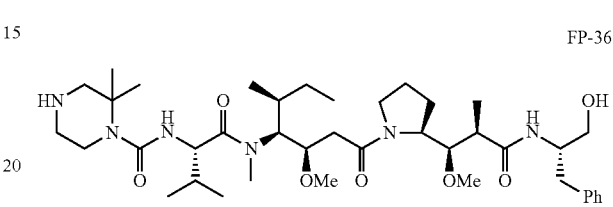

FP-36

Compound (FP-36) (MS m/z 745.5 (M+1); Retention time 0.976 min.) was prepared using the method described in Example 34 except tert-butyl 3,3-dimethylpiperazine-1-carboxylate was used in step 1 rather than (3S,5R)-tert-butyl 3,5-dimethylpiperazine-1-carboxylate.

EXAMPLE 36

(2R,6S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,4,6-trimethylpiperazine-1-carboxamide (FP-37)

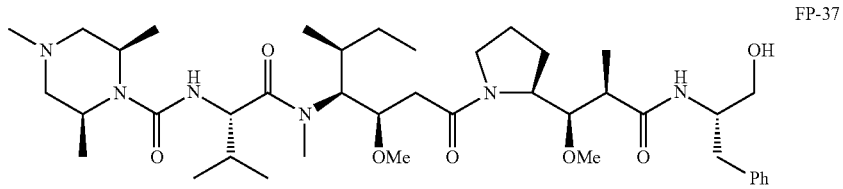

FP-37

Paraformaldehyde (1.7 mg, 56 µmol), acetic acid (5 µl, 90 µmol) and NaCNBH$_3$ (3.5 mg, 56 µmol) were added to (2R,6S)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,6-dimethylpiperazine-1-carboxamide HCl salt (FP-35) (4.4 mg, 56 µmol) in MeOH (2 ml), and then stirred at rt for 16 h. Preparative HPLC purification (10-45% acetonitrile-H$_2$O containing 0.05% TFA) followed by HCl treatment afforded the title compound (FP-37) as HCl salt. MS m/z 759.6 (M+1). Retention time 0.950 min.

EXAMPLE 37

N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,2,4-trimethylpiperazine-1-carboxamide (FP-38)

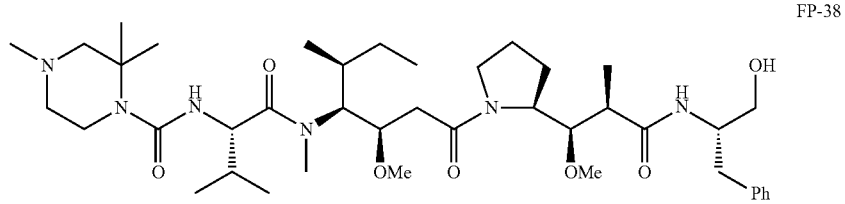

FP-38

Compound (FP-38) (MS m/z 759.6 (M+1); Retention time 0.980 min.) was prepared using the method described in Example 36 except compound (FP-37) was used rather than compound (FP-35).

EXAMPLE 38

(S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methylpiperazine-1-carboxamide (FP-39)

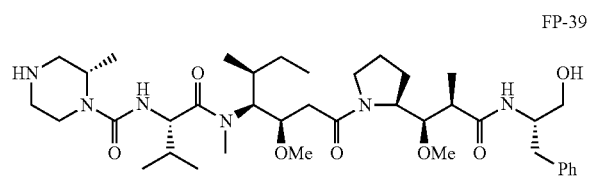

FP-39

Compound (FP-39) (MS m/z 731.6 (M+1); Retention time 0.934 min.) was prepared using the method described in Example 24 except (S)-t-butyl 3-methylpiperazine-1-carboxylate was used in step 1 rather than morpholine, and the boc protecting group was removed from the final intermediate by treatment with 5% HCl in 1:1 acetonitrile-water mixture (4 ml) and stirred for 2 h to afford the title compound as an HCl salt.

EXAMPLE 39

(R)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methylpiperazine-1-carboxamide (FP-40)

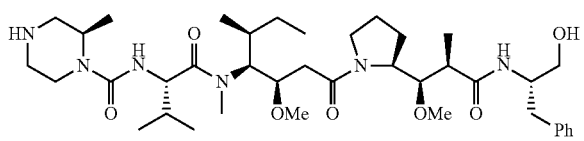

FP-40

Compound (FP-40) (MS m/z 731.5 (M+1); Retention time 0.932 min.) was prepared using the method described in Example 24 except (R)-t-butyl 3-methylpiperazine-1-carboxylate was used in step 1 rather than morpholine, and the boc protecting group was removed from the final intermediate by treatment with 5% HCl in 1:1 acetonitrile-water mixture (4 ml) and stirred for 2 h to afford the title compound as an HCl salt.

EXAMPLE 40

(S)-4-Acetyl-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methylpiperazine-1-carboxamide (FP-41)

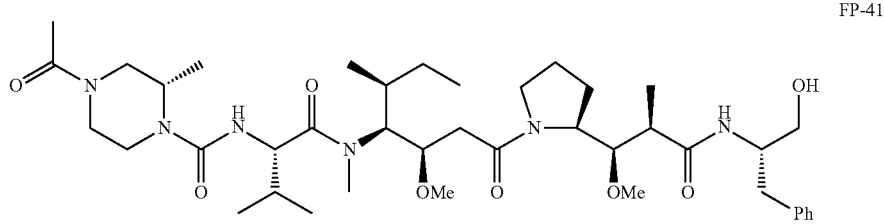

FP-41

To acetic acid (0.9 mg, 20 µmol) in DMF (0.5 ml) were added DIEA (3.9 mg, 30 µmol) and HATU (3.2 mg, 8 µmol). The resulting mixture was stirred at rt for 5 min and then added to compound (FP-39) HCl salt (5.8 mg, 7.6 µmol) in DMF (0.5 ml). The reaction mixture was stirred at rt for 1 h and then concentrated, and purified by preparative HPLC (10-60% acetonitrile-H₂O containing 0.05% TFA) to obtain the title compound (FP-41). MS m/z 773.5 (M+1). Retention time 1.061 min.

EXAMPLE 41

(R)-N-((S)-1-(((3R,4S,5S)-1-((S)-2-((1 R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2,4-dimethylpiperazine-1-carboxamide (FP-42)

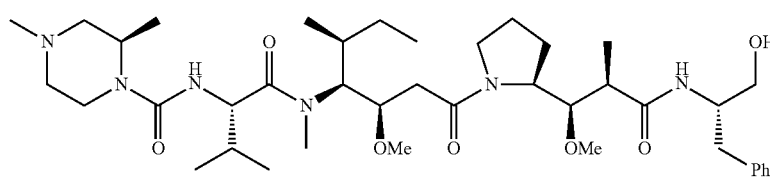

Compound (FP-42) (MS m/z 745.5 (M+1); Retention time 0.935 min.) was prepared using the method described in Example 36 except compound (FP-40) was used rather than compound (FP-35).

EXAMPLE 42

(S)-N-((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-(pyrimidin-2-ylamino)butanamide (FP-43)

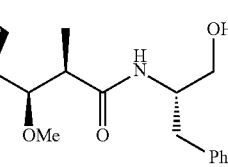

Step 1: 10% Pd on carbon (60 mg) was added to Cbz-Val-Dil-Dap-OMe (350 mg, 565 µmol) in MeOH (10 ml) and the reaction was stirred at rt for 1 h under hydrogen atmosphere and the catalyst was then removed by filtration. The filtrate was concentrated to give Val-Dil-Dap-OMe. MS m/z 486.3 (M+1). Retention time 1.070 min.

Step 2: A microwave reaction tube was charged with Val-Dil-Dap-OMe (274 mg, 565 µmol), 2-chloropyrimidine (194 mg, 1.69 mmol), DIEA (292 mg, 2.26 mmol) and sec-BuOH (5.0 ml). It was sealed and heated at 130° C. for 48 h. The reaction mixture was concentrated and purified by preparative HPLC (20-70% acetonitrile-H2O containing 0.05% TFA) to obtain (2R,3R)-methyl 3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanoate,

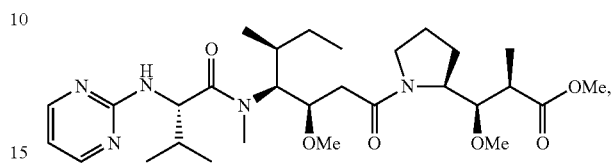

as TFA salt. MS m/z 564.4 (M+1). Retention time 1.274 min.

Step 3: Lithium hydroxide (120 mg, 5.0 mmol) was added to the product obtained in step 2 (383 mg, 565 µmol) in MeOH-H2O (1:1, 10 ml). The reaction was stirred at rt for 16 h and then heated at 60° C. for 1 h. The reaction mixture was then cooled to rt and concentrated. Hydrochloric acid (1 N) was added to the residue till precipitate was formed (pH~5). The mixture was concentrated and purified by preparative HPLC (20-60% acetonitrile-water containing 0.05% TFA)) to give (2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanoic acid,

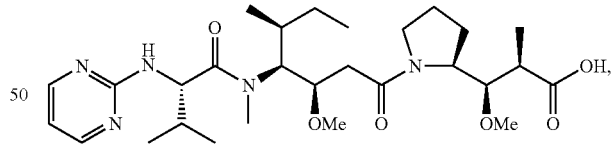

as TFA salt. MS m/z 550.3 (M+1). Retention time 1.152 min.

Step 4: DIEA (3.5 mg, 27 µmol) and then HATU (6.9 mg, 18 µmol) were added to the product obtained in step 3 (6.0 mg, 9 µmol) in DMF (0.5 ml). The mixture was stirred at rt for 5 min and then added to (S)-2-amino-3-phenylpropan-1-ol (4.1 mg, 27 µmol) in DMF (0.5 ml). The reaction mixture was stirred at rt for 16 h, and then purified by preparative HPLC (20-60% acetonitrile-H₂O containing 0.05% TFA) to obtain compound (FP-43) as TFA salt. MS m/z 683.4 (M+1). Retention time 1.264 min.

EXAMPLE 43

(S)-N-((3R,4S,5S)-1-((S)-2-((1R,2R)-3-(((S)-1-(3-aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)-N,3-dimethyl-2-(pyrimidin-2-ylamino)butanamide (FP-44)

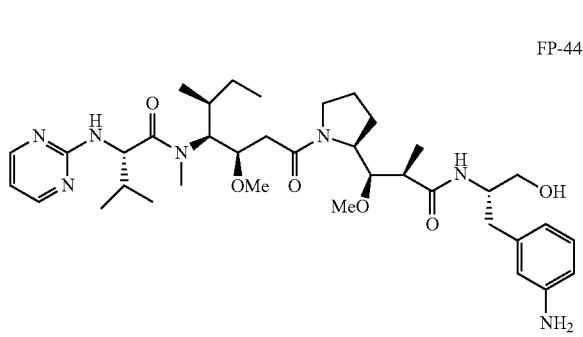

FP-44

Step 1: To a solution of (S)-2-((tert-butoxycarbonyl)amino)-3-(3-nitrophenyl)propanoic acid (562 mg, 1.81 mmol) in THF (10 ml) stirred at 0° C. under $N_2$ was added $BH_3$ in THF (1M, 10 ml) and the reaction was warmed to 50° C. and stirred for 1 h. The reaction was cooled to 0° C. and quenched with water. The quenched mixture was diluted with ethylacetate and washed with 10% aqueous $K_2CO_3$, dried over MgSO4, filtered and concentrated. The crude was purified by a silica gel column, eluted with 30-70% ethylacetate-hexanes to obtain (S)-t-butyl (1-hydroxy-3-(3-nitrophenyl)propan-2-yl)carbamate as white solid. MS m/z 319.1 (M+Na). Retention time 1.183 minute. 1H NMR (600 MHz, Chloroform-d) δ 8.13-8.04 (m, 2H), 7.57 (d, J=7.7 Hz, 1H), 7.46 (dd, J=8.9, 7.6 Hz, 1H), 4.76 (s, 1H), 3.87 (dq, J=8.0, 4.6, 4.1 Hz, 1H), 3.69 (dd, J=10.9, 3.9 Hz, 1H), 3.58 (dd, J=10.8, 4.7 Hz, 1H), 2.97 (td, J=13.1, 12.5, 7.3 Hz, 2H), 1.37 (s, 9H).

Step 2: To a solution of (S)-t-butyl (1-hydroxy-3-(3-nitrophenyl)propan-2-yl)carbamate (0.31 g, 1.046 mmol) in acetonitrile (5 ml) was added 10% HCl (5 ml). It was stirred at rt for 48 hours and then concentrated to give (S)-2-amino-3-(3-nitrophenyl)propan-1-ol as a HCl salt. MS m/z 197.2 (M+H). Retention time 0.775 minutes.

Step 3: (S)-2-amino-3-(3-nitrophenyl)propan-1-ol HCl salt (0.243 g, 1.046 mmol) obtained in step 2 was dissolved in MeOH (10 ml) and 10% palladium on carbon (50 mg, 0.047 mmol) was added. A 2 L hydrogen balloon was attached. The reaction was flushed with $H_2$ three times and then stirred at rt for 1 hour. LCMS indicated the reaction was complete. The reaction mixture was filtered through celite and then concentrated to give (S)-2-amino-3-(3-aminophenyl)propan-1-ol as HCl salt. MS m/z 167.2 (M+H). Retention time 0.373 minutes.

Step 4: (S)-2-amino-3-(3-aminophenyl)propan-1-ol HCl salt (0.212 g, 1.05 mmol) obtained in step 3 was dissolved in dioxane-water-AcOH (10:9:1, 20 ml). $Boc_2O$ (0.243 mL, 1.05 mmol) was added. The reaction was stirred at rt for 3 days. LCMS indicated still ¼ starting material remained. Additional $Boc_2O$ (150 mg) was added and the reaction was further stirred for 6 h. The reaction mixture was then concentrated and purified with preparative HPLC (10-40% acetonitrile in water with 0.05% TFA) to give (S)-t-butyl (3-(2-amino-3-hydroxypropyl)phenyl)carbamate as an oil. MS m/z 267.2 (M+H). Retention time 1.011 minutes.

Step 5: To (2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanoic acid,

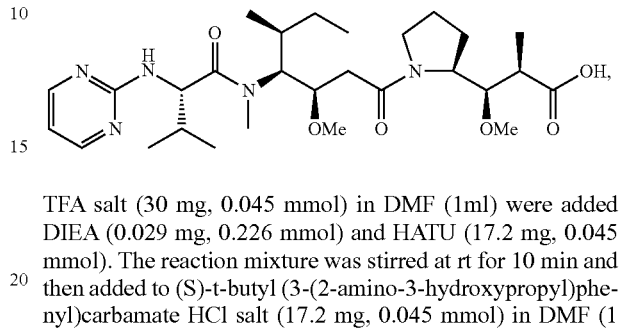

TFA salt (30 mg, 0.045 mmol) in DMF (1ml) were added DIEA (0.029 mg, 0.226 mmol) and HATU (17.2 mg, 0.045 mmol). The reaction mixture was stirred at rt for 10 min and then added to (S)-t-butyl (3-(2-amino-3-hydroxypropyl)phenyl)carbamate HCl salt (17.2 mg, 0.045 mmol) in DMF (1 ml). The reaction mixture was stirred at rt for 1 hour and then concentrated. The crude was purified by preparative HPLC (eluted with 10-70% acetonitrile-$H_2O$ containing 0.05% TFA) to obtain t-butyl (3-((S)-2-((2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanamido)-3-hydroxypropyl)phenyl)carbamate as TFA salt. MS m/z 798.5(M+H). Retention time 1.267 minutes.

Step 6: The compound obtained in step 5 (36.1 mg, 0.045 mmol) in acetonitrile-$H_2O$ (1:1, 5 ml) with 5% HCl was stirred at rt for 24 h. The reaction mixture was then concentrated and purified by preparative HPLC (eluted with 5-35% acetonitrile-$H_2O$ containing 0.05% TFA) to give compound (FP-44) as a TFA salt. MS m/z 698.5(M+H). Retention time 0.894 minutes.

EXAMPLE 44

(S)-N-((3R,4S,5S)-1-((S)-2-((1R,2R)-3-(((1S,2R)-1-Hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-(pyrimidin-2-ylamino)butanamide (FP-45)

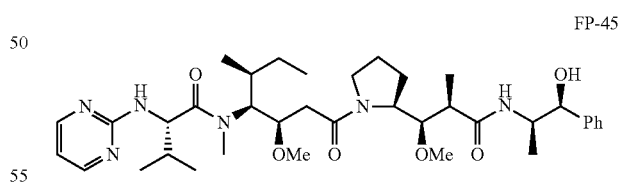

FP-45

To (2R,3R)-3-((S)-1-((3R,4S,5S)-4-((S)-N,3-dimethyl-2-(pyrimidin-2-ylamino)butanamido)-3-methoxy-5-methylheptanoyl)pyrrolidin-2-yl)-3-methoxy-2-methylpropanoic acid (8 mg, 0.015 mmol) in DMF (1 ml), were added DIEA (8.6 mg, 0.012 ml) and HATU (5.3 mg, 0.014 mmol). The reaction was stirred for 15 min and then (1S,2R)-(+)-norephedrine (2 mg, 0.013 mmol) was added. The reaction was stirred at rt for 1 h. The crude was purified by preparative HPLC (20-70% acetonitrile-$H_2O$ containing 0.05% TFA) to obtain compound (FP-45). MS m/z 683.4 (M+1). Retention time 1.241 minutes.

Synthetic Procedure for Example N-Terminal Linked Compounds of Formula (I)

EXAMPLE 45

Synthesis of (S)-2-((2R,3R)-3-((S)-1-((3R,4S,5S)-4-((S)-2-((E)-((dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-4)

MS m/z 276.1 (M+). Retention time 0.771 min. The product was used in the next step without further purification.

Step 2: The product obtained in Step 1 (0.462 g, 1.09 mmol) was added to a solution of 1H-benzo[d][1,2,3]triazol-1-ol (HOBt)(0.148 g, 1.09 mmol) and triethylamine (0.111 g, 1.09 mmol) in DCM (10 mL). The reaction was stirred at rt for 3 h, forming precipitates. The reaction mixture was concentrated, and the residue was washed with diethyl ether, affording Isouronium 1 hexafluorophosphate,

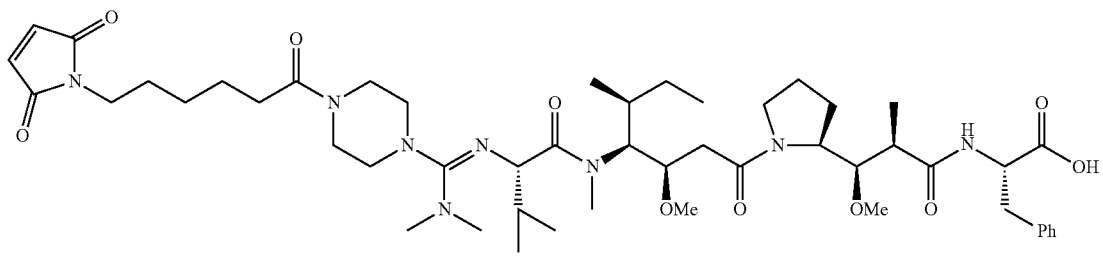

NL-4

Step 1: Oxalyl chloride (0.356 g, 2.80 mmol) in DCM (1 mL) was added dropwise to tert-butyl 4-(dimethylcarbamoyl)piperazine-1-carboxylate (0.361 g, 1.40 mmol) in DCM (5 mL) at rt over 5 min. The reaction was heated at reflux with stirring for 3 h. Conversion of the starting urea to the desired product was approximatly 70% as judged by LCMS analysis. The reaction mixture was concentrated, and treated with diethyl ether (10 mL). The solid thereby formed was sonicated and the ether layer was discarded. The solid was dissolved in DCM (10 mL and treated with saturated aq $KPF_6$ (0.8 g in 3.0 mL water). The mixture was shaken for 5 min. The DCM layer was separated, dried over $Na_2SO_4$, filtered and concentrated, affording N-((4-(tert-butoxycarbonyl)piperazin-1-yl)chloromethylene)-N-methylmethanaminium hexafluorophosphate,

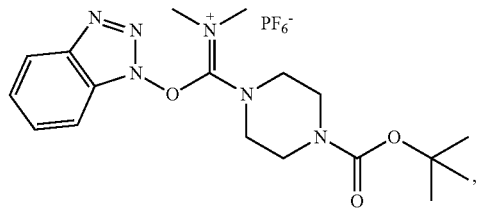

as solid. MS m/z 375.2 (M+). Retention time 0.826 min.

Step 3: To (S)-methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate (118 mg, 0.186 mmol) in DMF (5 mL) were added DIEA (120 mg, 0.928 mmol) and the product obtained in Step 2 (342 mg, 0.557 mmol). The reaction was heated at 40° C. for 12 h. The reaction mixture was concentrated and purified by ISCO using a C18 column with a 25-75% gradient of acetonitrile in $H_2O$ with 0.035% TFA to give tert-butyl 4-((E)-N'-((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)-N,N-dimethylcarbamimidoyl)piperazine-1-carboxylate (NL-1) as a TFA salt,

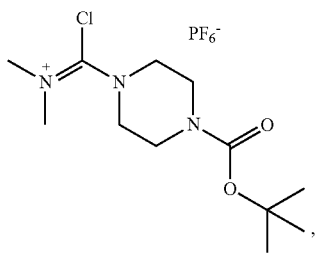

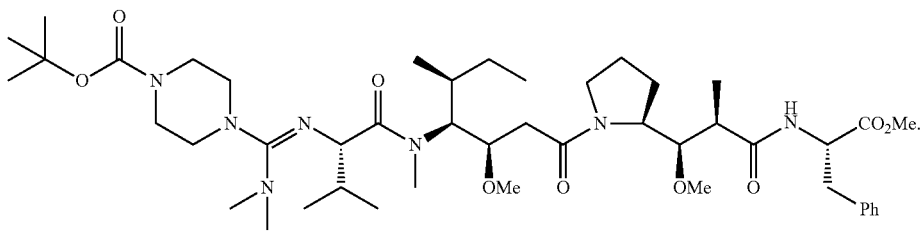

NL-1

MS m/z 872.5 (M+1). Retention time 1.159 min.
Step 4: tert-Butyl 4-((E)-N'-((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)-N,N-dimethylcarbamimidoyl)piperazine-1-carboxylate (NL-1) (0.157 g, 0.180 mmol) in DCM (10.0 mL) was treated with TFA (3.0 mL) at rt for 1 h. The reaction mixture was concentrated to obtain (S)-methyl 2-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoate (NL-2) as a TFA salt,

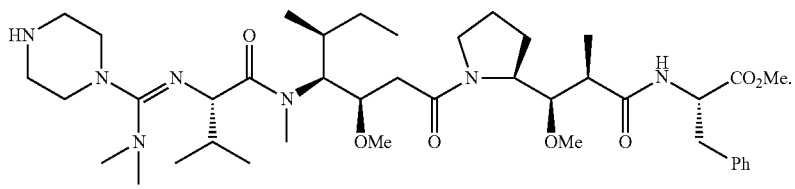

NL-2

MS m/z 772.5 (M+1). Retention time 0.924 min.
Step 5: (S)-Methyl 2-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoate (NL-2) (183 mg, 0.207 mmol) was dissolved in MeOH:H$_2$O (2:1, 9.0 ml) and LiOH (35.6 mg, 1.49 mmol) was added. The reaction mixture was stirred at rt for 2 h and concentrated. The residue was treated with acetic acid (0.060 mL) and purified by ISCO using a C18 column with a 10-70% gradient of acetonitrile in H$_2$O with 0.05% TFA to obtain (S)-2-((2R,3R)-3-((S)-1-((3R,4S,5S)-4-((S)-2-((E)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-3) as a TFA salt,

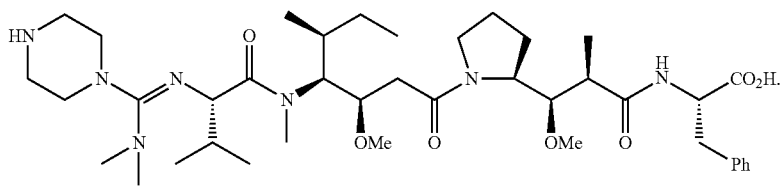

NL-3

MS m/z 758.5 (M+1). Retention time 0.860 min.

Step 6: To 6-(2,5-dioxo-2,5-dihydro-1H-pyrrol-1-yl)hexanoic acid (EMCA, 17 mg, 0.080 mmol) in DMF (2.0 mL) were added DIEA (0.042 mL, 0.241 mmol) and HATU (30.5 mg, 0.080 mmol). The reaction mixture was stirred at rt for 5 min and added to (S)-2-((2R,3R)-3-((S)-1-((3R,4S,5S)-4-((S)-2-((E)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-3) (70 mg, 0.080 mmol) in DMF (1.0 mL). The reaction was complete shortly. DMF was removed by evaporation. The residue was purified by ISCO using a C18 column with a 15-70% gradient of acetonitrile in water containing 0.05% TFA to give (S)-2-((2R,3R)-3-((S)-1-((3R,4S,5S)-4-((S)-2-((E)-((Dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-4), as a TFA salt. MS m/z 951.5 (M+1). Retention time 1.049 min.

EXAMPLE 46

Synthesis of (S)-2-((2R,3R)-3-((S)-1-((3R,4S,7S,E)-4-((S)-sec-butyl)-9-(dimethylamino)-19-(2,5-dioxo-2,5-dihydro-1H-pyrrol-1-yl)-7-isopropyl-3-methoxy-5,10,13-trimethyl-6,14-dioxo-5,8,10,13-tetraazanonadec-8-en-1-oyl)pyrrolidin-2-yl)-3-methoxy-2-methylpropanamido)-3-phenylpropanoic acid (NL-9)

diethyl ether (10 mL), and sonicated. After the ether layer was discarded, the residue was dissolved in DCM and treated with 1.5 mL saturated aq KPF$_6$ (0.38g in 1.5 mL water). The mixture was shaken for 5 min, and the DCM layer was separated, dried over Na$_2$SO$_4$, filtered and concentrated to afford N-(((2-((tert-butoxycarbonyl)(methyl)amino)ethyl)(methyl)amino)chloromethylene)-N-methylmethanaminium hexafluorophosphate. MS m/z 278.2 (M$^+$). Retention time 0.710 min. The product was used in the next step without further purification.

Step 3: The product obtained in Step 2 (179 mg, 0.422 mmol) was added to HOBt (56.9 mg, 0.421 mmol) and triethylamine (42.6 mg, 0.421 mmol) in DCM (10 mL). The reaction was stirred for 1 h. No precipitate was formed, but LCMS indicated formation of product. The reaction mixture was concentrated, and the residue was treated with diethyl ether. The insoluble residue was mainly the desired product, 2-(1H-benzo[d][1,2,3]triazol-1-yl)-1-(2-((tert-butoxycarbonyl)(methyl)amino)ethyl)-1,3,3-trimethylisouronium hexafluorophosphate,

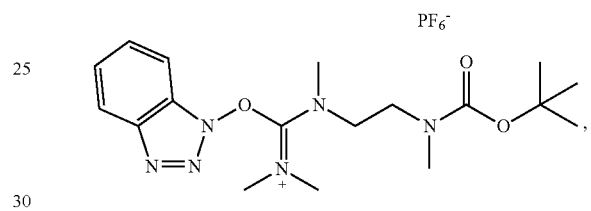

as judged by LCMS analysis. MS m/z 377.2 (M$^+$). Retention time 0.746 min. The residue was used in the next step without further purification.

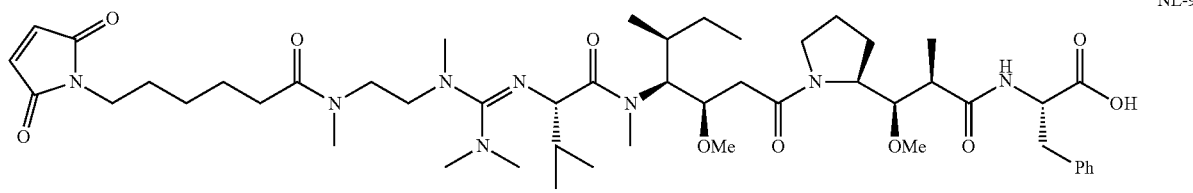

NL-9

Step 1: Dimethylcarbamic chloride (129 mg, 1.20 mmol) was added dropwise to tert-butyl(2-(dimethylamino)ethyl)carbamate (188 mg, 0.999 mmol) and triethylamine (0.139 mL, 0.999 mmol) in DCM (5 mL) at 0° C. with stirring. The reaction was stirred at rt for 1 h. The reaction mixture was basified with 1N aq NaOH, and the resulting two phases were separated. The aq phase was extracted with DCM. The combined DCM phases was washed succesively with water and saturated aq NaCl, dried over Na$_2$SO$_4$, filtered and concentrated to give tert-butyl methyl(2-(1,3,3-trimethylureido)ethyl)carbamate. MS m/z 260.2 (M+1). Retention time 1.042 min. The product was used in the next step without further purification.

Step 2: Oxalyl chloride (253 mg, 2.00 mmol) in DCM (1 mL) was added dropwise to the urea obtained in Step 1 (288 mg, 1.11 mmol) in DCM (5 mL) at rt over 5 min. The reaction mixture was heated at reflux with stirring for 3 h, and then concentrated. The residue was taken up in Step 4: DIEA (15.6 mg, 0.121 mmol) was added to the residue obtained in Step 3 (63.1 mg, 0.121 mmol) and (S)-methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate TFA salt (30 mg, 0.040 mmol) in DMF (2 mL). The reaction was stirred at rt for 2 h and then at 50° C. for 2 h. The crude material was purified by preparative HPLC using 30-55% gradient to obtain (S)-methyl 2-((2R,3R)-3-((S)-1-((11S,14S,15R,Z)-14-((S)-sec-butyl)-9-(dimethylamino)-11-isopropyl-15-methoxy-2,2,5,8,13-pentamethyl-4,12-dioxo-3-oxa-5,8,10,13-tetraazaheptadec-9-en-17-oyl)pyrrolidin-2-yl)-3-methoxy-2-methylpropanamido)-3-phenylpropanoate (NL-5) as a TFA salt.

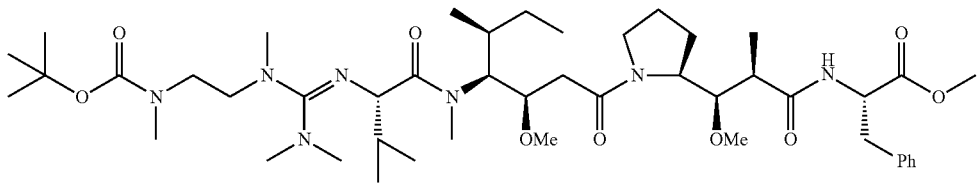

NL-5

MS m/z 874.5 (M+1). Retention time 1.179 min.

Step 5: (S)-Methyl 2-((2R,3R)-3-((S)-1-((11S,14S,15R,Z)-14-((S)-sec-butyl)-9-(dimethylamino)-11-isopropyl-15-methoxy-2,2,5,8,13-pentamethyl-4,12-dioxo-3-oxa-5,8,10,13-tetraazaheptadec-9-en-17-oyl)pyrrolidin-2-yl)-3-methoxy-2-methylpropanamido)-3-phenylpropanoate (NL-5) (17 mg, 0.020 mmol) in DCM (2 mL) was treated with TFA (2 mL). The reactiaon mixture was stirred at rt for 30 min, and concentrated to give (S)-methyl 2-((2R,3R)-3-((S)-1-((8S,11S,12R,Z)-11-((S)-sec-butyl)-6-(dimethylamino)-8-isopropyl-12-methoxy-5,10-dimethyl-9-oxo-2,5,7,10-tetraazatetradec-6-en-14-oyl)pyrrolidin-2-yl)-3-methoxy-2-methylpropanamido)-3-phenylpropanoate (NL-6) as TFA salt.

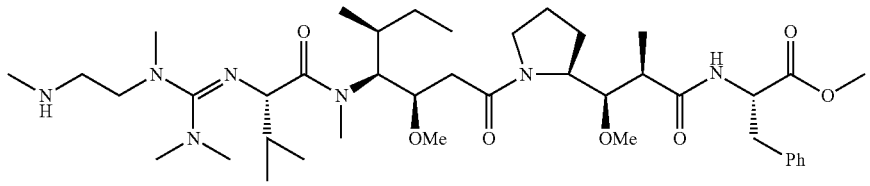

NL-6

MS m/z 774.5 (M+1). Retention time 0.899 min.

Step 6: LiOH (10 mg, 0.42 mmol) was added to (S)-methyl 2-((2R,3R)-3-((S)-1-((8S,11S,12R,Z)-11-((S)-sec-butyl)-6-(dimethylamino)-8-isopropyl-12-methoxy-5,10-dimethyl-9-oxo-2,5,7,10-tetraazatetradec-6-en-14-oyl)pyrrolidin-2-yl)-3-methoxy-2-methylpropanamido)-3-phenylpropanoate (NL-6) (24 mg, 0.027 mmol) in MeOH: H$_2$O (2:1, 6 mL). The reaction was stirred at rt for 0.5 h. LCMS indicated urea NL-8 formed along with NL-7. The reaction mixture was concentrated. The residue was purified by preparative HPLC using a 20-55% gradient. Fractions containing NL-7 and NL-8 were separately collected and concentrated to give (S)-2-((2R,3R)-3-((S)-1-((8S,11S,12R,Z)-11-((S)-sec-butyl)-6-(dimethylamino)-8-isopropyl-12-methoxy-5,10-dimethyl-9-oxo-2,5,7,10-tetraazatetradec-6-en-14-oyl)pyrrolidin-2-yl)-3-methoxy-2-methylpropanamido)-3-phenylpropanoic acid (NL-7) as a TFA salt,

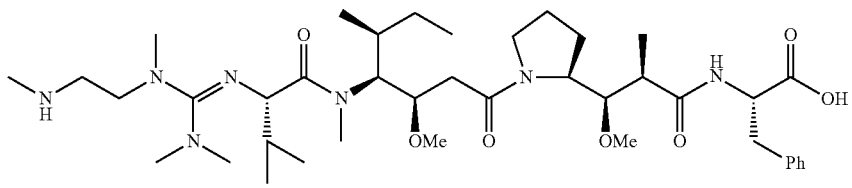

NL-7

MS m/z 760.5 (M+1), retention time 0.868 min; and (S)-2-((2R,3R)-3-((S)-1-((8S,11S,12R)-11-((S)-sec-butyl)-8-isopropyl-12-methoxy-5,10-dimethyl-6,9-dioxo-2,5,7,10-tetraazatetradecan-14-oyl)pyrrolidin-2-yl)-3-methoxy-2-methylpropanamido)-3-phenylpropanoic acid (NL-8) as a TFA salt.

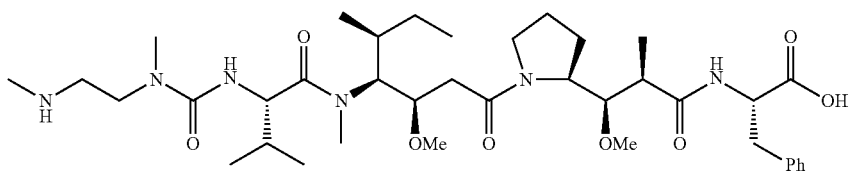

NL-8

MS m/z 733.4 (M+1). Retention time 0.954 min.

Step 7: To EMCA (2.4 mg, 0.011 mmol) in DMF (2 mL) were added DIEA (6.0 mg, 0.046 mmol) and HATU (4.0 mg, 0.010 mmol). The reaction mixture was stirred for 5 min, and added to (S)-2-((2R,3R)-3-((S)-1-((8S,11S,12R,Z)-11-((S)-sec-butyl)-6-(dimethylamino)-8-isopropyl-12-methoxy-5,10-dimethyl-9-oxo-2,5,7,10-tetraazatetradec-6-en-14-oyl)pyrrolidin-2-yl)-3-methoxy-2-methylpropanamido)-3-phenylpropanoic acid (NL-7) TFA salt (5.5 mg, 0.0056 mmol). The reaction was stirred at rt for 30 min. The crude material was purified by preparative HPLC using a 30-50% gradient to obtain (S)-2-((2R,3R)-3-((S)-1-((3R,4S,7S,E)-4-((S)-sec-Butyl)-9-(dimethylamino)-19-(2,5-dioxo-2,5-dihydro-1H-pyrrol-1-yl)-7-isopropyl-3-methoxy-5,10,13-trimethyl-6,14-dioxo-5,8,10,13-tetraazanonadec-8-en-1-oyl)pyrrolidin-2-yl)-3-methoxy-2-methylpropanamido)-3-phenylpropanoic acid (NL-9). MS m/z 953.5 (M+1). Retention time 1.057 min.

EXAMPLE 47

Synthesis of (S)-2-((E)-((dimethylamino)(4-(6-(2,5-dioxo-2,5-dihydro-1H-pyrrol-1-yl)hexanoyl)piperazin-1-yl)methylene)amino)-N-((3R,4S,5S)-3-methoxy-1-((S)-2-((1R,2R)-1-methoxy-2-methyl-3-oxo-3-(((S)-2-phenyl-1-(2H-tetrazol-5-yl)ethyl)amino)propyl)pyrrolidin-1-yl)-5-methyl-1-oxoheptan-4-yl)-N,3-dimethylbutanamide (NL-12)

remained. The aq layer was extracted twice with EtOAc. The combined organic layers was washed with water, dried over Na$_2$SO$_4$, and filtered. The solvent was removed by evapolation, and the residue was purified by silica gel flash chromatography (10% MeOH in DCM). Fractions containing the desired product were concentrated, re-dissolved in EtOAc, washed with brine, dried and concentrated to give (S)-tert-butyl (2-phenyl-1-(2H-tetrazol-5-yl)ethyl)carbamate. MS m/z 290.2 (M+1). Retention time 0.990 min. $^1$H NMR (400 MHz, CDCl$_3$) δ 7.40-7.24 (m, 3H), 7.22-7.12 (m, 2H), 5.22-5.02 (m, 2H), 3.49-3.24 (m, 2H), 1.40 (s, 9H).

Step 2: In a 15 mL round bottom flask were combined (S)-tert-butyl (2-phenyl-1-(2H-tetrazol-5-yl)ethyl)carbamate (30 mg, 0.104 mmol), TFA (2 mL) and DCM (4 mL), resulting in a clear solution. The solution was stirred at rt for 1 h, and concentrated to obtain (S)-2-phenyl-1-(2H-tetrazol-5-yl)ethanamine as TFA salt (M+1 190.2). Retention time 0.422 min. It was used without further purification in the next step.

Step 3: A 15 ml round bottom flask was charged with Boc-Val-Dil-Dap-OH (59.3 mg, 0.104 mmol), DIEA (0.072 mL, 0.415 mmol) and DMF (2 ml), followed by HATU (43.4 mg, 0.114 mmol). The reaction was stirred for 5 min, and (S)-2-phenyl-1-(2H-tetrazol-5-yl)ethanamine TFA salt obtained in Step 2 (0.104 mmol) was added. The reaction was stirred at rt for 72 h. The crude material was purified by preparative HPLC using a 10-70% gradient to obtain tert-butyl ((S)-1-(((3R,4S,5S)-3-methoxy-1-((S)-2-((1R,2R)-1-methoxy-2-methyl-3-oxo-3-(((S)-2-phenyl-1-(1H-tetrazol-5-ypethyl)amino)propyl)pyrrolidin-1-yl)-5-methyl-1-oxoheptan-4-yl)(methyl)amino)-3-methyl-1-oxobutan-2-yl)carbamate,

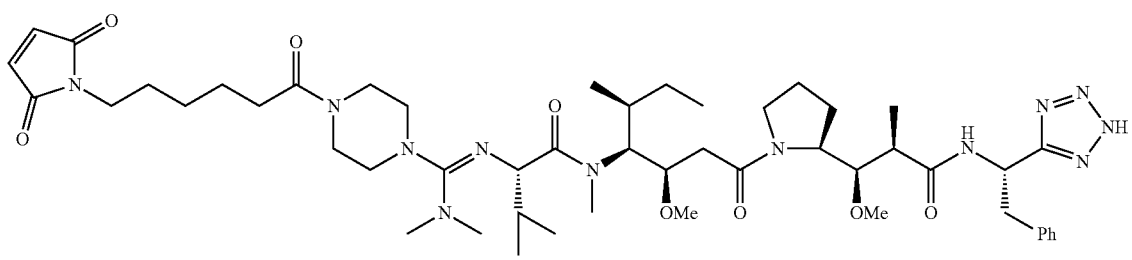

NL-12

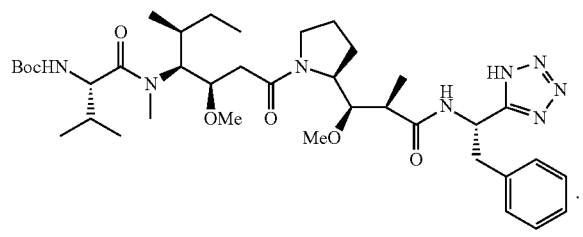

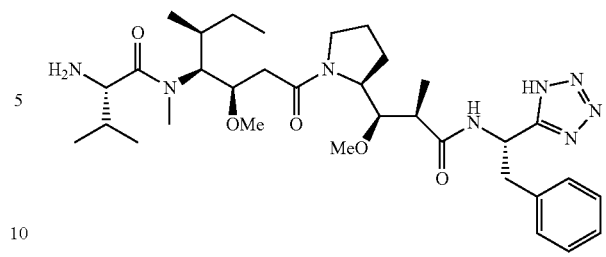

MS m/z 743.5 (M+1). Retention time 1.373 min.

Step 4: In a 15 mL round bottom flask were combined tert-butyl ((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)carbamate (46 mg, 0.056 mmol), TFA (2 mL and DCM (4 mL), resulting in a clear solution. The solution was stirred at rt for 1 h, and concentrated to obtain (S)-2-amino-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide as TFA salt, MS m/z 643.5 (M+1). Retention time 0.929 min. It was used in the next step without further purification.

Step 5: DIEA (0.028 ml, 0.16 mmol) was added to (S)-2-amino-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide TFA salt (40 mg, 0.053 mmol) and Isouronium 1 (27.6 mg, 0.053 mmol) in DMF (2 mL). The reaction was stirred at rt for 1 h. The crude material was purified by preparative HPLC using a 30-55% gradient to obtain tert-butyl 4-((E)-N'-((S)-1-(((3R,4S,5S)-3-methoxy-1-((S)-2-((1R,2R)-1-methoxy-2-methyl-3-oxo-3-(((S)-2-phenyl-1-(2H-tetrazol-5-yl)ethyl)amino)propyl)pyrrolidin-1-yl)-5-methyl-1-oxoheptan-4-yl)(methyl)amino)-3-methyl-1-oxobutan-2-yl)-N,N-dimethylcarbamimidoyl)piperazine-1-carboxylate (NL-10) as a TFA salt,

NL-10

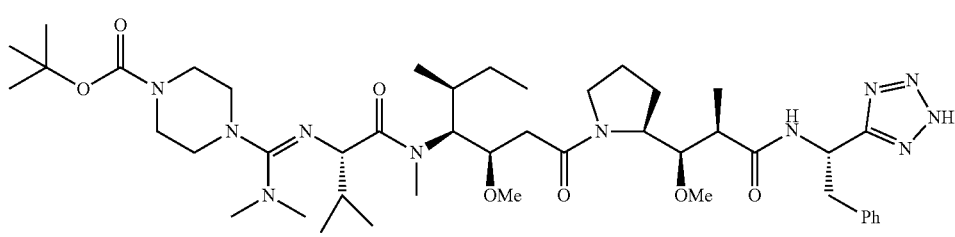

MS m/z 882.6 (M+1). Retention time 1.174 min.

Step 6: tert-Butyl 4-((E)-N'-((S)-1-(((3R,4S,5S)-3-methoxy-1-((S)-2-((1R,2R)-1-methoxy-2-methyl-3-oxo-3-(((S)-2-phenyl-1-(2H-tetrazol-5-yl)ethyl)amino)propyl)pyrrolidin-1-yl)-5-methyl-1-oxoheptan-4-yl)(methyl)amino)-3-methyl-1-oxobutan-2-yl)-N,N-dimethylcarbamimidoyl)piperazine-1-carboxylate (NL-10) (46.6 mg, 0.053 mmol) in DCM (1 mL) was treated with TFA (1 mL) at rt for 2 h and concentrated. The crude material was purified by preparative HPLC using a 10-45% gradient to obtain (S)-2-((Z)-((dimethylamino)(piperazin-1-yl)methylene)amino)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide (NL-11) as a TFA salt,

NL-11

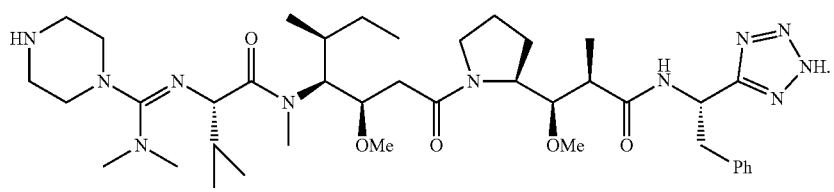

MS m/z 782.5 (M+1). Retention time 0.869 min.

Step 7: To EMCA (1.9 mg, 0.0092 mmol) in DMF (1 mL) were added DIEA (4.9 mg, 0.038 mmol) and HATU (3.5 mg, 0.0092 mmol). The reaction mixture was stirred for 5 min, and added to (S)-2-((Z)-((dimethylamino)(piperazin-1-yl)methylene)amino)-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide (NL-11) (5.0 mg, 0.0044 mmol). The reaction was complete within 10 min as judged by LCMS. The crude material was purified by preparative HPLC using a 30-50% gradient to obtain (S)-2-((E)-((dimethylamino)(4-(6-(2,5-dioxo-2,5-dihydro-1H-pyrrol-1-yl)hexanoyl)piperazin-1-yl)methylene)amino)-N-((3R,4S,5S)-3-methoxy-1-((S)-2-((1R,2R)-1-methoxy-2-methyl-3-oxo-3-(((S)-2-phenyl-1-(2H-tetrazol-5-yl)ethyl)amino)propyl)pyrrolidin-1-yl)-5-methyl-1-oxoheptan-4-yl)-N,3-dimethylbutanamide (NL-12). MS m/z 975.6 (M+1). Retention time 1.074 min.

EXAMPLE 48

Synthesis of (2R)-2-acetamido-3-((1-(6-(4-((E)-N'-((S)-1-(((3R,4S,5S)-1-((S)-2-((1R,2R)-3-(((S)-1-carboxy-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazin-1-yl)-6-oxohexyl)-2,5-dioxopyrrolidin-3-yl)thio)propanoic acid (NL-13)

NL-13

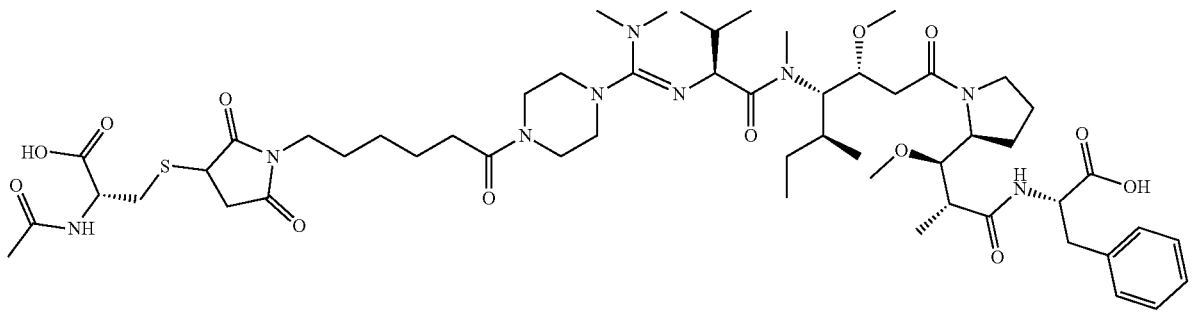

(S)-2-((2R,3R)-3-((S)-1-((3R,4S,5S)-4-((S)-2-((E)-((Dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-4) (3.6 mg, 0.0034 mmol) was dissolved in 50% acetonitrile in water (3 mL), and L-acetyl cysteine (1.1 mg, 0.0067 mmol) in pH7.5 phosphate buffer was added. LCMS analysis indicated that the product formed quantitatively. The crude material was purified by preparative HPLC using a 20-70% gradient to obtain (2R)-2-acetamido-3-((1-(6-(4-((E)-N'-((S)-1-(((3R,4S,5S)-1-((S)-2-((1R,2R)-3-(((S)-1-carboxy-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazin-1-yl)-6-oxohexyl)-2,5-dioxopyrrolidin-3-yl)thio)propanoic acid (NL-13). MS m/z 1114.6 (M+1). Retention time 0.973 min.

EXAMPLE 49

Synthesis of (S)-2-((2R,3R)-3-((S)-1-((3R,4S,5S)-4-((S)-2-((E)-((dimethylamino)(4-(4-(4-((2,5-dioxo-2,5-dihydro-1H-pyrrol-1-yl)methyl)-1H-1,2,3-triazol-1-yl)butanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-15)

NL-15

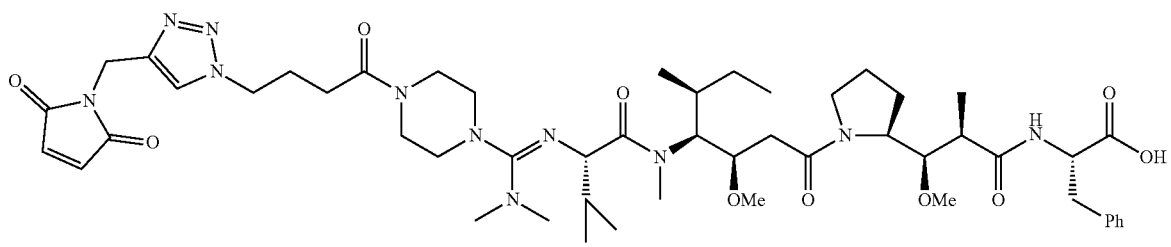

Step 1: To 4-azidobutanoic acid (1.9 mg, 0.015 mmol) in DMF (1 mL) was added DIEA (0.0076 ml, 0.044 mmol) and HATU (5.5 mg, 0.015 mmol). The reactio mixture was stirred at rt for 5 min, and added to a solution of (S)-2-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid TFA salt (NL-3)(12.7 mg, 0.015 mmol) and DIEA (0.010 ml) in DMF (1 mL). LCMS indicated the reaction was complete within 10 min. The crude material was purified by ISCO using a C18 column, with a gradient of 15-85% acetonitrile in water with 0.05% TFA to obtain (S)-2-((2R,3R)-3-((S)-1-((3R,4S,5S)-4-((S)-2-(((4-(4-azidobutanoyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-14) as a TFA salt, obtain (S)-2-((2R,3R)-3-((S)-1-((3R,4S,5S)-4-((S)-2-((E)-((dimethylamino)(4-(4-(4-((2,5-dioxo-2,5-dihydro-1H-pyrrol-1-yl)methyl)-1H-1,2,3-triazol-1-yl)butanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-15) as a TFA salt. MS m/z 1004.5 (M+1). Retention time 1.031 min.

NL-14

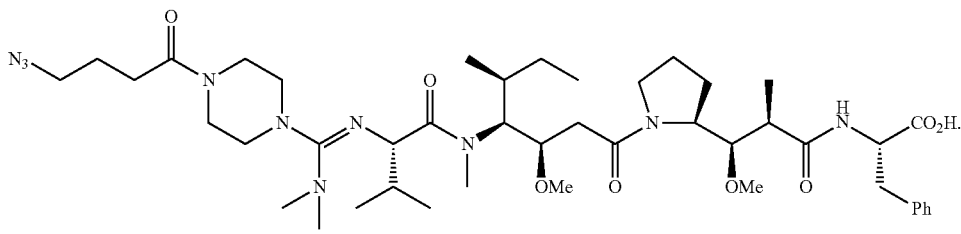

MS m/z 869.5 (M+1). Retention time 1.076 min.

Step 2: A solution of (S)-2-((2R,3R)-3-((S)-1-((3R,4S,5S)-4-((S)-2-(((4-(4-azidobutanoyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-3-phenylpropanoic acid (NL-14) TFA salt (11.6 mg, 0.012 mmol) and 1-(prop-2-yn-1-yl)-1H-pyrrole-2,5-dione (2.0 mg, 0.015 mmol) in 1:2 mixture of water and t-BuOH was degassed with Ar. Degassed aq solution of sodium L-ascorbate (5.9 mg, 0.030 mmol) and of CuSO₄ (0.5 mg, 0.003 mmol) were added. The reaction was stirred at rt for 30 min. The solvents were removed by evaporation. The residue was purified by preparative HPLC using a 20-45% gradient to

EXAMPLE 50

Synthesis of (2R)-2-acetamido-3-((1-((1-(4-(4-((Z)-N'-((S)-1-(((3R,4S,5S)-1-((S)-2-((1R,2R)-3-(((S)-1-carboxy-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazin-1-yl)-4-oxobutyl)-1H-1,2,3-triazol-4-yl)methyl)-2,5-dioxopyrrolidin-3-yl)thio)propanoic acid (NL-16)

NL-16

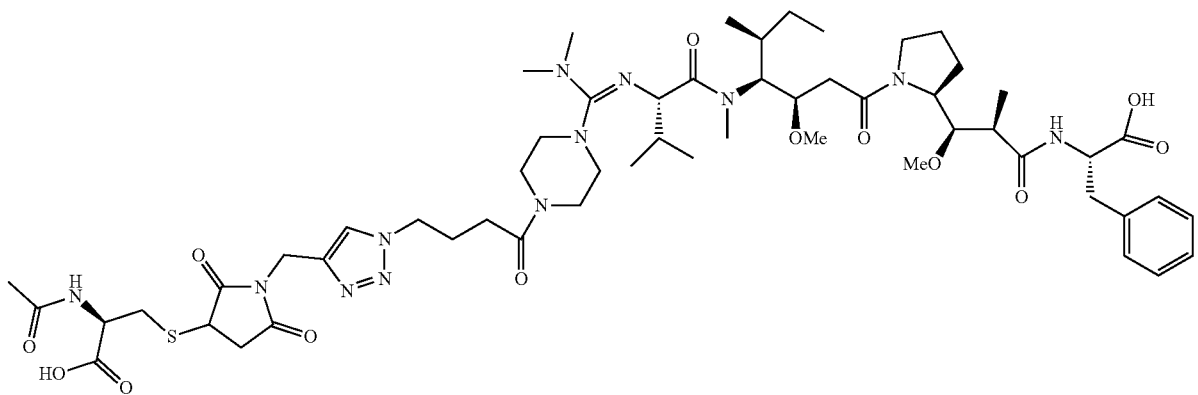

To (S)-2-((2R,3R)-3-((S)-1-((3R,4S,5S)-4-((S)-2-((E)-((dimethylamino)(4-(4-(4-((2,5-dioxo-2,5-dihydro-1H-pyrrol-1-yl)methyl)-1H-1,2,3-triazol-1-yl)butanoyl)piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanoic acid TFA salt (NL-15) (2.0 mg, 0.0018 mmol) in acetonitrile was added acetyl cysteine (0.3 mg, 0.002 mmol) in pH 7.5 phosphate buffer. Upon completion of the reaction, the desired product was purified by preparative HPLC usin a 20-50% gradient to obtain (2R)-2-acetamido-3-((1-((1-(4-(4-((Z)-N'-((S)-1-(((3R,4S,5S)-1-((S)-2-((1R,2R)-3-(((S)-1-carboxy-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazin-1-yl)-4-oxobutyl)-1H-1,2,3-triazol-4-Amethyl)-2,5-dioxopyrrolidin-3-yl)thio)propanoic acid (NL-16). MS m/z 1167.5 (M+1). Retention time 0.986 min.

EXAMPLE 51

Synthesis of ((R)-1-((2R,3R)-3-((S)-1-((3R,4S,5S)-4-((S)-2-((E)-((dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-19)

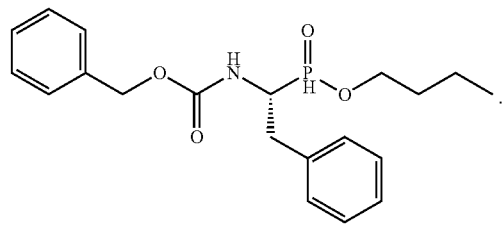

MS m/z 392.1 (M+1). Retention time 1.179 min. 1H NMR (400 MHz, CD$_3$CN) d 7.42-7.18 (m, 8H), 7.18-7.00 (m, 2H), 6.10 (s, 1H), 5.07-4.59 (m, 2H), 4.20-4.35 (m, 1H), 4.13-3.93 (m, 2H), 3.15-3.30 (m, 1H), 2.85-2.75 (s, 1H), 1.71-1.47 (m, 2H), 1.47-1.23 (m, 2H), 0.89 (t, J=7.3 Hz, 3H).

Step 2: To a solution of benzyl ((1R)-1-(butoxy(hydroxy)phosphoryl)-2-phenylethyl)carbamate (84.7 mg, 0.216 mmol) in MeOH (5 mL) was added 10% Pd/C (26 mg). The reaction was stirred at rt for 2 h under H$_2$ atmosphere. The catalyst was removed by filtration through Celite, and the filtrat was concentrated to give butyl hydrogen ((R)-1-amino-2-phenylethyl)phosphonate,

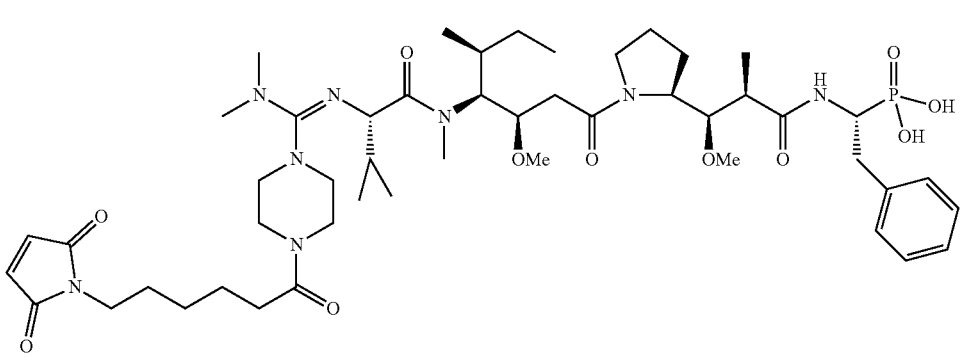

NL-19

Step 1: ((R)-1-(((benzyloxy)carbonyl)amino)-2-phenylethyl)phosphinic acid (synthesized by following the schemes described in J Organometallic Chem 646 (2002) 212 and J Chem Soc Perkin Trans I: Organic and Bio-Organic Chemistry (1984), (12), 2845) (100 mg, 0.313 mmol) was dissolved in pyridine (5 ml) and n-BuOH (35 mg, 0.46 mmol), followed by an addition of pivaloyl chloride (70 mg, 0.58 mmol). Three more equal portions of n-BuOH and pivaloyl chloride were added until all of the phosphinic acid was consumed as judged by LCMS. A solution of iodine (160 mg, 0.630 mmol) in 2 mL pyridine-H$_2$O (10% water) was added. The reaction was stirred for 20 min. LCMS indicated that the reaction was complete. Pyridine was removed by evapolation. Aq sodium thiosulfate was added and the reaction mixture was extracted with EtOAc. EtOAc layer was dried over Na2SO4, filtered, and concentrated. The residue was purified with ISCO using a C18 column with a 10%-60% gradient of acetonitrile in water with 0.5% TFA to obtain benzyl ((1R)-1-(butoxy(hydroxy)phosphoryl)-2-phenylethyl)carbamate as white solid,

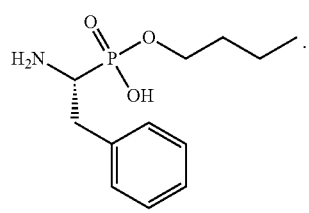

MS m/z 258.1 (M+1). Retention time 0.789 min. This material was used in step 3 without further purification.

Step 3: In a 15 mL round-bottomed flask was combined Boc-Val-Dip-Dap-OH (80 mg, 0.140 mmol), DIEA (62.9 mg, 0.487 mmol) and DMF (2 mL), followed by HATU (53 mg, 0.139 mmol). The reaction was stirred for 5 min, and the product obtained in Step 2 (41.9 mg, 0.163 mmol) was added. The resulting solution was stirred at rt for 16 h. The crude material was purified by preparative HPLC using a 40-60% gradient to obtain tert-butyl ((2S)-1-(((3R,4S,5S)-1-((2S)-2-((1R,2R)-3-((1-(butoxy(hydroxy)phosphoryl)-2-phenylethyl)amino)-1-methoxy-2-methyl- 3-oxopropyl)pyrrolidin-1-yl)-3-methoxy-5-methyl-1-oxoheptan-4-yl)(methyl)amino)-3-methyl-1-oxobutan-2-yl)carbamate,

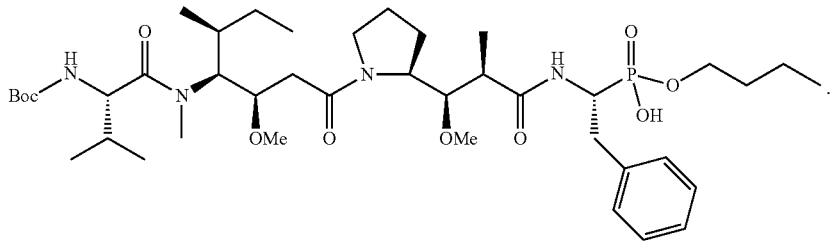

MS m/z 811.4 (M+1). Retention time 1.376 min.

Step 4: TFA (1 mL) was added to the product obtained in Step 3 (106 mg, 0.131 mmol) in DCM (3 mL). The reaction mixture was stirred at rt for 1 h, and concentrated to give ((R)-1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)phosphonic acid TFA salt,

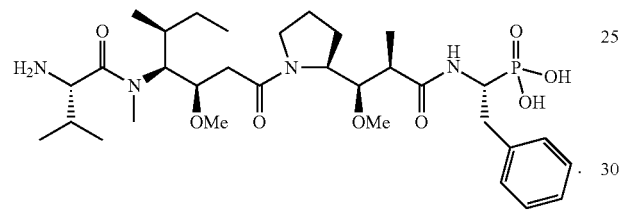

MS m/z 655.3 (M+1). Retention time 0.957 min.

Step 5: To the product obtained in Step 4 (22.6 mg, 0.029 mmol) in DMF (1 ml) were added Isouronium 1 (30.7 mg, 0.059 mmol) and DIEA (19.0 mg, 0.15 mmol). The reaction was heated at 40° C. for 2 h and the reaction mixture was purified by preparative HPLC using a 25-42% gradient to obtain ((R)-1-((2R,3R)-3-((S)-1-((3R,4S,5S)-4-((S)-2-((Z)-((4-(tert-butoxycarbonyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-17) as a TFA salt,

NL-17

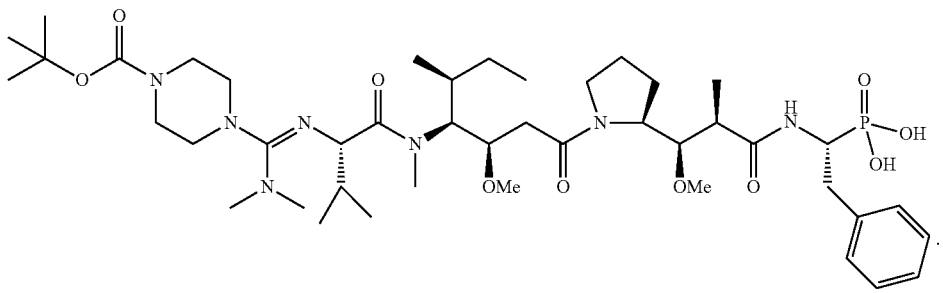

MS m/z 894.5 (M+1). Retention time 1.067 min.

Step 6: ((R)-1-((2R,3R)-3-((S)-1-((3R,4S,5S)-4-((S)-2-((Z)-((4-(tert-Butoxycarbonyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-17) TFA salt (9 mg, 0.01 mmol) was dissolved in DCM (2 ml) and TFA (1 ml) was added. The reaction mixture was stirred at rt for 1 h and concentrated to obtain ((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-18) as a TFA salt,

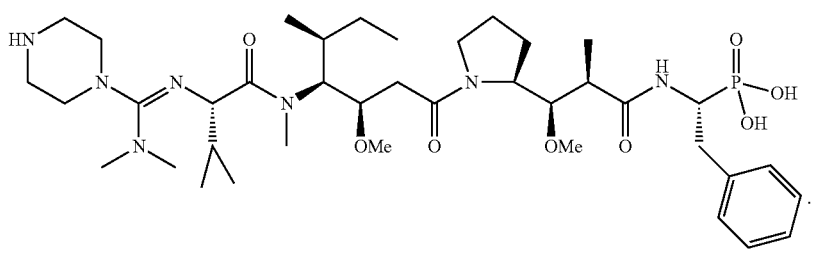

NL-18

MS m/z 794.5 (M+1). Retention time 0.842 min.

Step 7: To EMCA (0.7 mg, 0.003 mmol) in DMF (1 mL) was added DIEA (0.0017 mL, 0.0099 mmol) and HATU (1.4 mg, 0.0036 mmol). The reaction mixture was stirred for 5 min, and added to ((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-18) (3 mg, 0.003 mmol) in DMF (0.5 mL). The reaction was complete within 5 min as indicated by LCMS. The reaction mixture was purified by preparative HPLC using a 25-34% gradient to obtain ((R)-1-((2R,3R)-3-((S)-1-((3R,4S,5S)-4-((S)-2-((E)-((dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-19) as a TFA salt. MS m/z 987.5 (M+1). Retention time 1.042 min.

EXAMPLE 52

Synthesis of ((R)-1-((2R,3R)-3-((S)-1-((3R,4S,5S)-4-((S)-2-((E)-((dimethylamino)(4-(4-(4-((2,5-dioxo-2,5-dihydro-1H-pyrrol-1-yl)methyl)-1H-1,2,3-triazol-1-yl)butanoyl)piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-21)

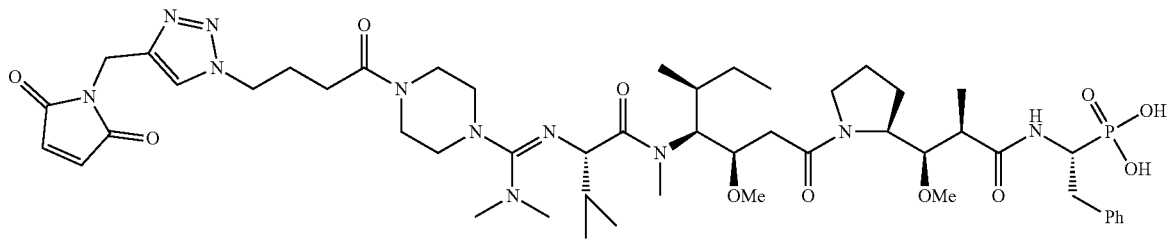

NL-21

Step 1: To 4-azidobutanoic acid (0.8 mg, 0.007 mmol) in DMF (1 mL) was added DIEA (2.6 mg, 0.020 mmol) and HATU (2.5 mg, 0.0066 mmol). The reaction mixture was stirred for 5 min, and added to ((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-18) TFA salt (6.0 mg, 0.0066 mmol) in DMF (0.5 mL). The reaction was complete within 5 min as indicated by LCMS. The crude material was purified by preparative HPLC using a 25-32% gradient to obtain ((R)-1-((2R,3R)-3-((S)-1-((3R,4S,5S)-4-((S)-2-((Z)-((4-(4-Azidobutanoyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-20) as a TFA salt,

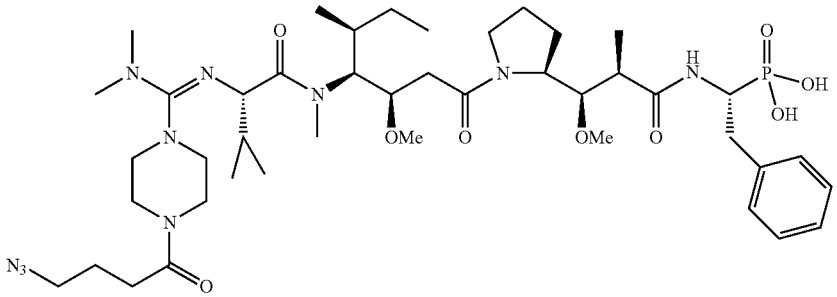

NL-20

MS m/z 905.5 (M+1). Retention time 1.048 min.

Step 2: A solution of ((R)-1-((2R,3R)-3-((S)-1-((3R,4S,5S)-4-((S)-2-((Z)-((4-(4-azidobutanoyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphonic acid (NL-20) TFA salt (4.0 mg, 0.0039 mmol) and 1-(prop-2-yn-1-yl)-1H-pyrrole-2,5-dione (1.1 mg, 0.0079 mmol) in 1:2 mixture of water-t-BuOH was degassed with Ar. To the degassed solution was added successively degassed solutions of sodium L-ascorbate (2.3 mg, 0.012 mmol) in water and of copper sulfate (0.7 mg, 0.004 mmol) in water. The reaction mixture was stirred at rt for 3 h, and concentrated. The residue was purified by preparative HPLC using a 20-32% gradient to obtain ((R)-1-((2R,3R)-3-((S)-1-((3R,4S,5S)-4-((S)-2-((E)-((dimethylamino)(4-(4-(4-((2,5-dioxo-2,5-dihydro-1H-pyrrol-1-yl)methyl)-1H-1,2,3-triazol-1-yl)butanoyl)piperazin-1-yl)methylene)amino)-N,3-dim ethylbutanamido)-3-methoxy-5-methylheptanoyl)pyrrolidin-2-yl)-3-methoxy-2-methylpropanamido)-2-phenylethyl)phosphonic acid (NL-21). MS m/z 1040.5 (M+1). Retention time 0.996 min.

EXAMPLE 53

Synthesis of (S)-2-((2R,3R)-3-((S)-1-((3R,4S,7S)-4-((S)-sec-butyl)-19-(2,5-dioxo-2,5-dihydro-1H-pyrrol-1-yl)-7-isopropyl-3-methoxy-5,10,13-trimethyl-6,9,14-trioxo-5,8,10,13-tetraazanonadecan-1-oyl)pyrrolidin-2-yl)-3-methoxy-2-methylpropanamido)-3-phenylpropanoic acid (NL-22)

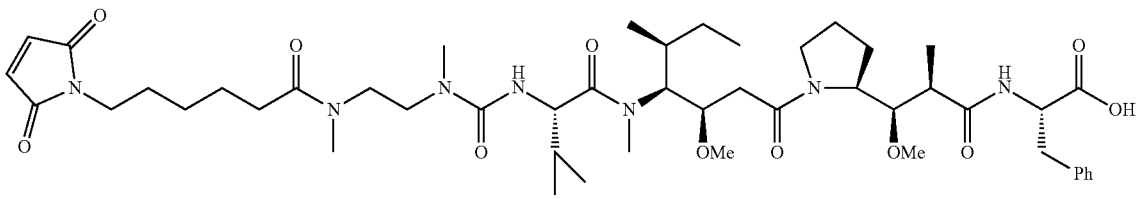

NL-22

To EMCA (2.1 mg, 0.0010 mmol) in DMF (2 mL) was added DIEA (0.0081 mL, 0.046 mmol) and HATU (3.7 mg, 0.0097 mmol). The reaction mixture was stirred for 5 min, and added to (S)-2-((2R,3R)-3-((S)-1-((8S,11S,12R)-11-((S)-sec-butyl)-8-isopropyl-12-methoxy-5,10-dimethyl-6,9-dioxo-2,5,7,10-tetraazatetradecan-14-oyl)pyrrolidin-2-yl)-3-methoxy-2-methylpropanamido)-3-phenylpropanoic acid (NL-8) TFA salt (4.3 mg, 0.0051 mmol). The reaction was stirred at rt for 30 min. The desired product was isolated by preparative HPLC using a linear gradient of 30-55%, affording (S)-2-((2R,3R)-3-((S)-1-((3R,4S,7S)-4-((S)-sec-Butyl)-19-(2,5-dioxo-2,5-dihydro-1H-pyrrol-1-yl)-7-isopropyl-3-methoxy-5,10,13-trimethyl-6,9,14-trioxo-5,8,10,13-tetraazanonadecan-1-oyl)pyrrolidin-2-yl)-3-methoxy-2-methylpropanamido)-3-phenylpropanoic acid (NL-22). MS m/z 926.4 (M+1). Retention time 1.141 min.

EXAMPLE 54

Synthesis of (S)-2-((2R,3R)-3-((S)-1-((3R,4S,5S)-4-((S)-2-(4-(6-(2,5-dioxo-2,5-dihydro-1H-pyrrol-1-yl)hexanoyl)piperazine-1-carboxamido)-N,3-dimethylbutanamido)-3-methoxy-5-methylheptanoyl)pyrrolidin-2-yl)-3-methoxy-2-methylpropanamido)-3-phenylpropanoic acid (NL-26)

NL-26

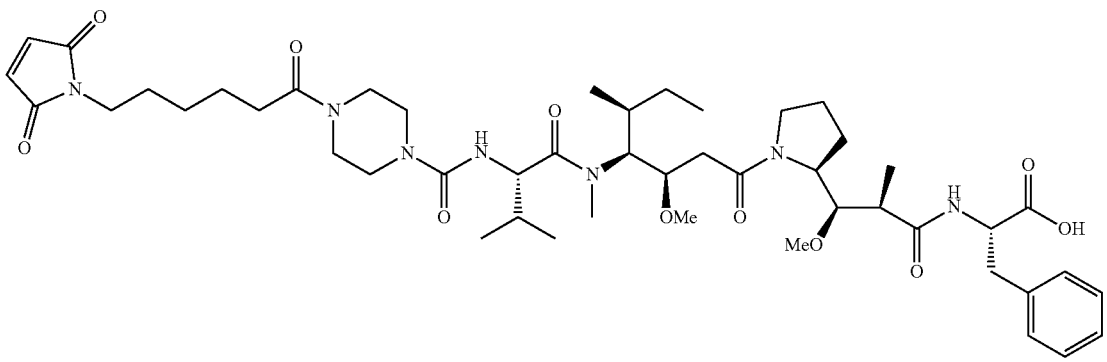

Step 1: DIEA (0.012 ml, 0.067 mmol) and 4-nitrophenyl carbonochloridate (4.5 mg, 0.022 mmol) were added to (S)-methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate HCl salt (15 mg, 0.022 mmol) in a mixture of DMF:THF (1:1, 2 mL). The reaction was stirred at rt for 1 h. LCMS indicated that formation of 4-nitrophenoxycarbamate was complete. MS m/z 798.4 (M+1). Retention time 1.409 min. To the reaction was added tert-butyl piperazine-1-carboxylate (6.3 mg, 0.034 mmol), and the reaction was stirred for an additional 1 h. The reaction mixture was purified by preparative HPLC using a 30-70% gradient to obtain tert-butyl 4-(((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)carbamoyl)piperazine-1-carboxylate (NL-23),

NL-23

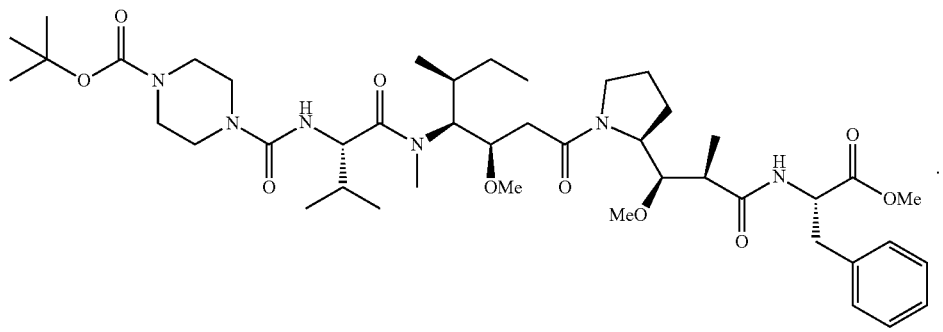

MS m/z 845.5 (M+1). Retention time 1.367 min.

Step 2: TFA (1 ml) was added to tert-butyl 4-(((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)carbamoyl)piperazine-1-carboxylate (NL-23) (14.9 mg, 0.018 mmol) in DCM (2 mL). The reaction mixture was stirred at rt for 1 h, and concentrated to give (S)-methyl 2-((2R,3R)-3-((S)-1-((3R,4S,5S)-4-((S)-N,3-dimethyl-2-(piperazine-1-carboxamido)butanamido)-3-methoxy-5-methylheptanoyl)pyrrolidin-2-yl)-3-methoxy-2-methylpropanamido)-3-phenylpropanoate (NL-24) as a TFA salt,

NL-24

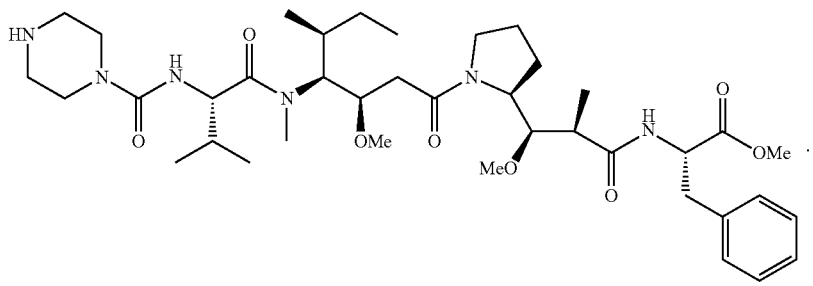

MS m/z 745.5 (M+1). Retention time 1.006 min.
Step 3: LiOH (15 mg, 0.63 mmol) was added to (S)-methyl 2-((2R,3R)-3-((S)-1-((3R,4S,5S)-4-((S)-N,3-dimethyl-2-(piperazine-1-carboxamido)butanamido)-3-methoxy-5-methylheptanoyl)pyrrolidin-2-yl)-3-methoxy-2-methylpropanamido)-3-phenylpropanoate (NL-24) TFA salt (15.5 mg, 0.018 mmol) in MeOH:H$_2$O (1:1, 2 mL). The reaction was stirred at rt for 18 h. The mixture was purified by preparative HPLC using a 20-45% gradient to obtain (S)-2-((2R,3R)-3-((S)-1-((3R,4S,5S)-4-((S)-N,3-dimethyl-2-(piperazine-1-carboxamido)butanamido)-3-methoxy-5-methylheptanoyl)pyrrolidin-2-yl)-3-methoxy-2-methylpropanamido)-3-phenylpropanoic acid (NL-25) as a TFA salt,

NL-25

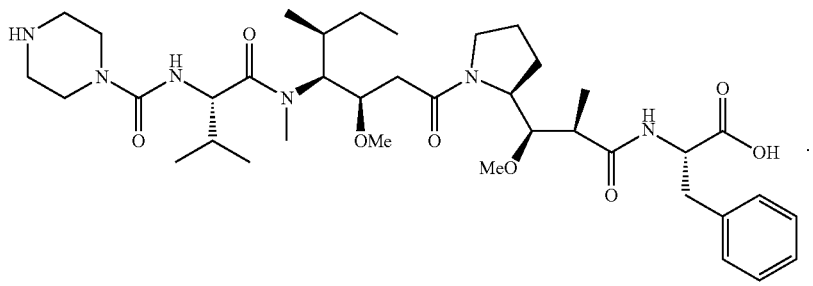

MS m/z 731.4 (M+1). Retention time 0.918 min.
Step 4: HATU (6.8 mg, 0.018 mmol) was added to EMCA (3.8 mg, 0.018 mmol) and DIEA (0.0094 ml, 0.054 mmol) in DMF (1 mL). The reaction mixture was stirred for 5 min, and added to (S)-2-((2R,3R)-3-((S)-1-((3R,4S,5S)-4-((S)-N,3-dimethyl-2-(piperazine-1-carboxamido)butanamido)-3-methoxy-5-methylheptanoyl)pyrrolidin-2-yl)-3-methoxy-2-methylpropanamido)-3-phenylpropanoic acid (NL-25) TFA salt (16 mg, 0.019 mmol). The reaction mixture was stirred for 2 h at rt, and purified by preparative HPLC using a 20-60% gradient to obtain (S)-2-((2R,3R)-3-((S)-1-((3R,4S,5S)-4-((S)-2-(4-(6-(2,5-dioxo-2,5-dihydro-1H-pyrrol-1-yl)hexanoyl)piperazine-1-carboxamido)-N,3-dimethylbutanamido)-3-methoxy-5-methylheptanoyl)pyrrolidin-2-yl)-3-methoxy-2-methylpropanamido)-3-phenylpropanoic acid (NL-26). MS m/z 924.6 (M+1). Retention time 1.152 min.

EXAMPLE 55

Synthesis of (S)-2-((2R,3R)-3-((S)-1-((3R,4S,7S)-4-((S)-sec-butyl)-20-(2,5-dioxo-2,5-dihydro-1H-pyrrol-1-yl)-7,10-diisopropyl-3-methoxy-5-methyl-6,9,15-trioxo-5,8,10,14-tetraazaicosan-1-oyl)pyrrolidin-2-yl)-3-methoxy-2-methylpropanamido)-3-phenylpropanoic acid (NL-30)

NL-30

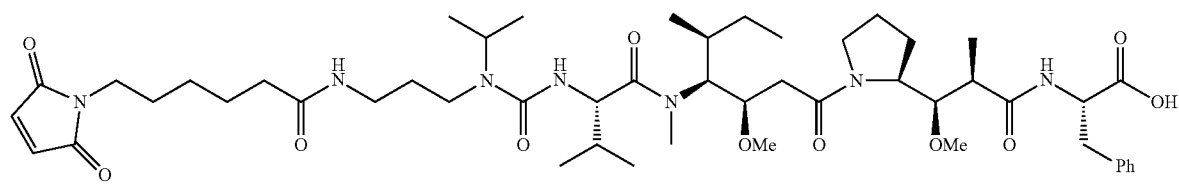

Step 1: DIEA (23 mg, 0.18 mmol) and 4-nitrophenyl carbonochloride (9.0 mg, 0.045 mmol) were added to (S)-methyl-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanoate HCl salt (30 mg, 0.045 mmol) in DMF:THF (1:1, 2 mL. The reaction was stirred at rt for 1 h. LCMS indicated that formation of 4-nitrophenoxycarbamate was complete. MS m/z 798.4 (M+1). Retention time 1.409 min. To the reaction was added tert-butyl (3-(isopropylamino)propyl)carbamate (9.7 mg, 0.045 mmol) and the reaction was stirred at rt for 70 h. The reaction mixture was purified by preparative HPLC using a 20-80% gradient to obtain (S)-methyl 2-((2R,3R)-3-((S)-1-((12S,15S,16R)-15-((S)-sec-butyl)-9,12-diisopropyl-16-methoxy-2,2,14-trimethyl-4,10,13-trioxo-3-oxa-5,9,11,14-tetraazaoctadecan-18-oyl)pyrrolidin-2-yl)-3-methoxy-2-methylpropanamido)-3-phenylpropanoate (NL-27),

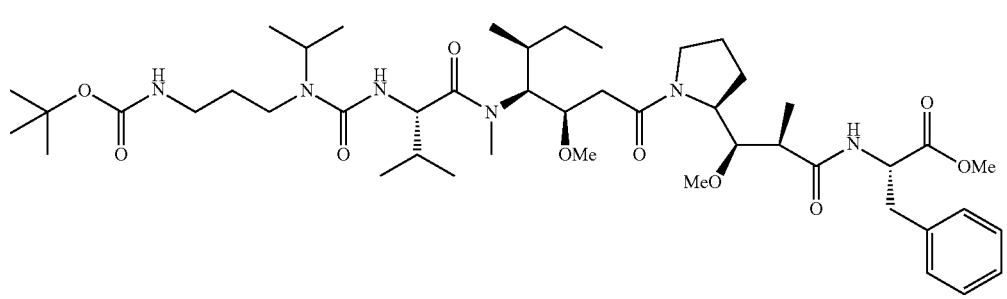

NL-27

MS m/z 875.6 (M+1). Retention time 1.371 min.

Step 2: TFA (1 mL) was added to (S)-methyl 2-((2R,3R)-3-((S)-1-((12S,15S,16R)-15-((S)-sec-butyl)-9,12-diisopropyl-16-methoxy-2,2,14-trimethyl-4,10,13-trioxo-3-oxa-5,9,11,14-tetraazaoctadecan-18-oyl)pyrrolidin-2-yl)-3-methoxy-2-methylpropanoate (NL-27) (19.1 mg, 0.022 mmol) in DCM (2 mL). The reaction mixture was stirred at rt for 1 h, and concentrated to give (S)-methyl 2-((2R,3R)-3-((S)-1-((3R,4S,5S)-4-((S)-2-(3-(3-aminopropyl)-3-isopropylureido)-N,3-dimethylbutanamido)-3-methoxy-5-methylheptanoyl)pyrrolidin-2-yl)-3-methoxy-2-methylpropanamido)-3-phenylpropanoate (NL-28) as a TFA salt,

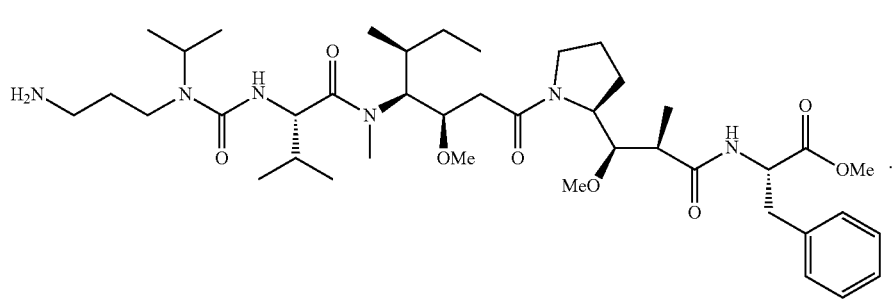

NL-28

MS m/z 775.6 (M+1). Retention time 1.064 min.

Step 3: LiOH (20 mg, 0.84 mmol) was added to (S)-methyl 2-((2R,3R)-3-((S)-1-((3R,4S,5S)-4-((S)-2-(3-(3-aminopropyl)-3-isopropylureido)-N,3-dimethylbutanamido)-3-methoxy-5-methylheptanoyl)pyrrolidin-2-yl)-3-methoxy-2-methylpropanamido)-3-phenylpropanoate (NL-28)TFA salt (19.0 mg, 0.022 mmol) in MeOH:H$_2$O (3:2, 2 mL). The reaction mixture was stirred at rt for 1 h, and purified by preparative HPLC using a 20-80% gradient to obtain (S)-2-((2R,3R)-3-((S)-1-((3R,4S,5S)-4-((S)-2-(3-(3-aminopropyl)-3-isopropylureido)-N,3-dimethylbutanamido)-3-methoxy-5-methylheptanoyl)pyrrolidin-2-yl)-3-methoxy-2-methylpropanamido)-3-phenylpropanoic acid (NL-29) as aTFA salt,

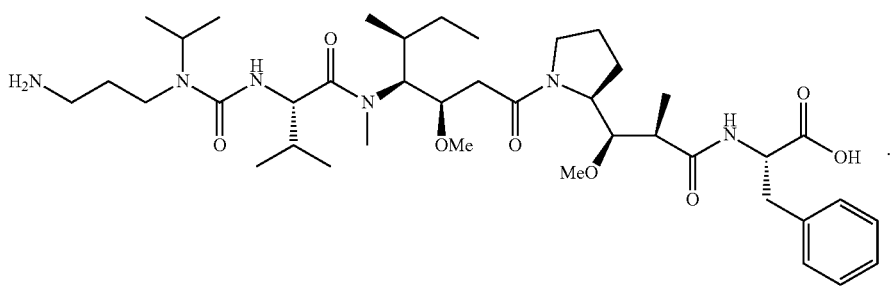

NL-29

MS m/z 761.5 (M+1). Retention time 0.993 min.

Step 4: To EMCA (3.1 mg, 0.015 mmol) in DMF (1 mL) were added DIEA (0.0070 ml, 0.040 mmol) and HATU (5.6 mg, 0.015 mmol). The reaction mixture was stirred at rt for 5 min, and added to (S)-2-((2R,3R)-3-((S)-1-((3R,4S,5S)-4-((S)-2-(3-(3-aminopropyl)-3-isopropylureido)-N,3-dimethylbutanamido)-3-methoxy-5-methylheptanoyl)pyrrolidin-2-yl)-3-methoxy-2-methylpropanamido)-3-phenylpropanoic acid (NL-29) (12 mg, 0.013 mmol). The reaction mixture was stirred at rt for 1 h, and purified by preparative HPLC using a 20-45% gradient to obtain (S)-2-((2R,3R)-3-((S)-1-((3R,4S,7S)-4-((S)-sec-butyl)-20-(2,5-dioxo-2,5-dihydro-1H-pyrrol-1-yl)-7,10-diisopropyl-3-methoxy-5-methyl-6,9,15-trioxo-5,8,10,14-tetraazaicosan-1-oyl)pyrrolidin-2-yl)-3-methoxy-2-methylpropanamido)-3-phenylpropanoic acid (NL-30). MS m/z 954.5 (M+1). Retention time 1.144 min.

EXAMPLE 56

Synthesis of (S)-2-((2R,3R)-3-((S)-1-((3R,4S,5S)-4-((S)-2-((5-((2-(6-(2,5-dioxo-2,5-dihydro-1H-pyrrol-1-yl)hexanamido)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-34)

Step 1: Oxalyl chloride (0.055 ml, 0.624 mmol) and DMF (0.0024 mL, 0.031 mmol) were added to 2-chloro-4-methylpyrimidine-5-carboxylic acid (59.2 mg, 0,343 mmol) in DCM (6.0 mL). The reaction was stirred for 20 h at rt. The reaction mixture was concentrated and the residue was dissolved in DCM (6.0 ml), tert-Butyl (2-aminoethyl)carbamate (50 mg, 0.312 mmol) in DCM (3 mL) was added, followed by trie.thylamine (0.13 mL, 0.936 mmol). The reaction was stirred at rt for 4 h. LCMS indicated completion of the reaction. The crude material was purified by preparative HPLC using a 20-70% gradient to obtain tert-butyl (2-(2-chloro-4-methylpyrimidine-5-carboxamido)ethyl)carbamate. MS m/z 315.1 (M+1). Retention time 0.951 min. $^1$H NMR (400 MHz, CD$_3$OD): δ 8.65 (s, 1H), 3.46-3.43 (m, 2H), 3.31-3.26 (m, 2H), 2.61 (s, 3H), 1.43 (s, 9H).

Step 2: Val-Dil-Dap-Phe-OMe (Step 2 of Example 1) (24 mg, 0.038 mmol), tert-butyl (2-(2-chloro-4-methylpyrimidine-5-carboxamido)ethyl)carbamate (23.9 mg, 0.076 mmol) and DIEA (0.066 ml, 0.38 mmol) in 2-propanol (2 mL) were heated in a sealed vial at 120° C. for 4 h. LCMS indicated completion of the reaction. The crude material was purified by preparative HPLC using a 20-70% gradient to obtain (S)-methyl 2-((2R,3R)-3-((S)-1-((3R,4S,5S)-4-((S)-2-((5-((2-((tert-butoxycarbonyl)amino)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-31),

NL-34

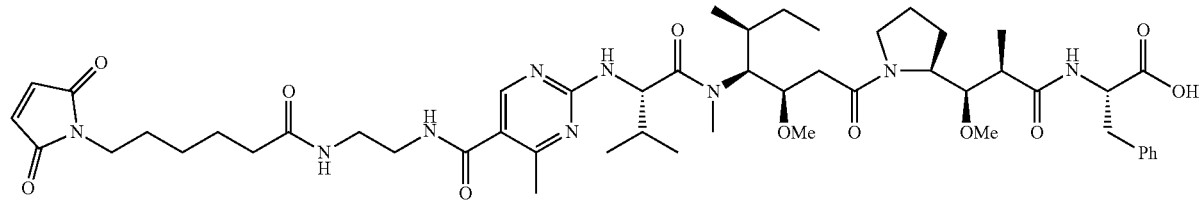

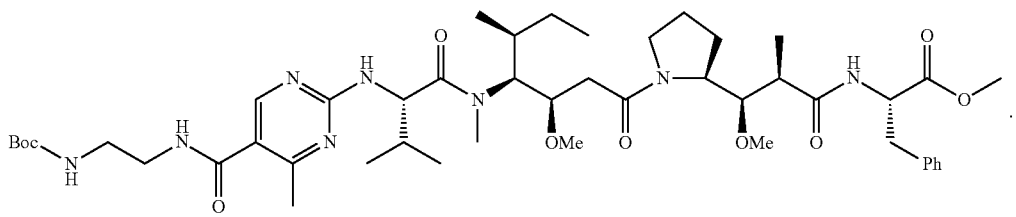

NL-31

MS m/z 911.6 (M+1). Retention time 1.295 min.

Step 3: (S)-Methyl 2-((2R,3R)-3-((S)-1-((3R,4S,5S)-4-((S)-2-((5-((2-((tert-butoxycarbonyl)amino)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-31) (11.8 mg, 0.013 mmol) was dissolved in methanolic HCl (3 M, 2 mL). The solvent was slowly evaporated. LCMS analysis indicated complete removal of the Boc group. The residue was taken up in acetonitrile and water and lyophilized to obtain (S)-methyl 2-((2R,3R)-3-((S)-1-((3R,4S,5S)-4-((S)-2-((5-((2-aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-32)

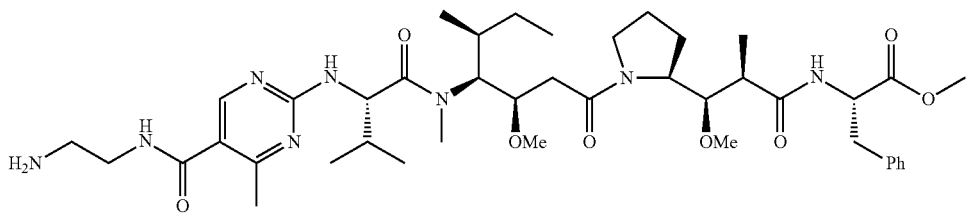

NL-32

MS m/z 811.5 (M+1). Retention time 1.009 min.

Step 4: (S)-Methyl 2-((2R,3R)-3-((S)-1-((3R,4S,5S)-4-((S)-2-((5-((2-aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-32) (11mg, 0.013 mmol) was dissolved mixture of THF (0.8 mL), MeOH (0.1 mL and H₂O (0.1 mL). LiOH (5.5 mg, 0.13 mmol) was added. The reaction was stirred for 4 h at rt. LCMS analysis indicated completion of the reaction. Hydrochloric acid (0.1N) was used to adjust pH of the reaction mixture to 7, and the mixture was concentrated. The residue was lyophilized from acetonitrile and water to obtain (S)-2-((2R,3R)-3-((S)-1-((3R,4S,5S)-4-((S)-2-((5-((2-Aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-33),

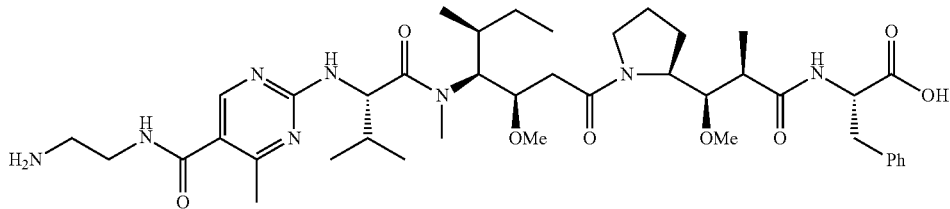

NL-33

MS m/z 797.6 (M+1). Retention time 0.942 min.

Step 5: DIEA (10 mg, 0.078 mmol) and HATU (12.3 mg, 0.032 mmol) were added to EMCA (8.2 mg, 0.039 mmol) in DMF (2 mL). After the reaction was stirred for 10 min, (S)-2-((2R,3R)-3-((S)-1-((3R,4S,5S)-4-((S)-2-((5-((2-aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-33) (10.3 mg, 0.013 mmol) was added. The reaction was stirred for 1 h at rt. LCMS indicated completion of the reaction. The crude material was purified by preparative HPLC using a 20-70% ACN-H$_2$O gradient to obtain (S)-2-((2R,3R)-3-((S)-1-((3R,4S,5S)-4-((S)-2-((5-((2-(6-(2,5-dioxo-2,5-dihydro-1H-pyrrol-1-yl)hexanamido)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-34). MS m/z 990.5 (M+1). Retention time 1.115 min.

EXAMPLE 57

Synthesis of (S)-2-((2R,3R)-3-((S)-1-((3R,4S,5S)-4-((S)-2-((4-((2-(6-(2,5-dioxo-2,5-dihydro-1H-pyrrol-1-yl)hexanamido)ethyl)carbamoyl)-6-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-38)

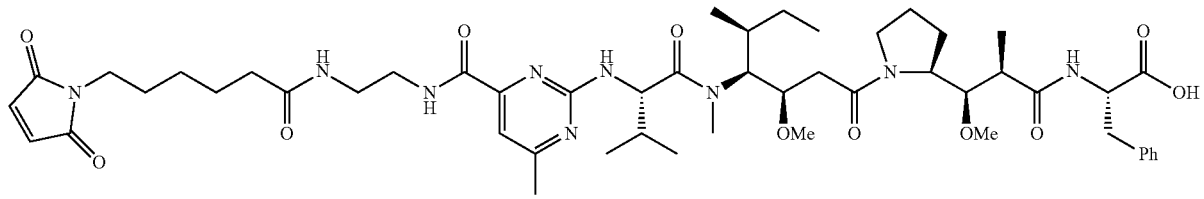

NL-38

Step 1: (S)-Methyl-2-((2R,3R)-3-((S)-1-((3R,4S,5)-4-((S)-2-((4-((2-((tert-butoxycarbonyl)amino)ethyl)carbamoyl)-6-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-35),

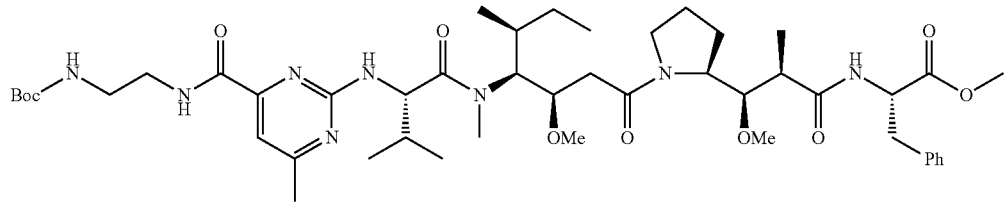

NL-35 was prepared using the method described for (S)-Methyl 2-((2R,3R)-3-((S)-1-((3R,4S,5S)-4-((S)-2-((5-((2-((tert-butoxycarbonyl)amino)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-31). MS m/z 911.5 (M+1). Retention time 1.405 min.

Step 2: (S)-Methyl 2-((2R,3R)-3-((S)-1-((3R,4S,5S)-4-((S)-2-((4-((2-aminoethyl)carbamoyl)-6-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-36),

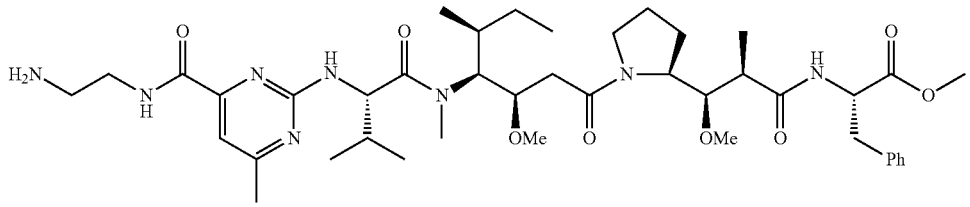

NL-36 was prepared by the method described for (S)-methyl 2-((2R,3R)-3-((S)-1-((3R,4S,5S)-4-((S)-2-((5-((2-aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoate (NL-32). MS m/z 811.5 (M+1). Retention time 1.131 min.

Step 3: (S)-2-((2R,3R)-3-((S)-1-((3R,4S,5S)-4-((S)-2-((4-((2-aminoethyl)carbamoyl)-6-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-37),

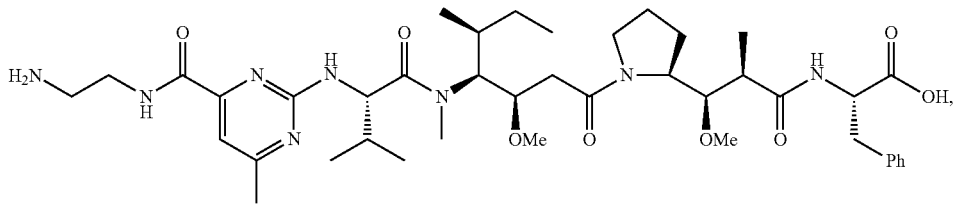

NL-37 was prepared by the method described for (S)-2-((2R,3R)-3-((S)-1-((3R,4S,5S)-4-((S)-2-((5-((2-aminoethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-33). MS m/z 797.5 (M+1). Retention time 1.038 min.

Step 4: (S)-2-((2R,3R)-3-((S)-1-((3R,4S,5S)-4-((S)-2-((4-((2-(6-(2,5-dioxo-2,5-dihydro-1H-pyrrol-1-yl)hexanamido)ethyl)carbamoyl)-6-methylpyrimidin-2yl)amino)-N,3-dimethylbutanamido)-3-methoxy-5-methylheptanoyl)pyrrolidin-2-yl)-3-methoxy-2-methylpropanamido)-3-phenylpropanoic acid (NL-38) was prepared by the method described for (S)-2-((2R,3R)-3-((S)-1-((3R,4S,5S)-4-((S)-2-((5-((2-(6-(2,5-dioxo-2,5-dihydro-1H-pyrrol-1-yl)hexanamido)ethyl)carbamoyl)-4-methylpyrimidin-2-yl)amino)-N,3-dimethylbutanamido)-3-methoxy-5-methylheptanoyl)pyrrolidin-2-yl)-3-methoxy-2-methylpropanamido)-3-phenylpropanoic acid (NL-34). MS m/z 990.5 (M+1). Retention time 1.183 min.

EXAMPLE 58

Synthesis of 2-(((R)-1-((2R,3R)-3-((S)-1-((3R,4S,5S)-4-((S)-2-((Z)-((dimethylamino)(4-(6-(2,5-dioxo-2,5-dihydro-1H-pyrrol-1-yl)hexanoyl)piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid (NL-42)

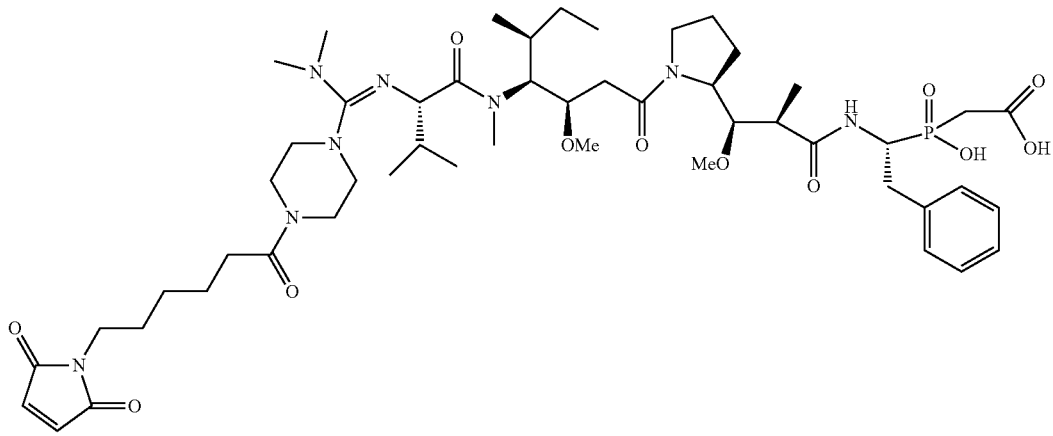

NL-42

Step 1: To ((R)-1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid TFA salt,

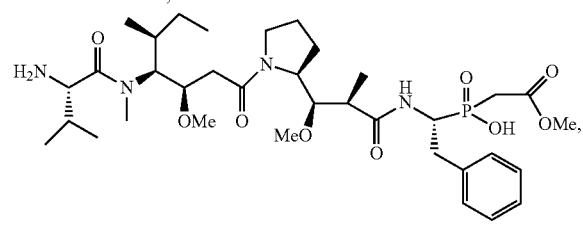

(17 mg, 0.021 mmol) in DMF (2 mL) were added Isouronium 1 (50 mg, 0.096 mmol) and DIEA (0.021 mL, 0.120 mmol). The reaction was stirred at 45° C. for 18 h. The crude material was purified by preparative HPLC using a 20-50% gradient to obtain ((R)-1-((2R,3R)-3-((S)-1-((3R,4S,5S)-4-((S)-2-((Z)-((4-(tert-butoxycarbonyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid (NL-39) as a TFA salt,

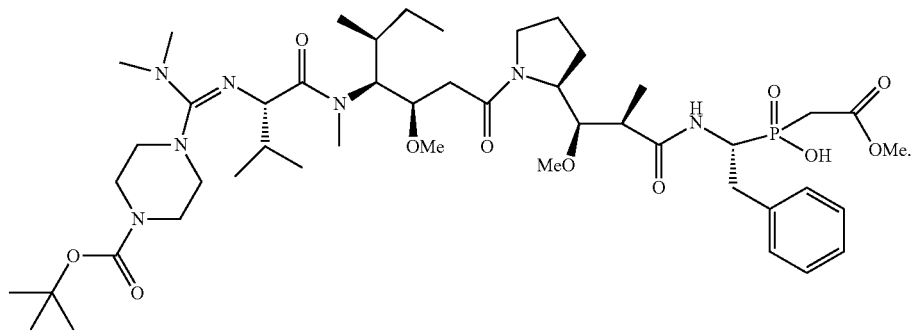

NL-39

MS m/z 950.4 (M+1). Retention time 1.252 min.

Step 2: ((R)-1-((2R,3R)-3-((S)-1-((3R,4S,5S)-4-((S)-2-((Z)-((4-(tert-Butoxycarbonyl)piperazin-1-yl)(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid (NL-39) TFA salt (7.6 mg, 0.0071 mmol) in DCM (2.0 mL) was treated with TFA (1.0 mL). The reaction was stirred at rt for 24 h. The reaction mixture was concentrated to obtain ((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid (NL-40) as a TFA salt,

NL-40

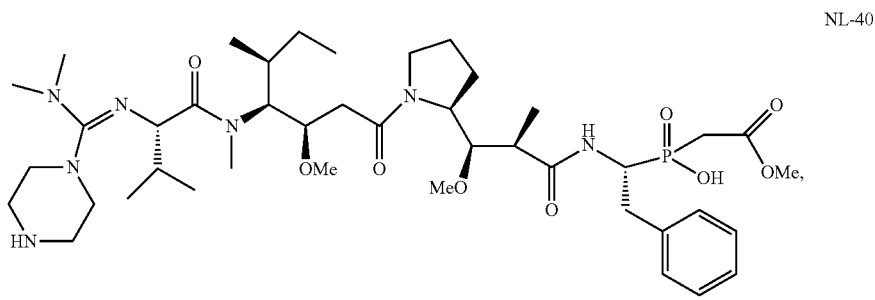

MS m/z 850.5 (M+1). Retention time 0.941 min.

Step 3: To ((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid (NL-40) TFA salt (6.9 mg, 0.0071 mmol) in MeOH:H₂O (2:1, 3 mL) was added LiOH (3.4 mg, 0.14 mmol). The reaction was stirred at rt for 18 h, resulting in a complete hydrolysis of the ester. After concentration, the residue was treated with 0.01 ml HOAc and purified by preparative HPLC with a 20-45% gradient to obtain 2-(((R)-1-((2R,3R)-3-((S)-1-((3R,4S,5S)-4-((S)-2-((Z)-((Dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid (NL-41) as a TFA salt,

NL-41

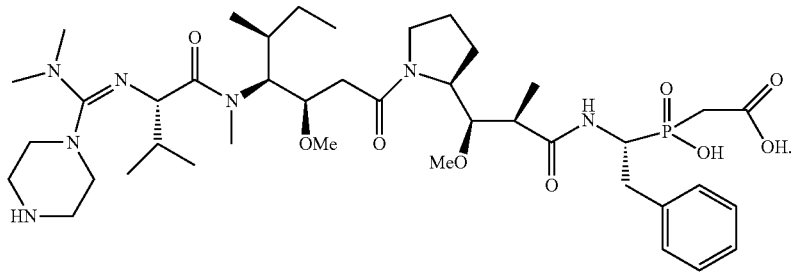

MS m/z 836.4 (M+1). Retention time 0.983 min.

Step 4: To EMCA (1.07 mg, 0.005 mmol) in DMF (1 mL) were added DIEA (0.0037 ml, 0.021 mmol) and HATU (1.9 mg, 0.005 mmol). The reaction mixture was stirred for 5 min, and added to 2-(((R)-1-((2R,3R)-3-((S)-1-((3R,4S,5S)-4-((S)-2-((Z)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid TFA salt (4 mg, 0.004 mmol) in DMF (0.5 mL) with DIEA (0.001 mL. The reaction was stirred at rt for 1 h. The crude material was purified by preparative HPLC using a 20-50% gradient to obtain 2-(((R)-1-((2R,3R)-3-((S)-1-((3R,4S,5S)-4-((S)-2-((Z)-((Dimethylamino)(4-(6-(2,5-dioxo-2,5-dihydro-1 H-pyrrol-1-yl)hexanoyl)piperazin-1-yl)methylene)amino)-N,3-dimethylbutanamido)-3-methoxy-5-methylheptanoyl) pyrrolidin-2-yl)-3-methoxy-2-methylpropanamido)-2-phenylethyl)(hydroxy)phosphoryl)acetic acid (NL-42) as a TFA salt. MS m/z 1029.5 (M+1). Retention time 1.089 min.

Synthetic Procedure for Example C-Terminal Linked Compounds of Formula (I)

EXAMPLE 59

Synthesis of N-(4-((R)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-1)

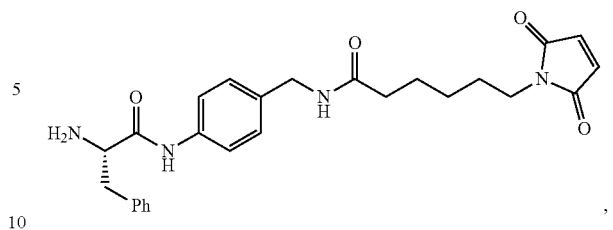

CL-1

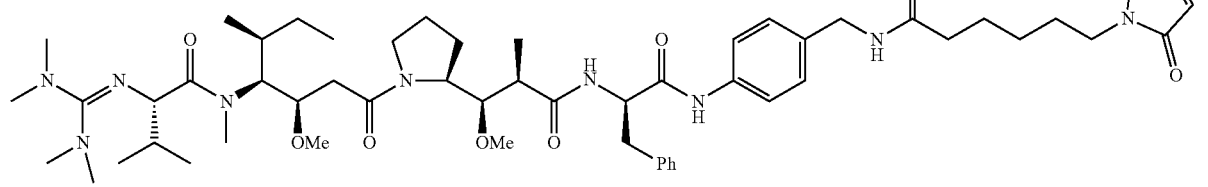

Step 1: DIEA (388 mg, 3.0 mmol) and HATU (571 mg, 1.5 mmol) were added to tert-butyl (4-(aminomethyl)phenyl)carbamate (111 mg, 0.50 mmol) and EMCA (127 mg, 0.60 mmol) in DMF (5 mL). The reaction was stired for 2 h at rt. The reaction mixture was diluted with EtOAc (30 mL) and washed with saturated aq NaHCO₃. The aq layer was extracted with EtOAc (2×30 mL). The combined organic phases was washed with H₂O (5×10 mL), dreid with MgSO₄, filtered and concentrated. The residue was purified by ISCO (EtOAc/Hexane 0-75%). The desired product, tert-butyl (4-(((6-(2,5-dioxo-2,5-dihydro-1H-pyrrol-1-yl)hexanamido)methyl)phenyl)carbamate (MS m/z 416.3 (M+1)), was obtained as a yellow oil. The oil was dissolved in DCM (2 mL) and treated with TFA (2 mL). After 1 h at rt, the reaction mixture was concentrated. The residue was dissolved in acetonitrile and H₂O, and lyophilized to obtained N-(4-aminobenzyl)-6-(2,5-dioxo-2,5-dihydro-1H-pyrrol-1-yl)hexanamide TFA salt as a yellow solid (MS m/z 316.2 (M+1)).

Step 2: DIEA (226 mg, 1.75 mmol) and HATU(265 mg, 0.698 mmol) were added to N-(4-aminobenzyl)-6-(2,5-dioxo-2,5-dihydro-1H-pyrrol-1-yl)hexanamide TFA salt (110 mg, 0.349 mmol) and (S)-2-((tert-butoxycarbonyl)amino)-3-phenylpropanoic acid (111 mg, 0.419 mmol) in DMF (2 mL). The reaction was stirred for 2 h at rt. The reaction mixture was diluted with EtOAc (20 mL), and washed with saturated aq NaHCO₃. The aq layer was extracted with EtOAc (2×20 mL). The combined organic phases was washed with H₂O (5×10 mL), dreid with MgSO₄, filtered, and concentrated. The residue was purified by ISCO (EtOAc/Hexane, 0-75%), affording (S)-tert-butyl (1-((4-(((6-(2,5-dioxo-2,5-dihydro-1H-pyrrol-1-yl)hexanamido)methyl)phenyl)amino)-1-oxo-3-phenylpropan-2-yl)carbamate (MS m/z 563.3 (M+1)). This product was dissolved in 3M HCl in MeOH (3 mL), and concentrated. The residue was taken up in acetonitrile and H₂O, and lyophilized to obtained (S)-N-(4-(2-amino-3-phenylpropanamido)benzyl)-6-(2,5-dioxo-2,5-dihydro-1H-pyrrol-1-yl)hexanamide as HCl salt, MS m/z 463.3 (M+1). ¹H NMR (400 MHz, CDCl₃): δ 7.76 (bs, 1H), 7.36-7.20 (m, 9H), 6.70 (s, 2H), 5.84 (s, 1H), 4.47 (bs, 1H), 4.41 (d, J=5.6 Hz, 2H), 3.52 (t, J=7.2 Hz, 2H), 3.17 (d, J=7.2 Hz, 2H), 2.23(t, J=7.6 Hz, 2H), 1.64-1.26 (m, 6H), 1.45 (s, 9H).

Step 3: DIEA (60.1 mg, 0.465 mmol) and HATU(70.7 mg, 0.186 mmol) were added to (S)-N-(4-(2-amino-3-phenylpropanamido)benzyl)-6-(2,5-dioxo-2,5-dihydro-1H-pyrrol-1-yl)hexanamide HCl salt (46.3 mg, 0.093 mmol) and BocVal-Dil-Dap-OH (53 mg, 0.093 mmol) in DMF (2 mL). The reaction was stirred for 1 hr at rt. The reaction mixture was puridfied by preparative HPLC to afford tert-butyl ((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate. MS m/z 1016.6 (M+1). The product was dissolved in 3M HCl in MeOH (2 mL), and concentrated. The residue was taken up in acetonitrile and H₂O, and lyophilized to obtain N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide as HCl salt,

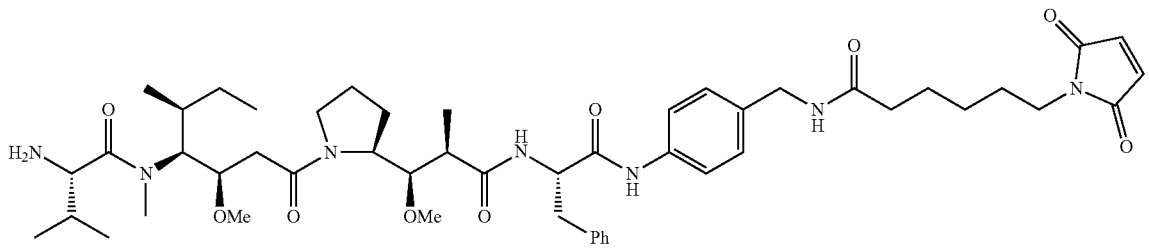

MS m/z 916.5 (M+1). Retention time 1.060 min.

Step 4: DIEA (1.7 mg, 0.013 mmol) and HATU (3.4 mg, 0.0089 mmol) were added to N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide HCl salt (4.6 mg, 0.0045 mmol) in DMF. The reaction was stirred at rt for 10 min. The crude material was purified by preparative HPLC using a 20-50% gradient to obtain N-(4-((R)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-1). MS m/z 1014.5 (M+1). Retention time 1.108 min.

EXAMPLE 60

Synthesis of N-(4-((S)-2-((2R,3R)-3-((S)-1-((3R,4S,5S)-4-((S)-2-((1,3-dimethylimidazolidin-2-ylidene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-2)

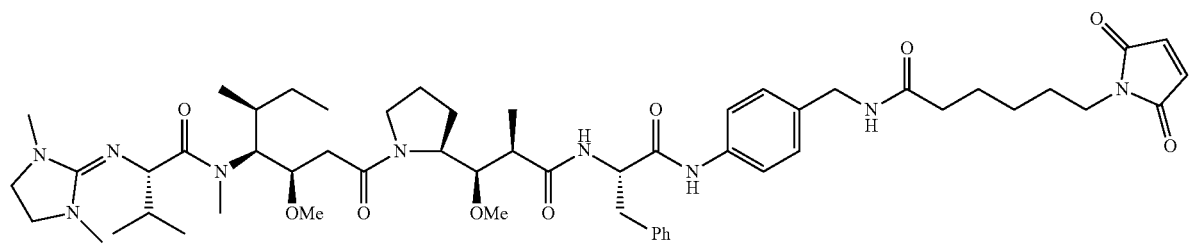

CL-2

To N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide HCl salt (4.5 mg, 0.0044 mmol) in DMF (1 mL) were added DIEA (20 mg, 0.16 mmol) and 2-chloro-1,3-dimethylimidazolinium hexafluorophosphate (4.6 mg, 0.017 mmol). The reaction was stirred at rt for 30 min. The crude material was purified by reverse phase HPLC using a 33-38% gradient to obtain N-(4-((S)-2-((2R,3R)-3-((S)-1-((3R,4S,5S)-4-((S)-2-((1,3-Dimethylimidazolidin-2-ylidene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-2). MS m/z 1012.6 (M+1). Retention time 1.122 min.

EXAMPLE 61

Synthesis of N-(4-((S)-2-((2R,3R)-3-((S)-1-((3R,4S,5S)-4-((S)-2-((Z)-((dimethylamino)(morpholino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-3)

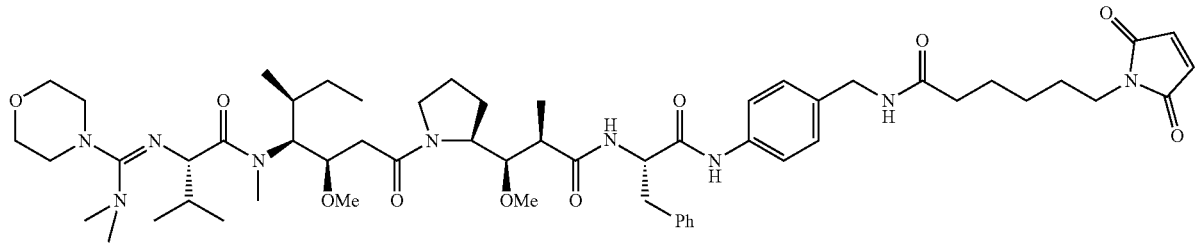

CL-3

Step 1: N,N-Dimethylcarbamoyl chloride (129 mg, 1.20 mmol) was added dropwise to a stirring mixture of morpholine (87 mg, 0.999 mmol) and triethylamine (0.139 ml, 0.999 mmol) in DCM (5 mL) at 0° C. When the addition was completed the temperature was raised to rt, and the reaction was stirred at rt for 18 h. The reaction mixture was basified with 10% aq NaOH. The organic layer was separated, and the aq layer was extracted with DCM. The combined DCM layers was washed successively with water and saturated aq NaCl, dried over $Na_2SO_4$, filtered and concentrated to give N,N-dimethylmorpholine-4-carboxamide. MS m/z 159.2 (M+1). Retention time 0.474 mins. The product was used in the next step without further purification.

Step 2: Oxalyl chloride (0.079 ml, 0.90 mmol) in DCM (1 mL) was added dropwise to N,N-dimethylmorpholine-4-carboxamide (158 mg, 0.999 mmol) in DCM (2 mL) at rt over 5 min. The reaction was heated at reflux for 3 h. The desired product N-(chloro(morpholino)methylene)-N-methylmethanaminium chloride formed cleanly. The solvent was evapolated, and the residue was washed with ether. The white solid thereby obtained was dissolved in DCM and saturated aq $KPF_6$ was added at rt with vigorous stirring. The aqueous solution was extracted with DCM three times. The organic layers were combined, dried over $Na_2SO_4$, filtered, and concentrated to obtain product N-(chloro(morpholino)methylene)-N-methylmethanaminium hexafluorophosphate. MS m/z 177.1 (M+1). Retention time 0.244 min.

Step 3: N-(Chloro(morpholino)methylene)-N-methylmethanaminium hexafluorophosphate (140 mg, 0.433 mmol) was added to a solution of 1-hydroxy-benzotriazole (58.5 mg, 0.433 mmol) and triethylamine (0.060 mL, 0.43 mmol) in DCM (20 mL). The reaction was stirred for 14 h. Precipitate formed immediately upon addition of HOBt. The white solid was collected by filtration to obtain Isouronium 2,

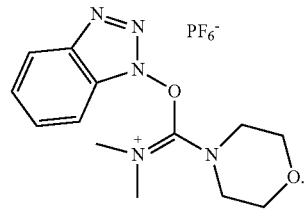

MS m/z 276 (M+). Retention time 0.375 min. The product was used in the next step without further purification.

Step 4: To N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide HCl salt (5.0 mg, 0.0049 mmol) in DMF (1 mL) were added DIEA (1.9 mg, 0.015 mmol) and Isouronium 2 (4.1 mg, 0.0097 mmol). The reaction was stirred at rt for 18 h. The crude material was purified by preparative HPLC using a 33-40% gradient to obtain N-(4-((S)-2-((2R,3R)-3-((S)-1-((3R,4S,5S)-4-((S)-2-((Z)-((dimethylamino)(morpholino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-3). MS m/z 1056.6 (M+1). Retention time 1.125 min.

EXAMPLE 62

Synthesis of tert-butyl 4-((E)-N'-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazine-1-carboxylate (CL-4)

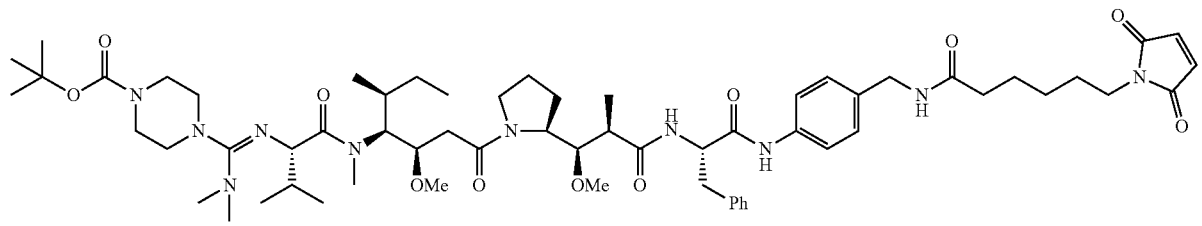

To N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide HCl salt (10 mg, 0.0097 mmol) in DMF (1 mL) were added DIEA (10 mg, 0.077 mmol) and Isouronium 1 (20 mg, 0.038 mmol). The reaction was stirred at 60° C. for 30 min. The crude material was purified by preparative HPLC using a 35-46% gradient to obtain tert-butyl 4-((E)-N'-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-N,N-dimethylcarbamimidoyl)piperazine-1-carboxylate (CL-4) as a TFA salt. MS m/z 1155.6 (M+1). Retention time 1.226 min.

EXAMPLE 63

Synthesis of N-(4-((S)-2-((2R,3R)-3-((S)-1-((3R,4S,5S)-4-((S)-2-((E)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-5)

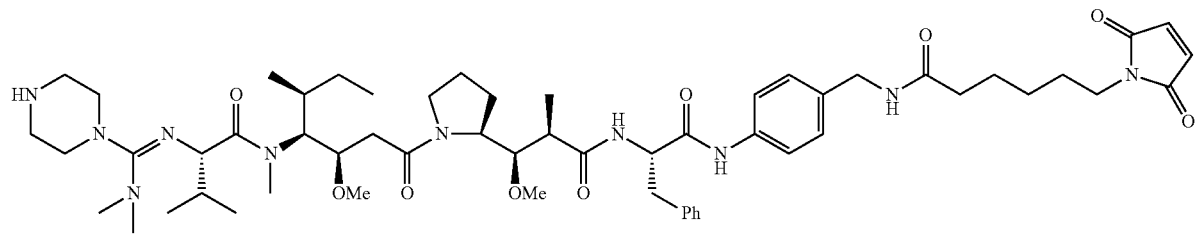

TFA (1 mL) was added to tert-butyl 4-((Z)-N'-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-m ethyl-1-oxobutan-2-yl)-N,N-dimethylcarbamimidoyl)piperazine-1-carboxylate TFA salt (5.1 mg, 0.004 mmol) in DCM (2 mL). The reaction mixture was stirred at rt for 1 h and concentrated. The residue was purified by preparative HPLC using a 25-35% gradient to obtain N-(4-((S)-2-((2R,3R)-3-((S)-1-((3R,4S,5S)-4-((S)-2-((E)-((dimethylamino)(piperazin-1-yl)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide (CL-5). MS m/z 1055.6 (M+1). Retention time 0.973 min.

EXAMPLE 64

Synthesis of N-(4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide (CL-6)

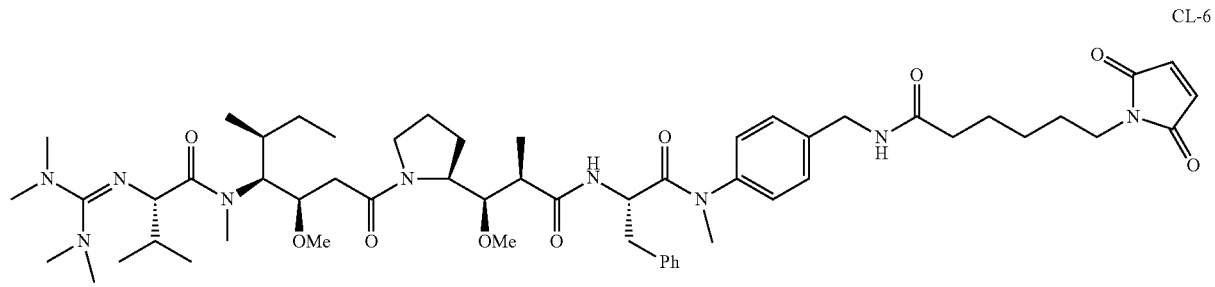

CL-6

Step 1: To EMCA (349 mg, 1.65 mmol) in DMF (10 mL) were added DIEA (820 mg, 6.35 mmol) and HATU (579 mg, 1.52 mmol). After 10 min at rt, tert-butyl (4-(aminomethyl)phenyl)(methyl)carbamate (300 mg, 1.27 mmol) was added. The reaction was stirred for an addtional 1 h at rt. The reaction mixture was diluted with EtOAc (30 mL), and washed with saturated aq NaHCO₃. The aqueous layer was extracted with EtOAc (2×30 ml). The combined organic phases was washed with H₂O (5×10 mL), dried with MgSO₄, filtered and concentrated. The residue was purified by ISCO (EtOAc/Hexane 0-80%), affording the desired product as yellow oil. MS m/z 374.2 (M-56.1 (isobutylene)+1). Retention time 1.156 min. This product was dissolved in DCM (3 mL), and treated with TFA (1 mL After 1 hour at rt, solvents were evapolated. The residue was taken up in acetonitrile and H₂O, and lyophilized to obtained 6-(2,5-dioxo-2,5-dihydro-1H-pyrrol-1-yl)-N-(4-(methylamino)benzyl)hexanamide TFA salt as a yellow solid. MS m/z 330.2 (M+1). Retention time 0.61 min.

Step 2: DIEA (356 mg, 2.76 mmol) and HATU (288 mg, 0.758 mmol) were added to Boc-Phenylalanine (219 mg, 0.827 mmol) in DMF (5 mL). After 10min at rt, 6-(2,5-dioxo-2,5dihydro-1H-pyrrol-1-yl)-N-(4-(methylamino) benzyphexanamide TFA salt (227 mg, 0.512 mmol) was added. The reaction was stirred for 2 h at rt. The reaction mixture was diluted with EtOAc (20 mL) and washed with saturated aq NaHCO₃. The aqueous layer was extracted with EtOAc (2×20 mL). The combined organic phases was washed with H₂O (5×10 mL), dreid with MgSO₄, filtered and concentrated. The residue was purified by ISCO (EtOAc/Hexane, 0-75%), affording (S)-tert-butyl (1-((4-((6-(2,5-dioxo-2,5-dihydro-1H-pyrrol-1-yl)hexanamido)methyl)phenyl)(methyl)amino)-1-oxo-3-phenylpropan-2-yl)carbamate. MS m/z 577.3 (M+1). Retention time 1.19 min. ¹H NMR (400 MHz, DMSO-d6): δ 10.00 (s, 1H), 8.24 (t, J=6.0 Hz, 1h), 7.52 (d, j=8.4 Hz, 2H), 7.32-7.09 (m, 7H), 7.01 (s, 2H), 4.31 (m, 1H), 4.19 (d, J=6.0 Hz, 2H), 3.38 (t, J=7.0 Hz, 2H), 3.17 (d, J=7.2 Hz, 2H), 3.00 (m, 1H), 2.85 (m, 1H), 2.10 (t, J=7.4 Hz, 2H), 1.54-1.44 (m, 4H), 1.31 (s, 9H), 1.22-1.15 (m, 4H). This product was dissolved in methanolic HCl (3M, 5 mL) and concentrated slowly. The residue was taken up in acetonitrile and H₂O and lyophilized to obtained (S)-N-(4-(2-amino-N-methyl-3-phenylpropanamido)benzyl)-6-(2,5-dioxo-2,5-dihydro-1H-pyrrol-1-yl)hexanamide as HCl salt. MS m/z 477.2 (M+1). Retention time 0.83 min.

Step 3: To Boc-Val-Dil-Dap-OH (347 mg, 0.607 mmol) in DMF (4 mL) were added DIEA (261 mg, 2.02 mmol) and HATU (282 mg, 0.49 mmol). The reaction was stirred for 15 min at rt before (S)-N-(4-(2-Amino-N-methyl-3-phenylpropanamido)benzyl)-6-(2,5-dioxo-2,5-dihydro-1H-pyrrol-1-yl)hexanamide HCl salt (193 mg, 0.376 mmol) was added. The reaction was stirred for an additional 2 h at rt. The reaction mixture was puridfied by preparative HPLC to afford tert-butyl ((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)(methyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate. MS m/z 1030.5 (M+1). Retention time 1.430 min. This product was dissolved in methanolic HCl (3M, 3 mL), and concentrated. The residue was taken up in acetonitrile and H₂O, and lyophilized to obtained N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide,

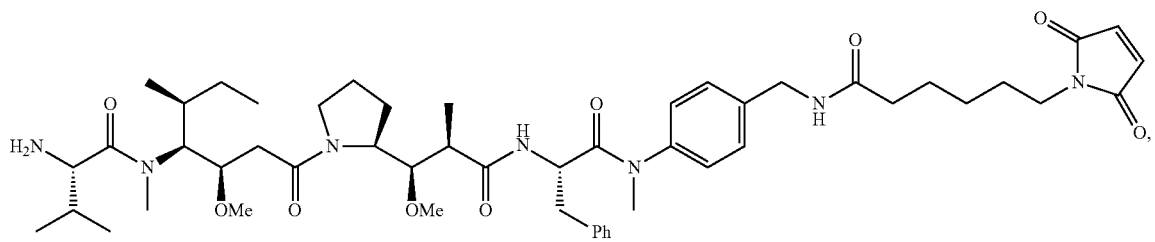

as HCl salt (MS m/z 930.5 (M+1), Retention time 1.07 min.

Step 4: DIEA (0.019 mL, 0.11 mmol) and HATU (12.3 mg, 0.032 mmol) were added to N-(4-((S)-2-((2R,3R)-3-((S)-1-((3R,4S,5S)-4-((S)-2-Amino-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide HCl salt (20 mg, 0.021 mmol) in DMF (2 mL). The reaction was stirred at rt for 2 h. The crude material was purified by preparative HPLC using a 10-90% gradient to obtain N-(4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide as TFA salt (CL-6). MS m/z 1028.6 (M+1). Retention time 1.129 min.

EXAMPLE 65

Synthesis of 6-(aminooxy)-N-(4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)hexanamide (CL-7)

benzylcarbamate as a white solid. MS m/z 404.2(M+1). $^1$H NMR (400 MHz, CD$_3$OD): δ 7.44-7.23 (m, 14H), 5.10 (s, 2H), 4.26 (s, 2H), 4.12 (d, J=7.4 Hz, 1H), 3.28-3.22 (m, 1H), 3.15-3.10 (m, 1H).

Step 2: DIEA (323 mg, 2.50 mmol) and HATU (342 mg, 0.90 mmol) were added were added to (S)-benzyl 4-(2-amino-3-phenylpropanamido)benzylcarbamate (202 mg, 0.50 mmol) and (2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanoic acid (429 mg, 0.75 mmol) in DMF (6 mL). The reaction mixture was stirred for 1 h at rt and purified by preparative HPLC to afford tert-butyl ((S)-1-(((3R,4S,5S)-1-((S)-2-((1R,2R)-3-(((S)-1-((4-((((benzyloxy)carbonyl)amino)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate. MS m/z 957.5 (M+1). Retention time 1.54 min. This product (393 mg, 0.41 mmol) was dissolved in methanolic HCl (3 M, 15 mL). The solvent was slowly evaporated. The LCMS analysis indicated the complete removal of the Boc group. The residue was dissolved in

CL-7

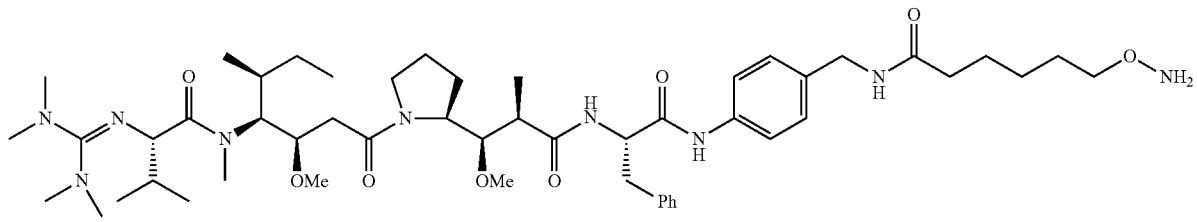

Step 1: To Boc-Phenylalanine (964 mg, 3.63 mmol) in DMF (10 mL) were added DIEA (1.27 g, 9.84 mmol) and HATU (1.13 g, 3.03 mmol) at rt. After 10 min, benzyl 4-aminobenzylcarbamate (388 mg, 1.51 mmol) was added. The reaction was stirred for 2 h at rt. The reaction acetonitrile and water, and lyophilized to obtain benzyl 4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzylcarbamate,

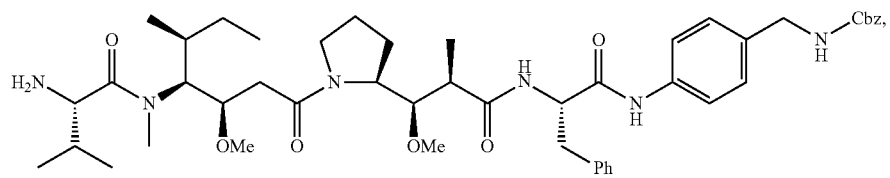

mixture was diluted with EtOAc (60 mL) and washed with saturated aq NaHCO$_3$. The aqueous layer was extracted with EtOAc (2×30 mL). The combined organic phases was washed with H$_2$O (5×10 mL), dreid over MgSO$_4$, filtered and concentrated to afford the crude product. The crude product was dissolved in DCM (5.0 mL) and treated with TFA (5.0 mL) for 1 h at rt. The reaction mixture was concentrated and purified by ISCO using 0-8% MeOH with 2M ammonia in DCM to obtained (S)-benzyl 4-(2-amino-3-phenylpropanamido)

as a HCl salt, MS m/z 857.5 (M+1). Retention time 1.16 min.

Step 3: DIEA (0.031 mL, 0.18 mmol) and HATU (20.0 mg, 0.053 mmol) were added to benzyl 4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzylcarbamate HCl salt (30 mg, 0.034 mmol) in DMF (2 mL). The reaction was stirred at rt for 2 h. LCMS indicated completion of the reaction. The crude material was purified by preparative HPLC using al 0-90% gradient to obtain benzyl 4-((S)-2-((2R,3R)-3-((S)-1-((3R,4S, 5S)-4-((S)-2-((bis(dimethylamino)methylene)amino)-N, 3-dimethylbutanamido)-3-methoxy-5-methylheptanoyl) pyrrolidin-2-yl)-3-methoxy-2-methylpropanamido)-3-phenylpropanamido)benzylcarbamate,

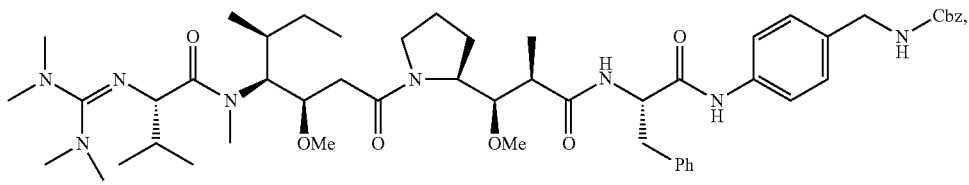

as TFA salt. MS m/z 955.6 (M+1). Retention time 1.232 min.

Step 4: Benzyl 4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzylcarbamate TFA salt (16 mg, 0.015 mmol) was dissolved in MeOH (1 ml). Pd/C (10%, wet, 7.1 mg) was added. The reaction was stirred under $H_2$ for 1 h. LCMS indicated completion of the reaction. The reaction mixture was filtered and concentrated to obtain (S)-N-((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((bis(dimethylamino)methylene)amino)-N,3-dimethylbutanamide,

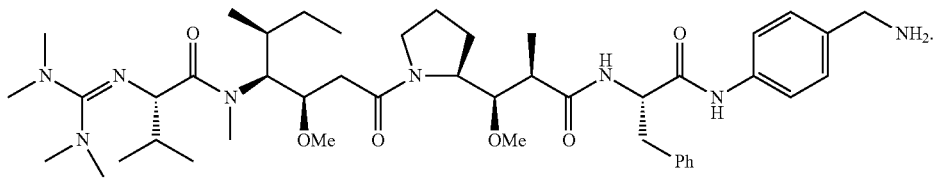

MS m/z 821.5 (M+1). Retention time 0.907 min.

Step 5: Lithium 6-(((1-ethoxyethylidene)amino)oxy)hexanoate (13.2 mg, 0.059 mmol) was suspended in DMF (2 mL), and HATU (18.75, 0.049 mmol) was added. The reaction was stirred 15 min at rt. DIEA (0.021 mL, 0.12 mmol) was added, followed by (S)-N-((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((bis(dimethylamino) methylene)amino)-N,3-dimethylbutanamide (16.2 mg, 0.020 mmol). The reaction was stirred till LCMS indicated completion of the reaction. The crude was purified by preparative HPLC using al 0-90% gradient to obtain ethyl N-(6-((4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)amino)-6-oxohexyl) oxyacetimidate,

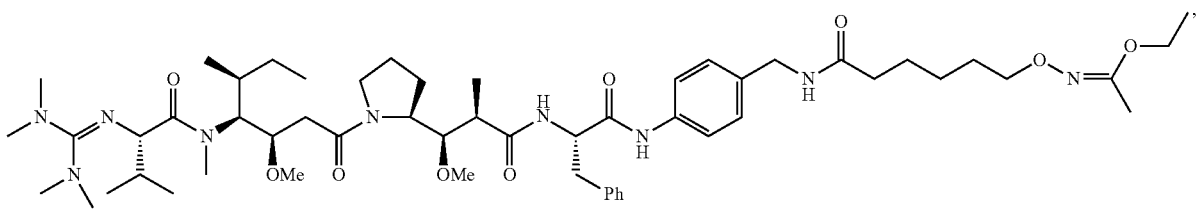

as TFA salt. MS m/z 1020.6 (M+1). Retention time 1.243 min.

Step 6: Ethyl N-(6-((4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)benzyl)amino)-6-oxohexyl) oxyacetimidate (11.4 mg, 0.0101 mmol) in MeOH (1.5 mL) was treated with hydrochloric acid (1 M, 0.061 ml) for 30 min ar rt. LCMS indicated completion of the reaction. The crude was purified by preparative HPLC using a 33-45% gradient to obtain 6-(aminooxy)-N-(4-((S)-2-((2R,3R)-3-((S)-1-((3R,4S,5S)-4-((S)-2-((bis(dimethylamino)methylene)amino-N,3-dimethylbutanamido)-3-methoxy-5-methylheptanoyl)pyrrolidin-2-yl)-3-methoxy-2-methylpropanamido)-3-phenylpropanamido)benzyl)hexanamide (CL-7) as a TFA salt. MS m/z 950.6 (M+1). Retention time 0.967 min.

EXAMPLE 66

Synthesis of (S)-2-((bis(dimethylamino)methylene) amino)-N-((3R,4S,5S)-1-((S)-2-((1R,2R)-3-(((S)-1-((4-((3-(6-(2,5-dioxo-2,5-dihydro-1H-pyrrol-1-yl) hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide (CL-8)

CL-8

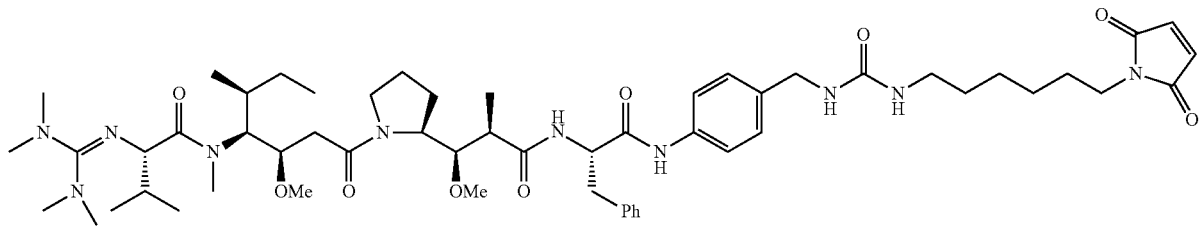

Step 1: (S)-N-((3R,4S,5S)-1-((S)-2-((1R,2R)-3-(((S)-1-((4-(Aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((bis (dimethylamino)methylene)amino)-N,3-dimethylbutanamide (6.4 mg) was dissolved in DMF(0.5 mL) and THF(0.5 mL). DIEA (0.0068 mL 0.039 mmol) and 4-nitrophenyl carbonochloridate (3.14 mg, 0.016 mmol) were added. The reaction was stirred for 2 h at rt. LCMS indicated completion of the reaction. The crude material was purified by preparative HPLC using a 10-90% gradient to obtain 4-nitrophenyl 4-((S)-2-((2R,3R)-3-((S)-1-((3R,4S,5S)-4-((S)-2-((bis(dimethylamino) methylene)amino)-N,3-dimethylbutanamido)-3-methoxy-5-methylheptanoyl)pyrrolidin-2-yl)-3-methoxy-2-methylpropanamido)-3-phenylpropanamido) benzylcarbamate, as TFA salt. MS m/z 986.5 (M+1). Retention time 1.206 min. pyrrole-2,5-dione (2.9 mg, 0.015 mmol). The reaction was stirred for 2 h at rt. LCMS indicated completion of the reaction. The crude material was purified by preparative HPLC using a 10-90% gradient to obtain (S)-2-((bis(dimethylamino)methylene)amino)-N-((3R,4S,5S)-1-((S)-2-((1R,2R)-3-(((S)-1-((4-((3-(6-(2,5-dioxo-2,5-dihydro-1H-pyrrol-1-yl)hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide (CL-8) as a TFA salt. MS m/z 1043.6 (M+1). Retention time 1.161 min.

Step 2: To 4-nitrophenyl 4-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido) benzylcarbamate TFA salt (2.4 mg, 0.0024 mmol) in DMF(0.5 mL) and THF(0.5 mL) were added DI EA (0.0085 mL, 0.049 mmol) and 1-(6-aminohexyl)-1H-

EXAMPLE 67

Synthesis of (S)-2-((bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-9)

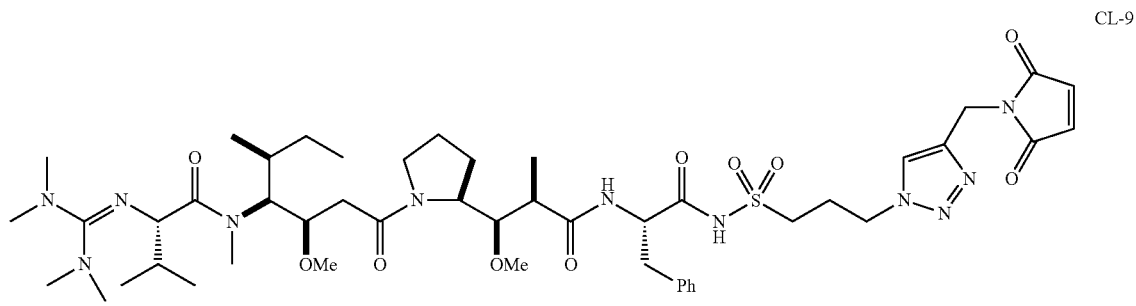

(S)-2-((Bis(dimethylamino)methylene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (FP-3) TFA salt (87.4 mg, 0.089 mmol) and 1-(prop-2-yn-1-yl)-1H-pyrrole-2,5-dione (24.2 mg, 0.0179 mmol) were suspensed in 3.0 mL each of t-BuOH and water. The reaction vessel was filled with $N_2$ by vacuum-fill cycle with $N_2$ five times. Degassed solutions of sodium L-ascorbate (17.7 mg, 0.089 mmol) in $H_2O$ (2.4 ml) and $CuSO_4$ (2.86 mg, 0.018 mmol) in $H_2O$ (0.6 ml) were added successively and the reaction was stirred at rt for 5 h. LCMS indicated completion of the reaction. The crude material was purified by preparative HPLC using a 20-45% gradient to obtain (S)-2-((bis (dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl) propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-9) as a TFA salt. MS m/z 998.5 (M+1). Retention time 1.014 min.

EXAMPLE 68

Synthesis of (S)-N-((3R,4S,5S)-1-((S)-2-((3R,4R,7S)-7-benzyl-21-(2,5-dioxo-2,5-dihydro-1H-pyrrol-1-yl)-4-methyl-5,8,19-trioxo-2,12,15-trioxa-6,9,18-triazahenicosan-3-yl)pyrrolidin-1-yl)-3-methoxy-5-methyl-1-oxoheptan-4-yl)-2-((bis(dimethylamino)methylene)amino)-N,3-dimethylbutanamide (CL-10)

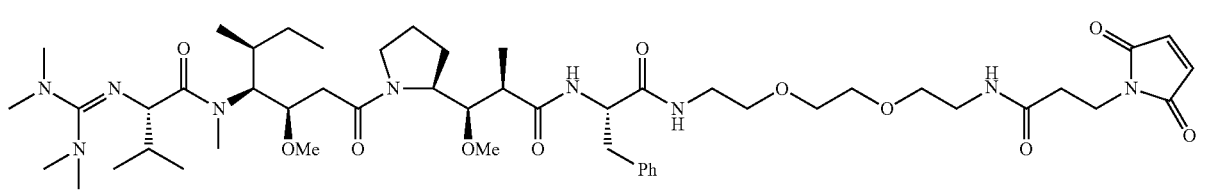

Step 1: To (S)-2-((tert-butoxycarbonyl)amino)-3-phenylpropanoic acid (482 mg, 1.82 mmol) in DMF (10 mL) were added DI EA (705 mg, 5.46 mmol) and HATU (622 mg, 1.64 mmol). After 10 min (9H-fluoren-9-yl)methyl (2-(2-(2-aminoethoxy)ethoxy)ethyl)carbamate (370 mg, 0.91 mmol) was added. The reaction was stirred for 2 h at rt. The crude material was purified by preparative HPLC using a 10-90% gradient to obtain tert-butyl (S)-(1-(9H-fluoren-9-yl)-3,14-dioxo-16-phenyl-2,7,10-trioxa-4,13-diazahexadecan-15-yl)carbamate. MS m/z 618.3 (M+1). Retention time 1.395 min. This product was dissolved in methanolic HCl (3 M, 5 ml) and concentrated slowly. LCMS analysis indicated complete removal of the Boc group. The residue was taken up in acetonitrile and H2O, and lyophilized to give (S)-(9H-fluoren-9-yl)methyl (2-(2-(2-(2-amino-3-phenylpropanamido)ethoxy)ethoxy)ethyl)carbamate as HCl salt. MS m/z 518.2 (M+1). Retention time 1.041 min.

Step 2: To Boc-Val-Dil-Dap-OH (189 mg, 0.33 mmol) in DMF (6 mL) were added DIEA (0.144 mL, 0.83 mmol) and HATU (113 mg, 0.297 mmol). After 15 min at rt (S)-(9H-fluoren-9-yl)methyl (2-(2-(2-(2-amino-3-phenylpropanamido)ethoxy)ethoxy)ethyl)carbamate HCl salt (91.5 mg, 0.165 mmol) was added. The reaction was stirred for an additional 2 h at rt. The crude material was purified by preparative HPLC using a 10-90% gradient to obtain tert-butyl ((S)-1-(((3R,4S,5S)-1-((S)-2-((15S,18R,19R)-15-benzyl-1-(9H-fluoren-9-yl)-18-methyl-3,14,17-trioxo-2,7,10,20-tetraoxa-4,13,16-triazahenicosan-19-yl)pyrrolidin-1-yl)-3-methoxy-5-methyl-1-oxoheptan-4-yl)(methyl)amino)-3-methyl-1-oxobutan-2-yl)carbamate. MS m/z 1071.6 (M+1). Retention time 1.577 min. This product (93 mg, 0.087 mmol) was dissolved in methanolic HCl (3 M, 3 ml) and concentrated slowly. LCMS analysis indicated complete removal of the Boc group. The residue was taken up in acetonitrile and water, and lyophilized to obtain (9H-fluoren-9-yl)methyl ((3R,4R,7S)-3-((S)-1-((3R,4S,5S)-4-((S)-2-amino-N,3-dimethylbutanamido)-3-methoxy-5-methylheptanoyl)pyrrolidin-2-yl)-7-benzyl-4-methyl-5,8-dioxo-2,12,15-trioxa-6,9-diazaheptadecan-17-yl)carbamate, Step 3: To (9H-fluoren-9-yl)methyl ((3R,4R,7S)-3-((S)-1-((3R,4S,5S)-4-((S)-2-amino-N,3-dimethylbutanamido)-3-methoxy-5-methylheptanoyl)pyrrolidin-2-yl)-7-benzyl-4-methyl-5,8-dioxo-2,12,15-trioxa-6,9-diazaheptadecan-17-yl)carbamate HCl salt (30 mg, 0.030 mmol) in DMF (2 mL) were added DIEA (0.027 mL 0.15 mmol) and HATU (23.5 mg, 0.062 mmol). The reaction was stirred at rt for 2 h. The crude material was purified by preparative HPLC using a 10-90% gradient to obtain (9H-fluoren-9-yl)methyl ((3R,4R,7S)-7-benzyl-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-4-methyl-5,8-dioxo-2,12,15-trioxa-6,9-diazaheptadecan-17-yl)carbamate. MS m/z 1069.6 (M+1). Retention time 1.255 min. The Fmoc group was removed form the product (13.6 mg, 0.011 mmol) by treatment with piperidine (0.2 mL) in DMF (2 mL) at rt for 30 min. Volatiles were removed by evaporation to obtain (S)-N-((3R,4S,5S)-1-((S)-2-((3R,4R,7S)-17-amino-7-benzyl-4-methyl-5,8-dioxo-2,12,15-trioxa-6,9-diazaheptadecan-3-yl)pyrrolidin-1-yl)-3-methoxy-5-methyl-1-oxoheptan-4-yl)-2-((bis(dimethylamino)methylene)amino)-N,3-dimethylbutanamide,

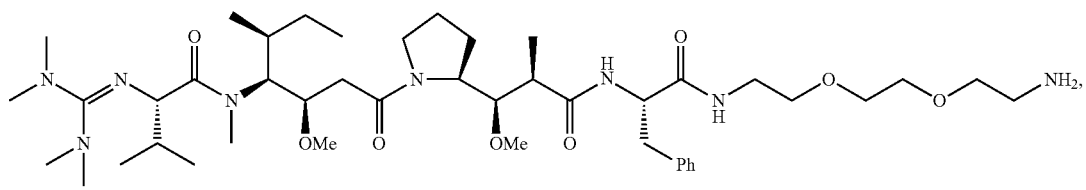

MS m/z 847.6 (M+1). Retention time 0.924 min. This material was used in the next step without further purification.

Step 4: To 3-(2,5-dioxo-2,5-dihydro-1H-pyrrol-1-yl)propanoic acid (5.83 mg, 0.034 mmol) in DMF (2 mL) were added DIEA (0.012 mL, 0.069 mmol) and HATU (10.9 mg, 0.029 mmol). After 15 min at rt the crude product obtained in Step 3 (9.74 mg) was added. The reaction was stirred at rt for 2 h. The crude material was purified by preparative HPLC using a 10-90% gradient to obtain (S)-N-((3R,4S,5S)-1-((S)-2-((3R,4R,7S)-7-benzyl-21-(2,5-dioxo-2,5-dihydro-1 H-pyrrol-1-yl)-4-methyl-5,8,19-trioxo-2,12,15-trioxa-6,9,18-triazahenicosan-3-yl)pyrro

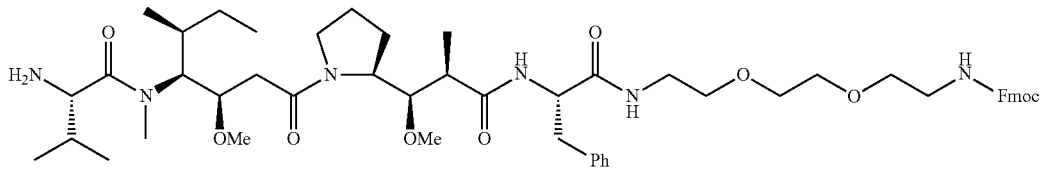

as HCl salt. MS m/z 971.6 (M+1). Retention time 1.195 min.

lidin-1-yl)-3-methoxy-5-methyl-1-oxoheptan-4-yl)-2-((bis(dimethylamino)methylene)amino)-N,3-dimethylbutanamide (CL-10). MS m/z 998.6 (M+1). Retention time 1.007 min.

EXAMPLE 69

Synthesis of (S)-2-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)propyl (2-(2-(2,5-dioxo-2,5-dihydro-1H-pyrrol-1-yl)ethoxy)ethyl)carbamate (CL-11)

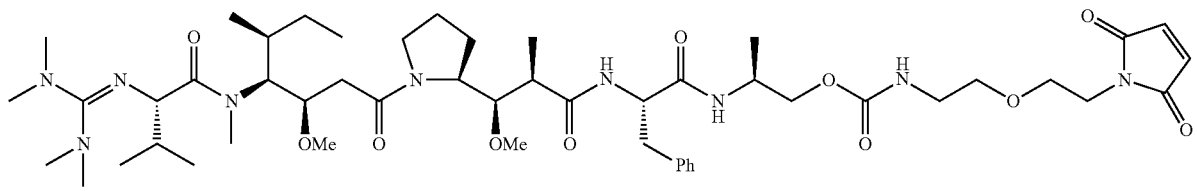

CL-11

Step 1-2: (S)-2-Amino-N-((3R,4S,5S)-1-((S)-2-((1R,2R)-3-(((S)-1-(((S)-1-hydroxypropan-2-yl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide,

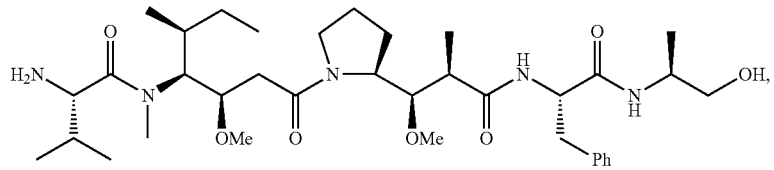

HCl salt was obtained by following Steps 1 and 2 in EXAMPLE 68 except (S)-2-aminopropan-1-ol was used in place of (9H-fluoren-9-yl)methyl (2-(2-(2-aminoethoxy)ethoxy)ethyl)carbamate, MS m/z 676.5 (M+1). Retention time 0.899 min.

Step 3: DIEA (0.026 mL, 0.15 mmol) and HBTU (14.6 mg, 0.038 mmol) were added to (S)-2-Amino-N-((3R,4S,5S)-1-((S)-2-((1R,2R)-3-(((S)-1-(((S)-1-hydroxypropan-2-yl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide HCl salt (20 mg, 0.028 mmol) in DMF (2 mL). The reaction was stirred at rt for 2 h. LCMS indicated completion of the reaction. The crude material was purified by preparative HPLC using a 10-90% gradient to obtain (S)-2-((bis(dimethylamino)methylene)amino)-N-((3R,4S,5S)-1-((S)-2-((1R,2R)-3-(((S)-1-(((S)-1-hydroxypropan-2-yl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide,

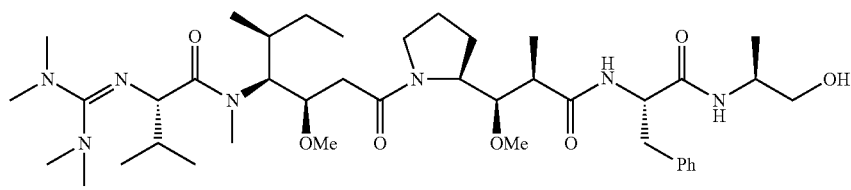

as TFA salt. MS m/z 774.6 (M+1). Retention time 0.984 min.

Step 4: To a stirred solution of 1-(2-(2-aminoethoxy)ethyl)-1H-pyrrole-2,5-dione (I-2) (12.5 mg, 0.057 mmol) and anhydrous pyridine (0.0092 mL, 0.11 mmol) in DCM (2.0 mL) was added phosgene (15% solution in toluene, 0.276 mL, 0.364 mmol). This mixture was stirred at rt for 20 min, and heated at reflux for 40 min. The reaction was cooled to rt and (S)-2-((bis(dimethylamino)methylene)amino)-N-((3R,4S,5S)-1-((S)-2-((1R,2R)-3-(((S)-1-(((S)-1-hydroxypropan-2-yl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide TFA salt (8.8 mg, 0.0099 mmol) in DCM (1.0 mL) was added. The reaction was heated at reflux for 1 h. The crude product was purified by preparative HPLC using a 10-90% gradient to obtain (S)-2-((S)-2-((2R,3R)-3-((S)-1-((3R,4S,5S)-4-((S)-2-((Bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)propyl (2-(2-(2,5-dioxo-2,5-dihydro-1H-pyrrol-1-yl)ethoxy)ethyl)carbamate (CL-11) as a TFA salt. MS m/z 984.6 (M+1). Retention time 1.065 min.

EXAMPLE 70

Synthesis of (S)-N-((3R,4S,5S)-1-((S)-2-((3R,4R,7S)-7-benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)-2-((bis(dimethylamino)methylene)amino)-N,3-dimethylbutanamide (CL-12)

CL-12

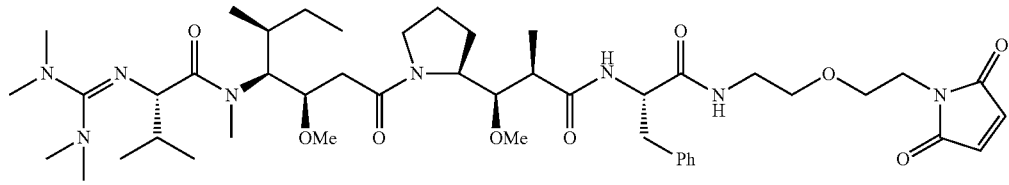

Step 1-2: (S)-2-Amino-N-((3R,4S,5S)-1-((S)-2-((3R,4R,7S)-7-benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)-N,3-dimethylbutanamide,

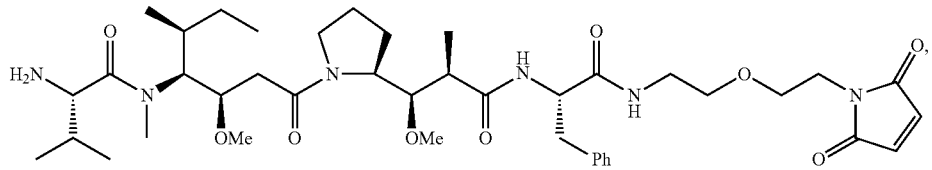

HCl salt was obtained by following Steps 1 and 2 of Example 68, except 1-(2-(2-aminoethoxy)ethyl)-1H-pyrrole-2,5-dione (I-2) was used in place of (9H-fluoren-9-yl)methyl (2-(2-(2-aminoethoxy)ethoxy)ethyl)carbamate. MS m/z 785.4 (M+1). Retention time 0.975 min.

Step 3: DIEA (0.019 ml, 0.11 mmol) and HATU (17.4 mg, 0.046 mmol) were added to (S)-2-amino-N-((3R,4S,5S)-1-((S)-2-((3R,4R,7S)-7-benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)-N,3-dimethylbutanamide HCl salt (15 mg, 0.018 mmol) in DMF (2 mL). The reaction was stirred at rt for 2 h. LCMS indicated completion of the reaction. The crude material was purified by preparative HPLC using a 10-90% gradient to obtain (S)-N-((3R,4S,5S)-1-((S)-2-((3R,4R,7S)-7-Benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)-2-((bis(dimethylamino)methylene)amino)-N,3-dimethylbutanamide (CL-12) as a TFA salt. MS m/z 883.5 (M+1). Retention time 1.061 min.

EXAMPLE 71

Synthesis of (R)-Ac-Cys-OH adduct of (S)-2-((bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-13)

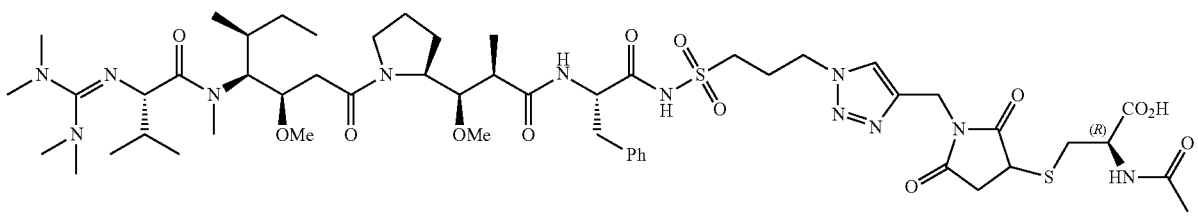

CL-13

(S)-2-((Bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-9) TFA salt (5 mg, 0.005 mmol) was dissolved in phosphate buffer (pH 7.5, 1 mL) containing 1.3mg of (R)-Ac-Cys-OH. The reaction was stirred for 1 h. The crude material was purified by preparative HPLC using a 10-90% gradient to obtain(R)-Ac-Cys-OH adduct of (S)-2-((bis(dimethylamino)methylene)amino)-1-(((3R,4S,5S)-1-((S)-2-((1 R,2R)-3-(((S)-N-1-(3-(4-((2,5-dioxo-2,5-dihydro-1 H-pyrrol-1-yl)methyl)-1 H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-13) as a TFA salt. MS m/z 1161.5 (M+1). Retention time 0.976 min.

EXAMPLE 72

Synthesis of ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((3-(6-(2,5-dioxo-2,5-dihydro-1H-pyrrol-1-yl)hexanamido)propyl)amino)-2-oxoethyl)phosphinic acid (CL-15)

Step 1: ((R)-1-(((Benzyloxy)carbonyl)amino)-2-phenylethyl)phosphinic acid (synthesized by following the schemes described in J Organometallic Chem 646 (2002) 212 and J Chem Soc Perkin Trans I: Organic and Bio-Organic Chemistry (1984), (12), 2845) (300 mg, 0.940 mmol) and hexamethyldisilazane (1.516 g, 9.40 mmol) were combined in a sealed vial and heated at 115° C. for 2 h. The temperature was lowered to 95° C. and methyl bromoacetate (719 mg, 4.70 mmol) was added dropwise to give a suspension. The reaction mixture was stirred for 1 h at 95° C., and concentrated. The residue was purified by ISCO using a C18 column (15.5g), and the desired product was eluted with 10-45% acetonitrile-$H_2O$ containing 0.05% TFA, affording (2-methoxy-2-oxoethyl)((R)-2-phenyl-1-(2-phenylacetamido)ethyl)phosphinic acid. MS m/z 392.1 (M+1). Retention time 1.010 min.

Step 2: To (2-methoxy-2-oxoethyl)((R)-2-phenyl-1-(2-phenylacetamido)ethyl)phosphinic acid (0.178 g, 0.454 mmol) in MeOH (10 mL) was added 10% Pd/C (0.048 g, 0.045 mmol). The reaction was stirred at rt for 1 h under $H_2$ atmosphere. The catalyst was removed by filtration through Celite, and the filtrate was evaporated to give ((R)-1-amino-2-phenylethyl)(2-methoxy-2-oxoethyl)phosphinic acid. MS m/z 258.1 (M+1). Retention time 0.565 min. This material was used in the next step without further purification.

Step 3: To Boc-Dap-OH (Small Molecules Inc.) (118 mg, 0.412 mmol) in DMF (5 mL) was added DIEA (160 mg, 1.236 mmol) and HATU (157 mg, 0.412 mmol). The reaction mixture was stirred at rt for 5 min, and added to ((R)-1-amino-2-phenylethyl)(2-methoxy-2-oxoethyl)phosphinic acid (106 mg, 0.412 mmol) in DMF. Upon completion of the reaction, the crude material was purified by preparative HPLC using a 20-34% gradient to give ((R)-1-((2R,3R)-3-((S)-1-(tert-butoxycarbonyl)pyrrolidin-2-yl)-3-methoxy-2-methylpropanamido)-2-phenylethyl)(2-methoxy-2-oxoethyl)phosphinic acid. MS m/z 527.2 (M+1). Retention time 1.144 min. During concentration the Boc group was partially lost from the product.

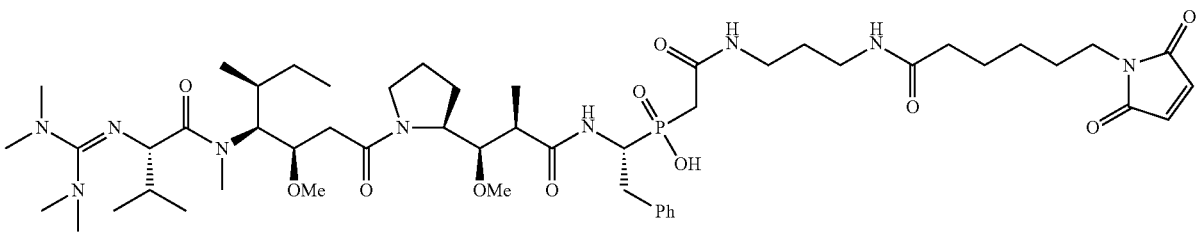

CL-15

Step 4: TFA (0.676 mL, 8.77 mmol) was added to the product obtained in Step 3 (155 mg, 0.294 mmol) in DCM (10 mL). The reaction mixture was stirred ar rt for 16 h, and concentrated to give ((R)-1-((2R,3R)-3-methoxy-2-methyl-3-((S)-pyrrolidin-2-yl)propanamido)-2-phenylethyl)(2-methoxy-2-oxoethyl)phosphinic acid,

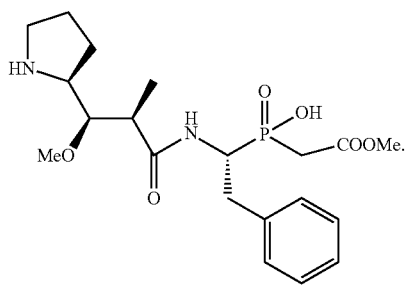

MS m/z 427.2 (M+1). Retention time 0.774 min.

Step 5: To Cbz-Val-Dil-OH (I-7) (108 mg, 0.247 mmol) in DMF (5 mL) was added DIEA (0.131 mL, 0.752 mmol) and HATU (94 mg, 0.25 mmol). The reaction mixture was stirred for 5 min and added to the amine obtained in Step 4 (133.5 mg, 0.247 mmol) in DMF (2 mL). The reaction was stirred at rt for 2 h. The crude material was purified by preparative HPLC using a 35-44% gradient to obtain ((R)-1-((2R,3R)-3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid,

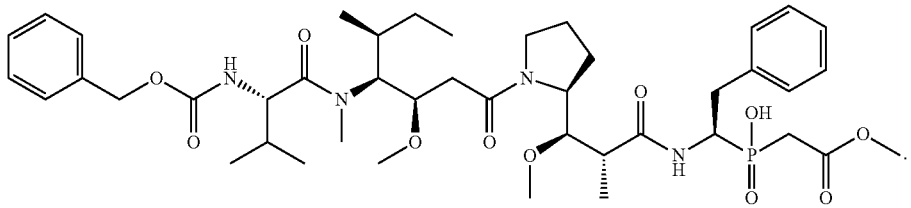

MS m/z 845.4 (M+1). Retention time 1.322 min.

Step 6: Pd/C (10%, 17.9 mg) was added to ((R)-1-((2R,3R)-3-((S)-1-((3R,4S,5S)-4-((S)-2-(((Benzyloxy)carbonyl)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid (143 mg, 0.169 mmol) in MeOH (5 mL). The reacation was stirred under H₂ for 1 h. LCMS indicated complete removal of the Cbz group. The reaction mixture was filtered through celite to remove Pd/C and concentrated. The residue was purified by ISCO using a C18 column (15.5 g), and the desired product was eluted with 10-50% acetonitrile in water with 0.05% TFA to give ((R)-1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid,

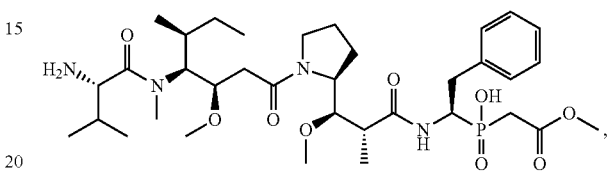

as TFA salt. MS m/z 711.4 (M+1). Retention time 1.009 min.

Step 7: To ((R)-1-((2R,3R)-3-((S)-1-((3R,4S,5S)-4-((S)-2-Amino-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid TFA salt (35 mg, 0.042 mmol) in DMF (1 mL were added DIEA (16 mg, 0.12 mmol) and HATU (16 mg, 0.042 mmol). The reaction was stirred at rt for 4 h and the desired product was isolated by preparative HPLC using a 20-45% gradient to obtain ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid,

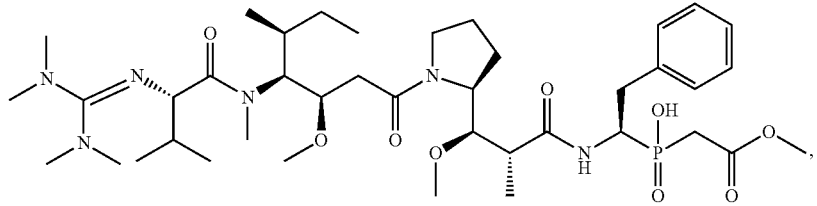

as TFA salt. MS m/z 809.5 (M+1). Retention time 1.044 min.

Step 8: LiOH (20 mg, 0.84 mmol) was added ((R)-1-((2R,3R)-3-((S)-1-((3R,4S,5S)-4-((S)-2-((bis(dimethylamino)

methylene)amino)-N,3-dimethylbutanamido)-3-methoxy-5-methylheptanoyl)pyrrolidin-2-yl)-3-methoxy-2-methylpropanamido)-2-phenylethyl)(2-methoxy-2-oxoethyl)phosphinic acid TFA salt (27 mg, 0.029 mmol) in MeOH—H$_2$O (2:1, 3 mL). The reaction mixture was stirred for 18 h at rt and concentrated. The residue was dissolved in acetonitrile-H$_2$O, and treated with AcOH (0.060 mL). The resulting solution was applied to a C18 column on ISCO, and the desired product was eluted with 5-50% acetonitrile-H$_2$O with 0.05% TFA to give 2-(((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid,

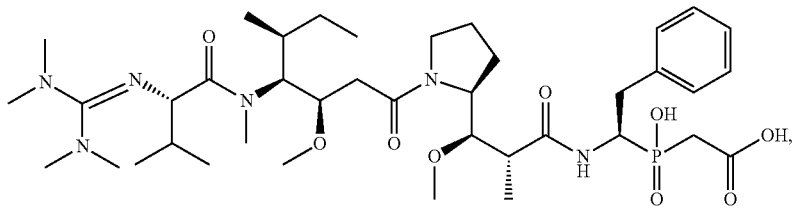

as TFA salt. MS m/z 795.4 (M+1). Retention time 1.010 min.

Step 9: DIEA (2.1 mg, 0.017 mmol) and HATU (2.1 mg, 0.0055 mmol) were added to 2-(((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid TFA salt (5.0 mg, 0.0055 mmol) in DMF (1 mL). The reaction mixture was stirred at rt for 5 min, and added to tert-butyl (3-aminopropyl)carbamate (1.0 mg, 0.0055 mmol) in DMF (0.2 mL). The reaction mixture was kept at rt for 18 h, and purified by preparative HPLC using a 20-55% gradient to obtain ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((3-((tert-butoxycarbonyl)amino)propyl)amino)-2-oxoethyl)phosphinic acid,

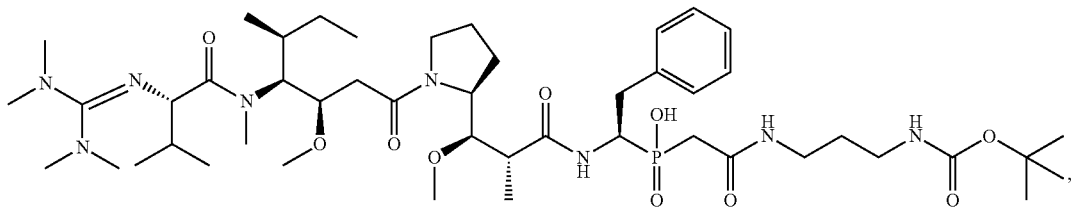

as TFA salt. MS m/z 951.0 (M+1). Retention time 1.074 min.

Step 10: TFA (1 mL) was added to ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((3-((tert-butoxycarbonyl)amino)propyl)amino)-2-oxoethyl)phosphinic acid TFA salt (3.5 mg, 0.0033 mmol) in DCM (1 mL). The resulting solution was stirred at rt for 2 h and concentrated to give (2-((3-aminopropyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphinic acid (CL-14),

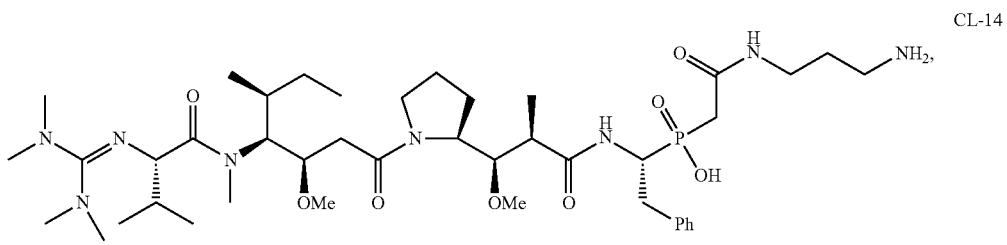

CL-14 as TFA salt MS m/z 851.1 (M+1). Retention time 0.971 min.

Step 11: To EMCA (1.0 mg, 0.0049 mmol) in DMF (1 mL) was added DIEA (0.0029 mL, 0.016 mmol) and HATU (1.9 mg, 0.0049 mmol). The reaction mixture was let stand at rt for 5 min and added to (2-((3-aminopropyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphinic acid (CL-14) TFA salt (4.2 mg, 0.0039 mmol). Upon completion of the reaction, the crude product was purified by preparative HPLC using a 20-50% gradient to obtain ((R)-1-((2R,3R)-3-((S)-1-((3R,4S,5S)-4-((S)-2-((Bis(dimethylamino)methylene)amino)-N,3-dimethylbutanam ido)-3-methoxy-5-methylheptanoyl)pyrrolidin-2-yl)-3-methoxy-2-methylpropanamido)-2-phenylethyl)(2-((3-(6-(2,5-dioxo-2,5-dihydro-1H-pyrrol-1-yl)hexanamido)propyl)amino)-2-oxoethyl)phosphinic acid (CL-15) as a TFA salt. MS m/z 1044.0 (M+1). Retention time 1.094 min.

EXAMPLE 73

Synthesis of ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((3-(4-((2,5-dioxo-2,5-dihydro-1H-pyrrol-1-yl)methyl)-1H-1,2,3-triazol-1-yl)propyl)amino)-2-oxoethyl)phosphinic acid (CL-17)

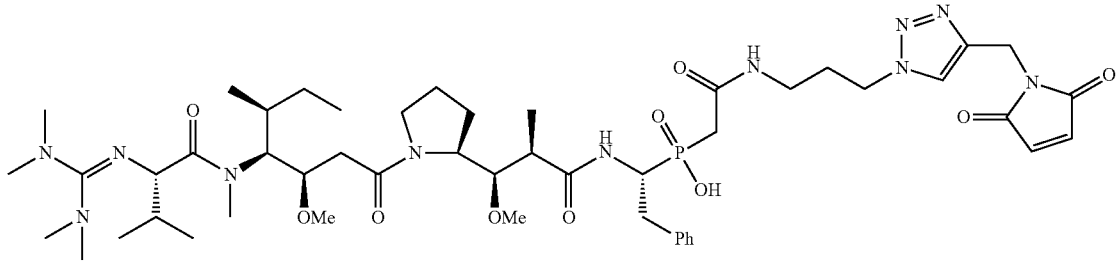

CL-17

Step 1: DIEA (2.1 mg, 0.017 mmol) and HATU (2.1 mg, 0.0055 mmol) were added to 2-(((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid TFA salt (5.0 mg, 0.0055 mmol) in DMF (1 mL). The reaction mixture was stirred at rt for 5 min and added to 3-azidopropan-1-amine (0.6 mg, 0.006 mmol) in DMF (0.2 mL). The reaction mixture was kept at rt for 18 h and purified by preparative HPLC using a 20-55% gradient to obtain (2-((3-azidopropyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphinic acid (CL-16),

CL-16

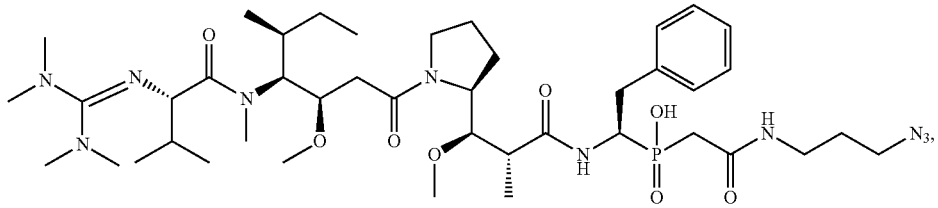

as TFA salt. MS m/z 877.0 (M+1). Retention time 1.141 min.

Step 2: A solution of (2-((3-azidopropyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl) phosphinic acid (CL-16) TFA salt (2.8 mg, 0.0028 mmol) and 1-(prop-2-yn-1-yl)-1H-pyrrole-2,5-dione (0.8 mg, 0.006 mmol) in 1:2 mixture of water-t-BuOH was degassed with Ar. To the degassed solution were add degassed aq solutions of sodium L-ascorbate (1.7 mg, 0.0085 mmol) and of copper sulfate (0.7 mg, 0.005 mmol). The reaction mixture was stirred at rt for 1 h, and concentrated. The residue was purified by preparative HPLC using a 20-45% gradient to obtain ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((3-(4-((2,5-dioxo-2,5-dihydro-1H-pyrrol-1-yl)methyl)-1H-1,2,3-triazol-1-yl)propyl)amino)-2-oxoethyl)phosphinic acid (CL-17) as a TFA salt. MS m/z 1012.0 (M+1). Retention time 1.059 min.

EXAMPLE 74

Synthesis of ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((2-(2-(4-((2,5-dioxo-2,5-dihydro-1H-pyrrol-1-yl)methyl)-1H-1,2,3-triazol-1-yl)ethoxy)ethyl)amino)-2-oxoethyl) phosphinic acid (CL-19)

CL-19

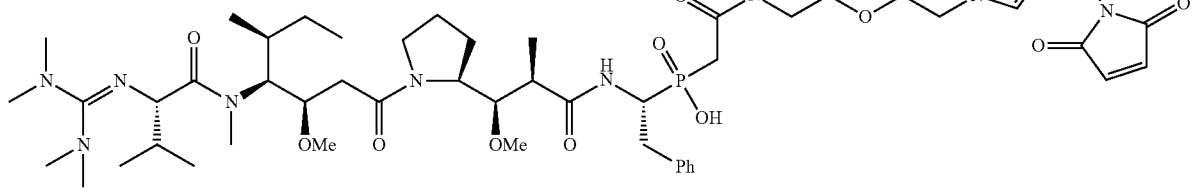

Step 1: DIEA (2.1 mg, 0.017 mmol) and then HATU (2.1 mg, 0.0055 mmol) were added to 2-(((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(hydroxy)phosphoryl)acetic acid TFA salt (5.0 mg, 0.0055 mmol) in DMF (1 mL). The reaction mixture was stirred at rt for 5 min and added to 2-(2-azidoethoxy)ethanamine (0.7 mg, 0.006 mmol) in DMF (0.2 mL). The reaction mixture was kept at rt for 18 h and purified by preparative HPLC using a 20-55% gradient to obtain (2-((2-(2-Azidoethoxy)ethyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)phosphinic acid (CL-18),

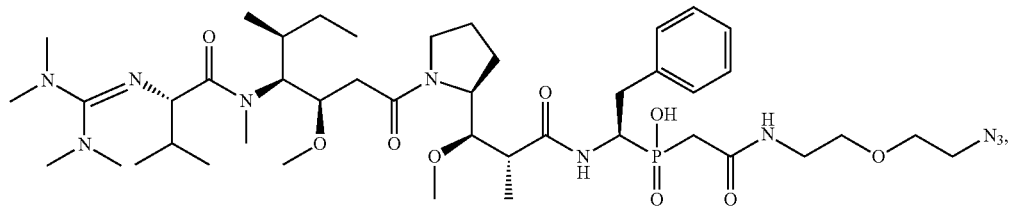

CL-18 as a TFA salt. MS m/z 907.0 (M+1). Retention time 1.121 min.

Step 2: A solution of 2-((2-(2-azidoethoxy)ethyl)amino)-2-oxoethyl)((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl) phosphinic acid (CL-18) TFA salt (4.6 mg, 0.0045 mmol) and 1-(prop-2-yn-1-yl)-1H-pyrrole-2,5-dione (1.2 mg, 0.0090 mmol) in 1:2 mixture of water-t-BuOH was degassed with Ar. To the degassed solution were added degassed aq solutions of sodium L-ascorbate (2.7 mg, 0.014 mmol) and of copper sulfate (0.7 mg, 0.005 mmol). The reaction mixture was stirred at rt for 1 h, and concentrated. The residue was purified by preparative HPLC using a 20-45% gradient to obtain ((R)-1-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-2-phenylethyl)(2-((2-(2-(4-((2,5-dioxo-2,5-dihydro-1H-pyrrol-1-yl)methyl)-1H-1,2,3-triazol-1-yl)ethoxy)ethyl)amino)-2-oxoethyl)phosphinic acid (CL-19) as a TFA salt. MS m/z 1042.0 (M+1). Retention time 1.057 min.

EXAMPLE 75

Synthesis of (S)-N-((3R,4S,5S)-1-((S)-2-((3R,4R,7S)-7-benzyl-20-(4-((2,5-dioxo-2,5-dihydro-1H-pyrrol-1-yl)methyl)-1H-1,2,3-triazol-1-yl)-4-methyl-5,8-dioxo-2,12,15,18-tetraoxa-6,9-diazaicosan-3-yl) pyrrolidin-1-yl)-3-methoxy-5-methyl-1-oxoheptan-4-yl)-2-((bis(dimethylamino)methylene)amino)-N,3-dimethylbutanamide (CL-21)

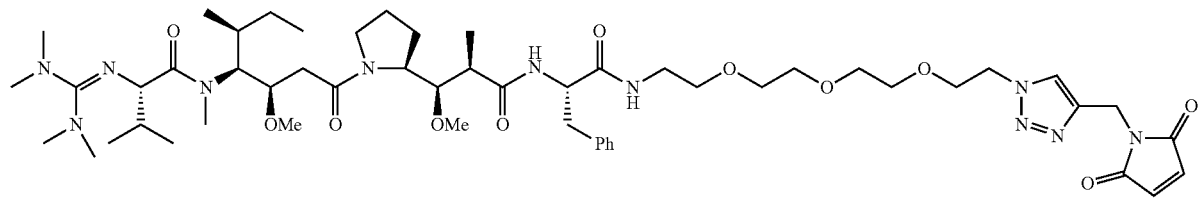

CL-21

Steps 1-3: (S)-N-((3R,4S,5S)-1-((S)-2-((3R,4R,7S)-20-Azido-7-benzyl-4-methyl-5,8-dioxo-2,12,15,18-tetraoxa-6,9-diazaicosan-3-Apyrrolidin-1-yl)-3-methoxy-5-methyl-1-oxoheptan-4-yl)-2-((bis(dimethylamino) methylene)amino)-N,3-dimethylbutanamide (CL-20),

CL-20

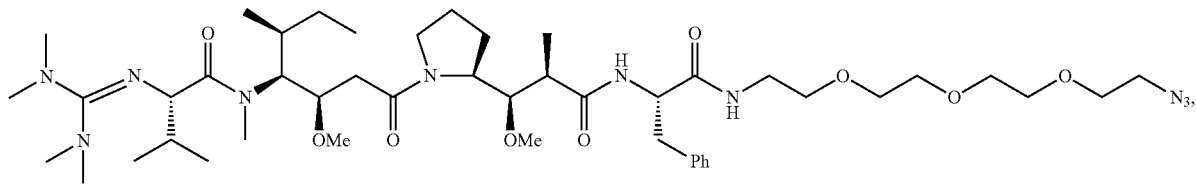

was prepared by the method described in Example 70 for (S)-N-((3R,4S,5S)-1-((S)-2-((3R,4R,7S)-7-benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)-2-((bis(dimethylamino)methylene)amino)-N,3-dimethylbutanamide (CL-12), except using 2-(2-(2-(2-azidoethoxy)ethoxy)ethoxy)ethanamine in place of 1-(2-(2-aminoethoxy)ethyl)-1H-pyrrole-2,5-dione (I-2). MS m/z 917.7 (M+1). Retention time 1.099 min.

Step 4: (S)-N-((3R,4S,5S)-1-((S)-2-((3R,4R,7S)-20-Azido-7-benzyl-4-methyl-5,8-dioxo-2,12,15,18-tetraoxa-6,9-diazaicosan-3-yl)pyrrolidin-1-yl)-3-methoxy-5-methyl-1-oxoheptan-4-yl)-2-((bis(dimethylamino)methylene)amino)-N,3-dimethylbutanamide (CL-20) (8.9 mg, 0.0097 mmol) and 1-(prop-2-yn-1-yl)-1H-pyrrole-2,5-dione (2.6 mg, 0.019 mmol) were suspended in t-BuOH (1.0 ml) and water (1.0 ml). The mixture was degassed by vacuum-fill cycle with $N_2$ five times. Degassed solutions of sodium L-ascorbate (1.9 mg, 0.0097 mmol) in $H_2O$ (0.4 mL) and $CuSO_4$ (0.31 mg, 0.0019 mmol) in $H_2O$ (0.4 mL were added and the reaction was stirred at rt for 3 h. The crude material was purified by preparative HPLC using a 20-70% gradient to obtain (S)-N-((3R,4S,5S)-1-((S)-2-((3R,4R,7S)-7-Benzyl-20-(4-((2,5-dioxo-2,5-dihydro-1H-pyrrol-1-yl)methyl)-1H-1,2,3-triazol-1-yl)-4-methyl-5,8-dioxo-2,12,15,18-tetraoxa-6,9-diazaicosan-3-Apyrrolidin-1-yl)-3-methoxy-5-methyl-1-oxoheptan-4-yl)-2-((bis(dimethylamino)methylene)amino)-N,3-dimethylbutanamide (CL-21) as a TFA salt. MS m/z 1052.3 (M+1). Retention time 0.998 min.

EXAMPLE 76

Synthesis of (S)-2-((bis(dimethylamino)methylene)amino)-1-(((3R,4S,5S)-1-((S)-2-((1R,2R)-3-(((S)-N-1-(3-(4-(aminoxymethyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-22)

Step 1: To ethyl N-hydroxyacetimidate (520 mg, 5.04 mmol) in DMF (8.3 mL) was added 3-bromoprop-1-yne (500 mg, 4.2 mmol), followed by NaOH (185 mg, 4.62 mmol). The reaction was stirred for 2 h at rt. LCMS indicated completion of the reaction. The reaction mixture was poured into saturated aq $NH_4Cl$ with ice (30 ml). The mixture was stirred until ice melted. The mixture was extracted with EtOAc (3×). The combined organic phases was washed with water and brine, dried with $MgSO_4$, filtered and concentrated to obtain ethyl N-prop-2-yn-1-yloxyacetimidate as a yellow oil. MS m/z 142.1 (M+1). Retention time 1.177 min. $^1$H NMR (400 MHz, $CDCl_3$): δ 4.52 (d, J=2.4 Hz, 2H), 4.06 (m, 2H), 2.42 (t, J=2.4 Hz, 1H), 1.96 (s, 3H), 1.30-1.24 (m, 3H). This material was used in the next step without further purification.

Step 2: (S)-2-((Bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (FP-3) (24 mg, 0.025 mmol) and ethyl N-prop-2-yn-1-yloxyacetimidate (6.9 mg, 0.049 mmol) were suspended in t-BuOH (0.5 mL) and water (1.0 mL). The reaction mixture was degassed by vacuum-fill cycle with $N_2$ five times. Degassed solutions of sodium L-ascorbate (4.9 mg, 0.025 mmol) in H2O (0.25 ml) and $CuSO_4$ (0.8 mg, 0.005 mmol) in $H_2O$ (0.25 ml) were added and the reaction was stirred at rt for 3 h. LCMS indicated completion of the reaction. The crude material was purified by preparative HPLC using a 20-70% gradient to obtain desired oxime product,

CL-22

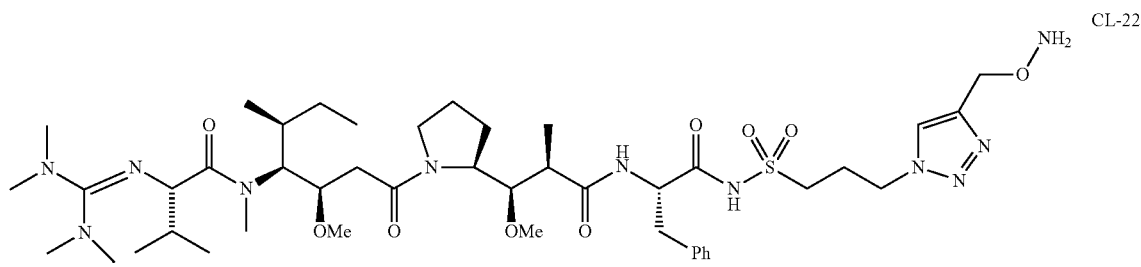

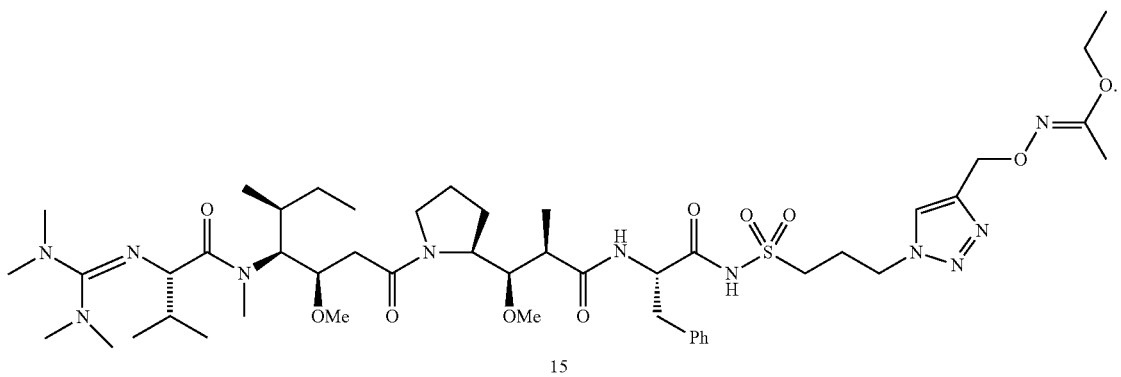

MS m/z 1004.0 (M+1). Retention time 1.226 min.

Step 3: To the product from Step 2 (17.5 mg, 0.017 mmol) in MeOH (3.0 mL) was added hydrochloric acid (1M, 0.095 mL). After 30 min at rt, LCMS indicated completion of the reaction. The crude material was purified by preparative HPLC using a 20-70% gradient to obtain (S)-2-((bis(dimethylamino)methylene)amino)-1-(((3R,4S,5S)-1-((S)-2-((1R,2R)-3-(((S)-N-1-(3-(4-(aminoxymethyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-22). MS m/z 934.3 (M+1). Retention time 0.882 min.

EXAMPLE 77

Synthesis of (S)-2-((4-methylpyrimidin-2-yl)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-24)

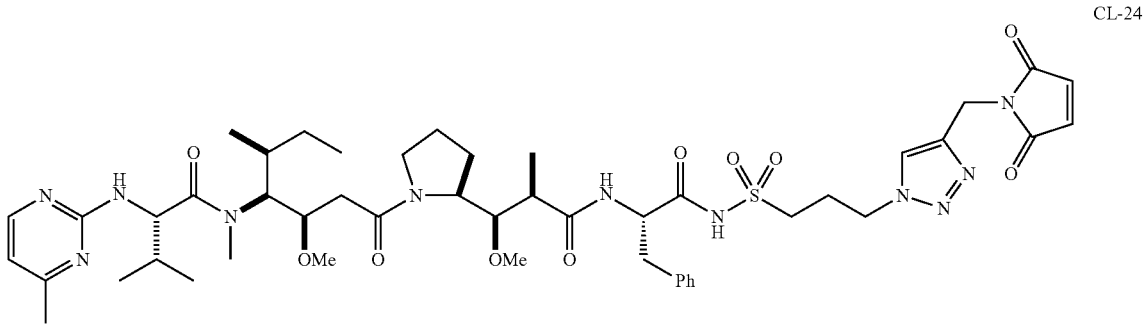

CL-24

Step 1: (S)-1-(((3R,4S,5S)-1-((S)-2-((1R,2R)-3-(((S)-N-1-(3-zidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane (7 mg, 0.009 mmol), 2-chloro-4-methylpyrimidine (5.6 mg, 0.044 mmol) and DIEA (0.031 mL, 0.18 mmol) in 2-propanol (2 mL). were heated in a sealed vial at 150° C. for overnight. The crude material was purified by preparative HPLC using a 20-70% gradient to obtain (S)-2-((4-Methylpyrimidin-2-yl)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-23),

CL-23

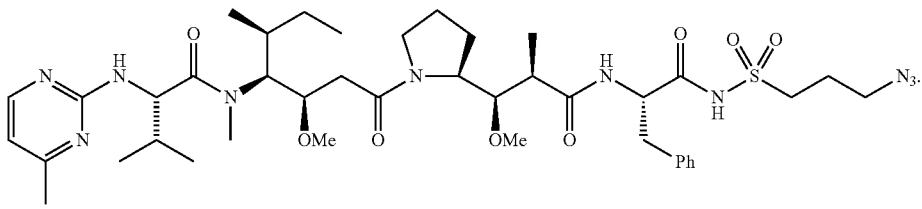

MS m/z 857.4 (M+1). Retention time 1.241 min.

Step 2: (S)-2-((4-Methylpyrimidin-2-yl)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-23) (2.8 mg, 0.0029 mmol) and 1-(prop-2-yn-1-yl)-1H-pyrrole-2,5-dione (1.2 mg, 0.0087 mmol) were suspensed in 0.5 mL each of t-BuOH and water. The mixture was degassed by vacuum-fill cycles with N₂ five times. Degassed solutions of sodium L-ascorbate (0.7 mg, 0.004 mmol) in water (0.4 mL) and CuSO₄ (0.1 mg, 0.0007 mmol) in water (0.1 mL) were added. The reaction was stirred at rt for 4 h. LCMS indicated completion of the reaction. The crude material was purified by reverse phase HPLC using a 20-70% gradient to obtain (S)-2-((4-methylpyrimidin-2-yl)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-24). MS m/z 992.5 (M+1). Retention time 1.077 min.

EXAMPLE 78

Synthesis of (S)-2-(3,3-diisopropylureido)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-26)

CL-26

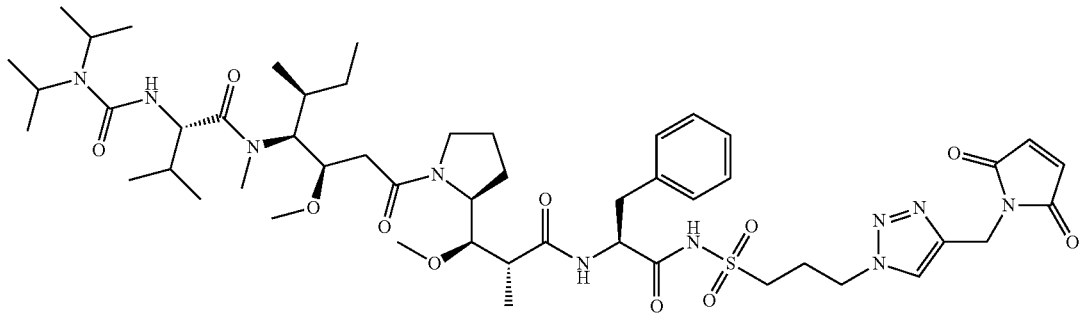

Step 1: To (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane HCl salt (7.5 mg, 0.0095 mmol) in THF:DMF (1:1, 1 mL) were added 4-nitrophenylchloroformate (3.2 mg, 0.016 mmol) and DIEA (6.0 mg, 0.047 mmol). After 10 min at rt LCMS indicated formation of the desired carbamate,

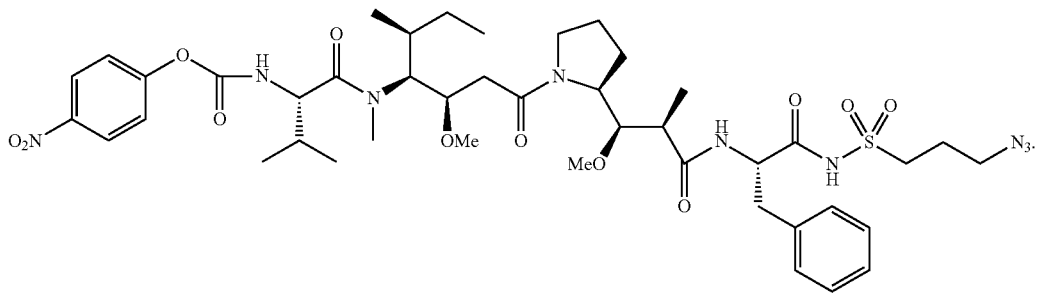

THF was removed by evapolation. Diisopropylamine (5.7 mg, 0.056 mmol) was added, and the reaction was stirred at rt for 1 h. The crude material was purified by preparative HPLC using a 40-80% gradient to obtain (S)-N-((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-(3,3-diisopropylureido)-N,3-dimethylbutanamide (CL-25),

CL-25

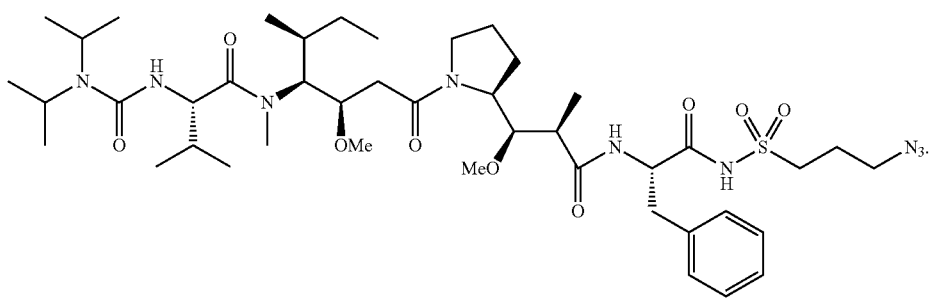

MS m/z 892.5 (M+1). Retention time 1.493 min.

Step 2: A solution of (S)-N-((3R,4S,5S)-1-((S)-2-((1R,2R)-3-(((S)-N-1-(3-azidopropylsulfonamido)-1-oxo-3-phenylpropan-2-yl)am ino)-1-methoxy-2-methyl-3-oxopropyl)pyrrolidin-1-yl)-3-methoxy-5-methyl-1-oxoheptan-4-yl)-2-(3,3-diisopropylureido)-N,3-dimethylbutanamide (CL-25) (6.2 mg, 0.007 mmol) and 1-(prop-2-yn-1-yl)-1H-pyrrole-2,5-dione (1.7 mg, 0.013 mmol) in 1:2 mixture of water-tBuOH (3 mL) was degassed with Ar. To the degassed solution were added degassed aq solutions of copper sulfate (2.0 mg, 0.013 mmol) and sodium ascorbate (4.1 mg, 0.021 mmol). The reaction mixture was stirred at rt for 1 h, and concentrated. The residue was purified by preparative HPLC using a 40-73% gradient to obtain (S)-2-(3,3-Diisopropylureido)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-26). MS m/z 1027.5 (M+1). Retention time 1.336 min.

EXAMPLE 79

Synthesis of N-((S)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)morpholine-4-carboxamide (CL-28)

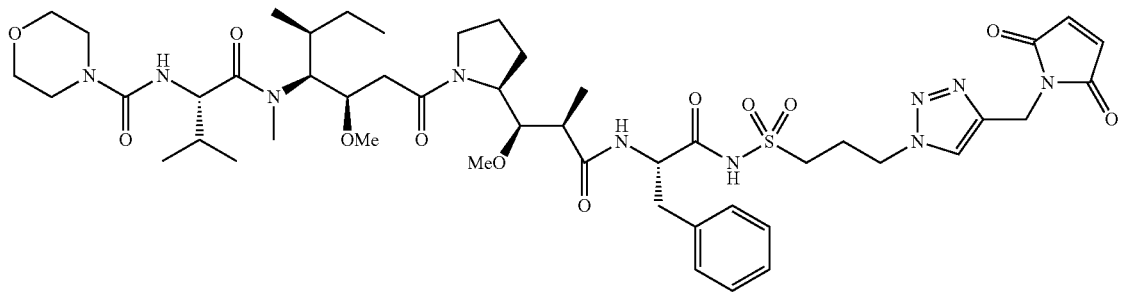

CL-28

Step 1: To (S)-1-(((3H,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane HCl salt (7.5 mg, 0.0095 mmol) in THF:DMF (1:1, 1 mL) were added 4-nitrophenylchloroformate (3.2 mg, 0.016 mmol) and DIEA (6.0 mg, 0.047 mmol). After 10 min at rt LCMS indicated formation of the desired carbamate. THF was evapolated. Morpholine (4.9 mg, 0.056 mmol) was added and the reaction was stirred at rt for 1 h. The crude material was purified by preparative HPLC using a 30-70% gradient to obtain N-((S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)morpholine-4-carboxamide (CL-27), phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)morpholine-4-carboxamide (CL-27) (6.3 mg, 0.007 mmol) and 1-(prop-2-yn-1-yl)-1H-pyrrole-2,5-dione (1.7 mg, 0.013 mmol) in 1:2 mixture of water-tBuOH (3 mL) was degassed with Ar. To the degassed solution were added degassed aq solutions of copper sulfate (1.9 mg, 0.013 mmol) and sodium ascorbate (1.9 mg, 0.0095 mmol). The reaction was stirred at rt for 1 h. The reaction mixture was concentrated and purified by preparative HPLC using a 30-60% gradient to obtain N-((S)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)

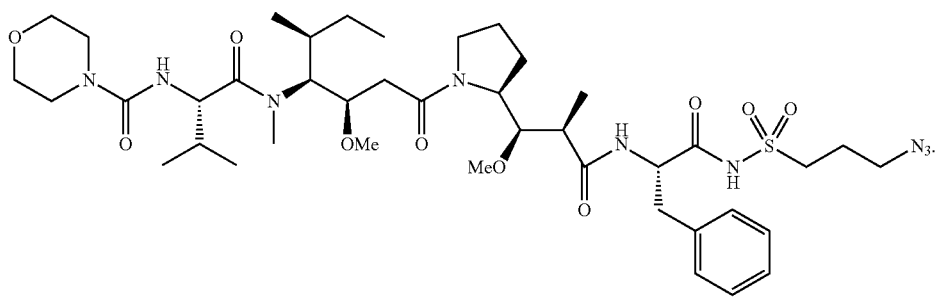

CL-27

MS m/z 878.4 (M+1). Retention time 1.310 min.

Step 2: A solution of N-((S)-1-(((3R,4S,5S)-1-((S)-2-((1R,2R)-3-(((S)-N-1-(3-azidopropylsulfonamido)-1-oxo-3- amino)-3-methyl-1-oxobutan-2-yl)morpholine-4-carboxamide (CL-28). MS m/z 1013.4(M+1). Retention time 1.122 min.

EXAMPLE 80

Synthesis of (S)-2-((1,3-dimethylimidazolidin-2-ylidene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-30)

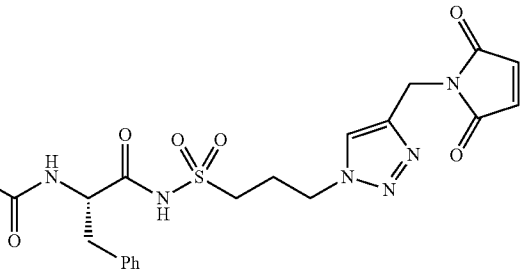

CL-30

Step 1: HOBt (27.8 mg, 0.206 mmol) in DCM (2 mL) was added to 2-chloro-1,3-dimethyl-4,5-dihydro-1H-imidazol-3-ium hexafluorophosphate (57.4 mg, 0.206 mmol) and triethylamine (0.029 mL, 0.21 mmol) in DCM (2 mL). The reaction was stirred at rt for overnight. The reaction mixture was filtered to collect 2-((1H-benzo[d][1,2,3]triazol-1-yl)oxy)-1,3-dimethyl-4,5-dihydro-1H-imidazol-3-ium hexafluorophosphate,

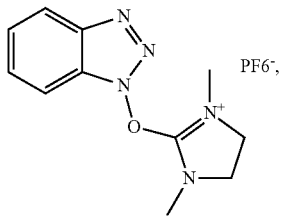

as white solid. MS m/z 232.1(M+). Retention time 0.324 min. This material was used in the next step without further purification.

Step 2: To (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl) amino)-2-amino-3-methyl-1-oxobutane hydrochloride (30.6 mg, 0.038 mmol) in DMF (2 mL) were added DIEA (0.033 mL, 0.191 mmol) and 2-((1H-benzo[d][1,2,3]triazol-1-yl)oxy)-1,3-dimethyl-4,5-dihydro-1H-imidazol-3-ium hexafluorophosphate (28.8 mg, 0.076 mmol). The reaction was stirred at rt for 2 h. LCMS indicated completion of the reaction. The crude material was purified by preparative HPLC using a 20-70% gradient to obtain (S)-2-((1,3-dimethylimidazolidin-2-ylidene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-29),

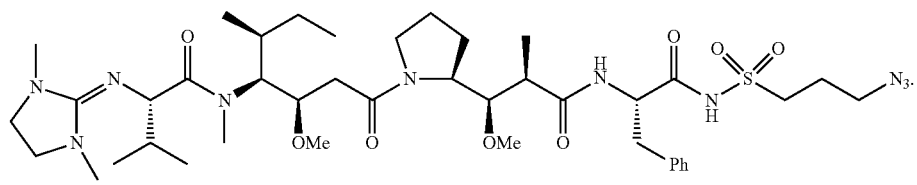

MS m/z 861.3 (M+1). Retention time 1.090 min.

Step 3: (S)-2-((1,3-Dimethylimidazolidin-2-ylidene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-30) was prepared by the method described for (S)-2-((bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-9) except using (S)-2-((1,3-dimethylimidazolidin-2-ylidene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl) amino)-3-methyl-1-oxobutane (CL-29). MS m/z 996.4 (M+1). Retention time 1.118 min.

EXAMPLE 81

Synthesis of N-hydroxysuccinimide (NHS) ester of (S)-2-((bis(dimethylamino)methylene)amino)-1-(((3R,4S,5S)-1-((S)-2-((1R,2R)-3-(((S)-N-1-(3-(4-carboxybutoyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-32)

CL-32

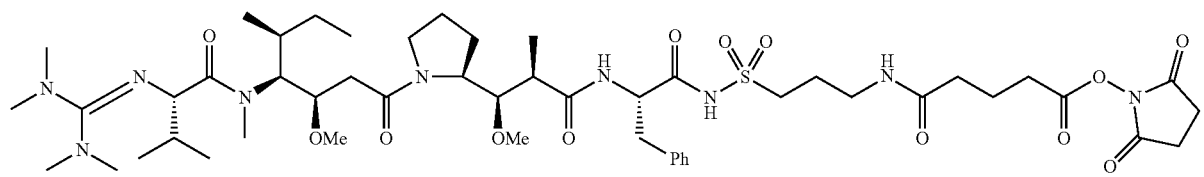

Step 1: Pd/C (10%, wet, 6.5 mg) was aaaeo to (S)-2-((Bis(dimethylamino)methylene)amino)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (FP-3) TFA salt (30 mg, 0.031 mmol) in water/ethanol (2 mL/2 mL). The reaction was stirred under H$_2$ for 3 h. The catalyst was removed by filtration. The filtrate was concentrated to afford (S)-2-((bis(dimethylamino)methylene)amino)-1-(((3R,4S,5S)-1-((S)-2-((1R,2R)-3-(((S)-N-1-(3-aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-31),

CL-31

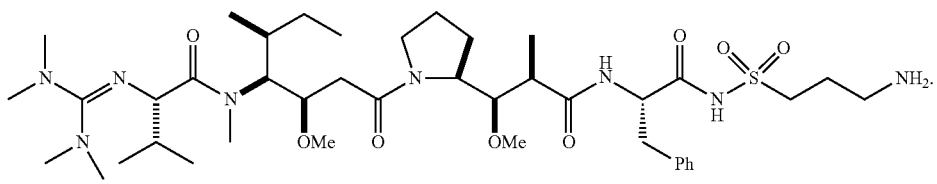

MS m/z 837.5 (M+1). Retention time 0.993 min.

Step 2: (S)-2-((Bis(dimethylamino)methylene)amino)-1-(((3R,4S,5S)-1-((S)-2-((1R,2R)-3-(((S)-N-1-(3-aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-31) (12 mg, 0.014 mmol) and DIEA (0.0125 mL, 0.0715 mmol) were dissolved in DMF (1 mL). The resulting solution was added to bis(2,5-dioxopyrrolidin-1-yl) glutarate (7.0 mg, 0.022 mmol) and DIEA (0.0125 mL, 0.0715 mmol) in DMF (1 mL). The reaction was stirred for 2 h at rt. LCMS indicated completion of the reaction. The crude material was purified by preparative HPLC using a 20-70% gradient to obtain (S)-2-((bis(dimethylamino)methylene)amino)-1-(((3R,4S,5S)-1-((S)-2-((1R,2R)-3-(((S)-N-1-(3-(5-((2,5-dioxopyrrolidin-1-yl)oxy)-5-oxopentanamido)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-32). MS m/z 1048.5 (M+1). Retention time 1.285 min.

EXAMPLE 82

Synthesis (S)-2-((bis(dimethylamino)methylene)amino)-1-(((3R,4S,5S)-1-((S)-2-((1R,2R)-3-(((S)-N-1-(3-((1R,8S,9s)-bicyclo[6.1.0]non-4-yn-9-ylmethyl-oxycarbonyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-33)

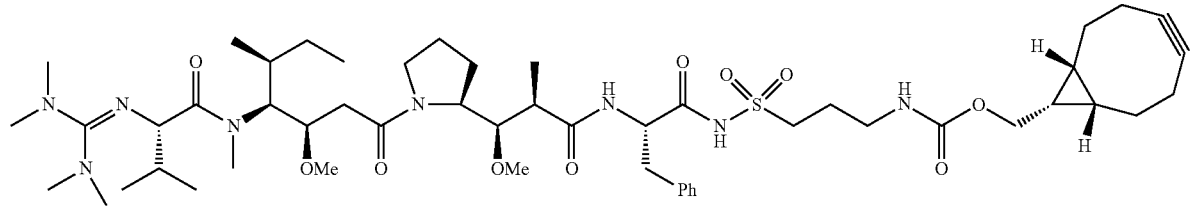

CL-33

A solution of (S)-2-((bis(dimethylamino)methylene)amino)-1-(((3R,4S,5S)-1-((S)-2-((1R,2R)-3-(((S)-N-1-(3-aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-32) (15 mg, 14 µmol) and DIEA (12 µl) in DMF (1 mL) was added to (1R,8S,9s)-bicyclo[6.1.0]non-4-yn-9-ylmethyl (2,5-dioxopyrrolidin-1-yl) carbonate (4.1 mg, 14 µmol) and DIEA (12 µl) in DMF (1 ml). The reaction was covered by aluminum foil and stirred for 1 h at rt. Purification by preparative HPLC (20-70% acetonitrile-H₂O containing 0.05% TFA) afforded compound (CL-33). MS m/z 1013.5(M+1). Retention time 1.203 min.

EXAMPLE 83

Synthesis of (1R,8S,9s)-bicyclo[6.1.0]non-4-yn-9-ylmethyl (3-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)propyl)carbamate (CL-34)

Step 1: To Boc-L-Phe-OH (65 mg, 0.25 mmol) in DMF (2 ml) were added DIEA (142 µl, 1.02 mmol) and HATU (85 mg, 0.225 mmol). The reaction was stirred for 15 min, and then benzyl (3-aminopropyl)carbamate (50 mg, 0.20 mmol) in DMF (1 ml) was added. The reaction mixture was stirred at rt for 1 h, and then purified by preparative HPLC (20-70% acetonitrile-H₂O containing 0.05% TFA) to obtain (S)-benzyl (3-(2-(tert-butoxycarbonyl)amino-3-phenylpropanamido)propyl)carbamate. MS m/z 456.3 (M+1). Retention time 1.225 min. The product thus obtained (81.2mg, 0.18 mmol) was dissolved in methanolic HCl (3M, 4 ml). The solvent was removed slowly under stream of N₂, resulting in removal of the Boc group. Lyophilization from acetonitrile water mixture afforded (S)-benzyl (3-(2-amino-3-phenylpropanamido)propyl) HCl salt. MS m/z 356.2(M+1). Retention time 0.857 min.

Step 2: To (2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoic acid (i-11) (14 mg) in DMF (2 ml) were added DIEA (12.4 mg, 122 µmol) and HATU (7.8 mg, 20 µmol). The reaction was stirred for 15 min, and then (S)-benzyl (3-(2-amino-3-phenylpropanamido)propyl)carbamate (8 mg, 20 µmol) was added. The reaction mixture was stirred at rt for 2 h and then purified by preparative HPLC (20-70% acetonitrile-H₂O containing 0.05% TFA) to obtain benzyl (3-((S)-2-((2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanamido)-3-phenylpropanamido)propyl)carbamate,

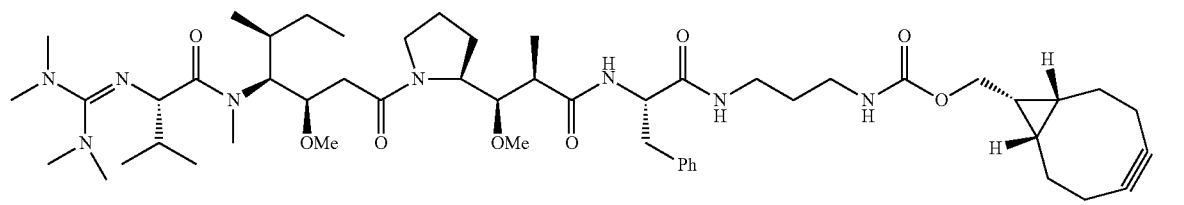

CL-34

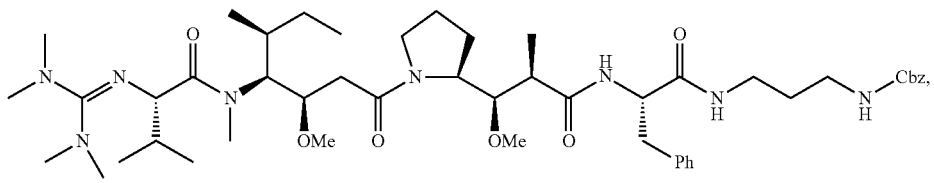

as TFA salt. MS m/z 907.6 (M+1). Retention time 1.149 minutes.

Step 3: To the product obtained in step 2 (16.2 mg, 16 μmol) in MeOH (2 ml) was added Pd/C (3.4 mg, 10% wet). The reaction atmosphere was replaced with $H_2$. The reaction mixture was stirred for 2 h at rt, then filtered and concentrated to give (S)-N-((3R,4S,5S)-1-((S)-2-((1R,2R)-3-(((S)-1-((3-aminopropyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((bis(dimethylamino)methylene)amino)-N,3-dimethylbutanamide,

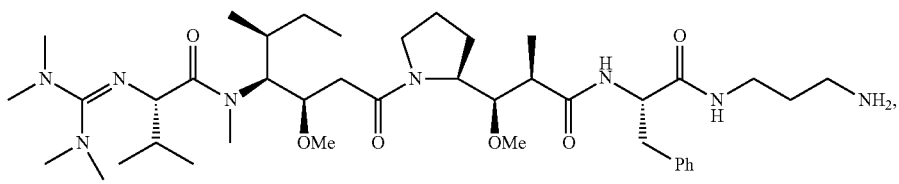

MS m/z 773.6(M+1). Retention time 0.872 min.

Step 4: The product obtained in step 3 (13.3 mg, 15 μmol) was dissolved in DMF (1 ml) and DIEA (13 μl) was added. (1R,8S,9s)-Bicyclo[6.1.0]non-4-yn-9-ylmethyl (2,5-dioxopyrrolidin-1-yl) carbonate,

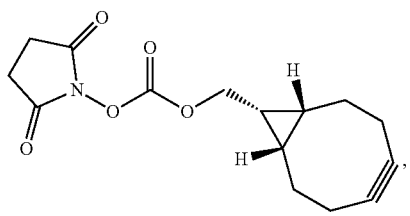

(4.4 mg, 15 μmol) was dissolved in DMF (1 ml), and DIEA (13 μl) was added. The two solutions were combined. The reaction mixture was stirred for 1 h at rt, and then purified by preparative HPLC (20-70% acetonitrile-$H_2O$ containing 0.05% TFA) to obtain compound (CL-34). MS m/z 949.6 (M+1). Retention time 1.190 min.

EXAMPLE 84

Synthesis of (S)-N-((3R,4S,5S)-1-((S)-2-((1R,2R)-3-(((S)-1-((2-(aminooxy)ethyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((bis(dimethylamino)methylene)amino)-N,3-dimethylbutanamide (CL-35)

CL-35

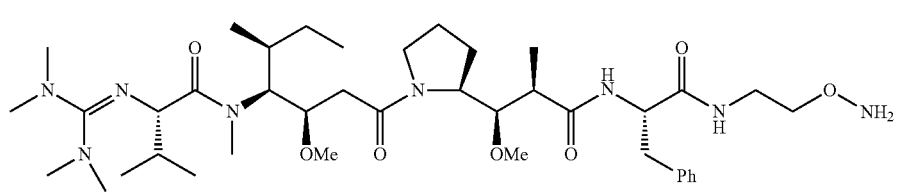

Step 1: Diisopropyl azodicarboxylate (1.26 ml, 6.51 mmol) was added dropwise to a suspension of N-(tert-butoxycarbonyl)ethanolamine (1.0 g, 6.2 mmol), N-hydroxyphthalimide (1.01 g, 6.2 mmol) and triphenylphosphine (1.71 g, 6.51 mmol) in tetrahydrofuran (10 ml) at 0° C. The reaction was stirred and allowed to warm to rt over 16 h. The reaction mixture was concentrated and purified by flash chromatography (SiO$_2$, ethyl acetate/hexane, 0% to 50%) to yield [2-(1,3-dioxo-1,3-dihydro-isoindol-2-yloxy)-ethyl]-carbamic acid tert-butyl ester as an white solid. MS m/z 207.1(M+1-Boc). Retention time 1.138 min. TFA (2 ml) was added to [2-(1,3-Dioxo-1,3-dihydro-isoindol-2-yloxy)-ethyl]-carbamic acid tert-butyl ester (1 g, approximately 60% pure, 2 mmol) in DCM (10 ml) at 0° C. The reaction was warmed to rt slowly and stirred for 2 h at rt. Concentration of the reaction mixture afforded 2-(2-aminoethoxy)isoindoline-1,3-dione as TFA salt. MS m/z 207.1(M+1). Retention time 0.780 min.

Step 2: To Boc-L-Phe-OH (519 mg, 1.96 mmol) in DMF (5 ml) were added DIEA (1.37 ml, 9.79 mmol) and HATU (745 mg, 1.96 mmol). The reaction was stirred for 15 min, and then 2-(2-aminoethoxy)isoindoline-1,3-dione (627 mg, 1.96 mmol) in DMF (3 ml) was added. The reaction mixture was stirred at rt for 1 h and purified by preparative HPLC (20-70% acetonitrile-H$_2$O containing 0.05% TFA) to obtain (S)-tert-butyl (1-((2-((1,3-dioxoisoindolin-2-yl)oxy)ethyl)amino)-1-oxo-3-phenylpropan-2-yl)carbamate. MS m/z 454.2(M+1). Retention time 1.215 min. The product thus obtained (0.66 g, 1.5 mmol) was dissolved in DCM (6 ml), and TFA (1.5 ml) was added at 0° C. The reaction was warmed to rt slowly and stirred for 2 h. Concentration of the reaction mixture afforded (S)-2-amino-N-(2-((1,3-dioxoisoindolin-2-yl)oxy)ethyl)-3-phenylpropanamide as TFA salt. MS m/z 354.2(M+1). Retention time 0.698 min.

Step 3: DIEA (36 μl, 0.20 mmol) and HATU (6.5 mg, 0.017 mmol) were added to (2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoic acid (i-11) (11.6 mg, 17 gmol) in DMF (1 ml). The reaction was stirred for 15 min, and then (S)-2-amino-N-(2-((1,3-dioxoisoindolin-2-yl)oxy)ethyl)-3-phenylpropanamide m(11.7 mg, 017 gmol) in DMF (1 ml). The reaction mixture was stirred at rt for 2 h, and then purified by preparative HPLC (20-70% acetonitrile-H$_2$O containing 0.05% TFA) to obtain (S)-2-((bis(dimethylamino)methylene)amino)-N-((3R,4S,5S)-1-((S)-2-((1R,2R)-3-(((S)-1-((2-((1,3-dioxoisoindolin-2-yl)oxy)ethyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide,

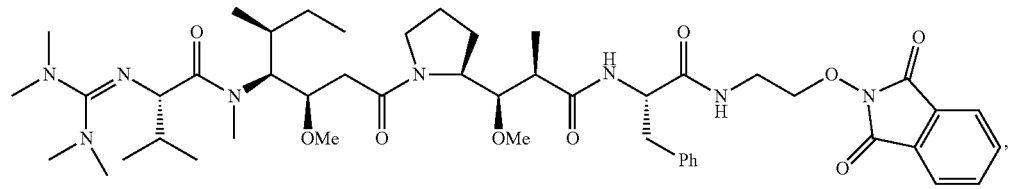

as TFA salt. MS m/z 905.5(M+1). Retention time 1.110 min.

Step 4: The product obtained in step 3 (86 mg, 84 μmol) in HCl (6 M, 6 ml) was stirred for 2 days at rt, resulting in a completion of the reaction. Purification by preparative HPLC (20-45% acetonitrile-H$_2$O containing 0.05% TFA) afforded compound (CL-35) as a TFA salt. MS m/z 775.5(M+1). Retention time 0.859 min.

EXAMPLE 85

Synthesis of (S)-2-((bis(dimethylamino)methylene)amino)-1-(((3R,4S,5S)-1-((S)-2-((1 R,2R)-3-(((S)-N-1-(3-(am inoxyacetyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)am ino)-3-methyl-1-oxobutane (CL-36)

CL-36

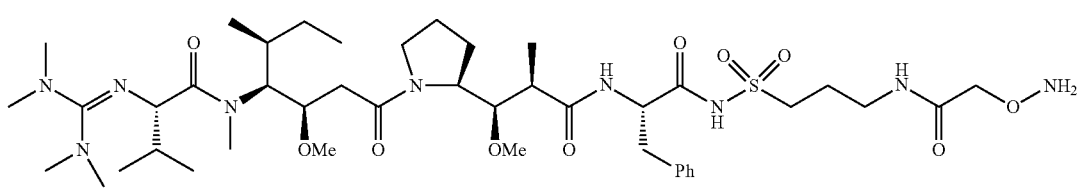

Step 1: A solution of (S)-2-((bis(dimethylamino)methylene)amino)-1-(((3R,4S,5S)-1-((S)-2-((1R,2R)-3-(((S)-N-1-(3-aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-31) (25 mg, 30 μmol) and DIEA (26 μl) in DMF (1.5 ml) was combined with a solution of 2,5-dioxopyrrolidin-1-yl 2-(((tert-butoxycarbonyl)amino)oxy)acetate (8.6 mg, 30 μmol) and DIEA (26 μl) in DMF (1.5 ml). The reaction mixture was stirred for 1 h at rt, and then purified by preparative HPLC (20-70% acetonitrile-H₂O containing 0.05% TFA) to obtain under hydrogen atmosphere. After removal of the spent catalyst by filtration, solvent was removed by concentration to give t-butyl 2-(2-aminoethoxy)ethoxycarbamate. MS m/z 221.2(M+1). Retention time 0.451 min.

Step 2: To Cbz-Phe (299 mg, 1.0 mmol) in DMF (2 ml) were added DIEA (0.793 ml, 4.54 mmol) and HATU (363 mg, 953 μmol). After being stirred for 15 min at rt, t-butyl 2-(2-aminoethoxy)ethoxycarbamate (200 mg, 0.908 mmol) in DMF (2 ml) was added. The reaction mixture was stirred for 2 h at rt, and then purified by preparative HPLC (20-70% acetonitrile-H₂O containing 0.05% TFA) to obtain (S)-t-butyl 2-(2-(2-benzyloxy carbonylamino-3-phenylpropanamido)ethoxy)ethoxycarbamate. MS m/z 502.3(M+1). Retention time 1.206 min. ¹H NMR (400 MHz, CDCl₃): δ 7.58 (s, 1H), 7.35-7.18 (m, 10H), 6.74 (s, 1H), 5.58 (d, J=7.6 Hz, 1H), 5.07 (s, 2H), 4.46-4.44 (m, 1H), 3.94-3.92 (m, 2H), 3.59-3.57 (m, 2H), 3.46-3.34 (m, 4H), 3.10-3.08 (m, 2H), 1.46 (s, 9H).

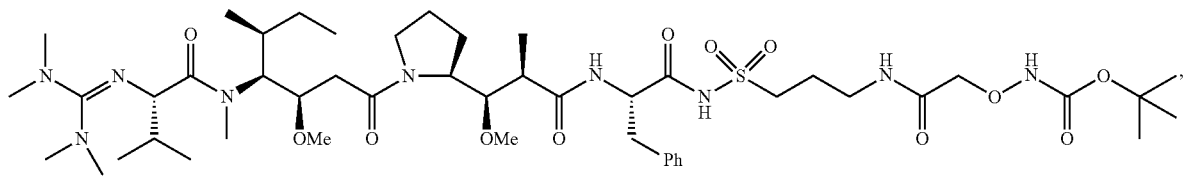

(S)-2-((bis(dimethylamino)methylene)amino)-1-(((3R,4S,5S)-1-((S)-2-((1R,2R)-3-(((S)-N-1-(3-(N-(t-butoxycarbonyl)aminoxyacetyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane, as a TFA salt. MS m/z 1011.5(M+1). Retention time 1.079 min.

Step 2: TFA (0.4 ml) was added to the product obtained in step 1 (15.3 mg, 14 μmol) in DCM (2 ml) at 0° C. The reaction was stirred at 0° C. for 30 min, then warmed up to rt and stirred for 1 h. Purification by preparative HPLC (20-70% acetonitrile-H₂O containing 0.05% TFA) afforded compound (CL-36) as a TFA salt. MS m/z 910.5(M+1). Retention time 0.919 min.

EXAMPLE 86

Synthesis of (S)-N-((3R,4S,5S)-1-((S)-2-((3R,4R,7S)-14-(aminooxy)-7-benzyl-4-methyl-5,8-dioxo-2,12-dioxa-6,9-diazatetradecan-3-yl)pyrrolidin-1-yl)-3-methoxy-5-methyl-1-oxoheptan-4-yl)-2-((bis(dimethylamino)methylene)amino)-N,3-dimethylbutanamide (CL-37)

Step 3: The Cbz group was removed by the method described in step 1 to give (S)-tert-butyl 2-(2-(2-amino-3-phenylpropanamido)ethoxy)ethoxycarbamate. MS m/z 368.5(M+1). Retention time 0.807 min.

Step 4: DIEA (19 μl) and HATU (8.3 mg, 22 μmol) were added to (2R,3R)-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-3-methoxy-2-methylpropanoic acid (i-11) (15 mg, 22 μmol) in DMF (1 ml). The reaction was stirred for 15 min, and then (S)-tert-butyl 2-(2-(2-amino-3-phenylpropanamido)ethoxy)ethoxycarbamate (8.1 mg, 22 μmol) in DMF (1 ml) was added. The reaction mixture was stirred at rt for 2 h, and then purified by preparative HPLC (20-70% acetonitrile-H₂O containing 0.05% TFA) to obtain tert-butyl ((3R,4R,7S)-7-benzyl-3-((S)-1-((3R,4S,5S)-4-((S)-2-((bis(dimethylamino)methylene)amino)-N,3-dimeth

CL-37

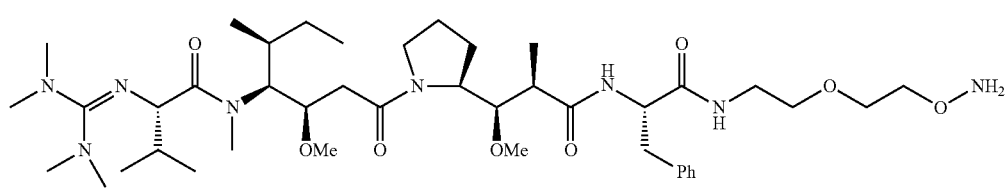

Step 1: t-Butyl 2-(2-benzyloxy carbonylaminoethoxy)ethoxycarbamate (1.5 g, 4.2 mmol) and 10% Pd—C (0.45 g, 0.42 mmol) in EtOAc (25 ml) were stirred for 5 h at rt ylbutanamido)-3-methoxy-5-methylheptanoyl)pyrrolidin-2-yl)-4-methyl-5,8-dioxo-2,12-dioxa-6,9-diazatetradecan-14-yl)oxycarbamate,

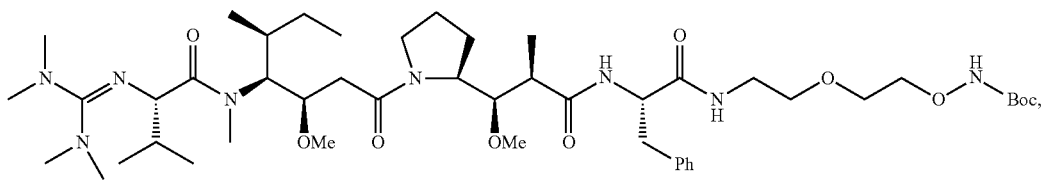

as a TFA salt. MS m/z 919.6(M+1). Retention time 1.139 min.

Step 5: TFA (0.4 ml) was added to the product obtained in step 4 (13.8 mg, 13 µmol) in DCM (2 ml) at 0° C. The reaction mixture was stirred at 0° C. for 30 min and then at rt for 1 h. Purification by preparative HPLC (20-70% acetonitrile-H₂O containing 0.05% TFA) afforded compound (CL-37) as a TFA salt. MS m/z 819.6(M+1). Retention time 0.868 min.

EXAMPLE 87

Synthesis of (3R,4R,7S)-2,5-Dioxopyrrolidin-1-yl 7-benzyl-3-((S)-1-((3R,4S,5S)-4-((S)-2-((bis(dimethylamino)methylene)amino)-N,3-dimethylbutanamido)-3-methoxy-5-methylheptanoyl)pyrrolidin-2-yl)-4,9,12-trimethyl-5,8,13-trioxo-2-oxa-6,9,12-triazaheptadecan-17-oate (CL-38)

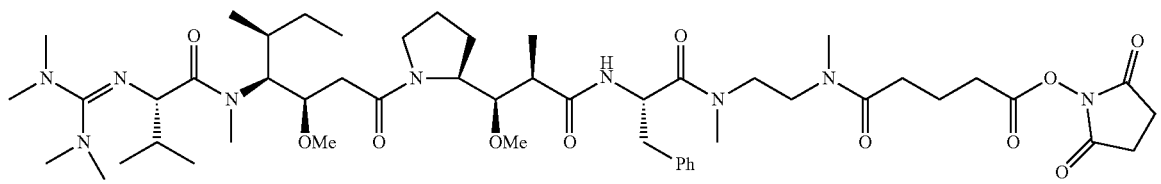

CL-38

Compound (CL-38) (MS m/z 998.5 (M+1); Retention time 1.022 min.) was prepared by the method described for step 2 of Example 81 except (S)-N-((3R,4S,5S)-1-((S)-2-((7S,10R,11R)-7-benzyl-5,10-dimethyl-6,9-dioxo-12-oxa-2,5,8-triazatridecan-11-yl)pyrrolidin-1-yl)-3-methoxy-5-methyl-1-oxoheptan-4-yl)-2-((bis(dimethylamino)methylene)amino)-N,3-dimethylbutanamide,

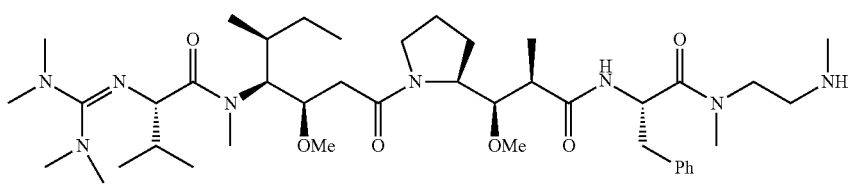

was used in place of compound (CL-31).

EXAMPLE 88

Synthesis of 2,3,5,6-tetraflulorphenyl ester of (S)-2-((bis(dimethylamino)methylene)amino)-1-(((3R,4S,5S)-1-((S)-2-((1R,2R)-3-(((S)-N-1-(3-(4-carboxybutoyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-39)

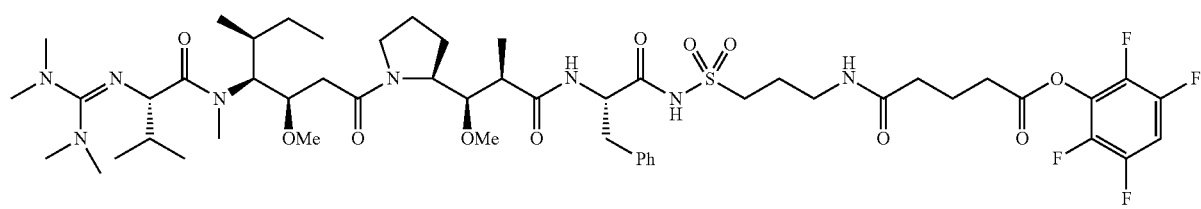

CL-39

Compound (CL-39) (MS m/z 1099.5 (M+1); Retention time 1.197 min.) was prepared by the method described for step 2 of Example 81 except bis(2,3,5,6-tetrafluorophenyl) glutarate was used in place of bis(2,5-dioxopyrrolidin-1-yl) glutarate.

EXAMPLE 89

Synthesis of perfluorophenyl ester of (S)-2-((bis(dimethylamino)methylene)amino)-1-(((3R,4S,5S)-1-((S)-2-((1R,2R)-3-(((S)-N-1-(3-(3-(2-carboxyethoxy)propanoyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-40)

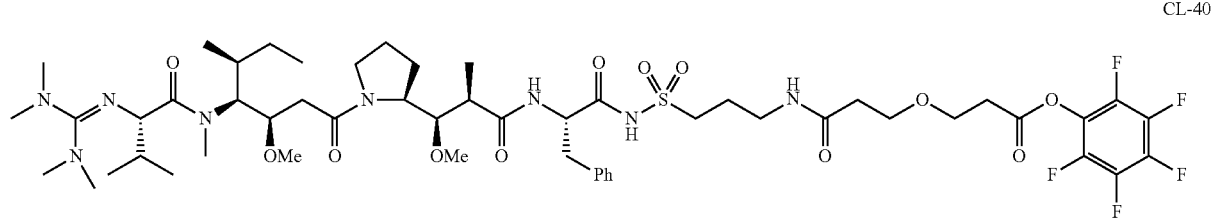

CL-40

Compound (CL-40) (MS m/z 1147.4 (M+1); Retention time 1.223 min.) was prepared by the method described for step 2 of Example 81 bis(perfluorophenyl) 3,3'-oxydipropanoate was used in place of bis(2,5-dioxopyrrolidin-1-yl) glutarate.

EXAMPLE 90

Synthesis of perflulorphenyl ester of (S)-2-((bis(dimethylamino)methylene)amino)-1-(((3R,4S,5S)-1-((S)-2-((1R,2R)-3-(((S)-N-1-(3-(4-carboxybutoyl)aminopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-41)

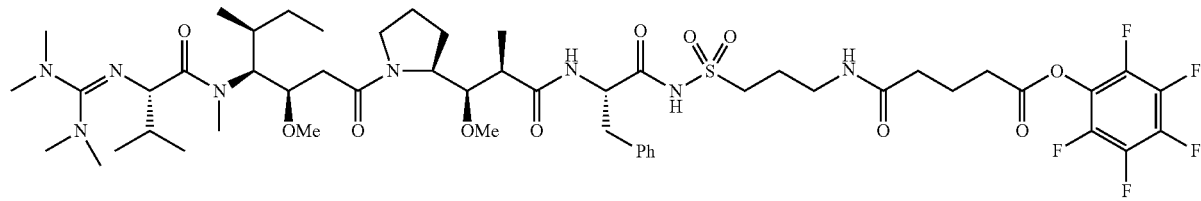

CL-41

Compound (CL-41) (MS m/z 1117.5 (M+1); Retention time 1.220 min.) was prepared by the method described for step 2 of Example 81 bis(perfluorophenyl) glutarate was used in place of bis(2,5-dioxopyrrolidin-1-yl) glutarate.

Synthetic Procedure for Coenzyme A Analogs

EXAMPLE 91

3-Buten-2-One Adduct of Coenzyme A (CoA-1)

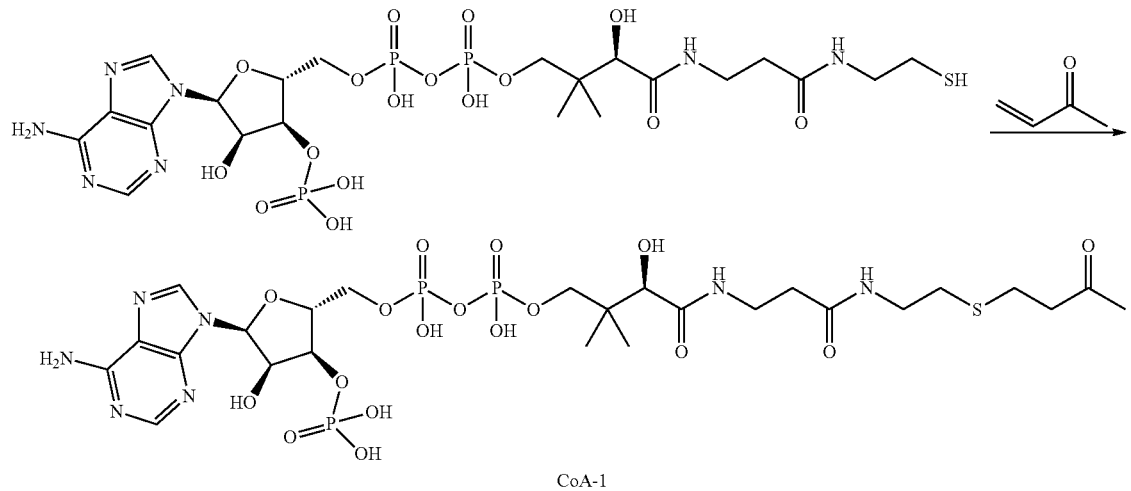

CoA-1

Coenzyme A trilithium salt (259 mg, Sigma, assay >93%) was dissolved in 2.0 mL of phosphate buffer with EDTA (100 mM phosphate, 5 mM EDTA, pH7.5). To The reaction mixture was added 3-buten-2-one (29.0 µL, Aldrich, 99%), and the reaction mixture was let stand at 20° C. for 75 min. The whole reaction mixture was loaded onto an ISCO C18 Aq Gold 15.5 g column which was pre-equilibrated with 100% $H_2O$. The desired product was eluted at 100% $H_2O$. The fractions containing the pure desired product were combined and lyophilized, affording compound CoA-1 as a crystalline solid. MS (ESI+) m/z 838.2 (M+1). H-NMR (400 MHz, $D_2O$) δ 8.525 (s, 1H), 8.235 (s, 1H), 6.140 (d, 1H, J=7.2 Hz), 4.746 (m, 1H), 4.546 (bs, 1H), 4.195 (bs, 1H), 3.979 (s, 1H), 3.786 (dd, 1H, J=4.8, 9.6 Hz), 3.510 (dd, 1H, J=4.8, 9.6 Hz), 3.429 (t, 2H, J=6.6 Hz), 3.294S (t, 2H, J=6.6 Hz), 2.812 (t, 2H, J=6.8 Hz), 2.676 (t, 2H, J=6.8 Hz), 2.604 (t, 2H, J=6.8 Hz), 2.420 (t, 2H, J=6.6 Hz), 2.168 (s, 3H), 0.842 (s, 3H), 0.711 (s, 3H) (note: some peaks which overlap with $D_2O$ are not reported).

EXAMPLE 92

(S)-2-((bis(dimethylamino)methylene)amino)-1-(((3R,4S,5S)-1-((S)-2-((1R,2R)-3-(((S)-N-1-(3-(4-((2,5-dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane adduct of Coenzyme A (CoA-2)

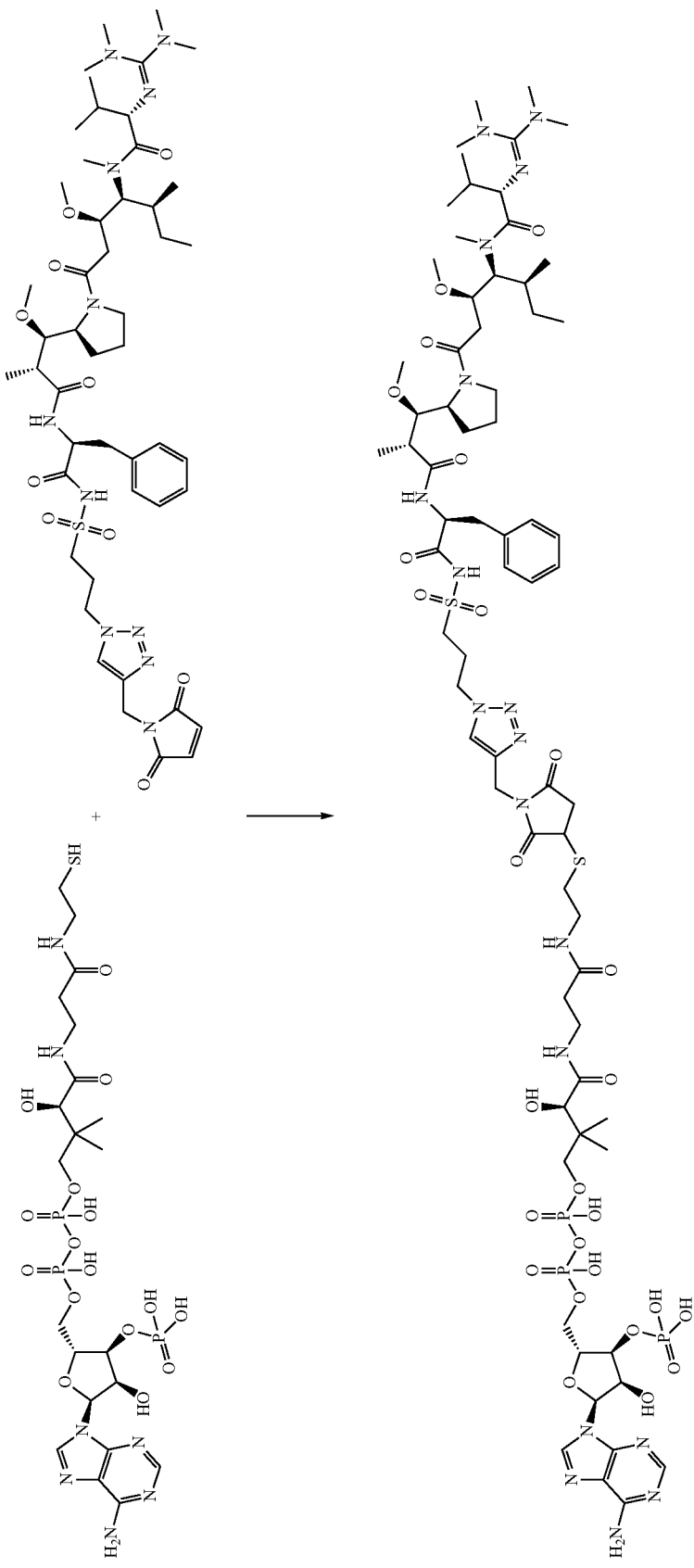

A solution of compound CL-9 (2.0 mg, 2.0 µmol) in 100 µL of DMSO was supplemented with Coenzyme A trilithium salt (2.4 mg, 3.0 µmol), which was dissolved in 120 µL of water. The reaction mixture was buffered by the addition of 750 µL of 75 mM sodium phosphate buffer (pH 7.0). After shaking the reaction at rt for 1 h, the product was purified on a preparative reverse phase C18 HPLC column using a linear gradient of 10-90% acetonitrile in water containing 0.05% TFA. Fractions containing the purified product were combined and lyophilized, affording compound CoA-2 as a crystalline solid. MS (ESI+) m/z 883.5 ((M+2)/2). Retention time 0.89 minutes.

EXAMPLE 93

Ketone-Coenzyme A Analog CoA-(i-12)

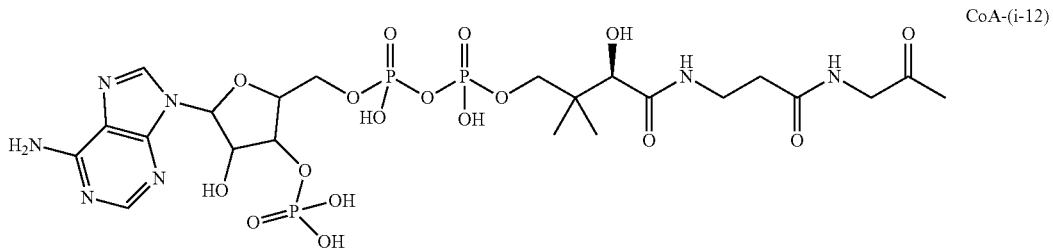

Compound (i-12) was converted into the ketone-functionalized CoA analog CoA-(i-12) by reacting 5 mM of compound (i-12) with 25 mM of ATP in the presence of 10 µM *Staphylococcus aureus* CoAA, 25 µM *Escherichia coli* CoAD, and 20 µM *Escherichia coli* CoAE for about 16 h at 37° C. in 50 mM HEPES buffer (pH 8.0) containing 20 mM MgCl$_2$. Precipitate was removed by centrifugation (20,817×g for 2 min). Enzymes were separated from the reaction mixture by ultrafiltration through an Amicon Ultra centrifugal filter with 10 kDa cutoff. The filtrate containing CoA-(i-12) was used without further purification. Enzymatic conversion of compound (i-12) into the CoA analog CoA-(i-12) was verified by formation of the anti-Her2-HC-ins388-ybbR-CoA-(i-12)-CL-35 ADC (see Table 11, Table 12 and Example 102).

EXAMPLE 94

Azide-Coenzyme A Analog CoA-(i-13)

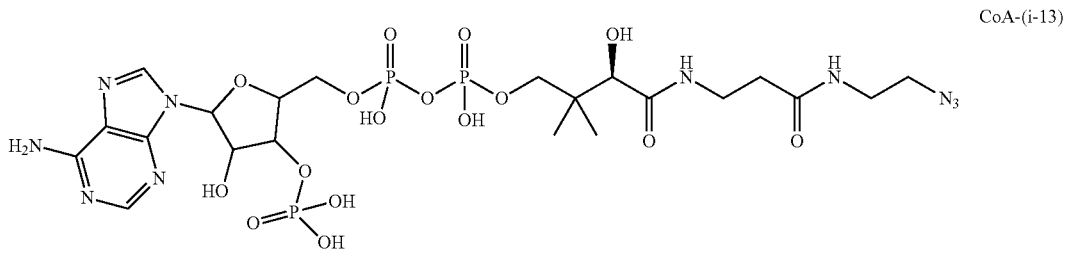

Compound (i-13) was converted into the ketone-functionalized CoA analog CoA-(i-13) using the procedure described in Example 93, except compound (i-13) was used in place of compound (i-12). Copper-free click chemistry using compound CL-33 was carried out for 3 h at 23° C. in 50% (v/v) DMSO/H$_2$O, and the reaction mixture was separated on a reverse-phase Acquity UPLC HSS T3 column (100 Å, 2.1 mm×50 mm, Waters) using gradient elution from 10 to 100% acetonitrile in water containing 0.05% TFA at a flow rate of 0.9 mL/min. Mass spectral analysis confirmed the structure of CoA analog CoA-(i-13). MS m/z 895.5 ((M+2)/2). Retention time 0.88 minutes.

EXAMPLE 95

Ketone-Coenzyme A Analog CoA-(i-14)

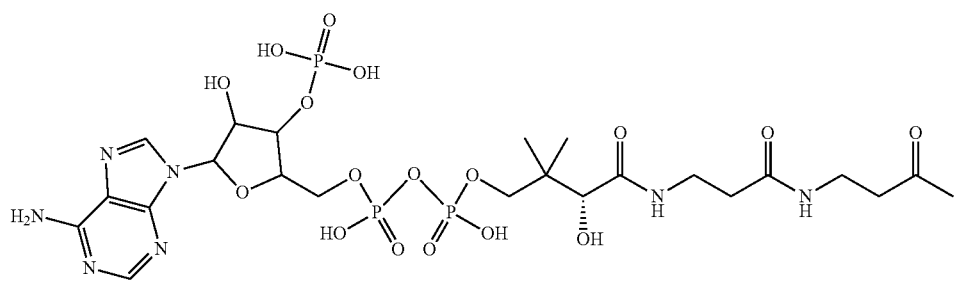

CoA-(i-14)

Compound (i-14) was converted into the ketone-functionalized CoA analog CoA-(i-14) using the procedure described in Example 93, except compound (i-14) was used in place of compound (i-12). Enzymatic conversion of compound (i-14) into the CoA analog CoA-(i-14) was verified by formation of the anti-Her2-HC-ins388-ybbR-CoA-(i-14)-CL-35 ADC (see Table 11, Table 12 and Example 102).

EXAMPLE 96

Ketone-Coenzyme A Analog CoA-(i-15)

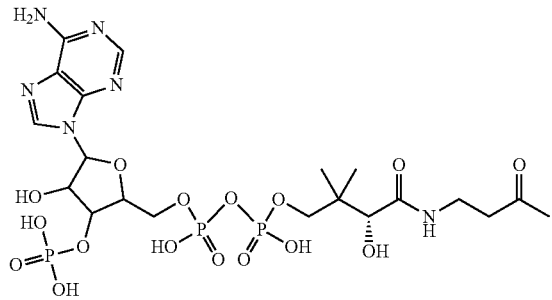

CoA-(i-15)

Compound (i-15) was converted into the ketone-functionalized CoA analog CoA-(i-15) using the procedure described in Example 93, except compound (i-15) was used in place of compound (i-12). Enzymatic conversion of compound (i-15) into the CoA analog CoA-(i-15) was verified by formation of the anti-Her2-HC-ins388-ybbR-CoA-(i-15)-CL-35 ADC (see Table 11, Table 12 and Example 102).

Synthetic Procedure Comparative Peptide

Synthesis of (S)-2-((2R,3R)-3-((S)-1-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)--methoxy-5-methylheptanoyl)pyrrolidin-2-yl)-3-methoxy-2-methylpropanamido)-3-phenylpropanoic acid (MC-MMAF)

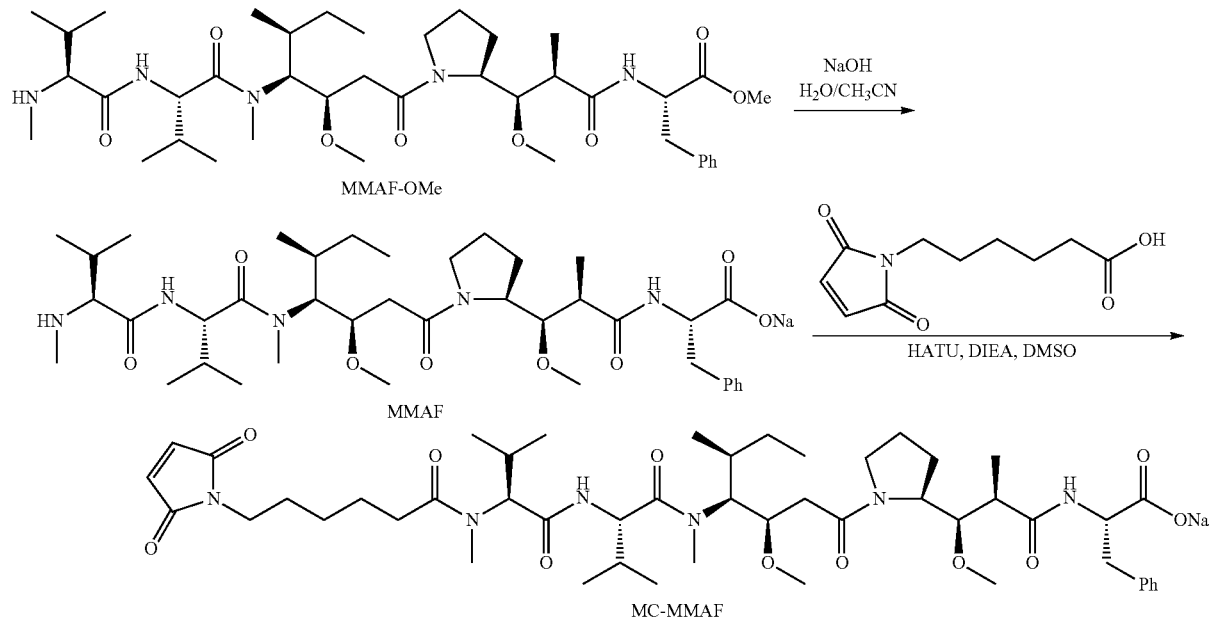

MMAF-OMe (135 mg, Concortis Biosystems) was dissoved in $CH_3CN$ (10 mL). To the resulting clear solution was added 5 mL water, followed by 0.375 mL of 1N aq NaOH (certified, Fisher Scientific). The reaction mixture was stirred magnetically at 21° C. for 18 h, at which time LCMS analysis indicated a complete reaction. The reaction mixture was lyophilized, affording MMAF sodium salt. LCMS retention time 0.911 min. MS (ESI+) m/z 732.5 (M+1). The whole MMAF sodium salt thus obtained in previous reaction was dissoved in 10 mL DMSO. In a separate reaction vessel, EMCA (95 mg) was treated with HATU (165 mg) and DIEA (0.126 mL) in 3.0 mL DMSO at 21° C. for 25 min. The whole reaction mixture of the activated ester was added to the solution of MMAF sodium salt, and the reaction mixture was stirred at 21° C. for 3 h. The reaction mixture was partitioned between 40 mL of EtOAc and 20 mL of 5% aq citric acid. The organic layer was separated, and the aqueous layer was extracted with 20 mL of EtOAc. The combined organic layers was washed with 10 mL saturated aq NaCl, dryed over anhydrous MgSO4, filtered and concentrated. The residue was purified on an ISCO CombiFlash instrument using an ISCO C18gold 15.5g column. The desired material was eluted with 50% $CH_3CN$ in $H_2O$, affording the desired compound as white solid. LCMS retention time 1.392 minutes. MS (ESI+) m/z 925.6 (M+1).

Antigen-Binding Moieties

The antigen-binding moiety (Ab) in Formula (II) or (III) can be any moiety that selectively binds to a targeted cell type. In some aspects, Ab is an antibody or antibody fragment (e.g. antigen binding fragment of an antibody) that specifically binds to an antigen predominantly or preferentially found on the surface of cancer cells, e.g., a tumor-associated antigen. In some aspects, Ab is an antibody or antibody fragment (e.g., antigen binding fragment) that specifically binds to a cell surface receptor protein or other cell surface molecules, a cell survival regulatory factor, a cell proliferation regulatory factor, a molecules associated with (for e.g., known or suspected to contribute functionally to) tissue development or differentiation, a lymphokine, a cytokine, a molecule involved in cell cycle regulation, a molecule involved in vasculogenesis or a molecule associated with (for e.g., known or suspected to contribute functionally to) angiogenesis. A tumor-associated antigen may be a cluster differentiation factor (i.e., a CD protein). In some aspects of the invention, the antigen binding moiety of the invention specifically binds to one antigen. In some aspects of the invention, the antigen binding moiety of the invention specifically binds to two or more antigens described herein, for example, the antigen binding moiety of the invention is a bispecific or multispecific antibody or antigen binding fragment thereof.

Exemplary antibodies or antigen binding fragments include but are not limited to anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In one embodiment, the antigen binding moiety of the antibody-drug conjugates (ADCs) of Formula (II) or (III) specifically binds to a receptor encoded by an ErbB gene. The antigen binding moiety may bind specifically to an ErbB receptor selected from EGFR, HER2, HER3 and HER4. The antigen binding moiety may be an antibody that will specifically bind to the extracellular domain (ECD) of the HER2 receptor and inhibit the growth of tumor cells which overexpress HER2 receptor. The antibody may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

Antigen-binding moieties in Formula (II) or (III) include, but are not limited to, antibodies or antibody fragments (e.g., antigen binding fragments) against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies and antibody fragments (e.g., antigen binding fragment) useful for the immunoconjugates of the invention include modified or engineered antibodies, such as an antibody modified to introduce a cysteine residue (Junutula J R, Raab H, Clark S, Bhakta S, Leipold D D, Weir S, Chen Y, Simpson M, Tsai S P, Dennis M S, Lu Y et al.: Nat Biotechnol 2008, 26:925-932), or other reactive amino acid, including Pcl, pyrrolysine, and non-natural amino acids, in place of at least one amino acid of the native sequence, thus providing a reactive site on the antibody or antigen binding fragment for conjugation to a compound of Formula (I) or subformulae thereof. For example, the antibodies or antibody fragments can be modified to incorporate Pcl or pyrrolysine (W. Ou et al. (2011) PNAS 108 (26), 10437-10442) or unnatural amino acids (J. Y. Axup, K. M. Bajjuri, M. Ritland, B. M. Hutchins, C. H. Kim, S. A. Kazane, R. Halder, J. S. Forsyth, A. F. Santidrian, K. Stafin, Y. Lu et al. Proc Natl Acad Sci U S A, 109 (2012), pp. 16101-16106; for review, see C. C. Liu and P. G. Schultz (2010) Annu Rev Biochem 79, 413-444; C. H. Kim, J. Y. Axup, P. G. Schultz (2013) Curr Opin Chem Biol. 17, 412-419) as sites for conjugation to a drug. Similarly, peptide tags for enzymatic conjugation methods can be introduced into an antibody (Strop P. et al. Chem Biol. 2013, 20(2)1 61-7; Rabuka D., Curr Opin Chem Biol. 2010 December; 14(6);790-6; Rabuka D, et al., Nat Protoc. 2012, 7(6)1052-67). One other example is the use of 4'-phosphopantetheinyl transferases (PPTase) for the conjugation of Co-enzyme A analogs to peptide tags such as S6, A1 and ybbR tags (Grunewald J. et al., SITE-SPECIFIC LABELING METHODS AND MOLECULES PRODUCED THEREBY, PCT/US2013/043684). Methods for conjugating such modified or engineered antibodies with payloads or linker-payload combinations are known in the art. The protein sequence of a mutated AcpS PPTase from *E. coli,* AcpS R26L-$C_{119}$S, is listed in Table 3 (SEQ ID NO:25). The recombinant enzyme contains a C-terminal $His_s$ tag.

Antigen-binding moieties (e.g., antibodies and antigen binding fragments) useful in the invention may also have other modifications or be conjugated to other moieties, such as but not limited to polyethylene glycol tags, albumin, and other fusion polypeptide.

The antibodies used in the examples herein have the heavy chain and light chain sequences listed in Table 3. Some of these antibodies were engineered to contain cysteine residues or PPTase enzyme tags for site-specific conjugation with compounds of the invention. The examples herein illustrate that these engineered antibodies are suitable antibodies for use in the immunoconjugates of Formula (II) or (III). In addition, non-engineered antibodies can also be used for the preparation of the immunoconjugates of Formula (II) or (III) through traditional methods (Carter P J, Senter P D, Antibody-drug conjugates for cancer therapy, *Cancer J.* 2008, 14(3):154-69; J. E. Stefano, M. Busch, L. Hou, A. Park, and D. A. Gianolio, p. 145-171, and M.-P. Brun and L. Gauzy-Lazo, p. 173-187 in Antibody-Drug Conjugate, Methods in Molecular Biology, Vol. 1045, Editor L. Ducry, Humana Press, 2013).

TABLE 3

Amino acid sequences of example antibodies and enzymes

SEQ ID NO: 1 (anti-Her2 heavy chain wild-type; CDR sequences underlined)
EVQLVESGGGLVQPGGSLRLSCAASGFNIKDTYIHWVRQAPGKGLEWVARIYPTNGY
TRYADSVKGRFTISADTSKNTAYLQMNSLRAEDTAVYYCSRWGGDGFYAMDYWGQ
GILVTVSSASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTH
TCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK SEQ ID NO: 2 (anti-Her2 light chain wild-type; CDR sequences underlined)
DIQMTQSPSSLSASVGDRVTITCRASQDVNTAVAWYQQKPGKAPKLLIYSASFLYSGV
PSRFSGSRSGTDFTLTISSLQPEDFATYYCQQHYTTPPTFGQGTKVEIKRTVAAPSVFI
FPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC SEQ ID NO: 3 (constant region of the heavy chain wild-type of antibody
20507 and anti-Her2)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 4 (constant region of the light chain wild-type of antibody
20507 and of anti-Her2)
KRTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC SEQ ID NO: 5 (constant region of the mutant light chain of anti-Her2
LC-S159C and antibody 20507 LC-S159C)
KRTVAAPSVFIFPPSDEQLKSGTASVVCLLNNFYPREAKVQWKVDNALQSGNCQESV
TEQDSKDSTYSLSSTLTLSKADYEKHKVYACEVTHQGLSSPVTKSFNRGEC SEQ ID NO: 6 (constant region of the mutant heavy chain of antibody
20507 HC-E1520)
SASTKGPSVFPLAPSSKSTSGGTAALGCLVKDYFPCPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 7 (constant region of the mutant heavy chain of antibody
20507 HC-S375C)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPCDIAVEWESNGQPENNYKTTPPVLDSDGS
FFLYSKLTVDKSRWQQGNVFSCSVMHEALHNHYTQKSLSLSPGK TABLE 3 -continued Amino acid sequences of example antibodies and enzymes SEQ ID NO: 8 (constant region of the mutant light chain of antibody
20507 LC-K107C)
CRTVAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC SEQ ID NO: 9 (constant region of the mutant heavy chain of antibody
20507 HC-K360C)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTCNQVSLTCLVKGFYPSDIAVEWESNGQPENNYKTTPPVLDSDGS
FFLYSKLTVDKSRWQQGNVFSCSVMHEALHNHYTQKSLSLSPGK SEQ ID NO: 10 (constant region of the mutant heavy chain of antibody
20507 HC-E152C-S375C and of anti-Her2 HC-E1520-S375C)
SASTKGPSVFPLAPSSKSTSGGTAALGCLVKDYFPCPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPCDIAVEWESNGQPENNYKTTPPVLDSDGS
FFLYSKLTVDKSRWQQGNVFSCSVMHEALHNHYTQKSLSLSPGK SEQ ID NO: 11 (constant region of the mutant heavy chain of
HC-ins388-A1 in anti-Her2 and antibody 20507)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPEGDSLDMLEWSLMNN
YKTTPPVLDSDGSFFLYSKLTVDKSRWQQGNVFSCSVMHEALHNHYTQKSLSLSPGK SEQ ID NO: 12 (A1 tag)
GDSLDMLEWSLM SEQ ID NO: 13 (signal sequence)
MKTFILLLWVLLLWVIFLLPGATA SEQ ID NO: 14 (constant region of the mutant heavy chain of
anti-Her2 HC-ins388-ybbR)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPEDSLEFIASKLANNYKT
TPPVLDSDGSFFLYSKLTVDKSRWQQGNVFSCSVMHEALHNHYTQKSLSLSPGK SEQ ID NO: 15 (constant region of the mutant heavy chain of
anti-Her2 HC-ins388-ybbR-S3900)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPEDCLEFIASKLANNYK
TTPPVLDSDGSFFLYSKLTVDKSRWQQGNVFSCSVMHEALHNHYTQKSLSLSPGK SEQ ID NO: 16 (constant region of the mutant heavy chain of
anti-Her2 HC-S119G-T120D-K121S-G122L-P123D-ins123-MLEW)
SAGDSLDMLEWSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTC
PPCPAPELLGGPSVFLFPPKPKDTLM ISRTPEVTCVVVDVSHEDPEVKFNWYVDGVE
VHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK SEQ ID NO: 17 (constant region of the mutant heavy chain of
anti-Her2 HC-P189G-S190D-S192L-L193S-G194W-T195L)
SASTKGPSVFPLAPSSKSTSGGTAALGCLVKDYFPEPVTVSWNSGALTSGVHTFPAV
LQSSGLYSLSSVVTVGDSLSWLQTYICNVNHKPSNTKVDKKVEPKSCDKTHTCPPCP
APELLGGPSVFLFPPKPKDTLM ISRTPEVTCVVVDVSHEDPEVKFNWYVDGVEVHNA
KTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK SEQ ID NO: 18 (constant region of the mutant heavy chain of
anti-Her2 HC-S190D-S192L-L193S-G194W-T195L)
SASTKGPSVFPLAPSSKSTSGGTAALGCLVKDYFPEPVTVSWNSGALTSGVHTFPAV
LQSSGLYSLSSVVTVPDSLSWLQTYICNVNHKPSNTKVDKKVEPKSCDKTHTCPPCP TABLE 3 -continued Amino acid sequences of example antibodies and enzymes

```
APELLGGPSVFLFPPKPKDTLM ISRTPEVTCVVVDVSHEDPEVKFNWYVDGVEVHNA
KTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO: 19 (constant region of the mutant heavy chain of
anti-Her 2HC-in5388-C)
SASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREP
QVYTLPPSREEMTKNQVSLTCLVKGFYPSDIAVEWESNGQPECNNYKTTPPVLDSDG
SFFLYSKLTVDKSRWQQGNVFSCSVMHEALHNHYTQKSLSLSPGK SEQ ID NO: 20 (ybbR tag)
DSLEFIASKLA SEQ ID NO: 21 (ybbR-S2C)
DCLEFIASKLA SEQ ID NO: 22 (A1-3aa)
GDSLDMLEW SEQ ID NO: 23 (S6-5aa)
GDSLSWL SEQ ID NO: 24 (S6-6aa)
DSLSWL SEQ ID NO: 25 (E. coli AcpSR26L-C119S)
MAILGLGTDIVEIARIEAVIARSGDLLARRVLSDNEWAIWKTHHQPVRFLAKRFAVKEAA
AKAFGTGIRNGLAFNQFEVFNDELGKPRLRLWGEALKLAEKLGVANMHVTLADERHY
ASATVIIESHHHHHH
```

SEQ ID NO:1 and SEQ ID NO:2 are the full length amino acid sequence of wild-type anti-Her2 antibody heavy chain (HC) and light chain (LC), respectively. SEQ ID NO:3, and SEQ ID NO:4 are the amino acid sequences of the constant regions for the HC and LC, respectively of antibody 20507 and anti-Her2 antibody. SEQ ID NO:5 is the amino acid sequence of the LC constant region of anti-Her2 LC-S159C and of antibody 20507-LC-S159C mutant antibody. SEQ ID NO:6 and SEQ ID NO:7 are the amino acid sequences of the constant regions for the heavy chain HC-E152C mutant antibody 20507 and anti-Her2 antibody and of the heavy chain HC-S375C mutant of both antibodies respectively. SEQ ID NO:8 is the amino acid sequence of the light chain LC-K107C mutants of antibody 20507 and of anti-Her2 antibody, respectively. SEQ ID NO:9 is the amino acid sequence of the heavy chain HC-K360C mutants of antibody 20507 and of anti-Her2 antibody, respectively. SEQ ID NO:10 is the amino acid sequence of the constant regions for the heavy chain double cysteine mutant HC-E152C and HC-S375C of antibody 20507 and of anti-Her2. SEQ ID NO:11 is the amino acid sequence of the constant region of the mutant heavy chain for both anti-Her2 and antibody 20507 HC-ins388-A1 antibodies wherein the A1 tag is inserted after the HC residue Glu388. SEQ ID NO:14 is the amino acid sequence of the constant region of the mutant heavy chain for anti-Her2 antibody wherein the ybbR tag is inserted after the HC residue Glu388. SEQ ID NO:15 is the amino acid sequence of the constant region of the mutant heavy chain for anti-Her2 antibody wherein the ybbR-S2C tag (SEQ ID NO:21) is inserted after the HC residue Glu388. SEQ ID NO:16 is the amino acid sequence of the constant region of the mutant heavy chain for anti-Her2 antibody wherein the A1-3aa tag (SEQ ID NO:22) replaces residues S119, T120, K121, G122, and P123. SEQ ID NO:17 is the amino acid sequence of the constant region of the mutant heavy chain for anti-Her2 antibody wherein the S6-5aa tag (SEQ ID NO:23) is introduced via the following mutations: P189G, S190D, S192L, L193S, G194W, and T195L. SEQ ID NO:18 is the amino acid sequence of the constant region of the mutant heavy chain for anti-Her2 antibody wherein the S6-6aa tag (SEQ ID NO:24) is introduced via the following mutations: S190D, S192L, L193S, G194W, and T195L. SEQ ID NO:19 is the amino acid sequence of the constant region of the mutant heavy chain for anti-Her2 antibody wherein a single cysteine residue is inserted after the HC residue Glu388. SEQ ID NO:12, SEQ ID NO:20, SEQ ID NO:21, SEQ ID NO:22, SEQ ID NO:23, and SEQ ID NO:24 are the amino acid sequences of A1 tag, ybbR tag, ybbR-S2C tag, A1-3aa tag, S6-5aa tag, and S6-6aa tag, respectively. SEQ ID NO:13 is the signal peptide used. Mutant or inserted Cys residues and the sequence tags of A1, ybbR, ybbR-S2C, A1-3aa, S6-5aa, and S6-6aa are shown in bold and are underlined in the sequences of corresponding mutant chains. CDR sequences are underlined in SEQ ID NO:1 and SEQ ID NO:2.

Antibody Production

The antibodies and antibody fragments (e.g., antigen binding fragments) of the invention can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein.

The polynucleotide sequences can be produced by de novo solid-phase DNA synthesis or by PCR mutagenesis of an existing sequence (e.g., sequences as described in the examples below) encoding an antibody or its binding fragment. Direct chemical synthesis of nucleic acids can be accomplished by methods known in the art, such as the phosphotriester method of Narang et al., *Meth. Enzymol.* 68:90, 1979; the phosphodiester method of Brown et al., *Meth. Enzymol.* 68:109, 1979; the diethylphosphoramidite method of Beaucage et al., *Tetra. Lett.,* 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, Calif., 1990; Mattila et al., *Nucleic Acids Res.* 19:967, 1991; and Eckert et al., *PCR Methods and Applications* 1:17, 1991.

Also provided in the invention are expression vectors and host cells for producing the antibodies or antibody fragments described above. Various expression vectors can be employed to express the polynucleotides encoding the antibody chains or binding fragments of the invention. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., *Nat Genet* 15:345, 1997). For example, nonviral vectors useful for expression of the polynucleotides and polypeptides in mammalian (e.g., human) cells include pThioHis A, B & C, pcDNA3.1/His, pEBVHis A, B & C (Life Tech., San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Smith, *Annu. Rev. Microbiol.* 49:807, 1995; and Rosenfeld et al., *Cell* 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment of the invention. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an antibody chain or fragment of the invention. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Enzymol.,* 153:516, 1987). For example, the SV40 enhancer or CMV enhancer may be used to increase expression in mammalian host cells.

The expression vectors may also provide a secretion signal sequence position to form a fusion protein with polypeptides encoded by inserted antibody sequences. More often, the inserted antibody sequences are linked to a signal sequences before inclusion in the vector. Vectors to be used to receive sequences encoding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibody chains of the invention can be either prokaryotic or eukaryotic. *E. coli* is one prokaryotic host useful for cloning and expressing the polynucleotides of the present invention. Other microbial hosts suitable for use include bacilli, such as *Bacillus subtilis,* and other enterobacteriaceae, such as *Salmonella, Serratia,* and various *Pseudomonas* species. In these prokaryotic hosts, one can also make expression vectors, which typically contain expression control sequences compatible with the host cell (e.g., an origin of replication). In addition, any number of a variety of well-known promoters may be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the antibodies or antibody fragments of the invention. Insect cells in combination with baculovirus vectors can also be used.

In one aspect, mammalian host cells are used to express and produce the antibodies and antibody fragments of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., *Immunol. Rev.* 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP pornl promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

EXAMPLE 97

Cloning of anti-Her2 and Antibody 20507 Cys and A1/ybbR-Tagged Mutant Antibodies for Conjugation Studies DNA oligonucleotides encoding variable regions of heavy and light chains of an anti-Her2 antibody (Carter P, Presta L, Gorman C M, Ridgway J B, Henner D, Wong W L, Rowland A M, Kotts C, Carver M E, Shepard H M. (1992) Proc. Natl. Acad. Sci. USA, 89, 4285-4289, Humanization of an anti-p185her2 antibody for human Cancer therapy) were chemically synthesized and cloned into two mammalian expression vectors, pOG-HC and pOG-LC that contain the constant regions of human IgG1 and human kappa light chain, resulting in two wild-type constructs, pOG-anti-Her2 antibody HC and pOG-anti-Her2 antibody LC, respectively. In these vectors, the expression of antibody heavy and light chain in mammalian cells is driven by a CMV promoter. The vectors encode a synthetic 24 amino acid signal sequence, MKTFILLLWVLLLWVIFLLPGATA (SEQ ID NO:13), at the N-termini of heavy chain and light chain to guide their secretion from mammalian cells. The signal sequence has been validated to be efficient in directing protein secretion in hundreds of mammalian proteins in 293 Freestyle™ cells (Gonzalez R, Jennings L L, Knuth M, Orth A P, Klock H E, Ou W, Feuerhelm J, Hull M V, Koesema E, Wang Y, Zhang J, Wu C, Cho C Y, Su Al, Batalov S, Chen H, Johnson K, Laffitte B, Nguyen D G, Snyder E Y, Schultz P G, Harris J L, Lesley S A. (2010) Proc Natl Acad Sci USA. 107:3552-7). Oligonucleotide directed mutagenesis was employed to prepare LC-S159C mutant of the anti-Her2 antibody. The sense and anti-sense primers (Table 4) that correspond to LC-S159C in the constant regions of human kappa light chain were chemically synthesized. PCR reactions were performed using PfuUltra II Fusion HS DNA Polymerase (Stratagene) with pOG-anti-Her2 antibody HC and pOG-anti-Her2 antibody LC as the templates. The PCR products were confirmed on agarose gels, and treated with DPN I followed by transformation in DH5a cells (Klock et al., (2009) Methods Mol Biol. 498:91-103).

The sequences of wild-type and the Cys mutant constructs were confirmed by DNA sequencing. The full-length amino acid sequence of wild-type anti-Her2 antibody heavy chain is shown as SEQ ID NO:1 and that of light chain is shown as SEQ ID NO:2 (Table 3). The amino acid sequence of LC-S159C mutant antibody is shown in Table 3 with C159 in bold and underlined (SEQ ID NO:5). Amino acid residues in human IgG1 heavy chain and human kappa light chain are numbered according to the Eu numbering system (Edelman et al, (1969) Proc Natl Aced Sci USA, 63:78-85). The anti-Her2 LC-S159C antibody was further cloned into vectors containing antibiotic selection markers for selection of stably transfected cell clones in media containing corresponding antibiotics. Additional single Cys mutants (HC-E152C, HC-S375C, LC-K107C) and two double Cys mutants (HC-E152/HC-S375C, HC-K360C/LC-K107C) were cloned using DNA primers listed in Table 4 and the above procedures. Furthermore, standard site-directed mutagenesis was employed to insert a single cysteine residue into a loop region of the CH3 domain. The sequences of the respective oligonucleotides are listed in Table 4.

Similarly, four single Cys mutants (HC-E152C, HC-S375C, LC-K107C, LC-S159C) and two double Cys mutants (HC-E152/HC-S375C, HC-K360C/LC-K107C) of a second antibody, antibody 20507 were cloned. Antibody 20507 contains a human IgG1 heavy chain and a human kappa light chain. The constant parts of heavy and light chain of antibody 20507 are identical in amino acid sequence to those in anti-Her2 antibody. The amino acid sequences of the constant regions of all Cys mutants are shown in Table 3 with the mutated Cys in bold and underlined.

DNA sequences encoding A1 tag (GDSLDMLEWSLM, SEQ ID NO:12) and ybbR tag (DSLEFIASKLA, SEQ ID NO:20) for PPTase-mediated conjugation was incorporated into the human IgG1 heavy chain using standard molecular biology techniques and confirmed by DNA sequencing. Table 4 lists the oligonucleotide sequences (SEQ ID NO:38, SEQ ID NO:39, SEQ ID NO:40, SEQ ID NO:41 used for PCR amplification of the plasmid pOG-anti-Her2 antibody HC, resulting in the expression vectors of the heavy chains of HC-ins388-A1 antibody and HC-ins388-ybbR antibody. Table 3 shows the amino acid sequences of the heavy chain constant regions of HC-ins388-A1 (SEQ ID NO:11) and HC-ins388-ybbR (SEQ ID NO:14). A1 and ybbR peptide tags (highlighted in bold and underlined) are inserted after residue Glu388 according to the Eu numbering system (Edelman et al, (1969) Proc Natl Aced Sci USA, 63:78-85). The serine residue at position 2 of the ybbR tag was further mutated to cysteine (DCLEFIASKLA, SEQ ID NO:21) using the oligonucleotides listed in Table 4 (SEQ ID NO:48, SEQ ID NO:49). The protein sequence of the resulting HC-ins388-ybbR-S390C antibody (SEQ ID NO:15) is shown in Table 3. Similarly, truncated versions of A1 (SEQ ID NO:22) and S6 (SEQ ID NO:23, SEQ ID NO:24) tags were cloned into the CH1 domain of anti-Her2 antibody using the oligonuctides listed in Table 4. The amino acid sequences of the constant regions of the mutated heavy chains (SEQ ID NO:16, SEQ ID NO:17, SEQ ID NO:18) are shown in Table 3 with the truncated peptide tag in bold and underlined.

The vector encoding the Al-tagged antibody 20507 (SEQ ID NO:11) was constructed by substituting the anti-Her2 variable region with that of antibody 20507. The respective protein sequence of the constant region is listed in Table 3.

DNA sequences encoding anti-Her2 HC-ins388-A1 and anti-Her2 HC-ins388-ybbR antibodies were further cloned into vectors that are suitable for the selection of cell lines stably expressing these peptide-tagged antibody constructs.

TABLE 4

DNA sequences of mutation primers used to clone Cys and peptide-tagged mutant antibodies.

| | | | |
|---|---|---|---|
| LC-S1590 | Sense | AGCGGCAACTGTCAGGAGAGCGT CACCGAGCAGGACAGCAA | SEQ ID NO: 26 |
| | Anti-sense | CTCTCCTGACAGTTGCCGCTCTGC AGGGCGTTGTCCACCT | SEQ ID NO: 27 |
| HC-E1520 | Sense | TACTTCCCCTGTCCCGTGACCGTG TCCTGGAACAGCGGA | SEQ ID NO: 28 |
| | Anti-sense | GGTCACGGGACAGGGGAAGTAGT CCTTCACCAGGCAGC | SEQ ID NO: 29 |
| HC-S3750 | Sense | TTCTACCCCTGCGACATCGCCGTG GAGTGGGAGAGCAACG | SEQ ID NO: 30 |
| | Anti-sense | GGCGATGTCGCAGGGGTAGAAGC CCTTCACCAGACAGGTCA | SEQ ID NO: 31 |
| HC-K3600 | Sense | AGCTGACCTGCAACCAGGTGTCCC TGACCTGTCTGGTGA | SEQ ID NO: 32 |
| | Anti-sense | CACCTGGTTGCAGGTCAGCTCGTC CCGGGATGGAGGCAGG | SEQ ID NO: 33 |
| LC-K107C | Sense | GTGGAGATCTGTCGAACGGTGGC CGCTCCCAGCGTGTTCA | SEQ ID NO: 34 |
| | Anti-sense | ACCGTTCGACAGATCTCCACCTTG GTACCCTGTCCGAAC | SEQ ID NO: 35 |
| HC-ins388-C | Sense | CCCGAGTGTAACAACTACAAGACC ACACCTCCAGTGCTG | SEQ ID NO: 36 |
| | Anti-sense | GTTGTTACACTCGGGCTGGCCGTT GCTCTCCCACTCCAC | SEQ ID NO: 37 |
| HC-ins388-A1 | Sense | CTGGACATGCTGGAGTGGAGCCT GATGAACAACTACAAGACCACACC TCCAG | SEQ ID NO: 38 |
| | Anti-sense | CCACTCCAGCATGTCCAGGCTGTC GCCCTCGGGCTGGCCGTTGCTC | SEQ ID NO: 39 |
| HC-ins388-ybbR | Sense | CTGGAGTTCATCGCCAGCAAGCTG GCCAACAACTACAAGACCACACCT CCAG | SEQ ID NO: 40 |
| | Anti-sense | CTTGCTGGCGATGAACTCCAGGCT GTCCTCGGGCTGGCCGTTGCTC | SEQ ID NO: 41 |
| anti-Her2 HC-S119G-T120D-K121S-G122L-P123D-ins123-MLEW | Sense | TGGACATGCTGGAGTGGAGCGTG TTCCCCCTGGCCCCCAGCAGC | SEQ ID NO: 42 |
| | Anti-sense | CTCCAGCATGTCCAGGCTGTCGCC AGCCGAGGAGACGGTGACCAGGG TTC | SEQ ID NO: 43 |
| anti-Her2 HC-P189G-S190D-S192L-L193S-G194W-T195L | Sense | GCGACAGCCTGAGCTGGCTGCAG ACCTACATCTGCAACGTGAAC | SEQ ID NO: 44 |
| | Anti-sense | CAGCCAGCTCAGGCTGTCGCCCA CTGTCACCACGCTGGACAG | SEQ ID NO: 45 |
| anti-Her2 HO-S190D-S192L-L193S-G194W-T195L | Sense | GACAGTGCCCGACAGCCTGAGCT GGCTGCAGACCTACATC | SEQ ID NO: 46 |
| | Anti-sense | GCTGTCGGGCACTGTCACCACGCT GGACAGGCTGTACAG | SEQ ID NO: 47 |
| HC-ins388-ybbR-S390C | Sense | CAGCCCGAGGACTGCCTGGAGTT CAT | SEQ ID NO: 48 |
| | Anti-sense | ATGAACTCCAGGCAGTCCTCGGGC TGG | SEQ ID NO: 49 |

EXAMPLE 98

Preparation of Anti-Her2 and Antibody 20507 Cys and A1 Tagged Mutant Antibodies Anti-Her2-LC-S159C, anti-Her2 HC-ins388-C, anti-Her2 HC-S119G-T120D-K121S-G122L-P123D-ins123-MLEW, anti-Her2 HC-P189G-S190D-S192L-L193S-G194W-T195L, anti-Her2 HC-S190D-S192L-L193S-G194W-T195L, anti-Her2 HC-ins388-ybbR-S390C, all antibody 20507 Cys mutants, and antibody 20507 HC-ins388-A1 were expressed in 293 Freestyle™ cells by co-transfecting heavy chain and light chain plasmids using transient transfection method as described previously (Meissner, et al., Biotechnol Bioeng. 75:197-203 (2001)). The DNA plasmids used in co-transfection were prepared using Qiagen plasmid preparation kit according to manufacturer's protocol. 293 Freestyle™ cells were cultured in suspension in FreestyleTM expression media (Invitrogen) at 37° C. under 5% $CO_2$. On the day before transfection, cells were split to $0.7 \times 10^6$ cells/mL into fresh media. On the day of transfection, the cell density typically reached $1.5 \times 10^6$ cells/mL. The cells were transfected with a mixture of heavy chain and light chain plasmids at the ratio of 1:1 using the PEI method (Meissner et al., 2001 supra). The transfected cells were further cultured for five days. The media from the culture was harvested by centrifugation of the culture at 2000×g for 20 min and filtered through 0.2 micrometer filters. The expressed antibodies were purified from the filtered media using Protein A-Sepharose™ (GE Healthcare Life Sciences). IgG antibodies were eluted from the Protein A-Sepharose™ column using a pH 3.0 elution buffer. Eluted IgG solutions were immediately neutralized with 1 M Tris-HCl (pH 8.0) followed by a buffer exchange to PBS.

Expression constructs for anti-Her2 LC-S159C, anti-Her2 HC-ins388-A1, and anti-Her2 HC-ins388-ybbR were transfected into CHO cells. Following standard protocols, cells stably expressing these antibodies were then selected using antibiotics. All anti-Her2 antibody constructs expressed in the selected CHO cell clones were purified by Protein A-Sepharose chromatography as described above.

Immunoconjugates

Immunoconjugates of the invention that comprise such compounds of Formula (I), and subformulae thereof, as a payload (drug) include conjugates of Formula (II):

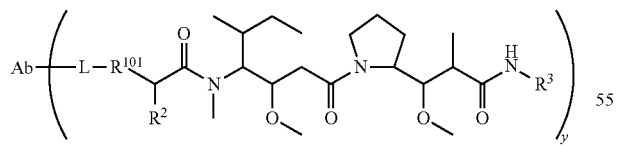

Formula (II)

wherein:
Ab represents an antigen binding moiety;
L is a linker selected from $-L_1L_2L_3L_4L_5L_6-$, $-L_6L_5L_4L_3L_2L_1-$, $-L_1L_2L_3L_4L_5-$, $-L_5L_4L_3L_2L_1-$, $-L_1L_2L_3L_4-$, $-L_4L_3L_2L_1-$, $-L_1L_2L_3-$, $-L_3L_2L_1-$, $-L_1L_2-$, $-L_2L_1-$ and $-L_1$, wherein $-L_1$, $L_2$, $L_3$, $L_4$, $L_5$, and $L_6$ are as defined herein;
y is an integer from 1 to 16;

$R^{101}$ is

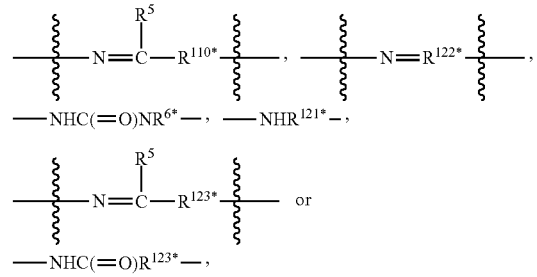

where the * denotes the point of attachment to L;
$R^2$ is $-C_1-C_6$alkyl;
$R^3$ is

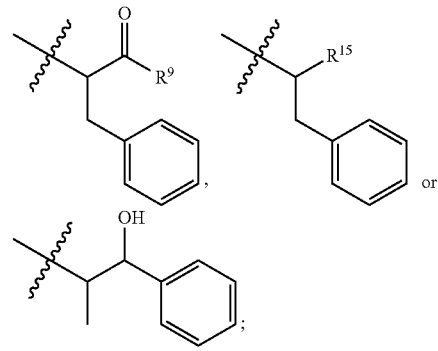

$R^5$ is $N(R^6)_2$;
each $R^6$ is independently selected from H and $-C_1-C_6$alkyl;
$R^9$ is $-OH$, $C_1-C_6$alkoxy, $-N(R^{12})_2$, $-R^{16}$, $-NR^{12}(CH_2)_mN(R^{12})_2$, $-NR^{12}(CH_2)_mR^{16}$, $-NHS(O)_2R^{18}$ or

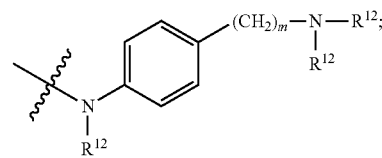

each $R^{12}$ is independently selected from H and $C_1-C_6$alkyl;
$R^{15}$ is tetrazolyl,

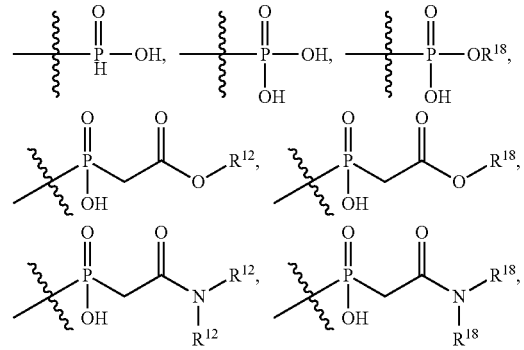

-continued

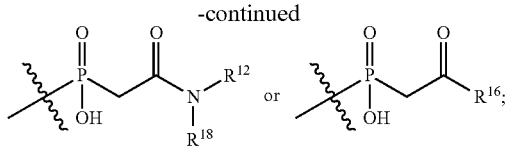

R[16] is an N-linked 4-8 membered heterocycloalkyl containing 1-2 heteroatoms independently selected from N, O, S, S(=O) and S(=O)$_2$, which is unsubstitituted or substituted with -LR[11]

each R[18] is independently selected from a $C_1$-$C_6$alkyl, a $C_1$-$C_6$alkyl which is substituted with azido and a $C_1$-$C_6$alkyl which is substituted with 1 to 5 hydroxyl;

R[110] is a bond or

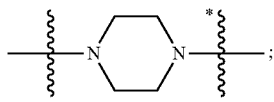

R[121] is a C-linked 5-6 membered heteroarylene having 1-2 N heteroatoms which is substituted with 0-2 substituents independently selected from $C_1$-$C_6$alkyl, $C_1$-$C_6$haloalkyl, halogen, —CN, NO$_2$, —C(=O)OR[6], —C(=O)N(R[6])$_2$ and $C_1$-$C_6$alkoxy;

R[122] is a C-linked 5-6 membered heterocycloalkylene having 1-2 heteroatoms independently selected from N, O and S which is substituted with 0-2 substituents independently selected from $C_1$-$C_6$alkyl, $C_1$-$C_6$haloalkyl, halogen and $C_1$-$C_6$alkoxy;

R[123] is an N-linked 5-6 membered heterocycloalkylene having 1-2 heteroatoms independently selected from N and O which is substituted with 0-2 substituents independently selected from $C_1$-$C_6$alkyl, $C_1$-$C_6$haloalkyl, halogen and $C_1$-$C_6$alkoxy;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Other Immunoconjugates of the invention that comprise such compounds of Formula (I), and subformulae thereof, as a payload (drug) include conjugates of Formula (III):

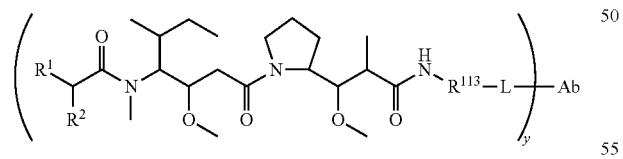

Formula (III)

wherein:
Ab represents an antigen binding moiety;
L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;
y is an integer from 1 to 16;
R[1] is —N=CR[4]R[5], —N=R[19], —N=CR[5]R[20], —NHC(=NR[6])R[4], —NHC(=O)R[4], —NHC(=O)R[20] or —NHR[8];

R[2] is —$C_1$-$C_6$alkyl;
R[4] is —N(R[6])$_2$ or —NR[6]R[7];
R[5] is N(R[8])$_2$;
each R[8] is independently selected from H and —$C_1$-$C_6$alkyl;
R[7] is an unsubstituted $C_3$-$C_8$cycloalkyl;
or R[7] is a $C_3$-$C_8$cycloalkyl substituted with 1-3 substituents independently selected from $C_1$-$C_6$alkyl, oxo, —C(=O)R[18], —(CH$_2$)$_m$OH, —C(=O)(CH$_2$)$_m$OH, —C(=O)((CH$_2$)$_m$O)$_n$R[12], —((CH$_2$)$_m$O)$_n$R[12] or a $C_1$-$C_6$alkyl which is optionally substituted with 1 to 5 hydroxyl;
R[8] is an unsubstituted C-linked 5-6 membered heteroaryl having 1-2 N heteroatoms;
or R[8] is a C-linked 5-6 membered heteroaryl having 1-2 N heteroatoms which is substituted with 1-3 substituents independently selected from $C_1$-$C_6$alkyl, $C_1$-$C_6$haloalkyl, halogen, —OH, —N(R[8])$_2$, —CN, —NO$_2$, —C(=O)OR[8] and $C_1$-$C_6$alkoxy;
each R[12] is independently selected from H and $C_1$-$C_6$alkyl;
R[19] is an unsubstituted C-linked 5-6 membered heterocycloalkyl having 1-2 heteroatoms independently selected from N and O;
or R[19] is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;
R[20] is an unsubstituted N-linked 5-6 membered heterocycloalkyl having 1-2 heteroatoms independently selected from N, O and S;
or R[20] is an N-linked 5-6 membered heterocycloalkyl having 1-2 heteroatoms independently selected from N, O and S, which is substituted with 1-2 substituents independently selected from $C_1$-$C_6$alkyl, $C_1$-$C_6$haloalkyl, halogen, —C(=O)OR[12], oxo, —OH and $C_1$-$C_6$alkoxy;
R[113] is

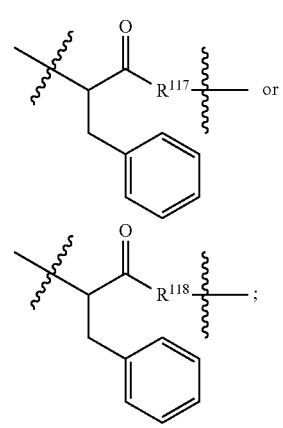

R[117] is a bond, —NH—, —NHS(=O)$_2$—,

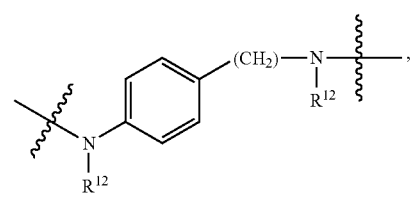

-continued

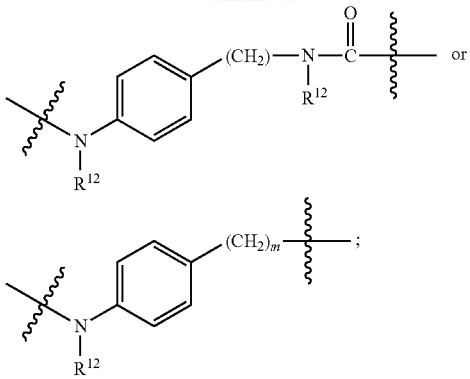
or $R^{118}$ is a bond, tetrazolyl,

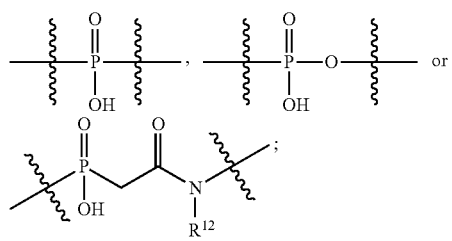
or each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

The invention provides immunoconjugates comprising one or more anti-mitotic cytotoxic peptides linked to an antigen-binding moiety, such as an antibody or antibody fragment. Preferred immunoconjugates of the invention are those of Formula (II) or (III) as described herein. Methods for making such immunoconjugates are well known in the art. Preferred immunoconjugates include, but are not limited to, those disclosed in Tables 6-14 and Examples 100 through 109, and variations thereof having another antigen binding moiety instead of anti-Her2 antibody, particularly such conjugates where anti-Her2 antibody is replaced by an antibody selected from the following list: anti-estrogen receptor antibody, anti-progesterone receptor antibody, anti-p53 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In some embodiments, an immunoconjugate of Formula (II) or Formula (III), or subformulae thereof, comprises an antibody or antibody fragment Ab having antigen-binding activity, where the linker L is attached to Ab at a cysteine sulfur atom of Ab. Typical reactive groups used for reaction with a cysteine sulfur group and the resulting group formed are given in Table 1. Non-limiting examples of linker components formed by reaction with a cysteine residue of the antigen binding moiety include, but are not limited to,

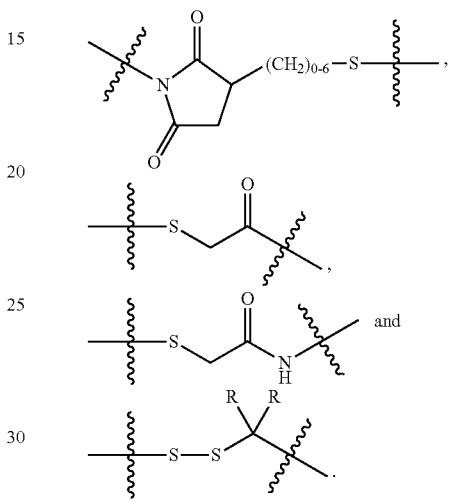

In some embodiments, an immunoconjugate of Formula (II) or Formula (III), or subformulae thereof, comprises an antibody or antibody fragment Ab having antigen-binding activity, where the linker is attached to Ab via a bridged disulfide of,

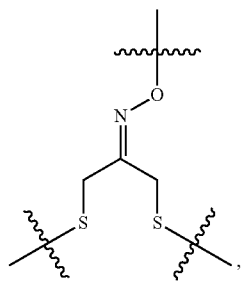

formed upon reaction of

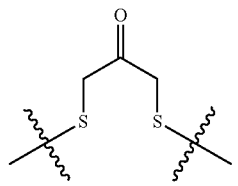

and a compound of Formula (I) which contains an hydroxylamine. In some embodiments, a linker component of linker, L, of immunoconjugates of Formula (II) and Formula (III) is

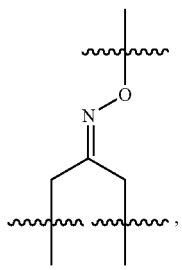

which is formed upon reaction of

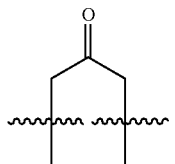

and a compound of Formula (I) which contains an hydroxylamine.

In some embodiments, an immunoconjugate of Formula (II) or Formula (III), or subformulae thereof, comprises an antibody or antibody fragment Ab having antigen-binding activity, where the linker L is attached to Ab at a free —$NH_2$ of lysine. The Linker components formed by reaction with the —$NH_2$ of a lysine residue of the antigen binding moiety, where each p is 1-10, and each R is independently H or $C_{1-4}$ alkyl (preferably methyl) include, but are not limited to,

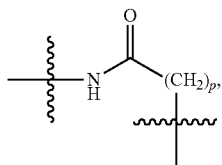

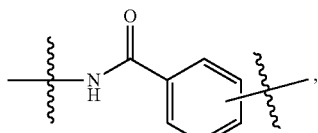

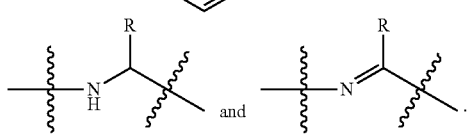

In some embodiments, an immunoconjugate of Formula (II) or Formula (III), or subformulae thereof, comprises an antibody or antibody fragment Ab having antigen-binding activity, where the linker L is attached to Ab at a Pcl or Pyl group engineered into an antibody. See e.g., Ou, et al., PNAS 108(26), 10437-42 (2011). Linker components formed by reaction with a Pcl or Pyl group include, but are not limited to,

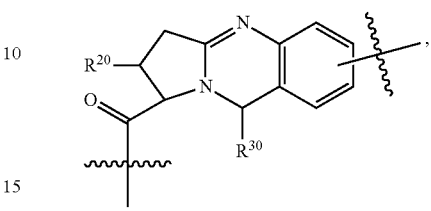

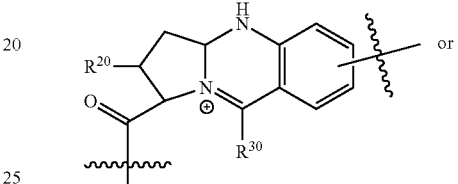

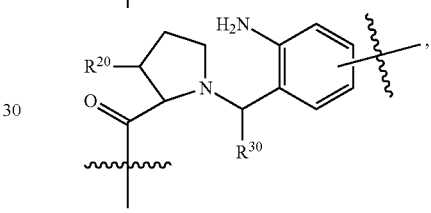

wherein $R^{20}$ is H or Me, and $R^{30}$ is H, Me or Phenyl, for linking, where the acyl group shown attaches to the lysine portion of a Pcl or Pyl in an engineered antibody.

In some embodiments, an immunoconjugate of Formula (II) or Formula (III), or subformulae thereof, comprises an antibody or antibody fragment Ab having antigen-binding activity, where the linker L is attached to Ab at serine residue in an S6, ybbR or A1 peptide engineered into an antibody. Linker components formed by reaction with such serine residues include, but are not limited to,

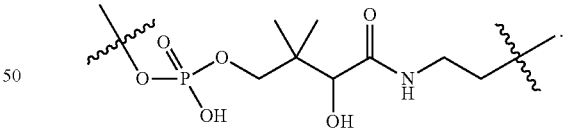

By way of example, one general reaction scheme for the formation of immunoconjugates of Formula (II) is shown in Scheme 32 below:

Scheme 32

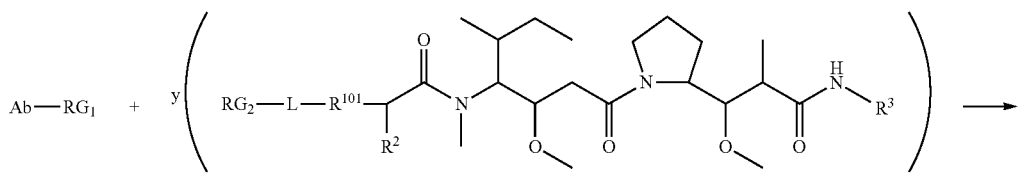

-continued

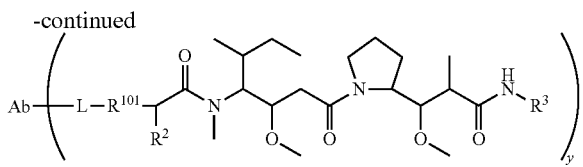

Formula (II)

where RG₁ is a reactive group 1 from Table 1 and RG₂ is a reactive group 2 from Table 1 and the reaction product of the respective groups (as seen in Table 1) is a linker component of linker L. $R^{101}$, $R^2$, $R^3$, L and Ab are as defined herein.

Another general reaction scheme for the formation of immunoconjugates of Formula (II) is shown in Scheme 33 below:

Scheme 33

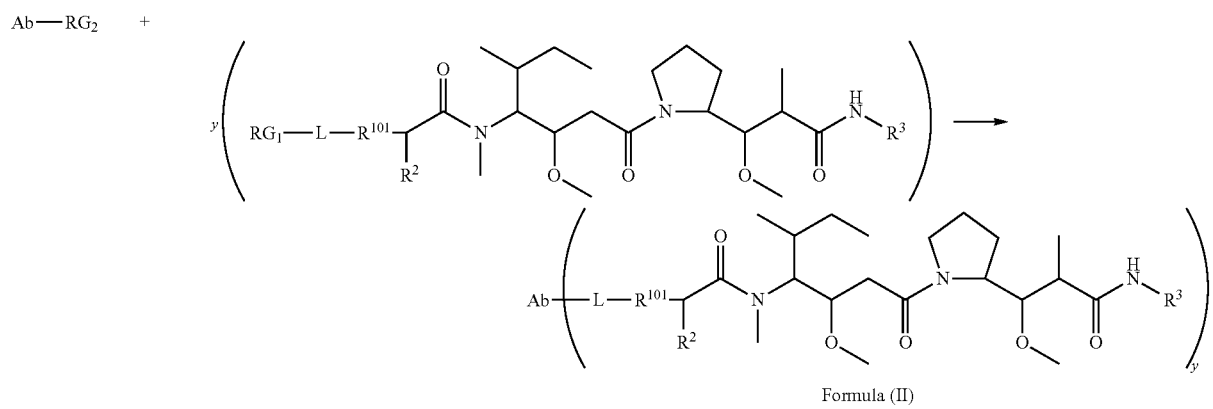

Formula (II)

where RG₁ is a reactive group 1 from Table 1 and RG₂ is a reactive group 2 from Table 1 and the reaction product of the respective groups (as seen in Table 1) is a linker component of linker L. $R^{101}$, $R^2$, $R^3$, L and Ab are as defined herein.

By way of example, one general reaction scheme for the formation of immunoconjugates of Formula (III) is shown in Scheme 34 below:

Scheme 34

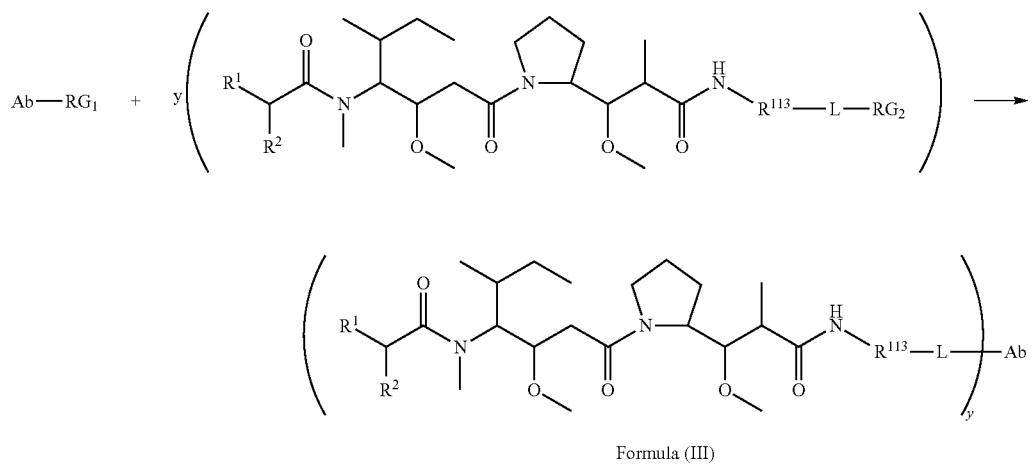

Formula (III)

where $RG_1$ is a reactive group 1 from Table 1 and $RG_2$ is a reactive group 1 from Table 1 and the reaction product of the respective groups (as seen in Table 1) is a linker component of linker L. $R^1$, $R^2$, $R^{113}$, L and Ab are as defined herein.

Another general reaction scheme for the formation of immunoconjugates of Formula (II) is shown in Scheme 35 below:

Scheme 35

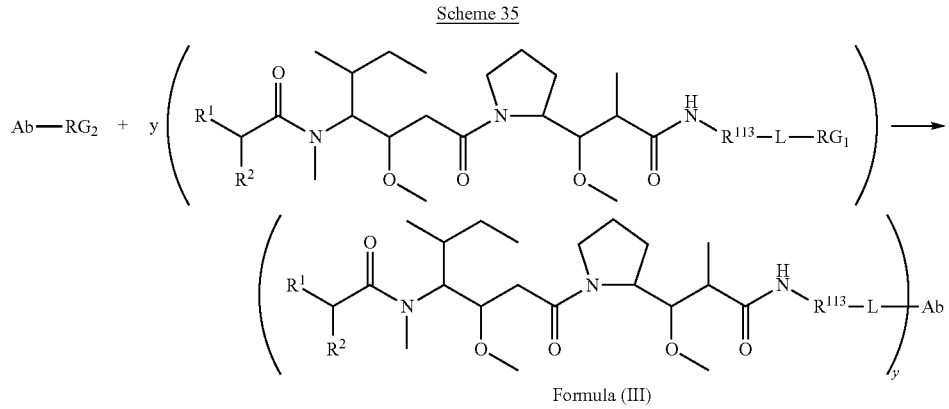

Formula (III)

where $RG_1$ is a reactive group 1 from Table 1 and $RG_2$ is a reactive group 2 from Table 1 and the reaction product of the respective groups (as seen in Table 1) is a linker component of linker L. $R^1$, $R^2$, $R^{113}$, L and Ab are as defined herein.

In another aspect, the present invention provides a pharmaceutical composition comprising an immunoconjugate of Formula (II) or Formula (III) of the present invention, or subformulae thereof, and at least one pharmaceutically acceptable carrier. The pharmaceutical composition can be formulated for particular routes of administration such as intravenous administration, parenteral administration, and the like.

The immunoconjugates of the invention are typically formulated as solutions or suspensions in aqueous buffer and/or isotonic aqueous solution. They are typically administered parenterally, either by injection or by infusion. Methods for their formulation and administration are similar to those for formulation and administration of other biologic-based pharmaceuticals such as antibody therapeutics, and are known to those of skill in the art.

Certain injectable compositions are aqueous isotonic solutions or suspensions, and suppositories are prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The in vitro cell killing potency given in Table 3 obtained for certain compounds of Formula (I) shows that such compounds of formula (I) exhibit valuable pharmacological activities, and as such these compounds can be used as the payload of an ADC. The immunoconjugates comprising a compound of formula (I), as demonstrated herein, exhibit substantial activity on targeted cells in vitro and on tumors in vivo, as demonstrated by potent growth inhibition of xenograft tumors representing different human cancers.

Thus the immunoconjugates of Formula (II) or (III) of the invention, comprising a payload of Formula (I), and subformulae thereof, linked to an antigen binding moiety such as an antibody, are also useful to treat cancers, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

An embodiment of the invention provides conjugation of a compound of formula (I), and subformulae thereof, to an antigen binding moiety and thereby forming an immunoconjugate of Formula (II) or Formula (III), as described herein.

The immunoconjugates of the invention comprising a compound of Formula (I), or subformulae thereof, are particularly useful for treating cancers known in the art to be inhibited by anti-mitotic toxins, and those tumor types demonstrated herein to be susceptible to inhibition by the compounds and conjugates of the invention. Suitable indications for treatment include, but are not limited to, gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. The immunoconjugates of the invention comprising a compound of Formula (I), or subformulae thereof, are particularly useful in therapy. In a further embodiment, the therapy is for a disease which may be treated by anti-mitotic toxins. In another embodiment, the compounds of the invention are useful to treat cancers, including but not limited to gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The methods typically comprise administering an effective amount of an immunoconjugate of the invention as described herein or a pharmaceutical composition comprising such immunoconjugates to a subject in need of such treatment. The immunoconjugate may be administered by any suitable method such as those described herein, and the administration may be repeated at intervals selected by a treating physician.

Thus, as a further embodiment, the present invention provides the use of a immunoconjugate of formula (II) or (III), or any of the embodiments of such compounds described herein, for the manufacture of a medicament. In a further embodiment, the medicament is for treatment of a disease which may be treated by anti-mitotic toxins. In another embodiment, the disease is selected from gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The pharmaceutical composition or combination of the present invention can be in unit dosage of about 1-1000 mg of active ingredient(s) for a subject of about 50-100 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, intravenously, e.g., as a suspension or in aqueous solution. The dosage in vitro may range between about $10^{-3}$ molar and $10^{-12}$ molar concentrations. A therapeutically effective amount in vivo may range depending on the route of administration, between about 0.1-500 mg/kg, or between about 1-100 mg/kg.

An immunoconjugate of Formula (II) or Formula (III), or subformulae thereof, of the present invention may be administered either simultaneously with, or before or after, one or more therapeutic co-agent(s). An immunoconjugate of Formula (II) or Formula (III), or subformulae thereof, of the present invention may be administered separately, by the same or different route of administration, or together in the same pharmaceutical composition as the co-agent(s).

In one embodiment, the invention provides a product comprising a compound of Formula (I), or subformulae thereof, and at least one other therapeutic co-agent as a combined preparation for simultaneous, separate or sequential use in therapy. In one embodiment, the therapy is the treatment of a disease or condition such as cancer with an anti-mitotic toxin. Products provided as a combined preparation include a composition comprising an immunoconjugate of Formula (II) or Formula (III), or subformulae thereof,and the other therapeutic co-agent(s) together in the same pharmaceutical composition, or the immunoconjugate of Formula (II) or Formula (III), or subformulae thereof,and the other therapeutic co-agent(s) in separate form, e.g. in the form of a kit.

In one embodiment, the invention provides a pharmaceutical composition comprising an immunoconjugate of Formula (II) or Formula (III), or subformulae thereof, and another therapeutic co-agent(s). Optionally, the pharmaceutical composition may comprise a pharmaceutically acceptable carrier, as described above.

Suitable co-agents for use with the compounds and conjugates of the invention include other anti-cancer agents, anti-allergic agents, anti-nausea agents (or anti-emetics), pain relievers, anti-inflammatory agents, cytoprotective agents, and combinations thereof.

Specific co-agents considered for use in combination with the conjugates disclosed herein include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, the invention provides a kit comprising two or more separate pharmaceutical compositions, at least one of which contains a Formula (II) or Formula (III), or subformulae thereof. In one embodiment, the kit comprises means for separately retaining said compositions, such as a container, divided bottle, or divided foil packet In the combination therapies of the invention, the immunoconjugate of Formula (II) or Formula (III), or subformulae thereof, of the invention and the other therapeutic co-agent may be manufactured and/or formulated by the same or different manufacturers. Moreover, the immunoconjugate of Formula (II) or Formula (III), or subformulae thereof, of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The invention also provides an immunoconjugate of Formula (II) or Formula (III), or subformulae thereof, for use in a method of treating a disease or condition with a cytotoxic peptide. The invention also provides an immunoconjugate of Formula (II) or Formula (III), or subformulae thereof, for use in a method of treating a disease or condition with a cytotoxic peptide, wherein the immunoconjugate of Formula (II) or Formula (III), or subformulae thereof, is prepared for administration with another therapeutic agent. The invention also provides another therapeutic co-agent for use in a method of treating a disease or condition with an a cytotoxic peptide, wherein the other therapeutic co-agent is prepared for administration with an immunoconjugate of Formula (II) or Formula (III), or subformulae thereof. The invention also provides an immunoconjugate of Formula (II) or Formula (III), or subformulae thereof, for use in a method of treating a disease or condition with an anti-mitotic toxin wherein the immunoconjugate of Formula (II) or Formula (III), or subformulae thereof, is administered with another therapeutic co-agent. The invention also provides another therapeutic co-agent for use in a method of treating a disease or condition with an anti-mitotic toxin, wherein the other therapeutic co-agent is administered with an immunoconjugate of Formula (II) or Formula (III), or subformulae thereof.

The invention also provides the use of an immunoconjugate of Formula (II) or Formula (III), or subformulae thereof, for treating a disease or condition with a cytotoxic peptide, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (II) or Formula (III), or subformulae thereof.

The invention also provides an immunoconjugate of Formula (II) or Formula (III), or subformulae thereof, for use in a method of treating a disease or condition with an anti-mitotic toxin. The invention also provides an immunoconjugate of Formula (II) or Formula (III), or subformulae thereof, for use in a method of treating a disease or condition with an anti-mitotic toxin, wherein the immunoconjugate of Formula (II) or Formula (III), or subformulae thereof, is prepared for administration with another therapeutic agent. The invention also provides another therapeutic co-agent for use in a method of treating a disease or condition with an anti-mitotic toxin, wherein the other therapeutic co-agent is prepared for administration with an immunoconjugate of Formula (II) or Formula (III), or subformulae thereof. The invention also provides an immunoconjugate of Formula (II) or Formula (III), or subformulae thereof, for use in a method of treating a disease or condition with an anti-mitotic toxin wherein the immunoconjugate of Formula (II) or Formula (III), or subformulae thereof, is administered with another therapeutic co-agent. The invention also provides another therapeutic co-agent for use in a method of treating a disease or condition with an anti-mitotic toxin, wherein the other therapeutic co-agent is administered with an immunoconjugate of Formula (II) or Formula (III), or subformulae thereof.

The invention also provides the use of an immunoconjugate of Formula (II) or Formula (III), or subformulae thereof, for treating a disease or condition with an anti-mitotic toxin, wherein the patient has previously (e.g. within 24 h) been treated with another therapeutic agent. The invention also provides the use of another therapeutic agent for treating a disease or condition with an anti-mitotic toxin, wherein the patient has previously (e.g. within 24 h) been treated with an immunoconjugate of Formula (II) or Formula (III), or subformulae thereof.

Conjugation of Linker-Payload (L-P) with an Antigen Binding Moiety

EXAMPLE 99

Preparation of Antibody Drug Conjugates using Engineered Cys Mutant Antibodies Numerous methods for conjugating linker-payloads to antigen binding moieties are known in the art (reviewed in for example: Antibody-Drug Conjugate, Methods in Molecular Biology, Vol. 1045, Editor L. Ducry, Humana Press (2013)). In this example, compounds described in the invention comprising a linker were conjugated to cysteine residues engineered into an antibody as described in Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932. As way of example, conjugation of the compounds of the invention is illustrated for only a small set of Cys antibody mutants but it is anticipated that the compounds can be conjugated to most if not all possible Cys antibody mutants.

Because engineered Cys in antibodies expressed in mammalian cells are modified by adducts (disulfides) such as glutathione (GSH) and/or cysteine during their biosynthesis (Chen et al. 2009), the modified Cys in the product as initially expressed is unreactive to thiol reactive reagents such as maleimido or bromo-or iodo-acetamide groups. To conjugate the engineered cysteine after expression, the glutathione or cysteine adducts need to be removed by reducing these disulfides, which generally entails reducing also the native disulfides in the expressed antibody. This can be accomplished by first exposing the antibody to a reducing agent such as dithiothreitol (DTT) followed by a procedure that allows for the re-oxidation of all native disulfide bonds of the antibody to restore and/or stabilize the functional antibody structure. Accordingly, in order to reduce all native disulfide bonds and the disulfide bound between the cysteine or GSH adducts of the engineered cysteine residue, freshly prepared DTT was added to purified anti-Her2 or antibody 20507 Cys mutant constructs, to a final concentration of 10 mM. After incubation with DTT at 37° C. for 1 h, the mixtures were dialyzed at 4° C. against PBS for three days with daily buffer exchange to remove DTT and re-oxidize the native disulfide bonds. An alternative method is to remove the reducing reagents through a desalting column such as Sephadex G-25. After the protein is reduced, 1 mM oxidized ascorbate (dehydro-ascorbic acid) is added to the desalted samples and the re-oxidation incubations are carried out for 20 h. All methods produce similar results. However, attempts to follow the re-oxidation protocols previously described in the literature using $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). Reoxidation restores intra-chain disulfides, while the dialysis removes cysteines and glutathiones initially connected to the engineered cysteine(s) of the antibody.

After re-oxidation, the antibody was conjugated with compounds of Formula (I) comprising a linker and a reactive moiety. By way of example, compounds having a linked maleimide moiety (10 molar equivalents relative to the antibody) were added to re-oxidized anti-Her2 or antibody 20507 Cys mutant antibodies in PBS buffer (pH 7.2). The incubations were carried out for 1 h. The conjugation process was monitored by reverse-phase HPLC, which is able to separate conjugated antibodies from unconjugated ones. The conjugation reaction mixtures were analyzed on a PLRP-S column (4000 Å, 50 mm×2.1 mm, Agilent) heated to 80° C. and elution from the column was carried out by a linear gradient of 30-60% acetonitrile in water containing 0.1% TFA at a flow rate of 1.5 mL/min. Antibody elution from the column was monitored at 280 nm, 254 nm and 215 nm.

Conjugation efficiency of various compounds having a linked maleimide to anti-Her2 or antibody 20507 Cys mutant antibodies varied depending on the solubility of the compounds used but most reactions resulted in more than 80% conjugate (Table 5 and 6). To evaluate the aggregation state, the resulting ADCs were analyzed by size exclusion chromatography (Agilent Bio SEC3, 300 Å, 7.8×150 mm) at a flow rate of 1 mL/min in PBS. All ADCs were mainly monomeric. The majority of the ADCs contained less than 3% dimeric and oligomeric material (Table 5 and 6), indicating that conjugation of the compounds to anti-Her2 or antibody 20507 Cys mutant antibodies did not cause significant aggregation.

The conjugates were also characterized in terms of average loading of a compound to the antibody binding moiety, generally referred to as drug to antibody ratio (DAR). The DAR value is extrapolated from reverse phase HPLC measurements or from LC-MS analysis. For most linker-payload molecules, ADCs with different number of drug molecules attached can readily be resolved by HPLC. LC/MS also allows quantitation of the average number of molecules of payload (drug) attached to an antibody in an ADC. For LC-MS analysis, ADCs are typically reduced and deglycosylated. LC separates heavy chain (HC) and light chain (LC) of the reduced antibody according to the number of linker-payload groups per chain. Mass spectral data enables identification of the component species in the mixture, e.g., LC, LC+1, LC+2, HC, HC+1, HC+2, etc. From the average loading on the LC and HC chains, the average DAR can be calculated for an ADC. The DAR for a given conjugate represents the average number of drug (payload) molecules attached to a typical antibody containing two light chains and two heavy chains. LC/MS and/or HPLC measurements were performed. The resulting DAR values are in agreement for both methods. Table 5 and 6 lists DAR values obtained by HPLC or ESI-MS for ADCs of anti-Her2 or antibody 20507 Cys mutant antibodies and certain compounds of Formula (I) having a linked maleimide.

As comparators, following the above protocol, anti-Her2-LC-S159C and antibody 20507-HC-E152C mutant antibodies were also conjugated with maleimidocaproyl monomethyl auristatin F (MC-MMAF; Doronina S O, Mendelsohn B A, Bovee T D, Cerveny C G, Alley S C, Meyer D L, Oflazoglu E, Toki B E, Sanderson R J, Zabinski R F, Wahl A F, Senter P D. Bioconjug. Chem. 2006 January-February; 17(1):114-24.). Selected properties of the two comparator ADCs are also listed in Table 5 and 6.

With a single Cys mutation site engineered in either heavy chain or light chain in our antibodies, up to two payload molecules can be conjugated to each antibody molecule to produce a DAR 2 ADC. To increase the numbers of payload per antibody, we have also created antibody constructs containing four Cys mutations per antibody molecule by introducing a Cys mutation site both in heavy chain and light chain, or two Cys mutation sites in the heavy chain. As way of example, anti-Her2-HC-E152C-S375C, antibody 20507-HC-K360C-LC-K107C and antibody 20507-HC-E152C-S375C Cys mutant antibodies were conjugated to compound CL-9. Selected properties of the three ADCs are shown in Table 5 and 6. Compound CL-9 was efficiently conjugated to the double Cys antibody mutants to produce ADCs with a DAR of 3.9 to 4. Conjugation of DAR 4 ADCs was as efficient and the resulting ADCs were as monomeric as DAR 2 ADCs (Table 5 and 6).

TABLE 5

Properties of various anti-Her2 Cys mutant ADCs

| Name of ADC[a] | Conjugation efficiency (%)[b] | DAR[c] | Oligomer (%)[d] |
| --- | --- | --- | --- |
| anti-Her2-LC-S159C-MC-MMAF | 95% | 1.9 | 1.4 |
| anti-Her2-LC-S159C-CL-1 | 95% | 1.9 | 2.0 |
| anti-Her2-LC-S159C-CL-2 | 80% | 1.6 | 1.6 |
| anti-Her2-LC-S159C-CL-3 | 100% | 2.0 | 1.6 |
| anti-Her2-LC-S159C-CL-5 | 100% | 2.0 | 1.5 |
| anti-Her2-LC-S159C-NL-4 | 95% | 1.9 | 1.5 |
| anti-Her2-LC-S159C-CL-6 | 100% | 2.0 | 2.0 |
| anti-Her2-LC-S159C-CL-8 | 95% | 1.9 | 3.0 |
| anti-Her2-LC-S159C-NL-9 | 60% | 1.2 | 1.7 |
| anti-Her2-LC-S159C-NL-22 | 85% | 1.7 | 2.1 |
| anti-Her2-LC-S159C-CL-9 | 95% | 1.9 | 1.2 |
| anti-Her2-LC-S159C-NL-26 | 85% | 1.7 | 4.0 |
| anti-Her2-LC-S159C-CL-10 | 85% | 1.7 | 3.3 |
| anti-Her2-LC-S159C-CL-11 | 80% | 1.6 | 3.2 |
| anti-Her2-LC-S159C-NL-12 | 80% | 1.6 | 3.4 |
| anti-Her2-LC-S159C-NL-34 | 80% | 1.6 | 2.8 |
| anti-Her2-LC-S159C-CL-12 | 90% | 1.8 | 2.7 |
| anti-Her2-LC-S159C-NL-38 | 90% | 1.8 | 1.9 |
| anti-Her2-LC-S159C-NL-30 | 95% | 1.9 | 1.5 |
| anti-Her2-LC-S159C-CL-24 | 85% | 1.7 | 4.1 |
| anti-Her2-LC-S159C-NL-19 | 85% | 1.7 | 1.5 |
| anti-Her2-LC-S159C-NL-21 | 100% | 2.0 | 2.0 |
| anti-Her2-LC-S159C-CL-15 | 96% | 1.9 | 2.5 |
| anti-Her2-LC-S159C-CL-17 | 96% | 1.9 | 1.6 |
| anti-Her2-LC-S159C-CL-19 | 97% | 1.9 | 1.6 |
| anti-Her2-HC-E152C-S375C-CL-9 | 98% | 3.9 | 0.3 |

[a]Name consists of a description of the mutated antibody and a description of the compound used in the chemical conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured by analytical size exclusion chromatography. Percent oligomer includes dimeric and oligomeric species.

TABLE 6

Properties of various antibody 20507 Cys mutant ADCs

| Name of ADC[a] | Conjugation efficiency (%)[b] | DAR[c] | Oligomer (%)[d] |
|---|---|---|---|
| Antibody 20507-HC-E152C-MC-MMAF | 100% | 2.0 | 0.8 |
| Antibody 20507-LC-S159C-MC-MMAF | 95% | 1.9 | 0.2 |
| Antibody 20507-LC-S159C-CL-1 | 100% | 2.0 | B.L.Q. |
| Antibody 20507-LC-S159C-CL-6 | 100% | 2.0 | 0.2 |
| Antibody 20507-LC-S159C-NL-4 | 100% | 2.0 | 0.8 |
| Antibody 20507-HC-E152C-NL-4 | 95% | 1.9 | 0.6 |
| Antibody 20507-HC-E152C-CL-9 | 95% | 1.9 | 0.6 |
| Antibody 20507-HC-S375C-CL-9 | 95% | 1.9 | 0.5 |
| Antibody 20507-LC-K107C-CL-9 | 95% | 1.9 | 0.1 |
| Antibody 20507-HC-K360C-LC-K107C-CL-9 | 100% | 4.0 | 1.5 |
| Antibody 20507-HC-E152C-S375C-CL-9 | 98% | 3.9 | B.L.Q. |

[a]Name consists of a description of the mutated antibody and a description of the compound used in the chemical conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured by analytical size exclusion chromatography. Percent oligomer includes dimeric and oligomeric species. B.L.Q, below limit of quantitation.

EXAMPLE 100

One-Step Preparation of Antibody Drug Conjugates through Enzymatic Conjugation of Peptide-Tagged Antibodies-Conjugation of ybbR-Tagged Anti-Her2 Mutant Antibody with Compound CoA-2

Some enzymatic processes that naturally lead to posttranslational modifications of proteins can be repurposed to efficiently conjugate structurally diverse small molecules to proteins (Rabuka D, Rush J S, deHart G W, Wu P, Bertozzi C R. Nat Protoc. (2012) 7:1052-1067) (Strop P, Liu S H, Dorywalska M, Delaria K, Dushin R G, Tran T T, Ho W H, Farias S, Casas M G, Abdiche Y, Zhou D, Chandrasekaran R, Samain C, Loo C, Rossi A, Rickert M, Krimm S, Wong T, Chin S M, Yu J, Dilley J, Chaparro-Riggers J, Filzen G F, O'Donnell C J, Wang F, Myers J S, Pons J, Shelton D L, Rajpal A. Chem Biol. (2013) 20:161-167) (Tsukiji S, Nagamune T. Chembiochem (2009) 10:787-798) (Yin J, Straight P D, McLoughlin S M, Zhou Z, Lin A J, Golan D E, Kelleher N L, Kolter R, Walsh C T (2005) Proc. Natl. Acad. Sci. U.S.A. 102:15815-15820), (Zhou Z, Cironi P, Lin A J, Xu Y, Hrvatin S, Golan D E, Silver P A, Walsh C T, Yin J. ACS Chem Biol. (2007) 2:337-346). For example, we have previously demonstrated that the posttranslational modification catalyzed by 4'-phosphopantetheinyl transferases (PPTases) can be utilized for the production of chemically defined, homogeneous ADCs (Gruenewald et al., WO2013184514). Site-specific conjugation of cytotoxic compounds was accomplished by inserting 11-12-mer A1, S6, or ybbR peptides into surface-exposed loops of the constant regions of IgG1 antibodies. These peptide tags served as recognition elements for Sfp and AcpS PPTases, which catalyzed the covalent attachment of the coenzyme A (CoA) linked cytotoxic drug to an invariant serine residue via phosphodiester bond formation. The bioorthogonality of PPTase catalysis further enabled the direct labelling of peptide-tagged antibodies with CoA analogues in cell culture medium. Although the following example describes PPTase-mediated ADC formation for only one site, the approach is expected to be applicable to many insertion sites within the antibody scaffold and is expected to be applicable to other antibodies.

PPTases as versatile enzymes that accept a variety of CoA-reporter analogs as substrates (La Clair J J, Foley T L, Schegg T R, Regan C M, Burkart M D (2004) Chem. Biol. 11:195-201). Cytotoxic CoA-peptide analog (CoA-2, CL-9 covalently linked to CoA, see Example 92) was enzymatically conjugated to the inserted ybbR sequence of anti-Her2 antibody. Specifically, 2.5 µM of anti-Her2-HC-ins388-ybbR antibody was conjugated with 50 µM of CoA-2 (20 molar equivalents relative to the antibody) in the presence of 2 µM of Sfp PPTase from Bacillus subtilis. The reaction was carried out at room temperature for approximately 16 hours in 75 mM Tris-HCl buffer (pH 8.0) supplemented with 20 mM NaCl and 12.5 mM $MgCl_2$. Following conjugation, Sfp PPTase and excess reagent were removed by Protein A affinity chromatography using rmp Protein A Sepharose Fast Flow resin (GE Healthcare Life Sciences). Elution from the affinity resin was carried out with approximately 6 bed volumes of 0.1 M of sodium acetate buffer (pH 2.8) followed by immediate neutralization with 25% (v/v) of 1 M Tris-HCl buffer (pH 8.0). The ADC was finally buffer-exchanged into PBS using PD-10 desalting columns (GE Healthcare).

The extent of payload conjugation was determined by reverse phase analytical HPLC on a PLRP-S column (4000 Å, 50 mm×2.1 mm, Agilent Technologies) heated to 80° C. using a linear gradient of 30-60% acetonitrile in water containing 0.1% TFA at a flow rate of 1.5 mL/min. Reverse-phase separation of conjugated and non-conjugated antibody was monitored at 280 nm, 254 nm, and 215 nm. The identity of the enzymatically labeled ADC was further confirmed by obtaining a deconvoluted ESI-MS spectrum of the reduced and deglycosylated sample. As shown in Table 8, the observed masses agree with the calculated molecular weights of the drug-labeled heavy chain of the anti-Her2-HC-ins388-ybbR antibody. Finally, the enzymatically labeled ADC was examined by analytical size-exclusion chromatography (AnSEC) on a Bio SEC-3 column (Agilent Technologies). The conjugation efficiency, DAR and % aggregation for this ADC is shown in see Table 7.

TABLE 7

Properties of ybbR-tagged anti-Her2 ADC

| Name of ADC[a] | Conjugation efficiency[b] (%) | DAR[c] | Aggregation[d] % |
|---|---|---|---|
| anti-Her2-HC-ins388-ybbR-CoA-2 | 95 | 1.9 | 1.8 |

[a]HC-ins388 refers to the insertion of the ybbR peptide tag after residue Glu388 in the heavy chain. The last number corresponds to the compound used in the enzymatic conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured by AnSEC and includes dimeric and oligomeric species.

TABLE 8

Mass spectrometric analysis of ybbR-tagged anti-Her2 ADC

| Name of ADC[a] | Observed mass (Da)[b] | Expected mass conjugate heavy chain with closed maleimide ring (Da)[c] | Expected mass conjugate heavy chain with hydrolyzed maleimide ring (Da)[c] | Expected mass unmodified heavy chain (Da)[d] |
|---|---|---|---|---|
| anti-Her2-HC-ins388-ybbR-CoA-2 | 51687.73<br>51668.94 | 51670.4 | 51688.4 | 50331.8 |

[a]HC-ins388 refers to the insertion of the ybbR peptide tag after residue Glu388 in the heavy chain. The last number corresponds to the compound used in the enzymatic conjugation step.
[b]Mass in Dalton as detected on an Agilent 6520 Q-TOF instrument (Agilent Technologies).
[c]Mass in Dalton as predicted for the conjugated heavy chain.
[d]Mass in Dalton as predicted for the uncoupled heavy chain.

EXAMPLE 101

Two-Step Preparation of Antibody-Drug Conjugates through Enzymatic Conjugation of Peptide-Tagged Antibodies-Conjugation of Peptide-Tagged Anti-Her2 and Antibody 20507 Mutant Antibodies with a Compound of Formula (I)

ADC preparation can be performed using a one-step approach (see Example 100), wherein a cytotoxic compound featuring a CoA moiety is directly and enzymatically conjugated, or ADC preparation can be performed using a two-step approach, wherein the antibody is first conjugated enzymatically with CoA or a CoA analog which is subsequently chemically modified in a second step with a cytotoxic compound.

One approach of the two-step method uses a stable cell line to co-secrete both an antibody tagged with an A1, S6, or ybbR peptide, or a truncated tag (see Table 3), and a PPTase into the culture medium. In the first step of this two-step approach, the culture medium is supplemented with a CoA analog which contains any one of the reactive group listed in Table 1. Subsequent PPTase catalysis affords the corresponding antibody functionalized with the reactive group from Table 1. In the second step, the purified, functionalized antibody is reacted with a cytotoxic drug that is activated with a complementary reactive group. The advantages of such a two-step approach are that it is not required to separately express and purify a PPTase enzyme, and non-toxic bioorthogonal CoA analogs can be used thereby allowing for the purification of a non-toxic, functionalized antibody prior to coupling of a cytotoxic payload. This can facilitate the scale up of PPTase-labeled ADCs to production levels.

Alternatively, the two-step method can involve the production of an antibody tagged with an A1, S6, or ybbR peptide, or a truncated tag (see Table 3), which is purified before being exposed to a mixture of CoA analog and a PPTase. The mixture contains a PPTase which covalently attaches a bioorthogonal CoA analog which contains any one of the reactive group listed in Table 1, thereby producing the corresponding antibody functionalized with the reactive group from Table 1. This functionalized antibody is then purified. In a second step, covalent conjugation/linking of a cytotoxic compound is achieved by reacting the purified functionalized antibody with a cytotoxic compound (payload) functionalized with a reactive group which reacts with the reactive group of the functionalized antibody from step 1. The resulting ADC is then purified.

To demonstrate the two-step approach, the latter method was used to site-specifically label ADCs prepared by enzymatically conjugating a ketone-CoA analogue (Example 91: compound CoA-1) to an A1 tagged antibody, thereby forming a ketone functionalized antibody which was subsequently purified and reacted with a compound of Formula (I) having a alkoxylamine moiety (Compound CL-22).

Specifically, two IgG1 antibodies (anti-Her2-HC-ins388-A1 and antibody 20507-HC-ins388-A1) with the A1 peptide inserted after residue Glu388 of the heavy chain (according to the Eu numbering system) were prepared (Example 98). Then 30 μM of a ketone-functionalized CoA (Compound CoA-1) (12 molar equivalents relative to the antibody) was reacted with 2.5 μM antibody 20507-HC-ins388-A1 in the presence of 2 μM B. subtilis Sfp. The same substrate and enzyme concentrations were used for the corresponding conjugation reaction with anti-Her2-HC-ins388-A1 antibody. Both enzymatic reactions were performed for approximately 16 h at 23° C. in 75 mM Tris buffer (pH 8.0) containing 12.5 mM $MgCl_2$ and 20 mM NaCl. Following conjugation, both antibody constructs were purified by Protein A affinity chromatography (Protein A-Sepharose™, GE Healthcare Life Sciences) in order to remove excess reagent and enzyme. Antibody elution was carried out with 75 mM sodium acetate buffer (pH 3.0). The acidic solution was immediately neutralized with 1 M Tris buffer (pH 8.0) followed by buffer exchange into PBS using PD-10 desalting columns (GE Healthcare). For ESI-MS analysis, the buffer exchanged antibody constructs were deglycosylated and reduced. ESI-MS analysis confirmed formation of the ketone-functionalized antibodies, anti-Her2-HC-ins388-A1-CoA-1 and antibody 20507-HC-ins388-A1-CoA-1) (Table 9).

To a solution of a ketone-functionalized antibody (25 μM anti-Her2-HC-ins388-A1-CoA-1 or antibody 20507-HC-ins388-A1-CoA-1) in 100 mM sodium acetate buffer (pH 5.0) containing 2.5% (v/v) DMSO was added 500 μM of the aminooxy-functionalized compound (Compound CL-22) (20-fold molar excess over antibody) and incubated for 2 days at 23° C. Excess reagent was removed by size-exclusion chromatography purification. ESI-MS analysis of deglycosylated and reduced samples confirm formation of the oxime-linked ADCs, anti-Her2-HC-ins388-A1-CoA-1-CL-22 and antibody 20507-HC-ins388-A1-CoA-1-CL-22 (Table 9). Similar to chemical conjugation to Cys mutant antibodies (Example 99), enzymatic conjugation through the inserted A1 peptide also proceeded with high efficiencies of around 95% (Table 11) and resulted in conjugates that were monomeric with less than 1% detectable aggregates (Table 10).

This two-step approach was also used to attach compounds of Formula (I) to anti-Her2 antibodies containing ybbR and S6-5aa tags at sites in the CH1 domain and CH3 domain. PPTase catalysis was used to enzymatically conjugate the bioorthogonal ketone group (CoA-1) site-specifically onto the embedded ybbR and S6-5aa tags of an anti-Her2 antibody. Anti-Her2-HC-ins388-ybbR antibody was conjugated with CoA-1 under exactly the same conditions as described above for enzymatic conjugation to the A1 tag except that a reduced concentration of 1.5 μM Sfp PPTase was used. Identical conditions as described above for enzymatic conjugation to the A1 tag were also used for the conjugation of anti-Her2 HC-P189G-S190D-S192L-

L193S-G194W-T195L (containing an S6-5aa tag), except that elevated concentrations of CoA-1 (100 μM) and Sfp PPTase (3 μM) were used. After removing Sfp PPTase and excess ketone-CoA analog (CoA-1) by Protein A affinity chromatography (MabSelect SuRe™ resin, GE Healthcare Life Sciences), the ketone-activated antibodies anti-Her2-HC-ins388-ybbR-CoA-1 and anti-Her2 HC-P189G-S190D-S192L-L193S-G194W-T195L-CoA-1 were eluted with IgG Elution buffer (Thermo Scientific). The neutralized antibody solutions were buffer-exchanged into PBS using PD-10 desalting columns (GE Healthcare).

The second step of the two-step method then involved site-specific attachment of a cytotoxic payload to the ketone-activated antibodies; anti-Her2-HC-ins388-ybbR-CoA-1, and anti-Her2-HC-P189G-S190D-S192L-L193S-G194W-T195L-CoA-1 via subsequent oxime ligation. Specifically, 67 μM of anti-Her2-HC-ins388-ybbR-CoA-1 was conjugated with a twenty-fold excess of compound CL-22 or compound CL-35 (1.33 mM) in 100 mM sodium acetate buffer (pH 4.0) containing 6.7% (v/v) DMSO for approximately 16-24 hours at 37° C. Identical conjugation conditions, with the exception of a lower DMSO concentration (5.0% (v/v)), were used to conjugate 1.0 mM of compound CL-35 to 67 μM of ketone-functionalized antibody anti-Her2 HC-P189G-S190D-S192L-L193S-G194W-T195L-CoA-1. Following conjugation, excess aminooxy reagent was removed by preparative size-exclusion chromatography on a HiLoad 26/600 Superdex 200 prep grade column (GE Healthcare) or on a HiLoad 16/600 Superdex 200 prep grade column (GE Healthcare). The drug-to-antibody ratio was determined by analytical reverse phase HPLC on a PLRP-S column (4000 Å, 5 μm, 50×4.6 mm, Agilent Technologies, 5-min linear gradient of 30-60% acetonitrile in water containing 0.1% trifluoroacetic acid at a flow rate of 1.5 mL/min and a column temperature of 80° C.). The HPLC trace was monitored at a wavelength of 280 nm followed by peak integration of conjugated and non-conjugated antibody. For the ADC's obtained using this two-step approach, Table 9 compares the expected mass with the observed mass and Table 10 shows the conjugation efficiency, DAR and aggregation.

TABLE 9

Characterization of enzymatically conjugated ADCs

| Name of Conjugate[a] | Observed mass (Da)[b] | Expected mass conjugated heavy chain (Da)[c] | Expected mass unmodified heavy chain (Da)[d] |
|---|---|---|---|
| anti-Her2-HC-ins388-A1-CoA-1 | 50942.8 | 50945.4 | 50535.0 |
| anti-Her2-HC-ins388-A1-CoA-1-CL-22 | 51857.8 | 51861.6 | 50535.0 |
| antibody 20507-HC-ins388-A1-CoA-1 | 50422.1 | 50424.8[e] | 50014.4[e] |
| antibody 20507-HC-ins388-A1-CoA-1-CL-22 | 51337.4 | 51341.0[e] | 50014.4[e] |
| anti-Her2-HC-ins388-ybbR-CoA-1 | 50742.1 | 50742.2 | 50331.8 |
| anti-Her2-HC-ins388-ybbR-CoA-1-CL-22 | 51653.7 | 51658.4 | 50331.8 |
| anti-Her2-HC-ins388-ybbR-CoA-1-CL-35 | 51494.5 | 51499.2 | 50331.8 |
| anti-Her2 HC-P189G-S190D-S192L-L193S-G194W-T195L-CoA-1 | 49692.1 49282.8 | 49696.0 | 49285.6 |
| anti-Her2 HC-P189G-S190D-S192L-L193S-G194W-T195L-CoA-1-CL-35 | 50451.4 | 50453.0 | 49285.6 |

[a]HC-ins388-A1 and HC-ins388-ybbR refers to the insertion of the A1 peptide or ybbR peprtide, respectively, after Glu388 of the heavy chain according to the Eu numbering system. The remaining numbers describe the CoA analogue and the compound used in the conjugation step. Anti-Her2-HC-ins388-A1, anti-Her2-HC-ins388-ybbR, anti-Her2 HC-P189G-S190D-S192L-L193S-G194W-T195L and antibody 20507-HC-ins388-A1 were first enzymatically conjugated with compound CoA-1 followed by oxime ligation with compound CL-22 or CL-35.
[b]Mass in Dalton as detected on an Agilent 6520 Q-TOF instrument (Agilent Technologies).
[c]Mass in Dalton predicted for the conjugated heavy chain.
[d]Mass in Dalton predicted for the uncoupled heavy chain.
[e]Predicted mass is based on pyroglutamate formation of the N-terminal glutamine residue.

TABLE 10

Properties of enzymatically conjugated ADCs

| Name of Conjugate[a] | Conjugation efficiency[b] (%) | DAR[c] | Aggregation[d] (%) |
|---|---|---|---|
| anti-Her2-HC-ins388-A1-CoA-1 | ND* | NA* | ND* |
| anti-Her2-HC-ins388-A1-CoA-1-CL-22 | 95 | 1.9[e] | 0.7 |
| antibody 20507-HC-ins388-A1-CoA-1 | ND* | NA* | ND* |
| antibody 20507-HC-ins388-A1-CoA-1-CL-22 | 96 | 1.9[e] | 0.6 |
| anti-Her2-HC-ins388-ybbR-CoA-1 | ND* | NA* | ND* |
| anti-Her2-HC-ins388-ybbR-CoA-1-CL-22 | 95 | 1.9[e] | 0.2 |
| anti-Her2-HC-ins388-ybbR-CoA-1-CL-35 | 92[e] | 1.8[e] | 0.1 |
| anti-Her2 HC-P189G-S190D-S192L-L193S-G194W-T195L-CoA-1 | ND* | NA* | ND* |

TABLE 10-continued

Properties of enzymatically conjugated ADCs

| Name of Conjugate[a] | Conjugation efficiency[b] (%) | DAR[c] | Aggregation[d] (%) |
|---|---|---|---|
| anti-Her2 HC-P189G-S190D-S192L-L193S-G194W-T195L-CoA-1-CL-35 | 95[e] | 1.9[e] | <1 |

[a]HC-ins388-A1 and HC-ins388-ybbR refers to the insertion of the A1 peptide or ybbR peprtide, respectively, after Glu$^{388}$ of the heavy chain according to the Eu numbering system. The remaining numbers describe the CoA analogue and the compound of Formula (1) used in the conjugation step. Anti-Her2-HC-ins388-A1, anti-Her2-HC-ins388-ybbR, anti-Her2 HC-P189G-S190D-S192L-L193S-G194W-T195L and antibody 20507-HC-ins388-A1 were first enzymatically conjugated with compound CoA-1 followed by oxime ligation with compound CL-22 or CL-35.
[b]Conjugation efficiency was measured by reverse-phase HPLC and describes the percentage of antibody converted to ADC.
[c]Drug-to-antibody ratio according to analytical reverse-phase HPLC.
[d]Aggregation was measured by analytical size exclusion chromatography and includes dimeric and oligomeric species.
[e]DAR and conjugation efficiency were estimated based on HPLC peak heights.
*ND: Not Determined and NA: Not Applicable

EXAMPLE 102

Two-Step Preparation of Antibody-Drug Conjugates Using Chemoenzymatically Synthesized CoA Analogs In another aspect of the two-step labeling approach, modified CoA analogs were prepared chemoenzymatically using the CoA biosynthetic enzymes CoAA, CoAD, and CoAE (Worthington A S, Burkart M D (2006) Org. Biomol. Chem. 4:44-46) (Kosa N M, Haushalter R W, Smith A R, Burkart M D (2012) Nat Methods 9:981-984). Adopting this approach, ketone-functionalized CoA analogs CoA-(i-12), CoA-(i-14), and CoA-(i-15) were prepared from the corresponding pantothenate precursor molecules i-12, i-14, and i-15, respectively (Examples 93, 95 and 96). Likewise, an azide-functionalized CoA analog CoA-(i-13) was chemoenzymatically synthesized from the respective pantothenate derivative i-13 (Example 94).

Crude preparations of CoA analogs CoA-(i-12), CoA-(i-13), and CoA-(i-14) (see Examples 93-95) were used for conjugation to anti-Her2-HC-ins388-ybbR antibody (2.5 μM) at a final concentration of approximately 30 μM. Labeling was performed in the presence of 1.5 μM B. subtilis Sfp PPTase for about 16 hours at 23° C. in 75 mM Tris-HCl buffer (pH 8.0), supplemented with 12.5 mM MgCl$_2$ and 20 mM NaCl. Similarly, approximately 25 μM of CoA-(i-15) (prepared in Example 96) was conjugated to 2.5 μM of anti-Her2-HC-ins388-ybbR antibody in the presence of 2μM Sfp enzyme under otherwise identical conditions. Conjugation of chemoenzymatically synthesized CoA analogs was further demonstrated for different labeling sites. Similar to the conjugation reactions described above, 2.5 pM of anti-Her2 HC-P189G-S190D-S192L-L193S-G194W-T195L antibody was coupled with approximately 100 μM of CoA-(i-12) in the presence of 3 μM Sfp enzyme in 75 mM Tris-HCl buffer (pH 8.0), supplemented with 12.5 mM MgCl$_2$ and 20 mM NaCl. The reaction mixture was incubated for about 16 hours at 23° C. In contrast to the aforementioned labeling reactions, mutated AcpS PPTase from E. coli, AcpS R26L-C119S, was used to conjugate CoA-(i-12) or CoA-(i-14) (400 μM each) to anti-Her2 HC-S190D-S192L-L193S-G194W-T195L antibody (10 μM). Using a final concentration of 40 μM of this mutant enzyme, the coupling reaction was carried out for 16 hours at 37° C. in the presence of 76 mM HEPES buffer (pH 7) containing 10 mM of MgCl$_2$. Identical reaction conditions were also used to conjugate anti-Her2 HC-S119G-T120D-K121S-G122L-P123D-ins123-MLEW antibody (10 μM) with CoA-(I-13) (333 μM) in the presence of 40 μM of AcpS R26L-C$_{119}$S mutant. All bioorthogonally labeled antibodies were affinity-purified using either MabSelect SuRe™ resin (GE Healthcare Life Sciences) or rProtein A Sepharose Fast Flow resin (GE Healthcare Life Sciences). Following purification, the neutralized antibody solutions were buffer-exchanged into PBS. Covalent attachment of the ketone and azide moieties to the engineered antibodies was confirmed by mass spectrometric analysis following sample treatment with PNGase F and TCEP (Table 11).

Site-specific antibody labeling with ketone and azide moieties enabled subsequent payload conjugation via oxime ligation and copper-free click chemistry, respectively, as the second step of the two-step method. The ketone-activated antibodies anti-Her2-HC-ins388-ybbR-CoA-(i-12) and anti-Her2-HC-ins388-ybbR-CoA-(i-14) (67 μM each) were reacted with a 20-fold excess of aminooxy-functionalized payloads CL-22 and CL-35 (1.33 mM each) in 100 mM sodium acetate buffer (pH 4) containing 7-13% (v/v) DMSO for approximately 16 hours at 37° C. The oxime ligations of anti-Her2-HC-ins388-ybbR-CoA-(i-14) with compounds CL-36 and CL-37 were carried out under identical conditions with the exception of a higher pH value of 5. Similarly, 67 μM of anti-Her2-HC-ins388-ybbR-CoA-(i-15) was reacted with 15-fold excess of CL-22 and CL-36 (1.0 mM each) in 100 mM sodium acetate buffer (pH 4) containing 5% (v/v) DMSO for about 16 hours at 37° C. The incubation time was extended to 2 days for the labeling of the same antibody construct with CL-37 (1.0 mM) and CL-35 (0.5 mM). Expanding the conjugation strategy to different labeling sites, anti-Her2 HC-S190D-S192L-L193S-G194W-T195L-CoA-(i-14) and anti-Her2 HC-S119G-T120D-K121S-G122L-P123D-ins123-MLEW-CoA-(i-14) (60 μM each) were conjugated with 15-fold excess of CL-22 payload (0.9 mM) in 190 mM sodium acetate buffer (pH 5) containing 5% (v/v) DMSO. Both oxime ligations were incubated for 4 days at 23° C. Anti-Her2 HC-S119G-T120D-K121S-G122L-P123D-ins123-MLEW-CoA-(i-14) (30 pM) was also conjugated with CL-35 (0.89 mM) for about 24 hours at 37° C. and pH 5. In addition, anti-Her2 HC-S119G-T120D-K121S-G122L-P123D-ins123-MLEW-CoA-(i-15) (33 μM) was conjugated to CL-22 payload (500 μM) for 2 days at 23° C. in 200 mM sodium acetate buffer (pH 4.0) containing 2.5% (v/v) DMSO. Finally, anti-Her2 HC-P189G-S190D-S192L-L193S-G194W-T195L-CoA-(i-12) and anti-Her2 HC-S190D-S192L-L193S-G194W-T195L-CoA-(i-12) (67 μM each) were conjugated for about 16-24 hours at 37° C. with 15 equivalents of CL-35 (1 mM) in 100 mM sodium acetate buffer (pH 4) containing 5% (v/v) DMSO.

Following antibody labeling, excess reagent was removed by preparative size-exclusion chromatography on a HiLoad 26/600 Superdex 200 prep grade column (GE Healthcare) or on a HiLoad 16/600 Superdex 200 prep grade column (GE Healthcare). The drug-to-antibody ratio (DAR) was determined by analytical reverse phase HPLC on a PLRP-S column (4000 Å, 5 µm, 50×4.6 mm, Agilent Technologies, 5-min linear gradient of 30-60% acetonitrile in water containing 0.1% trifluoroacetic acid at a flow rate of 1.5 mL/min and a column temperature of 80° C.). The HPLC trace was monitored at a wavelength of 280 nm followed by peak integration of conjugated and non-conjugated antibody. Table 11 shows the mass obtained for the ketone-activated anti-Her2 antibodies labeled with aminooxy-peptide analogs CL-22, CL-35, CL-36 and CL-37, and Table 12 shows the conjugation efficiency, DAR and aggregation observed for these labeled antibodies.

Site-specific attachment of an azide moiety to an engineered antibody allows subsequent payload conjugation via copper-free click chemistry. This was demonstrated using the strain-promoted alkyne-azide cycloaddition carried out with an azide-activated anti-Her2-HC-ins388-ybbR-CoA-(i-13) antibody in the presence of the bicyclo[6.1.0]nonyne (BCN)-functionalized payload CL-33, where 127 µM anti-Her2-HC-ins388-ybbR-CoA-(i-13) was added to a 10-fold molar excess of BCN-functionalized payload CL-33 (1.27 mM) in 100 mM sodium phosphate buffer (pH 7.5) supplemented with 1 M NaCl and 6% (v/v) DMSO. After approximately 16 hours of incubation at 23° C., excess BCN reagent was removed by Protein A affinity chromatography using MabSelect SuRe™ resin (GE Healthcare Life Sciences). Elution was carried out with IgG Elution Buffer (Thermo Scientific), followed by neutralization with 1 M Tris-HCl buffer (pH 8) and buffer exchange into PBS. The mass obtained for this azide-activated anti-Her2 antibody labeled with BCN-functionalized payload CL-33 is shown in Table 11, and Table 12 shows the conjugation efficiency, DAR and aggregation observed for this ADC. DAR values were obtained using 10 µg of this azide-activated anti-Her2 antibody labeled with BCN-functionalized payload CL-33 in 10 µL of 50% slurry of IgG Sepharose 6 Fast Flow (GE Healthcare). Resin binding was performed under mild agitation for 1 h at 23° C. After washing the resin with PBS, the affinity-bound ADC was deglycosylated by addition of 5 µg of PNGase F and subsequent incubation at 37° C. for 3 hours. PNGase F enzyme was removed by washing the affinity resin with PBS. Next, the deglycosylated sample was eluted using 1% formic acid followed by immediate neutralization with 10 M ammonium acetate (pH 5). To effectively reduce the antibody construct to heavy and light chains, 20 µL of eluate was supplemented with 10 µL of 100 mM sodium formate buffer (pH 4.0) containing 6 M guanidine hydrochloride and 5 µL of 0.66 M TCEP in 10 M ammonium acetate (pH 5). After incubation for at least 30 min at 23° C., the reduced and deglycosylated sample was injected onto a 6550 iFunnel Q-TOF LC/MS system (Agilent Technologies). MassHunter Qualitative Analysis Software (Agilent Technologies) was used for processing of the spectral record and spectral deconvolution.

TABLE 11

Mass spectrometric analysis of antibodies and ADCs containing bioorthogonal CoA analogs

| Name of Conjugate[a] | Observed mass (Da)[b] | Expected mass conjugated heavy chain (Da)[c] | Expected mass unmodified heavy chain (Da)[d] |
|---|---|---|---|
| anti-Her2-HC-ins388-ybbR-CoA-(i-12) | 50669.5 | 50668.1 | 50331.8 |
| anti-Her2-HC-ins388-ybbR-CoA-(i-12)-CL-22 | 51582.6 | 51584.3 | 50331.8 |
| anti-Her2-HC-ins388-ybbR-CoA-(i-12)-CL-35 | 51422.8 | 51425.1 | 50331.8 |
| anti-Her2-HC-ins388-ybbR-CoA-(i-13) | 50678.3 50654.2[e] | 50681.1 | 50331.8 |
| anti-Her2-HC-ins388-ybbR-CoA-(i-13)-CL-33 | 51696.0 | 51694.4 | 50331.8 |
| anti-Her2-HC-ins388-ybbR-CoA-(i-14) | 50681.8 | 50682.1 | 50331.8 |
| anti-Her2-HC-ins388-ybbR-CoA-(i-14)-CL-22 | 51593.1 | 51598.3 | 50331.8 |
| anti-Her2-HC-ins388-ybbR-CoA-(i-14)-CL-35 | 51436.2 | 51439.1 | 50331.8 |
| anti-Her2-HC-ins388-ybbR-CoA-(i-14)-CL-36 | 51574.3 | 51574.3 | 50331.8 |
| anti-Her2-HC-ins388-ybbR-CoA-(i-14)-CL-37 | 51484.1 | 51483.2 | 50331.8 |
| anti-Her2-HC-ins388-ybbR-CoA-(i-15) | 50604.2 | 50611.0 | 50331.8 |
| anti-Her2-HC-ins388-ybbR-CoA-(i-15)-CL-22 | 51522.9 | 51527.2 | 50331.8 |
| anti-Her2-HC-ins388-ybbR-CoA-(i-15)-CL-36 | 51502.0 | 51503.2 | 50331.8 |
| anti-Her2-HC-ins388-ybbR-CoA-(i-15)-CL-37 | 51408.2 | 51412.1 | 50331.8 |
| anti-Her2-HC-ins388-ybbR-CoA-(i-15)-CL-35 | 51364.0 | 51368.0 | 50331.8 |
| anti-Her2 HC-P189G-S190D-S192L-L193S-G194W-T195L-CoA-(i-12) | 49622.0 49286.4 | 49621.9 | 49285.6 |
| anti-Her2 HC-P189G-S190D-S192L-L193S-G194W-T195L-CoA-(i-12)-MBJ437 | 50376.0 49282.9 | 50378.9 | 49285.6 |
| anti-Her2 HC-S190D-S192L-L193S-G194W-T195L-CoA-(i-12) | 49660.0 49324.0 | 49662.0 | 49325.7 |
| anti-Her2 HC-S190D-S192L-L193S-G194W-T195L-CoA-(i-12)-CL-35 | 50414.6 | 50419.0 | 49325.7 |
| anti-Her2 HC-S190D-S192L-L193S-G194W-T195L-CoA-(i-14) | 49677.0 49327.0 | 49676.0 | 49325.7 |
| anti-Her2 HC-S190D-S192L-L193S-G194W-T195L-CoA-(i-14)-CL-22 | 50588.1 | 50592.2 | 49325.7 |
| anti-Her2 HC-S119G-T120D-K121S-G122L-P123D-ins123-MLEW-CoA-(i-14) | 50083.1 | 50083.3 | 49733.0 |

TABLE 11-continued

Mass spectrometric analysis of antibodies and ADCs containing bioorthogonal CoA analogs

| Name of Conjugate[a] | Observed mass (Da)[b] | Expected mass conjugated heavy chain (Da)[c] | Expected mass unmodified heavy chain (Da)[d] |
|---|---|---|---|
| anti-Her2-HC-S119G-T120D-K121S-G122L-P123D-ins123-MLEW-CoA-(i-14)-CL-35 | 50839.4 | 50840.3 | 49733.0 |
| anti-Her2 HC-S119G-T120D-K121S-G122L-P123D-ins123-MLEW-CoA-(il-14)-CL-22 | 50998.1 | 50999.5 | 49733.0 |
| anti-Her2 HC-S119G-T120D-K121S-G122L-P123D-ins123-MLEW-CoA-(i-15) | 50007.9 | 50012.2 | 49733.0 |
| anti-Her2 HC-S119G-T120D-K121S-G122L-P123D-ins123-MLEW-CoA-(i-15)-CL-22 | 50923.4 | 50928.4 | 49733.0 |

[a]HC-ins388-ybbR refers to the insertion of a ybbR peptide after Glu$^{388}$ of the heavy chain according to the Eu numbering system. The remaining numbers describe the CoA analog and the compound used in the conjugation step. For instance, anti-Her2-HC-ins388-ybbR-CoA-(i-12)-CL-22 was first enzymatically conjugated with compound CoA-(i-12) followed by oxime ligation with compound CL-22.
[b]Mass in Dalton as detected on an Agilent 6520 Q-TOF instrument (Agilent Technologies).
[c]Mass in Dalton as predicted for the conjugated heavy chain.
[d]Mass in Dalton as predicted for the uncoupled heavy chain.
[e]Observed mass most likely corresponds to primary amine of CoA analog with an expected mass of 50655.1 Da (derived from reduction of azide moiety).

TABLE 12

Properties of antibodies and ADCs containing bioorthogonal CoA analogs

| Name of Conjugate[a] | Conjugation efficiency[b] (%) | DAR[c] | Aggregation[d] (%) |
|---|---|---|---|
| anti-Her2-HC-ins388-ybbR-CoA-(i-12) | ND* | NA* | ND* |
| anti-Her2-HC-ins388-ybbR-CoA-(i-12)-CL-22 | 91 | 1.8[e] | 0.2 |
| anti-Her2-HC-ins388-ybbR-CoA-(i-12)-CL-35 | 84[g] | 1.7[g] | 0.1 |
| anti-Her2-HC-ins388-ybbR-CoA-(i-13) | ND* | NA* | ND* |
| anti-Her2-HC-ins388-ybbR-CoA-(i-13)-CL-33 | 100[e] | 2.0[f] | 10 |
| anti-Her2-HC-ins388-ybbR-CoA-(i-14) | ND* | NA* | ND* |
| anti-Her2-HC-ins388-ybbR-CoA-(i-14)-CL-22 | 98 | 2.0[e] | 0.1 |
| anti-Her2-HC-ins388-ybbR-CoA-(i-14)-CL-35 | 96[g] | 1.9[g] | 0.1 |
| anti-Her2-HC-ins388-ybbR-CoA-(i-14)-CL-36 | 100 | 2.0[e] | <1 |
| anti-Her2-HC-ins388-ybbR-CoA-(i-14)-CL-35 | 100 | 2.0[e] | <1 |
| anti-Her2-HC-ins388-ybbR-CoA-(i-15) | ND* | NA* | ND* |
| anti-Her2-HC-ins388-ybbR-CoA-(i-15)-CL-22 | 90[g] | 1.8[g] | <1 |
| anti-Her2-HC-ins388-ybbR-CoA-(i-15)-CL-36 | 95[g] | 1.9[g] | <1 |
| anti-Her2-HC-ins388-ybbR-CoA-(i-15)-CL-37 | 94[g] | 1.9[g] | <1 |
| anti-Her2-HC-ins388-ybbR-CoA-(i-15)-CL-35 | 91[g] | 1.8[g] | <1 |
| anti-Her2 HC-P189G-S190D-S192L-L193S-G194W-T195L-CoA-(i-12) | ND* | NA* | ND* |
| anti-Her2 HC-P189G-S190D-S192L-L193S-G194W-T195L-CoA-(i-12)-CL-35 | 89[g] | 1.8[g] | <1 |
| anti-Her2 HC-S190D-S192L-L193S-G194W-T195L-CoA-(i-12) | ND* | NA* | ND* |
| anti-Her2 HC-S190D-S192L-L193S-G194W-T195L-CoA-(i-12)-CL-35 | 90 | 1.8[e] | <1 |
| anti-Her2 HC-S190D-S192L-L193S-G194W-T195L-CoA-(i-14) | ND* | NA* | ND* |
| anti-Her2 HC-S190D-S192L-L193S-G194W-T195L-CoA-(i-14)-CL-22 | 90[e] | 1.8[f] | <1 |
| anti-Her2-HC-S119G-T120D-K121S-G122L-P123D-ins123-MLEW-CoA-(i-14) | ND* | NA* | ND* |
| anti-Her2-HC-S119G-T120D-K121S-G122L-P123D-ins123-MLEW-CoA-(i-14)-CL-35 | 98 | 2.0 | <1 |
| anti-Her2 HC-S119G-T120D-K121S-G122L-P123D-ins123-MLEW-CoA-(i-14)-CL-22 | 100[e] | 2.0[f] | <1 |
| anti-Her2 HC-S119G-T120D-K121S-G122L-P123D-ins123-MLEW-CoA-(i-15) | ND* | NA* | ND* |

TABLE 12-continued

Properties of antibodies and ADCs containing bioorthogonal CoA analogs

| Name of Conjugate[a] | Conjugation efficiency[b] (%) | DAR[c] | Aggregation[d] (%) |
|---|---|---|---|
| anti-Her2 HC-S119G-T120D-K121S-G122L-P123D-ins123-MLEW-CoA-(i-15)-CL-22 | 100[e] | 2.0[f] | <1 |

[a]HC-ins388-ybbR refers to the insertion of a ybbR peptide after Glu[388] of the heavy chain according to the Eu numbering system. The remaining numbers describe the CoA analog and the compound used in the conjugation step. For instance, anti-Her2-HC-ins388-ybbR-CoA-(i-12)-CL-22 was first enzymatically conjugated with compound CoA-(i-12) followed by oxime ligation with compound CL-22.
[b]Conjugation efficiency was measured by analytical reverse phase HPLC and describes the percentage of antibody converted to ADC.
[c]Drug-to-antibody ratio (DAR) according to analytical reverse phase HPLC.
[d]Aggregation was measured by analytical size exclusion chromatography and includes dimeric and oligomeric species.
[e]Conjugation efficiency was measured by ESI-MS and describes the percentage of antibody converted to ADC.
[f]Drug-to-antibody ratio according to ESI-MS.
[g]DAR and conjugation efficiency were estimated based on HPLC peak heights.
*ND: not determined; NA: not applicable

EXAMPLE 103

Preparation of Antibody Drug Conjugates Through Partial Reduction of Native Disulfide Bonds of Non-Engineered Antibodies Cytotoxic drugs of the invention can also be conjugated to native cysteine residues of non-engineered antibodies using a procedure that involves partial reduction of the antibodies (Doronina, S. O., Toki, B. E., Torgov, M. Y., Mendelsohn, B. A., Cerveny, C. G., Chace, D. F., DeBlanc, R. L., Gearing,R. P., Bovee, T. D., Siegall, C. B., Francisco, J. A., Wahl, A. F., Meyer, D. L., and Senter, P. D. (2003) Development of potent monoclonal antibody auristatin conjugates for cancer therapy. *Nat. Biotechnol.* 21, 778-84). In this example, inter- and intra-chain disulfides bonds of anti-Her2 and antibody 20507 antibodies at a concentration of 5 to 10 mg/ml were first partially reduced in PBS containing 2 mM EDTA by adding solid mercaptoethylamine to a final concentration of 50 mM and incubating the mixture at 37° C. for 1 hour. After desalting and addition of 1% w/v PS-20 detergent, the partially reduced antibodies (1-2 mg/ml) were reacted overnight at 4° C. with 0.5 to 1 mg CL-9 per 10 mg antibody. The resulting ADCs were purified by Protein A chromatography. After base-line washing with PBS, the conjugates were eluted with 50 mM citrate, pH 2.7, 140 mM NaCl, neutralized and sterile filtered. The average DAR of the resulting ADCs, anti-Her2-CL-9 and antibody 20507-CL-9 were determined to be 4.1 and 3.9, respectively. Selected properties of anti-Her2-CL-9 and antibody 20507-CL9 ADCs are summarized in Table 13.

EXAMPLE 104

Preparation of Antibody Drug Conjugates Using 1,3-dichloropropan-2-one to Reconnect Native Disulfide Bonds of Non-Engineered Antibodies Conjugation to native cysteine residues of non-engineered antibodies using the procedure in Example 103 has the disadvantage that some native disulfide bonds that naturally stabilize the antibody are broken and remain so after drug conjugation. In an alternative method that overcomes this disadvantage, inter- and intra-chain disulfides bonds of the antibody are first reduced and then chemically reconnected through a reaction with 1,3-dichloropropan-2-one. In the process, the four native interchain disulfide bonds in an antibody are replaced by a three carbon "ketone bridge" (Scheme 36). The ketone group can then specifically be conjugated with a cytotoxic drug in the second step. The resulting ADC has up to four drugs attached specifically at the location of the four native, interchain disulfide bonds of an antibody. In contrast to traditional conjugation to partially reduced native disulfides (Example 103), ADCs prepared in the example are more stable.

In one example, non-engineered, recombinant antibody 20507 was prepared by standard methods and as described above. After purification, antibody 20507 was conjugated to a cytotoxic drug in two steps following Scheme 36:

Scheme 36

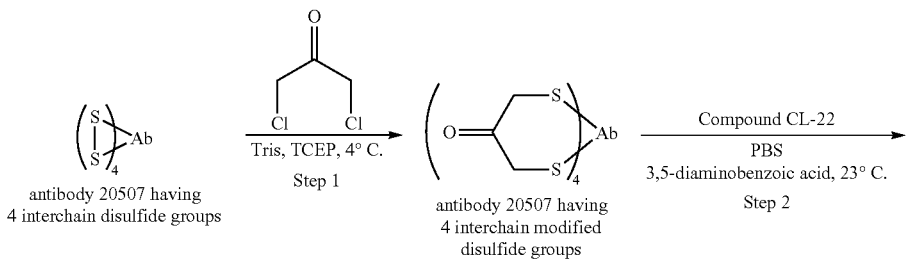

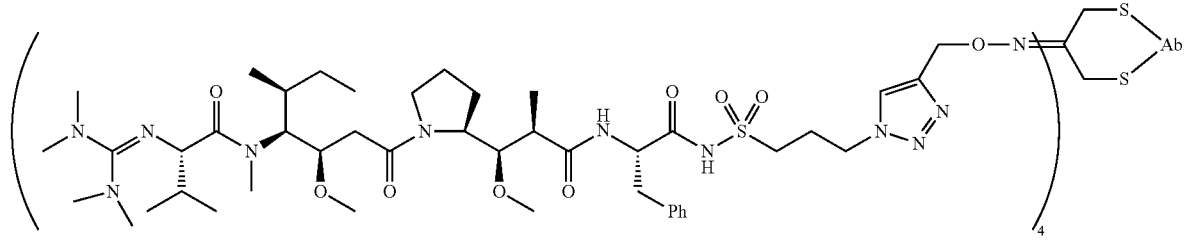

Step 1—Reduction of native disulfide bridges and re-bridging using 1,3-dichloropropan-2-one: TCEP.HCl (41.4 μg, 0.144 μmol) was added to a solution of antibody 20507 (1770 μg, 0.012 μmol, 147 μL in 0.25 M Tris pH 7.4) and 1,3-dichloropropan-2-one (193 μg, 1.443 μmol) at 4° C. The resulting mixture was kept at 4"C for 4 h. The reaction mixture was then desalted using a Zeba spin column 7K MWCO (0.5 mL) with PBS (pH 7.4) as the eluting buffer for 4 times to give the modified antibody 20507: 144483 Da (after deglycosylation by PNGase F (New England Biolabs)). ESI (Eluent A: water+0.1% Formic acid, Eluent B: Acetonitrile+0.04% Formic acid. Gradient: from 3 to 80% B in 2 min Flow 1.0 mL/min. Column: Proswift Monolith 4.6*50 mm 40° C.).

Step 2—Conjugation of the cytotoxic drug: A solution of (S)-2-((Bis(dimethylamino)methylene)amino)-1-(((3R,4S,5S)-1-((S)-2-((1R,2R)-3-(((S)-N-1-(3-(4-(aminoxymethyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutane (CL-22) (304 μg, 0.326 μmol, 3.04 μL, in DMSO) and 3,5-diaminobenzoic acid (681 μg, 4.48 μmol, 2.27 μL, in DMSO) were added to a solution of the modified antibody from step 1 (1200 μg, 0.0081 μmol, 118 μL in PBS pH 7.4). The resulting mixture was kept at 23° C. for 15 h. The reaction mixture was then desalted (3x) using a Zeba spin column 7K MWCO (2 mL) with PBS (pH 7.4) as the eluting buffer. The resulting ADC, antibody 20507-CL-22, has an average DAR 3.8 as determined by MS. Some properties of the ADC are shown in Table 13.

EXAMPLE 105

Preparation of Antibody Drug Conjugates Using Lysine Reactive Compounds of Formula (I)

Cytotoxic drugs of the invention can also be conjugated to native lysine residues of non-engineered antibodies. This can be accomplished, for example, by reacting a cytotoxic drug linked to an NHS ester or a pentafluorophenyl (PFP) ester group with non-engineered antibodies under neutral pH in PBS buffer devoid of free amines. The NHS or PFP ester group in the drugs readily reacts with lysine residues in antibodies (Hermanson, G. T. Bioconjugate Techniques; Academic Press: New York, 1996; Baslé E, Joubert N, Pucheault M. Chem Biol. 2010, 17:213-227. Protein chemical modification on endogenous amino acids). In one example, non-engineered anti-Her2 and antibody 20507 antibodies were reacted with compound CL-32 or CL-41 at the molar compound to antibody ratio of 10:1 and 4:1, respectively. The resulting ADCs, anti-Her2-CL-32, anti-Her2-CL-41 and antibody 20507-CL-32, had an average DAR 4.7, DAR1.3 and DAR 2.7, respectively (Table 13).

Some of the properties of anti-Her2-CL-32 and antibody20507-CL-32 are listed in Table 13.

TABLE 13

Properties of various ADCs prepared with non-engineered antibodies

| Name of ADC$^a$ | DAR$^c$ | Oligomer (%)$^d$ |
|---|---|---|
| Anti-Her2-CL-9 | 4.1 | 2.3 |
| Antibody 20507-CL-9 | 3.9 | 2.7 |
| Anti-Her2-CL-32 | 4.7 | 1.0 |
| Antibody 20507-CL-32 | 2.7 | 1.0 |
| Antibody 20507-CL-22 | 3.8 | 3.0 |
| Anti-Her2-CL-41 | 1.3 | 1.0 |

While the immunoconjugates of Formula (II) and Formula (III) disclosed in Tables 5 and 6 were obtained by conjugating anti-Her2 and antibody 20507 Cys mutant antibodies with certain compounds of Formula (I) having a linked maleimide moiety, other linker-payload combinations of the invention have also been used as exemplified by the immunoconjugates disclosed in Tables 8-13. In addition conjugation to-non-engineered antibodies is also possible, in particular at cysteine or lysine residues using methods know in the art and as shown in Example 103, Example 104 and Example 105 and exemplified by the immunoconjugates in Table 13.

All example ADCs were tested for in vitro cell killing potency as described in Example 107. Pharmacokinetic studies (Example 108) and in vivo efficacy studies (Example 109) were preformed for selected immunoconjugates of the invention.

EXAMPLE 106

In Vitro Cell Killing Assay of Compounds of Formula (I)

For evaluation of the cell killing potency of the compounds of Formula (I) in vitro, cell proliferation assays were performed in parallel with 8 cell lines: MDA-MB231 clone 16, clone 40, JimT1, HCC1954, NCl-H526, KU812, CMK11-5 cells and Jurkat cells. The cell lines are described in more detail in Example 107 and were also used to assess the in vitro potency of immunoconjugates of the invention. The cell proliferation assays were conducted with Cell-Titer-Glo™ (Promega) five days after cells were incubated with various concentrations of the compound (Riss et al., (2004) *Assay Drug Dev Technol.* 2:51-62). In some studies, the cell based assays are high throughput and conducted on an automated system (Melnick et al., (2006) Proc Natl Acad Sci USA. 103:3153-3158). The in vitro cell killing potency obtained for certain examples of compounds of Formula (I) are given in Table 14.

TABLE 14

In vitro cell killing (IC$_{50}$ [nM]) of certain compounds of Formula (I)

| Cmpd No. | CMK-11-5 | HCC1 954 | JimT1 | JURKAT | KU812 | MDA-MB-231 clone 16 | MDA-MB-231 clone 40 | NCI-H526 |
|---|---|---|---|---|---|---|---|---|
| 1 | 1.23 | 0.131 | 0.675 | 0.151 | 0.281 | 1.24 | 2.49 | 1.08 |
| 2 | 182 | 46.2 | 202 | 162 | 279 | 735 | 442 | 218 |
| 3 | 14.7 | 10.8 | 42.1 | 3.01 | 6.78 | 12.7 | 23.9 | 22 |
| 5 | 74.8 | 47 | 44.7 | 49.9 | 106 | 83.5 | 139 | 204 |
| 46 | 10.4 | 2.3 | 14.2 | 6.1 | 8.4 | 8.1 | 11.7 | 29.5 |

EXAMPLE 107

Cell Proliferation Assays to Measure In Vitro Cell Killing Potency of ADCs

Cells that naturally express target antigens or cell lines engineered to express target antigens are frequently used to assay the activity and potency of ADCs. For evaluation of the cell killing potency of anti-Her2 antibody ADCs in vitro, two engineered cell lines, MDA-MB-231 clone 16 and clone 40, and two endogenous cell lines, JimT-1 and HCC1954 cells were employed (Clinchy B, Gazdar A, Rabinovsky R, Yefenof E, Gordon B, Vitetta E S. Breast Cancer Res Treat. (2000) 61:217-228). MDA-MB-231 clone 16 cells stably express high copy numbers (~5×10$^5$ copies/cell) of recombinant human Her2 on the cell surface, while clone 40 expresses human Her2 at low levels (~5×10$^3$ copies/cell). HCC1954 cells endogenously express high levels (~5×10$^5$ copies/cell) of recombinant human Her2 in the surface while JimT-1 cells express human Her2 at a medium level (~8×10$^4$ copies/cell). NCI-N87 cells express high levels of Her2 while A375 cell express low levels of Her2. An ADC should kill cells in an antigen-dependent manner, meaning that only cells that express sufficient antigen in the cell surface but not cells lacking the antigen will be killed. Therefore cell killing should not be observed MDA-MB-231 clone 40 cells.

To measure antigen-dependent cell killing, cell proliferation assays were conducted with Cell-Titer-Glo™ (Promega) five days after different cell types were incubated with various concentrations of ADCs (Riss et al., (2004) Assay Drug Dev Technol. 2:51-62). In some studies, the cell based assays are high throughput and conducted on an automated system (Melnick et al., (2006) Proc Natl Acad Sci USA. 103:3153-3158).

Anti-Her2 ADCs prepared with compounds of the invention and conjugated site-specifically to anti-Her2 Cys mutant antibodies (see Table 5) were assayed in the aforementioned four cell lines to evaluate their cytotoxicity. All ADCs except two (anti-Her2-LC-S159C-NL-34 and -CL-6) specifically killed the two cell lines which have high levels of Her2 expression; MDA-MB231 clone 16 and HCC1954, but did not kill MDA-MB-231 clone 40 cells which express a low level of Her2 (FIG. 1, Table 15). IC$_{50}$ values of the anti-Her2 ADCs in MDA-MB-231 clone 16 and HCC1954 cell assays ranged from 20 pM to 300 pM (Table 15). ADCs prepared with two payloads (anti-Her2-LC-S159C-NL-34 and -CL-6) did not show cytotoxicity toward any cell lines in the assays. In JimT-1 cells, a cell line with a medium level of Her2 expression, the cell killing activities by the ADCs varied widely. ADCs with some payloads (Compounds: CL-5, NL-38, NL-30, NL-19, NL-21, CL-24) were active in HCC1954 and MDAMB231-16 cells but not in JimT-1 cells. Many ADCs killed JimT-1 cell as effectively as HCC1954 and MDAMB231-16 cells (FIG. 1, Table 15). In JimT-1 cell proliferation assays (Table 15), anti-Her2 ADCs with many payloads of the invention displayed higher cytotoxicity than anti-Her2-MMAF, the ADC that contains a well-characterized reference payload (Svetlana O. Doronina, Brian A. Mendelsohn, Tim D. Bovee, Charles G. Cerveny, Stephen C. Alley, Damon L. Meyer, Ezogelin Oflazoglu, Brian E. Toki, Russell J. Sanderson, Roger F. Zabinski, Alan F. Wahl, and Peter D. Senter, Bioconjugate Chem. 2006, 17, 114-124). The significant differences of cytotoxic potency observed in JimT-1 cell amoung anti-Her2-LC-S159C ADCs have made it possible to rank the potency of the payloads. The results indicate that the anti-Her2 ADCs with various compounds of the invention killed Her2+ cells in a Her2 dependent manner and the ADCs are highly active towards multiple cell types. This is in contrast to the in vitro cell killing of both high and low Her2 expressing cell lines by free, unconjugated compounds of the invention (see Example 106, Table 14).

To verify whether compounds of Formula (I) were also active when conjugated to other antibodies, several compounds (CL-1, CL-6, CL-9, NL-4) were conjugated to antibody 20507 Cys mutant antibodies (Table 6), whose target antigen was expressed in H526, KU812 and CMK11-5 cells, but not in Jurkat cells and therefore cell killing should not be observed for the Jurkat cell line. As shown in FIG. 2 and Table 16, payload linker combinations (CL-1, CL9, NL-4) that show cell killing activities in Her2+ cells are also active when conjugated to antibody 20507, killing cells that express the target antigen. In agreement with the observation that anti-Her2-CL-6 ADC had no cytotoxicity in Her2+ cells, the antibody 20507-CL-6 ADC is also not active in cell killing assays with antigen expressing cells (Table 16). The results indicate that the compounds described herein show cytotoxicity towards a broad range of cell types.

Since cytotoxic drug payload in an ADC is the primary cause for cellular toxicity, increasing the drug to antibody ratio (DAR) should enhace the ADC's cytotoxic potency. We tested the cytotoxic activity of two DAR 4 ADCs, antibody 20507-HC-K360C-LC-K107C-CL-9 and antibody 20507-HC-E152C-S375C-CL-9, in cell proliferation assays. As shown in Table 16, the two DAR 4 ADCs inhibited cell proliferation in an antigen-dependent manner with IC$_{50}$ values lower than corresponding DAR 2 ADCs, indicating that conjugation of four CL-9 payload molecules to each antibody, as expected, increases cytotoxic potency of the ADCs without sacrificing the specificity of the antibody.

Compounds of the invention can be effectively utitlized as ADC payloads in conjunction with a broad array of conjugations methods. In addition to the highly potent ADCs prepared with Cys engineered antibodies (discussion above; Example 99), immunoconjugates of the invention were prepared with four other conjugation methods: conjugation using an enzymatic method using tagged antibodies (Examples 101-103), and conjugation of non-engineered antibodies through partial reduction of native disulfide bonds (Example 103), through "ketone-bridging" of reduced native disulfide bonds (Example 104), and through native lysine residues (Example 105).

In addition to Cys engineered ADCs, ADCs prepared with the latter four methods also proved to be highly cytotoxic and killed cells in an antigen-dependent manner. In particular, payload CL-22 has a similar core structure to CL-9 and contains a hydroxyl amine moiety to replace the maleimide moiety. CL-22 was conjugated to antibody 20507 through an enzyme-mediated conjugation method as described in Examples 101-103 and a ketone bridge-based method as described in Example 104. The resulting two ADCs are antibody 20507-HC-ins388-A1-CoA-1-CL-22 and antibody 20507-CL-22. The two ADCs were tested in cell proliferation assays as described above. While having an identical conjugate ratio (DAR 2), the enzymatically conjugated ADC, antibody 20507-HC-ins388-A1-CoA-1-CL-22, displays 2-3 fold higher $IC_{50}$ values compared to the corresponding CL-9-conjugated DAR 2 Cys ADCs (Table 16). On the other hand, the ketone bridged ADC, antibody 20507-CL-22, which has a DAR of 4, showed a similar potency in terms of $IC_{50}$ to DAR 2 CL-9 Cys ADCs, and was less potent than DAR 4 CL-9 Cys ADCs (Table 16). CL-9 is a potent payload when it is site-specifically conjugated to anti-Her2 and antibody 20507. CL-9 was also conjugated to native Cys residues of anti-Her2 and antibody 20507 through a partial reduction method as described in Example 103. The average DAR ratio for the two resulting ADCs: anti-Her2-CL-9 and antibody 20507-CL-9 are DAR 4.1 and DAR 3.9 respectively (Table 13). Both ADCs are potent in vitro cell based assays with an $IC_{50}$ similar to that of site-specific, Cys engineered CL-9 ADCs (Tables 15 and 16). Conjugation to lysine residues in antibodies with NHS ester and PFP ester containing drug payloads is a common method in ADC preparation. ADCs were prepared by conjugating CL-32 or CL-41 to anti-Her2 and antibody 20507. The resulting ADCs, anti-Her2-CL-32, anti-Her2-CL-41 and antibody 20507-CL-32 (Table 13) showed high, antigen-dependent cytotoxicity in cell based assays (Table 15 and Table 16).

Our results demonstrate that the class of payloads described in the invention is suitable for preparation of active ADCs with various conjugation methods as mentioned above. Potent ADCs can be prepared from the payloads conjugating to a large number of diverse conjugation sites in antibodies including engineered cysteine residues, native cysteine residues, lysine residues, and certain serine residues.

TABLE 15

ADC potency in in vitro cell killing assay: $IC_{50}$ of anti-Her2 ADCs in MDA-MB231 clone 40, MDA-MB231 clone 16, HCC1954, JimT-1 NCI-N87, and A375 cell proliferation assays.

| Name of ADC | HCC1954 $IC_{50}$ (nM) | JimT-1 $IC_{50}$ (nM) | MDA-MB-231-16 $IC_{50}$ (nM) | MDA-MB-231-40 $IC_{50}$ (nM) | NCI-N87 $IC_{50}$ (nM) | A375 $IC_{50}$ (nM) |
|---|---|---|---|---|---|---|
| anti-Her2-LC-S159C-MC-MMAF | 0.054 | 0.13 | 0.057 | >67 | ND | ND |
| anti-Her2-LC-S159C-NL-26 | 0.057 | 0.079 | 0.047 | >67 | ND | ND |
| anti-Her2-LC-S159C-CL-12 | 0.057 | 0.046 | 0.053 | 47 | ND | ND |
| anti-Her2-LC-S159C-CL-10 | 0.055 | 0.053 | 0.053 | >67 | ND | ND |
| anti-Her2-LC-S159C-CL-11 | 0.061 | 0.12 | 0.058 | >67 | ND | ND |
| anti-Her2-LC-S159C-NL-38 | 0.17 | >67 | 0.15 | >67 | ND | ND |
| anti-Her2-LC-S159C-CL-9 | 0.053 | 0.041 | 0.050 | >67 | ND | ND |
| anti-Her2-LC-S159C-NL-12 | 0.057 | 0.051 | 0.053 | >67 | ND | ND |
| anti-Her2-LC-S159C-CL-1 | 0.058 | 0.079 | 0.052 | >67 | ND | ND |
| anti-Her2-LC-S159C-NL-4 | 0.020 | 0.041 | 0.019 | >67 | ND | ND |
| anti-Her2-LC-S159C-CL-5 | 0.18 | >67 | 0.19 | >67 | ND | ND |
| anti-Her2-LC-S159C-CL-2 | 0.054 | 0.068 | 0.051 | >67 | ND | ND |
| anti-Her2-LC-S159C-CL-3 | 0.056 | 0.065 | 0.052 | >67 | ND | ND |
| anti-Her2-LC-S159C-CL-6 | >67 | >67 | >67 | >67 | ND | ND |
| anti-Her2-LC-S159C-NL-34 | >67 | 23 | >67 | >67 | ND | ND |
| anti-Her2-LC-S159C-NL-9 | 0.063 | 0.23 | 0.076 | >67 | ND | ND |
| anti-Her2-LC-S159C-NL-22 | 0.063 | 0.52 | 0.049 | >67 | ND | ND |
| anti-Her2-LC-S159C-NL-19 | 0.19 | >67 | 0.29 | 67 | ND | ND |
| anti-Her2-LC-S159C-NL-21 | 0.10 | >67 | 0.17 | 67 | ND | ND |
| anti-Her2-LC-S159C-CL-24 | 0.082 | >67 | 0.15 | 67 | ND | ND |
| anti-Her2-LC-S159C-NL-30 | 0.13 | >67 | 0.11 | 67 | ND | ND |
| anti-Her2-LC-S159C-CL-8 | 0.068 | 0.11 | 0.077 | 67 | ND | ND |
| anti-Her2-HC-E152C-S375C-CL-9 | 0.084 | 0.21 | 0.10 | >67 | ND | ND |
| anti-Her2-HC-ins388-A1-CoA-1-CL-22 | 0.14 | 0.17 | 0.14 | 61 | ND | ND |
| anti-Her2-CL-9 | 0.16 | 0.19 | 0.17 | >67 | ND | ND |
| anti-Her2-CL-32 | 0.15 | 0.18 | 0.16 | >67 | ND | ND |
| anti-Her2-CL-41 | 0.12 | 0.16 | ND | ND | ND | ND |
| anti-Her2-HC-ins388-ybbR-CoA-1-CL-22 | 0.084 | 0.25 | ND | ND | 0.11 | >44 |
| anti-Her2-HC-ins388-ybbR-CoA-1-CL-35 | 0.19 | 0.39 | ND | ND | 0.48 | >52 |
| anti-Her2-HC-ins388-ybbR-CoA-(i-12)-CL-22 | 0.061 | 0.16 | ND | ND | 0.089 | >41 |

TABLE 15-continued

ADC potency in in vitro cell killing assay: IC$_{50}$ of anti-Her2 ADCs in MDA-MB231 clone 40, MDA-MB231 clone 16, HCC1954, JimT-1 NCI-N87, and A375 cell proliferation assays.

| Name of ADC | HCC1954 IC$_{50}$ (nM) | JimT-1 IC$_{50}$ (nM) | MDA-MB-231-16 IC$_{50}$ (nM) | MDA-MB-231-40 IC$_{50}$ (nM) | NCI-N87 IC$_{50}$ (nM) | A375 IC$_{50}$ (nM) |
|---|---|---|---|---|---|---|
| anti-Her2-HC-ins388-ybbR-CoA-(i-12)-CL-35 | 0.11 | 0.41 | ND | ND | 0.14 | >43 |
| anti-Her2-HC-ins388-ybbR-CoA-(i-13)-CL-33 | 0.047 | 0.22 | 0.14 | >61 | ND | ND |
| anti-Her2-HC-ins388-ybbR-CoA-(i-14)-CL-22 | 0.13 | 0.21 | ND | ND | 0.15 | >44 |
| anti-Her2-HC-ins388-ybbR-CoA-(i-14)-CL-35 | 0.093 | 0.26 | ND | ND | 0.11 | >47 |
| anti-Her2-HC-ins388-ybbR-CoA-(i-14)-CL-36 | 0.075 | 0.16 | ND | ND | 0.11 | >67 |
| anti-Her2-HC-ins388-ybbR-CoA-(i-14)-CL-35 | 0.029 | 0.14 | ND | ND | 0.077 | >67 |
| anti-Her2 HC-ins388-ybbR-CoA-(i-15)-CL-22 | 0.033 | 0.16 | ND | ND | 0.081 | >67 |
| anti-Her2 HC-ins388-ybbR-CoA-(i-15)-CL-36 | 0.057 | 0.15 | ND | ND | 0.10 | >67 |
| anti-Her2 HC-ins388-ybbR-CoA-(i-15)-CL-37 | 0.059 | 0.19 | ND | ND | 0.16 | >67 |
| anti-Her2 HC-ins388-ybbR-CoA-(i-15)-CL-35 | 0.043 | 0.28 | ND | ND | 0.092 | >67 |
| anti-Her2-HC-P189G-S190D-S192L-L193S-G194W-T195L-CoA-1-CL-35 | 0.49 | 0.67 | ND | ND | 0.82 | >63 |
| anti-Her2-HC-P189G-S190D-S192L-L193S-G194W-T195L-CoA-(i-12)-CL-35 | 0.47 | 1.3 | ND | ND | 1.4 | >69 |
| anti-Her2-HC-S190D-S192L-L193S-G194W-T195L-CoA-(i-12)-CL-35 | 0.25 | ND | ND | ND | 0.57 | ND |
| anti-Her2-HC-S190D-S192L-L193S-G194W-T195L-CoA-(i-14)-CL-22 | 0.096 | 0.20 | ND | ND | 0.13 | >62 |
| anti-Her2-HC-S119G-T120D-K121S-G122L-P123D-ins123-MLEW-CoA-(i-14)-CL-35 | 0.19 | 0.45 | ND | ND | 0.36 | >67 |
| anti-Her2-HC-S119G-T120D-K121S-G122L-P123D-ins123-MLEW-CoA-(i-14)-CL-22 | 0.068 | 0.12 | ND | ND | 0.11 | >61 |

The highest concentration used in the assay was 67 nM for all Cys ADCs and 61 nM for anti-Her2-HC-ins388-A1-CoA-1-CL-22. IC$_{50}$ values of 67 nM indicate inactivity of the ADC in the assay.
ND: Not determined

TABLE 16

ADC potency in in vitro cell killing assay: IC$_{50}$ of antibody 20507 ADCs in Jurkat, H526, KU812 and CMK11-5 cell proliferation assays.

| Name of ADC | JURKAT IC$_{50}$ (nM) | NCI-H526 IC$_{50}$ (nM) | KU812 IC$_{50}$ (nM) | CMK-11-5 IC$_{50}$ (nM) |
|---|---|---|---|---|
| Antibody 20507-LC-S159C-MC-MMAF | >67 | 0.050 | 0.060 | 0.054 |
| Antibody 20507-LC-S159C-CL-1 | >67 | 0.050 | 0.061 | 0.057 |
| Antibody 20507-LC-S159C-CL-6 | >67 | >67 | >67 | >67 |
| Antibody 20507-LC-S159C-NL-4 | >67 | >67 | 0.067 | >67 |
| Antibody 20507-HC-E152C-NL-4 | >67 | >67 | 0.044 | >67 |
| Antibody 20507-LC-K107C-CL-9 | >67 | 0.056 | 0.060 | 0.063 |
| Antibody 20507-HC-S375C-CL-9 | >67 | 0.056 | 0.074 | 0.10 |
| Antibody 20507-HC-E152C-CL-9 | >67 | 0.064 | 0.061 | 0.062 |
| Antibody 20507-HC-K360C-LC-K107C-CL-9 | >67 | 0.018 | 0.017 | 0.018 |
| Antibody 20507-HC-E152C-S375C-CL-9 | >67 | 0.018 | 0.016 | 0.016 |
| Antibody 20507-HC-ins388-A1-CoA-1-CL-22 | 48 | 0.16 | 0.14 | 0.15 |
| Antibody 20507-CL-22 | >67 | 0.15 | 0.095 | 0.052 |

TABLE 16-continued

ADC potency in in vitro cell killing assay: IC$_{50}$ of antibody 20507 ADCs in Jurkat, H526, KU812 and CMK11-5 cell proliferation assays.

| Name of ADC | JURKAT IC$_{50}$ (nM) | NCI-H526 IC$_{50}$ (nM) | KU812 IC$_{50}$ (nM) | CMK-11-5 IC$_{50}$ (nM) |
|---|---|---|---|---|
| Antibody 20507-CL-9 | >67 | 0.18 | 0.13 | 0.054 |
| Antibody 20507-CL-32 | >67 | 0.22 | 0.16 | 0.16 |

The highest concentration used in the assay was 67 nM. IC$_{50}$ values of 67 nM therefore indicate inactivity of the ADC in the assay.

EXAMPLE 108

ADC Pharmacokinetic Study

It has been demonstrated that a long serum half-life is critical for high in vivo efficacy of ADCs (Hamblett, et al., "Effects of drug loading on the antitumor activity of a monoclonal antibody drug conjugate," *Clin Cancer Res.*, 10:7063-7070 (2004); Alley et al., *Bioconjug Chem.* 19:759-765 (2008)). Attaching a hydrophobic drug payload to an antibody could affect the properties of an antibody, and this may lead to a fast clearance of the ADCs in vivo (Hamblett et al., 2004) and poor in vivo efficacy. To evaluate the effects of conjugation of various compounds of Formula (I) on clearance of the ADCs in vivo, pharmacokinetic studies in non-tumor bearing mice were carried out. To detect the immunoconjugates in murine plasma, an anti-MMAF antibody was generated which recognizes various compounds described in this invention. ELISA assays for the detection of immunoconjugates were developed on a Gyros™ platform using an anti-hIgG antibody to capture human IgG molecules from the plasma and a second anti-human IgG antibody and an anti-MMAF antibody for signal detection in two separate assays. The anti-MMAF antibody recognizes the compounds of the invention and therefore can be used to detect ADCs with the compounds attached ("intact" ADC). Hence, the two ELISA assays measure the serum concentration of the human antibody and the "intact" ADC respectively.

Examples of PK studies are shown in FIG. 3. Three mice per group were administered with a single dose of the indicated ADCs. Eight anti-Her2 DAR 2 ADCs, anti-Her2-LC-S159C-CL-9, anti-Her2-LC-S159C-NL-4, anti-Her2-LC-S159C-CL-1, anti-Her2-LC-S159C-CL-6, anti-Her2-LC-S159C-CL-10, anti-Her2-LC-S159C-CL-11, anti-Her2-LC-S159C-CL-12, and anti-Her2-LC-S159C-NL-38 (FIG. 3A, B), two antibody 20507 DAR 2 ADCs, antibody 20507-HC-E152C-CL-9, and antibody 20507-HC-E152C-NL-4 (FIG. 3C), two antibody 20507 DAR 4 ADCs, antibody 20507-HC-E152C-S375C-CL-9 and antibody 20507-HC-K360C-LC-K107C-CL-9 (FIG. 3D), two enzymatically conjugated ADCs, anti-Her2-HC-ins388-A1-CoA-1-CL-22 and antibody 20507-HC-ins388-A1-CoA-1-CL-22 (FIG. 3E), anti-Her2-CL-9 ADC prepared by partial reduction of native disulfide bonds (FIG. 3F), anti-Her2-CL-32 ADC conjugated through native lysine residues (FIG. 3F) as well as unconjugated, wild-type anti-Her2 antibody were administered into mice at 1 mg/kg. Plasma samples were collected over the course of three weeks and assayed by ELISA assays using an anti-hIgG antibody to capture the IgG molecules including ADCs and naked anti-Her2 antibody and antibody 20507. The anti-MMAF and an anti-hIgG antibody were then used for detection in two separate assays. The anti-MMAF antibody assay measures the concentration of the conjugates only and the anti-hIgG quantitates both conjugates and antibodies that lack payloads. Standard curves were generated for each ADC separately using the same material as injected into the mice. The assays with anti-MMAF and anti-hIgG should therefore yield identical concentration readouts if no changes to the drug loading of the ADCs occur after injection into mice. For ADCs that lost some of the payload, the assay with the anti-MMAF antibody will measure a lower concentration than the anti-hIgG assay. A comparison of the two concentration readouts therefore allows to measure drug-release from ADC during in vivo incubation in the mouse. For comparison, a PK study with unconjugated, wild-type anti-Her2 was also performed (FIG. 3F).

Figure 3A:
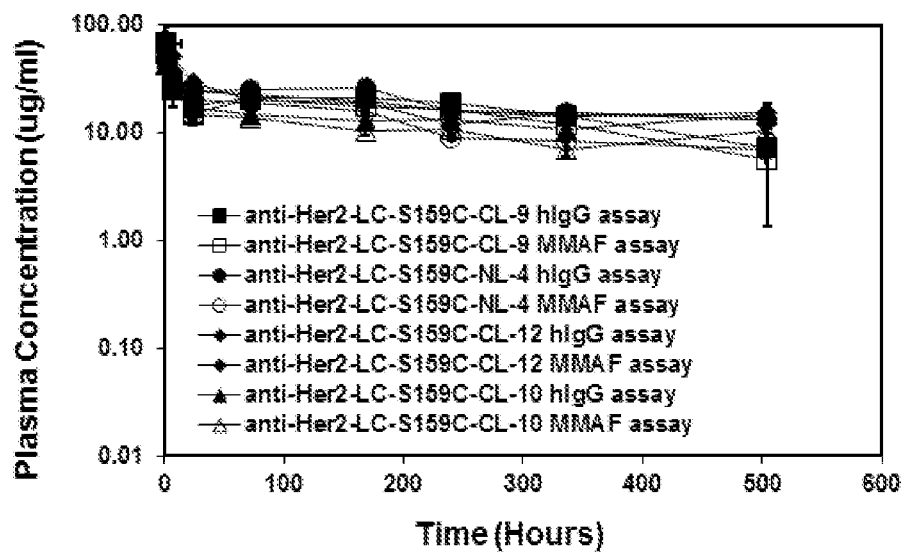
FIG. 3A-3F: Pharmacokinetic studies of anti-Her2 and antibody 20507 ADCs and antibodies using anti-hIgG assay and anti-MMAF assays: Anti-Her2 ADCs (A and B) and antibody 20507 ADCs (C and D) conjugated through engineered Cys residues, conjugated enzymatically (E) and conjugated through partial reduction of native disulfide bonds and conjugated through lysine residues (F). Non-conjugate anti-Her2 antibody (anti-Her2) is included as reference in Figure (F)
Figure 3B:
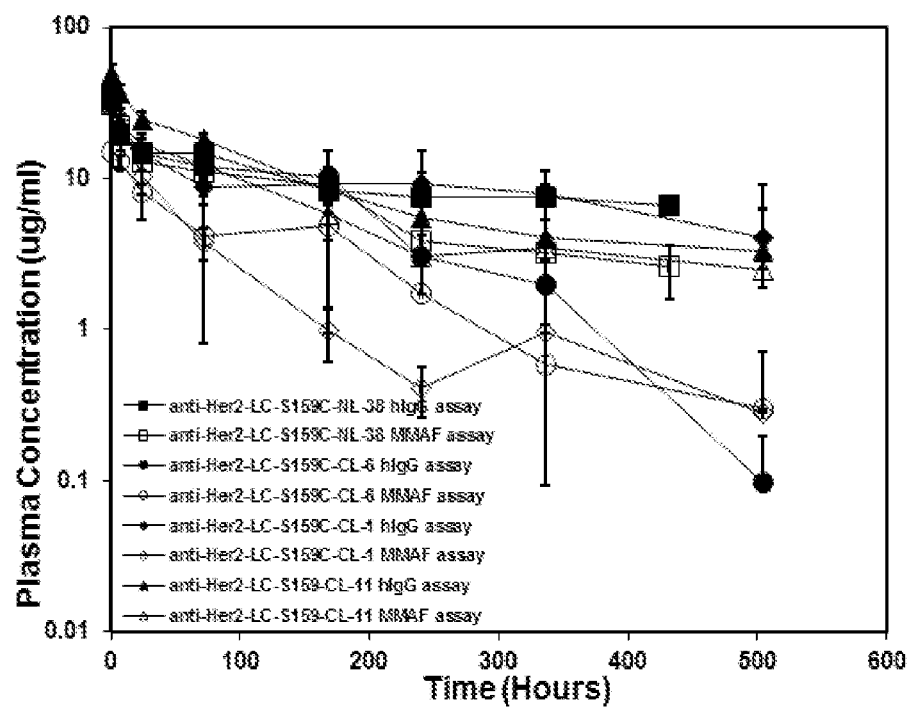
Figure 3C:
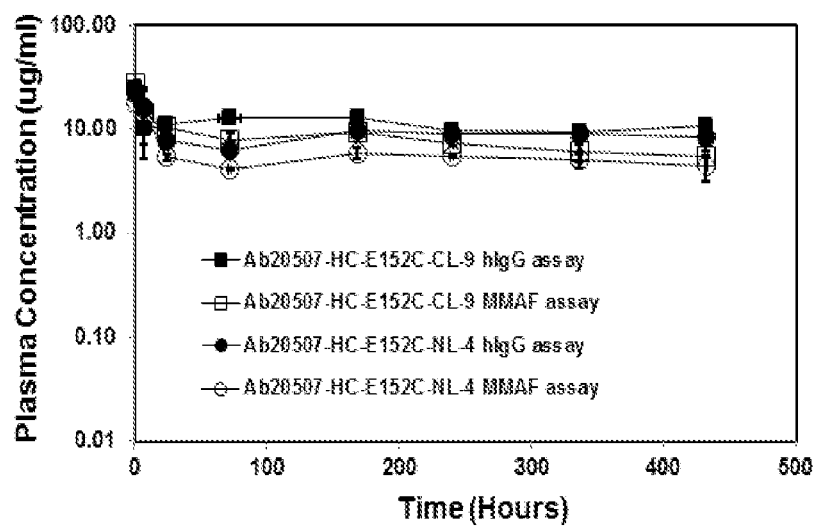
Figure 3D:
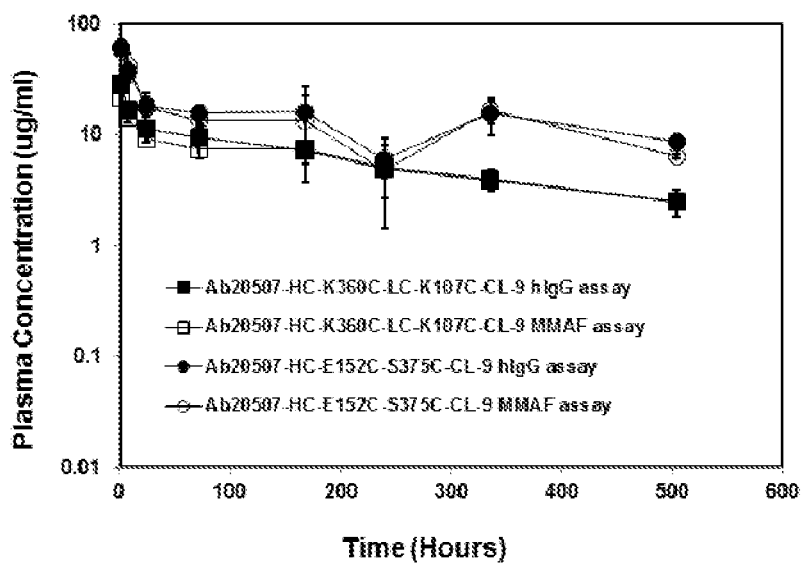
Figure 3E:
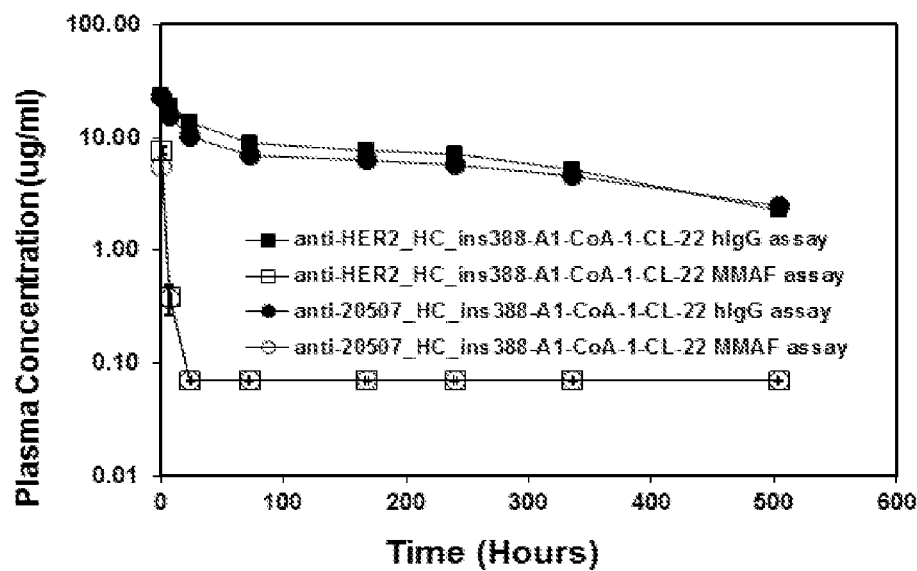
Figure 3F:
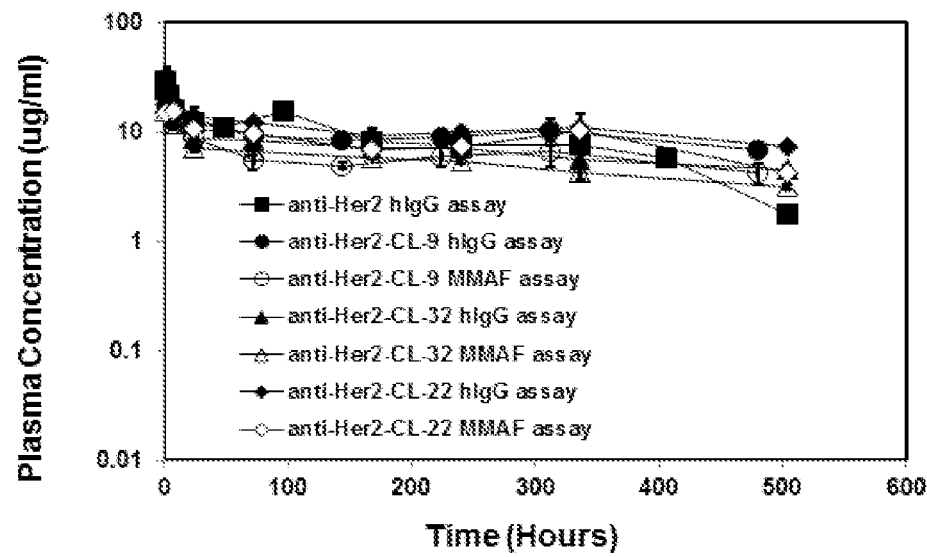

Most anti-Her2 ADCs of the invention exhibit similar pharmacokinetics as those of the wild-type, unconjugated antibody (see FIG. 3F). As shown in FIGS. 3A and B, for six ADCs (anti-Her2-LC-S159C-CL-9, anti-Her2-LC-S159C-NL-4, anti-Her2-LC-S159C-CL-10, anti-Her2-LC-S159C-CL-11, anti-Her2-LC-S159C-CL-12, and anti-Her2-LC-S159C-NL-38), plasma concentrations obtained by both anti-hIgG assay and anti-MMAF assay match closely, indicating that there is a minimal drug loss in the six ADCs during the testing period, and indicating that the six payloads (CL-9, CL10, CL-11, CL-12 and NL-4, NL-38) and that the linkers of the payloads are stable during circulation in mice. However, for one ADC (anti-Her2-LC-S159C-CL-1), results of the anti-MMAF assay and the anti-hIgG assay differ significantly from each other, suggesting that CL-1 payload is lost from the antibody (FIG. 3B). MS analysis of anti-Her2-LC-S159C-CL-1 ADC isolated from mice plasma three weeks after administered with the ADC indicates that the amide bond in CL-1 linker was cleaved, confirming the results from anti-MMAF assay.

The anti-MMAF and anti-hIgG assays data (FIG. 3B) showed that anti-Her2-LC-S159C-CL-6 cleared more rapidly from circulation in mice than unconjugated anti-Her2 antibody (squares, FIG. 3F). The PK studies clearly have identified stable payload-linker combinations for six payloads (CL-9, CL10, CL-11, CL-12 and NL-4, NL-38). Two of these payloads (CL-9 and NL-4) were conjugated to a second antibody, antibody 20507 in DAR 2 and DAR 4 formats. PK studies of the four antibody 20507 ADCs (antibody 20507-HC-E152C-CL-9, antibody 20507-HC-E152C-NL-4, antibody 20507-HC-E152C-S375C-CL-9 and antibody 20507-HC-K360C-LC-K107C-CL-9) verified excellent linker stability for the four linker-payload combinations in the context of a second antibody (FIG. 3C, D). Compared to the DAR 2 antibody 20507 ADCs (FIG. 3C), DAR 4 antibody 20507 ADCs (FIG. 3D), antibody 20507-HC-K360C-LC-K107C-CL-9 in particular, appear to clear slightly more rapidly from circulation in mice. However, the results indicate that conjugation of either two or four CL-9 or NL-4 payloads to each antibody molecule in the described sites does not alter the biochemical properties nor does it change of pharmacokinetics of the antibodies significantly.

In another example, payload compound CL-22 was conjugated to anti-Her2 and antibody 20507 antibodies through an enzyme mediated conjugation method as described in Examples 101-103. The two ADCs (anti-Her2-HC-ins388-A1-CoA-1-CL-22 and antibody 20507-ins388-A1-CoA-1-CL-22) were subjected to mouse PK studies. As shown in FIG. 3E, while the anti-hIgG assay data show a PK profile similar to that of unconjugated, wild-type anti-Her2 antibody (FIG. 3F) over a period of three weeks, the anti-MMAF assays showed that the level of both ADCs in mice plasma dropped below detection level whithin 24 hours, indicating that CL-22 payload was released from the two antibodies. MS analysis indicates that the linker in CL-22 was cleaved at the sulfonamide and oxime linker groups. This finding was unexpected as the closely related compound CL-9 experiences no cleavage when conjugated to engineered Cys residues (FIGS. 3A, C and D) or native Cys residues (FIG. 3F). In the latter example, payload compound CL-9 was conjugated to native cysteine residues of partially reduced anti-Her2 antibody (Example 103). PK study with the resulting ADC, anti-Her2-CL-9 showed that profiles of both anti-IgG and anti-MMAF assays are similar to that of unconjugated, wild-type anti-Her2 (FIG. 3F), indicating that the ADC despite partially reduced native disulfide bonds has good PK properties.

Compared to CL-9 ADCs, the two CL-22 ADCs (anti-Her2-HC-ins388-A1-CoA-1-CL-22 and antibody 20507-ins388-A1-CoA-1-CL-22) contain a longer linker between the compound and the conjugation site on the antibody (Example 91, scheme 49). The long and flexible linker in the two CL-22 ADCs prepared by the enzymatic method (Examples 101-103) could potentially make the linker more accessible to enzymes that could facilitate linker cleavage. On the other hand, anti-Her2-CL-22, a CL-22 ADC prepared with the conjugation method described in Example 104 contains a shorter linker between the compound and the conjugation sites on the antibody compared to the enzymatically prepared CL-22 ADCs. When anti-Her2-CL-22 was subjected to PK study, a good PK profile resembling that of WT anti-Her2 was demonstrated for both anti-hIgG assay and anti-MMAF assay (FIG. 3F), indicating that CL-22 payload in anti-Her2-CL-22 is not released from the ADC throughout the PK study. Therefore the length and the chemical composition of the linker may be an important factor for the stability of the ADCs.

We have also performed PK studies with anti-Her2-CL-32, an ADC with payload CL-32 conjugated to the lysine residues of the anti-Her2 antibody (Example 105). The profiles of both anti-IgG and anti-MMAF assays (FIG. 3F) overlapped with each other, indicating that the payload CL-32 is stably conjugated to the antibody and demonstrating excellent PK properties for the ADC in mouse circulation Taken together, the findings in our PK studies clearly demonstrate that among the payloads described in the invention there are significant differences in terms of the stability of the ADCs in mouse circulation. The linkers in payloads CL-1 and CL-22 were found to be cleaved in circulation in mice. Payload CL-6 caused ADC to be cleared more rapidly than the unconjugated antibody from circulation. However, ADCs prepared with payloads CL-9, CL 10, CL-11, CL-12, CL-32, NL-4, and NL-38 using different conjugation methods, are stable in circulation in mice and exhibit excellent PK properties. ADCs prepared with payloads CL-9, CL10, CL-11, CL-12, NL-4, and NL-38 are stable in mice

EXAMPLE 109

In Vivo Efficacy Studies

In vivo xenograft tumor models simulate biological activity observed in humans by grafting relevant and well characterized human primary tumors or tumor cell lines into immune-deficient nude mice. Studies on treatment of tumor xenograft mice with anti-cancer reagents have provided valuable information regarding in vivo efficacy of the tested reagents (Sausville and Burger, Cancer Res. 2006, 66:3351-3354). NCI-N87 cells overexpress Her2 antigen on the cell surface and have been utilized as a model for both in vitro and in vivo efficacy studies for anti-Her2 antibodies (Kasprzyk, P., Song, S. V., DiFiore, P. P. & King, C. R., Cancer Res. 1992, 52: 2771-2776). The NCI-N87 cell line was used as model for testing ADCs made with the anti-Her2 antibody in vivo. H526 cells express the antigen of antibody 20507 on their surface and are selectively killed by antibody 20507 ADCs (FIG. 2, Table 16). The cell line was used as a second xenograft model to evaluate the in vivo activity of ADCs made with antibody 20507. All animal studies were conducted in accordance with the Guide for the Care and Use of Laboratory Animals (NIH publication; National Academy Press, $8^{th}$ edition, 2001). NCI-N87 or H526 cells were implanted in nu/nu mice subcutaneously (Morton and Houghton, Nat. Protoc. 2007; 2:247-250). After the tumor size reached ~200 mm$^3$, ADCs were administered into the mice by IV injection in a single dose at dosage as indicated in each study. The tumor growth was then measured periodically after ADC administration. Examples of in vivo efficacy studies with anti-Her2 ADCs in the NCI-N87 xenograft model are shown in FIGS. 4A and 4B and examples of in vivo efficacy studies with antibody 20507 ADCs in the H526 xenograft model are shown in FIGS. 4C, 4D and 4E.

Figure 4A:
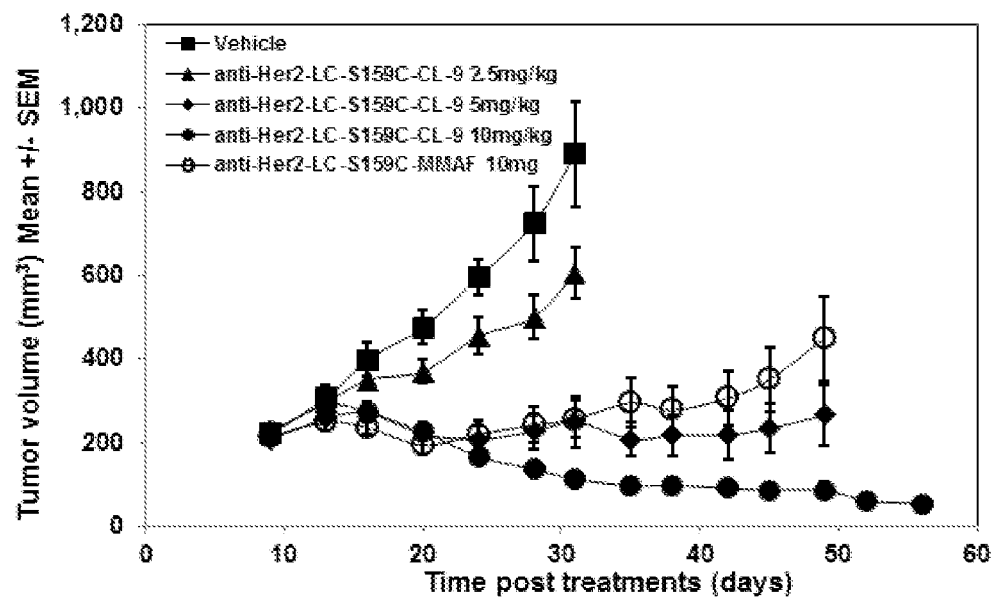
FIG. 4A-4E: In vivo efficacy studies of anti-Her2 ADCs in NCI-N87 xenograft model (A and B) and of antibody 20507 ADCs in H526 xenograft model (C, D and E). A single dose was administered at day 0.
Figure 4B:
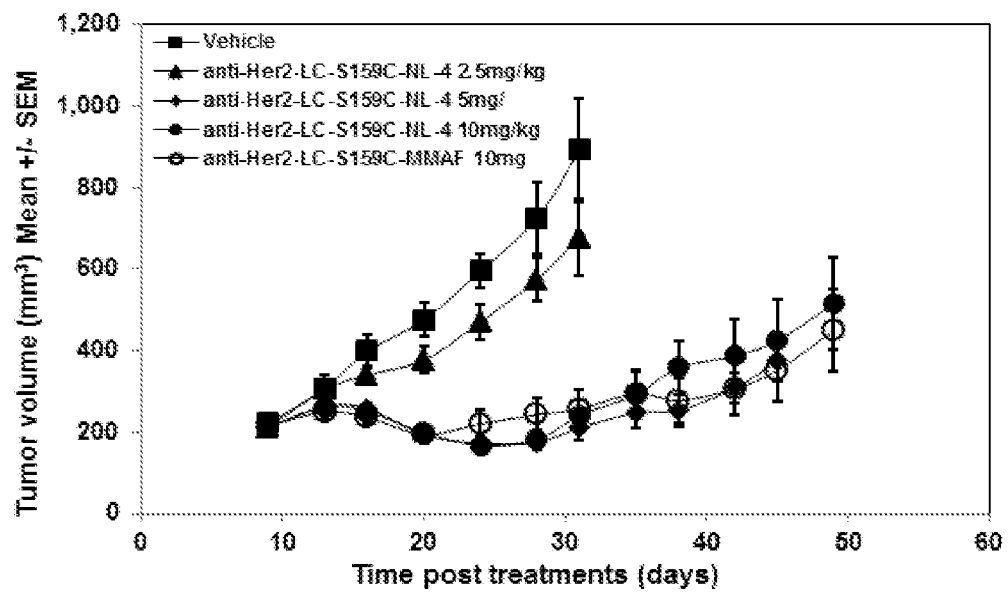
Figure 4C:
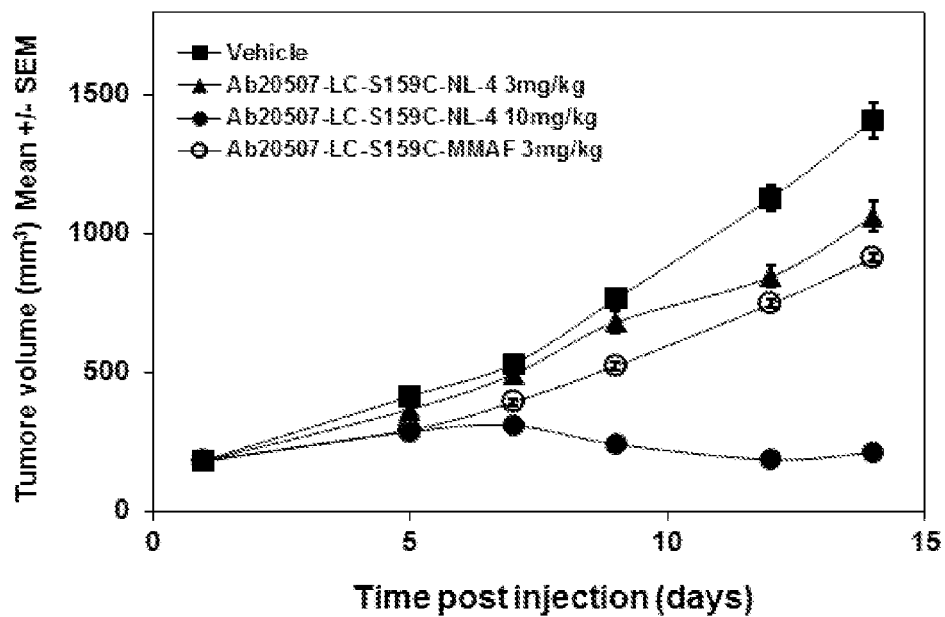
Figure 4D:
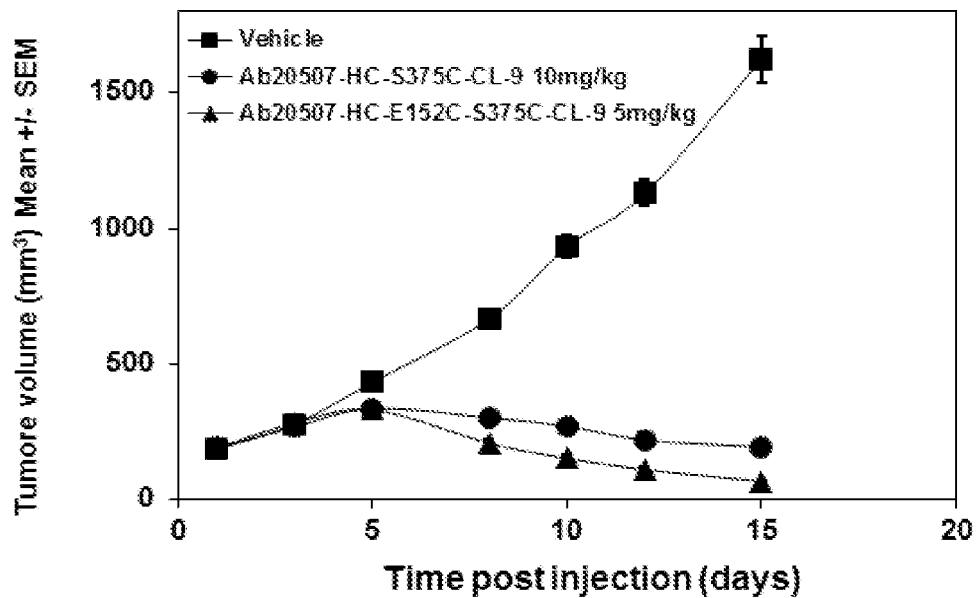
Figure 4E:
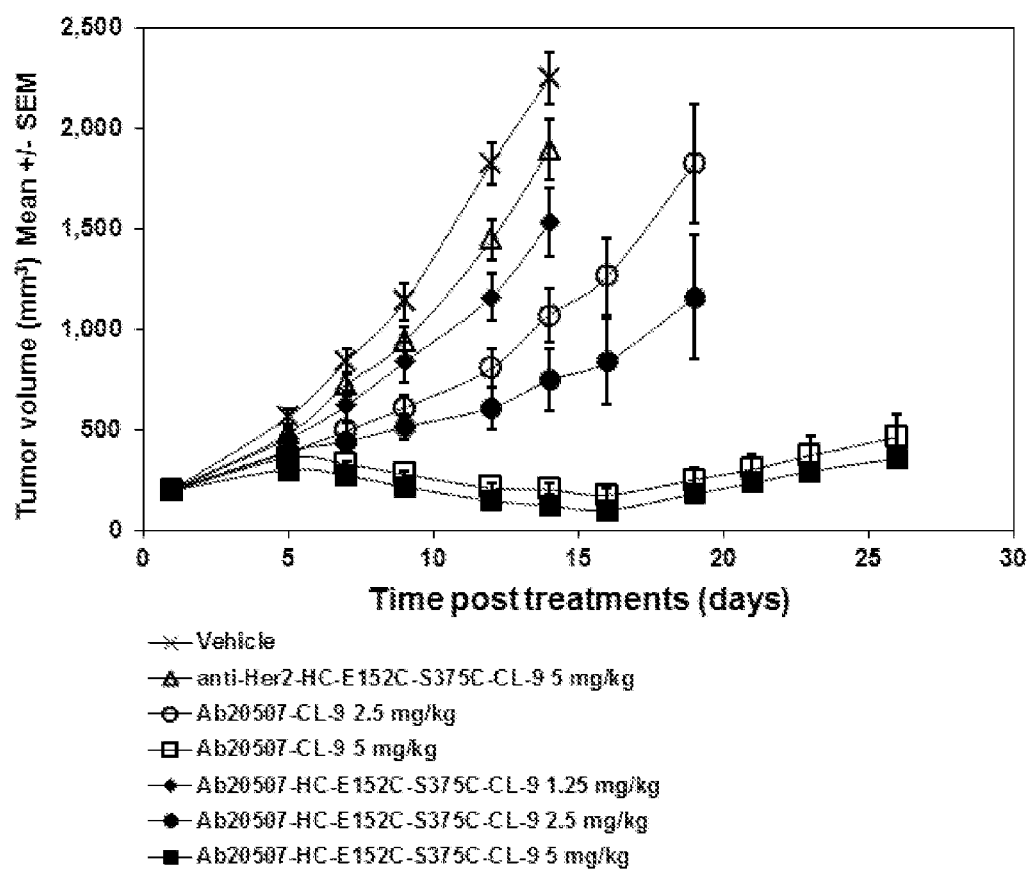

The NCI-N87 xenograft study showed that treatment of mice with anti-Her2-LC-S159C-CL-9 and anti-Her2-LC-S159C-NL-4 caused dose-dependent tumor inhibition and regression in NCI-N87 tumors (FIGS. 4A and 4B). Inhibition of NCI-N87 tumor was observed with the administration of 2.5 mg/kg anti-Her2-LC-S159C-CL-9 while treatment with the same ADC at 5 mg/kg induced stasis of the tumors (FIG. 4A). Persistent tumor regression was seen at 10 mg/kg anti-Her2-LC-S159C-CL-9 for 50 days. As comparison, when mice were treated with 10 mg/kg anti-Her2-LC-S159C-MMAF, which contains the literature reference compound MMAF, the NCI-N87 tumors initially regressed but grew back after 30 days (FIG. 4A). Thus, the tumor regression caused by anti-Her2-LC-S159C-CL-9 is sustained significantly longer than when anti-Her2-LC-S159C-MMAF ADC is administered at the same dosage. Treatment of mice with an ADC containing another payload, NL-4, also caused a dose-dependent inhibition of NCI-N87 tumors (anti-Her2-LC-S159C-NL-4, FIG. 4B). A weak inhibition of NCI-N87 tumor growth was observed after a single dose of 2.5 mg/kg while tumor stasis was observed for doses of 5 mg/kg and 10 mg/kg anti-Her2-LC-S159C-NL-4. The degree of tumor inhibition caused by anti-Her2-LC-S159C-NL-4 is similar to that caused by anti-Her2-LC-S159C-MMAF (FIG. 4B).

To investigate if the ADCs containing the above two payloads are efficacious in another tumor model in vivo, ADCs were prepared with payloads CL-9 and NL-4 conjugated to antibody 20507, whose antigen is highly expressed on H526 cells (Example 107). ADCs with two different antibody-to-drug ratios, namely DAR 2 and DAR 4, were prepared and tested in the H526 tumor model. As shown in FIG. 4C, similar to the results of the above study with anti-Her2 ADCs in NCI-N87 model, antibody 20507-LC-S159C-NL-4 ADC (DAR 2) inhibited H526 tumor growth in a dose dependent manner. Antibody 20507-LC-S159C-NL-4 inhibited H526 tumor growth after a single dose of 3 mg/kg, and caused tumor regression at 10 mg/kg. The inhibition of H526 tumors caused by 3 mg/kg antibody 20507-LC-S159C-NL-4 ADC is similar to that caused by a reference ADC, antibody 20507-LC-S159C-MMAF at the same dosage.

A DAR 4 ADC has twice as much cytotoxic drug attached to an antibody as a DAR 2 ADC and should hence deliver twice the drug dose per antibody. To illustrate this feature, the efficacy of DAR 2 and DAR 4 ADCs were compared in vivo in the H526 xenograft model (FIG. 4D). In the study, treatment of mice with a DAR 4 ADC, antibody 20507-HC-E152C-S375C-CL-9 at 5 mg/kg caused comparable tumor regression than the DAR 2 ADC, antibody 20507-HC-S375C-CL-9 at 10 mg/kg. The results indicate that the payload, CL-9, prepared either as DAR 2 or DAR 4 ADCs, is efficacious in vivo. Tumor inhibition and regression caused by CL-9 ADCs are dependent on the amounts of CL-9 that are delivered by the ADCs in experimental animals.

In Example 107, we have shown that ADCs prepared with the payloads of the invention by various conjugation methods were potent in vitro cell based assays. In another example, ADCs with payload CL-9 in antibody 20507 prepared by two different conjugation methods were evaluated in H526 tumor model for their in vivo efficacy in inhibition of tumor growth (FIG. 4E): Antibody 20507-HC-E152C-S375C-CL-9 was prepared by conjugating CL-9 to four engineered Cys residues in antibody 20507 as described in Example 99 and antibody 20507-CL-9 ADC was prepared by conjugating CL-9 to native Cys residues by the partial reduction method as described in Example 103. Because H526 tumor cells do not express Her2 antigen in the surface, anti-Her2-HC-E152C-S375C-CL-9 was prepared in the same manner as antibody 20507-HC-E152C-S375C-CL-9 and used as the negative control ADC in the study. The three ADCs contain the same CL-9 drug to antibody ratio (DAR 3.9). When administered in H526 tumor bearing mice, as expected, anti-Her2-HC-E152C-S375C-CL-9 did not affect tumor growth when dosed at 5 mg/kg, while antibody 20507-HC-E152C-S375C-CL-9 and antibody 20507-CL-9 ADCs caused tumor regression in a dose-dependent manner (FIG. 4E). At 2.5 mg/kg dosage, both antibody 20507 ADCs displayed an inhibition on H526 tumor growth. A complete tumor regression was observed at 5 mg/kg for both antibody 20507 ADCs.

From the results of the in vivo xenograft models in NCI-N87 and H526 tumors with ADCs prepared with two different antibodies, it is clear that ADCs prepared with CL-9 showed a higher efficacy in tumor inhibition and regression as compared to the reference MMAF ADCs. CL-9 ADCs are able to cause a more sustainable tumor regression than MMAF ADCs. ADCs prepared with payload NL-4 displayed in vivo efficacy similar to that of the reference MMAF ADCs. We have also shown that ADCs prepared with payload CL-9 using two different mothods are able to cause tumor regression in vivo, confirming the observations from in vitro studies (Example 107). The results in Example 107 and Example 109 suggest that ADCs prepared with compound payloads disclosed in this invention are potent both in vitro and in vivo for different antibodies and multiple tumor cell lines. It is anticipated that the compounds of the invention will be broadly applicable for many different tumor settings and indications. The compounds can be used to prepare potent ADCs using many established conjugation methods including site-specific engineered Cys method (Example 99), partial reduction method (Example 103), enzyme-mediated conjugation method (Examples 101-103), cysteine ketone bridge method (Example 104) and NHS-lysine conjugation method (Example 105). It is anticipated that the compounds of the invention can be combined with many different antibodies or antigen targeting moieties.

Certain aspects and examples of the invention are provided in the following listing of enumerated embodiments. It will be recognized that features specified in each embodiment may be combined with other specified features to provide further embodiments of the present invention.

1. A compound or stereoisomer and tautomers thereof having the structure of Formula (I)

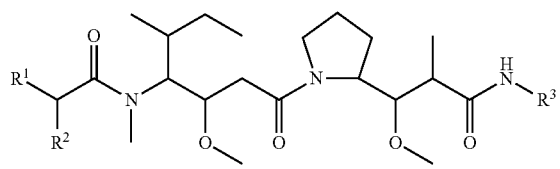

Formula (I)

wherein:
$R^1$ is —N=$CR^4R^5$, —N=$R^{19}$, —N=$CR^5$ $R^{20}$, —N=$CR^5NR^{12}(CH_2)_mN(R^{12})C(O)OR^{12}$, —N=$CR^5NR^{12}(CH_2)_mN(R^{12})_2$, —NHC(=$NR^6$)$R^4$, —NHC(=O)$R^4$, —NHC(=O)$R^{20}$ or —NH$R^8$;
$R^2$ is —$C_1$-$C_6$alkyl;
$R^3$ is

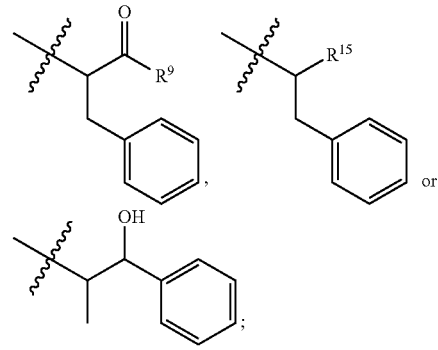

$R^4$ is —N($R^6$)$_2$ or —N$R^6R^7$;
$R^5$ is N($R^6$)$_2$;
each $R^6$ is independently selected from H and —$C_1$-$C_6$alkyl;
$R^7$ is —$(CH_2)_mN(R^{12})_2$, —$(CH_2)_mN(R^{12})C(=O)OR^{12}$ or an unsubstituted $C_3$-$C_8$cycloalkyl;
or $R^7$ is a $C_3$-$C_8$cycloalkyl substituted with 1-3 substituents independently selected from $C_1$-$C_6$alkyl, oxo, —C(=O)$R^{18}$, —$(CH_2)_mOH$, —C(=O)$(CH_2)_mOH$, —C(=O)$((CH_2)_mO)_nR^{12}$, —$((CH_2)_mO)_nR^{12}$ or a $C_1$-$C_6$alkyl which is optionally substituted with 1 to 5 hydroxyl;
$R^8$ is an unsubstituted C-linked 5-6 membered heteroaryl having 1-2 N heteroatoms;

or R⁸ is a C-linked 5-6 membered heteroaryl having 1-2 N heteroatoms which is substituted with 1-3 substituents independently selected from $C_1$-$C_6$alkyl, $C_1$-$C_6$haloalkyl, halogen, $C_1$-$C_6$alkoxy, —OH, —CN, —NO₂, —C(=O)OR⁶, —C(=O)N(R⁶)₂, —C(=O)NR⁶(CH₂)$_m$N(R⁶)C(O)OR⁶ and —C(=O)NR⁶(CH₂)$_m$N(R⁶)₂;

R⁹ is —OH, $C_1$-$C_6$alkoxy, —NHS(O)₂(CH₂)$_m$N₃, —NHS(O)₂(CH₂)$_m$NH₂, —N(R¹²)₂, —R¹⁶, —NR¹²(CH₂)$_m$N(R¹²)₂, —NR¹²(CH₂)$_m$R¹⁶, —NHS(O)₂R¹⁸ or

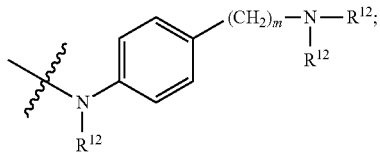

each R¹² is independently selected from H and $C_1$-$C_6$alkyl;

R¹³ is —S(CH₂)$_n$CHR¹⁴NHC(=O)R¹² or

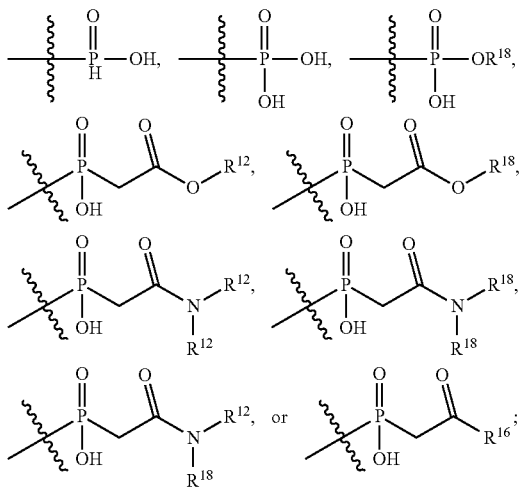

R¹⁴ is R¹² or —C(=O)OR¹²;

R¹⁵ is tetrazolyl, —CN, —C(=O)OR¹²,

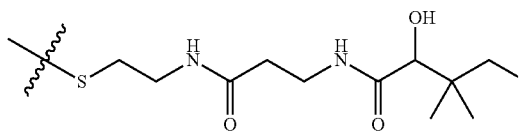

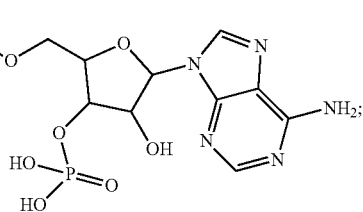

R¹⁶ is an N-linked 4-8 membered heterocycloalkyl containing 1-2 heteroatoms independently selected from N, O, S, S(=O) and S(=O)₂;

R¹⁷ is 2-pyridyl or 4-pyridyl;

each R¹⁸ is independently selected from a $C_1$-$C_6$alkyl, a $C_1$-$C_6$alkyl which is substituted with azido and a $C_1$-$C_6$alkyl which is substituted with 1 to 5 hydroxyl;

R¹⁹ is an unsubstituted C-linked 5-6 membered heterocycloalkyl having 1-2 heteroatoms independently selected from N and O;

or R¹⁹ is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;

R²⁰ is an unsubstituted N-linked 5-6 membered heterocycloalkyl having 1-2 heteroatoms independently selected from N, O and S;

or R²⁰ is an N-linked 5-6 membered heterocycloalkyl having 1-2 heteroatoms independently selected from N, O and S, which is substituted with 1-2 substituents independently selected from $C_1$-$C_6$alkyl, —C(=O)OR¹², —C(=O)(CH₂)$_m$N₃, $C_1$-$C_6$haloalkyl, halogen, oxo, —OH and $C_1$-$C_6$alkoxy;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18.

2. The compound according to embodiment 1, wherein:
R¹ is —N=CR⁴R⁵, —N=R¹⁹, —N=CR⁵NR¹²(CH₂)$_m$N(R¹²)C(O)OR¹², —N=CR⁵NR¹²(CH₂)$_m$N(R¹²)₂ or —N=CR⁵R²⁰.

3. The compound according to embodiment 1, wherein:
R¹ is —NHC(=NR⁶)R⁴, —NHC(=O)R⁴ or —NHC(=O)R²⁰.

4. The compound according to embodiment 1, wherein:
R¹ is —N=CR⁴R⁵;
R⁴ is is —N(R⁶)₂;
R⁵ is N(R⁶)₂;
and
each R⁶ is independently selected from —$C_1$-$C_6$alkyl.

5. The compound according to embodiment 1, wherein R¹ is

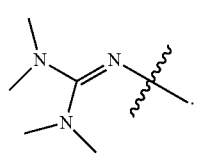

6. The compound according to embodiment 1, wherein R¹ is —NHR⁸.

7. The compound according to any one of embodiments 1 to 6, wherein $R^3$ is

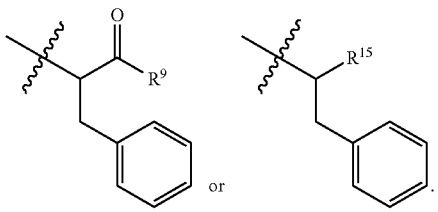

8. The compound according to any one of embodiments 1 to 3, wherein $R^7$ is —$(CH_2)_mN(R^{12})_2$, —$(CH_2)_mN(R^{12})C(=O)OR^{12}$.
9. The compound according to any one of embodiments 1 to 3, wherein $R^7$ is a $C_3$-$C_8$cycloalkyl substituted with —$(CH_2)_mOH$.
10. The compound according to any one of embodiments 1, 3 or 6, wherein $R^8$ is an unsubstituted C-linked pyridinyl, an unsubstituted C-linked pyrimidinyl or an unsubstituted C-linked pyrazinyl.
11. The compound according to any one of embodiments 1, 3 or 6, wherein $R^8$ is a C-linked pyridinyl, a C-linked pyrimidinyl or a C-linked pyrazinyl, each of which is substituted with 1-3 substituents independently selected from $C_1$-$C_6$alkyl, $C_1$-$C_6$haloalkyl, halogen, $C_1$-$C_6$alkoxy, —$C(=O)NR^6(CH_2)_mN(R^6)C(O)OR^6$ and —$C(=O)NR^6(CH_2)_mN(R^6)_2$.
12. The compound according to any one of embodiments 1, 2 or 7, wherein $R^{19}$ is a C-linked imidazolidinyl or a C-linked piperazinyl, each of which is substituted with 1-3 substituents independently selected from $C_1$-$C_6$alkyl.
13. The compound according to any one of embodiments 1, 2, 3 or 7, wherein $R^{20}$ is an unsubstituted piperazinyl.
14. The compound according to any one of embodiments 1, 2, 3 or 7, wherein $R^{20}$ is an N-linked piperazinyl substituted with 1-2 substituents independently selected from —$C(=O)OR^{12}$ and —$C(=O)(CH_2)_mN_3$.
15. The compound according to any one of embodiments 1 to 14, wherein $R^9$ is —OH, $C_1$-$C_6$alkoxy, —$NHS(O)_2(CH_2)_mN_3$ or —$NHS(O)_2(CH_2)_mNH_2$.
16. The compound according to any one of embodiments 1 to 14, wherein $R^{15}$ is tetrazolyl or

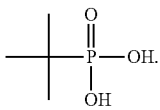

17. A compound or stereoisomer thereof having the structure of Formula (I)

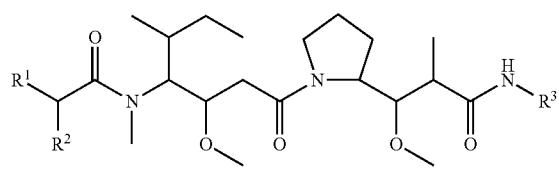

Formula (I)

wherein:
$R^1$ is —$N=CR^4R^5$, —$N=R^{19}$, —$N=CR^5$ $R^{20}$, —$N=CR^5NR^{12}(CH_2)_mN(R^{12})C(O)OR^{12}$, —$N=CR^5NR^{12}(CH_2)_mN(R^{12})_2$, —$NHC(=NR^8)R^4$, —$NHC(=O)R^4$, —$NHC(=O)R^{20}$, —$NHR^8$, —$NHLR^{11}$, —$NHR^{21}$, —$N=CR^5R^{10}$, —$N=R^{22}$, —$N=CR^5R^{23}$ or —$NHC(=O)R^{23}$;
$R^2$ is —$C_1$-$C_6$alkyl;
$R^3$ is

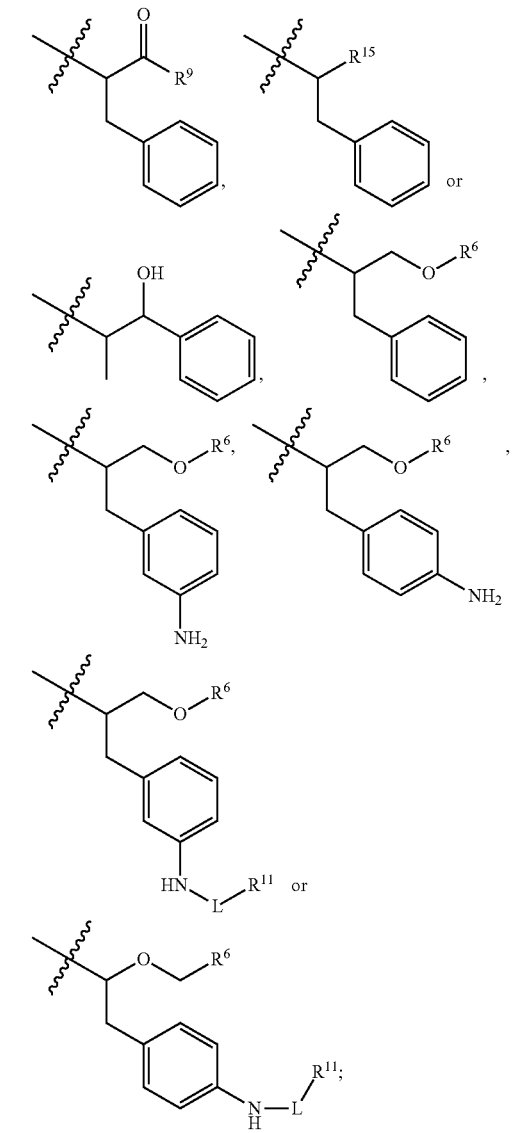

$R^4$ is —$N(R^6)_2$ or —$NR^6R^7$;
$R^5$ is $N(R^6)_2$;
each $R^6$ is independently selected from H and —$C_1$-$C_6$alkyl;
$R^7$ is —$(CH_2)_mN(R^{12})_2$, —$(CH_2)_mN(R^{12})C(=O)OR^{12}$ or an unsubstituted $C_3$-$C_8$cycloalkyl;
or $R^7$ is a $C_3$-$C_8$cycloalkyl substituted with 1-3 substituents independently selected from $C_1$-$C_6$alkyl, oxo, —$C(=O)R^{18}$, —$(CH_2)_mOH$, —$C(=O)(CH_2)_mOH$, —$C(=O)((CH_2)_mO)_nR^{12}$, —$((CH_2)_mO)_nR^{12}$ or a $C_1$-$C_6$alkyl which is optionally substituted with 1 to 5 hydroxyl;
$R^8$ is an unsubstituted C-linked 5-6 membered heteroaryl having 1-2 N heteroatoms;
or $R^8$ is a C-linked 5-6 membered heteroaryl having 1-2 N heteroatoms which is substituted with 1-3 substituents independently selected from $C_1$-$C_6$alkyl, $C_1$-$C_6$haloalkyl, halogen, $C_1$-$C_6$alkoxy, —OH, —CN, —$NO_2$, —$C(=O)$ $OR^6$, $-C(=O)N(R^6)_2$, $-C(=O)NR^6(CH_2)_mN(R^6)C(O)OR^6$ and $-C(=O)NR^6(CH_2)_mN(R^6)_2$;
$R^9$ is $-OH$, $C_1$-$C_6$alkoxy, $-NHS(O)_2(CH_2)_mN_3$, $-NHS(=O)_2LR^{11}$, $-NHLR^{11}$, $-NHS(O)_2(CH_2)_2NH_2$, $-N(R^{12})_2$, $-R^{16}$, $-NR^{12}(CH_2)_mN(R^{12})_2$, $-NR^{12}(CH_2)_mR^{16}$, $-LR^{11}$, $-NHS(O)_2R^{18}$,
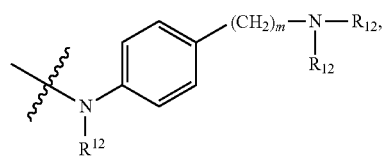
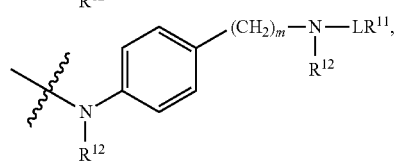
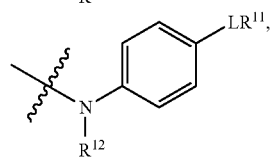
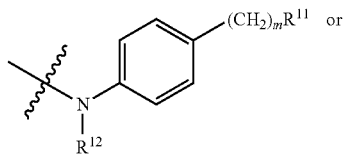
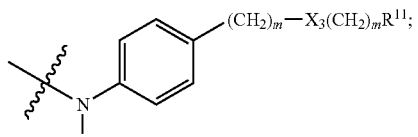
$R^{10}$ is $LR^{11}$ or
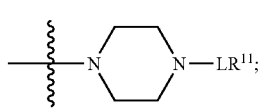
$R^{11}$ is
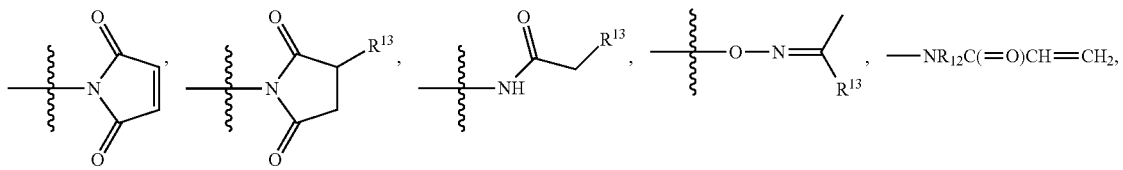
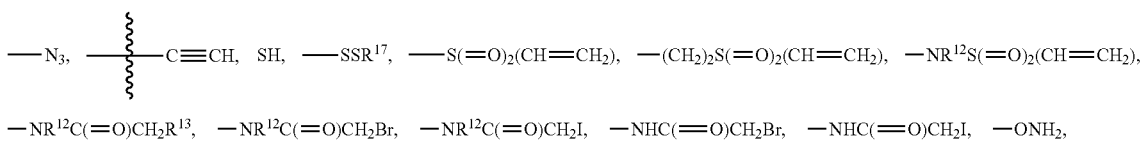
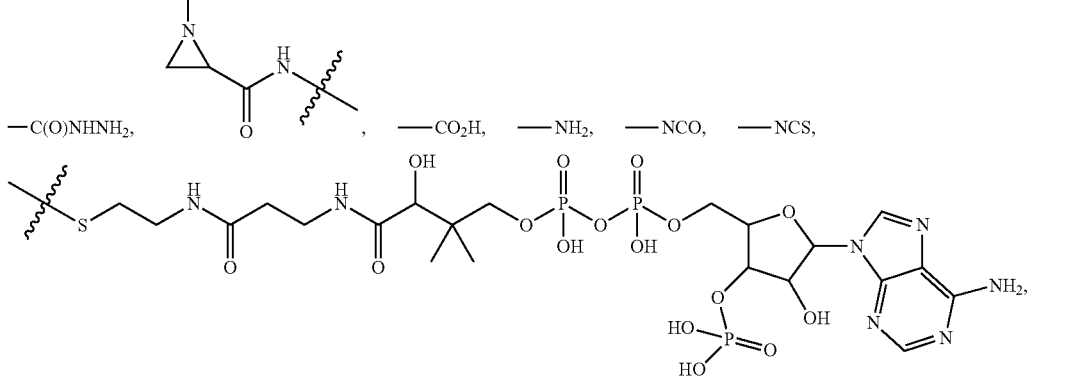
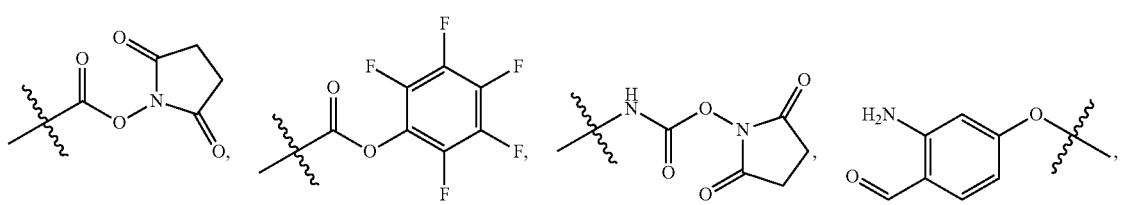

367
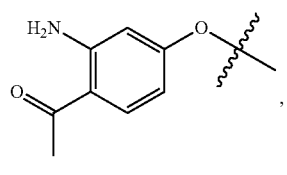
-continued
368
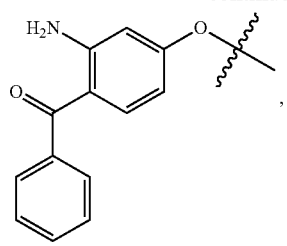
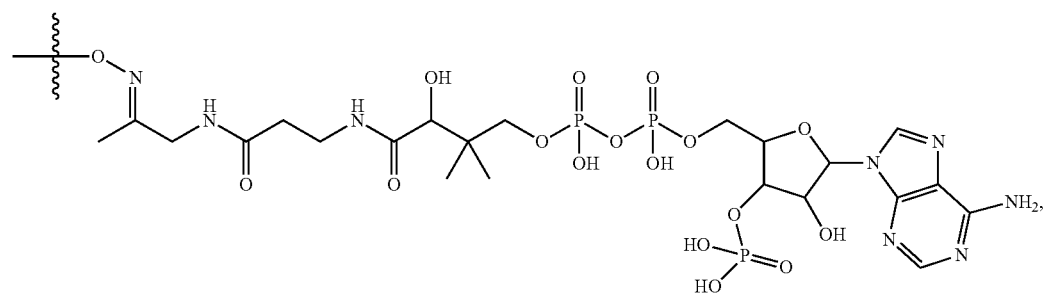
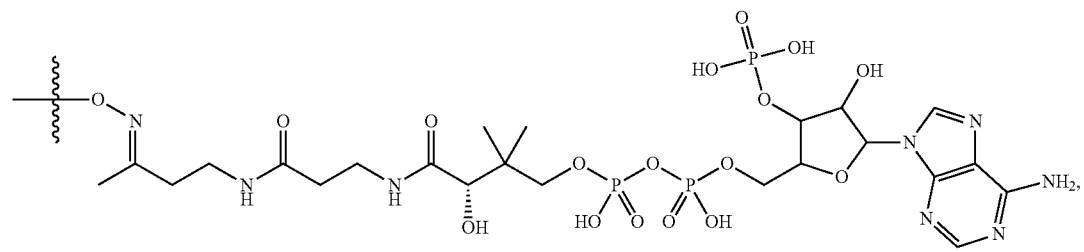
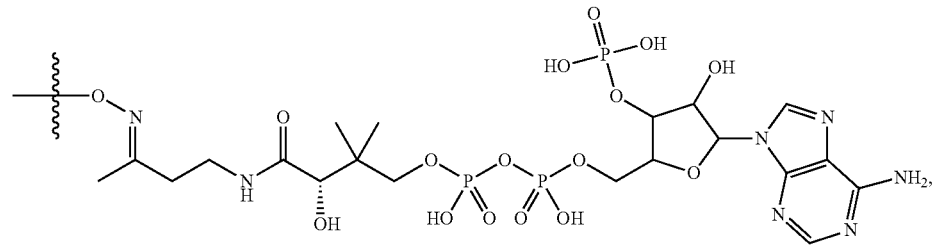
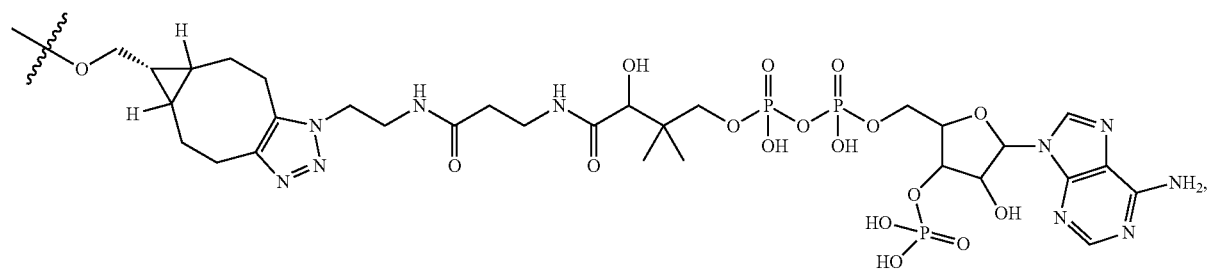
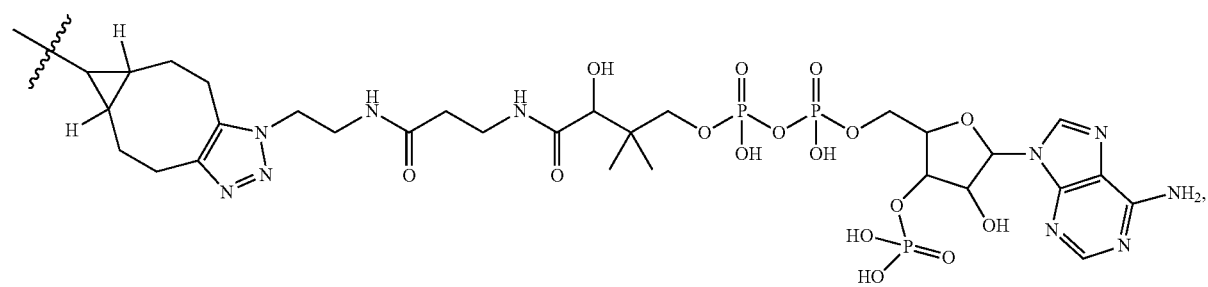

-continued
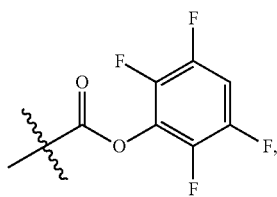 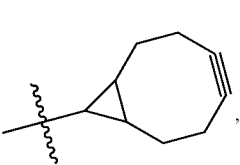 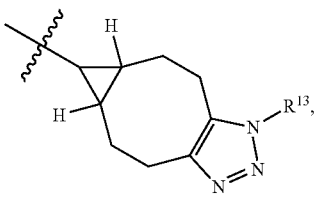
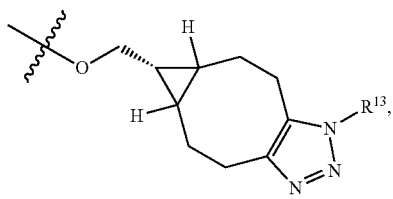
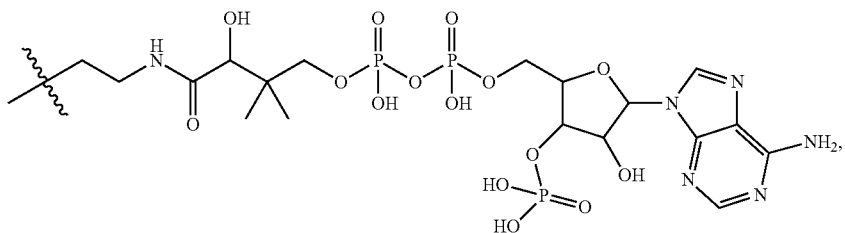
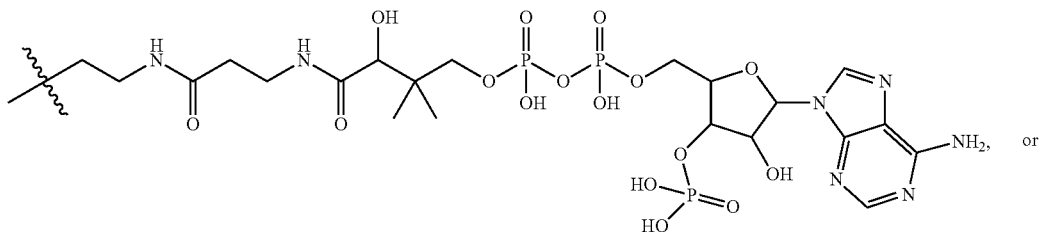 or
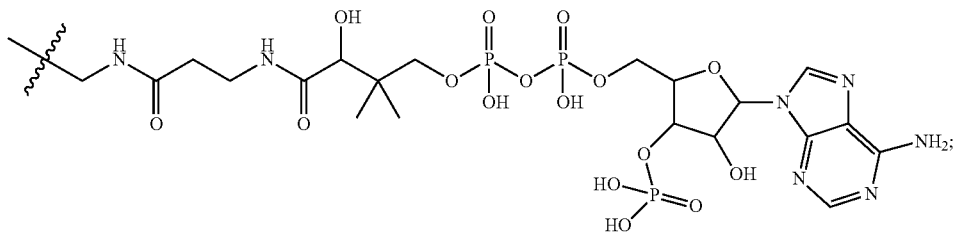
each $R^{12}$ is independently selected from H and $C_1$-$C_6$alkyl;
$R^{13}$ is —S(CH$_2$)$_n$CHR$^{14}$NHC(=O)R$^{12}$,
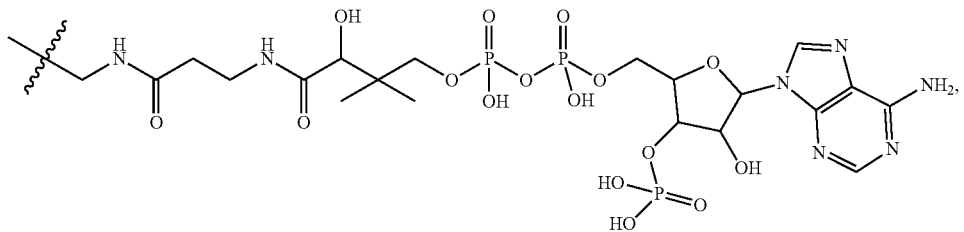

-continued

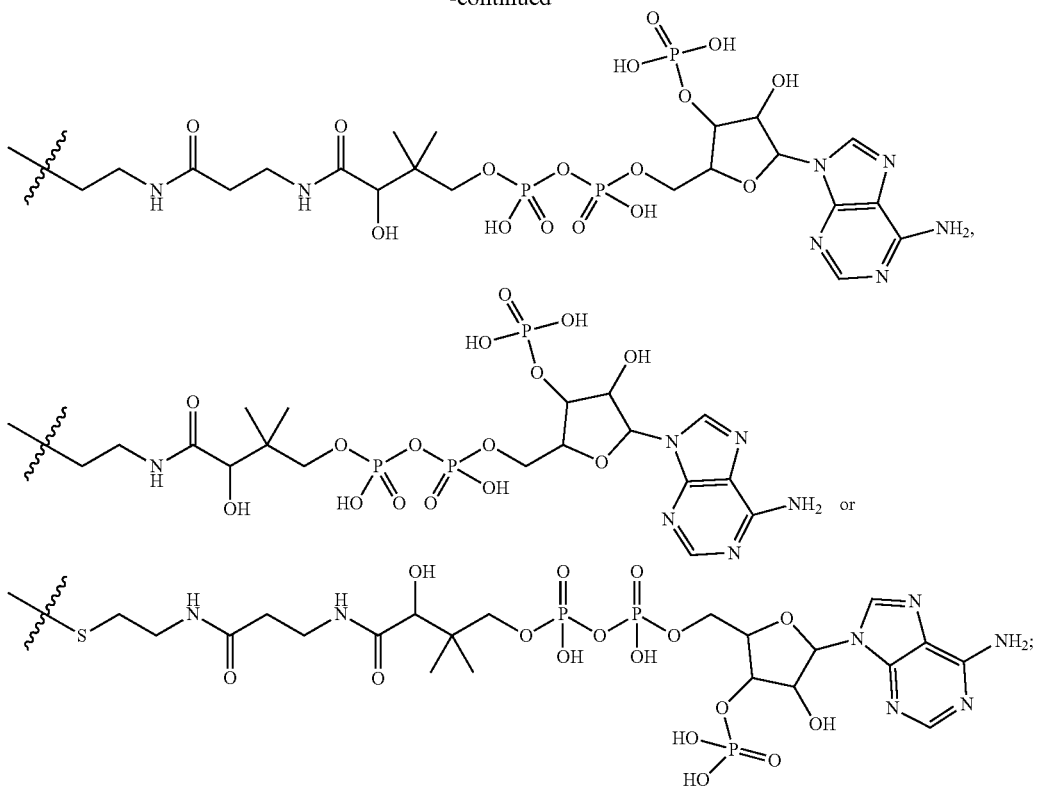

$R^{14}$ is $R^{12}$ or —C(=O)OR$^{12}$;
$R^{15}$ is tetrazolyl, —CN, —C(=O)OR$^{12}$,

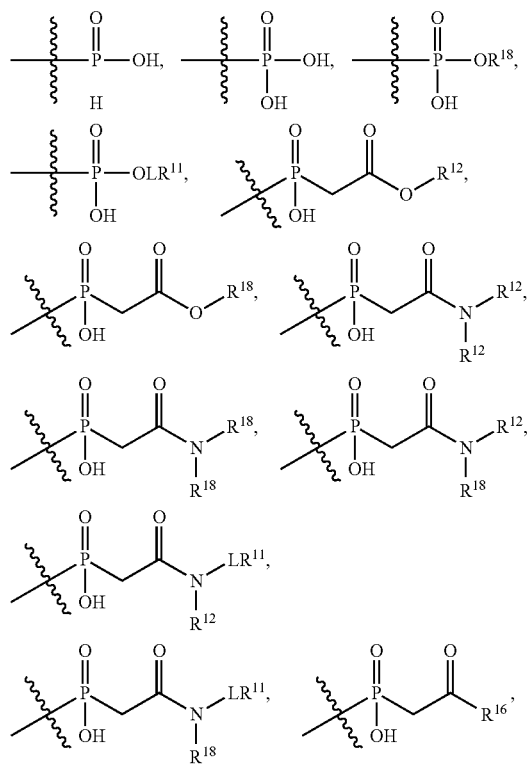

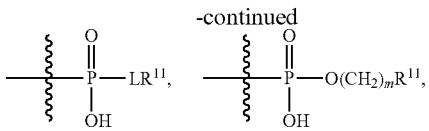

-LR$^{11}$ or —X$_4$LR$^{11}$;
each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;
$R^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;
$R^{17}$ is 2-pyridyl or 4-pyridyl;
each $R^{18}$ is independently selected from a C$_1$-C$_6$alkyl, a C$_1$-C$_6$alkyl which is substituted with azido and a C$_1$-C$_6$alkyl which is substituted with 1 to 5 hydroxyl;
$R^{19}$ is an unsubstituted C-linked 5-6 membered heterocycloalkyl having 1-2 heteroatoms independently selected from N and O;
or $R^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;
$R^{20}$ is an unsubstituted N-linked 5-6 membered heterocycloalkyl having 1-2 heteroatoms independently selected from N, O and S;
or $R^{20}$ is an N-linked 5-6 membered heterocycloalkyl having 1-2 heteroatoms independently selected from N, O and S, which is substituted with 1-3 substituents independently selected from C$_1$-C$_6$alkyl, —C(=O)OR$^{12}$, —C(=O)(CH$_2$)$_m$N$_3$, C$_1$-C$_6$haloalkyl, halogen, oxo, —OH and C$_1$-C$_6$alkoxy;

R$^{21}$ is a C-linked 5-6 membered heteroaryl having 1-2 N heteroatoms which is substituted with LR$^{11}$ and 0-2 substituents independently selected from C$_1$-C$_6$alkyl, C$_1$-C$_6$haloalkyl, halogen, —CN, NO$_2$, —C(=O)OR$^6$, —C(=O)N(R$^6$)$_2$ and C$_1$-C$_6$alkoxy;

R$^{22}$ is a C-linked 5-6 membered heterocycloalkyl having 1-2 heteroatoms independently selected from N, O and S which is substituted with LR$^{11}$ and 0-2 substituents independently selected from C$_1$-C$_6$alkyl, C$_1$-C$_6$haloalkyl, halogen and C$_1$-C$_6$alkoxy;

R$^{23}$ is an N-linked 5-6 membered heterocycloalkyl having 1-2 heteroatoms independently selected from N and O which is substituted with LR$^{11}$ and 0-2 substituents independently selected from C$_1$-C$_6$alkyl, C$_1$-C$_6$haloalkyl, halogen and C$_1$-C$_6$alkoxy;

X$_3$ is

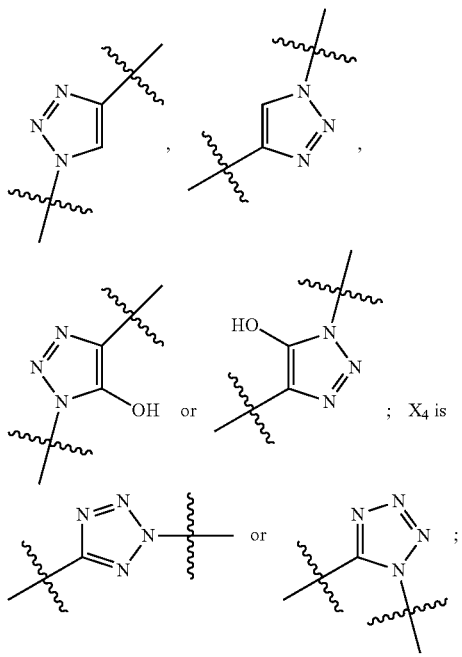

; X$_4$ is each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18, or a tautomer, a hydrate, or a pharmaceutically acceptable salt thereof.

18. A compound or stereoisomer thereof having the structure of Formula (I)

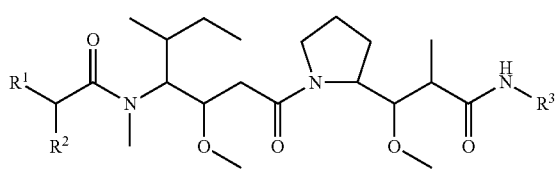

Formula (I)

wherein,

R$^1$ is —N=CR$^4$R$^5$, —N=R$^{19}$, —N=CR$^5$R$^{20}$, —N=CR$^5$NR$^{12}$(CH$_2$)$_m$N(R$^{12}$)C(O)OR$^{12}$, —N=CR$^5$NR$^{12}$(CH$_2$)$_m$N(R$^{12}$)$_2$, —NHC(=NR$^6$)R$^4$, —NHC(=O)R$^4$, —NHC(=O)R$^{20}$, —NHR$^8$, —NHLR$^{11}$, —NHR$^{21}$, —N=CR$^5$R$^{10}$, —N=R$^{22}$, —N=CR$^5$R$^{23}$ or —NHC(=O)R$^{23}$;

R$^2$ is —C$_1$-C$_6$alkyl;

R$^3$ is

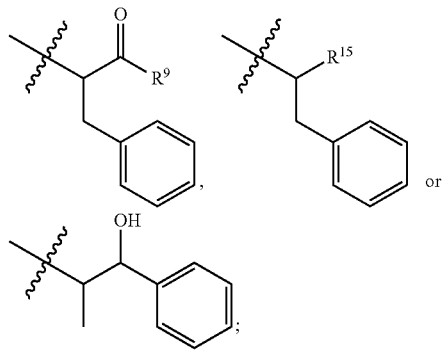

R$^4$ is —N(R$^6$)$_2$ or —NR$^6$R$^7$;

R$^5$ is N(R$^6$)$_2$;

each R$^6$ is independently selected from H and —C$_1$-C$_6$alkyl;

R$^7$ is —(CH$_2$)$_m$N(R$^{12}$)$_2$, —(CH$_2$)$_m$N(R$^{12}$)C(=O)OR$^{12}$ or an unsubstituted C$_3$-C$_8$cycloalkyl;

or R$^7$ is a C$_3$-C$_8$cycloalkyl substituted with 1-3 substituents independently selected from C$_1$-C$_6$alkyl, oxo, —C(=O)R$^{18}$, —(CH$_2$)$_m$OH, —C(=O)(CH$_2$)$_m$OH, —C(=O)((CH$_2$)$_m$O)$_n$R$^{12}$, —((CH$_2$)$_m$O)$_n$R$^{12}$ or a C$_1$-C$_6$alkyl which is optionally substituted with 1 to 5 hydroxyl;

R$^8$ is an unsubstituted C-linked 5-6 membered heteroaryl having 1-2 N heteroatoms;

or R$^8$ is a C-linked 5-6 membered heteroaryl having 1-2 N heteroatoms which is substituted with 1-3 substituents independently selected from C$_1$-C$_6$alkyl, C$_1$-C$_6$haloalkyl, halogen, C$_1$-C$_6$alkoxy, —OH, —CN, —NO$_2$, —C(=O)OR$^6$, —C(=O)N(R$^6$)$_2$, —C(=O)NR$^6$(CH$_2$)$_m$N(R$^6$)C(O)OR$^6$ and —C(=O)NR$^6$(CH$_2$)$_m$N(R$^6$)$_2$;

R$^9$ is —OH, C$_1$-C$_6$alkoxy, —NHS(O)$_2$(CH$_2$)$_m$N$_3$, —NHS(O)$_2$(CH$_2$)$_m$NH$_2$, —N(R$^{12}$)$_2$, —R$^{16}$, —NR$^{12}$(CH$_2$)$_m$N(R$^{12}$)$_2$, —NR$^{12}$(CH$_2$)$_m$R$^{16}$, -LR$^{11}$, —NHS(O)$_2$R$^{19}$, —NHS(=O)$_2$LR$^{11}$,

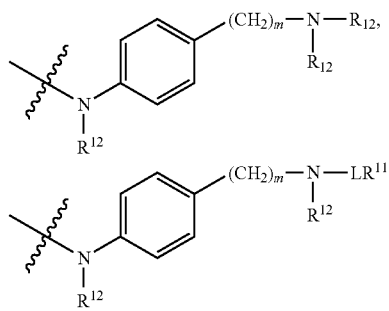

375
-continued
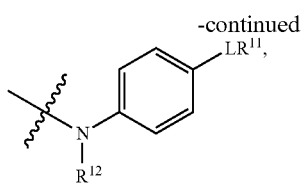
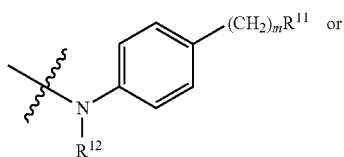
376
-continued
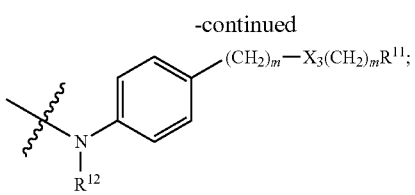
$R^{10}$ is $LR^{11}$ or
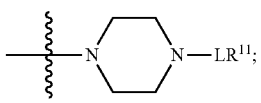
$R^{11}$ is
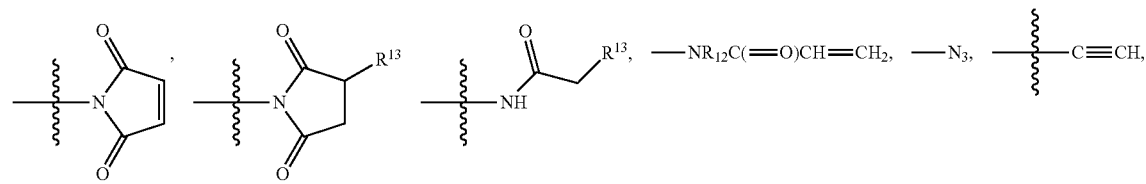
SH, —$SSR^{17}$, —$S(=O)_2(CH=CH_2)$, —$(CH_2)_2S(=O)_2(CH=CH_2)$, —$NR^{12}S(=O)_2(CH=CH_2)$,
—$NR^{12}C(=O)CH_2R^{13}$, —$NR^{12}C(=O)CH_2Br$, —$NR^{12}C(=O)CH_2I$, —$NHC(=O)CH_2Br$, —$NHC(=O)CH_2I$,
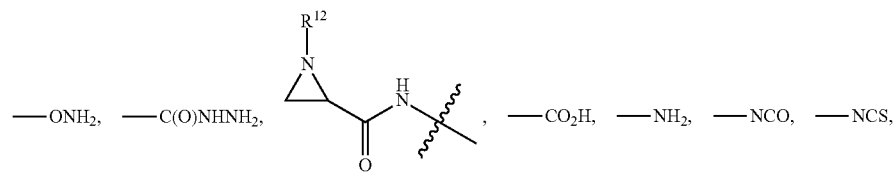
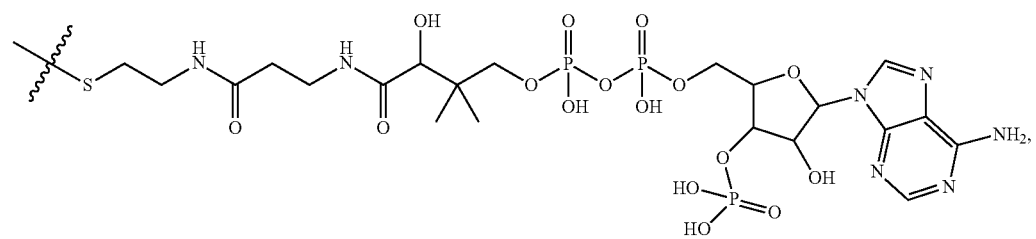
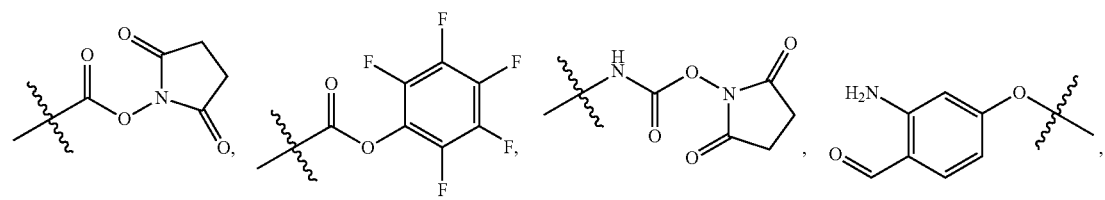
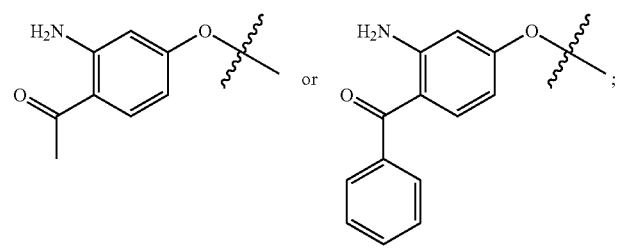

each $R^{12}$ is independently selected from H and $C_1$-$C_6$alkyl;

$R^{13}$ is $S(CH_2)_n CHR^{14}NHC(=O)R^{12}$ or

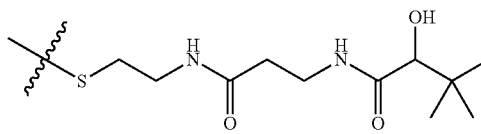

$R^{14}$ is $R^{12}$ or $-C(=O)OR^{12}$;

$R^{15}$ is tetrazolyl, $-CN$, $-C(=O)OR^{12}$,

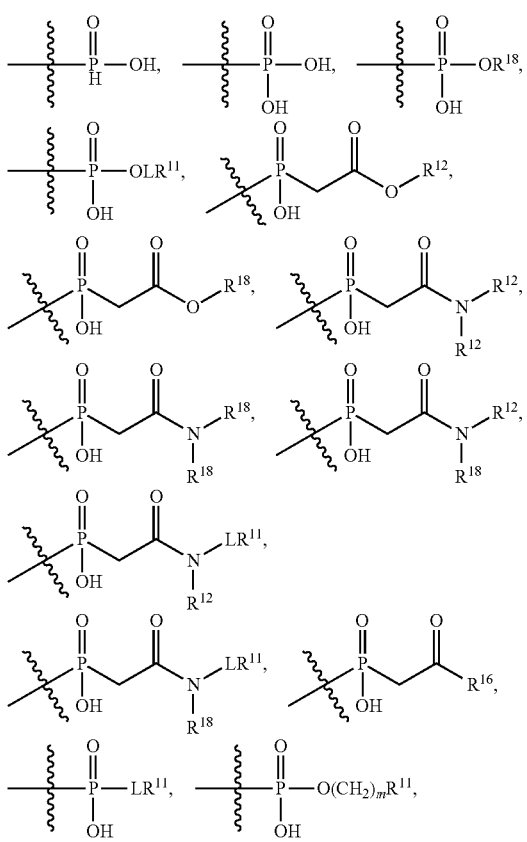

$-LR^{11}$ or $X_4LR^{11}$;

$R^{16}$ is an N-linked 4-8 membered heterocycloalkyl containing 1-2 heteroatoms independently selected from N, O, S, S(=O) and S(=O)$_2$, which is unsubstitituted or substituted with $-LR^{11}$;

$R^{17}$ is 2-pyridyl or 4-pyridyl;

each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

$R^{19}$ is an unsubstituted C-linked 5-6 membered heterocycloalkyl having 1-2 heteroatoms independently selected from N and O;

or $R^{19}$ is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;

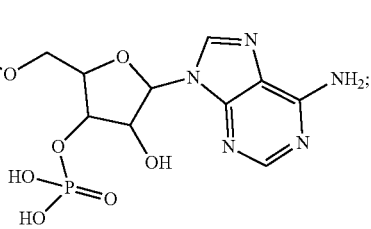

$R^{20}$ is an unsubstituted N-linked 5-6 membered heterocycloalkyl having 1-2 heteroatoms independently selected from N, O and S;

or $R^{20}$ is an N-linked 5-6 membered heterocycloalkyl having 1-2 heteroatoms independently selected from N, O and S, which is substituted with 1-2 substituents independently selected from $C_1$-$C_6$alkyl, $-C(=O)OR^{12}$, $-C(=O)(CH_2)_m N_3$, $C_1$-$C_6$haloalkyl, halogen, oxo, $-OH$ and $C_1$-$C_6$alkoxy;

$R^{21}$ is a C-linked 5-6 membered heteroaryl having 1-2 N heteroatoms which is substituted with $LR^{11}$ and 0-2 substituents independently selected from $C_1$-$C_6$alkyl, $C_1$-$C_6$haloalkyl, halogen, $-CN$, $NO_2$, $-C(=O)OR^6$, $-C(=O)N(R^6)_2$ and $C_1$-$C_6$alkoxy;

$R^{22}$ is a C-linked 5-6 membered heterocycloalkyl having 1-2 heteroatoms independently selected from N, O and S which is substituted with $LR^{11}$ and 0-2 substituents independently selected from $C_1$-$C_6$alkyl, $C_1$-$C_6$haloalkyl, halogen and $C_1$-$C_6$alkoxy;

$R^{23}$ is an N-linked 5-6 membered heterocycloalkyl having 1-2 heteroatoms independently selected from N and O which is substituted with $LR^{11}$ and 0-2 substituents independently selected from $C_1$-$C_6$alkyl, $C_1$-$C_6$haloalkyl, halogen and $C_1$-$C_6$alkoxy;

each L is independently selected from $-L_1L_2L_3L_4L_5L_6-$, $-L_6L_5L_4L_3L_2L_1-$, $-L_1L_2L_3L_4L_5-$, $-L_5L_4L_3L_2L_1-$, $-L_1L_2L_3L_4-$, $-L_4L_3L_2L_1-$, $-L_1L_2L_3-$, $-L_3L_2L_1-$, $-L_1L_2-$, $-L_2L_1-$ and $-L_1$, wherein $-L_1$, $L_2$, $L_3$, $L_4$, $L_5$, and $L_6$ are as defined herein;

$X_3$ is

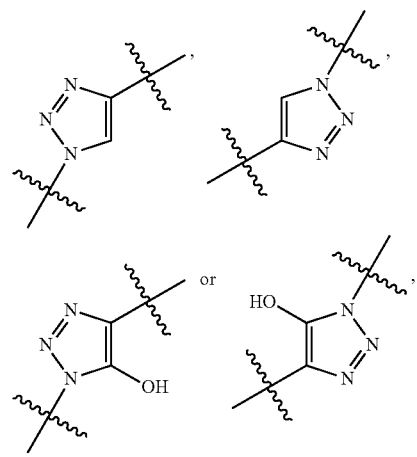

and X₄ is

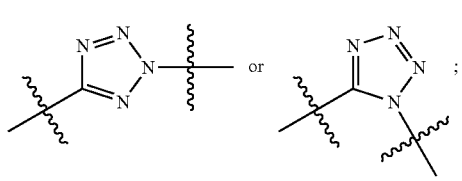 or ;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18, or a tautomer, a hydrate, a solvate or a pharmaceutically acceptable salt thereof.

19. The compound according to any one of embodiments 1 to 17, wherein the compound is a compound having the structure of Formula (Ia):

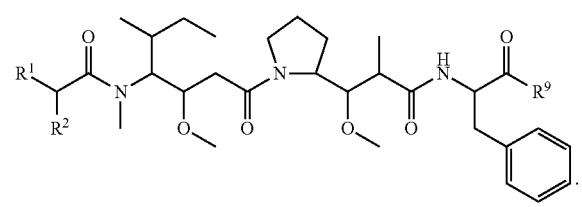

Formula (Ia)

20. The compound according to any one of embodiments 1 to 18, wherein the compound is a compound having the structure of Formula (Ib):

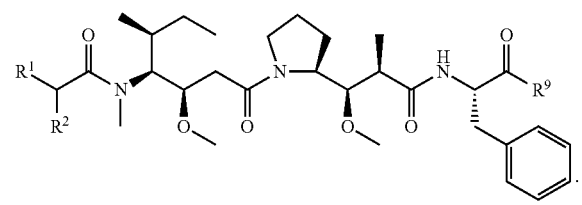

Formula (Ib)

21. The compound according to any one of embodiments 1 to 6, wherein the compound is a compound having the structure of Formula (Ic):

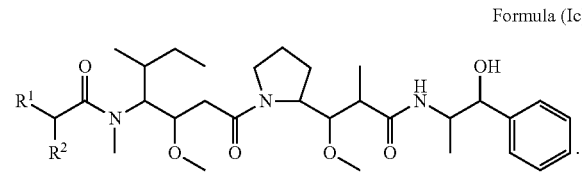

Formula (Ic)

22. The compound according to any one of embodiments 1 to 6, and 20, wherein the compound is a compound having the structure of Formula (Id):

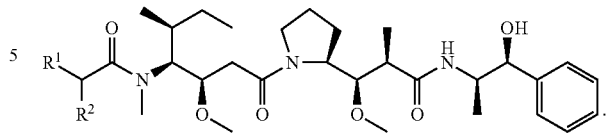

Formula (Id)

23. The compound according to any one of embodiments 1 to 17, wherein the compound is a compound having the structure of Formula (Ie):

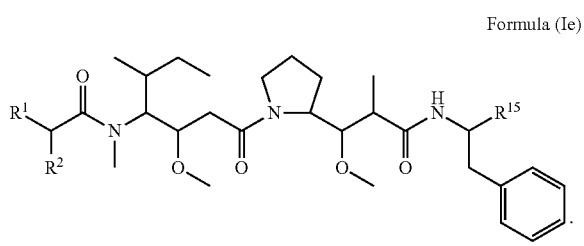

Formula (Ie)

24. The compound according to any one of embodiments 1 to 17, and 22, wherein the compound is a compound having the structure of Formula (If):

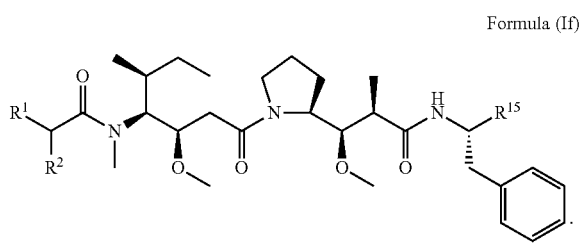

Formula (If)

25. The compound according to any one of embodiments 17 to 23, wherein each L is independently selected from -$L_1L_2L_3L_4L_5L_6$- and -$L_6L_5L_4L_3L_2L_1$-, and wherein -$L_1$, $L_2$, $L_3$, $L_4$, $L_5$, and $L_6$ are as defined herein.

26. The compound according to any one of embodiments 17 to 23, wherein each L is independently selected from -$L_1L_2L_3L_4L_5$-, -$L_5L_4L_3L_2L_1$-, -$L_1L_2L_3L_4$-, -$L_4L_3L_2L_1$-, -$L_1L_2L_3$- and -$L_3L_2L_1$-, wherein -$L_1$, $L_2$, $L_3$, $L_4$, $L_5$, and $L_6$ are as defined herein.

27. The compound according to any one of embodiments 17 to 23, wherein each L is independently selected from -$L_1L_2$- and -$L_2L_1$-, and wherein -$L_1$ and $L_2$ are as defined herein.

28. The compound according to any one of embodiments 17 to 23, wherein L is -$L_1$-, wherein -$L_1$ is as defined herein.

29. The compound according to any one of embodiments 17 to 27, wherein:
$R^1$ is —N=CR⁴R⁵, —N=R¹⁹, —N=CR⁵R²⁰, —N=CR⁵R¹⁰, —N=R²² or —N=CR⁵R²³.

30. The compound according to any one of embodiments 17 to 27, wherein:
$R^1$ is N=CR⁵R¹⁰, —N=R²² or —N=CR⁵R²³.

31. The compound according to any one of embodiments 17 to 27, wherein:
$R^1$ is N=CR⁵R¹⁰, N=R²², —NHLR¹¹, —NHR²¹, N=CR⁵R²³ or —NHC(=O)R²³.

32. The compound according to any one of embodiments 17 to 27, wherein:
$R^1$ is —NHC(=NR$^6$)R$^4$, —NHC(=O)R$^4$, —NHC(=O)R$^{20}$ or —NHC(=O)R$^{23}$.
33. The compound according to any one of embodiments 17 to 27, wherein:
$R^1$ is —NHC(=O)R$^{23}$.
34. The compound according to any one of embodiments 17 to 27, wherein:
$R^1$ is —NNR$^8$, —NHLR$^{11}$ or —NHR$^{21}$.
35. The compound according to any one of embodiments 17 to 27, wherein:
$R^1$ is —NNR$^8$.
36. The compound according to any one of embodiments 17 to 27, wherein:
$R^1$ is —NHLR$^{11}$ or —NHR$^{21}$.
37. The compound according to any one of embodiments 17 to 27, wherein:
$R^1$ is —N=CR$^4$R$^5$; R$^4$ is is —N(R$^6$)$_2$; R$^5$ is N(R$^6$)$_2$; and each R$^6$ is independently selected from —C$_1$—C$_6$alkyl.
38. The compound according to any one of embodiments 17 to 27, wherein:
$R^1$ is

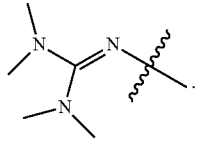

39. The compound according to any one of embodiments 17 to 27, wherein R$^7$ is —(CH$_2$)$_m$N(R$^{12}$)$_2$, —(CH$_2$)$_m$N(R$^{12}$)C(=O)OR$^{12}$.
40. The compound according to any one of embodiments 17 to 27, wherein R$^7$ is a C$_3$-C$_8$cycloalkyl substituted with —(CH$_2$)$_m$OH.
41. The compound according to any one of embodiments 17 to 27, 33 or 34, wherein R$^8$ is an unsubstituted C-linked pyridinyl, an unsubstituted C-linked pyrimidinyl or an unsubstituted C-linked pyrazinyl.
42. The compound according to any one of embodiments 17 to 27, 33 or 34, wherein R$^8$ is a C-linked pyridinyl, a C-linked pyrimidinyl or a C-linked pyrazinyl, each of which is substituted with 1-3 substituents independently selected from C$_1$-C$_6$alkyl, C$_1$-C$_6$haloalkyl, halogen, C$_1$-C$_6$alkoxy, —OH, —CN, —NO$_2$, —C(=O)OR$^6$, —C(=O)N(R$^6$)$_2$, —C(=O)NR$^6$(CH$_2$)$_m$N(R$^6$)C(O)OR$^6$ and —C(=O)NR$^6$(CH$_2$)$_m$N(R$^6$)$_2$.
43. The compound according to any one of embodiments 17 to 28, wherein R$^{19}$ is a C-linked imidazolidinyl or a C-linked piperazinyl, each of which is substituted with 1-3 substituents independently selected from C$_1$-C$_6$alkyl.
44. The compound according to any one of embodiments 17 to 28, or 31, wherein R$^{20}$ is an unsubstituted piperazinyl.
45. The compound according to any one of embodiments 17 to 28, or 31, wherein R$^{20}$ is an N-linked piperazinyl substituted with 1-2 substituents independently selected from —C(=O)OR$^{12}$ and —C(=O)(CH$_2$)$_m$N$_3$.
46. The compound according to any one of embodiments 17 to 27, 30 or 33, wherein R$^{21}$ is a C-linked pyridinyl, a C-linked pyrimidinyl or a C-linked pyrazinyl, each of which is substituted with -LR$^{11}$ and 0-2 substituents independently selected from C$_1$-C$_6$alkyl, C$_1$-C$_6$haloalkyl, halogen, C$_1$-C$_6$alkoxy, —OH, —CN, —NO$_2$, —C(=O)OR$^6$, —C(=O)N(R$^6$)$_2$ and C$_1$-C$_6$alkoxy.

47. The compound according to any one of embodiments 17 to 30, wherein R$^{22}$ is a C-linked imidazolidinyl or a C-linked piperazinyl, each of which is substituted with LR$^{11}$ and 0-2 substituents independently selected from C$_1$-C$_6$alkyl, C$_1$-C$_6$haloalkyl, halogen and C$_1$-C$_6$alkoxy.
48. The compound according to any one of embodiments 17 to 32, wherein R$^{23}$ is an N-linked piperazinyl substituted with substituted with LR$^{11}$ and 0-2 substituents independently selected from C$_1$-C$_6$alkyl, C$_1$-C$_6$haloalkyl, halogen and C$_1$-C$_6$alkoxy.
49. The compound according to any one of embodiments 17 to 30, wherein R$^{10}$ is LR$^{11}$.
50. The compound according to any one of embodiments 17 to 49, wherein:
$R^3$ is

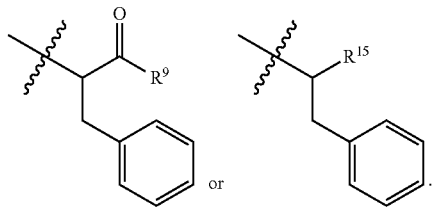

51. The compound according to any one of embodiments 17 to 50, wherein R$^9$ is —OH, C$_1$-C$_6$alkoxy, —NHS(O)$_2$(CH$_2$)$_m$N$_3$ or —NHS(O)$_2$(CH$_2$)$_m$NH$_2$.
52. The compound according to any one of embodiments 17 to 50, wherein R$^9$ is -LR$^{11}$, —NHS(=O)$_2$LR$^{11}$,

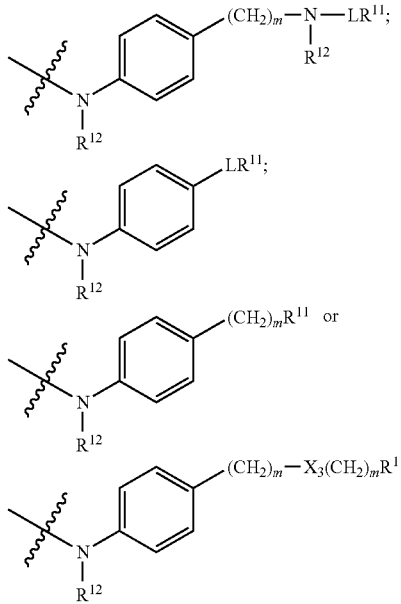

53. The compound according to any one of embodiments 17 to 50, wherein R$^{15}$ is tetrazolyl or

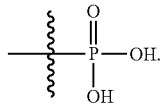

54. The compound according to any one of embodiments 17 to 50, wherein $R^{15}$ is

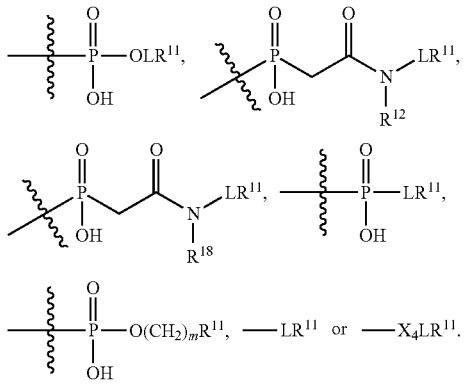

55. The compound according to any one of embodiments 17 to 50, wherein $R^{15}$ is tetrazolyl, —CN, —C(=O)OR$^{12}$,

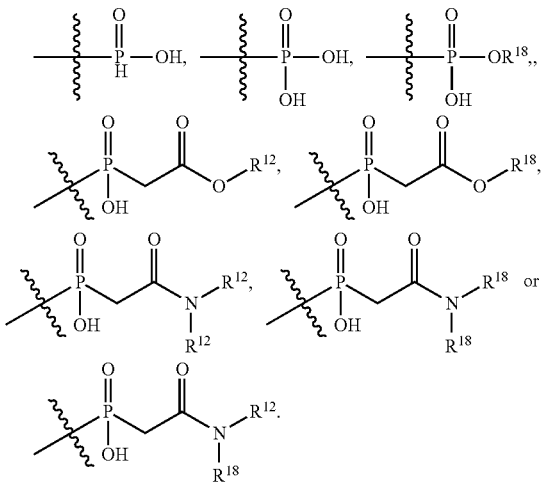

56. The compound according to any one of embodiments 17 to 55, wherein $R^{11}$ is

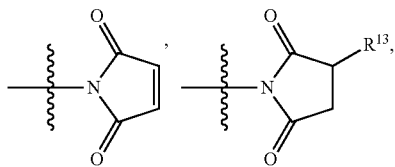

—N$_3$, —ONH$_2$, —NH$_2$, or

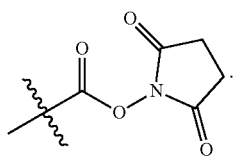

57. An immunoconjugate of Formula (II):

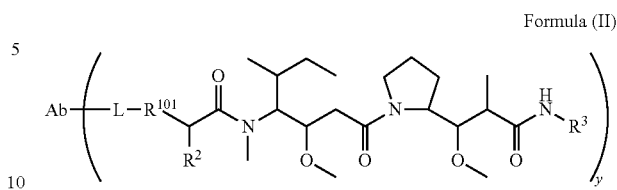

Formula (II)

wherein:
Ab represents an antigen binding moiety;
L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;
$R^{101}$ is

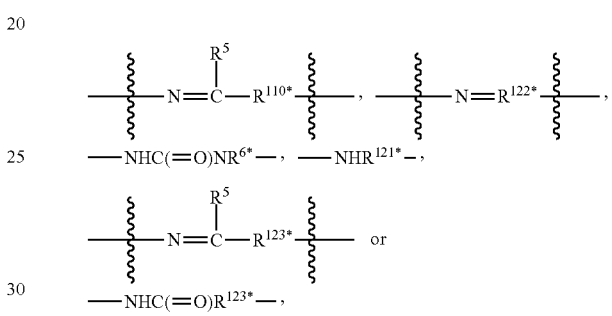

where the * denotes the point of attachment to L;
$R^2$ is —C$_1$-C$_6$alkyl;
$R^3$ is

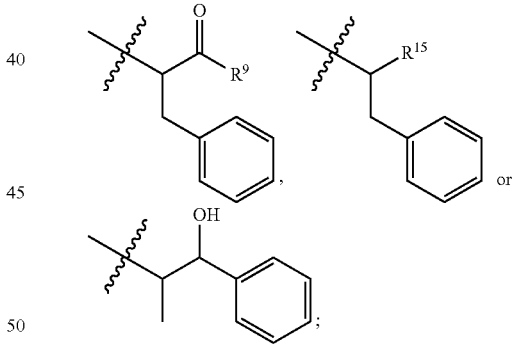

$R^5$ is N(R$^6$)$_2$;
each $R^6$ is independently selected from H and —C$_1$-C$_6$alkyl;
$R^9$ is —OH, C$_1$-C$_6$alkoxy, —N(R$^{12}$)$_2$, —R$^{16}$, —NR$^{12}$(CH$_2$)$_m$N(R$^{12}$)$_2$, —NR$^{12}$(CH$_2$)$_m$R$^{16}$, —NHS(O)$_2$R$^{18}$ or

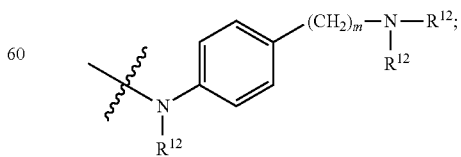

each $R^{12}$ is independently selected from H and C$_1$-C$_6$alkyl;
$R^{15}$ is tetrazolyl,

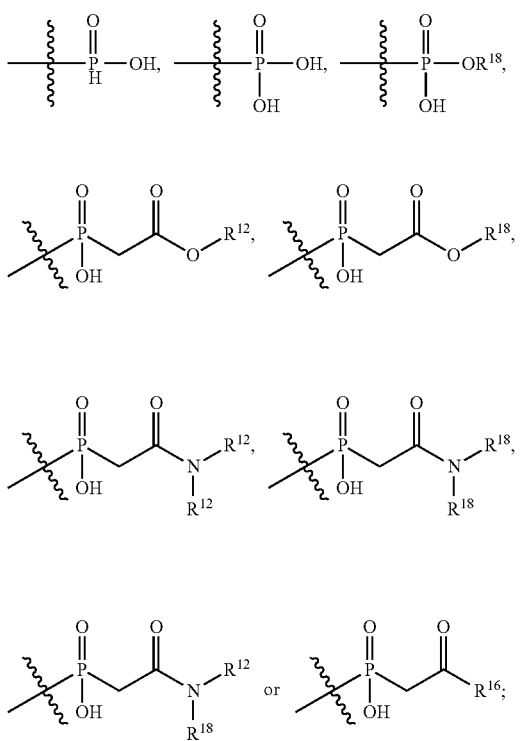

$R^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$ each $R^{18}$ is independently selected from a $C_1$-$C_6$alkyl, a $C_1$-$C_6$alkyl which is substituted with azido and a $C_1$-$C_6$alkyl which is substituted with 1 to 5 hydroxyl;

$R^{110}$ is a bond or

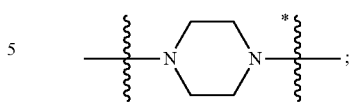

$R^{121}$ is a C-linked 5-6 membered heteroarylene having 1-2 N heteroatoms which is substituted with 0-2 substituents independently selected from $C_1$-$C_6$alkyl, $C_1$-$C_6$haloalkyl, halogen, —CN, NO$_2$, —C(=O)OR$^6$, —C(=O)N(R$^6$)$_2$ and $C_1$-$C_6$alkoxy;

$R^{122}$ is a C-linked 5-6 membered heterocycloalkylene having 1-2 heteroatoms independently selected from N, O and S which is substituted with 0-2 substituents independently selected from $C_1$-$C_6$alkyl, $C_1$-$C_6$haloalkyl, halogen and $C_1$-$C_6$alkoxy;

$R^{123}$ is an N-linked 5-6 membered heterocycloalkylene having 1-2 heteroatoms independently selected from N and O which is substituted with 0-2 substituents independently selected from $C_1$-$C_6$alkyl, $C_1$-$C_6$haloalkyl, halogen and $C_1$-$C_6$alkoxy;

y is an integer from 1 to 16;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

58. The immunoconjugate according to embodiment 57, wherein L is -L$_1$L$_2$L$_3$L$_4$L$_5$L$_6$- or -L$_6$L$_5$L$_4$L$_3$L$_2$L$_1$-, and wherein -L$_1$, L$_2$, L$_3$, L$_4$, L$_5$, and L6 are as defined herein.

59. The immunoconjugate according to embodiment 57, wherein L is selected from -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$- and -L$_3$L$_2$L$_1$-, wherein -L$_1$, L$_2$, L$_3$, L$_4$, L$_5$, and L$_6$ are as defined herein.

60. The immunoconjugate according to any one of embodiments 57 to 59, wherein the immunoconjugate of Formula (II) is an immunoconjugate of Formula (IIa):

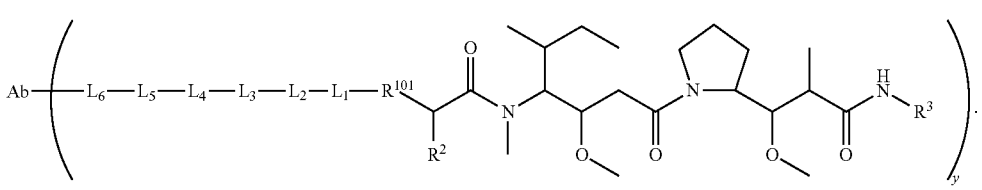

Formula (IIa)

61. The immunoconjugate according to any one of embodiments 57 to 60, wherein L is -L$_1$L$_2$- or and wherein -L$_1$ and L$_2$ are as defined herein.

62. The immunoconjugate according to any one of embodiments 57 to 61, wherein the immunoconjugate of Formula (II) is an immunoconjugate of Formula (IIb):

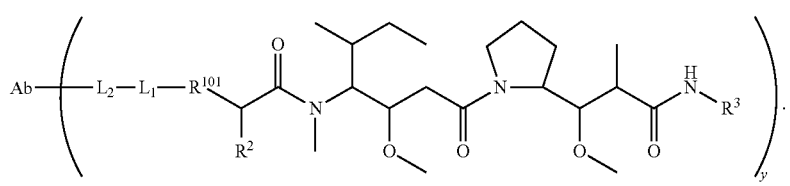

Formula (IIb)

63. The immunoconjugate according to any one of embodiments 57 to 62, wherein the immunoconjugate of Formula (II), Formula (IIa) or Formula (IIb) is an immunoconjugate having the structure of Formula (IIc):

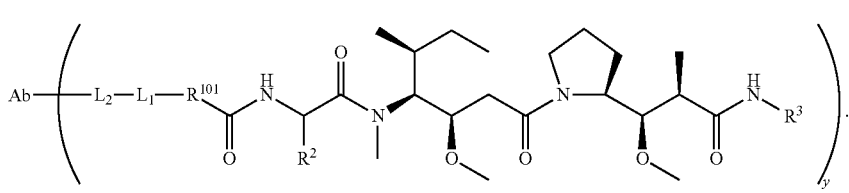

64. The immunoconjugate according to any one of embodiments 57 to 63, wherein $R^{101}$ is

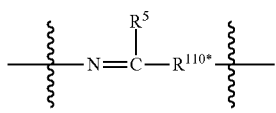

and $R^{110}$ is a bond.

65. The immunoconjugate according to any one of embodiments 57 to 63, wherein $R^{101}$ is

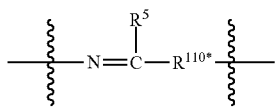

and $R^{110}$ is

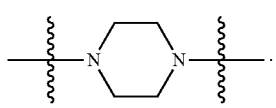

66. The immunoconjugate according to any one of embodiments 57 to 63, wherein $R^{101}$ is —NHR$^{121}$*— and $R^{121}$ is a C-linked pyrimidinylene, a C-linked pyazinylene or a C-linked pyridinylene, each of which is substituted with 0-2 substituents independently selected from $C_1$-$C_6$alkyl, $C_1$-$C_6$haloalkyl, halogen, —CN, $NO_2$, —C(=O)OR$^6$, —C(=O)N(R$^6$)$_2$ and $C_1$-$C_6$alkoxy.

67. The immunoconjugate according to any one of embodiments 57 to 63, wherein $R^{101}$ is —NHC(=O)R$^{123}$*— and $R^{123}$ is a N-linked piperazinylene which is substituted with 0-2 substituents independently selected from $C_1$-$C_6$alkyl, $C_1$-$C_6$haloalkyl, halogen and $C_1$-$C_6$alkoxy.

68. The immunoconjugate according to any one of embodiments 57 to 63, wherein $R^{101}$ is —NHC(=O)NR$^{6}$*—.

69. The immunoconjugate according to any one of embodiments 57 to 68, wherein $R^9$ is —OH, $C_1$-$C_6$alkoxy, —N(R$^{14}$)$_2$, —R$^{16}$, —NR$^{12}$(CH$_2$)$_m$N(R$^{12}$)$_2$, —NHS(O)2R$^{18}$, or —NR$^{12}$(CH$_2$)R$^{16}$; and $R^{15}$ is tetrazolyl,

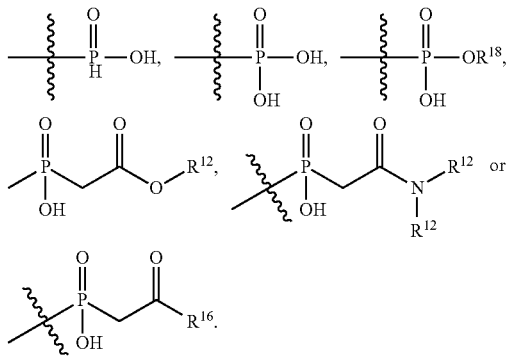

70. The immunoconjugate according to any one of embodiments 57 to 69, wherein $R^3$ is

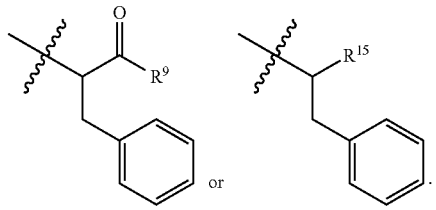

71. The immunoconjugate according to any one of embodiments 57 to 70, wherein $R^9$ is —OH, $C_1$-$C_6$alkoxy, —N(R$^{14}$)$^2$, —R$_{16}$, —NR$^{12}$(CH$_2$)$_m$N(R$^{14}$)$_2$, or —NR$^{12}$(CH$_2$)$_m$R$^{16}$.

72. The immunoconjugate according to any one of embodiments 57 to 71, wherein $R^9$ is —OH or —OCH$_3$.

73. The immunoconjugate according to any one of embodiments 57 to 70, wherein $R^{15}$ is

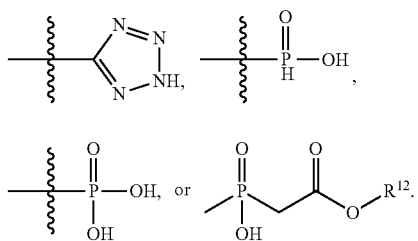

74. An immunoconjugate of Formula (III):

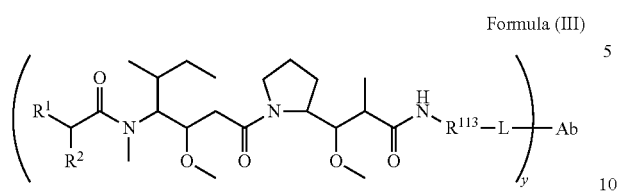
Formula (III)

wherein:
Ab represents an antigen binding moiety;
L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;
y is an integer from 1 to 16;
R$^1$ is —N=CR$^4$R$^5$, —N=R$^{19}$, —N=CR$^5$R$^{20}$, —NHC(=NR$^6$)R$^4$, —NHC(=O)R$^4$, —NHC(=O)R$^{20}$ or —NHR$^8$;
R$^2$ is —C$_1$-C$_6$alkyl;
R$^4$ is —N(R$^6$)$_2$ or —NR$^6$R$^7$;
R$^5$ is N(R$^6$)$_2$;
each R$^6$ is independently selected from H and —C$_1$-C$_6$alkyl;
R$^7$ is an unsubstituted C$_3$-C$_8$cycloalkyl;
or R$^7$ is a C$_3$-C$_8$cycloalkyl substituted with 1-3 substituents independently selected from C$_1$-C$_6$alkyl, oxo, —C(=O)R$^{18}$, —(CH$_2$)$_m$OH, —C(=O)(CH$_2$)$_m$OH, —C(=O)((CH$_2$)$_m$O)$_n$R$^{12}$, —((CH$_2$)$_m$O)$_n$R$^{12}$ or a C$_1$-C$_6$alkyl which is optionally substituted with 1 to 5 hydroxyl;
R$^8$ is an unsubstituted C-linked 5-6 membered heteroaryl having 1-2 N heteroatoms;
or R$^8$ is a C-linked 5-6 membered heteroaryl having 1-2 N heteroatoms which is substituted with 1-3 substituents independently selected from C$_1$-C$_6$alkyl, C$_1$-C$_6$haloalkyl, halogen, —OH, —N(R$^6$)$_2$, —CN, —NO$_2$, —C(=O)OR$^6$ and C$_1$-C$_6$alkoxy;
each R$^{12}$ is independently selected from H and C$_1$-C$_6$alkyl;
R$^{19}$ is an unsubstituted C-linked 5-6 membered heterocycloalkyl having 1-2 heteroatoms independently selected from N and O;
or R$^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_1$-C$_6$alkoxy;
R$^{20}$ is an unsubstituted N-linked 5-6 membered heterocycloalkyl having 1-2 heteroatoms independently selected from N, O and S;
or R$^{20}$ is an N-linked 5-6 membered heterocycloalkyl having 1-2 heteroatoms independently selected from N, O and S, which is substituted with 1-3 substituents independently selected from C$_1$-C$_6$alkyl, C$_1$-C$_6$haloalkyl, halogen, —C(=O)OR$^{12}$, oxo, —OH and C$_1$-C$_6$alkoxy;
R$^{113}$ is

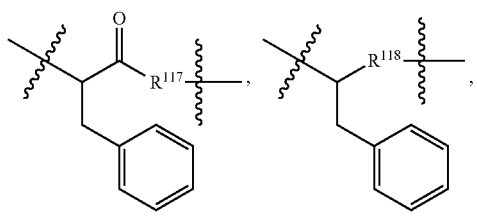

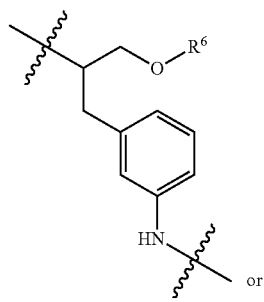
or

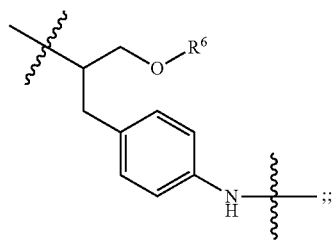

R$^{117}$ is a bond, —NH—, —NHS(=O)$_2$—, —NHS(=O)$_2$(CH$_2$)$_m$X$_3$(CH$_2$)$_m$—, -, —NHS(=O)$_2$(CH$_2$)$_m$NHC(=O)—, —NHS(=O)$_2$(CH$_2$)$_m$NHC(=O)O(CH$_2$)$_m$—,

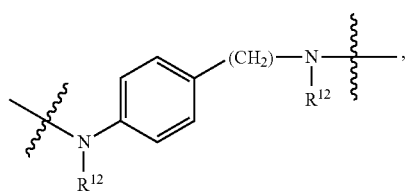

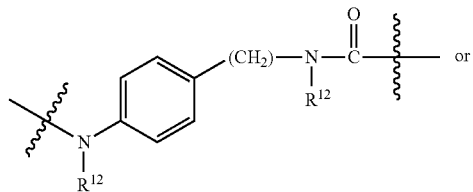
or

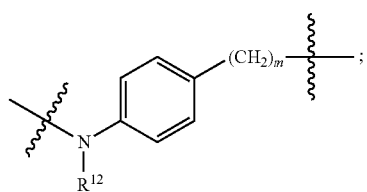

R$^{118}$ is a bond, tetrazolyl,

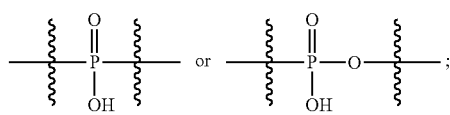

$R_{26}$ is

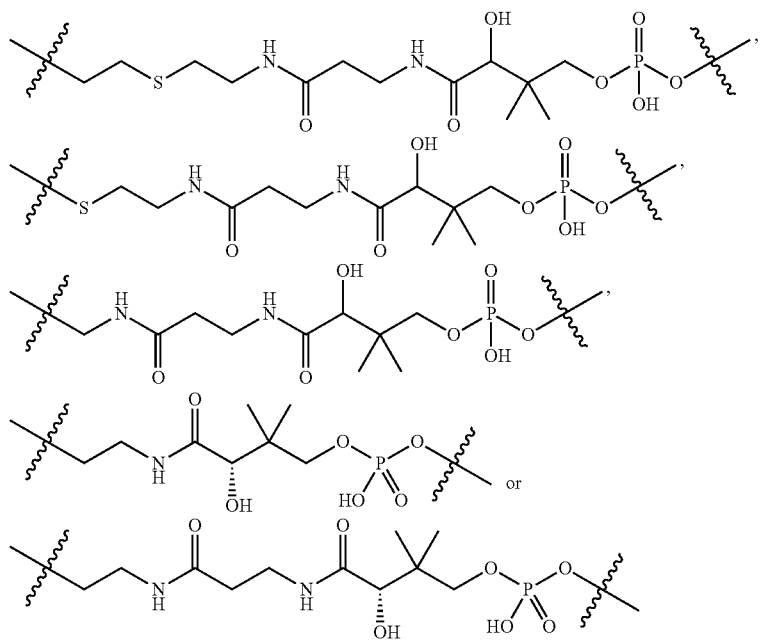

each m is independently selected from 1, 2, 3, 4, 5, 6, 7, 8, 9 and 10,
and
each n is independently selected from 1, 2, 3, 4, 5, 6, 7, 8, 9, 10, 11, 12, 13, 14, 15, 16, 17 and 18.

75. An immunoconjugate of Formula (III):

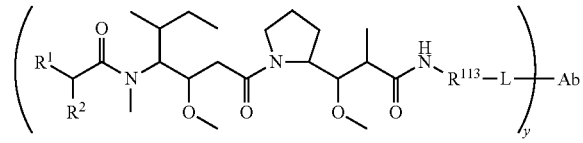

Formula (III)

wherein:
Ab represents an antigen binding moiety;
$R^1$ is $-N{=}CR^4R^5$, $-N{=}R^{19}$, $-N{=}CR^5R^{20}$, $-NHC(=NR^6)R^4$, $-NHC(=O)R^4$, $-NHC(=O)R^{20}$ or $-NHR^8$;
$R^2$ is $-C_1$-$C_6$alkyl;
$R^4$ is $-N(R^6)_2$ or $-NR^6R^7$;
$R^5$ is $N(R^6)_2$;
each $R^6$ is independently selected from H and $-C_1$-$C_6$alkyl;
$R^7$ is an unsubstituted $C_3$-$C_8$cycloalkyl;
or $R^7$ is a $C_3$-$C_8$cycloalkyl substituted with 1-3 substituents independently selected from $C_1$-$C_6$alkyl, oxo, $-C(=O)R^{18}$, $-(CH_2)_mOH$, $-C(=O)(CH_2)_mOH$, $-C(=O)((CH_2)_mO)_nR^{12}$, $-((CH_2)_mO)_nR^{12}$ or a $C_1$-$C_6$alkyl which is optionally substituted with 1 to 5 hydroxyl;
$R^8$ is an unsubstituted C-linked 5-6 membered heteroaryl having 1-2 N heteroatoms;
or $R^8$ is a C-linked 5-6 membered heteroaryl having 1-2 N heteroatoms which is substituted with 1-3 substituents independently selected from $C_1$-$C_6$alkyl, $C_1$-$C_6$haloalkyl, halogen, $-OH$, $-N(R^6)_2$, $-CN$, $-NO_2$, $-C(=O)OR^6$ and $C_1$-$C_6$alkoxy;

each $R^{12}$ is independently selected from H and $C_1$-$C_6$alkyl;
$R^{19}$ is an unsubstituted C-linked 5-6 membered heterocycloalkyl having 1-2 heteroatoms independently selected from N and O;
or $R^{19}$ is a C-linked 5-6 membered heterocycloalkyl having 1-2 heteroatoms independently selected from N and O which is substituted with 1-3 substituents independently selected from $C_1$-$C_6$alkyl, $C_1$-$C_6$haloalkyl, halogen and $C_1$-$C_6$alkoxy;
$R^{20}$ is an unsubstituted N-linked 5-6 membered heterocycloalkyl having 1-2 heteroatoms independently selected from N, O and S;
or $R^{20}$ is an N-linked 5-6 membered heterocycloalkyl having 1-2 heteroatoms independently selected from N, O and S, which is substituted with 1-2 substituents independently selected from $C_1$-$C_6$alkyl, $C_1$-$C_6$haloalkyl, halogen, $-C(=O)OR^{12}$, oxo, $-OH$ and $C_1$-$C_6$alkoxy;
$R^{113}$ is

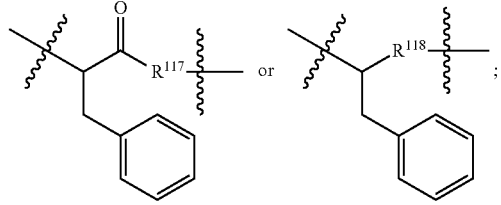

$R^{117}$ is a bond, $-NH-$, $-NHS(=O)_2-$,

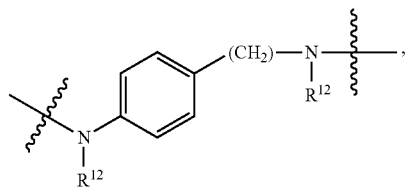

-continued

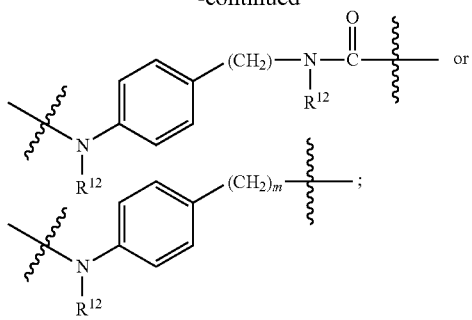

$R^{118}$ is a bond, tetrazolyl,

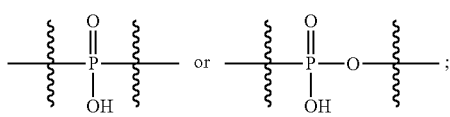

L is selected from -L₁L₂L₃L₄L₅L₆-, -L₆L₅L₄L₃L₂L₁-, -L₁L₂L₃L₄L₅-, -L₅L₄L₃L₂L₁-, -L₁L₂L₃L₄-, -L₄L₃L₂L₁-, -L₁L₂L₃-, -L₃L₂L₁-, -L₁L₂-, -L₂L₁- and -L₁, wherein -L₁, L₂, L₃, L₄, L₅, and L₆ are as defined herein;

y is an integer from 1 to 16;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

76. The immunoconjugate according to embodiment 74, wherein L is -L₁L₂L₃L₄L₅L₆- or -L₆L₅L₄L₃L₂L₁-, and wherein -L₁, L₂, L₃, L₄, L₅, and L₆ are as defined herein.

77. The immunoconjugate according to any one of embodiments 74 to 75, wherein L is selected from -L₁L₂L₃L₄L₅-, -L₅L₄L₃L₂L₁-, -L₁L₂L₃L₄-, -L₄L₃L₂L₁-, -L₁L₂L₃- and -L₃L₂L₁-, wherein -L₁, L₂, L₃, L₄, L₅, and L₆ are as defined herein.

78. The immunoconjugate according to any one of embodiments 74 to 76, wherein the immunoconjugate of Formula (III) is an immunoconjugate of Formula (IIIa):

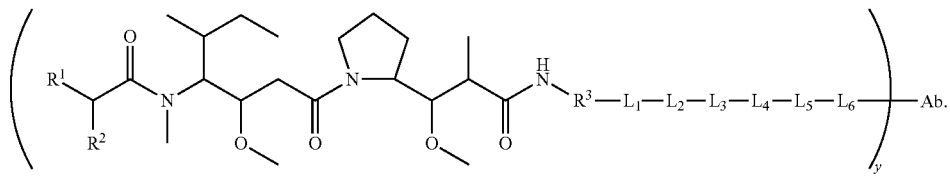

Formula (IIIa)

79. The immunoconjugate according to any one of embodiments 74 to 76, wherein L is -L₁L₂- or L₂L₁-, and wherein -L₁ and L₂ are as defined herein.

80. The immunoconjugate according to any one of embodiments 74 to 76 or 78, wherein the immunoconjugate of Formula (III) or Formula (IIIa) is an immunoconjugate of Formula (IIIb):

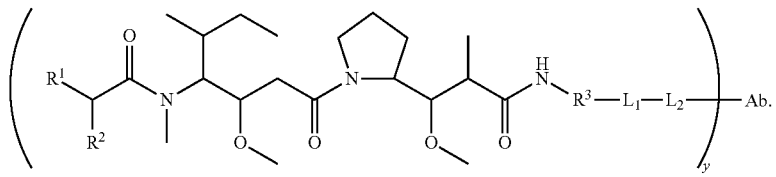

Formula (IIIb)

81. The immunoconjugate according to any one of embodiments 74 to 79, wherein the immunoconjugate of Formula (III), Formula (IIIa) or Formula (IIIb) is an immunoconjugate of Formula (IIIc):

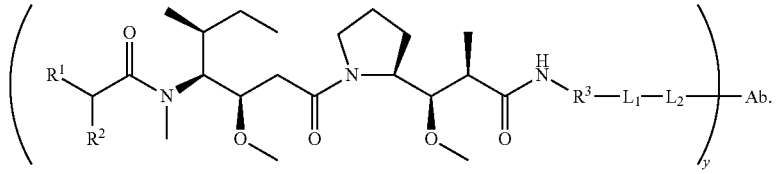

Formula (IIIc)

82. The immunoconjugate according to any one of embodiments 74 to 80, wherein $R^1$ is —N=$CR^4R^5$, —N=$R^{19}$ or —N=$CR^5R^{20}$.

83. The immunoconjugate according to any one of embodiments 74 to 80, wherein $R^1$ is —NHC(=$NR^6$)$R^4$, —NHC(=O)$R^4$ or —NHC(=O)$R^{20}$.

84. The immunoconjugate according to any one of embodiments 74 to 80, wherein $R^1$ is —$NHR^8$.

85. The immunoconjugate according to any one of embodiments 74 to 80, wherein $R^1$ is —N=$CR^4R^5$; $R^4$ is is —N($R^6$)$_2$; $R^5$ is N($R^6$)$_2$; and each $R^6$ is independently selected from —$C_1$-$C_6$alkyl.

86. The immunoconjugate according to any one of embodiments 74 to 80, wherein $R^1$ is

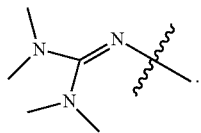

87. The immunoconjugate according to any one of embodiments 74 to 85, wherein $R^{13}$ is

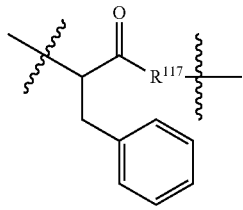

and $R^{117}$ is —NH—, —NHS(=O)$_2$— or

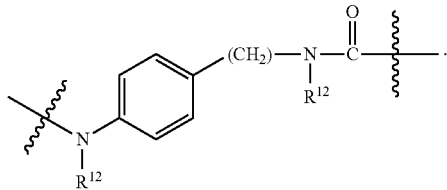

88. The immunoconjugate according to any one of embodiments 74 to 85, wherein $R^{113}$ is

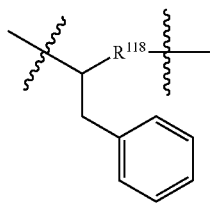

and $R^{118}$ is

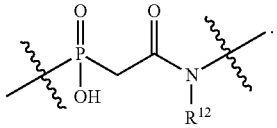

89. The compound of any one of embodiments 17 to 56, and the immunoconjugate according to any one of embodiments 57 to 87, wherein $L_1$ is selected from —(CH$_2$)$_m$—, —C(=O)(CH$_2$)$_m$—, —NR$^{12}$C(=O)(CH$_2$)$_m$—, —C(=O)X$_1$X$_2$C(=O)(CH$_2$)$_m$—, —C(=O)X$_1$X$_2$C(=O)(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NR$^{12}$C(=O)(CH$_2$)$_m$—, —C(=O)X$_1$X$_2$((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NR$^{12}$((CH$_2$)$_m$O)$_n$(CH$_2$)$_m$—, —C(=O)X$_1$X$_2$C(=O)(CH$_2$)$_m$NR$^{12}$((CH$_2$)$_m$O)$_n$(CH$_2$)$_m$X$_3$(CH$_2$)$_m$—, —(CH$_2$)$_m$NR$^{12}$C(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NR$^{12}$(CH$_2$)$_m$—, —C(=O)NR$^{12}$(CH$_2$)$_m$—, —C(=O)NR$^{12}$(CH$_2$)$_m$X$_3$(CH$_2$)$_m$—, —C(=O)NR$^{12}$(CH$_2$)$_m$NR$^{12}$C(=O)X$_1$X$_2$C(=O)(CH$_2$)$_m$—, —C(=O)X$_1$C(=O)NR$^{12}$(CH$_2$)$_m$NR$^{12}$C(=O)(CH$_2$)$_m$—, —C(=O)X$_1$C(=O)NR$^{12}$(CH$_2$)$_m$X$_3$(CH$_2$)$_m$—, —C(=O)NR$^{12}$(CH$_2$)$_m$NR$^{12}$C(=O)(CH$_2$)$_m$—, —C(=O)NR$^{12}$(CH$_2$)$_m$NR$^{12}$C(=O)(CH$_2$)$_m$X$_3$(CH$_2$)$_m$—, —(CH$_2$)$_m$C(=O)NR$^{12}$(CH$_2$)$_m$NR$^{12}$C(=O)(CH$_2$)$_m$—, —(CH$_2$)$_m$C(=O)—, —C(=O)(CH$_2$)$_m$NR$^{12}$(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^{12}$(CH$_2$)$_m$—, —(CH$_2$)$_m$C(=O)NR$^{12}$(CH$_2$)$_m$X$_3$(CH$_2$)$_m$—, —(CH$_2$)$_m$X$_3$(CH$_2$)$_m$NR$^{12}$C(=O)(CH$_2$)$_m$—, —(CH$_2$)$_m$C(=O)NR$^{12}$(CH$_2$)$_m$X$_3$—, —X$_3$(CH$_2$)$_m$NR$^{12}$C(=O)(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$—, —((C(R$^{12}$)$_2$)$_m$OC(=O)NR$^{12}$(CH$_2$)$_m$O(CH$_2$)$_m$—, —(CH$_2$)$_m$(O(CH$_2$)$_m$)$_n$NR$^{12}$C(=O)O(C(R$^{12}$)$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^{12}$(CH$_2$)$_m$C(=O)—, —(CH$_2$)$_m$O(CH$_2$)$_m$NR$^{12}$C(=O)O((C(R$^{12}$)$_2$)$_m$—, —(CH$_2$)$_m$NR$^{12}$C(=O)—, —(CH$_2$)$_m$C(=O)X$_2$X$_1$C(=O)NR$^{12}$(CH$_2$)$_m$NR$^{12}$C(=O)—, —(CH$_2$)$_m$C(=O)NR$^{12}$(CH$_2$)$_m$NR$^{12}$C(=O)X$_1$—, —(CH$_2$)$_m$C(=O)NR$^{12}$(CH$_2$)$_m$NR$^{12}$C(=O)—,

397

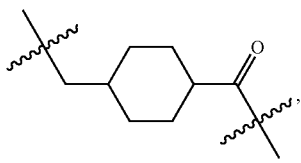

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$C(=O)NR$^{12}$(CH$_2$)$_m$O)$_n$(CH$_2$)$_m$X$_3$—, —X$_3$(CH$_2$)$_m$(O(CH$_2$)$_m$)$_n$NR$^{12}$C(=O)(CH$_2$)$_m$—, —(CH$_2$)$_m$C(=O)NR$^{12}$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$NR$^{12}$C(=O)—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —(CH$_2$)$_m$X$_3$—, —X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —(CH$_2$)$_m$C(=O)NR$^{12}$(CH$_2$)$_m$NR$^{12}$C(=O)NR$^{12}$—, —(CH$_2$)$_m$C(=O)NR$^{12}$(CH$_2$)$_m$NR$^{12}$C(=O)—, —(CH$_2$)$_m$C(=O)X$_2$X$_1$C(=O)—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —(CH$_2$(O(CH$_2$)$_m$)$_n$NR$^{12}$—, —(C(R$_{12}$)$_2$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^{12}$(CH$_2$)$_m$NR$^{12}$C(=O)—,

—(CH$_2$)$_m$X$_3$(CH$_2$)$_m$C(=O)NR$^{12}$(CH$_2$)$_m$C(=O)—, —C(=O)(CH$_2$)$_m$NR$^{12}$C(=O)(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NR$^{12}$C(=O)(CH$_2$)$_m$—, —(CH$_2$)$_m$C(=O)NR$^{12}$(CH$_2$)$_m$C(=O)X$_1$—, —C(=O)CHR$^{aa}$NR$^{12}$—, —NR$^{12}$CHR$^{aa}$C(=O)—, —C(=O)NR$^{12}$—, —C(=O)O—, —S—, —SCH$_2$(C=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NR$^{12}$C(=S)—, —(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$—, —NR$_{12}$S(=O)$_2$(CH$_2$)$_m$X$_3$(CH$_2$)$_m$—, and —(CH$_2$)$_m$X$_3$(CH$_2$)$_m$S(=O)$_2$NR$_{12}$—, and L$_1$ is selected from the groups shown in Table 2, wherein:

X$_1$ is self immolative spacer selected from

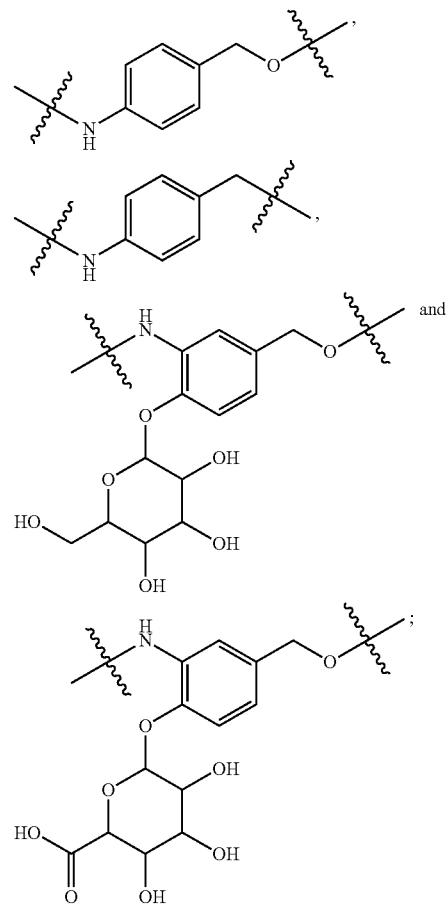

$X_2$ is dipeptide selected from

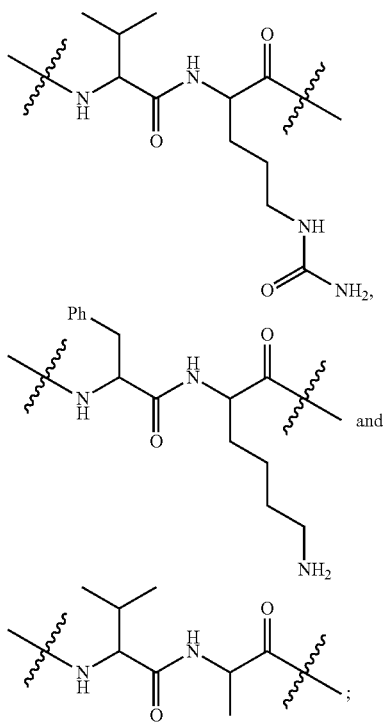

$X_3$ is

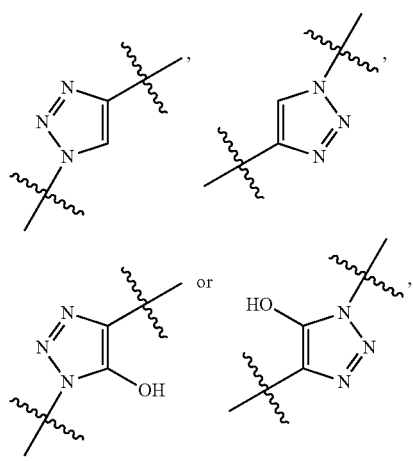

and
$X_4$ is

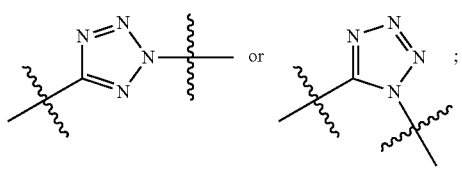

and
$L_2$, $L_3$, $L_4$, $L_5$, and $L_6$ are each independently selected from a bond and $L_1$.

90. The compound of any one of embodiments 17 to 56, and the immunoconjugate according to any one of embodiments 57 to 87, wherein L1 is selected from a group shown in Table 2, —(CH$_2$)$_m$—, —C(=O)(CH$_2$)$_n$—, —NHC(=O)(CH$_2$)$_m$—, —C(=O)X$_1$X$_2$C(=O)(CH$_2$)$_m$—, —C(=O)X$_1$X$_2$C(=O)(CH$_2$)$_m$NHC(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NHC(=O)(CH$_2$)$_m$—, —C(=O)X$_1$X$_2$C(=O)((CH$_2$)$_m$O)$_n$(CH$_2$)$_m$NHC(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NHC(=O)((CH$_2$)$_m$O)$_n$(CH$_2$)$_m$—, —C(=O)X$_1$X$_2$C(=O)(CH$_2$)$_m$NHC(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NHC(=O)(CH$_2$)$_m$—, —C(=O)X$_1$X$_2$((CH$_2$)$_m$O)$_n$(CH$_2$)$_m$NHC(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NH((CH$_2$)$_m$O)$_n$(CH$_2$)$_m$—, —C(=O)X$_1$X$_2$C(=O)(CH$_2$)$_m$NH((CH$_2$)$_m$O)$_n$(CH$_2$)$_m$X$_3$(CH$_2$)$_m$—, —(CH$_2$)$_m$NHC(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_n$—, —C(=O)(CH$_2$)$_m$NH(CH$_2$)$_m$—, —C(=O)NH(CH$_2$)$_m$—, —C(=O)NH(CH$_2$)$_m$X$_3$(CH$_2$)$_m$—, —C(=O)NH(CH$_2$)$_m$NHC(=O)X$_1$X$_2$C(=O)(CH$_2$)$_m$—, —C(=O)X$_1$C(=O)NH(CH$_2$)$_m$NHC(=O)(CH$_2$)$_m$—, —C(=O)X$_1$C(=O)NH(CH$_2$)$_m$X$_3$(CH$_2$)$_m$—, —C(=O)NH(CH$_2$)$_m$NHC(=O)(CH$_2$)$_m$—, —C(=O)NH(CH$_2$)$_m$NHC(=O)(CH$_2$)$_m$X$_3$(CH$_2$)$_m$—,

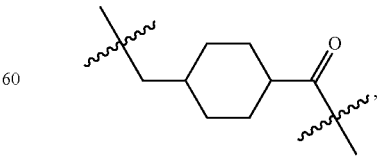

—(CH$_2$)$_m$C(=O)NH(CH$_2$)$_m$NHC(=O)(CH$_2$)$_m$—, —(CH$_2$)$_m$C(=O)—, —C(=O)(CH$_2$)$_m$NH(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NH(CH$_2$)$_m$—, —(CH$_2$)$_m$C(=O)NH(CH$_2$)$_m$X$_3$(CH$_2$)$_m$—, —(CH$_2$)$_m$X$_3$(CH$_2$)$_m$NHC(=O)(CH$_2$)$_m$—, —(CH$_2$)$_m$C(=O)NH(CH$_2$)$_m$X$_3$—, —X$_3$(CH$_2$)$_m$NHC(=O)(CH$_2$)$_m$—, —(CH$_2$)$_m$X$_3$(CH$_2$)$_m$C(=O)NH(CH$_2$)$_m$—, —(CH$_2$)$_m$NHC(=O)(CH$_2$)$_m$X$_3$(CH$_2$)$_m$—, —(CH$_2$)$_m$O)$_n$(CH$_2$)$_m$NHC(=O)(CH$_2$)$_m$—, —(CH$_2$)$_m$C(=O)NH(CH$_2$)$_m$(O(CH$_2$)$_m$)$_n$—, —(CH$_2$)$_m$OC(=O)NH(CH$_2$)$_m$O(CH$_2$)$_m$—, —(CH$_2$)$_m$(O(CH$_2$)$_m$)$_n$NHC(=O)O(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NH(CH$_2$)$_m$C(=O)—, —(CH$_2$)$_m$O(CH$_2$)$_m$NHC(=O)O((CH$_2$)$_m$—, —(CH$_2$)$_m$NHC(=O)—, —(CH$_2$)$_m$C(=O)X$_2$X$_1$C(=O)NH(CH$_2$)$_m$NHC(=O)—, —(CH$_2$)$_m$C(=O)NH(CH$_2$)$_m$NHC(=O)X$_1$—, —(CH$_2$)$_m$C(=O)NH(CH$_2$)$_m$NHC(=O)—,

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—,

—C(=O)(CH$_2$)$_m$X$_3$(CH$_2$)$_m$—, —(CH$_2$)$_m$C(=O)NH(CH$_2$)$_m$O)$_n$(CH$_2$)$_m$X$_3$—, —X$_3$(CH$_2$)$_m$(O(CH$_2$)$_m$)$_n$NHC(=O)(CH$_2$)$_m$—, —(CH$_2$)$_m$C(=O)NH(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NHC(=O)(CH$_2$)$_m$—, —(CH$_2$)$_m$X$_3$(CH$_2$)$_m$(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NH(CH$_2$)$_m$C(=O)—, —C(=O)(CH$_2$)$_m$NHC(=O)(CH$_2$)$_m$—, —(CH$_2$)$_m$C(=O)NH(CH$_2$)$_m$(O(CH$_2$)$_m$)$_n$C(=O)—, —C(=O)((CH$_2$)$_m$O)$_n$(CH$_2$)$_m$NHC(=O)(CH$_2$)$_m$—, —(CH$_2$)$_m$C(=O)NH(CH$_2$)$_m$C(=O)NH(CH$_2$)$_m$—, —(CH$_2$)$_m$NHC(=O)(CH$_2$)$_m$NHC(=O)(CH$_2$)$_m$—, —C(=O)NH(CH$_2$)$_m$NHC(=O)—, —(CH$_2$)$_m$S(CH$_2$)$_m$—, —NHC(=O)(CH$_2$)$_m$—, —NHC(=O)(CH$_2$)$_m$X$_3$(CH$_2$)$_m$—, —(CH$_2$)$_m$X$_3$(CH$_2$)$_m$C(=O)NH—, —(CH$_2$)$_m$C(=O)NH—, —(CH$_2$)$_m$NH(CH$_2$)$_m$—, —(CH$_2$)$_m$X$_3$(CH$_2$)$_m$—, —(CH$_2$)$_m$X$_3$—, —X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NH(CH$_2$)$_m$—, —NHCH$_2$(CH$_2$)$_m$—, —(CH$_2$)$_m$CH$_2$NH—, —(CH$_2$)$_m$C(=O)NH(CH$_2$)$_m$NH—, —(CH$_2$)$_m$C(=O)NH(CH$_2$)$_m$NHC(=O)NH—, —(CH$_2$)$_m$C(=O)NH(CH$_2$)$_m$NHC(=O)—, —(CH$_2$)$_m$C(=O)X$_2$X$_1$C(=O)—, —NH(CH$_2$)$_m$NHC(=O)(CH$_2$)$_m$—, —NHCH$_2$(CH$_2$)$_m$NHC(=O)(CH$_2$)$_m$—, —(CH$_2$)$_m$C(=O)NH(CH$_2$)$_m$CH$_2$NH—, —NH(CH$_2$)$_m$X$_3$(CH$_2$)$_m$—, —NHCH$_2$(CH$_2$)$_m$X$_3$(CH$_2$)$_m$—, —(CH$_2$)$_m$X$_3$(CH$_2$)$_m$CH$_2$NH—, —NHCH$_2$(CH$_2$)$_m$OC(=O)NH(CH$_2$)$_m$—, —(CH$_2$)$_m$NHC(=O)O(CH$_2$)$_m$CH$_2$NH—, —NHCH$_2$(CH$_2$)$_m$OC(=O)NH(CH$_2$)$_m$X$_3$(CH$_2$)$_m$—, —(CH$_2$)$_m$X$_3$(CH$_2$)$_m$NHC(=O)O(CH$_2$)$_m$CH$_2$NH—, —NHCH$_2$(CH$_2$)$_m$OC(=O)NH((CH$_2$)$_m$O)$_n$(CH$_2$)$_m$—, —(CH$_2$)$_m$(O(CH$_2$)$_m$)$_n$NHC(=O)O(CH$_2$)$_m$CH$_2$NH—, —NHCH$_2$(CH$_2$)$_m$OC(=O)NH((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NHC(=O)O(CH$_2$)$_m$CH$_2$NH—, —(CH$_2$)$_m$X$_3$(CH$_2$)$_m$NH—, —NH((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NH—, —(CH$_2$)$_m$NH—, —NH((CH$_2$)$_m$O)$_n$(CH$_2$)$_m$—, —NH((CH$_2$)$_m$O)$_n$(CH$_2$)$_m$NHC(=O)(CH$_2$)$_m$—, —(CH$_2$)$_m$C(=O)NH(CH$_2$)$_m$(O(CH$_2$)$_m$)$_n$NH—, —(CH$_2$)$_m$(O(CH$_2$)$_m$)$_n$NH—, —(CH$_2$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NHC(=O)(CH$_2$)$_m$—, —(CH$_2$)$_m$C(=O)NH(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NH(CH$_2$)$_m$NHC(=O)—, —(CH$_2$)$_m$X$_3$(CH$_2$)$_m$C(=O)NH(CH$_2$)$_m$C(=O)—, —C(=O)(CH$_2$)$_m$NHC(=O)(CH$_2$)$_m$X$_3$(CH$_2$)$_m$—, —(CH$_2$)$_m$X$_3$(CH$_2$)$_m$C(=O)NH(CH$_2$)$_m$(O(CH$_2$)$_m$)$_n$C(=O)—, —C(=O)((CH$_2$)$_m$O)$_n$(CH$_2$)$_m$NHC(=O)(CH$_2$)$_m$X$_3$(CH$_2$)$_m$—, —(CH$_2$)$_m$NHC(=O)X$_1$X$_2$C(=O)(CH$_2$)$_m$—, —(CH$_2$)$_m$C(=O)X$_2$X$_1$C(=O)NH(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NH—, —NHCHR$^{aa}$C(=O)—, —C(=O)NH—, —C(=O)O—, —S—, —SCH$_2$(C=O)NH—, —NHC(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S(=O)$_2$CH$_2$CH$_2$—, —NHC(=S)—, —(CH$_2$)$_m$X$_3$(O(CH$_2$)$_m$)$_n$C(=O)—, —C(=O)((CH$_2$)$_m$O)$_n$X$_3$(CH$_2$)$_m$—,

—(CH$_2$)$_m$NHC(=O)((CH$_2$)$_m$O)$_n$(CH$_2$)$_m$—, —(CH$_2$)$_m$(O(CH$_2$)$_m$)$_n$C(=O)NH(CH$_2$)$_m$—, —(CH$_2$)$_m$NHC(=O)NH(CH$_2$)$_m$—, —(CH$_2$)$_m$X$_3$(CH$_2$)$_m$NHC(=O)—, —C(=O)NH(CH$_2$)$_m$X$_3$(CH$_2$)$_m$—, —NHS(=O)$_2$(CH$_2$)$_m$X$_3$(CH$_2$)$_m$— and —(CH$_2$)$_m$X$_3$(CH$_2$)$_m$S(=O)$_2$NH—;

wherein,

X$_1$ is self immolative spacer selected from

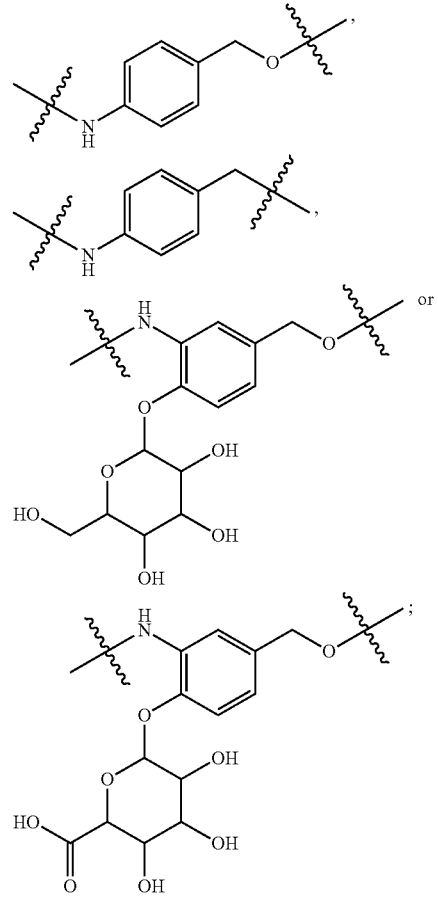

X$_2$ is dipeptide selected from

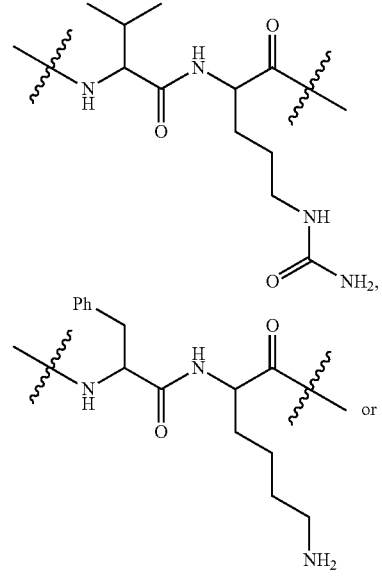

-continued

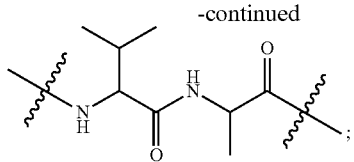

$X_3$ is

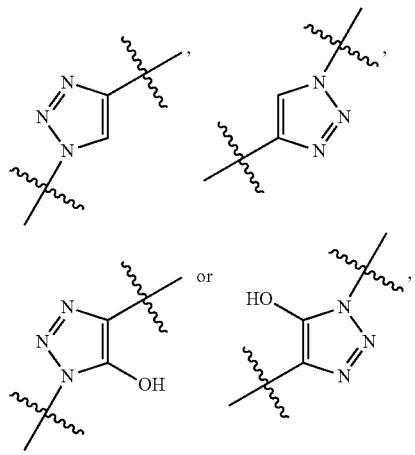

and
$X_4$ is

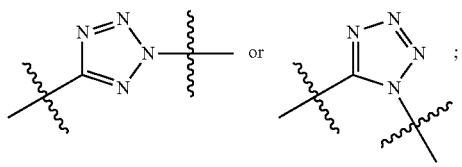

and
$L_2$, $L_3$, $L_4$, $L_5$, and $L_6$ are each independently selected from a bond and $L_1$.

91. The compound of any one of embodiments 17 to 56, and the immunoconjugate according to any one of embodiments 57 to 87, wherein $L_1$ is selected from $-(CH_2)_m-$, $-C(=O)(CH_2)_m-$, $-NR^{12}C(=O)(CH_2)_m-$, $-C(=O)X_1X_2C(=O)(CH_2)_m-$, $-C(=O)X_1X_2C(=O)(CH_2)_mNR^{12}C(=O)(CH_2)_m-$, $-C(=O)X_1X_2C(=O)(CH_2)_mX_3(CH_2)_m-$, $-C(=O)X_1X_2C(=O)((CH_2)_mO)_n(CH_2)_m-$, $-C(=O)X_1X_2C(=O)((CH_2)_mO)_n(CH_2)_mNR^{12}C(=O)(CH_2)_m-$, $-C(=O)X_1X_2C(=O)((CH_2)_mO)_n(CH_2)_mNR^{12}C(=O)(CH_2)_mX_3(CH_2)_m-$, $-C(=O)X_1X_2C(=O)((CH_2)_mO)_n(CH_2)_mX_3(CH_2)_m-$, $-C(=O)X_1X_2C(=O)(CH_2)_mNR^{12}C(=O)((CH_2)_mO)_n(CH_2)_m-$, $-C(=O)X_1X_2C(=O)(CH_2)_mNR^{12}C(=O)((CH_2)_mO)_n(CH_2)_mX_3(CH_2)_m-$, $-C(=O)X_1X_2(CH_2)_mX_3(CH_2)_m-$, $-C(=O)X_1X_2((CH_2)_mO)_n(CH_2)_m-$, $-C(=O)X_1X_2((CH_2)_mO)_n(CH_2)_mNR^{12}C(=O)(CH_2)_m-$, $-C(=O)X_1X_2((CH_2)_mO)_n(CH_2)_mNR^{12}C(=O)(CH_2)_mX_3(CH_2)_m-$, $-C(=O)X_1X_2((CH_2)_mO)_n(CH_2)_mX_3(CH_2)_m-$, $-C(=O)X_1X_2(CH_2)_mNR^{12}((CH_2)_mO)_n(CH_2)_m-$, $-C(=O)X_1X_2C(=O)(CH_2)_mNR^{12}((CH_2)_mO)_n(CH_2)_mX_3(CH_2)_m-$, $-(CH_2)_mNR^{12}C(=O)(CH_2)_m-$, $-C(=O)((CH_2)_mO)_n(CH_2)_m-$, $-(CH_2)_mS(=O)_2((CH_2)_mO)_n(CH_2)_m-$, $-C(=O)(CH_2)_mNR^{12}(CH_2)_m-$, $-C(=O)NR^{12}(CH_2)_m-$, $-C(=O)NR^{12}(CH_2)_mX_3(CH_2)_m-$, $-C(=O)NR^{12}(CH_2)_mNR^{12}C(=O)X_1X_2C(=O)(CH_2)_m-$, $-C(=O)X_1C(=O)NR^{12}(CH_2)_mNR^{12}C(=O)(CH_2)_m-$, $-C(=O)X_1C(=O)NR^{12}(CH_2)_mX_3(CH_2)_m-$, $-C(=O)NR^{12}(CH_2)_mNR^{12}C(=O)(CH_2)_m-$, $-C(=O)NR^{12}(CH_2)_mNR^{12}C(=O)(CH_2)_mX_3(CH_2)_m-$,

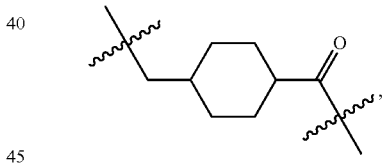

$-(CH_2)_mC(=O)NR^{12}(CH_2)_mNR^{12}C(=O)(CH_2)_m-$, $-(CH_2)_mC(=O)-$, $-C(=O)(CH_2)_mNR^{12}(CH_2)_mC(=O)X_2X_1C(=O)-$, $-(CH_2)_mX_3(CH_2)_mC(=O)X_2X_1C(=O)-$, $-(CH_2)_mC(=O)NR^{12}(CH_2)_m-$, $-(CH_2)_mC(=O)NR^{12}(CH_2)_mX_3(CH_2)_m-$, $-(CH_2)_mX_3(CH_2)_mNR^{12}C(=O)(CH_2)_m-$, $-(CH_2)_mC(=O)NR^{12}(CH_2)_mX_3-$, $-X_3(CH_2)_mNR^{12}C(=O)(CH_2)_m-$, $-(CH_2)_mX_3(CH_2)_mC(=O)NR^{12}(CH_2)_m-$, $-(CH_2)_mNR^{12}C(=O)(CH_2)_mX_3(CH_2)_m-$, $-(CH_2)_mO)_n(CH_2)_mNR^{12}C(=O)(CH_2)_m-$, $-(CH_2)_mC(=O)NR^{12}(CH_2)_m(O(CH_2)_m)_n-$, $-((C(R^{12})_2)_mOC(=O)NR^{12}(CH_2)_mO(CH_2)_m-$, $-(CH_2)_m(O(CH_2)_m)_nNR^{12}C(=O)O(C(R^{12})_2)_m-$, $-(CH_2)_m(O(CH_2)_m)_nC(=O)-$, $-(CH_2)_m(O(CH_2)_m)_nS(=O)_2(CH_2)_m-$, $-(CH_2)_mNR^{12}(CH_2)_mC(=O)-$, $-(CH_2)_mO(CH_2)_mNR^{12}C(=O)O((C(R^{12})_2)_m-$, $-(CH_2)_mNR^{12}C(=O)-$, $-(CH_2)_mC(=O)X_2X_1C(=O)NR^{12}(CH_2)_mNR^{12}C(=O)-$, $-(CH_2)_mC(=O)NR^{12}(CH_2)_mNR^{12}C(=O)X_1-$, $-(CH_2)_mC(=O)NR^{12}(CH_2)_mNR^{12}C(=O)-$, $-((CH_2)_mO)_n(CH_2)_m-$, $-(CH_2)_m(O(CH_2)_m)_n-$, $-(CH_2)_m(O(CH_2)_m)_nX_3(CH_2)_m-$, $-(CH_2)_mX_3((CH_2)_mO)_n(CH_2)_m-$, $-(CH_2)_mX_3(CH_2)_mC(=O)-$, $-C(=O)(CH_2)_mX_3(CH_2)_m-$, $-(CH_2)_mC(=O)NR^{12}(CH_2)_mO)_n(CH_2)_mX_3-$, $-X_3(CH_2)_m(O(CH_2)_m)_nNR^{12}C(=O)(CH_2)_m-$, $-(CH_2)_mC(=O)NR^{12}(CH_2)_mO)_n(CH_2)_mX_3(CH_2)_m-$, $-(CH_2)_mX_3(CH_2)_m(O(CH_2)_m)_nNR^{12}C(=O)(CH_2)_m-$, $-(CH_2)_mX_3(CH_2)_m(O(CH_2)_m)_nC(=O)-$, $-C(=O)((CH_2)_mO)_n(CH_2)_mX_3(CH_2)_m-$, $-(CH_2)_mC(=O)NR^{12}(CH_2)_mC(=O)-$, $-C(=O)(CH_2)_mNR^{12}C(=O)(CH_2)_m-$, $-(CH_2)_mC(=O)NR^{12}(CH_2)_m(O(CH_2)_m)_nC(=O)-$, $-C(=O)((CH_2)_mO)_n(CH_2)_mNR^{12}C(=O)(CH_2)_m-$, $-(CH_2)_mC(=O)NR^{12}(CH_2)_mC(=O)NR^{12}(CH_2)_m-$, $-(CH_2)_mNR^{12}C(=O)(CH_2)_mNR^{12}C(=O)(CH_2)_m-$, $-C(=O)NR^{12}(CH_2)_mNR^{12}C(=O)-$, $-(CH_2)_mS(CH_2)_m-$, $-NR^{12}C(=O)(CH_2)_m-$, $-NR^{12}C(=O)(CH_2)_mX_3(CH_2)_m-$, $-(CH_2)_mX_3(CH_2)_mC(=O)NR^{12}-$, $-(CH_2)_mC(=O)NR^{12}-$, $-(CH_2)_mNR^{12}(CH_2)_m-$, $-(CH_2)_mX_3(CH_2)_m-$, $-(CH_2)_mX_3-$, $-X_3(CH_2)_m-$, $-((CH_2)_mO)_n(CH_2)_mX_3(CH_2)_m-$,

—(CH₂)ₘX₃(CH₂)ₘ(O(CH₂)ₘ)ₙ—, —NR¹²(CH₂)ₘ—, —NR¹²C(R¹²)₂(CH₂)ₘ—, —(CH₂)ₘC(R¹²)₂NR¹²—, —(CH₂)ₘC(=O)NR¹²(CH₂)ₘNR¹²—, —(CH₂)ₘNR¹²C(=O)NR¹²(CH₂)ₘNR¹²C(=O)—, —(CH₂)ₘC(=O)NR¹²(CH₂)ₘNR¹²C(=O)—, —(CH₂)ₘC(=O)X₂X₁C(=O)—, —NR¹²(CH₂)ₘNR¹²C(=O)(CH₂)ₘ—, —NR¹²C(R¹²)₂(CH₂)ₘNR¹²C(=O)(CH₂)ₘ—, —(CH₂)ₘC(=O)NR¹²(CH₂)ₘC(R¹²)₂NR¹²—, —NR¹²(CH₂)ₘX₃(CH₂)ₘ—, —NR¹²C(R¹²)₂(CH₂)ₘX₃(CH₂)ₘ—, —(CH₂)ₘX₃(CH₂)ₘC(R¹²)₂NR¹²—, —NR¹²C(R¹²)₂(CH₂)ₘOC(=O)NR¹²(CH₂)ₘ—, —(CH₂)ₘNR¹²C(=O)O(CH₂)ₘC(R¹²)₂NR¹²—, —NR¹²C(R¹²)₂(CH₂)ₘOC(=O)NR¹²(CH₂)ₘX₃(CH₂)ₘ—, —(CH₂)ₘX₃(CH₂)ₘNR¹²C(=O)O(CH₂)ₘC(R¹²)₂NR¹²—, —NR¹²C(R¹²)₂(CH₂)ₘOC(=O)NR¹²((CH₂)ₘO)ₙ(CH₂)ₘ—, —(CH₂)ₘ(O(CH₂)ₘ)ₙNR¹²C(=O)O(CH₂)ₘC(R¹²)₂NR¹²—, —NR¹²C(R¹²)₂(CH₂)ₘOC(=O)NR¹²((CH₂)ₘO)ₙ(CH₂)ₘX₃(CH₂)ₘ—, —(CH₂)ₘX₃(CH₂)ₘ(O(CH₂)ₘ)ₙNR¹²C(=O)O(CH₂)ₘC(R¹²)₂NR¹²—, —(CH₂)ₘX₃(CH₂)ₘNR¹²—, —NR¹²((CH₂)ₘO)ₙ(CH₂)ₘX₃(CH₂)ₘ—, —(CH₂)ₘX₃(CH₂)ₘ(O(CH₂)ₘ)ₙNR¹²—, —(CH₂)ₘNR¹²—, —NR¹²((CH₂)ₘO)ₙ(CH₂)ₘ—, —NR¹²((CH₂)ₘO)ₙ(CH₂)ₘNR¹²C(=O)(CH₂)ₘ—, —(CH₂)ₘC(=O)NR¹²(CH₂)ₘ(O(CH₂)ₘ)ₙNR¹²—, —(CH₂)ₘ(O(CH₂)ₘ)ₙNR¹²—, —(CR₁₂)₂)ₘ—, —(CH₂CH₂O)ₙ—, —(OCH₂CH₂)ₙ—, —(CH₂)ₘO(CH₂)ₘ—, —S(=O)₂(CH₂)ₘ—, —(CH₂)ₘS(=O)₂—, —S(=O)₂(CH₂)ₘNR¹²C(=O)(CH₂)ₘ—, —(CH₂)ₘC(=O)NR¹²(CH₂)ₘS(=O)₂—, —S(=O)₂(CH₂)ₘX₃(CH₂)ₘ—, —(CH₂)ₘX₃(CH₂)ₘS(=O)₂—, —(CH₂)ₘX₂X₁C(=O)—, —C(=O)X₁X₂(CH₂)ₘ—, —(CH₂)ₘ(O(CH₂)ₘ)ₙC(=O)X₂X₁C(=O)—, —C(=O)X₁X₂C(=O)((CH₂)ₘO)ₙ(CH₂)ₘ—, —(CH₂)ₘ(O(CH₂)ₘ)ₙX₂X₁C(=O)—, —(CH₂)ₘX₃(CH₂)ₘX₂X₁C(=O)—, —C(=O)X₁X₂(CH₂)ₘX₃(CH₂)ₘ—, —(CH₂)ₘX₃(CH₂)ₘ(O(CH₂)ₘ)ₙX₂X₁C(=O)—, —(CH₂)ₘX₃(CH₂)ₘC(=O)NR¹²(CH₂)ₘNR¹²C(=O)—, —(CH₂)ₘX₃(CH₂)ₘC(=O)NR¹²(CH₂)ₘC(=O)—, —C(=O)(CH₂)ₘNR¹²C(=O)(CH₂)ₘX₃(CH₂)ₘ—, —(CH₂)ₘX₃(CH₂)ₘC(=O)NR¹²(CH₂)ₘ(O(CH₂)ₘ)ₙC(=O)—, —C(=O)((CH₂)ₘO)ₙ(CH₂)ₘNR¹²C(=O)(CH₂)ₘX₃(CH₂)ₘ—, —(CH₂)ₘNR¹²C(=O)X₁X₂C(=O)(CH₂)ₘ—, —(CH₂)ₘC(=O)X₂X₁C(=O)NR¹²(CH₂)ₘ—, —X₄X₁X₂C(=O)(CH₂)ₘ—, —(CH₂)ₘC(=O)X₂X₁X₄—, —X₁C(=O)(CH₂)ₘNR¹²C(=O)(CH₂)ₘ—, —(CH₂)ₘC(=O)NR¹²(CH₂)ₘC(=O)X₁—, —C(=O)CHRᵃᵃNR¹²—, —NR¹²CHRᵃᵃC(=O)—, —C(=O)NR¹²—, —C(=O)O—, —S—, —SCH₂(C=O)NR¹²—, —NR¹²C(=O)CH₂S—, —S(=O)₂CH₂H2S—, —SCH₂CH₂S(=O)₂—, —(CH₂)₂S(=O)₂CH₂CH₂S—, —SCH₂CH₂S(=O)₂CH₂CH₂—, —NR¹²C(=S)—, —(CH₂)ₘX₃(O(CH₂)ₘ)ₙC(=O)—, —C(=O)((CH₂)ₘO)ₙX₃(CH₂)ₘ—, —(CH₂)ₘNR¹²C(=O)((CH₂)ₘO)ₙ(CH₂)ₘ—, —(CH₂)ₘ(O(CH₂)ₘ)ₙC(=O)NR¹²(CH₂)ₘ—, —(CH₂)ₘNR¹²C(=O)NR¹²(CH₂)ₘ—, —(CH₂)ₘX₃(CH₂)ₘNR¹²C(=O)—, —C(=O)NR¹²(CH₂)ₘX₃(CH₂)ₘ—, —NR₁₂S(=O)₂(CH₂)ₘX₃(CH₂)ₘ—, and —(CH₂)ₘX₃(CH₂)ₘS(=O)₂NR₁₂—; wherein, X₁ is self immolative spacer selected from

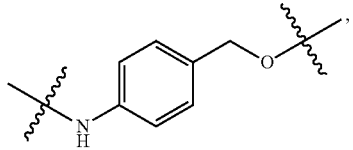

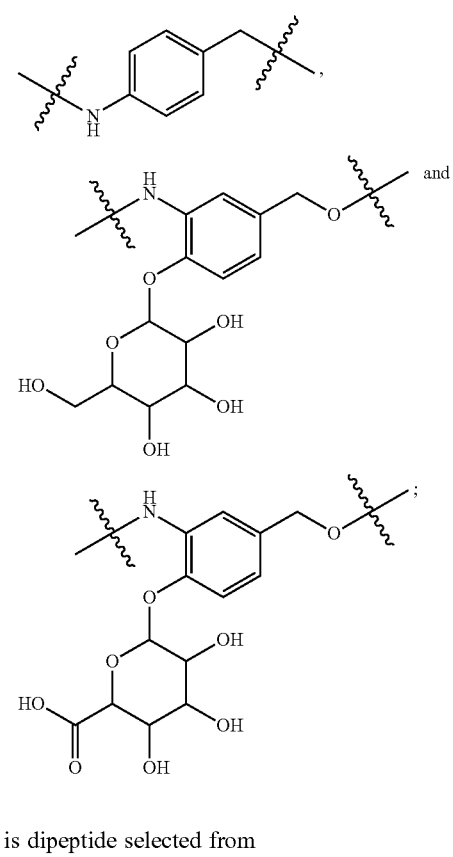

X₂ is dipeptide selected from

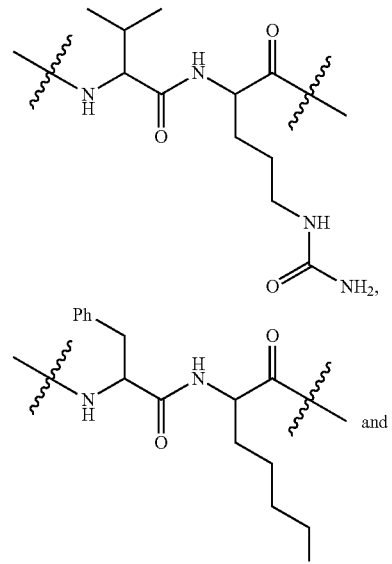

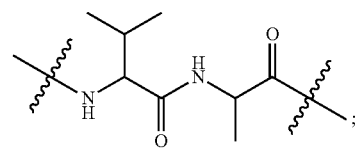

$X_3$ is

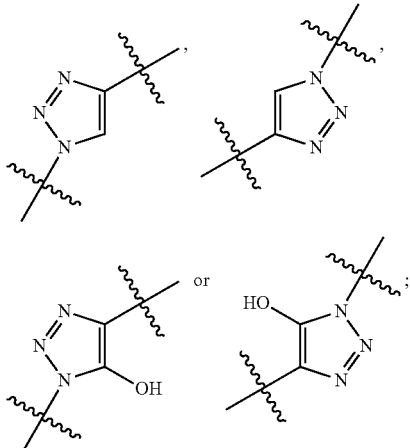

$X_4$ is

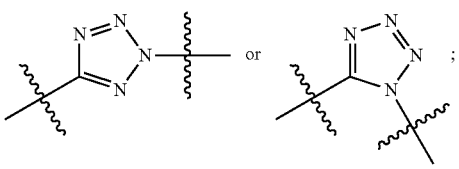

$L_2$, $L_3$, $L_4$, $L_5$, and $L_6$ are each independently selected from a bond and a group shown in Table 2.

92. The compound of any one of embodiments 17 to 56, and the immunoconjugate according to any one of embodiments 57 to 87, wherein $L_1$ is selected from —$(CH_2)_m$—, —C(=O)$(CH_2)_m$—, —NHC(=O)$(CH_2)_m$—, —C(=O)$X_1X_2$C(=O)$(CH_2)_m$—, —C(=O)$X_1X_2$C(=O)$(CH_2)_m$NHC(=O)$(CH_2)_m$—, —C(=O)$X_1X_2$C(=O)$(CH_2)_mX_3(CH_2)_m$—, —C(=O)$X_1X_2$C(=O)$((CH_2)_mO)_n(CH_2)_m$—, —C(=O)$X_1X_2$C(=O)$((CH_2)_mO)_n(CH_2)_m$NHC(=O)$(CH_2)_m$—, —C(=O)$X_1X_2$C(=O)$((CH_2)_mO)_n(CH_2)_m$NHC(=O)$(CH_2)_mX_3(CH_2)_m$—, —C(=O)$X_1X_2$C(=O)$((CH_2)_mO)_n(CH_2)_mX_3(CH_2)_m$—, —C(=O)$X_1X_2$C(=O)$(CH_2)_m$NHC(=O)$((CH_2)_mO)_n(CH_2)_m$—, —C(=O)$X_1X_2$C(=O)$(CH_2)_m$NHC(=O)$((CH_2)_mO)_n(CH_2)_mX_3(CH_2)_m$—, —C(=O)$X_1X_2(CH_2)_mO_n(CH_2)_mX_3(CH_2)_m$—, —C(=O)$X_1X_2((CH_2)_mO)_n(CH_2)_m$NHC(=O)$(CH_2)_m$—, —C(=O)$X_1X_2((CH_2)_mO)_n(CH_2)_m$NHC(=O)$(CH_2)_mX_3(CH_2)_m$—, —C(=O)$X_1X_2((CH_2)_mO)_n(CH_2)_mX_3(CH_2)_m$—, —C(=O)$X_1X_2(CH_2)_m$NH$((CH_2)_mO)_n(CH_2)_m$—, —C(=O)$X_1X_2$C(=O)$(CH_2)_m$NH$((CH_2)_mO)_n(CH_2)_mX_3(CH_2)_m$—, —$(CH_2)_m$NHC(=O)$(CH_2)_m$—, —C(=O)$((CH_2)_mO)_n(CH_2)_m$—, —$(CH_2)_mS$(=O)$_2((CH_2)_mO)_n(CH_2)_n$—, —C(=O)$(CH_2)_m$NH$(CH_2)_m$—, —C(=O)NH$(CH_2)_m$—, —C(=O)NH$(CH_2)_mX_3(CH_2)_m$—, —C(=O)NH$(CH_2)_m$NHC(=O)$X_1X_2$C(=O)$(CH_2)_m$—, —C(=O)XiC(=O)NH$(CH_2)_m$NHC(=O)$(CH_2)_m$—, —C(=O)$X_1$C(=O)NH$(CH_2)_mX_3(CH_2)_m$—, —C(=O)NH$(CH_2)_m$NHC(=O)$(CH_2)_m$—, —C(=O)NH$(CH_2)_m$NHC(=O)$(CH_2)_mX_3(CH_2)_m$—,

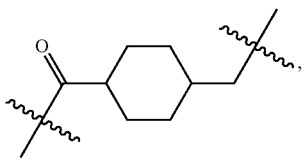

—$(CH_2)_m$C(=O)NH$(CH_2)_m$NHC(=O)$(CH_2)_m$—, —$(CH_2)_m$C(=O)—, —C(=O)$(CH_2)_m$NH$(CH_2)_m$C(=O)$X_2X_1$C(=O)—, —$(CH_2)_mX_3(CH_2)_m$C(=O)$X_2X_1$C(=O)—, —$(CH_2)_m$C(=O)NH$(CH_2)_m$—, —$(CH_2)_m$C(=O)NH$(CH_2)_mX_3(CH_2)_m$—, —$(CH_2)_mX_3(CH_2)_m$NHC(=O)$(CH_2)_m$—, —$(CH_2)_m$C(=O)NH$(CH_2)_mX_3$—, —$X_3(CH_2)_m$NHC(=O)$(CH_2)_m$—, —$(CH_2)_mX_3(CH_2)_m$C(=O)NH$(CH_2)_m$—, —$(CH_2)_m$NHC(=O)$(CH_2)_mX_3(CH_2)_m$—, —$(CH_2)_mO)_n(CH_2)_m$NHC(=O)$(CH_2)_m$—, —$(CH_2)_m$C(=O)NH$(CH_2)_m(O(CH_2)_m)_n$—, —$(CH_2)_m$OC(=O)NH$(CH_2)_mO(CH_2)_m$—, —$(CH_2)_m(O(CH_2)_m)_n$NHC(=O)O$(CH_2)_m$—, —$(CH_2)_m(O(CH_2)_m)_n$C(=O)—, —$(CH_2)_m(O(CH_2)_m)_nS$(=O)$_2(CH_2)_m$—, —$(CH_2)_n$NH$(CH_2)_m$C(=O)—, —$(CH_2)_mO(CH_2)_m$NHC(=O)O$((CH_2)_m$—, —$(CH_2)_m$NHC(=O)—, —$(CH_2)_m$C(=O)$X_2X_1$C(=O)NH$(CH_2)_m$NHC(=O)—, —$(CH_2)_m$C(=O)NH$(CH_2)_m$NHC(=O)$X_1$—, —$(CH_2)_m$C(=O)NH$(CH_2)_m$NHC(=O)—,

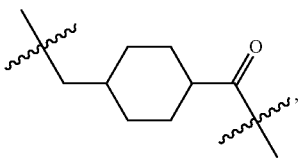

—$((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_m$C(=O)—, —C(=O)$(CH_2)_mX_3(CH_2)_m$—, —$(CH_2)_m$C(=O)NH$(CH_2)_mO)_n(CH_2)_mX_3$—, —$X_3(CH_2)_m(O(CH_2)_m)_n$NHC(=O)$(CH_2)_m$—, —$(CH_2)_m$C(=O)NH$(CH_2)_mO)_n(CH_2)_mX_3(CH_2)_m$—, —$(CH_2)_mX_3(CH_2)_m$(O$(CH_2)_m)_n$NHC(=O)$(CH_2)_m$—, —C(=O)$(CH_2)_mX_3(CH_2)_m$(O$(CH_2)_m)_nC$(=O)—, —C(=O)$((CH_2)_mO)_n(CH_2)_mX_3(CH_2)_m$—, —$(CH_2)_m$C(=O)NH$(CH_2)_m$C(=O)—, —C(=O)$(CH_2)_m$NHC(=O)$(CH_2)_m$—, —$(CH_2)_m$C(=O)NH$(CH_2)_m(O(CH_2)_m)_nC$(=O)—, —C(=O)$((CH_2)_mO)_n(CH_2)_m$NHC(=O)$(CH_2)_m$—, —$(CH_2)_m$C(=O)NH$(CH_2)_m$C(=O)NH$(CH_2)_m$—, —$(CH_2)_m$NHC(=O)$(CH_2)_m$NHC(=O)$(CH_2)_m$—, —C(=O)N H$(CH_2)_m$NHC(=O)—, —$(CH_2)_mS(CH_2)_m$—, —NHC(=O)$(CH_2)_m$—, —NHC(=O)$(CH_2)_mX_3(CH_2)_m$—, —$(CH_2)_mX_3(CH_2)_m$C(=O)NH—, —$(CH_2)_m$C(=O)NH—, —$(CH_2)_m$NH$(CH_2)_m$—, —$(CH_2)_mX_3(CH_2)_m$—, —$(CH_2)_mX_3$—, —$X_3(CH_2)_m$—, —$((CH_2)_mO)_n(CH_2)_mX_3(CH_2)_m$—, —$(CH_2)_mX_3(CH_2)_m(O(CH_2)_m)_n$—NH$(CH_2)_m$—, —NHCH$_2(CH_2)_m$—, —$(CH_2)_m$CH$_2$NH—, —$(CH_2)_m$C(=O)NH$(CH_2)_m$NH—, —$(CH_2)_m$C(=O)NH$(CH_2)_m$NHC(=O)NH—, —$(CH_2)_m$C(=O)NH$(CH_2)_m$NHC(=O)—, —$(CH_2)_m$C(=O)$X_2X_1$C(=O)—, —NH$(CH_2)_m$NHC(=O)$(CH_2)_m$—, —NHCH$_2(CH_2)_m$NHC(=O)$(CH_2)_m$—, —$(CH_2)_m$C(=O)NH$(CH_2)_m$CH$_2$NH—, —NH$(CH_2)_mX_3(CH_2)_m$—, —NHCH$_2(CH_2)_mX_3(CH_2)_m$—, —$(CH_2)_mX_3(CH_2)_m$CH$_2$NH—, —NHCH$_2(CH_2)_m$OC(=O)NH (CH₂)ₘ—, —(CH₂)ₘNHC(=O)O(CH₂)ₘCH₂NH—, —NHCH₂(CH₂)ₘOC(=O)NH(CH₂)ₘX₃(CH₂)ₘ—, —(CH₂)ₘX₃(CH₂)ₘNHC(=O)O(CH₂)ₘCH₂NH—, —NHCH₂(CH₂)ₘOC(=O)NH((CH₂)ₘO)ₙ(CH₂)ₘ—, —(CH₂)ₘ(O(CH₂)ₘ)ₙNHC(=O)O(CH₂)ₘCH₂NH—, —NHCH₂(CH₂)ₘOC(=O)NH((CH₂)ₘO)ₙ(CH₂)ₘX₃(CH₂)ₘ—, —(CH₂)ₘX₃(CH₂)ₘ(O(CH₂)ₘ)ₙNHC(=O)O(CH₂)ₘCH₂NH—, —(CH₂)ₘX₃(CH₂)ₘNH—, —NH((CH₂)ₘO)ₙ(CH₂)ₘX₃(CH₂)ₘ—, —(CH₂)ₘX₃(CH₂)ₘ(O(CH₂)ₘ)ₙNH—, —(CH₂)ₘNH—, —NH((CH₂)ₘO)ₙ(CH₂)ₘ—, —NH((CH₂)ₘO)ₙ(CH₂)ₘNHC(=O)(CH₂)ₘ—, —(CH₂)ₘC(=O)NH(CH₂)ₘ(O(CH₂)ₘ)ₙNH—, —(CH₂)ₘ(O(CH₂)ₘ)ₙNH—, —(CH₂)ₘ—, —(CH₂CH₂O)ₙ—, —(OCH₂CH₂)ₙ—, —(CH₂)ₘO(CH₂)ₘ—, —S(=O)₂(CH₂)ₘ—, —(CH₁₂)ₘS(=O)₂—, —S(=O)₂(CH₂)ₘNHC(=O)(CH₂)ₘ—, —(CH₂)ₘC(=O)NH(CH₂)ₘS(=O)₂—, —S(=O)₂(CH₂)ₘX₃(CH₂)ₘ—, —(CH₂)ₘX₃(CH₂)ₘS(=O)₂—, —(CH₂)ₘX₂X₁C(=O)—, —C(=O)X₁X₂(CH₂)ₘ—, —(CH₂)ₘ(O(CH₂)ₘ)ₙC(=O)X₂X₁C(=O)—, —C(=O)X₁X₂C(=O)((CH₂)ₘO)ₙ(CH₂)ₘ—, —(CH₂)ₘ(O(CH₂)ₘ)ₙX₂X₁C(=O)—, —(CH₂)ₘX₃(CH₂)ₘX₂X₁C(=O)—, —C(=O)X₁X₂(CH₂)ₘX₃(CH₂)ₘ—, —(CH₂)ₘX₃(CH₂)ₘ(O(CH₂)ₘ)ₙX₂X₁C(=O)—, —(CH₂)ₘX₃(CH₂)ₘC(=O)NH(CH₂)ₘNHC(=O)—, —(CH₂)ₘX₃(CH₂)ₘC(=O)NH(CH₂)ₘC(=O)—, —C(=O)(CH₂)ₘNHC(=O)(CH₂)ₘX₃(CH₂)ₘ—, —(CH₂)ₘX₃(CH₂)ₘC(=O)NH(CH₂)ₘ(O(CH₂)ₘ)ₙC(=O)—, —C(=O)((CH₂)ₘO)ₙ(CH₂)ₘNHC(=O)(CH₂)ₘX₃(CH₂)ₘ—, —(CH₂)ₘNHC(=O)X₁X₂C(=O)(CH₂)ₘ—, —(CH₂)ₘC(=O)X₂X₁C(=O)NH(CH₂)ₘ—, —X₄X₁X₂C(=O)(CH₂)ₘ—, —(CH₂)ₘC(=O)X₂X₁X₄—, —X₁C(=O)(CH₂)ₘNHC(=O)(CH₂)ₘ—, —(CH₂)ₘC(=O)NH(CH₂)ₘC(=O)X₁—, —C(=O)CHR$^{aa}$NH—, —NHCHR$^{aa}$C(=O)—, —C(=O)NH—, —C(=O)O—, —S—, —SCH₂(C=O)NH—, —NHC(=O)CH₂S—, —S(=O)₂CH₂CH₂S—, —SCH₂CH₂S(=O)₂—, —(CH₂)₂S(=O)₂CH₂CH₂S—, —SCH₂CH₂S(=O)₂CH₂CH₂—, —NHC(=S)—, —(CH₂)ₘX₃(O(CH₂)ₘ)ₙC(=O)—, —C(=O)((CH₂)ₘO)ₙX₃(CH₂)ₘ—, —(CH₂)ₘNHC(=O)((CH₂)ₘO)ₙ(CH₂)ₘ—, —(CH₂)ₘ(O(CH₂)ₘ)ₙC(=O)NH(CH₂)ₘ—, —(CH₂)ₘNHC(=O)NH(CH₂)ₘ—, —(CH₂)ₘX₃(CH₂)ₘNHC(=O)—, —C(=O)NH(CH₂)ₘX₃(CH₂)ₘ—, —NHS(=O)₂(CH₂)ₘX₃(CH₂)ₘ—, and —(CH₂)ₘX₃(CH₂)ₘS(=O)₂NH—;

X₁ is self immolative spacer selected from

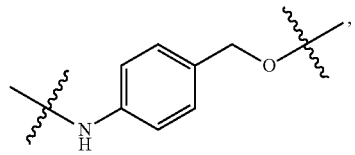

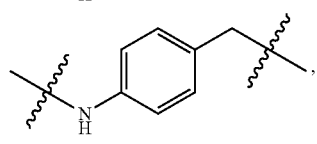

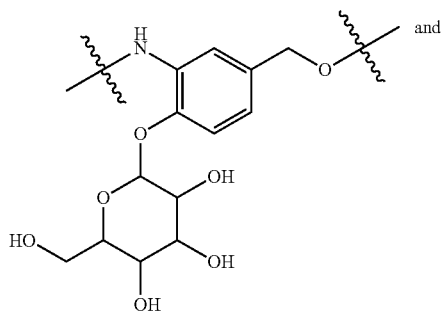 and

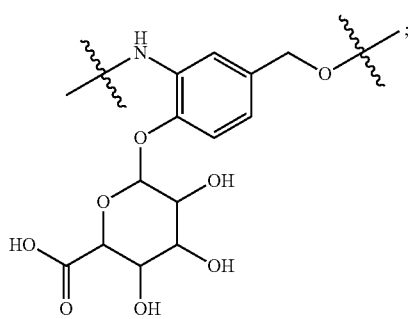;

X₂ is dipeptide selected from

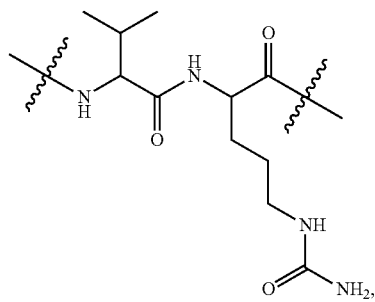

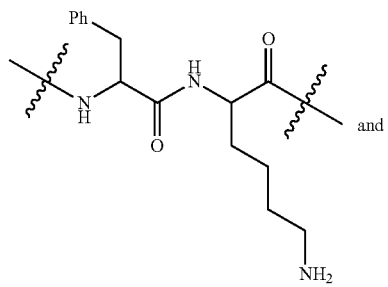 and

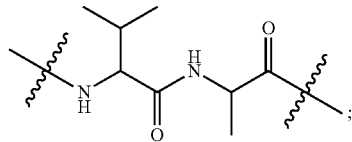;

$X_3$ is

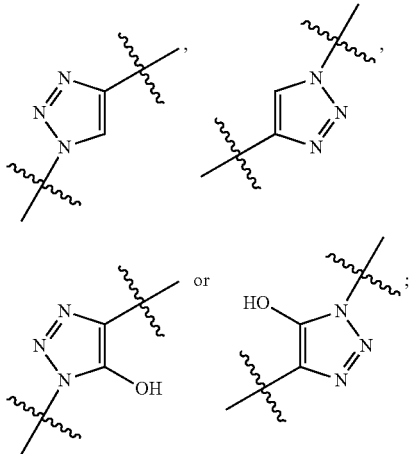

$X_4$ is

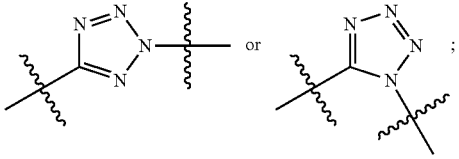

$L_2$, $L_3$, $L_4$, $L_5$, and $L_6$ are each independently selected from a bond and a group shown in Table 2.

93. The compound of any one of embodiments 17 to 56, wherein L is -$L_1$- and -$L_1$- is selected from —$(CH_2)_mC(=O)$—, —$C(=O)(CH_2)_m$—, —$(CH_2)_m$—, —$(CH_2)_mC(=O)X_2X_1C(=O)$—, —$C(=O)X_1X_2C(=O)(CH_2)_m$—, —$(CH_2)_m(O(CH_2)_m)_nC(=O)$—, —$C(=O)((CH_2)_mO)_n(CH_2)_m$—, —$(CH_2)_mX_3(O(CH_2)_m)_nC(=O)$—, —$C(=O)((CH_2)_mO)_nX_3(CH_2)_m$—,

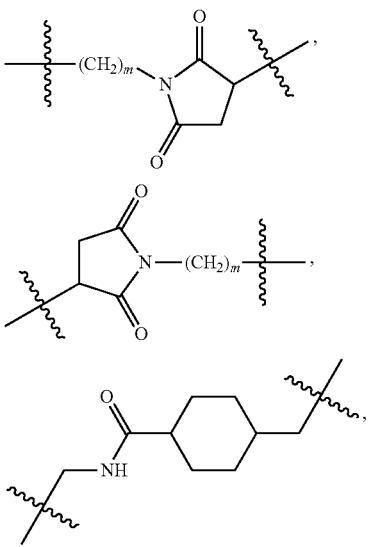

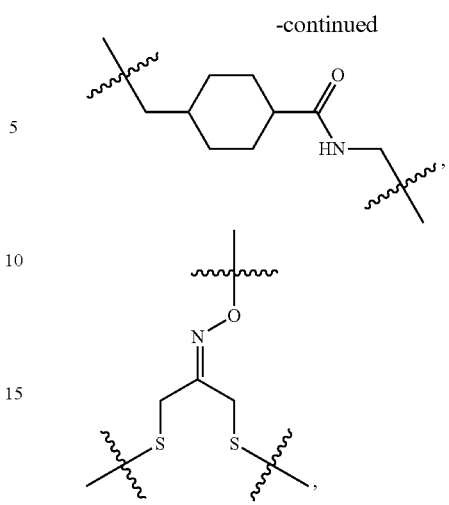

—$(CH_2)_m(O(CH_2)_m)_nS(=O)_2(CH_2)_m$—, —$(CH_2)_mS(=O)_2((CH_2)_mO)_n(CH_2)_m$—, —$(CH_2)_mNH(CH_2)_mC(=O)$—, —$C(=O)(CH_2)_mNH(CH_2)_m$—, —$(CH_2)_mNR^{12}(CH_2)_mC(=O)$—, —$C(=O)(CH_2)_mNR^{12}(CH_2)_m$—, —$(CH_2)_mC(=O)NR^{12}(CH_2)_m$—, —$(CH_2)_mC(=O)NH(CH_2)_m$—, —$(CH_2)_mNR^{12}C(=O)(CH_2)_m$—, —$(CH_2)_mNHC(=O)(CH_2)_m$—, —$C(=O)NR^{12}(CH_2)_mNR^{12}C(=O)(CH_2)_m$—, —$(CH_2)_mNHC(=O)((CH_2)_mO)_n(CH_2)_m$—, —$(CH_2)_m(O(CH_2)_m)_nC(=O)NH(CH_2)_m$—, —$(CH_2)_mNHC(=O)NH(CH_2)_m$—, —$(CH_2)_mS(=O)_2$—, —$S(=O)_2(CH_2)_m$—, —$(CH_2)_mX_3(CH_2)_mS(=O)_2$—, —$S(=O)_2(CH_2)_mX_3(CH_2)_m$—, —$(CH_2)_mNHC(=O)(CH_2)_mX_3(CH_2)_m$—, —$(CH_2)_mX_3(CH_2)_mC(=O)NH(CH_2)_m$—, —$(CH_2)_mX_2X_1C(=O)$—, —$C(=O)X_1X_2(CH_2)_m$—, —$(CH_2)_m(O(CH_2)_m)_nC(=O)X_2X_1C(=O)$—, —$C(=O)X_1X_2C(=O)((CH_2)_mO)_n(CH_2)_m$—, —$(CH_2)_m(O(CH_2)_m)_nX_2X_1C(=O)$—, —$C(=O)X_1X_2((CH_2)_mO)_n(CH_2)_m$—, —$(CH_2)_m(O(CH_2)_m)_nS(=O)_2(CH_2)_m$—, —$(CH_2)_mS(=O)_2((CH_2)_mO)_n(CH_2)_m$—, —$((CH_2)_mO)_n(CH_2)_m$—, —$(CH_2)_m(O(CH_2)_m)_n$—, —$(CH_2)_mX_3(CH_2)_m$—, —$(CH_2)_mX_3(CH_2)_mC(=O)$—, —$C(=O)(CH_2)_mX_3(CH_2)_m$—, —$(CH_2)_mX_3(CH_2)_mC(=O)X_2X_1C(=O)$—, —$C(=O)X_1X_2C(=O)(CH_2)_mX_3(CH_2)_m$—, —$(CH_2)_mX_3(CH_2)_mX_2X_1C(=O)$—, —$C(=O)X_1X_2(CH_2)_mX_3(CH_2)_m$—, —$(CH_2)_mX_3(CH_2)_m(O(CH_2)_m)_nX_2X_1C(=O)$—, —$C(=O)X_1X_2((CH_2)_mO)_n(CH_2)_mX_3(CH_2)_m$—, —$(CH_2)_mNHC(=O)$—, —$C(=O)NH(CH_2)_m$—, —$(CH_2)_mX_3(CH_2)_m(O(CH_2)_m)_nC(=O)$—, —$C(=O)((CH_2)_mO)_n(CH_2)_mX_3(CH_2)_m$—, —$(CH_2)_mX_3((CH_2)_mO)_n(CH_2)_m$—, —$(CH_2)_m(O(CH_2)_m)_nX_3(CH_2)_m$—, —$(CH_2)_mX_3(CH_2)_mC(=O)NH(CH_2)_m$—, —$(CH_2)_mNHC(=O)(CH_2)_mX_3(CH_2)_m$—, —$(CH_2)_mC(=O)NR^{12}(CH_2)_mNR^{12}C(=O)$—, —$(CH_2)_mC(=O)NH(CH_2)_mNHC(=O)$—, —$((CH_2)_mO)_n(CH_2)_mX_3(CH_2)_m$—, —$(CH_2)_mX_3(CH_2)_m(O(CH_2)_m)_n$—, —$NR^{12}C(R^{12})_2(CH_2)_mOC(=O)NR^{12}((CH_2)_mO)_n(CH_2)_m$—, —$(CH_2)_m(O(CH_2)_m)_nNR^{12}C(=O)O(CH_2)_mC(R^{12})_2NR^{12}$—, —$NR^{12}((CH_2)_mO)_n(CH_2)_mNR^{12}C(=O)(CH_2)_m$—, —$(CH_2)_mC(=O)NR^{12}(CH_2)_m(O(CH_2)_m)_nNR^{12}$—, —$C(=O)NH(CH_2)_mNHC(=O)(CH_2)_m$—, —$(CH_2)_mX_3(CH_2)_mNHC(=O)$—, —$C(=O)NH(CH_2)_mX_3(CH_2)_m$—, —$(CH_2)_mC(=O)NH(CH_2)_mC(=O)$—, —$C(=O)(CH_2)_mNHC(=O)(CH_2)_m$—, —$(CH_2)_mX_3(CH_2)_mC(=O)NH(CH_2)_mNHC(=O)$—, —$C(=O)NH(CH_2)_mNHC(=O)(CH_2)_mX_3$ $-(CH_2)_m-$, $-(CH_2)_mX_3(CH_2)_mC(=O)NH(CH_2)_mC(=O)-$, $-C(=O)(CH_2)_mNHC(=O)(CH_2)_mX_3(CH_2)_m-$, $-(CH_2)_mC(=O)NH(CH_2)_mO(CH_2)_m)_nC(=O)-$, $-C(=O)((CH_2)_mO)_n(CH_2)_mNHC(=O)(CH_2)_m-$, $-(CH_2)_mX_3(CH_2)_mC(=O)NH(CH_2)_m(O(CH_2)_m)_nC(=O)-$, $-C(=O)((CH_2)_mO)_n(CH_2)_mNHC(=O)(CH_2)_mX_3(CH_2)_m$, $-(CH_2)_mC(=O)NH(CH_2)_mNHC(=O)(CH_2)_m-$, $-(CH_2)_mC(=O)NH(CH_2)_mC(=O)NH(CH_2)_m-$, $-(CH_2)_mNHC(=O)(CH_2)_mNHC(=O)(CH_2)_m$, $-NR_{12}S(=O)_2(CH_2)_mX_3(CH_2)_m-$, $-(CH_2)_mX_3(CH_2)_mS(=O)_2NR_{12}-$, $-(CH_2)_mX_3(CH_2)_mC(=O)NH(CH_2)_m-$ and $-(CH_2)_mNHC(=O)(CH_2)_mX_3(CH_2)_m-$.

94. The compound of any one of embodiments 17 to 56, wherein L is -$L_1$- and -$L_1$- is selected $-(CH_2)_mC(=O)-$, $-C(=O)(CH_2)_m-$, $-(CH_2)_m-$, $-(CH_2)_mC(=O)X_2X_1C(=O)-$, $-C(=O)X_1X_2C(=O)(CH_2)_m-$, $-(CH_2)_m(O(CH_2)_m)_nC(=O)-$, $-C(=O)((CH_2)_mO)_n(CH_2)_m-$, $-(CH_2)_mX_3(O(CH_2)_m)_nC(=O)-$, $-C(=O)((CH_2)_mO)_nX_3(CH_2)_m-$,

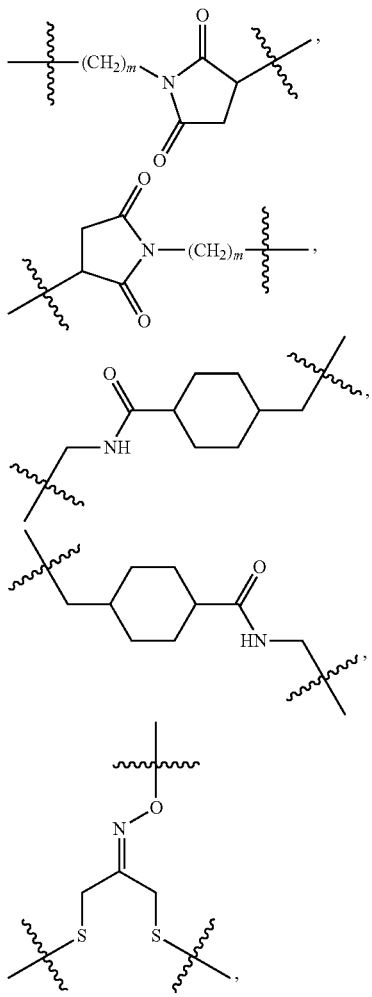

$-(CH_2)_m(O(CH_2)_m)_nS(=O)_2(CH_2)_m-$, $-(CH_2)_mS(=O)_2((CH_2)_mO)_n(CH_2)_m-$, $-(CH_2)_mNH(CH_2)_mC(=O)-$, $-C(=O)(CH_2)_mNH(CH_2)_m-$, $-(CH_2)_mNR^{12}(CH_2)_mC(=O)-$, $-C(=O)(CH_2)_mNR^{12}(CH_2)_m-$, $-(CH_2)_mC(=O)NR^{12}(CH_2)_m-$, $-(CH_2)_mC(=O)NH(CH_2)_m-$, $-(CH_2)_mNR^{12}C(=O)(CH_2)_m-$, $-(CH_2)_mNHC(=O)(CH_2)_m-$, $-(CH_2)_mNR^{12}C(=O)-$, $-(CH_2)_mC(=O)NR^{12}(CH_2)_m-$, $-(CH_2)_mC(=O)NH(CH_2)_mNHC(=O)-$, $-(CH_2)_mX_3(CH_2)_mC(=O)-$, $-C(=O)(CH_2)_mX_3(CH_2)_m-$, $-(CH_2)_mX_3(CH_2)_m-$, $-((CH_2)_mO)_n(CH_2)_mX_3(CH_2)_m-$, $-(CH_2)_mX_3(CH_2)_m(O(CH_2)_m)_n-$, $-NR^{12}C(R^{12})_2(CH_2)_mOC(=O)NR^{12}((CH_2)_mO)_n(CH_2)_m-$, $-(CH_2)_m(O(CH_2)_m)_nNR^{12}C(=O)OC(CH_2)_mC(R^{12})_2NR^{12}-$, $-NR^{12}((CH_2)_mO)_n(CH_2)_mNR^{12}C(=O)(CH_2)_m-$, $-(CH_2)_mC(=O)NR^{12}(CH_2)_m(O(CH_2)_m)_nNR^{12}-$, $-(CH_2)_mNR^{12}C(=O)(CH_2)_m-$, $-(CH_2)_mC(=O)NR^{12}(CH_2)_m-$, $-(CH_2)_m(O(CH_2)_m)_nNR^{12}-$, $-C(=O)NR^{12}(CH_2)_m-$, $-(CH_2)_mNR^{12}C(=O)(CH_2)_m-$, $-(CH_2)_mNHC(=O)(CH_2)_m-$, $-((CH_2)_mO)_n(CH_2)_m-$, $-(CH_2)_mO(CH_2)_m)_nC(=O)NH(CH_2)_m-$, $-(CH_2)_mNHC(=O)NH(CH_2)_m-$, $-(CH_2)_mS(=O)_2-$, $-S(=O)_2(CH_2)_m-$, $-(CH_2)_mX_3(CH_2)_mS(=O)_2-$ and $-S(=O)_2(CH_2)_mX_3(CH_2)_m-$.

95. The compound of any one of embodiments 17 to 56, wherein L is -$L_1$- and -$L_1$- is selected from $-(CH_2)_mC(=O)-$, $-C(=O)(CH_2)_m-$, $-(CH_2)_mC(=O)NR^{12}(CH_2)_m-$, $-(CH_2)_mC(=O)NH(CH_2)_m-$, $-(CH_2)_mNR^{12}C(=O)(CH_2)_m-$, $-(CH_2)_mNHC(=O)(CH_2)_m-$, $-(CH_2)_mC(=O)NR^{12}(CH_2)_mNR^{12}C(=O)-$, $-(CH_2)_mC(=O)NH(CH_2)_mNHC(=O)-$, $-(CH_2)_mX_3(CH_2)_mC(=O)-$, $-C(=O)(CH_2)_mX_3(CH_2)_m-$, $-((CH_2)_mO)_n(CH_2)_mX_3(CH_2)_m-$, $-(CH_2)_mX_3(CH_2)_m(O(CH_2)_m)_n-$, $-NR^{12}C(R^{12})_2(CH_2)_mOC(=O)NR^{12}((CH_2)_mO)_n(CH_2)_m-$, $-(CH_2)_m(O(CH_2)_m)_nNR^{12}C(=O)O(CH_2)_mC(R^{12})_2NR^{12}-$, $-NR^{12}((CH_2)_mO)_n(CH_2)_mNR^{12}C(=O)(CH_2)_m-$, and $-(CH_2)_mC(=O)NR^{12}(CH_2)_m(O(CH_2)_m)_nNR^{12}-$.

96. The compound of any one of embodiments 17 to 56, and the immunoconjugate according to any one of embodiments 57 to 73, wherein $L_1$ is $-(CH_2)_mNHC(=O)(CH_2)_mX_3(CH_2)_m*-$, $-(CH_2)_mC(=O)*-$, $-(CH_2)_m-$, $-(CH_2)_mC(=O)X_2X_1C(=O)*-$, $-(CH_2)_mX_2X_1C(=O)*-$, $-(CH_2)_m(O(CH_2)_m)_nC(=O)*-$, $-(CH_2)_m(O(CH_2)_m)_nC(=O)X_2X_1C(=O)*-$, $-(CH_2)_m(O(CH_2)_m)_nX_2X_1C(=O)*-$, $-(CH_2)_m(O(CH_2)_m)_nS(=O)_2(CH_2)_m*-$, $-(CH_2)_mNR^{12}(CH_2)_mC(=O)*-$, $-X_3(CH_2)_m*-$, $-(CH_2)_mC(=O)NH*-$, $-(CH_2)_mNH(CH_2)_mC(=O)*-$, $-((CH_2)_mO)_n(CH_2)_m*-$, $-(CH_2)_mX_3(CH_2)_mC(=O)*-$, $-(CH_2)_mC(=O)NR^{12}(CH_2)_mNR^{12}*-$, $-(CH_2)_mC(=O)NR^{12}(CH_2)_mNR^{12}C(=O)NH*-$, $-(CH_2)_mX_3(CH_2)_m-$, $-(CH_2)_mX_3(CH_2)_mC(=O)X_2X_1C(=O)*-$, $-(CH_2)_mX_3(CH_2)_mX_2X_1C(=O)*-$, $-(CH_2)_mX_3(CH_2)_m(O(CH_2)_m)_nX_2X_1C(=O)*-$, $-(CH_2)_mNHC(=O)*-$, $-(CH_2)_mX_3(CH_2)_m(O(CH_2)_m)_nC(=O)*-$, $-(CH_2)_mX_3((CH_2)_mO)_n(CH_2)_m*-$, $-(CH_2)_mC(=O)NH(CH_2)_m*-$, $-(CH_2)_mX_3(CH_2)_mC(=O)NH(CH_2)_m*-$, $-(CH_2)_mC(=O)NH(CH_2)_mNHC(=O)*-$, $-(CH_2)_mX_3(CH_2)_mNHC(=O)*-$, $-(CH_2)_mC(=O)NH(CH_2)_mC(=O)*-$, $-(CH_2)_mX_3(CH_2)_mC(=O)NH(CH_2)_mNHC(=O)*-$, $-(CH_2)_mX_3(CH_2)_mC(=O)NH(CH_2)_mC(=O)*-$, $-(CH_2)_mC(=O)NH(CH_2)_m(O(CH_2)_m)_nC(=O)*-$, $-(CH_2)_mX_3(CH_2)_mC(=O)NH(CH_2)_m(O(CH_2)_m)_nC(=O)*-$, $-(CH_2)_mC(=O)NH(CH_2)_mNHC(=O)(CH_2)_m*-$, $-(CH_2)_mX_3(CH_2)_mNHC(=O)(CH_2)_m*-$, $-X_3(CH_2)_mNHC(=O)(CH_2)_m*-$, $-(CH_2)_m(O(CH_2)_m)_n*-$, $-(CH_2)_mC(=O)NH(CH_2)_m(O(CH_2)_m)_n*-$, $-X_3(CH_2)_m(O(CH_2)_m)_nNHC(=O)(CH_2)_m*-$, $-(CH_2)_mX_3(CH_2)_m(O(CH_2)_m)_nNHC(=O)(CH_2)_m*-$, $-(CH_2)_mC(=O)NH(CH_2)_mC(=O)NH(CH_2)_m*-$, $-(CH_2)_mX_3(CH_2)_mC(=O)NH(CH_2)_m*-$, $-(CH_2)_mO(CH_2)_mNHC(=O)O((C(R^{12})_2)_m*-$, $-(CH_2)_mS(=O)_2*-$ or $-(CH_2)_mX_3(CH_2)_mS(=O)_2*-$, wherein in the immunoconjugate embodiments the * indicates the point of attachment to $R^{101}$;

$L_2$ is

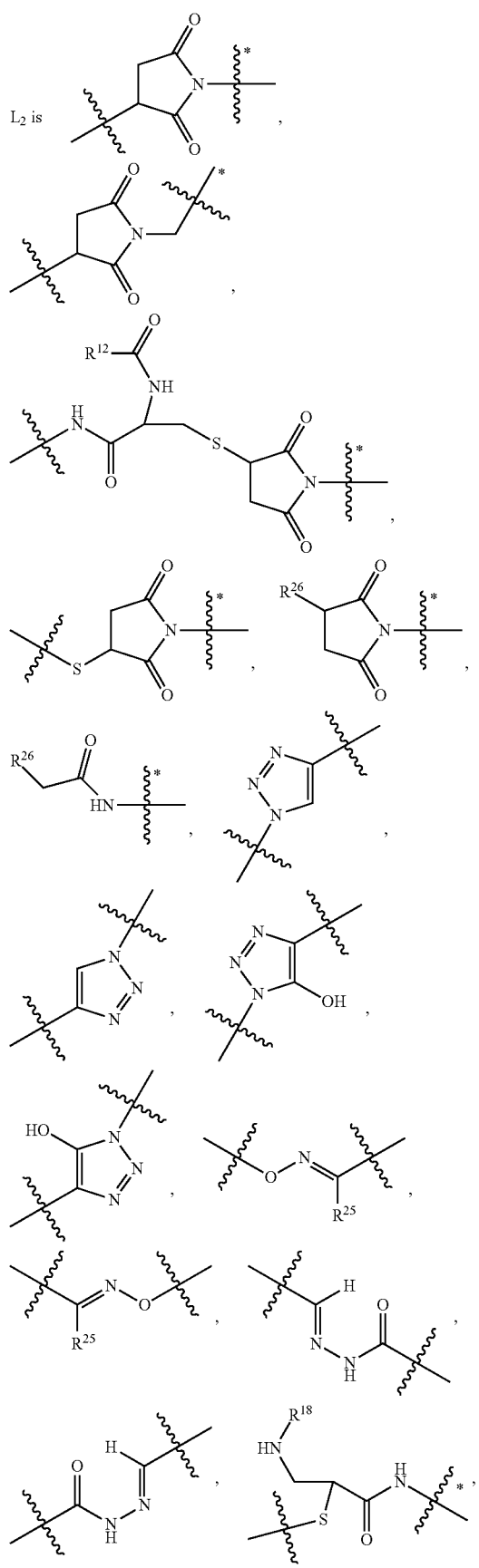

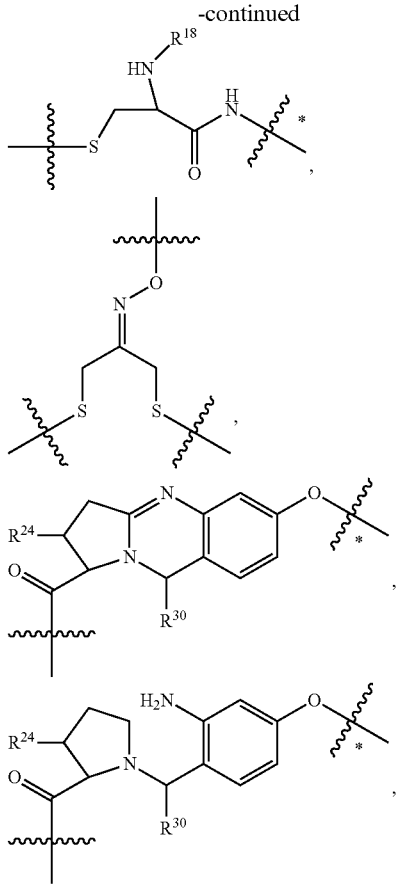

—S—, —SCH$_2$C(=O)NH—, —NHC(=O)CH$_2$S—, —NH(=O)CH$_2$CH$_2$S—, —SCH$_2$CH$_2$C(=O)NH—, —S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * of $L_2$ indicates the point of attachment to $L_1$;

and $L_3$, $L_4$, $L_5$ and $L_6$ are a bond.

97. The compound of any one of embodiments 17 to 56, and the immunoconjugate according to any one of embodiments 57 to 73, wherein $L_1$ is selected from —(CH$_2$)$_m$C(=O)*—, —(CH$_2$)$_m$X$_3$(CH$_2$)$_m$C(=O)*—, —(CH$_2$)$_m$C(=O)NR$^{12}$(CH$_2$)$_m$NR$^{12}$*—, —(CH$_2$)$_m$C(=O)NR$^{12}$(CH$_2$)$_m$NR$^{12}$C(=O)NH*—, —(CH$_2$)$_m$C(=O)NH(CH$_2$)$_m$NHC(=O)*—, —(CH$_2$)$_m$—, —(CH$_2$)$_m$C(=O)X$_2$X$_1$C(=O)*—, —(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*—, —(CH$_2$)$_m$NR$^{12}$(CH$_2$)$_m$C(=O)*—, —X$_3$(CH$_2$)$_m$*—, —(CH$_2$)$_m$C(=O)NH*—, —(CH$_2$)$_m$C(=O)NH(CH$_2$)$_m$NHC(=O)(CH$_2$)$_m$*—, —(CH$_2$)$_m$X$_3$(CH$_2$)$_m$NHC(=O)(CH$_2$)$_m$*—, —X$_3$(CH$_2$)$_m$NHC(=O)(CH$_2$)$_m$*—, —(CH$_2$)$_m$(O(CH$_2$)$_m$)$_n$*—, —(CH$_2$)$_m$C(=O)NH(CH$_2$)$_m$(O(CH$_2$)$_m$)$_n$*—, —(CH$_2$)$_m$O(CH$_2$)$_m$NHC(=O)O((C(R$^{12}$)$_2$)$_m$*—, —X$_3$(CH$_2$)$_m$(O(CH$_2$)$_m$)$_n$NHC(=O)(CH$_2$)$_m$*— and —(CH$_2$)$_m$X$_3$(CH$_2$)$_m$(O(CH$_2$)$_m$)$_n$NHC(=O)(CH$_2$)$_m$*—, wherein in the immunoconjugate embodiments the * indicates the point of attachment to $R^{101}$;

$L_2$

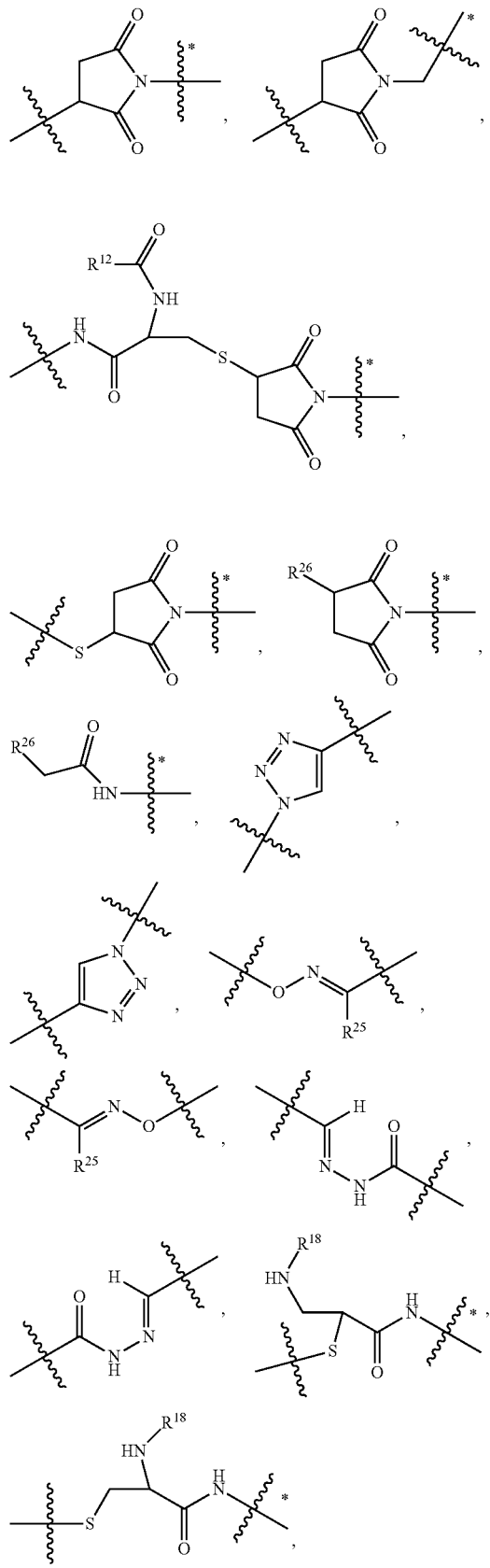

-continued

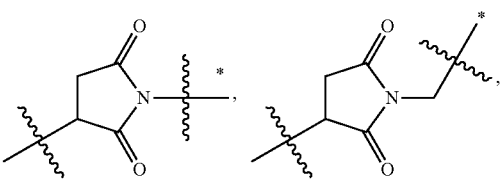

—S—, —SCH$_2$C(=O)NH—, —NHC(=O)CH$_2$S—, —NH(=O)CH$_2$CH$_2$S—, —SCH$_2$CH$_2$C(=O)NH—, —S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * of $L_2$ indicates the point of attachment to $L_1$, and $L_3$, $L_4$, $L_5$ and $L_6$ are a bond.

98. The compound of any one of embodiments 17 to 56, and the immunoconjugate according to any one of embodiments 57 to 73, wherein $L_1$ is selected from —(CH$_2$)$_m$C(=O)*—, —(CH$_2$)$_m$X$_3$(CH$_2$)$_m$C(=O)*—, —(CH$_2$)$_m$C(=O)NR$^{12}$(CH$_2$)$_m$NR$^{12}$*—, —(CH$_2$)$_m$C(=O)NR$^{12}$(CH$_2$)$_m$NR$^{12}$C(=O)NH*—, —(CH$_2$)$_m$C(=O)NH(CH$_2$)$_m$NHC(=O)*—, —(CH$_2$)$_m$—, —(CH$_2$)$_m$C(=O)X$_2$X$_1$C(=O)*—, —(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*—, —(CH$_2$)$_m$NR$^{12}$(CH$_2$)$_m$C(=O)*—, —X$_3$(CH$_2$)$_m$*—, —(CH$_2$)$_m$C(=O)NH*—, —(CH$_2$)$_m$C(=O)NH(CH$_2$)$_m$NHC(=O)(CH$_2$)$_m$*—, —(CH$_2$)$_m$X$_3$(CH$_2$)$_m$NHC(=O)(CH$_2$)$_m$*—, —X$_3$(CH$_2$)$_m$NHC(=O)(CH$_2$)$_m$*—, —(CH$_2$)$_m$(O(CH$_2$)$_m$)$_n$*—, —(CH$_2$)$_m$C(=O)NH(CH$_2$)$_m$(O(CH$_2$)$_m$)$_n$*—, —(CH$_2$)$_m$O(CH$_2$)$_m$NHC(=O)O((CR$^{12}$)$_2$)$_m$*—, —X$_3$(CH$_2$)$_m$(O(CH$_2$)$_m$)$_n$NHC(=O)(CH$_2$)$_m$*— and —(CH$_2$)$_m$X$_3$(CH$_2$)$_m$(O(CH$_2$)$_m$)$_n$NHC(=O)(CH$_2$)$_m$*—, wherein in the immunoconjugate embodiments the * indicates the point of attachment to $R^{101}$;

$L_2$ is

-continued

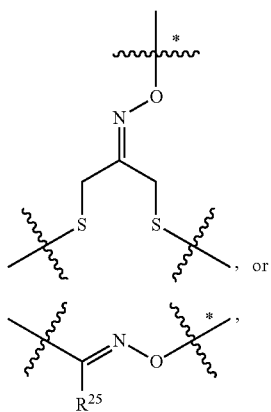

, or wherein the * of L₂ indicates the point of attachment to L₁,
and L₃, L₄, L₅ and L₆ are a bond.

99. The compound of any one of embodiments 17 to 56, and the immunoconjugate according to any one of embodiments 57 to 73, L₁ is selected from —(CH₂)$_m$C(=O)*—, —(CH₂)$_m$X₃(CH₂)$_m$C(=O)*—, —(CH₂)—C(=O)NR¹² (CH₂)$_m$NR¹²*—, —(CH₂)$_m$C(=O)NR¹²(CH₂)$_m$NR¹²C (=O)NH*—, and —(CH₂)$_m$C(=O)NH(CH₂)$_m$NHC (=O)*—, wherein in the immunoconjugate embodiments the * indicates the point of attachment to R¹⁰¹;

L₂ is

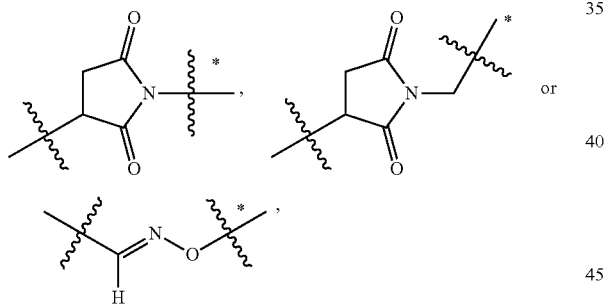

wherein the * of L₂ indicates the point of attachment to L₁,
and L₃, L₄, L₅ and L₆ are a bond.

100. The compound of any one of embodiments 17 to 56, and the immunoconjugate according to any one of embodiments 74 to 87, wherein L₁ is selected from —*(CH₂)$_m$X₃(CH₂)$_m$—, —*(CH₂)$_m$X₃—, —*C(=O) (CH₂),—, -*NHC(=O)(CH₂)$_m$—, —(CH₂)$_m$—, —*(CH₂)$_m$C(=O)NH(CH₂)$_m$NHC(=O)(CH₂)$_m$—, —*(CH₂)$_m$C(=O)NH(CH₂)$_m$X₃(CH₂)$_m$—, —*(CH₂)$_m$C (=O)NH(CH₂)$_m$X₃—, —*(CH₂)$_m$O)$_n$(CH₂)$_m$—, —*(CH₂)$_m$O)$_n$(CH₂)$_m$NHC(=O)(CH₂)$_m$—, —*((C (R¹²)₂)$_m$OC(=O)NH(CH₂)$_m$O(CH₂)$_m$—, —*(CH₂)$_m$C (=O)NH(CH₂)$_m$O)$_n$(CH₂)$_m$X₃—, —*(CH₂)$_m$C(=O)NH (CH₂)$_m$O)$_n$(CH₂)$_m$X₃(CH₂)$_m$—, —*(CH₂)$_m$NHC(=O) X₁X₂C(=O)(CH₂)$_m$—, —*X₄X₁X₂C(=O)(CH₂)$_m$—, —*X₁C(=O)(CH₂)$_m$NHC(=O)(CH₂)$_m$—, —*S(=O)₂ (CH₂)mX₃(CH₂)$_m$—, —*C(=O)((CH₂)$_m$O)$_n$(CH₂)$_m$—, —*C(=O)NH (CH₂)$_m$—, —*C(=O)X₁X₂C(=O)(CH₂)$_m$—, —*C (=O)((CH₂)$_m$O)$_n$(CH₂)$_m$—, —*(CH₂)$_m$S(=O)₂ ((CH₂)$_m$O)$_n$(CH₂)$_m$—, —*C(=O)(CH₂)$_m$NR¹² (CH₂)$_m$—, —*C(=O)(CH₂)$_m$NH(CH₂)$_m$—, —*(CH₂)$_m$ (O(CH₂)$_m$)$_n$—, —*C(=O)(CH₂)$_m$X₃(CH₂)$_m$—, —*C (=O)NH(CH₂)$_m$—, —*C(=O)((CH₂)$_m$O)$_n$(CH₂)$_m$X₃ (CH₂)$_m$—, —*(CH₂)$_m$NHC(=O)(CH₂)$_m$—, —*C(=O) NH(CH₂)$_m$NHC(=O)(CH₂)$_m$—, —*C(=O) (CH₂)$_m$NHC(=O)(CH₂)$_m$—, —*C(=O)((CH₂)$_m$O)$_n$ (CH₂)$_m$NHC(=O)(CH₂)$_m$—, —(CH₂)$_m$C(=O)NH (CH₂)$_m$NHC(=O)(CH₂)$_m$—, —*NH₂S(=O)₂(CH₂)$_m$X₃ (CH₂)$_m$—, —*(CH₂)$_m$NHC(=O)(CH₂)$_m$NHC(=O) (CH₂)$_m$— and —C(=O)NH(CH₂)$_m$NHC(=O)—, wherein in the immunoconjugate embodiments the * indicates the point of attachment to R³;

L₂ is a bond,

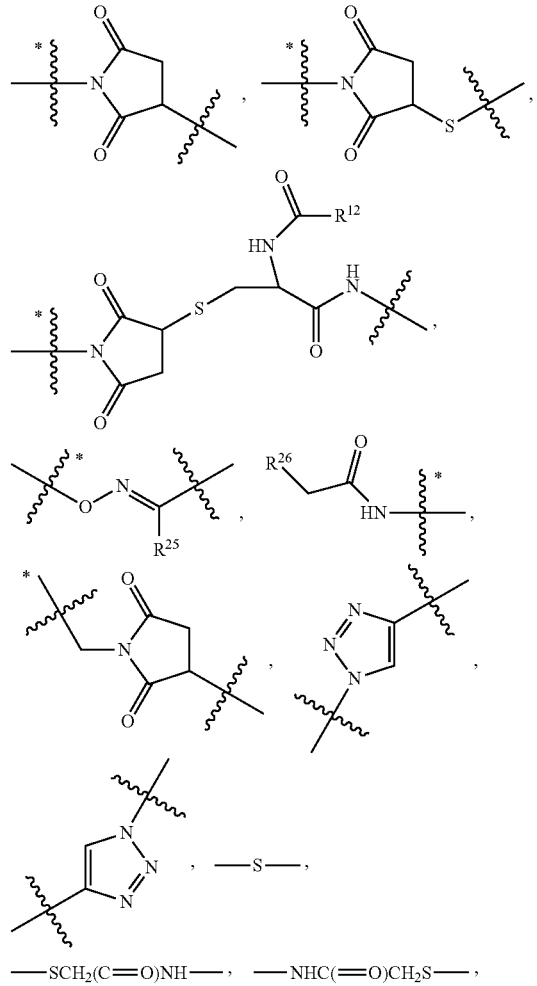

—SCH₂(C=O)NH—, —NHC(=O)CH₂S—,

-continued

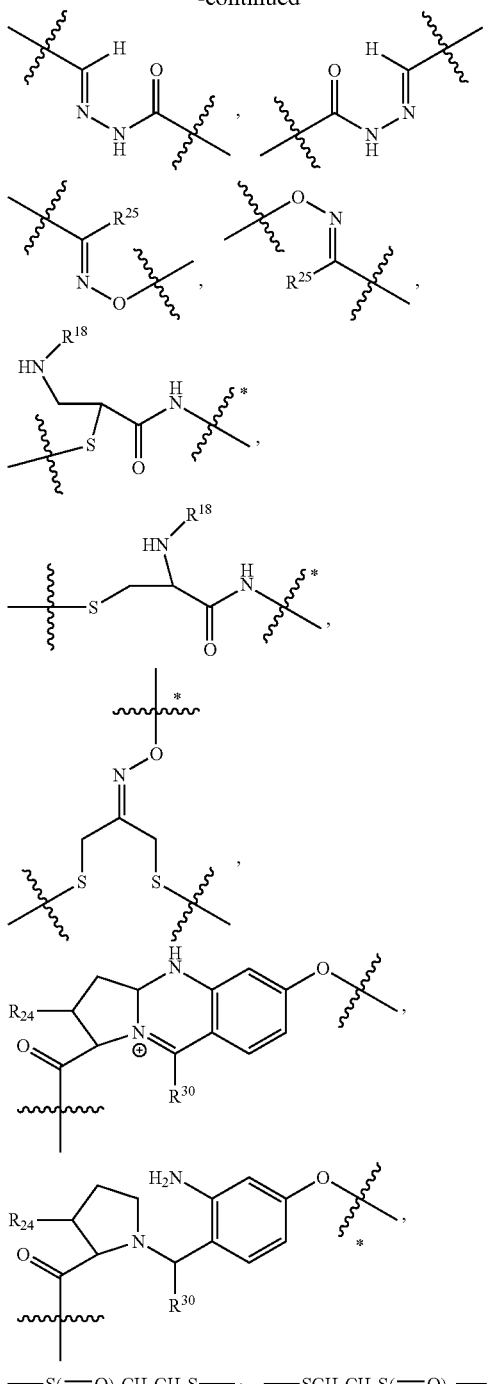

—S(=O)₂CH₂CH₂S—, —SCH₂CH₂S(=O)₂—,
—(CH₂)₂S(=O)₂CH₂CH₂S— or
—SCH₂CH₂S(=O)₂CH₂CH₂—, wherein the * of L₂ indicates the point of attachment to L₁,
and L₃, L₄, L₅ and L₆ are a bond.

101. The compound of any one of embodiments 17 to 56, and the immunoconjugate according to any one of embodiments 74 to 87, wherein L₁ is selected from —*(CH₂)ₘX₃(CH₂)ₘ—, —*(CH₂)ₘX₃—, —*C(=O)(CH₂)ₘ—, —*NHC(=O)(CH₂)ₘ—, —(CH₂)ₘ—, —*(CH₂)ₘC(=O)NH(CH₂)ₘNHC(=O)(CH₂)ₘ—,
—*(CH₂)ₘC(=O)NH(CH₂)ₘX₃(CH₂)ₘ—, —*(CH₂)ₘC(=O)NH(CH₂)ₘX₃—, —*(CH₂)ₘO)ₙ(CH₂)ₘ—, —*(CH₂)ₘO)ₙ(CH₂)ₘNHC(=O)(CH₂)ₘ—, —*((CR¹²)₂)ₘOC(=O)NH(CH₂)ₘO(CH₂)ₘ—, —*(CH₂)ₘC(=O)NH(CH₂)ₘO)ₙ(CH₂)ₘX₃—, —*(CH₂)ₘC(=O)NH(CH₂)ₘO)ₙ(CH₂)ₘX₃(CH₂)ₘ—, —*(CH₂)ₘNHC(=O)X₁X₂C(=O)(CH₂)ₘ—, —*X₄ X₁X₂C(=O)(CH₂)ₘ—, —*X₁C(=O)(CH₂)ₘNHC(=O)(CH₂)ₘ—, —*S(=O)₂(CH₂)ₘX₃(CH₂)ₘ—,

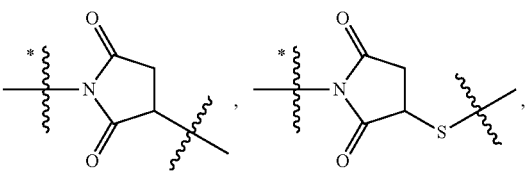

—*NH₂S(=O)₂(CH₂)ₘX₃(CH₂)ₘ—, —*C(=O)((CH₂)ₘO)ₙ(CH₂)ₘ)— and —*C(=O)NH(CH₂)ₘ)—, wherein in the immunoconjugate embodiments the * indicates the point of attachment to R³;

L₂ is

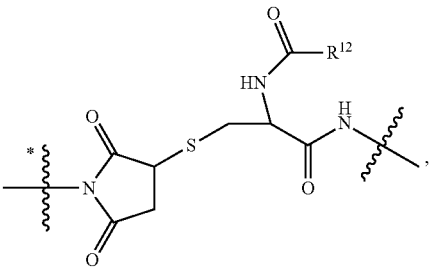

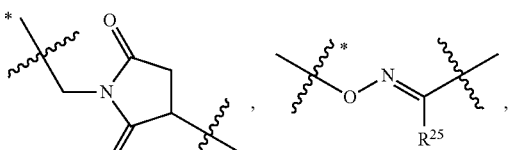

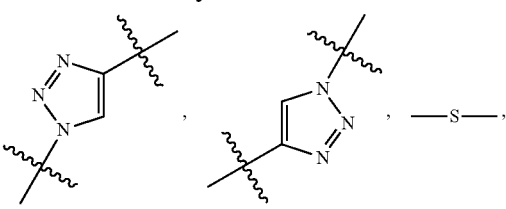

—SCH₂(C=O)NH—, —NHC(=O)CH₂S—,

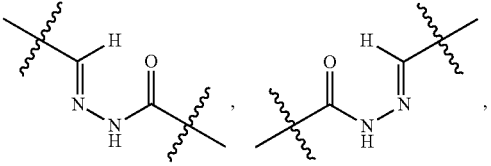

-continued

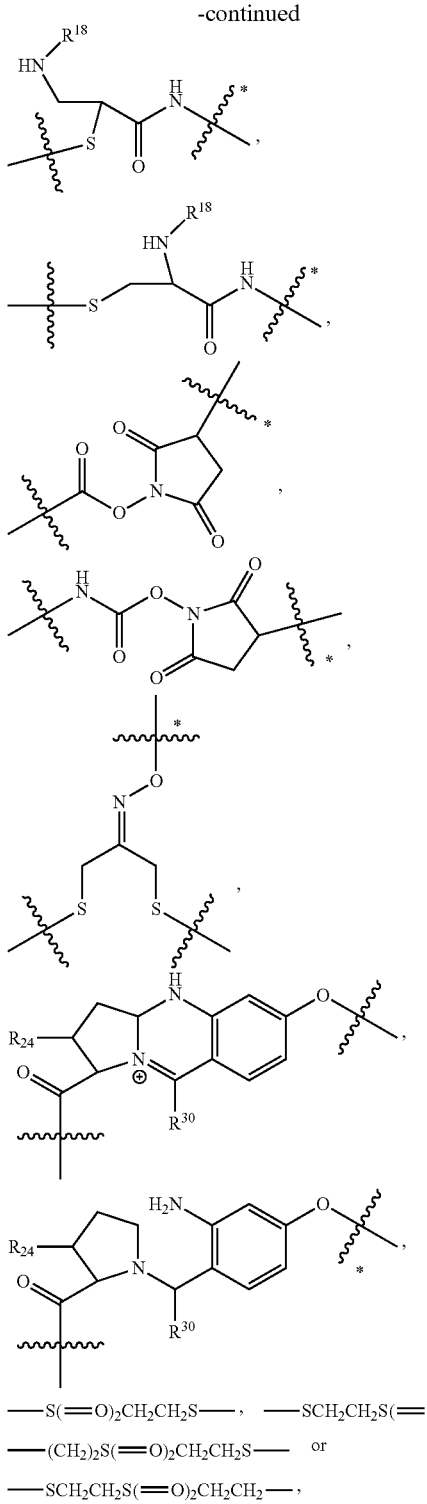

—S(=O)₂CH₂CH₂S—, —SCH₂CH₂S(=O)₂—,
—(CH₂)₂S(=O)₂CH₂CH₂S— or
—SCH₂CH₂S(=O)₂CH₂CH₂—, wherein the * of L₂ indicates the point of attachment to L₁, and L₃, L₄, L₅ and L₆ are a bond.

102. The compound of any one of embodiments 17 to 56, and the immunoconjugate according to any one of embodiments 74 to 87, wherein L₁ is selected from —*(CH₂)$_m$X₃(CH₂)—, —*(CH₂)$_m$X₃—, —*C(=O)(CH₂)$_m$—, —*NHC(=O)(CH₂)$_m$—, —(CH₂)$_m$—, —*(CH₂)$_m$C(=O)NH(CH₂)$_m$NHC(=O)(CH₂)$_m$—, —*(CH₂)$_m$C(=O)NH(CH₂)$_m$X₃(CH₂)$_m$—, —*(CH₂)$_m$C(=O)NH(CH₂)$_m$X₃—, —*(CH₂)$_m$O)$_n$(CH₂)$_m$—, —*(CH₂)$_m$O)$_n$(CH₂)$_m$NHC(=O)(CH₂)$_m$—, —*((CR¹²)₂)$_m$OC(=O)NH(CH₂)$_m$O(CH₂)$_m$—, —*(CH₂)$_m$C(=O)NH(CH₂)$_m$O$_n$(CH₂)$_m$X₃—, —*(CH₂)$_m$C(=O)NH(CH₂)$_m$O)$_n$(CH₂)$_m$X₃(CH₂)$_m$—, —*(CH₂)$_m$NHC(=O)X₁X₂C(=O)(CH₂)$_m$—, —*X₄ X₁X₂C(=O)(CH₂)$_m$—, —*X₁C(=O)(CH₂)$_m$NHC(=O)(CH₂)$_m$—, —*S(=O)₂(CH₂)mX₃(CH₂)$_m$—,

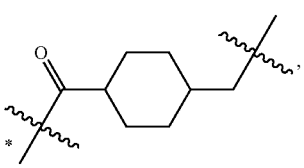

—*NH₂S(=O)₂(CH₂)$_m$X₃(CH₂)$_m$—, —*C(=O)((CH₂)$_m$O)$_n$(CH₂)$_m$)— and —*C(=O)NH(CH₂)$_m$)—, wherein in the immunoconjugate embodiments the * indicates the point of attachment to R³;

L₂ is

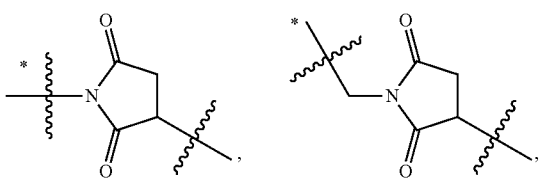

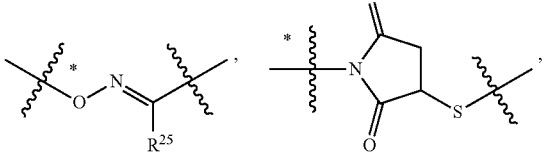

or

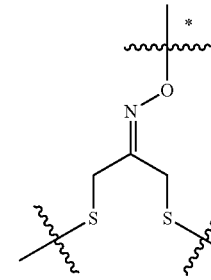

wherein the * of L₂ indicates the point of attachment to L₁, and L₃, L₄, L₅ and L₆ are a bond.

103. The compound of any one of embodiments 17 to 56, and the immunoconjugate according to any one of embodiments 74 to 87, wherein L₁ is selected from —*(CH₂)$_m$X₃(CH₂)$_m$—, —*(CH₂)$_m$X₃—, —*C(=O)(CH₂)$_m$—, —*NHC(=O)(CH₂)$_m$—, —(CH₂)$_m$—, —*(CH$_2$)$_m$C(=O)NH(CH$_2$)$_m$NHC(=O)(CH$_2$)$_m$—, —*(CH$_2$)$_m$C(=O)NH(CH$_2$)$_m$X$_3$(CH$_2$)$_m$—, —*(CH$_2$)$_m$C(=O)NH(CH$_2$)$_m$X$_3$—, —*(CH$_2$)$_m$O)$_n$(CH$_2$)$_m$—, —*(CH$_2$)$_m$O)$_n$(CH$_2$)$_m$NHC(=O)(CH$_2$)$_m$—, —*((CR$^{12}$)$_2$)$_m$OC(=O)NH(CH$_2$)$_m$O(CH$_2$)$_m$—, —*(CH$_2$)$_m$C(=O)NH(CH$_2$)$_m$O)$_n$(CH$_2$)$_m$X$_3$—, —*(CH$_2$)$_m$C(=O)NH(CH$_2$)$_m$O)$_n$(CH$_2$)$_m$X$_3$(CH$_2$)$_m$—, —*(CH$_2$)$_m$NHC(=O)X$_1$X$_2$C(=O)(CH$_2$)$_m$—, —*X$_4$ X$_1$X$_2$C(=O)(CH$_2$)$_m$—, —*X$_1$C(=O)(CH$_2$)$_m$NHC(=O)(CH$_2$)$_m$—, —*S(=O)$_2$(CH$_2$)mX$_3$(CH$_2$)$_m$—,

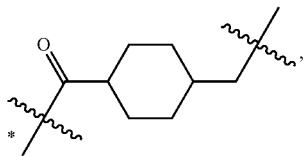

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein in the immunoconjugate embodiments the * indicates the point of attachment to R$^3$;
L2 is

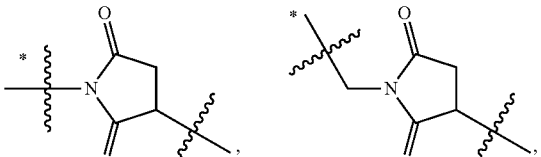

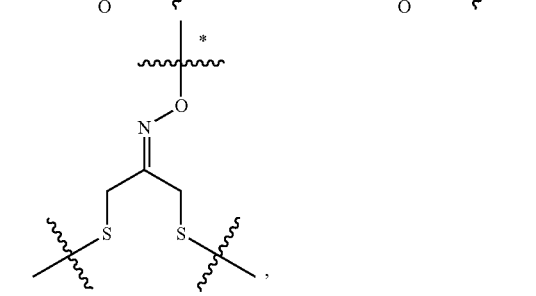

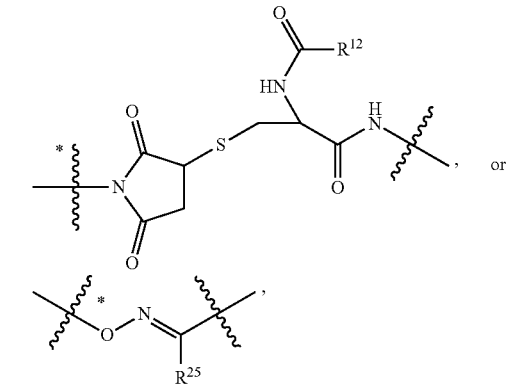

wherein the * of L$_2$ indicates the point of attachment to L$_1$,
and L$_3$, L$_4$, L$_5$ and L$_6$ are a bond.

104. The compound of any one of embodiments 17 to 56, and the immunoconjugate according to any one of embodiments 74 to 87, wherein L$_1$ is selected from —*(CH$_2$)$_m$X$_3$(CH$_2$)$_m$—, —*(CH$_2$)$_m$X$_3$—, —*C(=O)(CH$_2$)$_m$—, —*NHC(=O)(CH$_2$)$_m$—, —(CH$_2$)$_m$—, —*(CH$_2$)$_m$C(=O)NH(CH$_2$)$_m$NHC(=O)(CH$_2$)$_m$—, —*(CH$_2$)$_m$C(=O)NH(CH$_2$)$_m$X$_3$(CH$_2$)$_m$—, —*(CH$_2$)$_m$C(=O)NH(CH$_2$)$_m$X$_3$—, —*(CH$_2$)$_m$O)$_n$(CH$_2$)$_m$—, —*(CH$_2$)$_m$O)$_n$(CH$_2$)$_m$NHC(=O)(CH$_2$)$_m$—, —*((CR$^{12}$)$_2$)$_m$OC(=O)NH(CH$_2$)$_m$O(CH$_2$)$_m$—, —*(CH$_2$)$_m$C(=O)NH(CH$_2$)$_m$O)$_n$(CH$_2$)$_m$X$_3$—, and —*(CH$_2$)$_m$C(=O)NH(CH$_2$)$_m$O)$_n$(CH$_2$)$_m$X$_3$(CH$_2$)$_m$—, wherein in the immunoconjugate embodiments the * indicates the point of attachment to R$^3$;

L$_2$ is

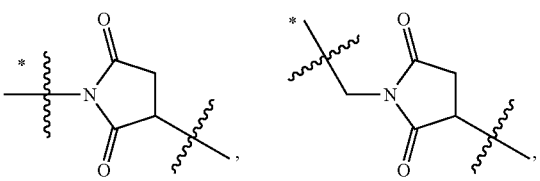

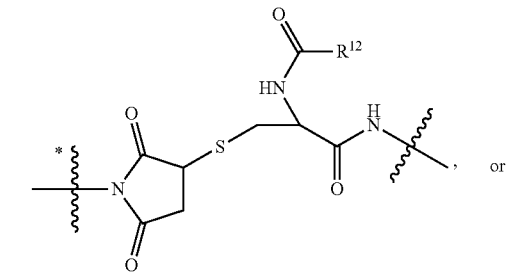

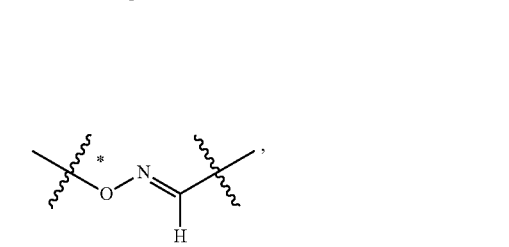

wherein the * of L$_2$ indicates the point of attachment to L$_1$,
and L$_3$, L$_4$, L$_5$ and L$_6$ are a bond.

105. The compound according to any one of embodiments 1 to 56 or 88 to 106, or the immunoconjugate of any one of embodiments 57 to 87 or 88 to 106, wherein R$^6$ is H, methyl, ethyl, isopropyl or sec-butyl.

106. The compound according to any one of embodiments 1 to 56 or 88 to 107, or 88, or the immunoconjugate of any one of embodiments 57 to 88 or 88 to 107, wherein R$^{12}$ is H, methyl, ethyl, isopropyl or sec-butyl.

107. The compound according to any one of embodiments 1 to 56 or 88 to 108, 88 or 89, or the immunoconjugate of any one of embodiments 57 to 89 or 88 to 108, wherein R$^2$ is methyl, ethyl, isopropyl or sec-butyl.

108. The compound of any one of embodiments 1 to 56, and 88 to 109, wherein the compound is selected from

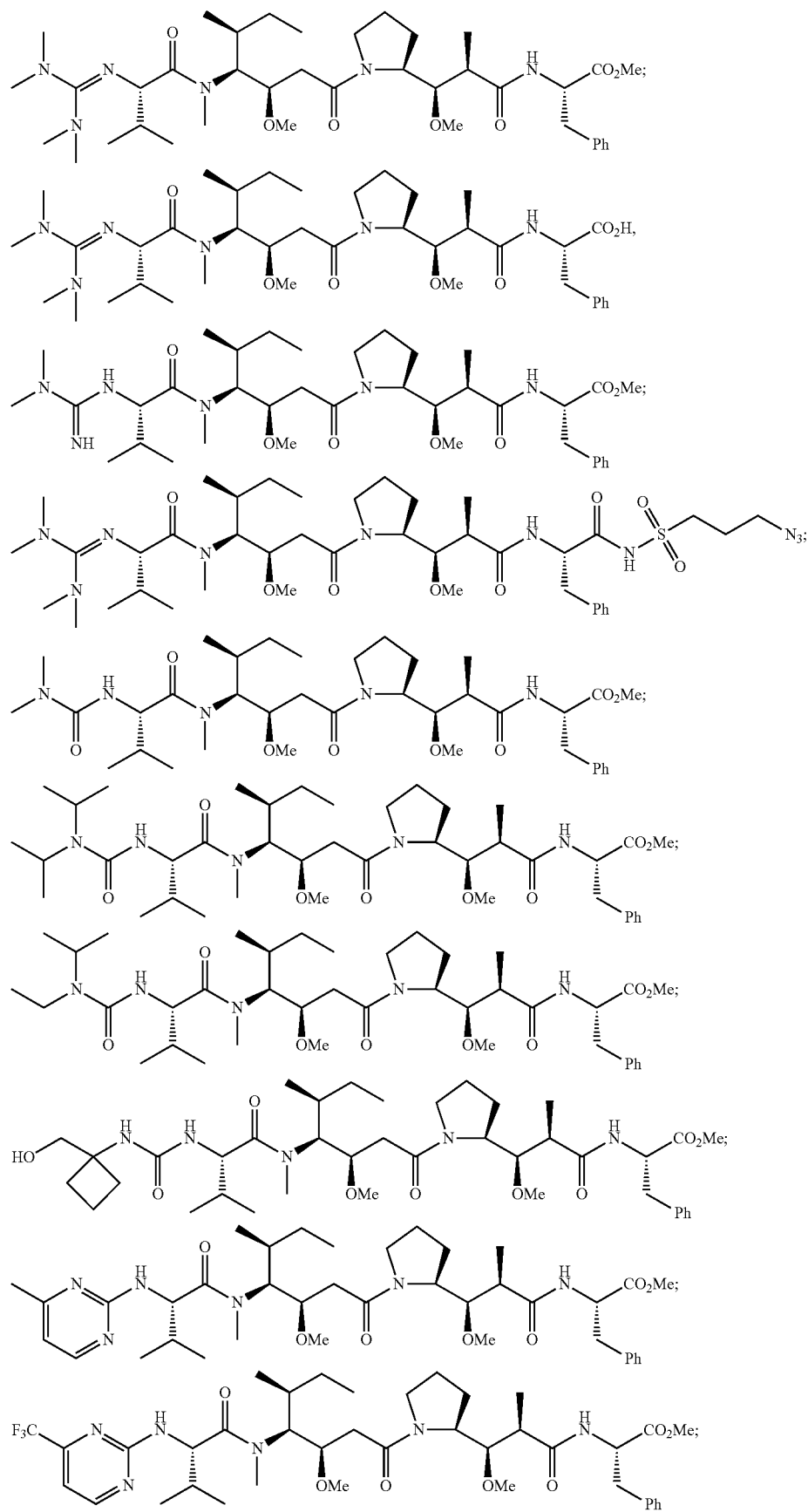

-continued
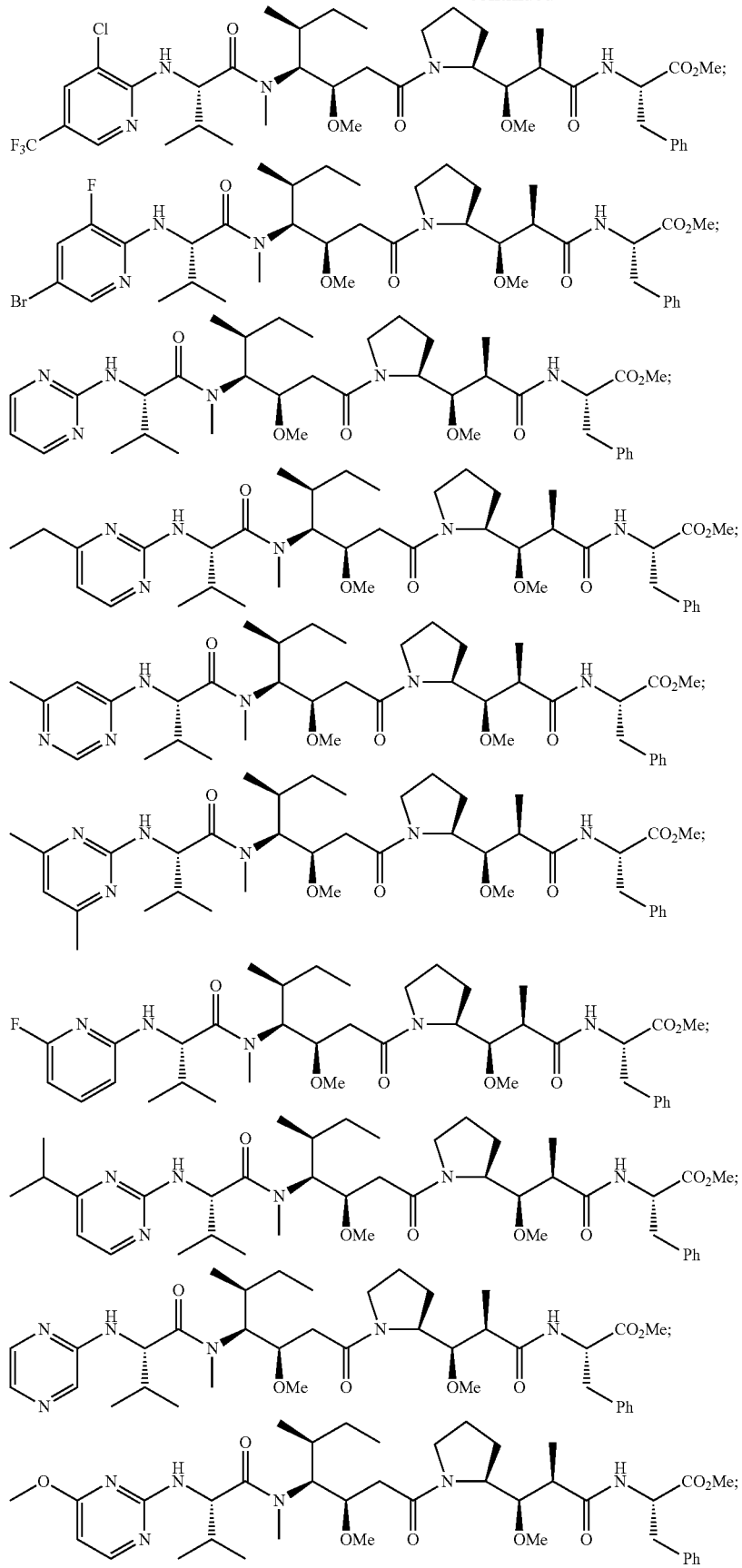

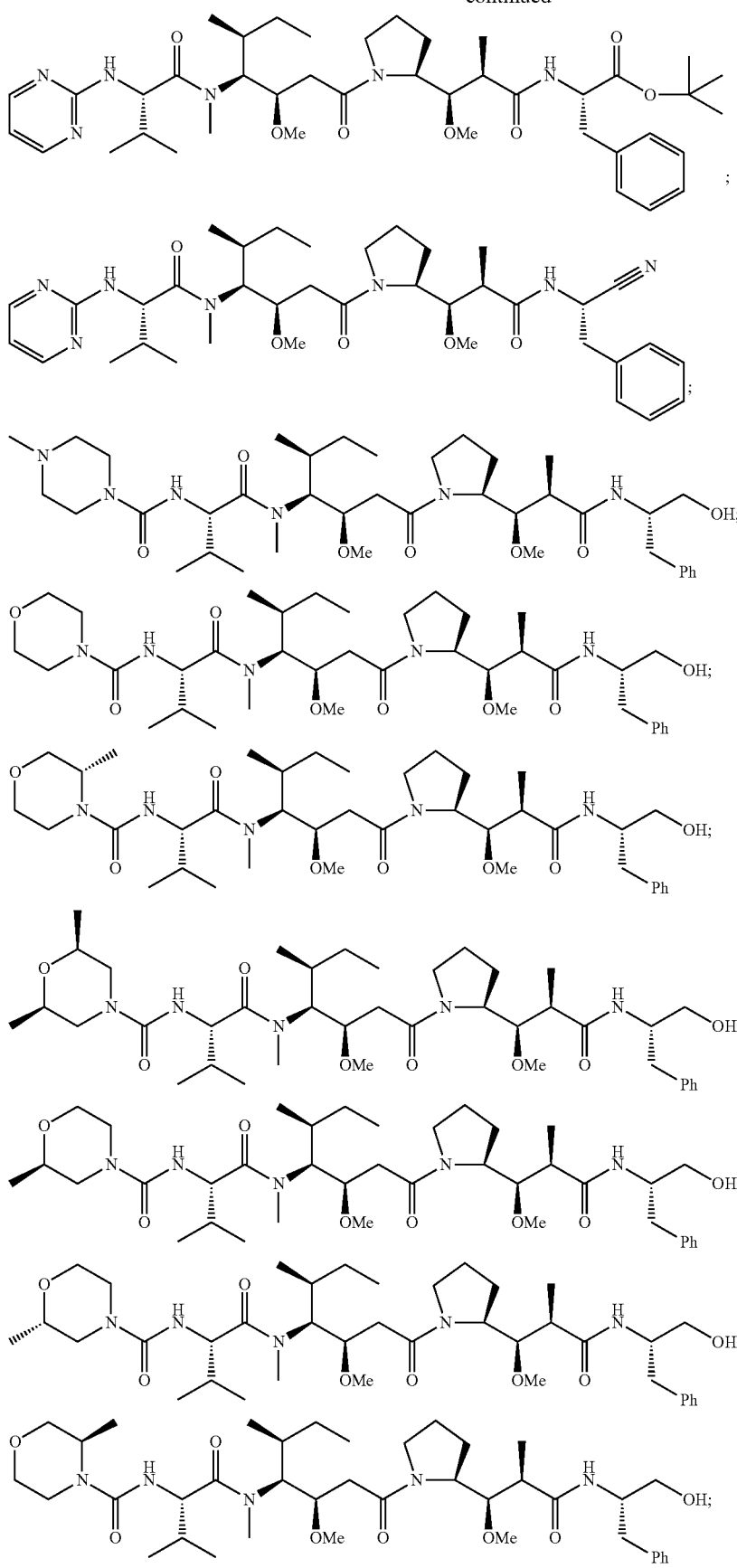

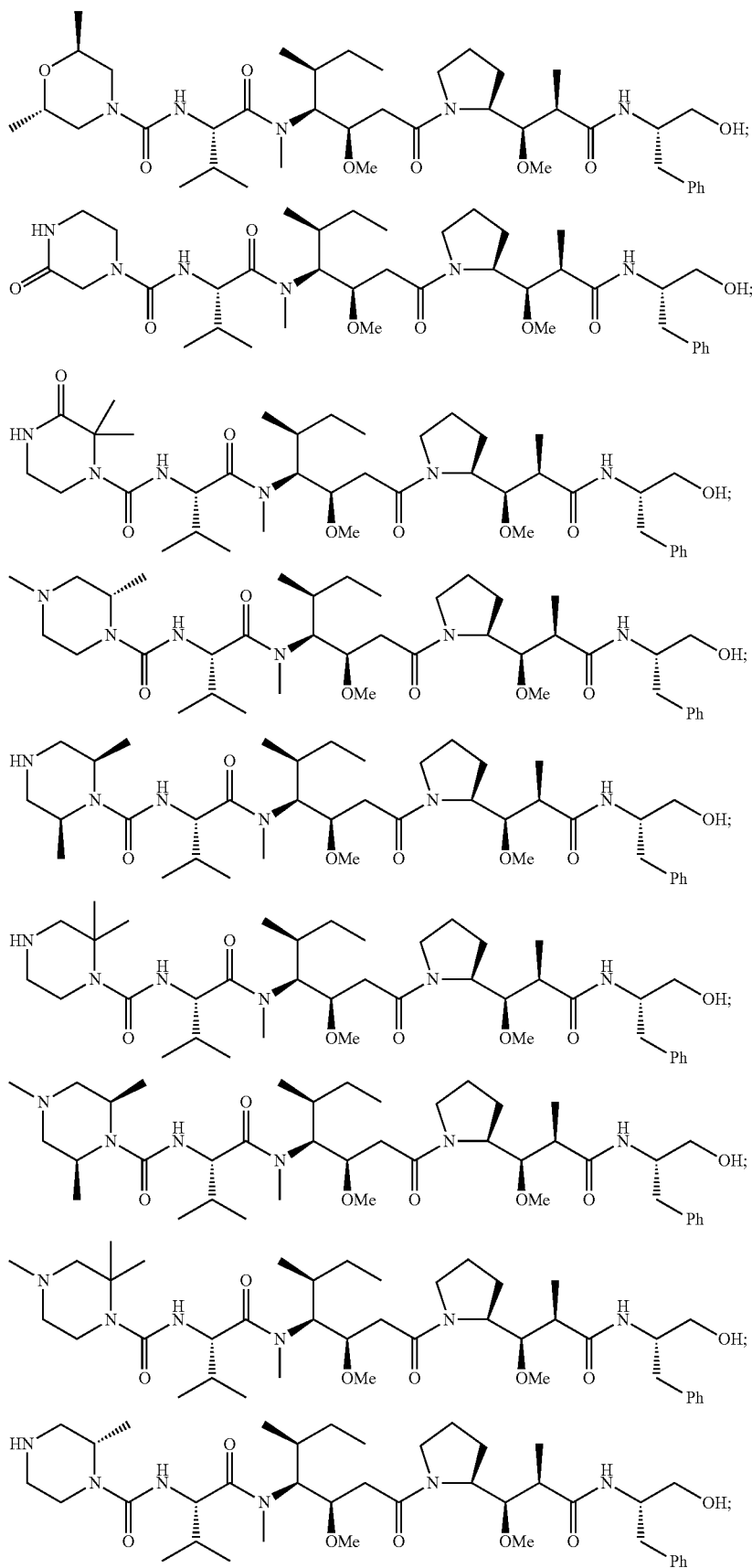

-continued
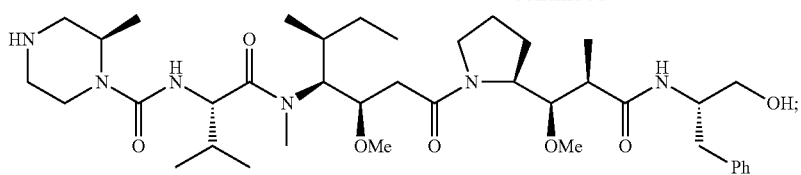
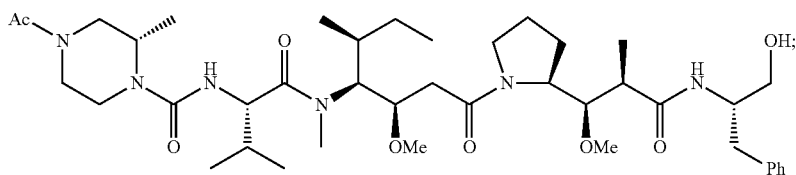
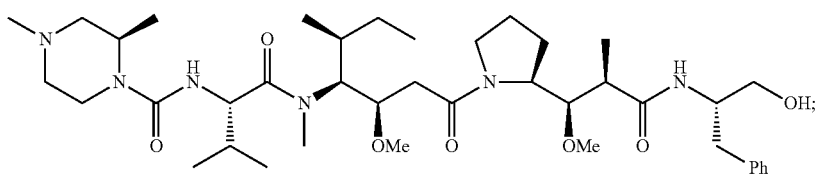
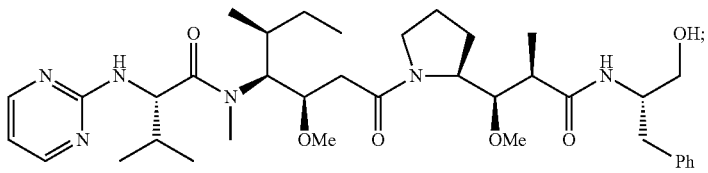
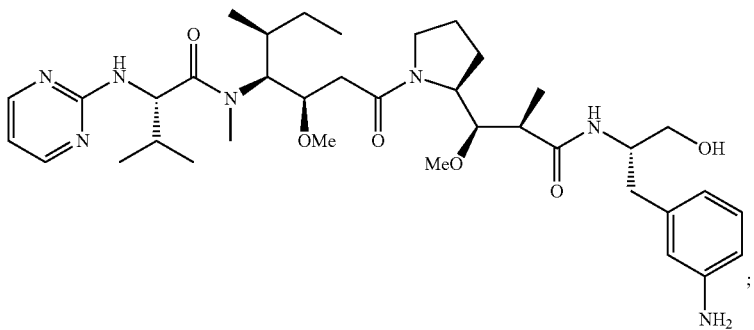
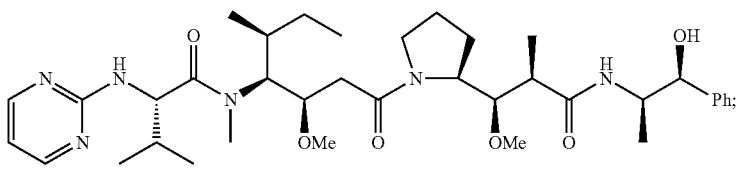
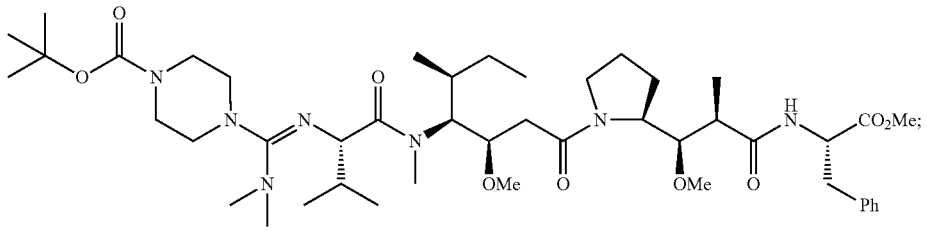
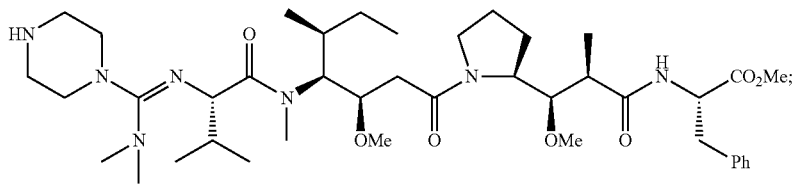

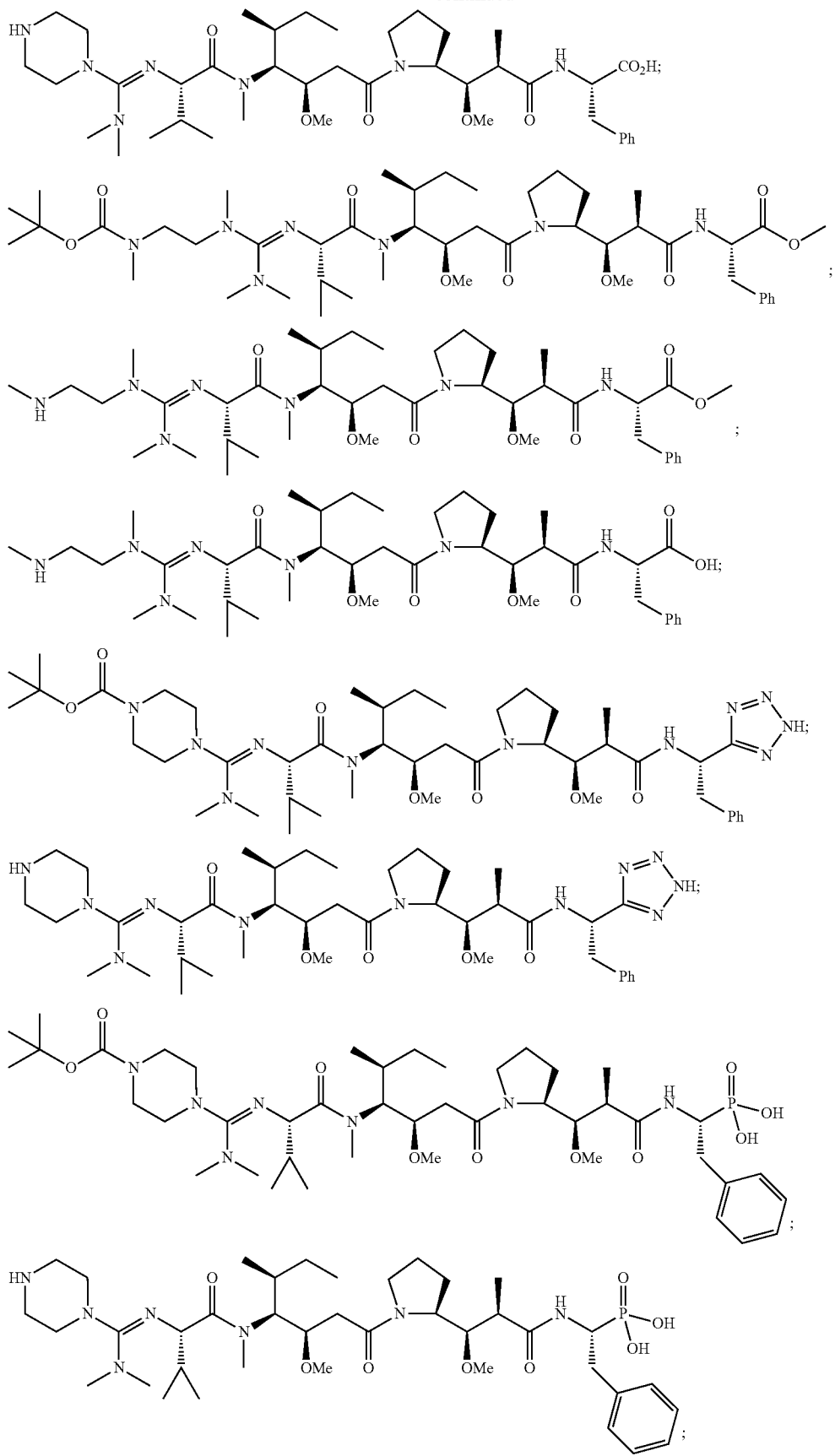

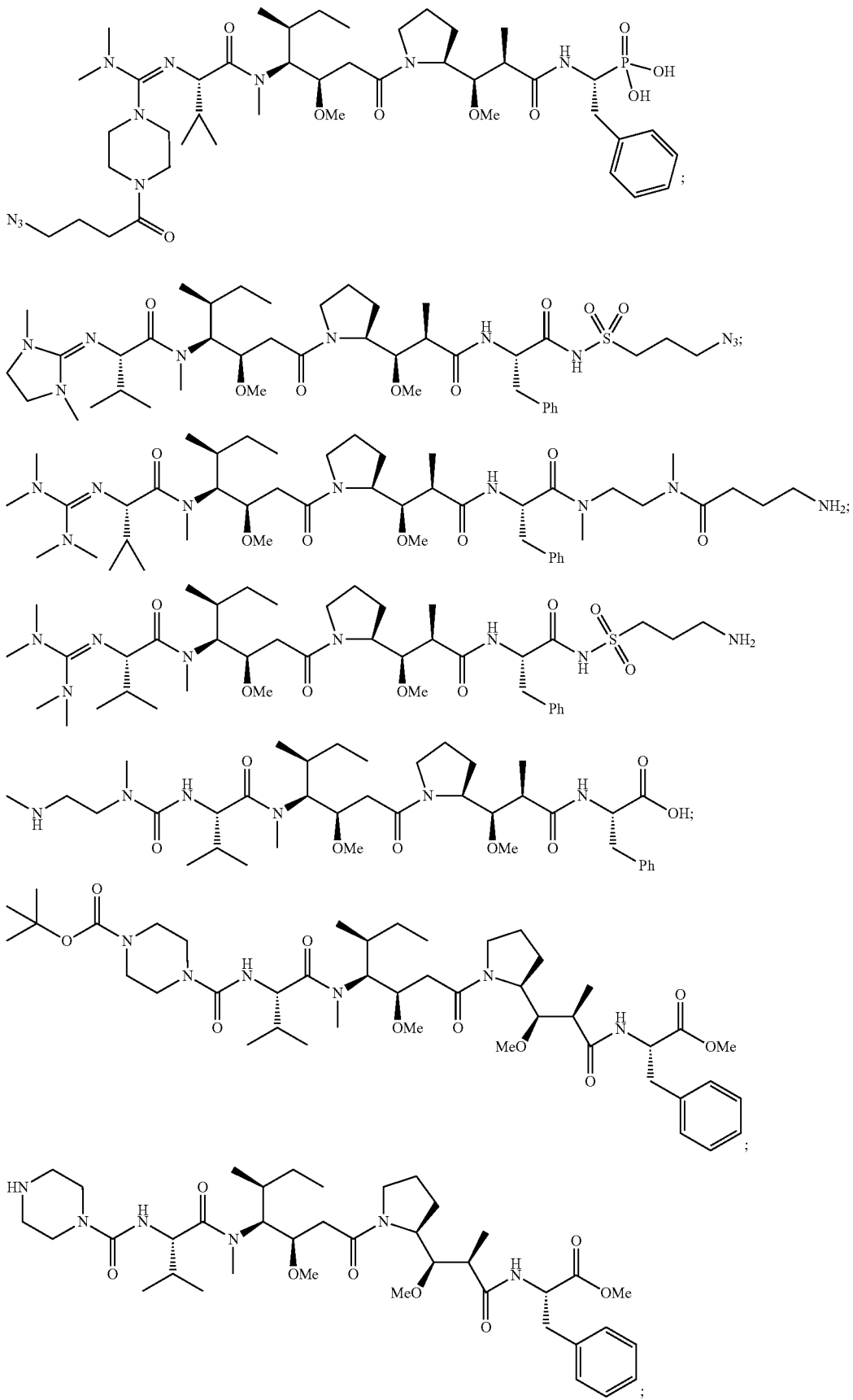

441 442
-continued
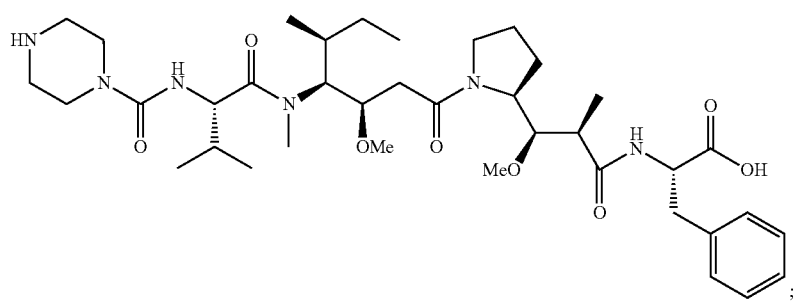
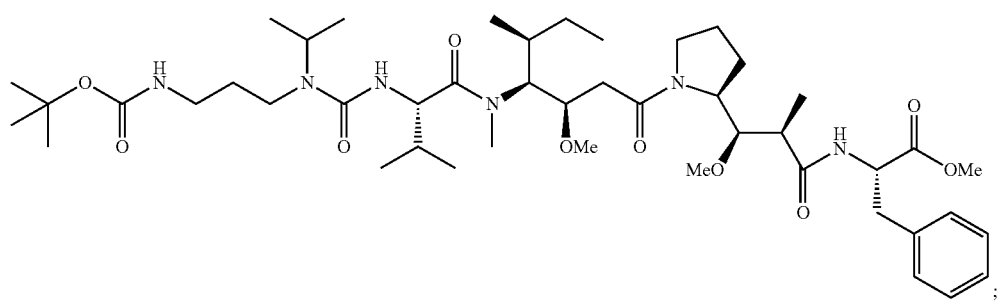
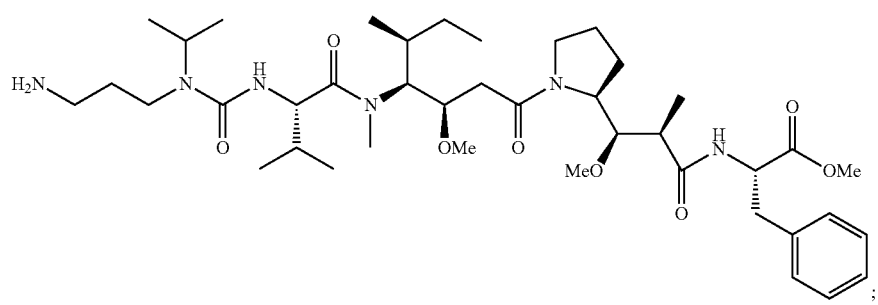
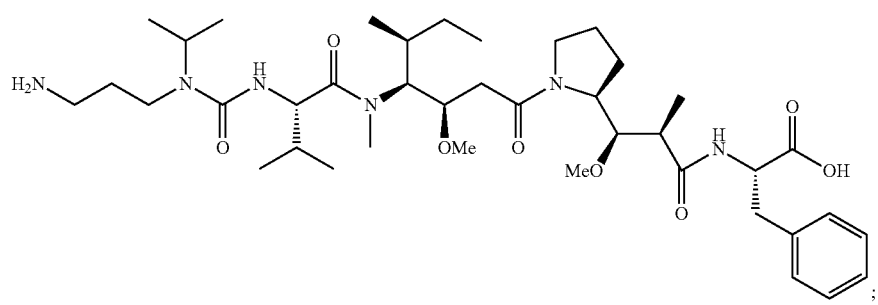
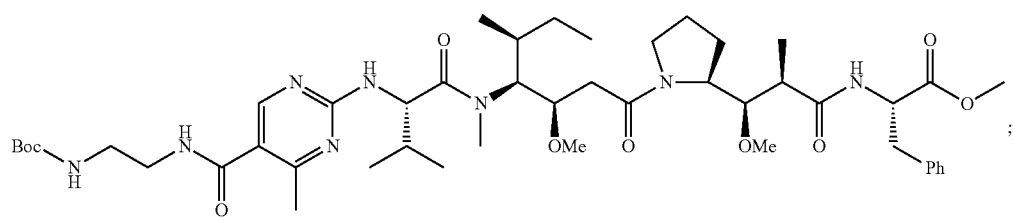
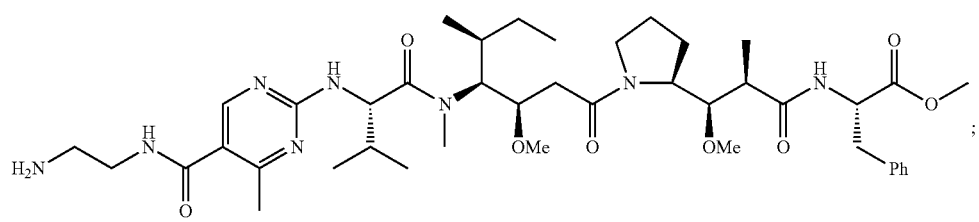

-continued
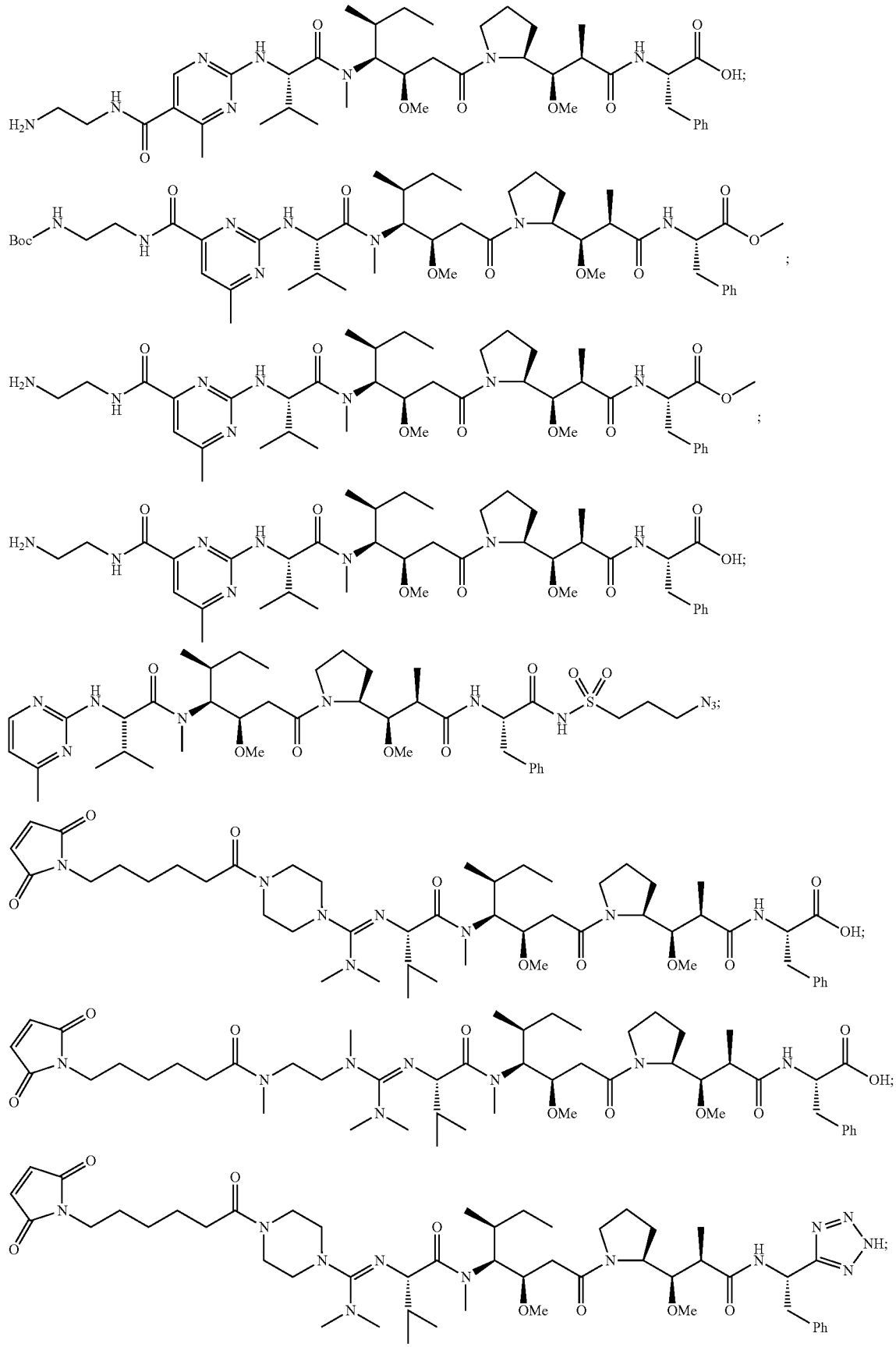

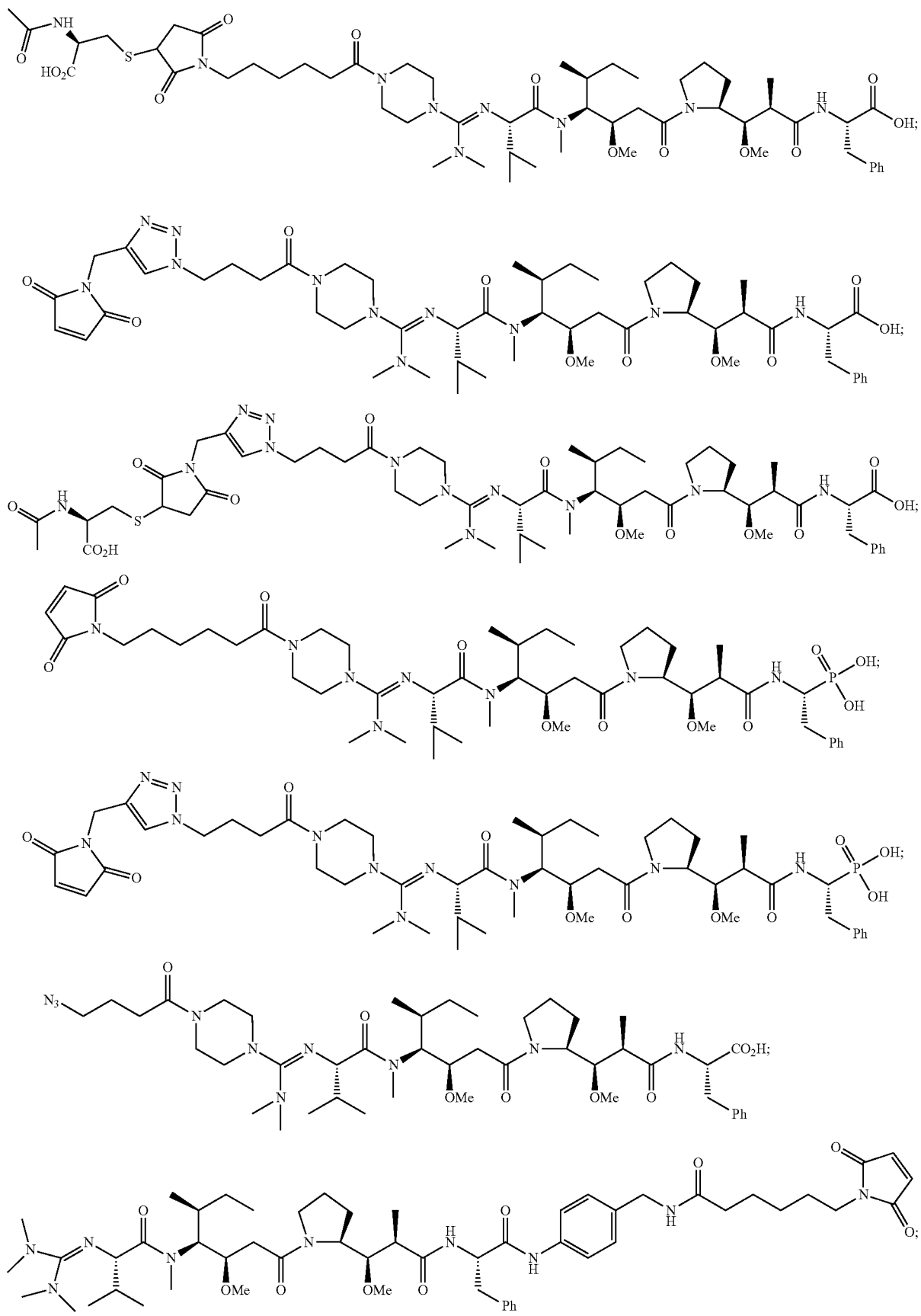

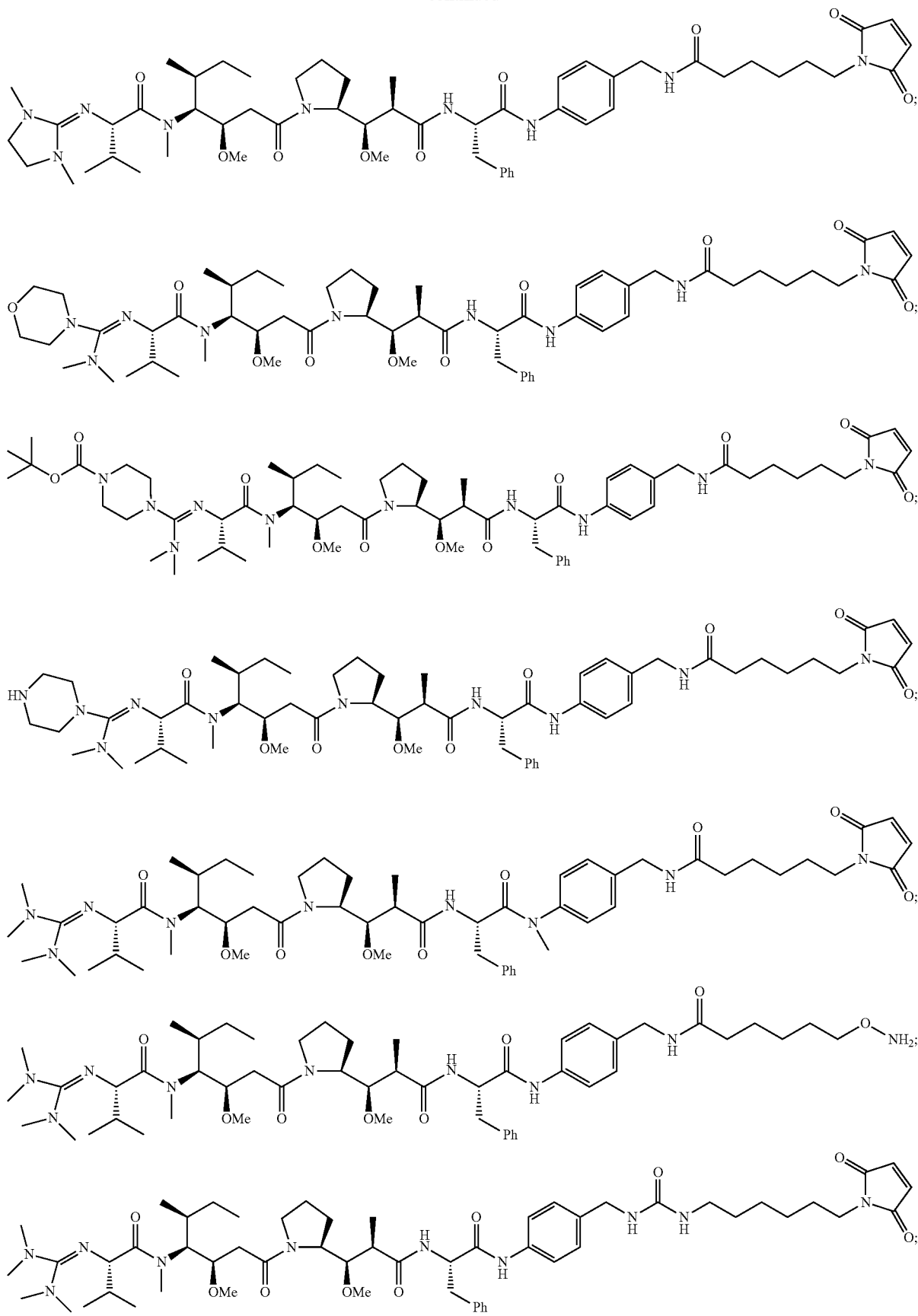

-continued
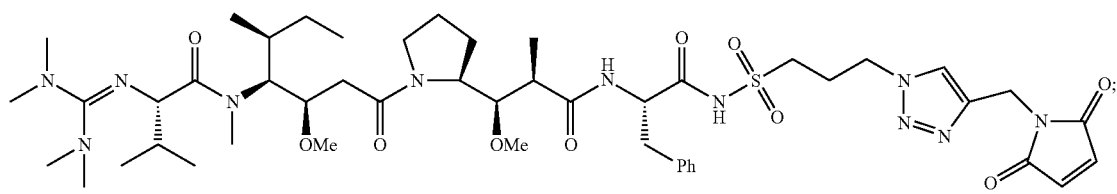
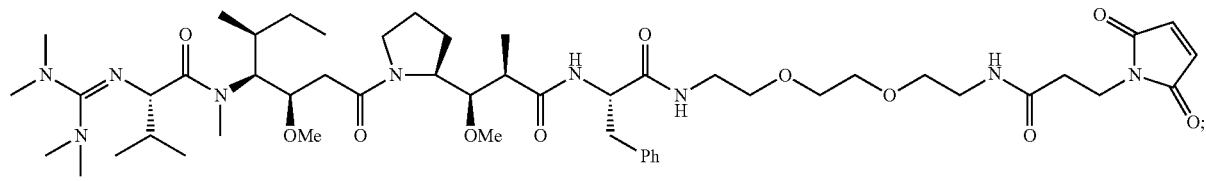
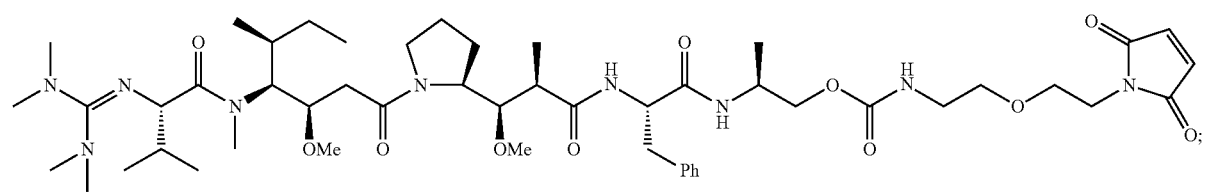
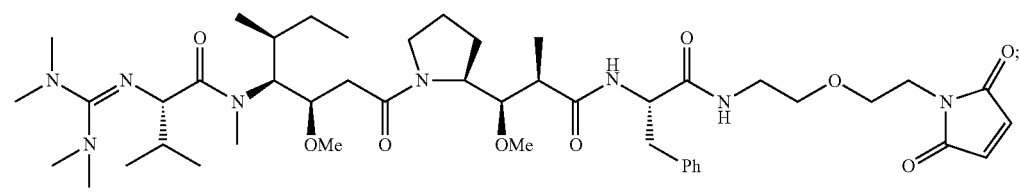
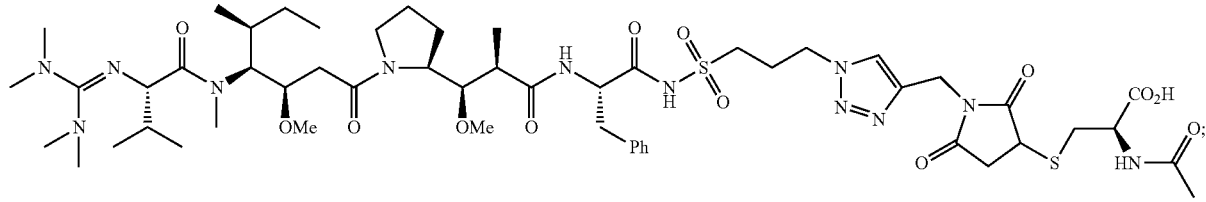
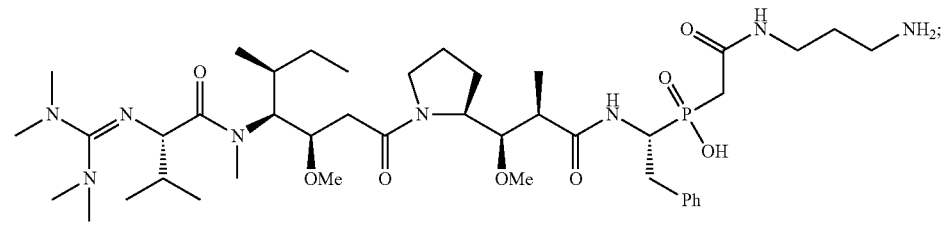
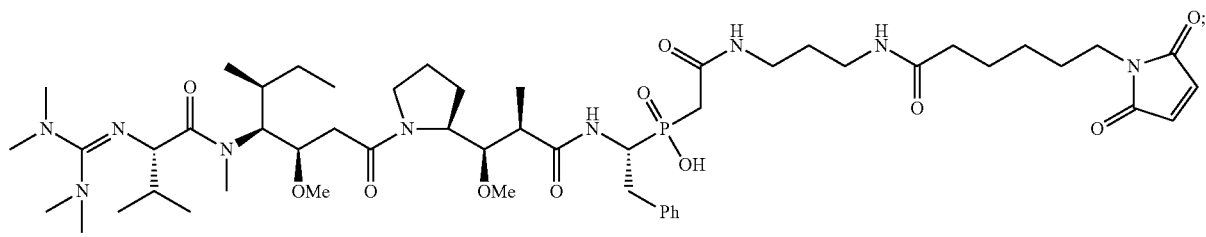
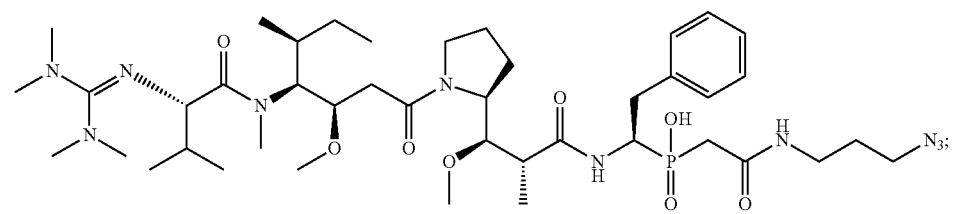

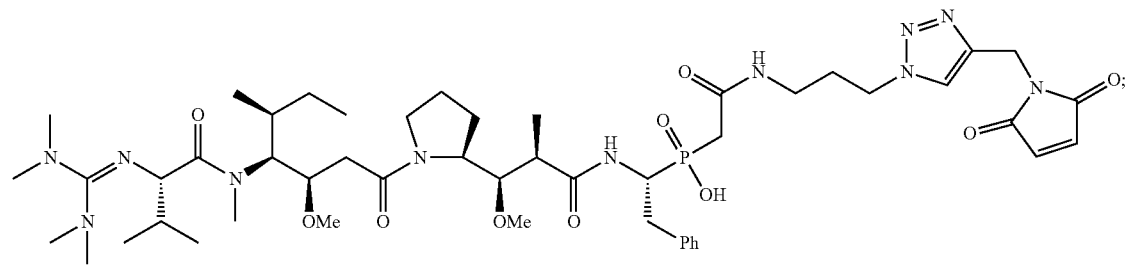
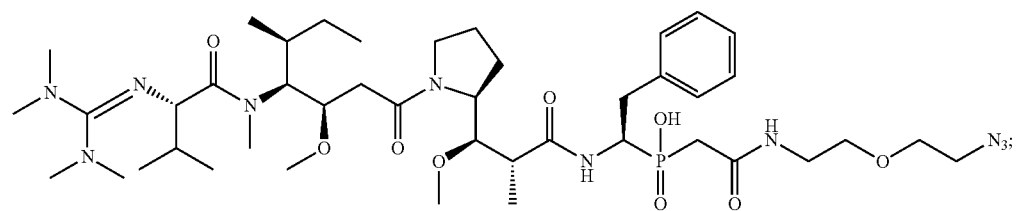
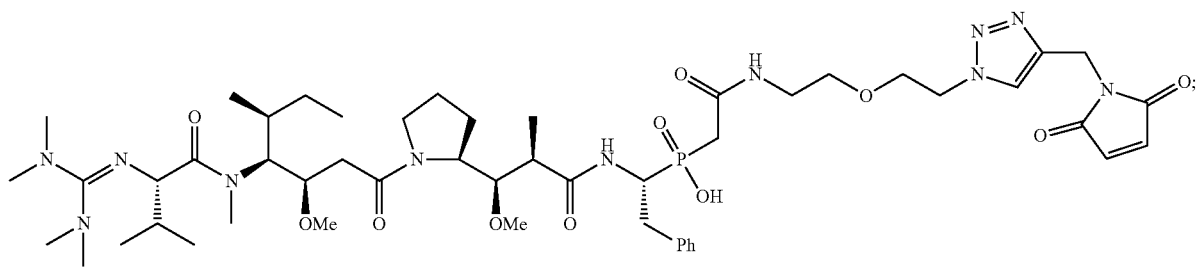
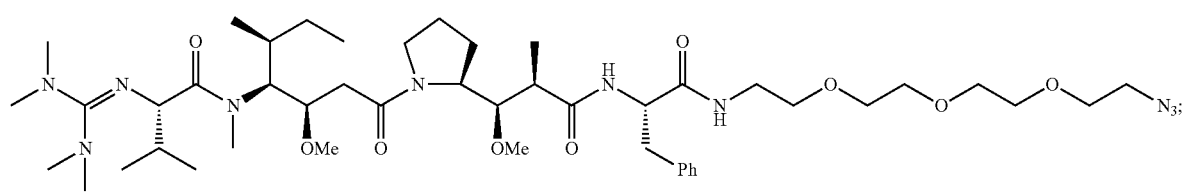
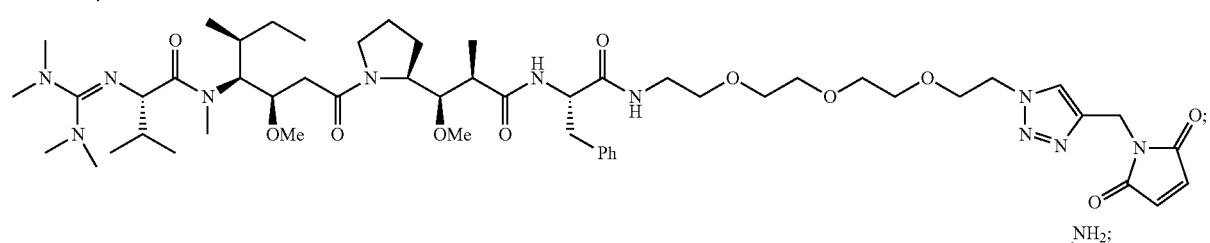
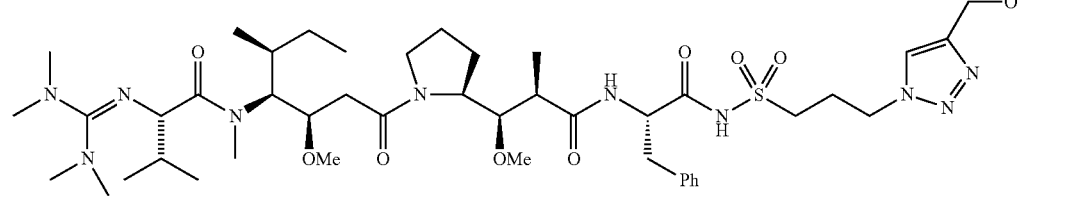
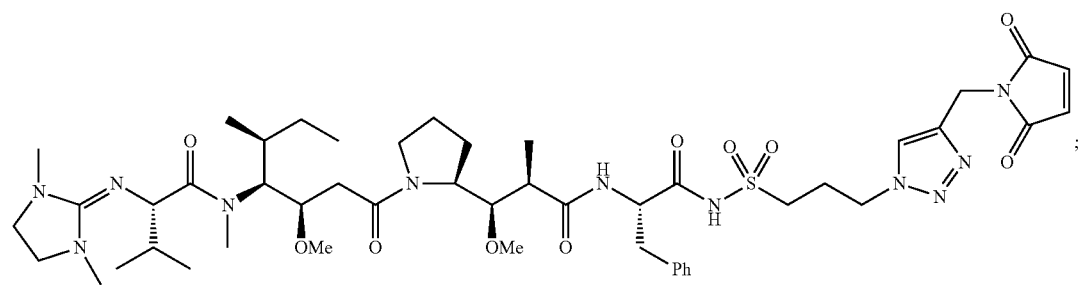

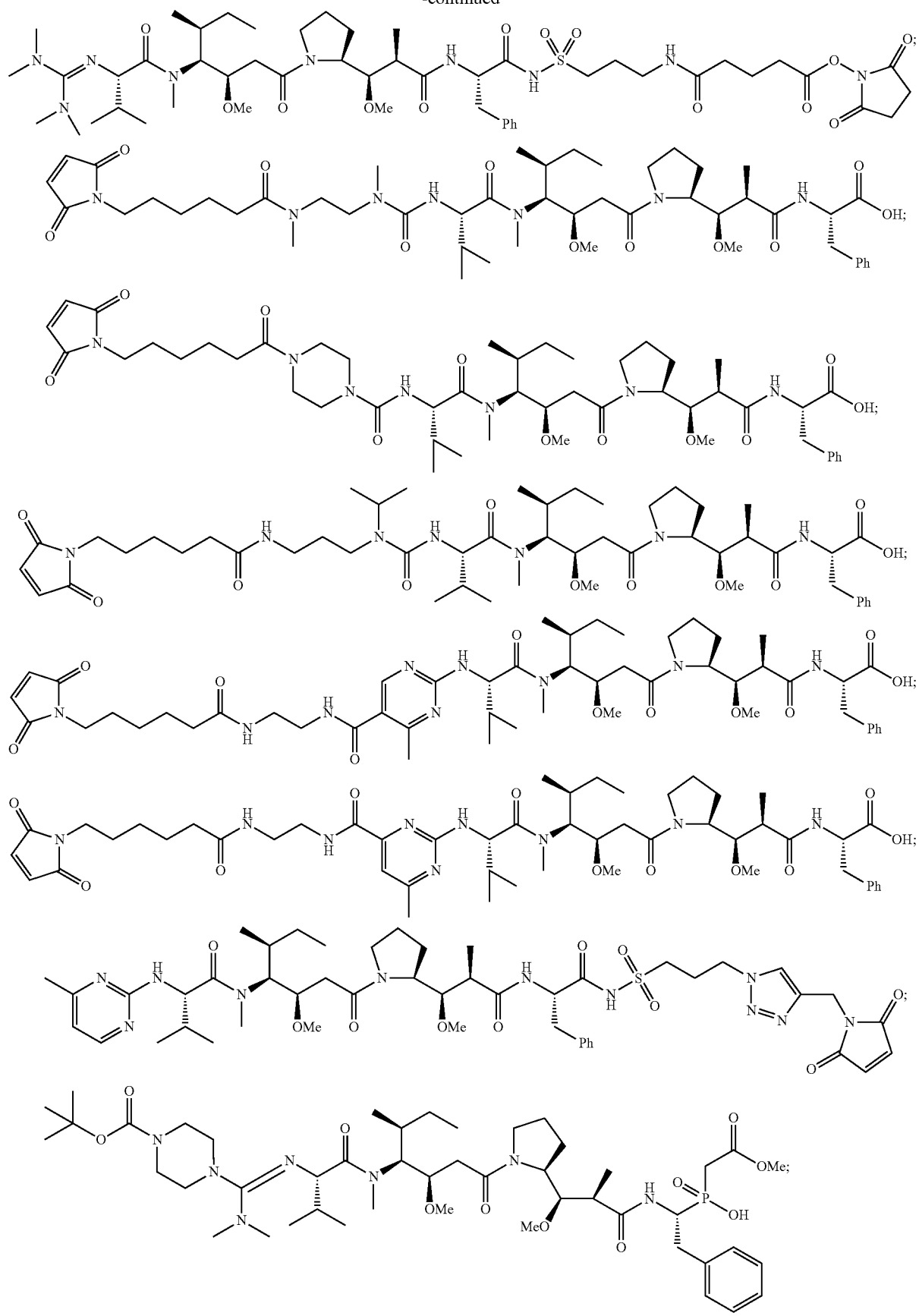

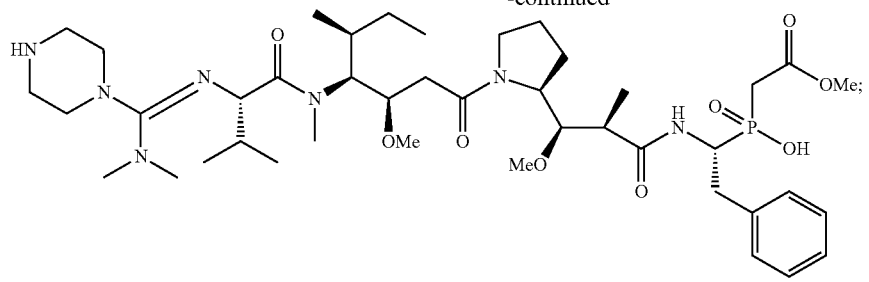
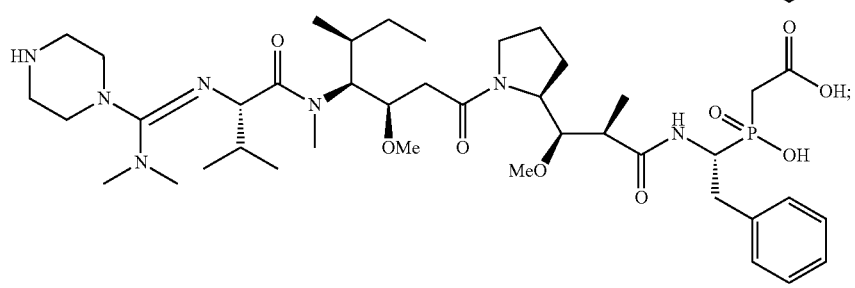
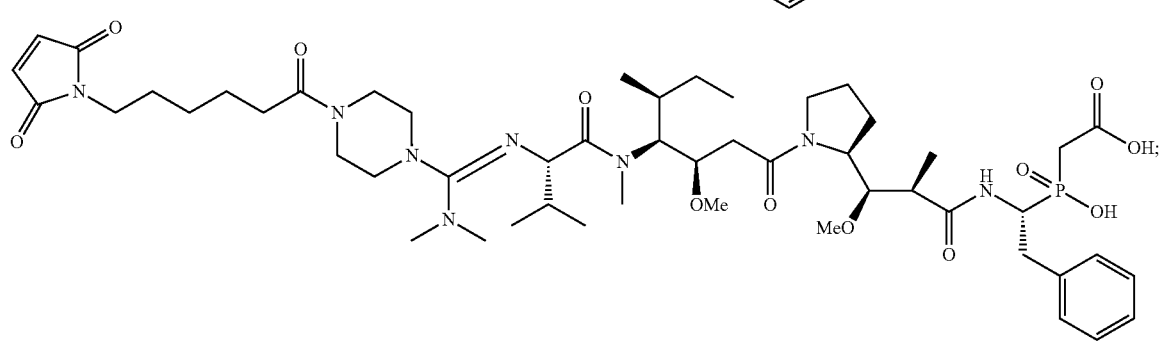
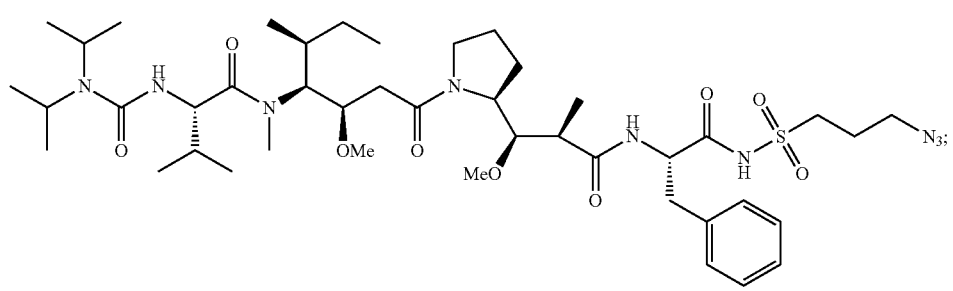
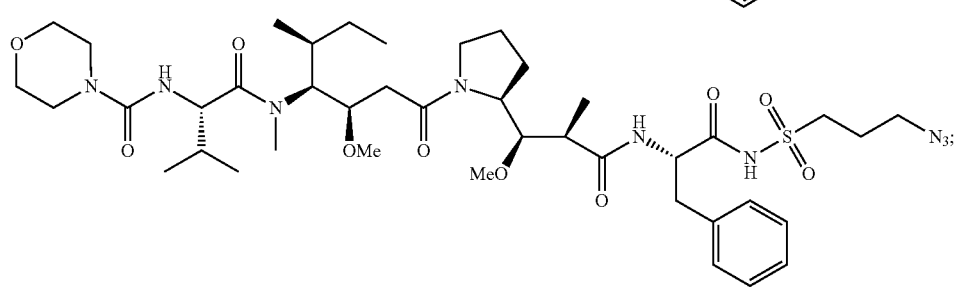
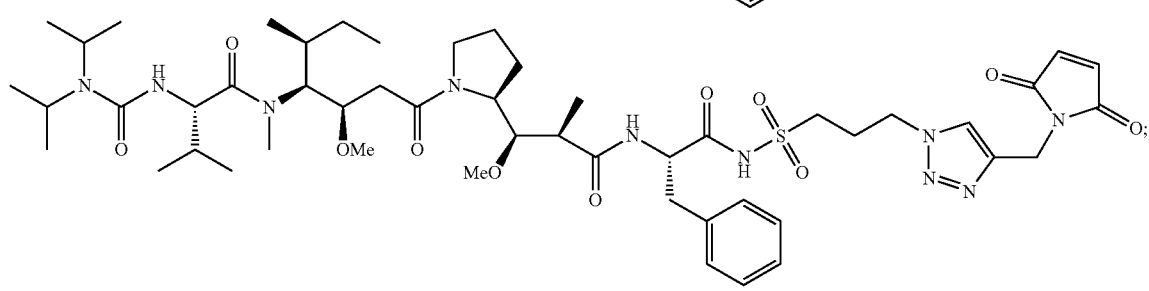

457                                                                                                    458
-continued
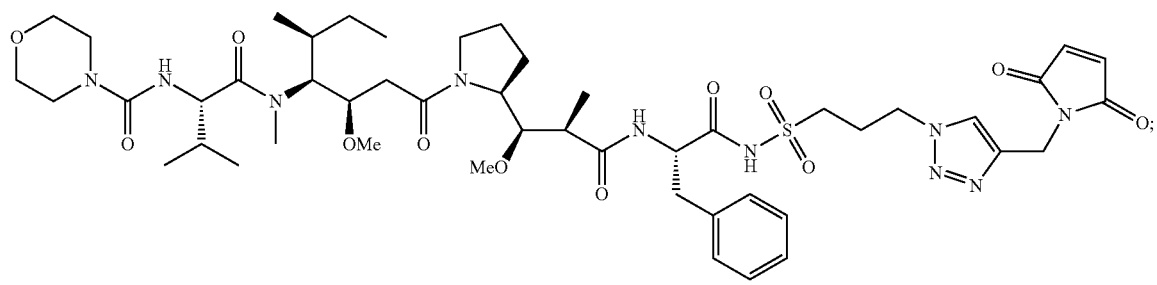
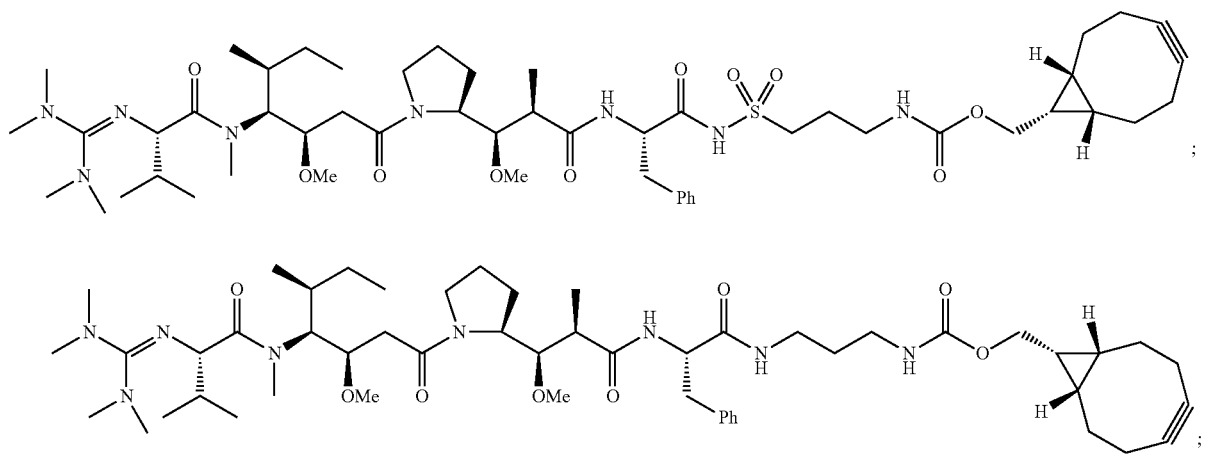
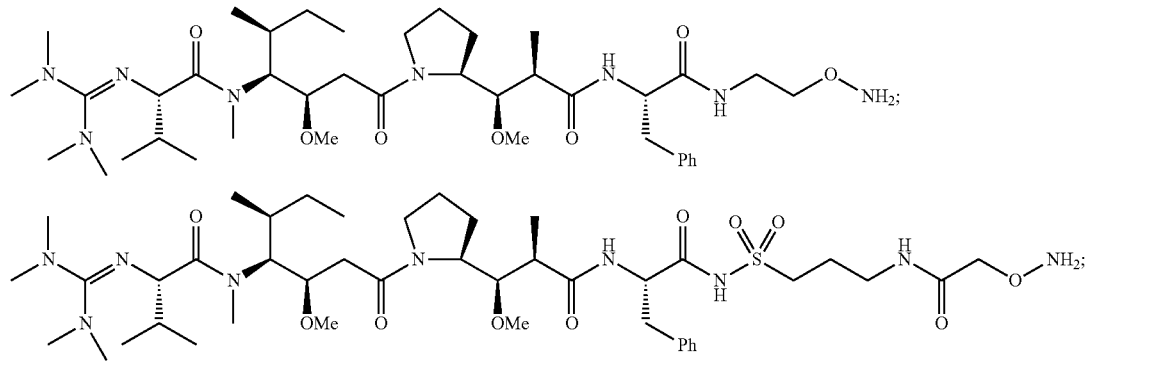
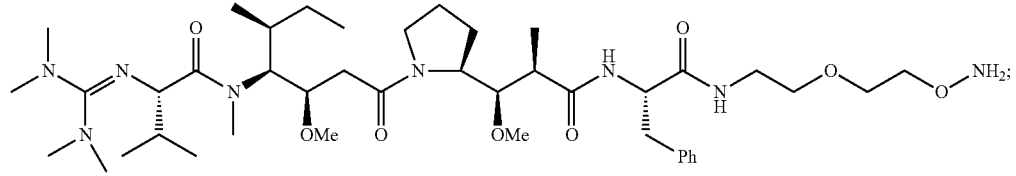
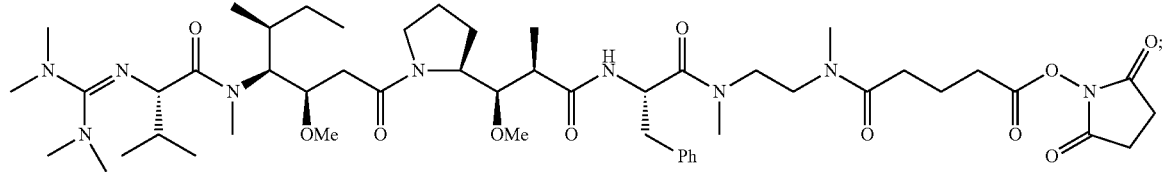
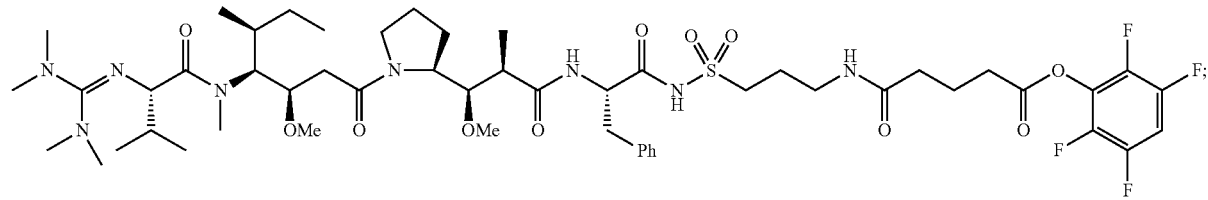

-continued

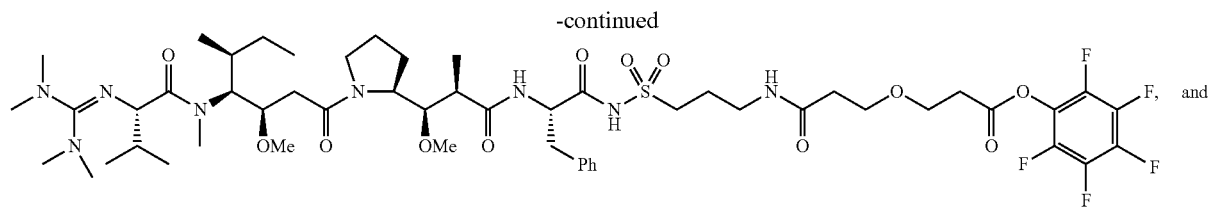

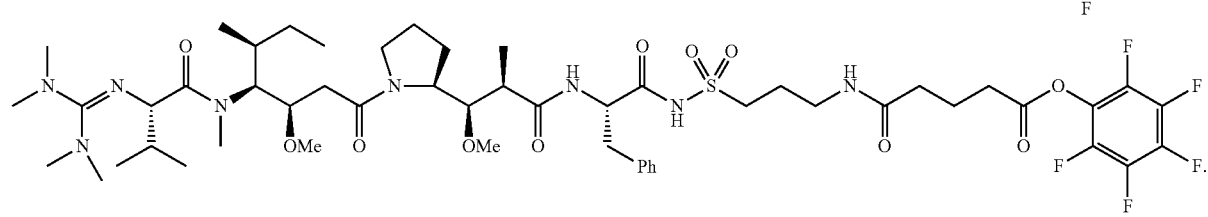

109. A pharmaceutical composition comprising an immunoconjugate of any one of embodiments 57 to 87, and one or more pharmaceutically acceptable carriers.

110. A combination comprising a therapeutically effective amount of an immunoconjugate of any one of embodiments 57 to 87, and one or more therapeutically active co-agents.

111. A method of treating a cell proliferation disorder, comprising administering to a subject in need thereof a therapeutically effective amount of an immunoconjugate of any one of embodiments 57 to 87.

112. An immunoconjugate of any one of embodiments 57 to 87 for use as a medicament.

113. The immunoconjugate according to embodiment 114, wherein the medicament is for use in the treatment of cancer.

114. An immunoconjugate of any one of embodiments 57 to 87 for use to treat cancer.

115. An immunoconjugate according to embodiments 57 to 87, having a formula selected from

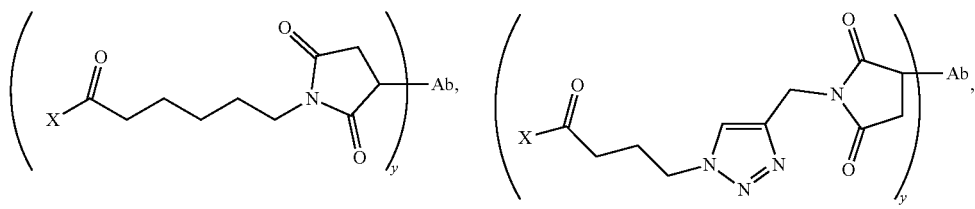

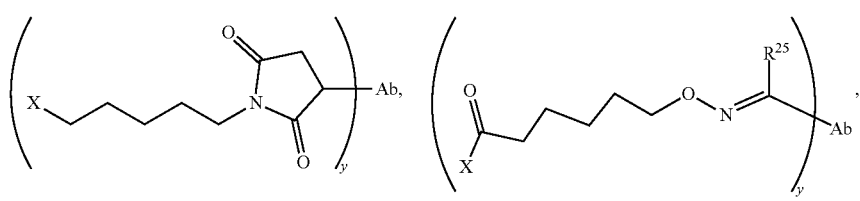

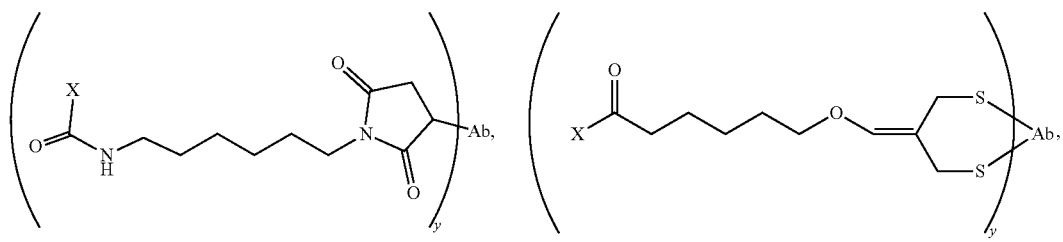

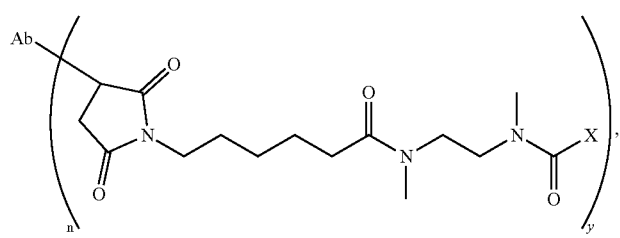

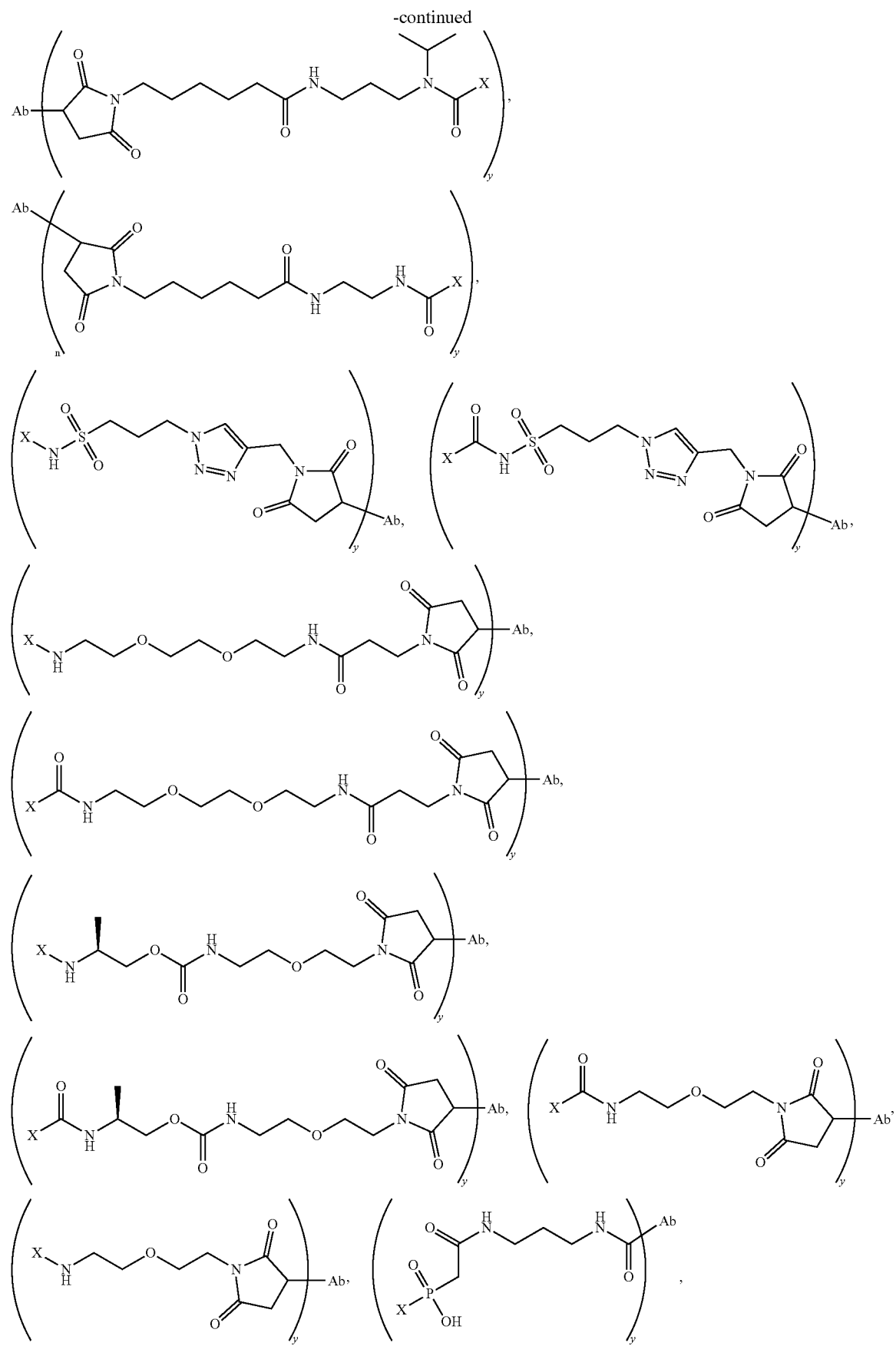

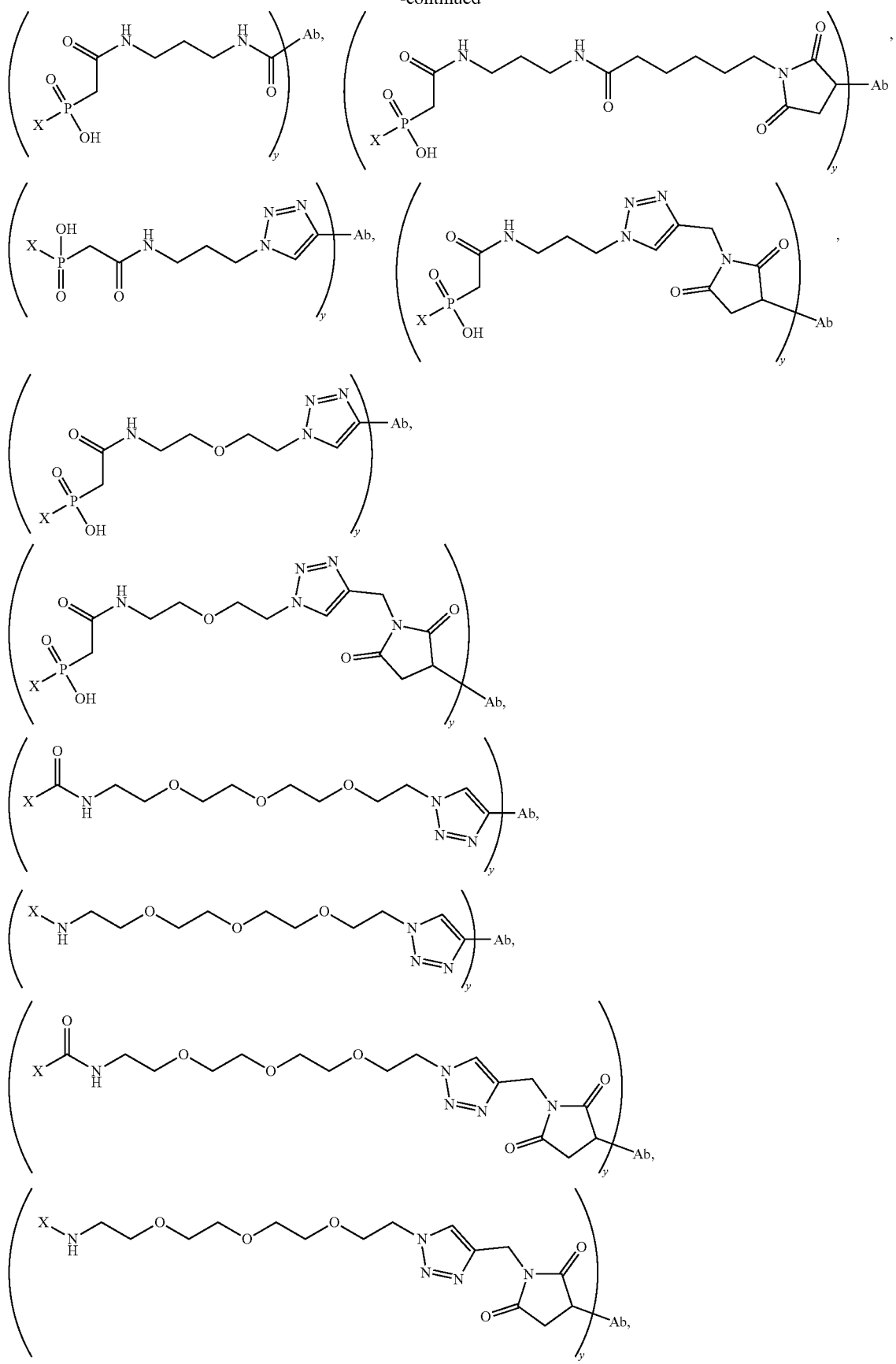

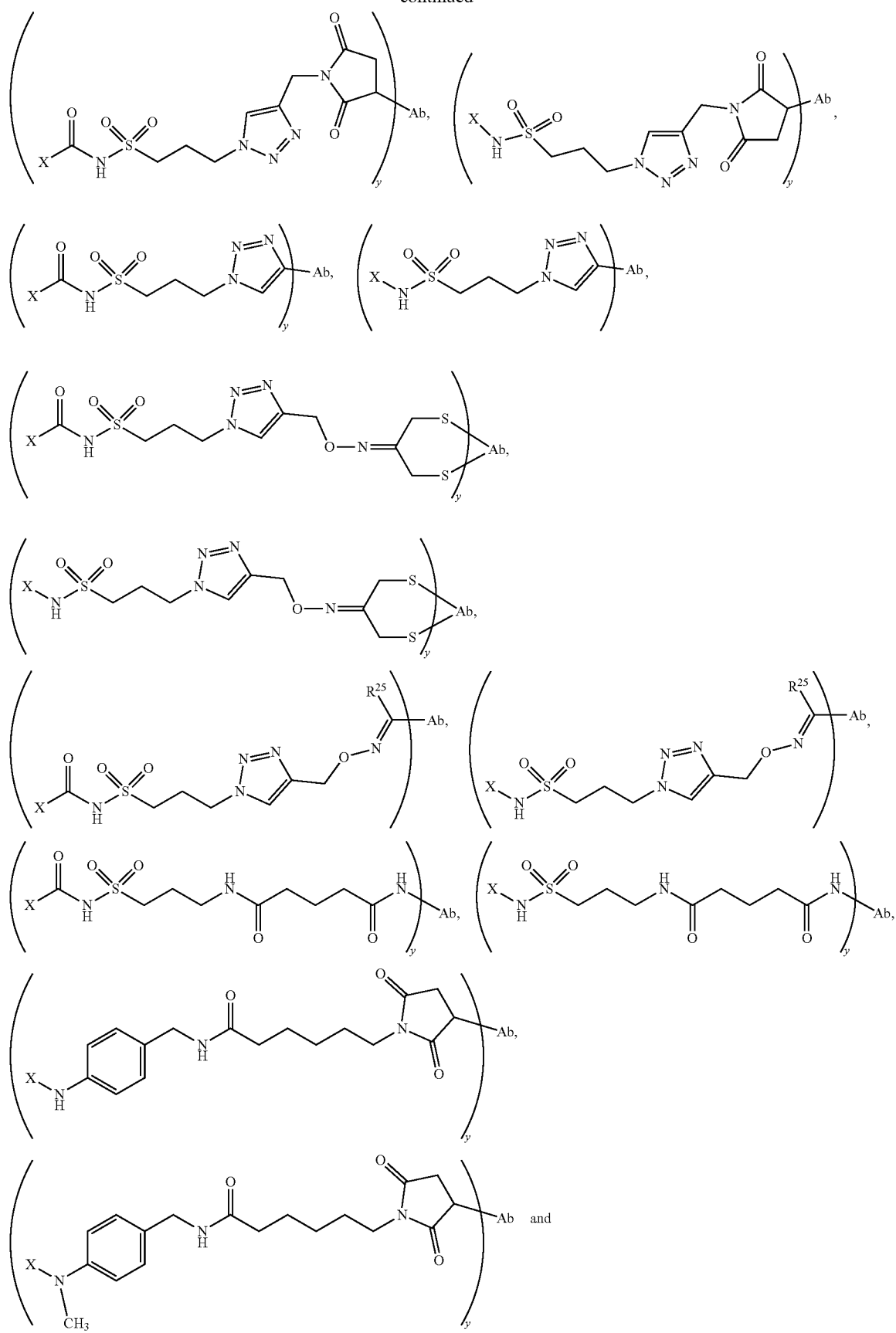

-continued

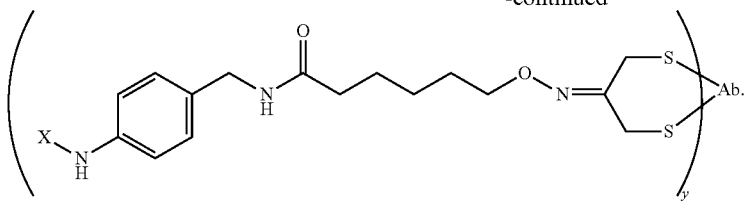

116. In embodiment 117, X is

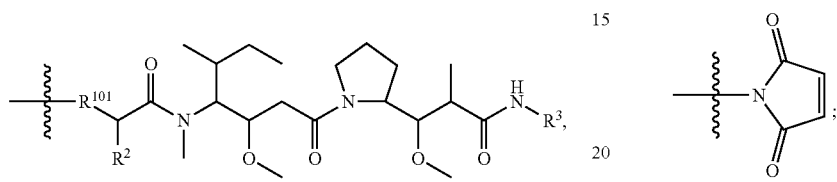

wherein $R^{101}$, $R^2$ and $R^3$ are as defined in embodiments 57 to 73.

117. In embodiment 117, X is

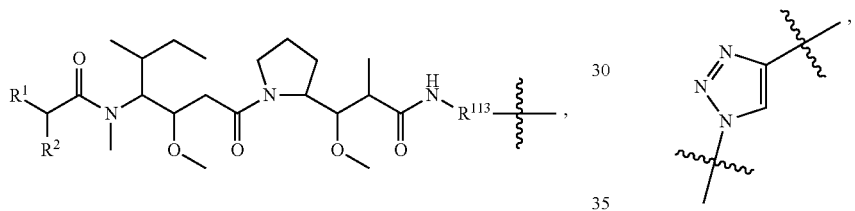

wherein $R^1$, $R^2$ and $R^3$ are as defined in embodiments 74 to 87.

118. A compound or stereoisomer thereof having the structure of Formula (I)

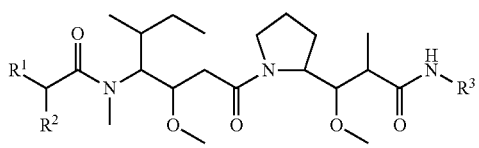

Formula (I)

wherein:
$R^1$ is —N=CR$^4$R$^5$; $R^2$ is —C$_1$-C$_6$alkyl; $R^3$ is

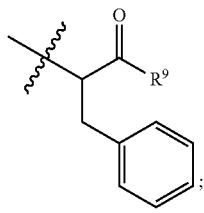

$R^4$ is —N(R$^6$)$_2$;
each $R^6$ is independently selected from H and —C$_1$-C$_6$alkyl;

$R^9$ is —NHS(=O)$_2$LR$^{11}$; $R^{11}$ is

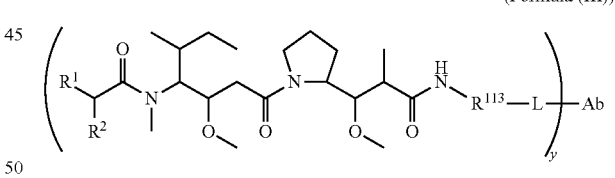

L is —(CH$_2$)$_m$X$_3$(CH$_2$)$_m$—; X$_3$ is and each m is independently selected from 1, 2 and 3.

119. An immunoconjugate of Formula (III)

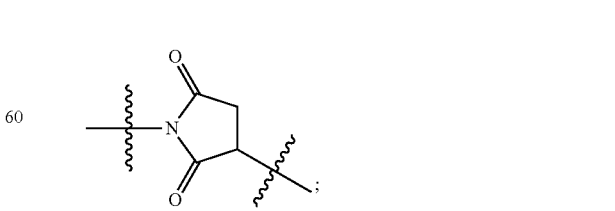

(Formula (III))

wherein:
Ab represents an antigen binding moiety;
L is y is an integer from 1 to 16; $R^1$ is —N=CR$^4$R$^5$; $R^2$ is —C$_1$-C$_6$alkyl;

$R^{113}$ is

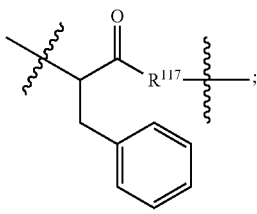

$R^4$ is —N(R$^6$)$_2$;
each $R^6$ is independently selected from H and —C$_1$-C$_6$alkyl;
$R^{117}$ is —NHS(=O)$_2$(CH$_2$)$_m$X$_3$(CH$_2$)$_m$—;
each m is independently selected from 1, 2 and 3.

120. An immunoconjugate of Formula (III)

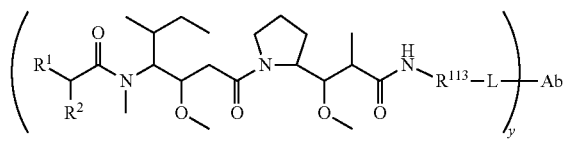

(Formula (III))

wherein:
Ab represents an antigen binding moiety;
L is -L$_1$L$_2$-; L$_1$ is —NHS(=O)$_2$(CH$_2$)$_m$X$_3$(CH$_2$)$_m$—; L$_2$ is

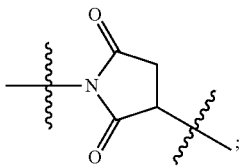

y is an integer from 1 to 16;
$R^1$ is —N=CR$^4$R$^5$; $R^2$ is —C$_1$-C$_6$alkyl;
$R^{113}$ is

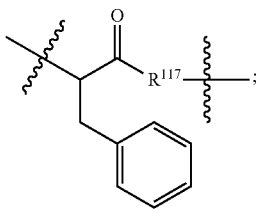

$R^4$ is —N(R$^6$)$_2$;
each $R^6$ is independently selected from H and —C$_1$-C$_6$alkyl;
$R^{117}$ is a bond;
each m is independently selected from 1, 2 and 3.

121. In any one of embodiments 57 to 87 and 117 to 119, unless otherwise described, Ab can be any antigen binding moiety, and is preferably an antigen or antigen fragment that recognizes a cell surface marker such as those described herein that is characteristic of a targeted cell, such as a cancer cell.

122. In any one of embodiments 57 to 87 and 117 to 119, unless otherwise described, Ab can be any antigen binding moiety, typically one that recognizes an antigen characteristic of cells to be targeted for pharmaceutical intervention, such as cancer cells. Many suitable antigens are well known in the art; specific ones of special interest are described herein. Typically, Ab is an antibody, which may be isolated or constructed, and may be natural or modified (engineered), or an antibody fragment that retains antigen binding activity similar to the antibody.

123. In any one of the above embodiments, each m is independently selected from 1, 2, 3, 4, 5 and 6. In any of the above embodiments, each m is independently selected from 1, 2, 3, 4 and 5. In any of the above embodiments, each m is independently selected from 1, 2, 3 and 4. In any of the above embodiments, each m is independently selected from 1, 2 and 3. In any of the above embodiments, each m is independently selected from 1 and 2.

124. In any of the above embodiments, each n is independently selected from 1, 2, 3, 4, 5, 6, 7, 8, 9, 10, 11 and 12. In any of the above embodiments, each n is independently selected from 1, 2, 3, 4, 5, 6, 7, 8, 9, 10 and 11. In any of the above embodiments, each n is independently selected from 1, 2, 3, 4, 5, 6, 7, 8, 9 and 10. In any of the above embodiments, each n is independently selected from 1, 2, 3, 4, 5, 6, 7, 8 and 9. In any of the above embodiments, each n is independently selected from 1, 2, 3, 4, 5, 6, 7 and 8. In any of the above embodiments, each n is independently selected from 1, 2, 3, 4, 5, 6 and 7. In any of the above embodiments, each n is independently selected from 1, 2, 3, 4, 5 and 6. In any of the above embodiments, each n is independently selected from 1, 2, 3, 4 and 5. In any of the above embodiments, each n is independently selected from 1, 2, 3 and 4. In any of the above embodiments, each n is independently selected from 1, 2 and 3. In any of the above embodiments, each n is independently selected from 1 and 2.

125. In any one of embodiments 38 to 95, each y is independently selected from 1, 2, 3, 4, 5, 6, 7, 8, 9, 10, 11 and 12. In any of the above embodiments, each y is independently selected from 1, 2, 3, 4, 5, 6, 7, 8, 9, 10 and 11. In any of the above embodiments, each y is independently selected from 1, 2, 3, 4, 5, 6, 7, 8, 9 and 10. In any of the above embodiments, each y is independently selected from 1, 2, 3, 4, 5, 6, 7, 8 and 9. In any of the above embodiments, each y is independently selected from 1, 2, 3, 4, 5, 6, 7 and 8. In any of the above embodiments, each y is independently selected from 1, 2, 3, 4, 5, 6 and 7. In any of the above embodiments, each y is independently selected from 1, 2, 3, 4, 5 and 6. In any of the above embodiments, each y is independently selected from 1, 2, 3, 4 and 5. In any of the above embodiments, each y is independently selected from 1, 2, 3 and 4. In any of the above embodiments, each y is independently selected from 1, 2 and 3. In any of the above embodiments, each y is independently selected from 1 and 2.

We claim:

1. A compound or stereoisomer thereof having the structure of Formula (I)

Formula (I)

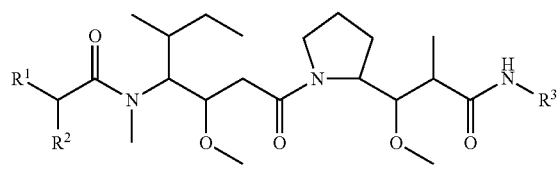

wherein:

R$^1$ is —N=CR$^4$R$^5$, —N=R$^{19}$, —N=CR$^5$ R$^{20}$, —N=CR$^5$NR$^{12}$(CH$_2$)$_m$N(R$^{12}$)C(O)OR$^{12}$, —N=CR$^5$NR$^{12}$(CH$_2$)$_m$N(R$^{12}$)$_2$, —NHC(=NR$^6$)R$^4$, —NHC(=O)R$^4$, —NHC(=O)R$^{20}$, —NHR$^8$, —NHR$^{21}$, —N=CR$^5$R$^{10}$, —N=R$^{22}$, —N=CR$^5$R$^{23}$ or —NHC(=O)R$^{23}$ ;

R$^2$ is —C$_1$-C$_6$alkyl;

R$^3$ is

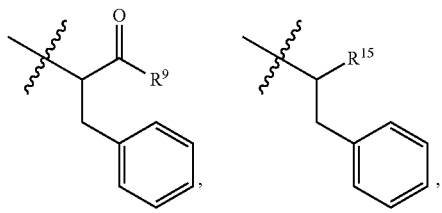

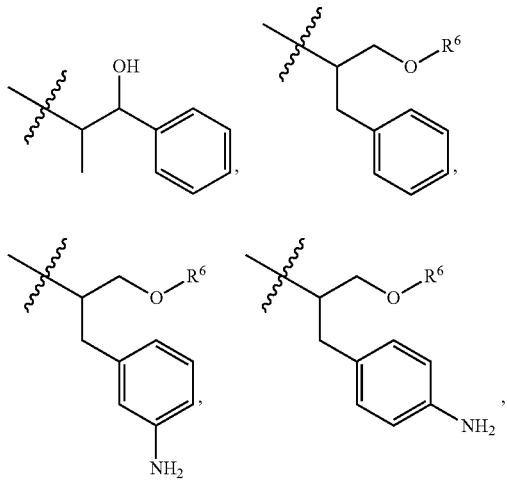

or

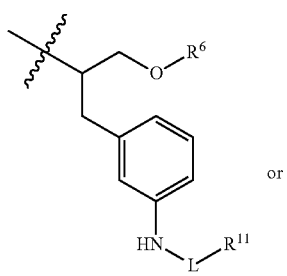

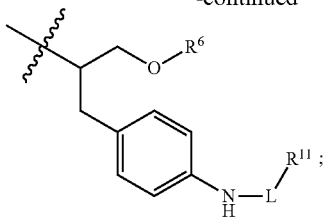

R$^4$ is —N(R$^6$)$_2$ or —NR$^6$R$^7$;

R$^5$ is N(R$^6$)$_2$;

each R$^6$ is independently selected from H and —C$_1$-C$_6$alkyl;

R$^7$ is —(CH$_2$)$_m$N(R$^{12}$)$_2$, —(CH$_2$)$_m$N(R$^{12}$)C(=O)OR$^{12}$ or an unsubstituted C$_3$-C$_8$cycloalkyl;

or R$^7$ is a C$_3$-C$_8$cycloalkyl substituted with 1-3 substituents independently selected from C$_1$-C$_6$alkyl, oxo, —C(=O)R$^{18}$, —(CH$_2$)$_m$OH, —C(=O)(CH$_2$)$_m$OH, —C(=O)((CH$_2$)$_m$O)$_n$R$^{12}$, —((CH$_2$)$_m$O)$_n$R$^{12}$ or a C$_1$-C$_6$alkyl which is optionally substituted with 1 to 5 hydroxyl;

R$^8$ is an unsubstituted C-linked 5-6 membered heteroaryl having 1-2 N heteroatoms;

or R$^8$ is a C-linked 5-6 membered heteroaryl having 1-2 N heteroatoms which is substituted with 1-3 substituents independently selected from C$_1$-C$_6$alkyl, C$_1$-C$_6$haloalkyl, halogen, C$_1$-C$_6$alkoxy, —OH, —CN, —NO$_2$, —C(=O)OR$^6$, —C(=O)N(R$^6$)$_2$, —C(=O)NR$^6$(CH$_2$)$_m$N(R$^6$)C(O)OR$^6$ and —C(=O)NR$^6$(CH$_2$)$_m$N(R$^6$)$_2$;

R$^9$ is —OH, C$_1$-C$_6$alkoxy, —NHS(O)$_2$(CH$_2$)$_m$N$_3$, —NHS(O)$_2$(CH$_2$)$_m$NH$_2$, —N(R$^{12}$)$_2$, —R$^{16}$, —NR$^{12}$(CH$_2$)$_m$N(R$^{12}$)$_2$, —NR$^{12}$(CH$_2$)$_m$R$^{16}$, —LR$^{11}$, —NHS(O)$_2$R$^{18}$—NHS(=O)$_2$LR$^{11}$,

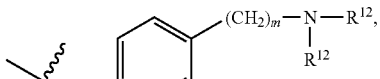

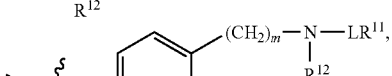

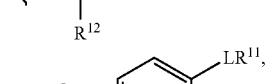

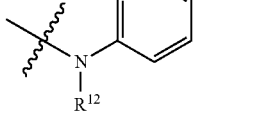

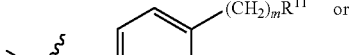

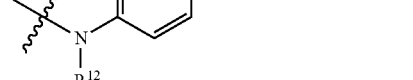

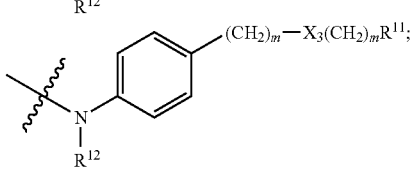

$R^{10}$ is $LR^{11}$ or

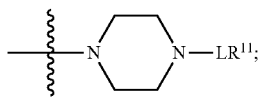

$R^{11}$ is

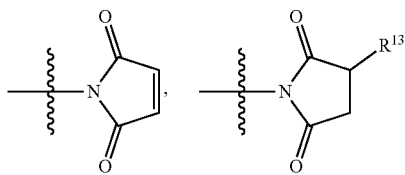

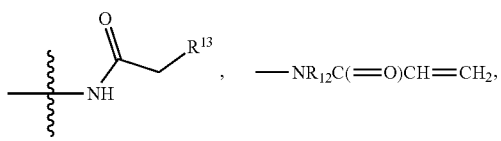, $-NR_{12}C(=O)CH=CH_2$, $-N_3$, —C≡CH, SH, $-SSR^{17}$, $-S(=O)_2(CH=CH_2)$, $-(CH_2)_2S(=O)_2(CH=CH_2)$, $-NR^{12}S(=O)_2(CH=CH_2)$, $-NR^{12}C(=O)CH_2R^{13}$, $-NR^{12}C(=O)CH_2Br$, $-NR^{12}C(=O)CH_2I$, $-NHC(=O)CH_2Br$, $-NHC(=O)CH_2I$,

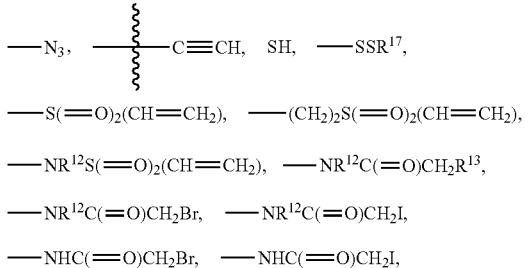

$-ONH_2$, $-C(O)NHNH_2$, $-CO_2H$, $-NH_2$, $-NCO$, $-NCS$,

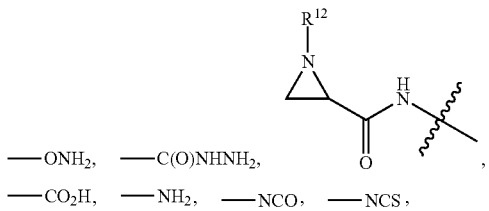

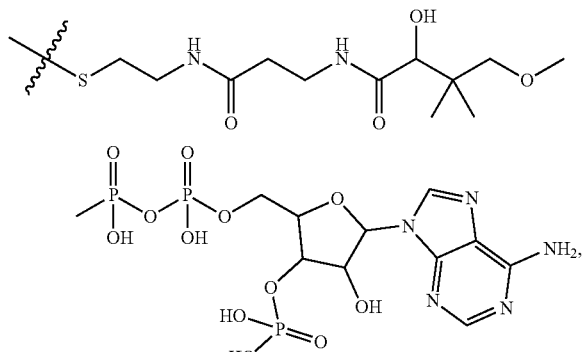

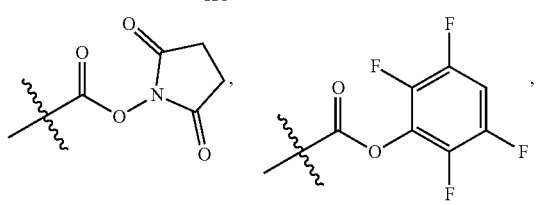

-continued

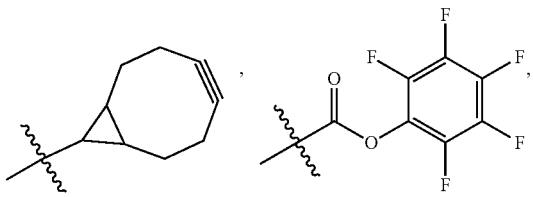

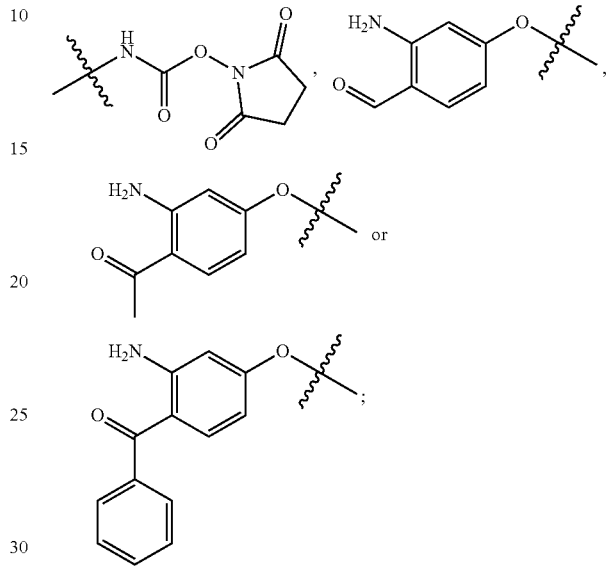

each $R^{12}$ is independently selected from H and $C_1$-$C_6$alkyl;

$R^{13}$ is $-S(CH_2)_nCHR^{14}NHC(=O)R^{12}$ or

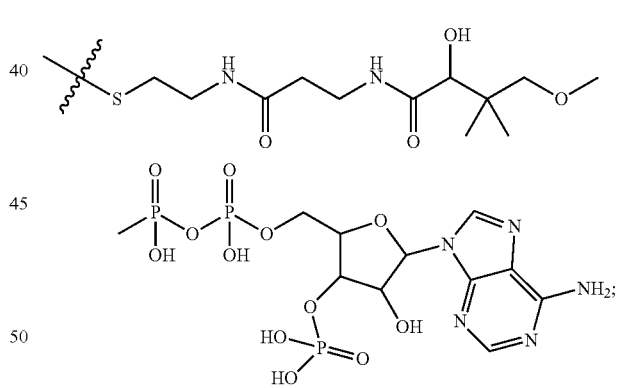

$R^{14}$ is $R^{12}$ or $-C(=O)OR^{12}$;

$R^{15}$ is tetrazolyl, $-CN$, $-C(=O)OR^{12}$,

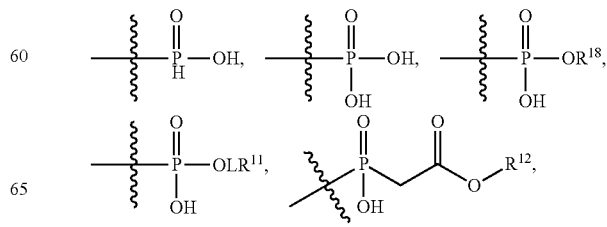

-continued

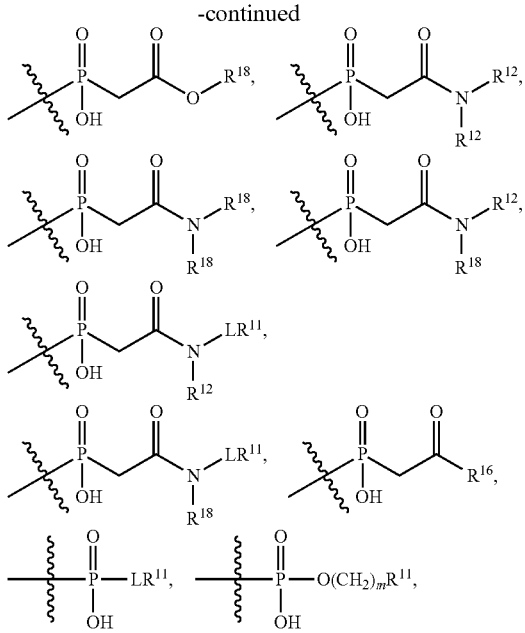

-LR$^{11}$ or —X$_4$LR$^{11}$;

R$^{16}$ is an N-linked 4-8 membered heterocycloalkyl containing 1-2 heteroatoms independently selected from N, O, S, S(=O) and S(=O)$_2$, which is unsubstitituted or substituted with -LR$^{11}$;

R$^{17}$ is 2-pyridyl or 4-pyridyl;

each R$^{18}$ is independently selected from a C$_1$-C$_6$alkyl, a C$_1$-C$_6$alkyl which is substituted with azido and a C$_1$-C$_6$alkyl which is substituted with 1 to 5 hydroxyl;

R$^{19}$ is an unsubstituted C-linked 5-6 membered heterocycloalkyl having 1-2 heteroatoms independently selected from N and O;

or R$^{19}$ is a C-linked 5-6 membered heterocycloalkyl having 1-2 heteroatoms independently selected from N and O which is substituted with 1-3 substituents independently selected from C$_1$-C$_6$alkyl, C$_1$-C$_6$haloalkyl, halogen and C$_{1\text{-}6}$alkoxy;

R$^{20}$ is an unsubstituted N-linked 5-6 membered heterocycloalkyl having 1-2 heteroatoms independently selected from N, O and S;

or R$^{20}$ is an N-linked 5-6 membered heterocycloalkyl having 1-2 heteroatoms independently selected from N, O and S, which is substituted with 1-2 substituents independently selected from C$_1$-C$_6$alkyl, —C(=O) OR$^{12}$, —C(=O)(CH$_2$)$_m$N$_3$, C$_1$-C$_6$haloalkyl, halogen, oxo, —OH and C$_1$-C$_6$alkoxy;

R$^{21}$ is a C-linked 5-6 membered heteroaryl having 1-2 N heteroatoms which is substituted with LR$^{11}$ and 0-2 substituents independently selected from C$_1$-C$_6$alkyl, C$_1$-C$_6$haloalkyl, halogen, —CN, NO$_2$, —C(=O)OR$^6$, —C(=O)N(R$^6$)$_2$ and C$_1$-C$_6$alkoxy;

R$^{22}$ is a C-linked 5-6 membered heterocycloalkyl having 1-2 heteroatoms independently selected from N, O and S which is substituted with LR$^{11}$ and 0-2 substituents independently selected from C$_1$-C$_6$alkyl, C$_1$-C$_6$haloalkyl, halogen and C$_1$-C$_6$alkoxy;

R$^{23}$ is an N-linked 5-6 membered heterocycloalkyl having 1-2 heteroatoms independently selected from N and O which is substituted with LR$^{11}$ and 0-2 substituents independently selected from C$_1$-C$_6$alkyl, C$_1$-C$_6$haloalkyl, halogen and C$_1$-C$_6$alkoxy;

each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein L1 is selected from:

—(CH$_2$)$_m$—, —C(=O)(CH$_2$)$_m$—, —NR$^{12}$C(=O)(CH$_2$)$_m$—, —C(=O)X$_1$X$_2$C(=O)(CH$_2$)$_m$—, —C(=O)X$_1$X$_2$C(=O)(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NR$^{12}$C(=O)(CH$_2$)$_m$—, —C(=O)X$_1$X$_2$((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NR$^{12}$((CH$_2$)$_m$O)$_n$(CH$_2$)$_m$—, —C(=O)X$_1$X$_2$C(=O)(CH$_2$)$_m$NR$^{12}$((CH$_2$)$_m$O)$_n$(CH$_2$)$_m$X$_3$(CH$_2$)$_m$—, —(CH$_2$)$_m$NR$^{12}$C(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NR$^{12}$(CH$_2$)$_m$—, —C(=O)NR$^{12}$(CH$_2$)$_m$—, —C(=O)NR$^{12}$(CH$_2$)$_m$X$_3$(CH$_2$)$_m$—, —C(=O)NR$^{12}$(CH$_2$)$_m$NR$^{12}$C(=O)X$_1$X$_2$C(=O)(CH$_2$)$_m$—, —C(=O)X$_1$C(=O)NR$^{12}$(CH$_2$)$_m$NR$^{12}$C(=O)(CH$_2$)$_m$—, —C(=O)X$_1$C(=O)NR$^{12}$(CH$_2$)$_m$X$_3$(CH$_2$)$_m$—, —C(=O)NR$^{12}$(CH$_2$)$_m$NR$^{12}$C(=O)(CH$_2$)$_m$—, —C(=O)NR$^{12}$(CH$_2$)$_m$NR$^{12}$C(=O)(CH$_2$)$_m$X$_3$(CH$_2$)$_m$—,

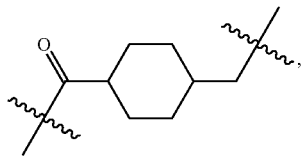

(CH$_2$)$_m$C(=O)NR$^{12}$(CH$_2$)$_m$NR$^{12}$C(=O)(CH$_2$)$_m$—, —(CH$_2$)$_m$C(=O)—, —C(=O)(CH$_2$)$_m$NR$^{12}$(CH$_2$)$_m$C(=O) X$_2$X$_1$C(=O)—, —(CH$_2$)$_m$X$_3$(CH$_2$)$_m$C(=O)X$_2$X$_1$C (=O)—, —(CH$_2$)$_m$C(=O)NR$^{12}$(CH$_2$)$_m$—, —(CH$_2$)$_m$C (=O)NR$^{12}$(CH$_2$)$_m$X$_3$(CH$_2$)$_m$—, —(CH$_2$)$_m$X$_3$ (CH$_2$)$_m$NR$^{12}$C(=O)(CH$_2$)$_m$—, —(CH$_2$)$_m$C(=O)NR$^{12}$ (CH$_2$)$_m$X$_3$—, —X$_3$(CH$_2$)$_m$NR$^{12}$C(=O)(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$O)$_n$ (CH$_2$)$_m$NR$^{12}$C(=O)(CH$_2$)$_m$—, —(CH$_2$)$_m$C(=O)NR$^{12}$ (CH$_2$)$_m$O(CH$_2$)$_m$)$_n$—, —((C(R$^{12}$)$_2$)$_m$OC(=O)NR$^{12}$ (CH$_2$)$_m$O(CH$_2$)$_m$—, —(CH$_2$)$_m$(O(CH$_2$)$_m$)$_n$NR$^{12}$C(=O)O(C (R$^{12}$)$_2$)$_m$—, —(CH$_2$)$_m$(O(CH$_2$)$_m$)$_n$C(=O)—, —(CH$_2$)$_m$(O (CH$_2$)$_m$)$_n$S(=O)$_2$(CH$_2$)$_m$—, —(CH$_2$)$_m$NR$^{12}$(CH$_2$)$_m$C (=O)—, —(CH$_2$)$_m$O(CH$_2$)$_m$NR$^{12}$C(=O)O((C(R$^{12}$)$_2$)$_m$—, —(CH$_2$)$_m$NR$^{12}$C(=O)—, —(CH$_2$)$_m$C(=O)X$_2$X$_1$C(=O) NR$^{12}$(CH$_2$)$_m$NR$^{12}$C(=O)—, —(CH$_2$)$_m$C(=O)NR$^{12}$ (CH$_2$)$_m$NR$^{12}$C(=O)X$_1$—, —(CH$_2$)$_m$C(=O)NR$^{12}$ (CH$_2$)$_m$NR$^{12}$C(=O)—,

517

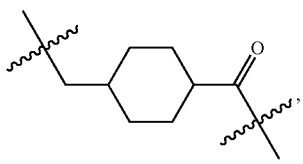

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$C(=O)NR$^{12}$(CH$_2$)$_m$O)$_n$(CH$_2$)$_m$X$_3$—, —X$_3$(CH$_2$)$_m$(O(CH$_2$)$_m$)$_n$NR$^{12}$C(=O)(CH$_2$)$_m$—, —(CH$_2$)$_m$C(=O)NR$^{12}$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$NR$^{12}$C(=O)—, —C(=O)NR$^{12}$(CH$_2$)$_m$NR$^{12}$C(=O)(CH$_2$)$_m$—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —(CH$_2$)$_m$X$_3$—, —X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —(CH$_2$)$_m$C(=O)NR$^{12}$(CH$_2$)$_m$NR$^{12}$C(=O)NR$^{12}$—, —(CH$_2$)$_m$C(=O)NR$^{12}$(CH$_2$)$_m$NR$^{12}$C(=O)—, —(CH$_2$)$_m$C(=O)X$_2$X$_1$C(=O)—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —(CH$_2$)$_m$(O(CH$_2$)$_m$)$_n$NR$^{12}$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —(CH$_2$)$_m$(O(CH$_2$)$_m$)$_n$NR$^{12}$—, —(C(R$_{12}$)$_2$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C

518

(=O)—, —C(=O)X$_1$X$_2$(CH$_2$)$_m$X$_3$(CH$_2$)$_m$—, —(CH$_2$)$_m$X$_3$(CH$_2$)$_m$O(CH$_2$)$_m$)$_n$X$_2$X$_1$C(=O)—, —(CH$_2$)$_m$X$_3$(CH$_2$)$_m$C(=O)NR$^{12}$(CH$_2$)$_m$NR$^{12}$C(=O)—, —(CH$_2$)$_m$X$_3$(CH$_2$)$_m$C(=O)NR$^{12}$(CH$_2$)$_m$C(=O)—, —C(=O)(CH$_2$)$_m$NR$^{12}$C(=O)(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NR$^{12}$C(=O)(CH$_2$)$_m$—, —(CH$_2$)$_m$C(=O)NR$^{12}$(CH$_2$)$_m$C(=O)X$_1$—, —C(=O)CHR$^{aa}$NR$^{12}$—, —NR$^{12}$CHR$^{aa}$C(=O)—, —C(=O)NR$^{12}$—, —C(=O)O—, —S—, —SCH$_2$C(=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NR$^{12}$C(=S)—, —(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$—, —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—,

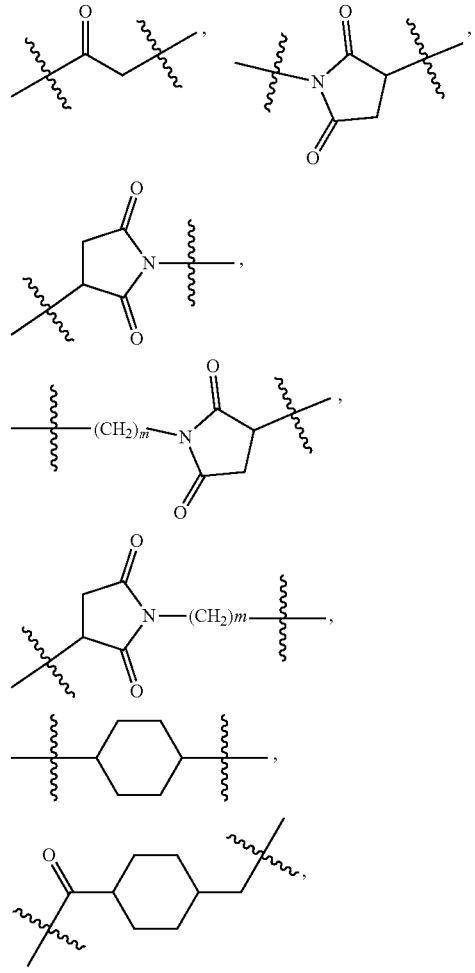

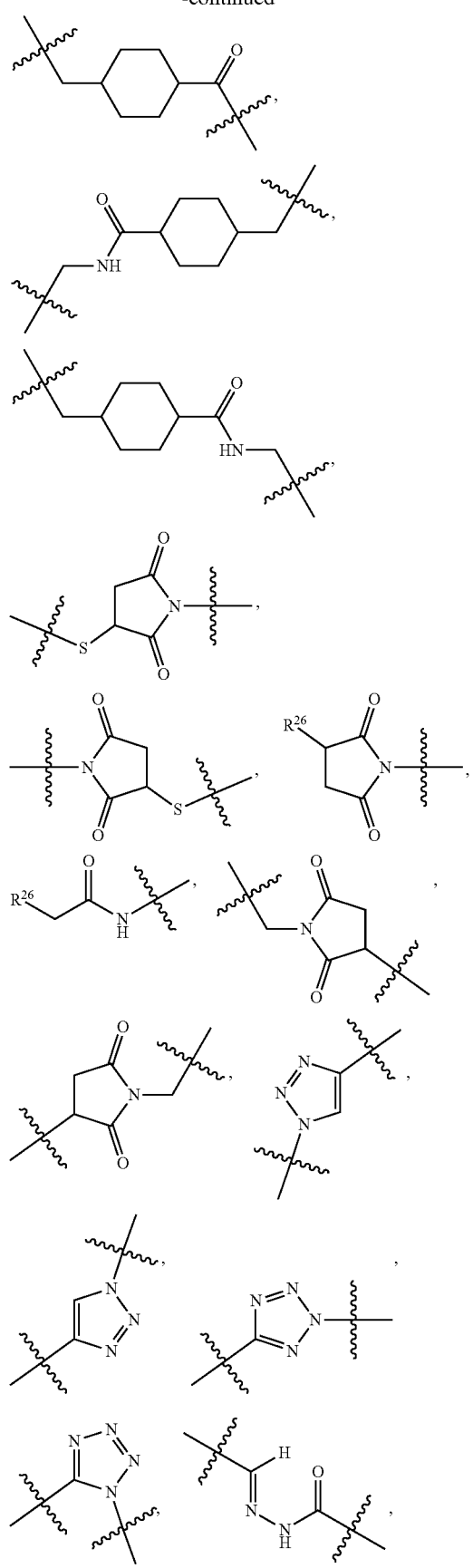
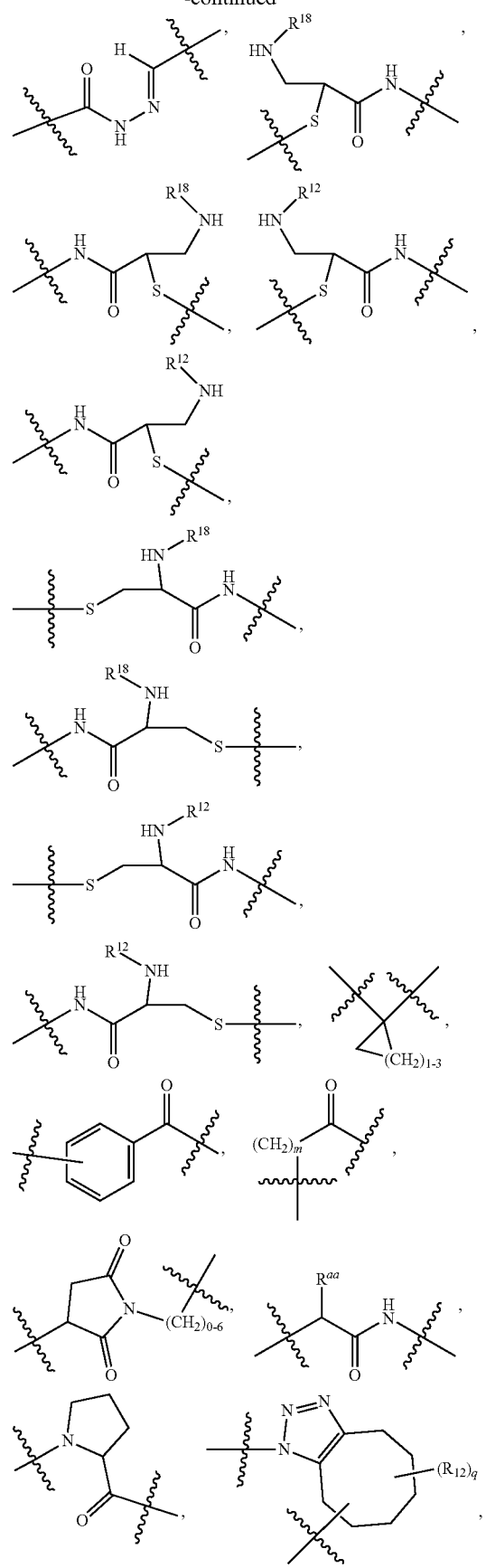

521
-continued
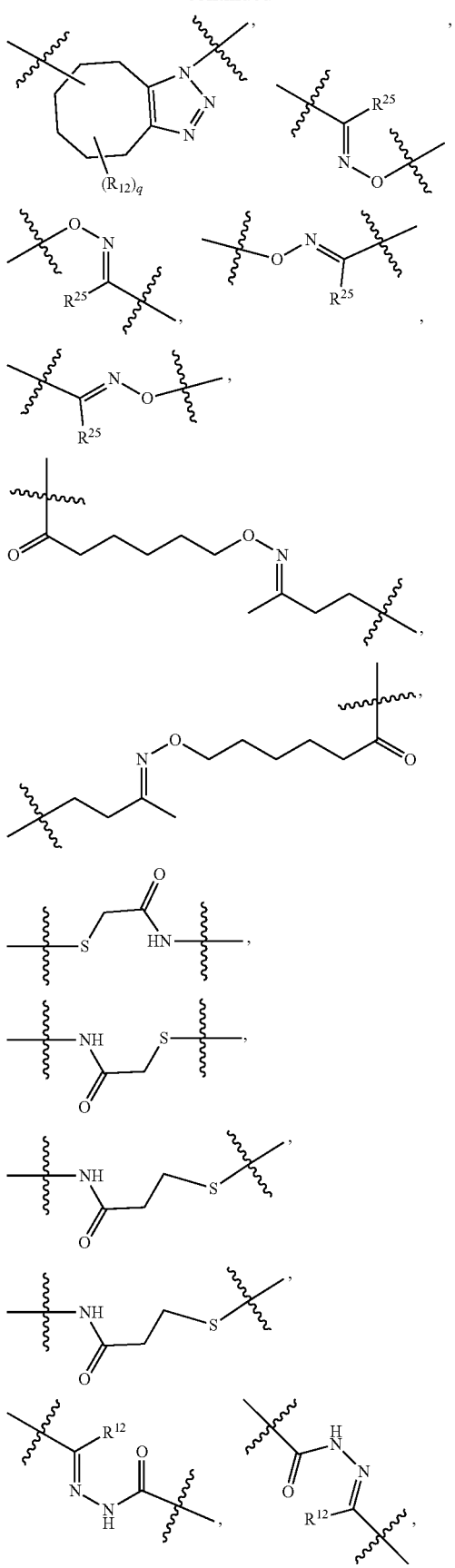
522
-continued
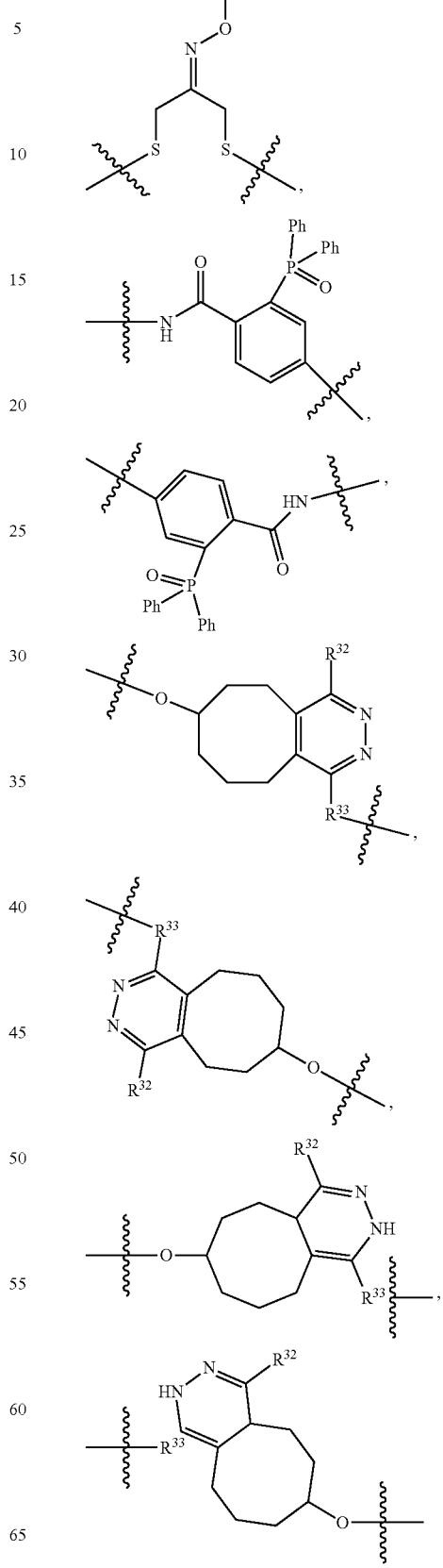

523
-continued
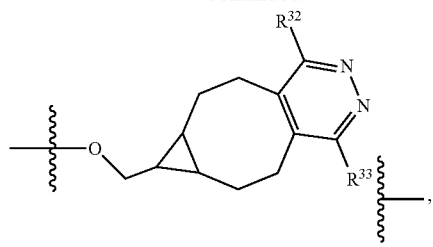
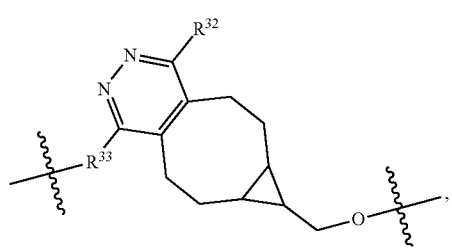
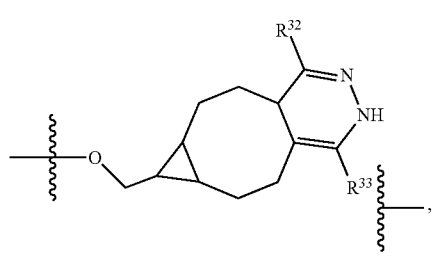
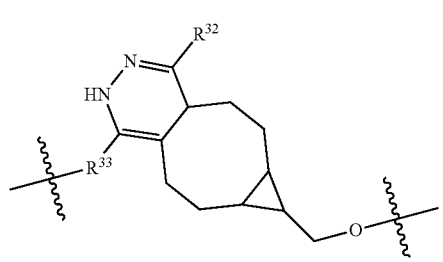
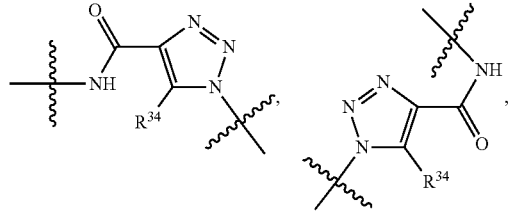
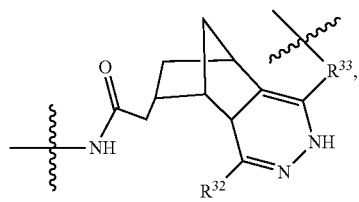
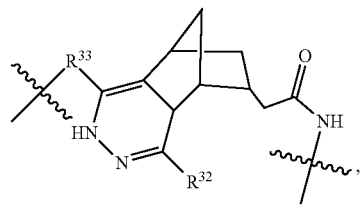
524
-continued
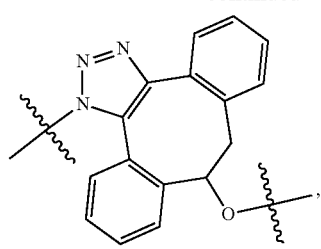
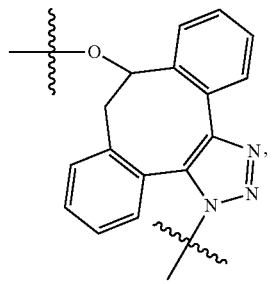
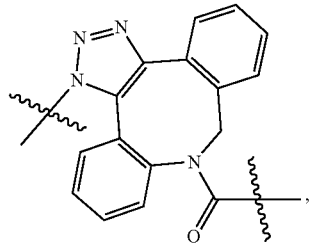
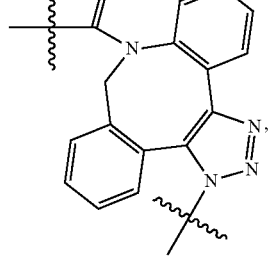
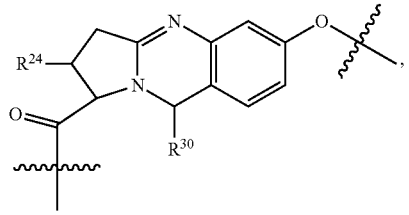
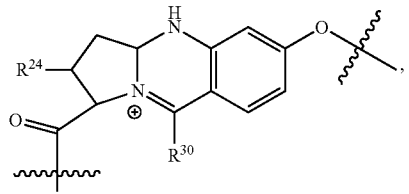
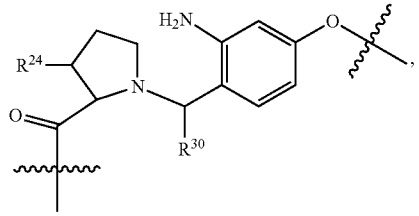

-continued

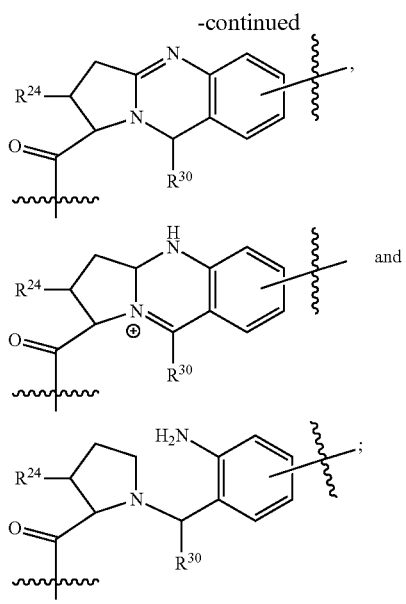

and

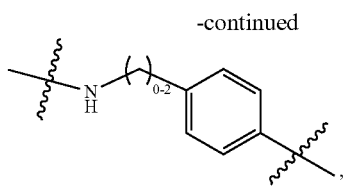

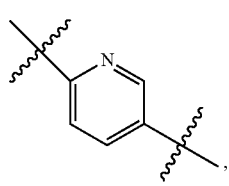

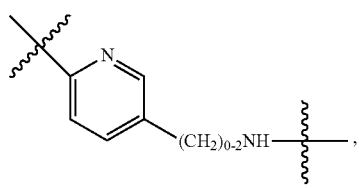

R²⁴ is H or Me;
each R²⁵ is independently selected from H or C₁₋₄ alkyl;
R²⁶ is

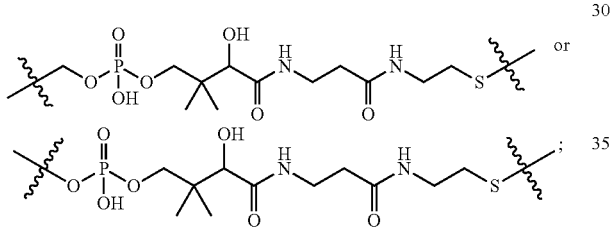 or

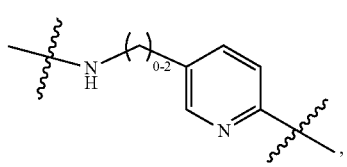

Rᵃᵃ is H or a side chain of an amino acid selected from alanine, tryptophan, tyrosine, phenylalanine, leucine, isoleucine, valine, asparagine, glutamic acid, glutamine, aspatic acid, histidine, arginine, lysine, cysteine, methionine, serine, threonine, citrulline, ornithine, phenylglycine and t-butylglycine;

R³⁰ is H, —CH₃ or phenyl;
R³² is independently selected from H, C₁₋₄ alkyl, phenyl, pyrimidine and pyridine;
R³³ is independently selected from

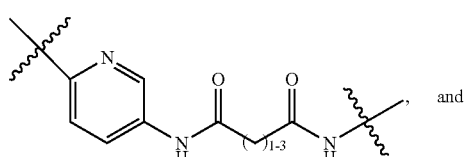

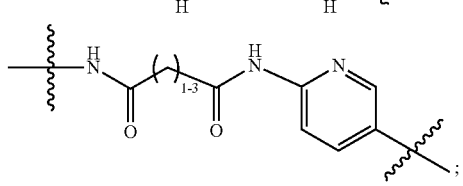

R³⁴ is independently selected from H, C₁₋₄ alkyl, and C₁₋₆ haloalkyl;
X₁ is self immolative spacer selected from

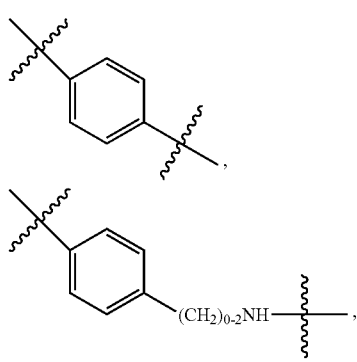

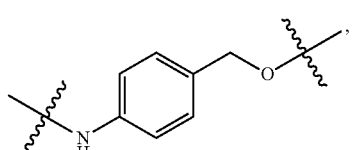

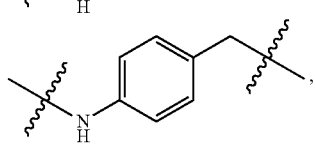

-continued

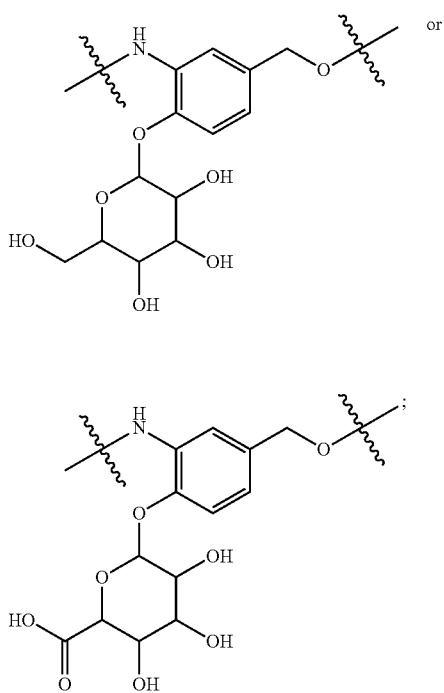

or $X_2$ is dipeptide selected from

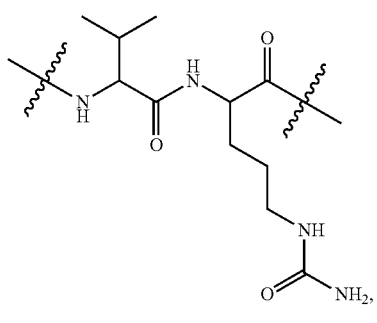

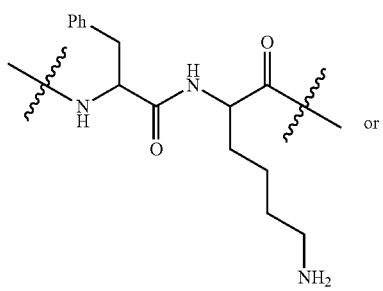

or

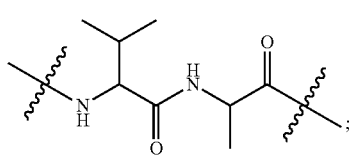

$X_3$ is

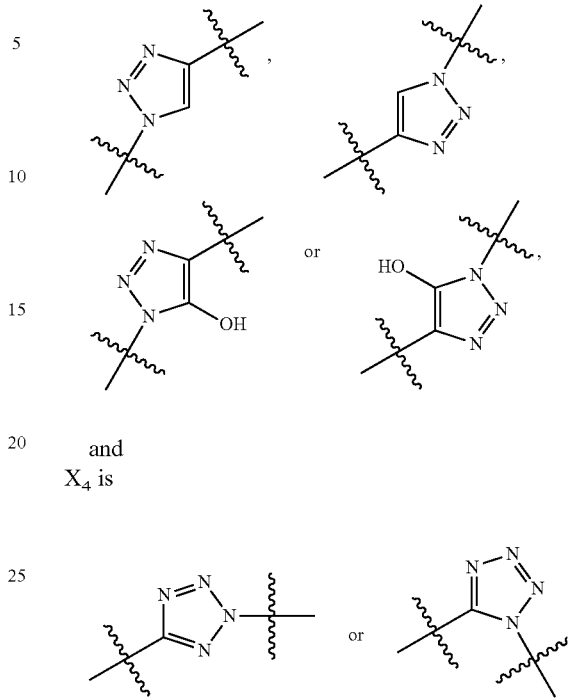

and
$X_4$ is $L_2$, $L_3$, $L_4$, $L_5$, and $L_6$ are each independently selected from a bond and $L_1$;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18, or a tautomer, a hydrate, or a pharmaceutically acceptable salt thereof.

2. The compound of claim 1, wherein each L is independently selected from -$L_1L_2$- and -$L_2L_1$-, or L is -$L_1$-.

3. The compound of claim 1, wherein:
$R^1$ is —N=$CR^4R^5$, —N=$R^{19}$, —N=$CR^5R^{20}$, —N=$CR^5R^{10}$, —N=$R^{22}$ or —N=$CR^5R^{23}$.

4. The compound of claim 1, wherein:
$R^1$ is —N=$CR^5R^{10}$, —N=$R^{22}$, —$NHR^{21}$, —N=$CR^5R^{23}$ or —NHC(=O)$R^{23}$.

5. The compound of claim 1, wherein:
$R^1$ is —NHC(=$NR^6$)$R^4$, —NHC(=O)$R^4$, —NHC(=O)$R^{20}$ or —NHC(=O)$R^{23}$.

6. The compound of claim 1, wherein:
$R^1$ is —$NHR^8$ or —$NHR^{21}$.

7. The compound of claim 1, wherein:
$R^1$ is —N=$CR^5R^{10}$, —N=$R^{22}$, —$NHR^{21}$, —N=$CR^5R^{23}$ or —NHC(=O)$R^{23}$.

8. The compound of claim 1, wherein:
$R^1$ is —N=$CR^4R^5$;
$R^4$ is —N($R^6$)$_2$;
$R^5$ is N($R^6$)$_2$;
and
each $R^6$ is independently selected from —$C_1$-$C_6$alkyl.

9. The compound of claim 1, wherein $R^9$ is —OH, $C_1$-$C_6$alkoxy, —NHS(O)$_2$(CH$_2$)$_m$N$_3$, —NHS(O)$_2$(CH$_2$)$_m$NH$_2$, —NHS(=O)$_2$L$R^{11}$ or

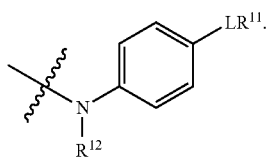

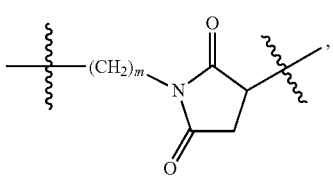

10. The compound of claim 1, wherein —$R^{15}$ is

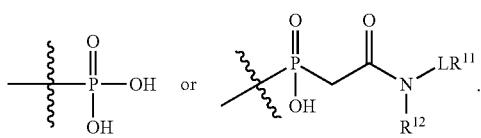

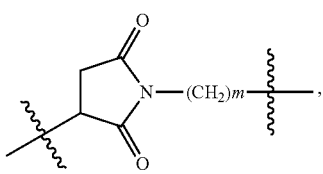

11. The compound of claim 1, wherein $R^{11}$ is

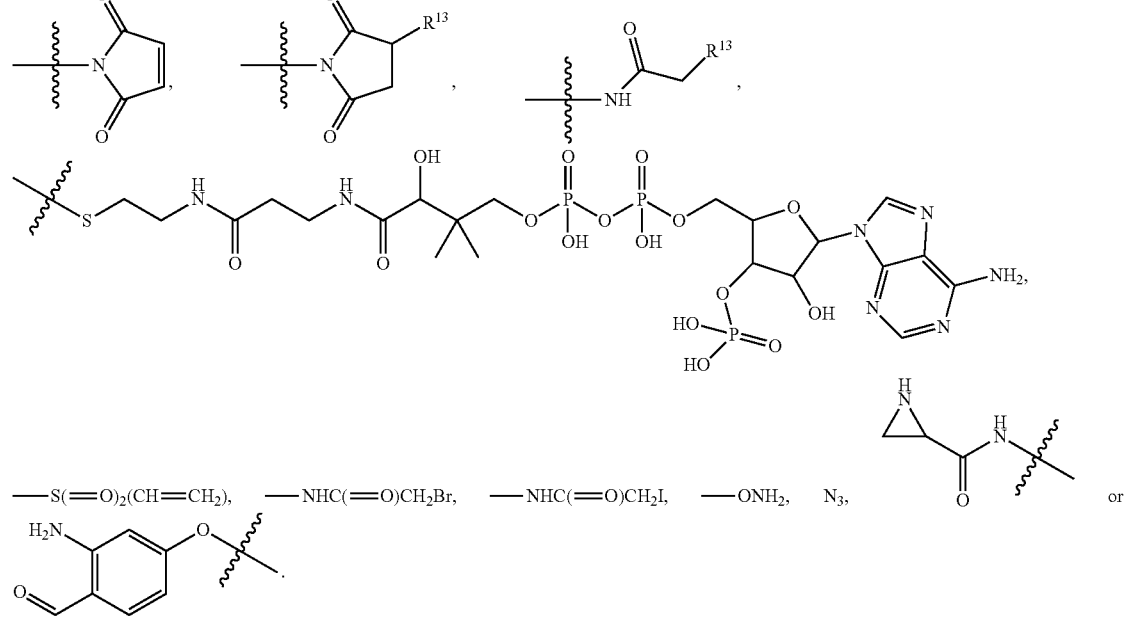

—$S(=O)_2(CH=CH_2)$, —$NHC(=O)CH_2Br$, —$NHC(=O)CH_2I$, —$ONH_2$, $N_3$,

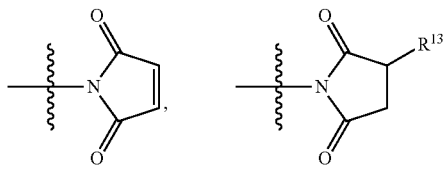 or

12. The compound of claim 1, wherein —$R^{11}$ is

-continued

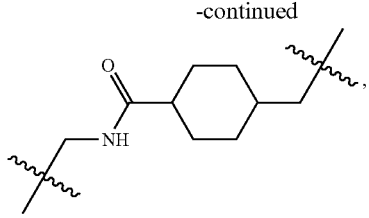

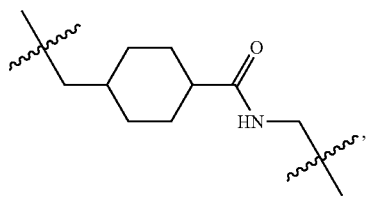

or —$ONH_2$.

13. The compound of claim 1, wherein L is -$L_1$- and -$L_1$- is selected from:

—$(CH_2)_mC(=O)$—, —$C(=O)(CH_2)_m$—, —$(CH_2)_m$—,
—$(CH_2)_mC(=O)X_2X_1C(=O)$—, —$C(=O)X_1X_2C(=O)(CH_2)_m$—, —$(CH_2)_m(O(CH_2)_m)_nC(=O)$—,
—$C(=O)((CH_2)_mO)_n(CH_2)_m$—, —$(CH_2)_mX_3(O(CH_2)_m)_nC(=O)$—, —$C(=O)((CH_2)_mO)_nX_3(CH_2)_m$—,

-continued

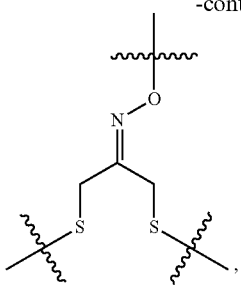

—(CH$_2$)$_m$(O(CH$_2$)$_m$)$_n$S(=O)$_2$(CH$_2$)$_m$—, —(CH$_2$)$_m$S(=O)$_2$((CH$_2$)$_m$O)$_n$(CH$_2$)$_m$—, —(CH$_2$)$_m$NH(CH$_2$)$_m$C(=O)—, —C(=O)(CH$_2$)$_m$NH(CH$_2$)$_m$—, —(CH$_2$)$_m$NR$^{12}$(CH$_2$)$_m$C(=O)—, —C(=O)(CH$_2$)$_m$NR$^{12}$(CH$_2$)$_m$—, —(CH$_2$)$_m$C(=O)NR$^{12}$(CH$_2$)$_m$—, —(CH$_2$)$_m$C(=O)NH(CH$_2$)$_m$—, —(CH$_2$)$_m$NR$^{12}$C(=O)(CH$_2$)$_m$—, —(CH$_2$)$_m$NHC(=O)(CH$_2$)$_m$—, —C(=O)NR$^{12}$(CH$_2$)$_m$NR$^{12}$C(=O)(CH$_2$)$_m$—, —(CH$_2$)$_m$NHC(=O)((CH$_2$)$_m$O)$_n$(CH$_2$)$_m$—, —(CH$_2$)$_m$(O(CH$_2$)$_m$)$_n$C(=O)NH(CH$_2$)$_m$—, —(CH$_2$)$_m$NHC(=O)NH(CH$_2$)$_m$—, —(CH$_2$)$_m$S(=O)$_2$—, —S(=O)$_2$(CH$_2$)$_m$—, —(CH$_2$)$_m$X$_3$(CH$_2$)$_m$S(=O)$_2$—, —S(=O)$_2$(CH$_2$)$_m$X$_3$(CH$_2$)$_m$—, —(CH$_2$)$_m$NHC(=O)(CH$_2$)$_m$X$_3$(CH$_2$)$_m$—, —(CH$_2$)$_m$X$_3$(CH$_2$)$_m$C(=O)NH(CH$_2$)$_m$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —C(=O)X$_1$X$_2$((CH$_2$)$_m$O)$_n$(CH$_2$)$_m$—, —(CH$_2$)$_m$(O(CH$_2$)$_m$)$_n$S(=O)$_2$(CH$_2$)$_m$—, —(CH$_2$)$_m$S(=O)$_2$((CH$_2$)$_m$O)$_n$(CH$_2$)$_m$—, —((CH$_2$)$_m$O)$_n$(CH$_2$)$_m$—, —(CH$_2$)$_m$(O(CH$_2$)$_m$)$_n$—, —(CH$_2$)$_m$X$_3$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$C(=O)X$_2$X$_1$C(=O)—, —C(=O)X$_1$X$_2$C(=O)(CH$_2$)$_m$X$_3$(CH$_2$)$_m$—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —C(=O)X$_1$X$_2$((CH$_2$)$_m$O)$_n$(CH$_2$)$_m$X$_3$(CH$_2$)$_m$—, —(CH$_2$)$_m$NHC(=O)—, —C(=O)NH(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$X$_3$((CH$_2$)$_m$O)$_n$(CH$_2$)$_m$—, —(CH$_2$)$_m$(O(CH$_2$)$_m$)$_n$X$_3$(CH$_2$)$_m$—, —(CH$_2$)$_m$X$_3$(CH$_2$)$_m$C(=O)NH(CH$_2$)$_m$—, —(CH$_2$)$_m$NHC(=O)(CH$_2$)$_m$X$_3$(CH$_2$)$_m$—, —(CH$_2$)$_m$C(=O)NR$^{12}$(CH$_2$)$_m$NR$^{12}$C(=O)—, —(CH$_2$)$_m$C(=O)NH(CH$_2$)$_m$NHC(=O)—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —C(=O)NH(CH$_2$)$_m$NHC(=O)(CH$_2$)$_m$—, —(CH$_2$)$_m$X$_3$(CH$_2$)$_m$NHC(=O)—, —C(=O)NH(CH$_2$)$_m$X$_3$(CH$_2$)$_m$—,—(CH$_2$)$_m$C(=O)NH(CH$_2$)$_m$C(=O)—, —C(=O)(CH$_2$)$_m$NHC(=O)(CH$_2$)$_m$—, —(CH$_2$)$_m$X$_3$(CH$_2$)$_m$C(=O)NH(CH$_2$)$_m$NHC(=O)—, —C(=O)NH(CH$_2$)$_m$NHC(=O)(CH$_2$)$_m$X$_3$(CH$_2$)$_m$—, —(CH$_2$)$_m$X$_3$(CH$_2$)$_m$C(=O)NH(CH$_2$)$_m$C(=O)—, —C(=O)(CH$_2$)$_m$NHC(=O)(CH$_2$)$_m$X$_3$(CH$_2$)$_m$—, —(CH$_2$)$_m$C(=O)NH(CH$_2$)$_m$(O(CH$_2$)$_m$)$_n$C(=O)—, —C(=O)((CH$_2$)$_m$O)$_n$(CH$_2$)$_m$NHC(=O)(CH$_2$)$_m$—, —(CH$_2$)$_m$X$_3$(CH$_2$)$_m$C(=O)NH(CH$_2$)$_m$(O(CH$_2$)$_m$)$_n$C(=O)—,

—C(=O)((CH$_2$)$_m$O)$_n$(CH$_2$)$_m$NHC(=O)(CH$_2$)$_m$X$_3$(CH$_2$)$_m$—, —(CH$_2$)$_m$C(=O)NH(CH$_2$)$_m$NHC(=O)(CH$_2$)$_m$—, —(CH$_2$)$_m$C(=O)NH(CH$_2$)$_m$C(=O)NH(CH$_2$)$_m$—, —(CH$_2$)$_m$NHC(=O)(CH$_2$)$_m$NHC(=O)(CH$_2$)$_m$—, —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—, —(CH$_2$)$_m$X$_3$(CH$_2$)$_m$C(=O)NH(CH$_2$)$_m$— and —(CH$_2$)$_m$NHC(=O)(CH$_2$)$_m$X$_3$(CH$_2$)$_m$—.

14. The compound of claim 1, wherein L is -L$_1$- and -L$_1$- is selected from:

—(CH$_2$)$_m$C(=O)—, —C(=O)(CH$_2$)$_m$—, —(CH$_2$)$_m$—, —(CH$_2$)$_m$C(=O)X$_2$X$_1$C(=O)—, —C(=O)X$_1$X$_2$C(=O)(CH$_2$)$_m$—, —(CH$_2$)$_m$(O(CH$_2$)$_m$)$_n$C(=O)—, —C(=O)((CH$_2$)$_m$O)$_n$(CH$_2$)$_m$—, —(CH$_2$)$_m$X$_3$(O(CH$_2$)$_m$)$_n$C(=O)—, —C(=O)((CH$_2$)$_m$O)$_n$X$_3$(CH$_2$)$_m$—,

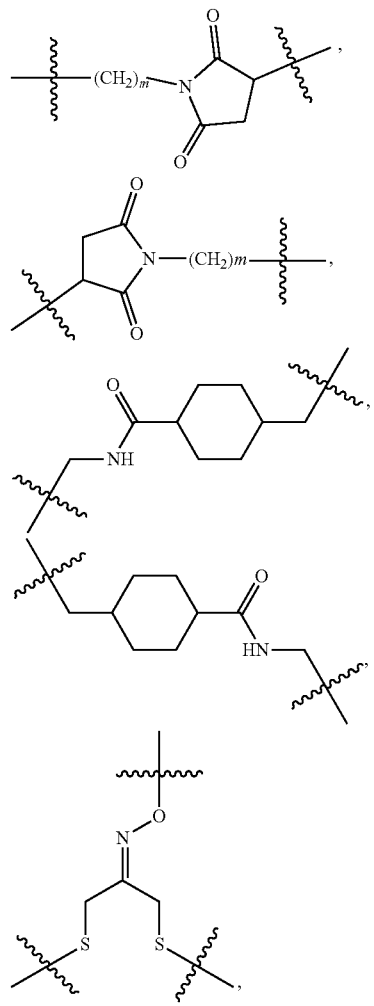

—(CH$_2$)$_m$(O(CH$_2$)$_m$)$_n$S(=O)$_2$(CH$_2$)$_m$—, —(CH$_2$)$_m$S(=O)$_2$((CH$_2$)$_m$O)$_n$(CH$_2$)$_m$—, —(CH$_2$)$_m$NH(CH$_2$)$_m$C(=O)—, —C(=O)(CH$_2$)$_m$NH(CH$_2$)$_m$—, —(CH$_2$)$_m$NR$^{12}$(CH$_2$)$_m$C(=O)—, —C(=O)(CH$_2$)$_m$NR$^{12}$(CH$_2$)$_m$—, —(CH$_2$)$_m$C(=O)NR$^{12}$(CH$_2$)$_m$—, —(CH$_2$)$_m$C(=O)NH(CH$_2$)$_m$—, —(CH$_2$)$_m$NR$^{12}$C(=O)(CH$_2$)$_m$—, —(CH$_2$)$_m$NHC(=O)(CH$_2$)$_m$—, —(CH$_2$)$_m$C(=O)NR$^{12}$(CH$_2$)$_m$NR$^{12}$C(=O)—, —(CH$_2$)$_m$C(=O)NH(CH$_2$)$_m$NHC(=O)—,

—(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —C(=O)NR$^{12}$(CH$_2$)$_m$NR$^{12}$C(=O)(CH$_2$)$_m$—, —(CH$_2$)$_m$NHC(=O)((CH$_2$)$_m$O)$_n$(CH$_2$)$_m$—, —(CH$_2$)$_m$(O(CH$_2$)$_m$)$_n$C(=O)NH(CH$_2$)$_m$—, —(CH$_2$)$_m$NHC(=O)NH(CH$_2$)$_m$—, —(CH$_2$)$_m$S(=O)$_2$—, —S(=O)$_2$(CH$_2$)$_m$—, —(CH$_2$)$_m$X$_3$(CH$_2$)$_m$S(=O)$_2$— and —S(=O)$_2$(CH$_2$)$_m$X$_3$(CH$_2$)$_m$—.

15. The compound of claim 1, wherein L is -L$_1$- and -L$_1$- is selected from:

—(CH$_2$)$_m$C(=O)—, —C(=O)(CH$_2$)$_m$—, —(CH$_2$)$_m$C(=O)NR$^{12}$(CH$_2$)$_m$—, —(CH$_2$)$_m$C(=O)NH(CH$_2$)$_m$—, —(CH$_2$)$_m$NR$^{12}$C(=O)(CH$_2$)$_m$—, —(CH$_2$)$_m$NHC(=O)(CH$_2$)$_m$—, —(CH$_2$)$_m$C(=O)NR$^{12}$(CH$_2$)$_m$NR$^{12}$C(=O)—, —(CH$_2$)$_m$C(=O)NH(CH$_2$)$_m$NHC(=O)—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$((CH$_2$)$_m$O)$_n$(CH$_2$)$_m$NR$^{12}$C(=O)(CH$_2$)$_m$—, and —(CH$_2$)$_m$C(=O)NR$^{12}$(CH$_2$)$_m$(O(CH$_2$)$_m$)$_n$NR$^{12}$—.

16. The compound of claim 1, wherein R$^{12}$ is H, —CH$_3$ or —CH$_2$CH$_3$.

17. The compound of claim 1, wherein R$^2$ is methyl, ethyl, isopropyl or sec-butyl.

18. The compound of claim 1, wherein:

R$^1$ is —N=CR$^4$R$^5$;
R$^2$ is —C$_1$-C$_6$alkyl;
R$^3$ is

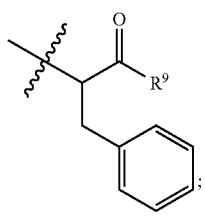

R$^4$ is —N(R$^6$)$_2$;
R$^5$ is N(R$^6$)$_2$;
each R$^6$ is independently selected from —C$_1$-C$_6$alkyl
R$^9$ is —OH, C$_1$-C$_6$alkoxy, —NHS(O)$_2$(CH$_2$)$_m$N$_3$, —NHS(O)$_2$(CH$_2$)$_m$NH$_2$, —NHS(=O)$_2$LR$^{11}$ or

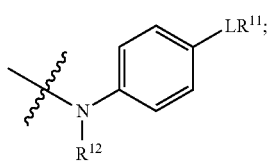

R$^{11}$ is

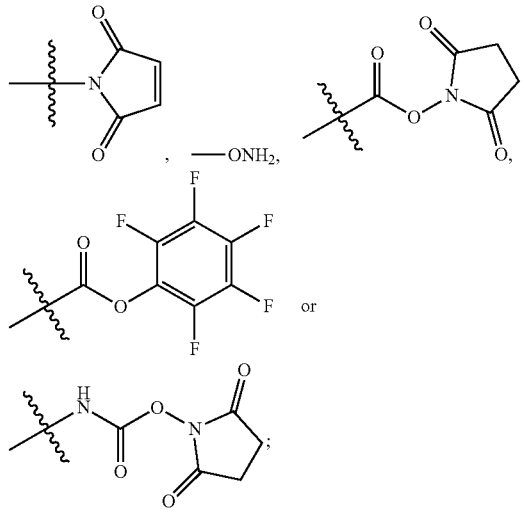

each R$^{12}$ is independently selected from H and C$_1$-C$_6$alkyl;
L is -L$_1$- and -L$_1$- is selected from:
—(CH$_2$)$_m$C(=O)—, —C(=O)(CH$_2$)$_m$—, —(CH$_2$)$_m$C(=O)NR$^{12}$(CH$_2$)$_m$—, —(CH$_2$)$_m$C(=O)NH(CH$_2$)$_m$—, —(CH$_2$)$_m$NR$^{12}$C(=O)(CH$_2$)$_m$—, —(CH$_2$)$_m$NHC(=O)(CH$_2$)$_m$—, —(CH$_2$)$_m$C(=O)NR$^{12}$(CH$_2$)$_m$NR$^{12}$C(=O)—, —(CH$_2$)$_m$C(=O)NH(CH$_2$)$_m$NHC(=O)—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$((CH$_2$)$_m$O)$_n$(CH$_2$)$_m$NR$^{12}$C(=O)(CH$_2$)$_m$—, and —(CH$_2$)$_m$C(=O)NR$^{12}$(CH$_2$)$_m$(O(CH$_2$)$_m$)$_n$NR$^{12}$—;
X$_3$ is

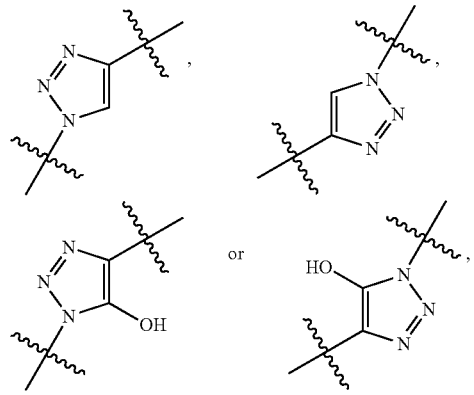

and
each m is independently selected from 1, 2, 3, 4, 5, 6, 7, 8, 9 and 10; and
each n is independently selected from 1, 2, 3, 4, 5, 6, 7, 8, 9, 10, 11, 12, 13, 14, 15, 16, 17 and 18.

19. The compound of claim 1, wherein:
R$^1$ is —N=CR$^4$R$^5$;
R$^2$ is isopropyl R³ is

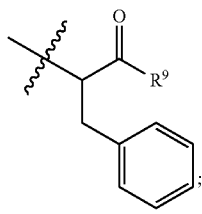

R⁴ is —N(R⁶)₂;
R⁵ is N(R⁶)₂;
each R⁶ is methyl
R⁹ is —NHS(=O)₂LR¹¹ or

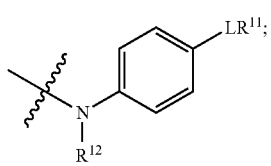

R¹¹ is

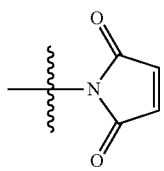

or —ONH₂;
each R¹² is independently selected from H and methyl;
L is -L₁- and -L₁- is selected from:
—(CH₂)$_m$C(=O)—, —C(=O)(CH₂)$_m$—, —(CH₂)$_m$C(=O)NR¹²(CH₂)$_m$—, —(CH₂)$_m$C(=O)NH(CH₂)$_m$—, —(CH₂)$_m$NR¹²C(=O)(CH₂)$_m$—, —(CH₂)$_m$NHC(=O)(CH₂)$_m$—, —(CH₂)$_m$C(=O)NR¹²(CH₂)$_m$NR¹²C(=O)—, —(CH₂)$_m$C(=O)NH(CH₂)$_m$NHC(=O)—, —(CH₂)$_m$X₃(CH₂)$_m$C(=O)—, —C(=O)(CH₂)$_m$X₃(CH₂)$_m$—, —(CH₂)$_m$X₃(CH₂)$_m$—, —((CH₂)$_m$O)$_n$(CH₂)$_m$X₃(CH₂)$_m$—, —(CH₂)$_m$X₃(CH₂)$_m$(O(CH₂)$_m$)$_n$—, —NR¹²C(R¹²)₂(CH₂)$_m$OC(=O)NR¹²((CH₂)$_m$O)$_n$(CH₂)$_m$—, —(CH₂)$_m$(O(CH₂)$_m$)$_n$NR¹²C(=O)O(CH₂)$_m$C(R¹²)₂NR¹²—, —NR¹²((CH₂)$_m$O)$_n$(CH₂)$_m$NR¹²C(=O)(CH₂)$_m$—, and —(CH₂)$_m$C(=O)NR¹²(CH₂)$_m$(O(CH₂)$_m$)$_n$NR¹²—;

X₃ is

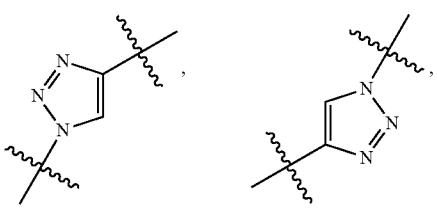

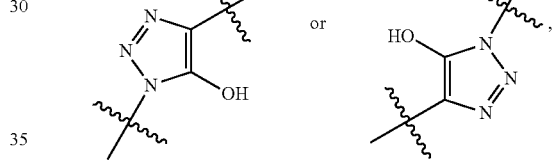

and
each m is independently selected from 1, 2, 3, 4, 5, and 6; and
each n is independently selected from 1, 2, 3 and 4.

20. The compound of claim 1 selected from,

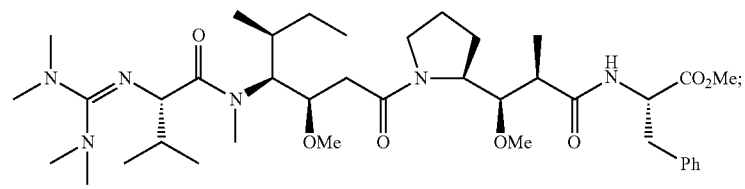

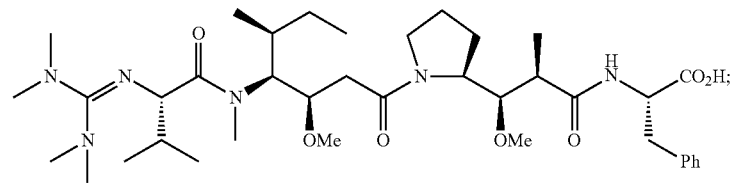

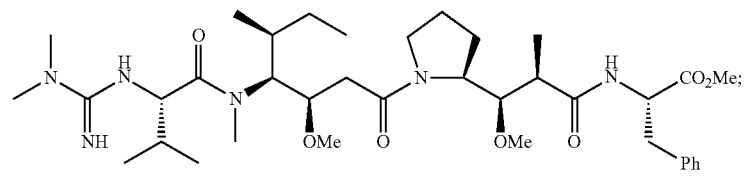

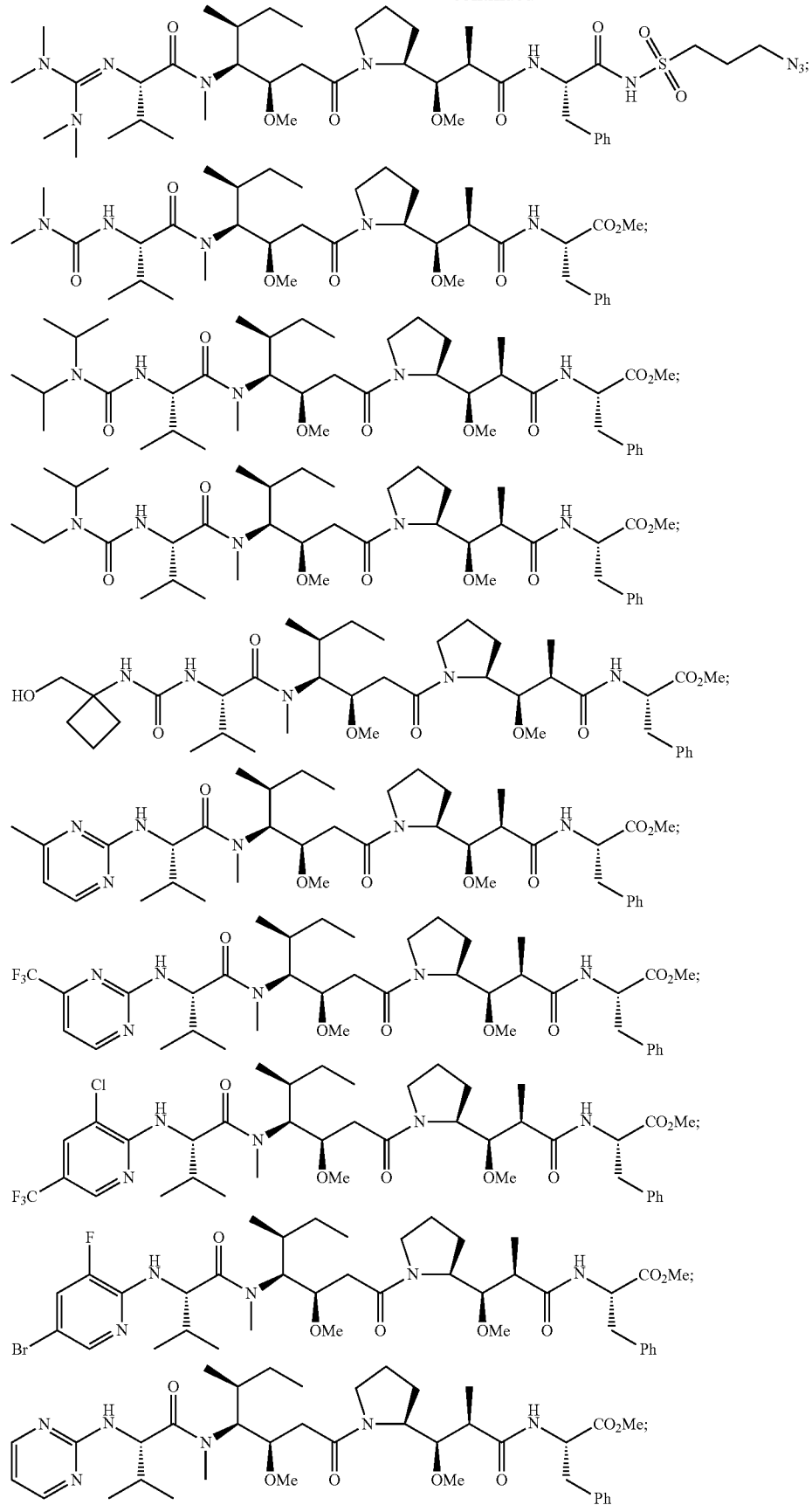

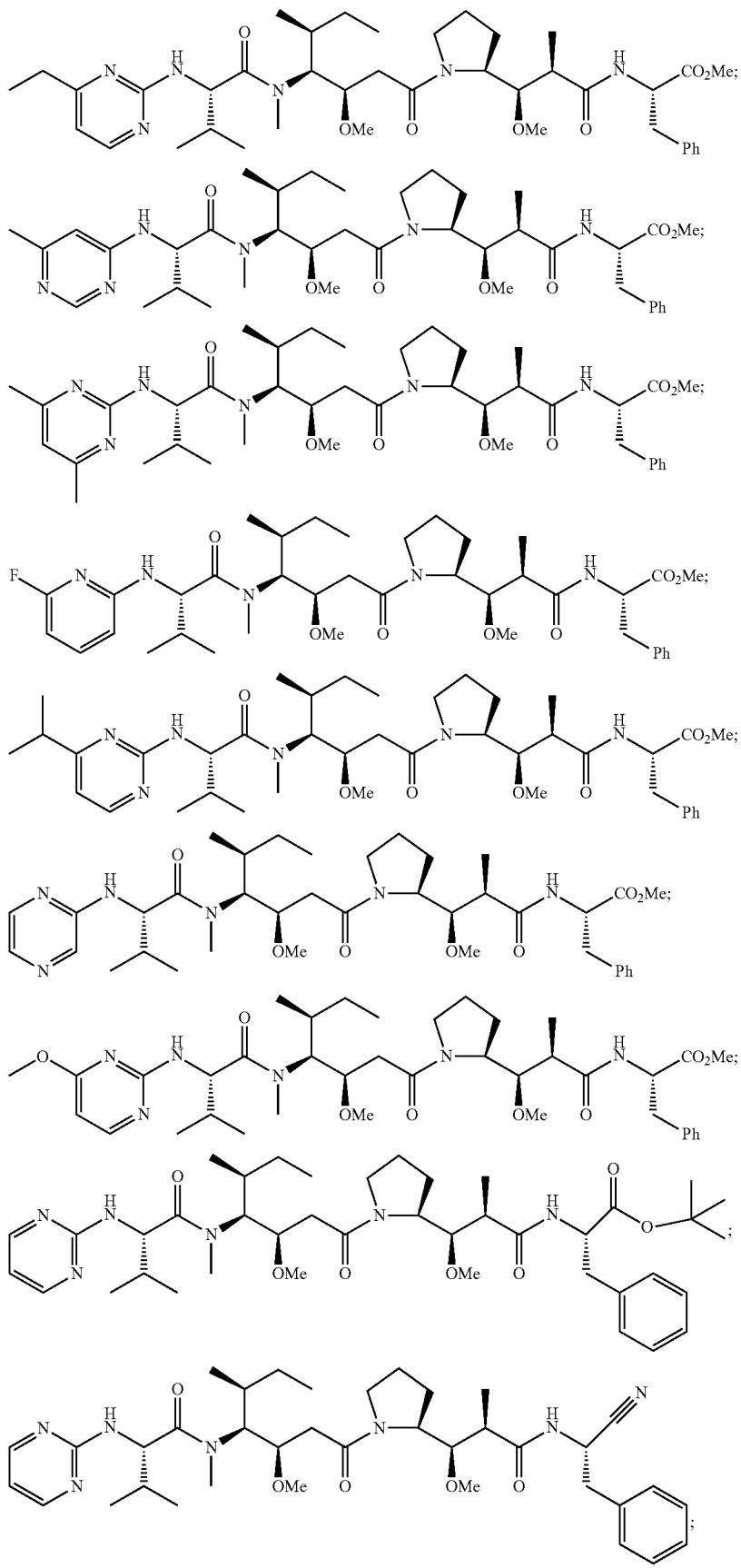

-continued
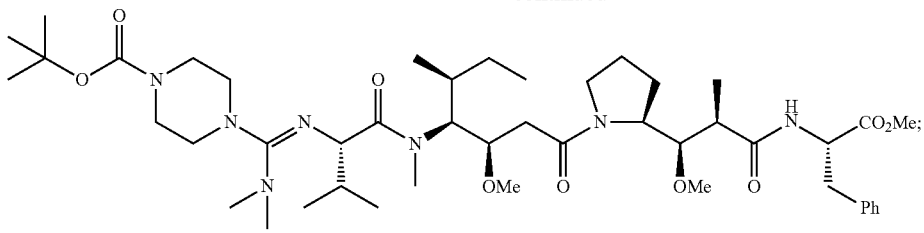
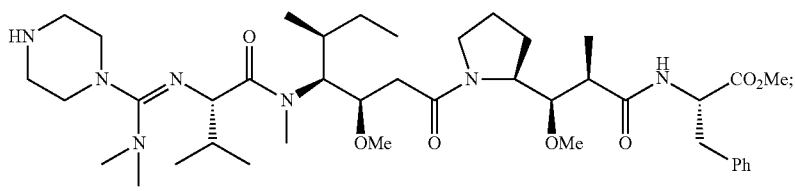
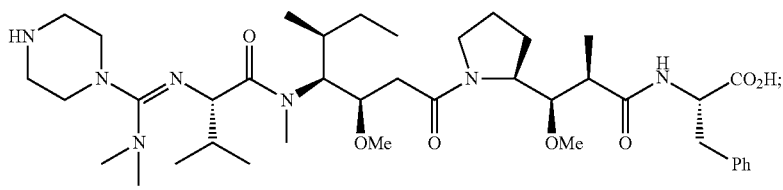
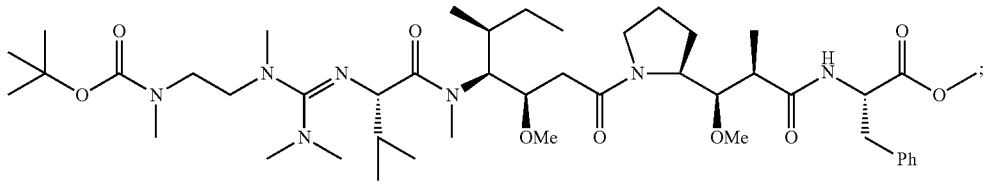
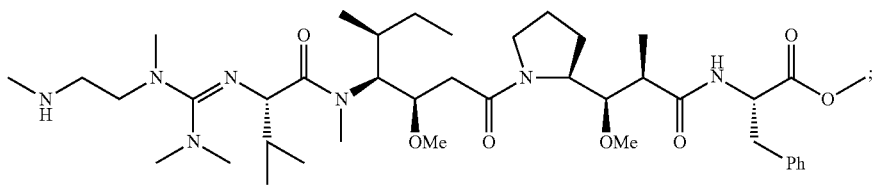
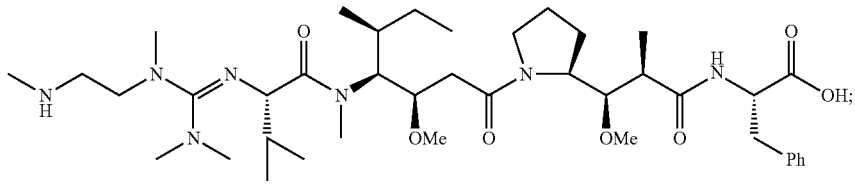
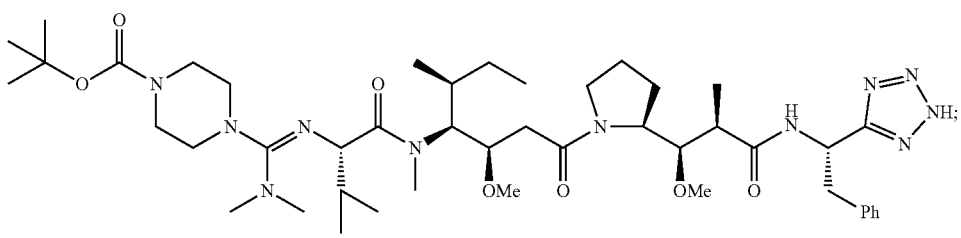
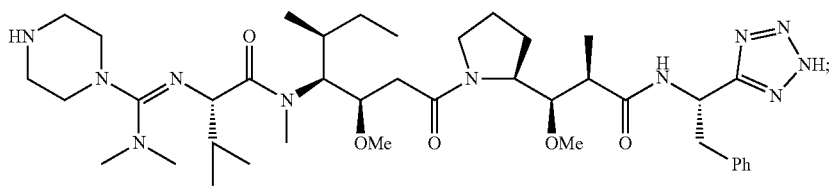

-continued
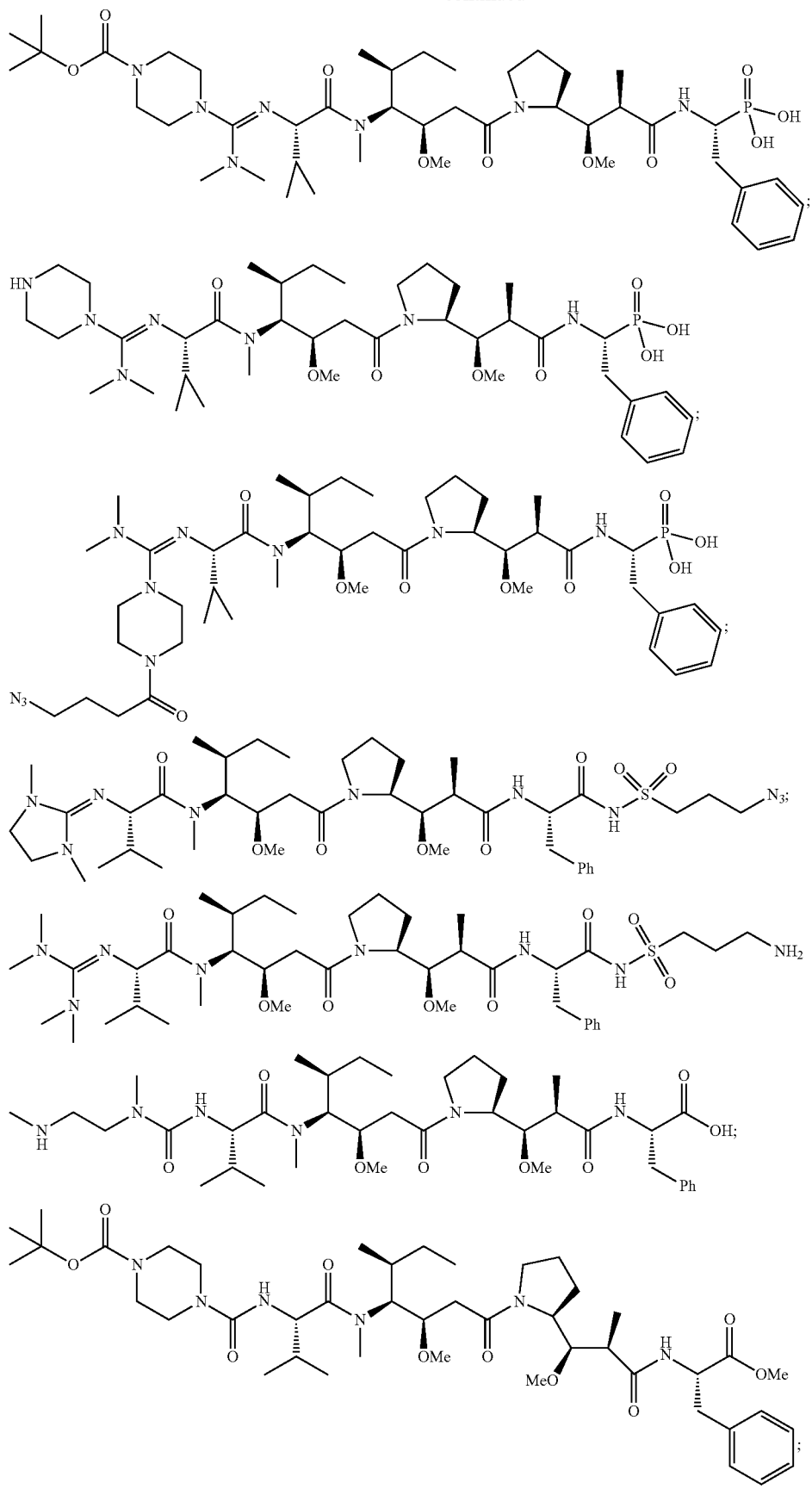

-continued
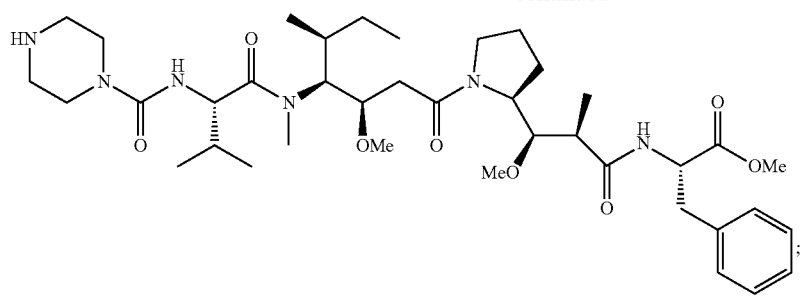
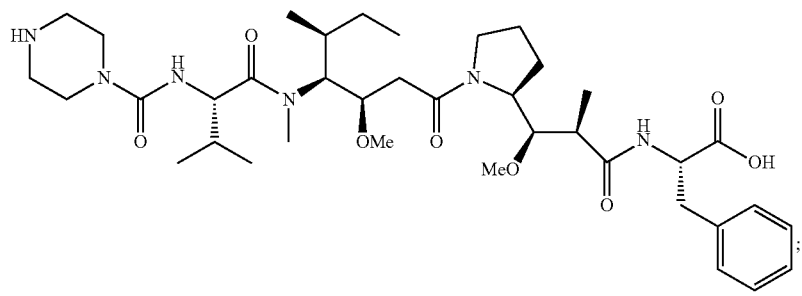
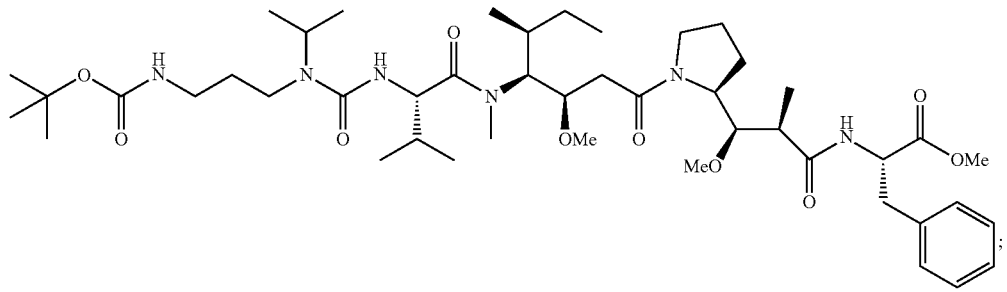
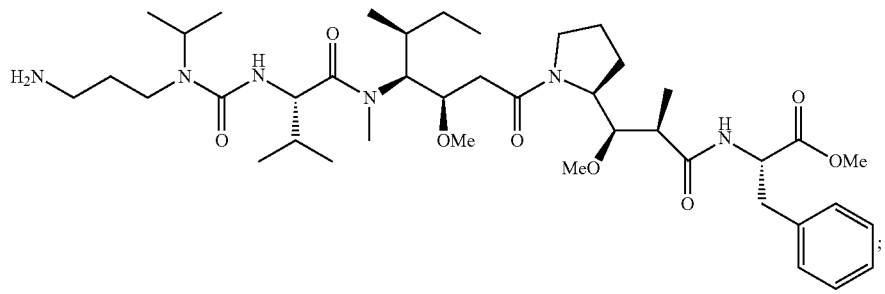
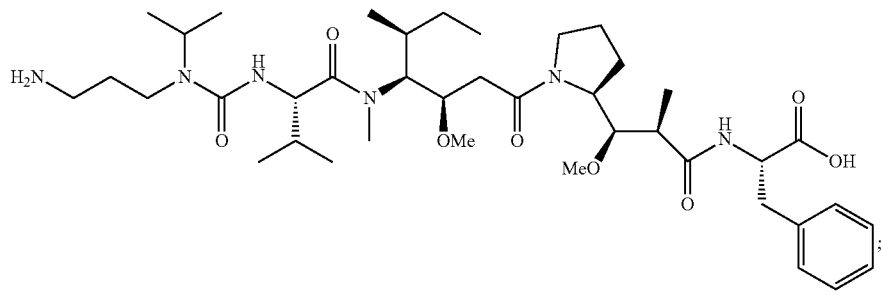
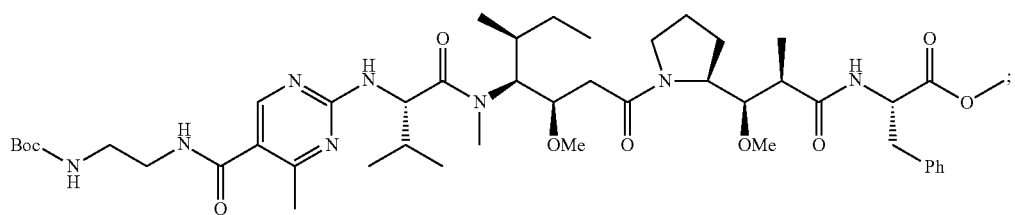

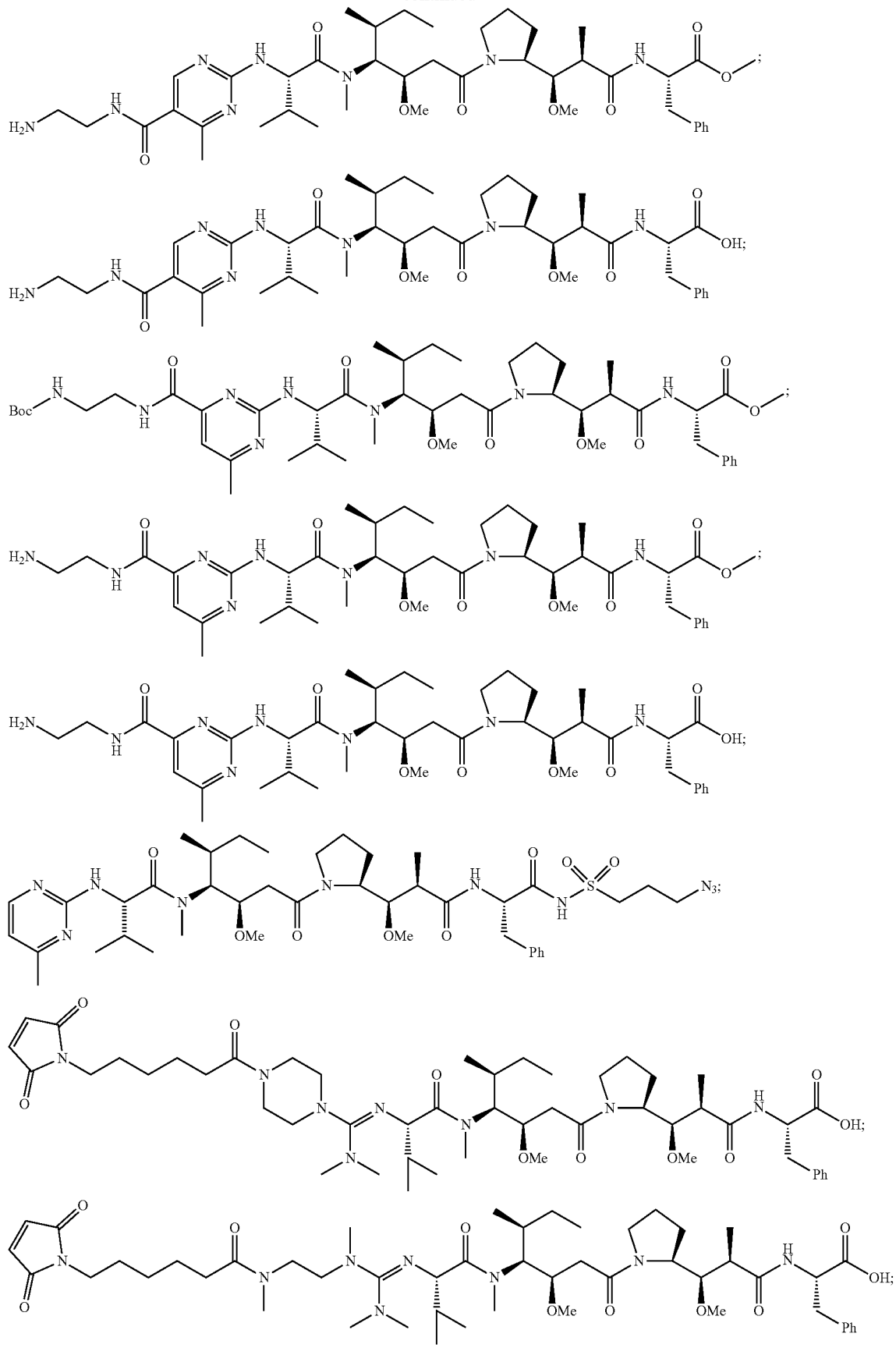

549
550
-continued
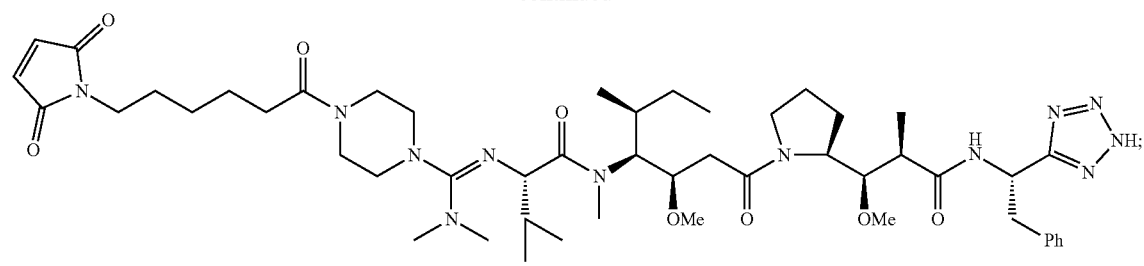
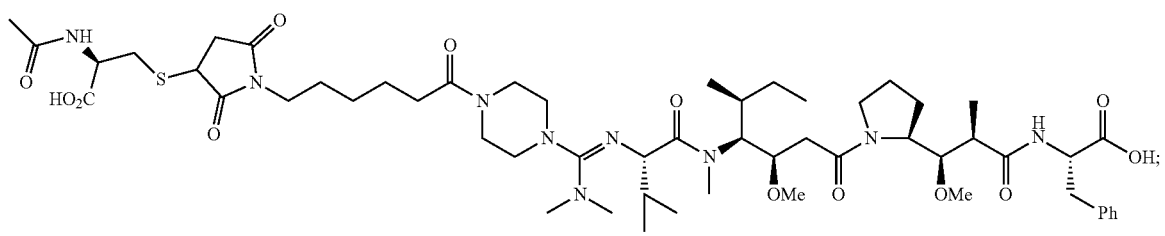
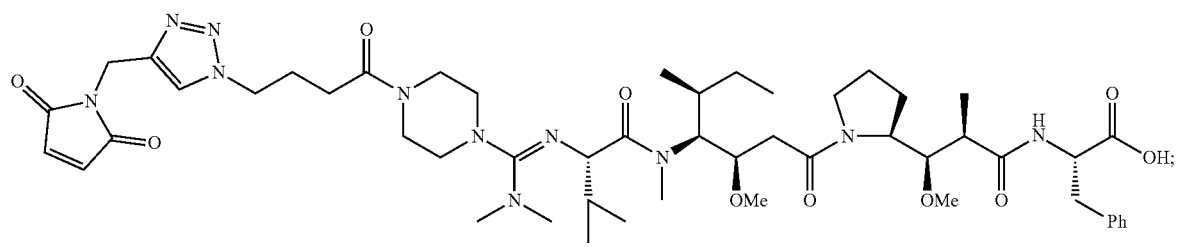
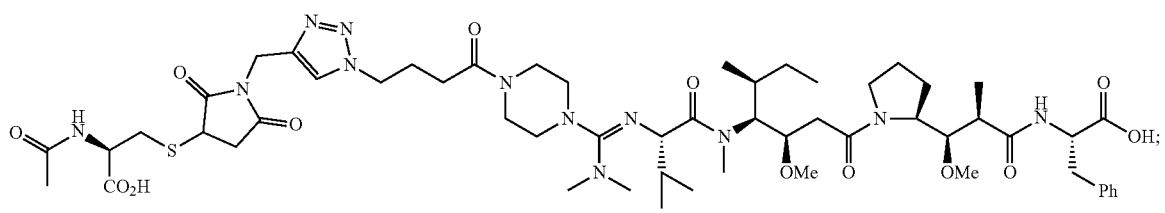
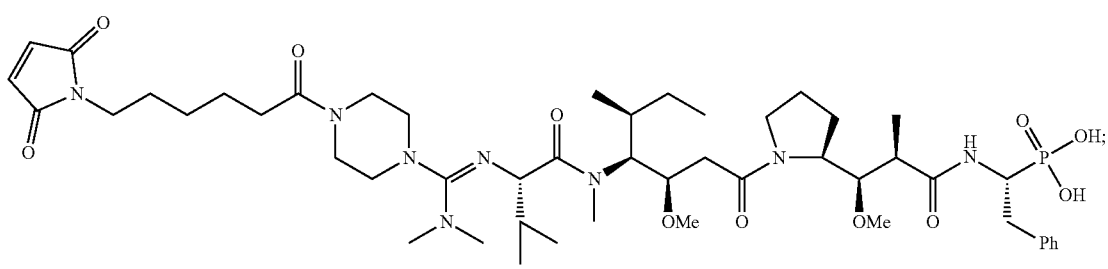
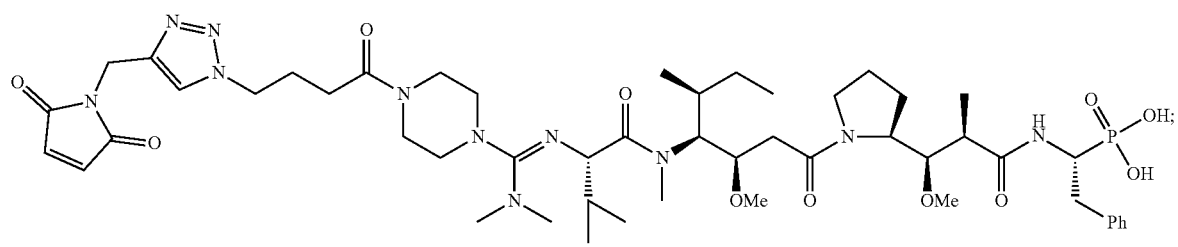
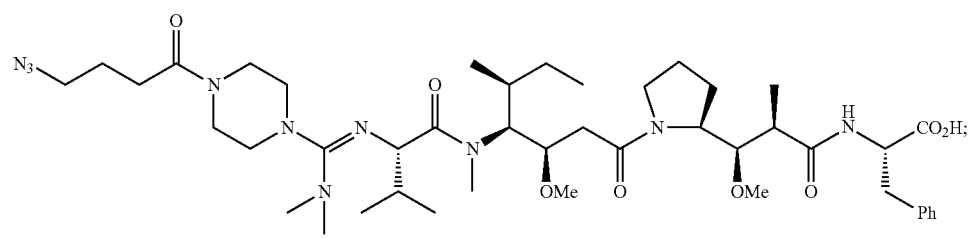

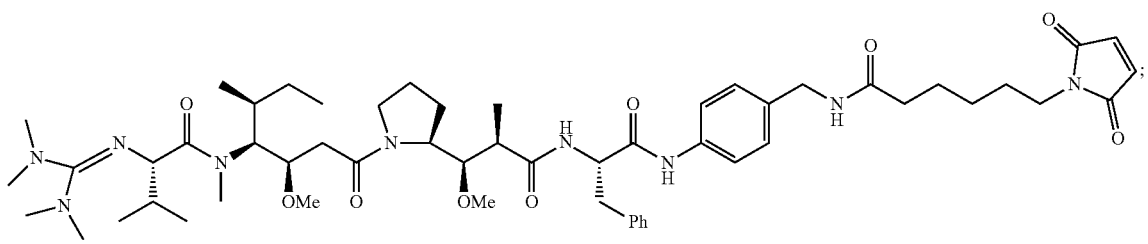
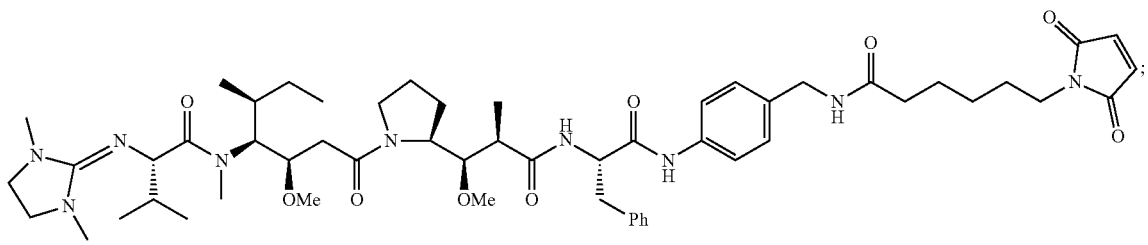
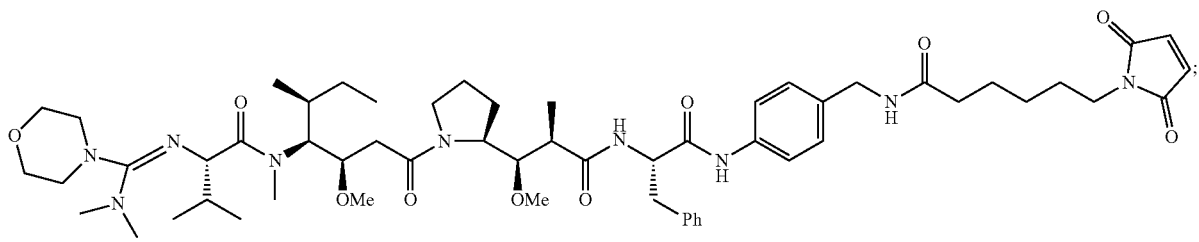
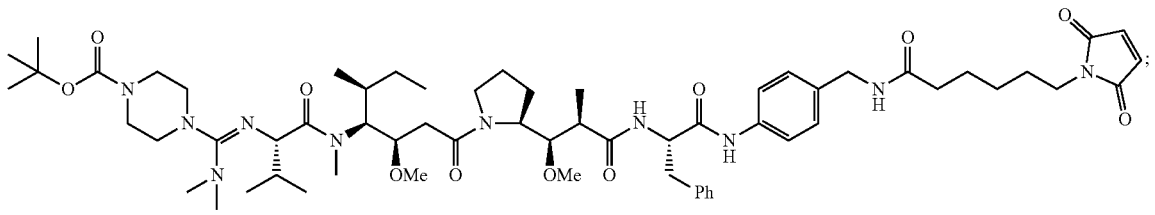
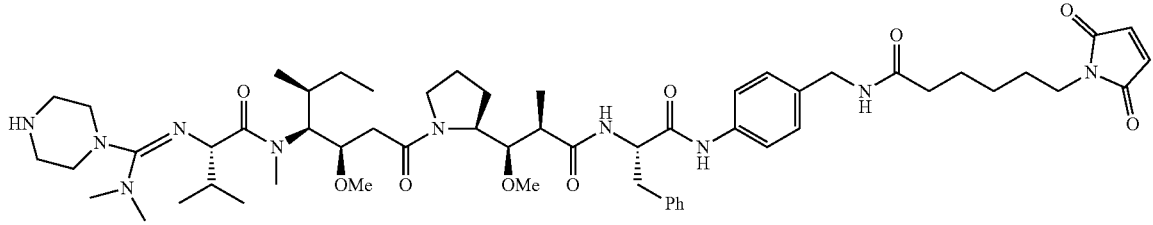
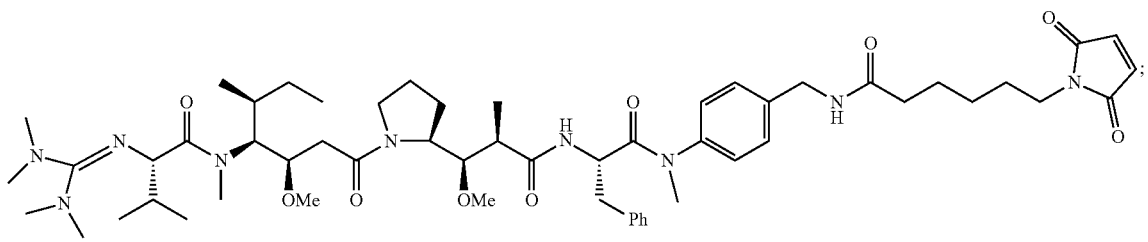
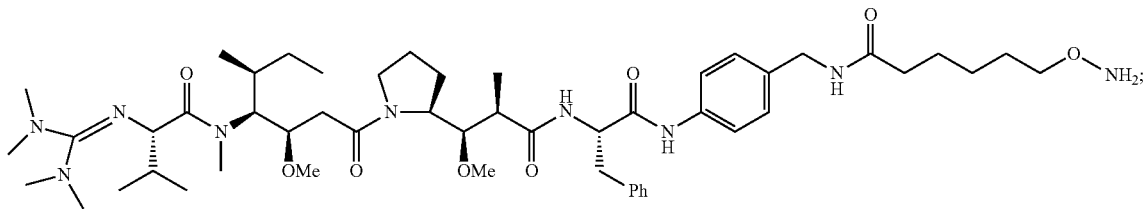

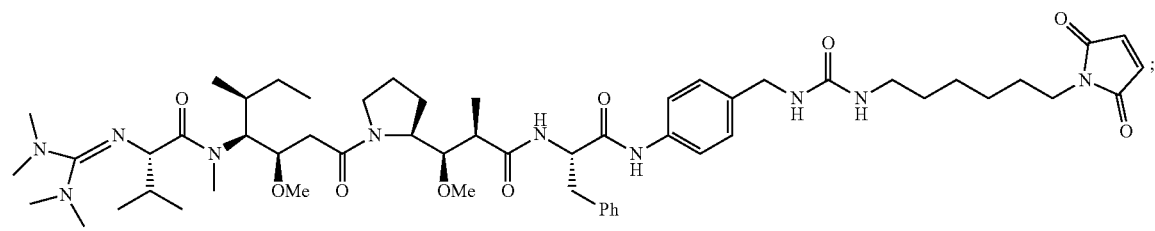
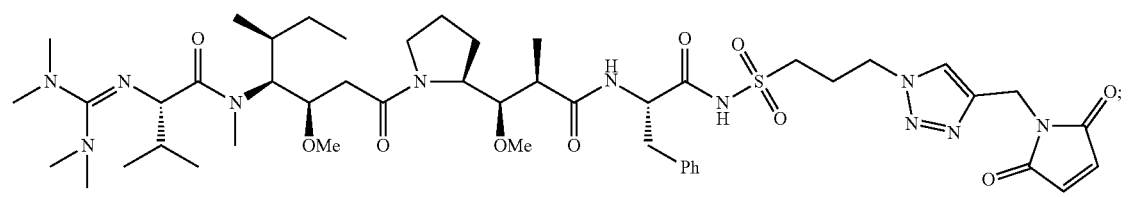
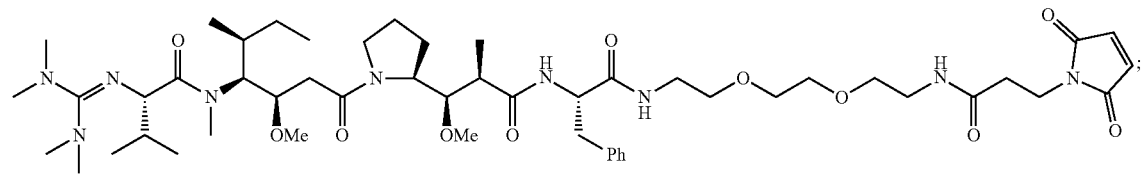
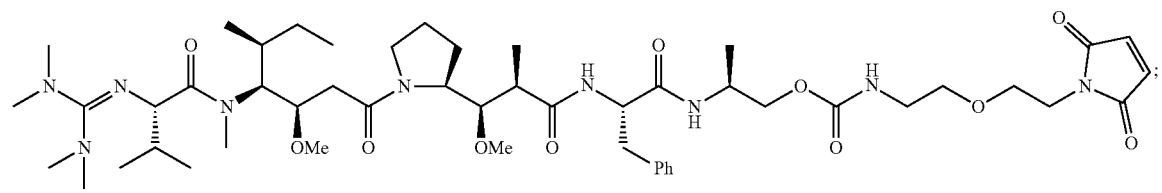
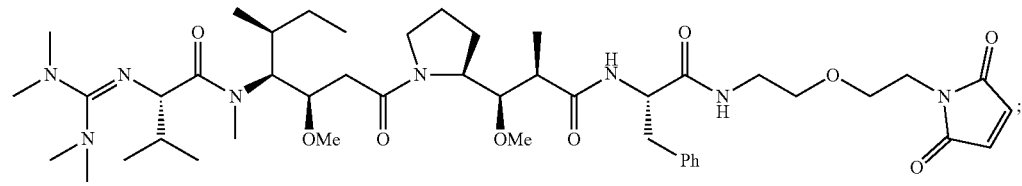
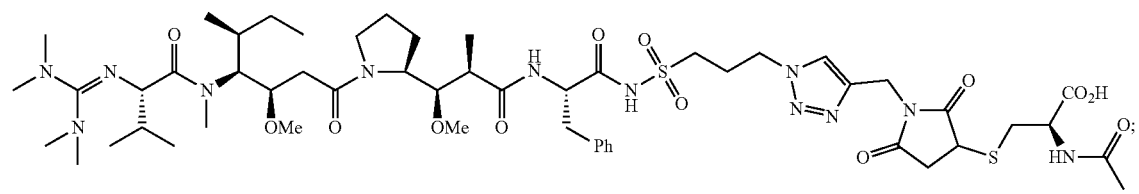
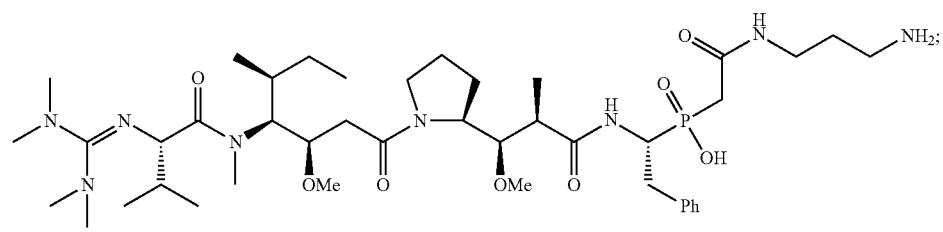
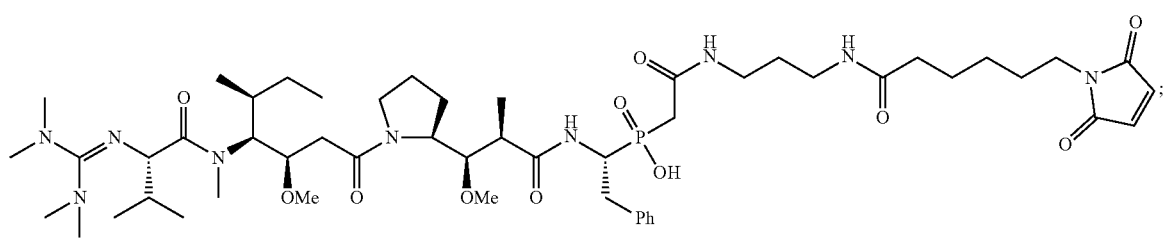

555
-continued
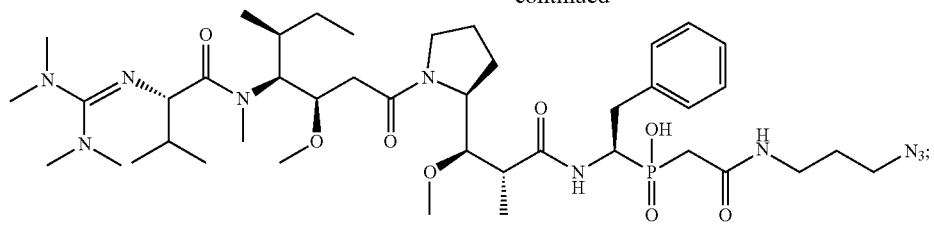
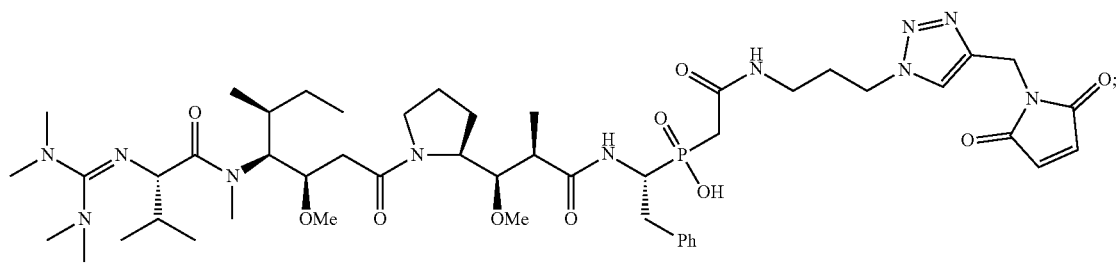
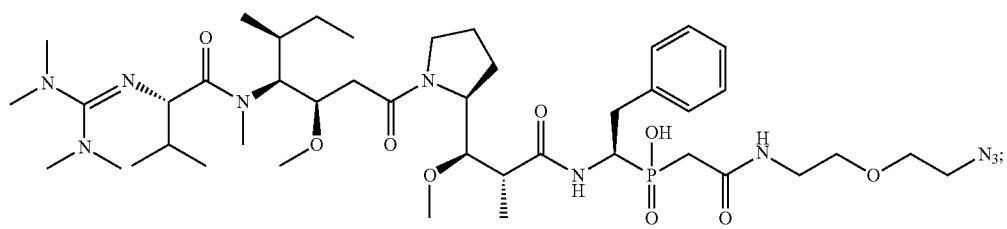
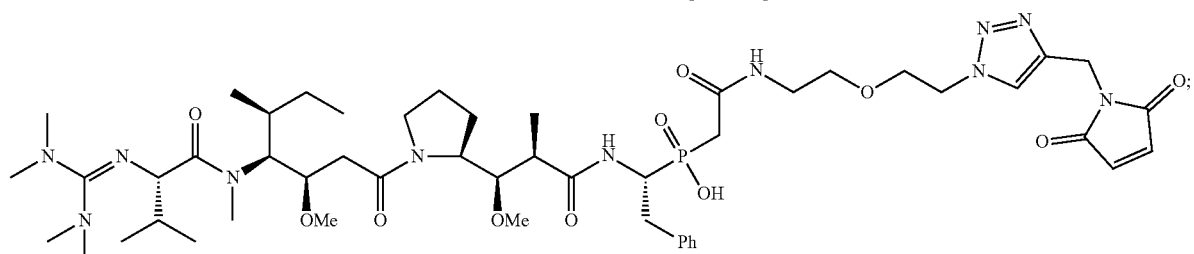
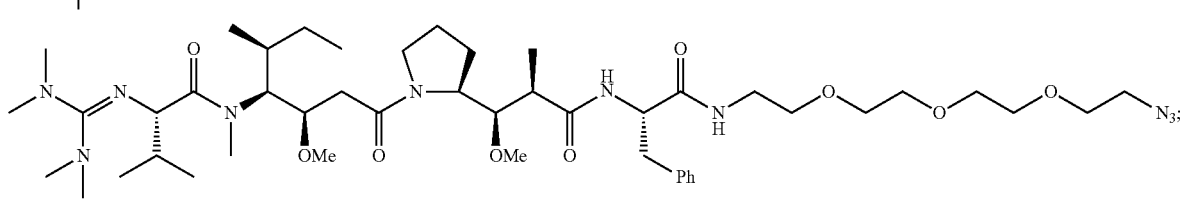
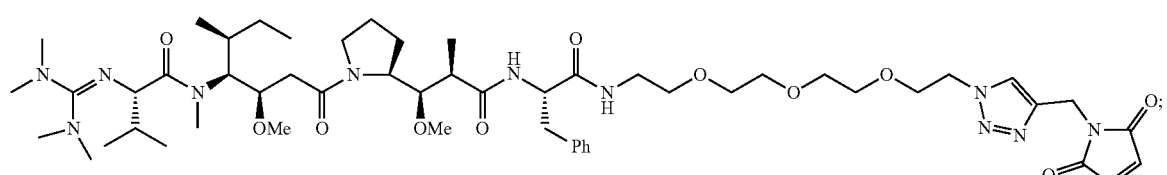
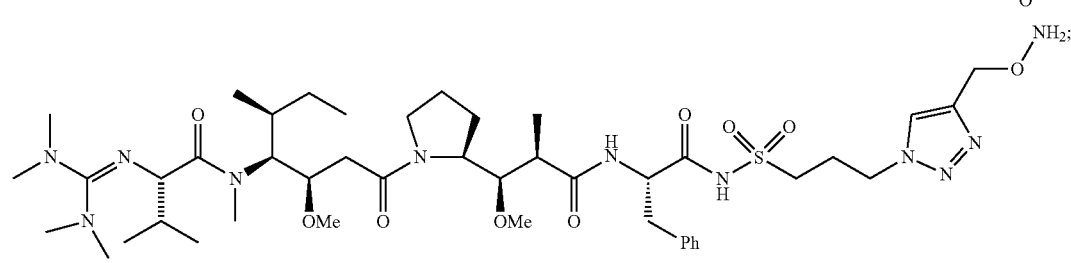

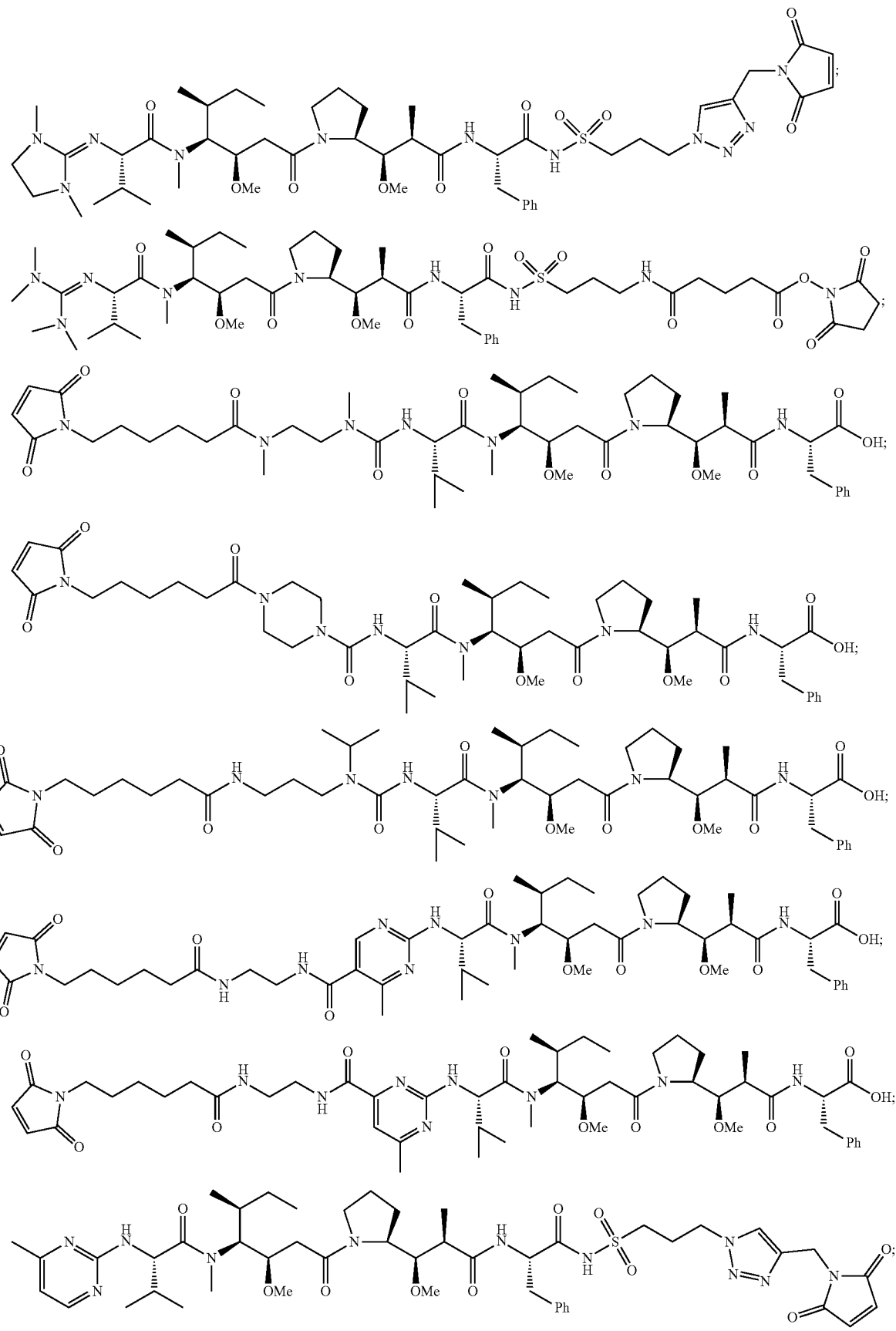

-continued
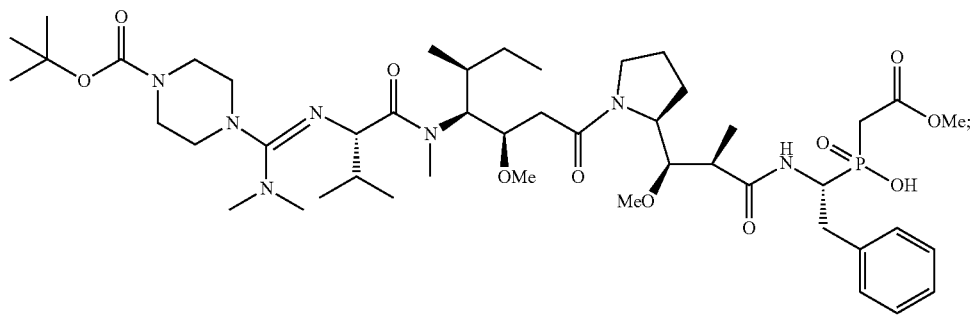
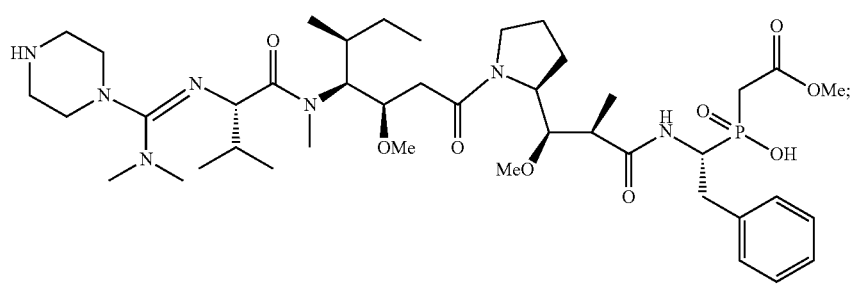
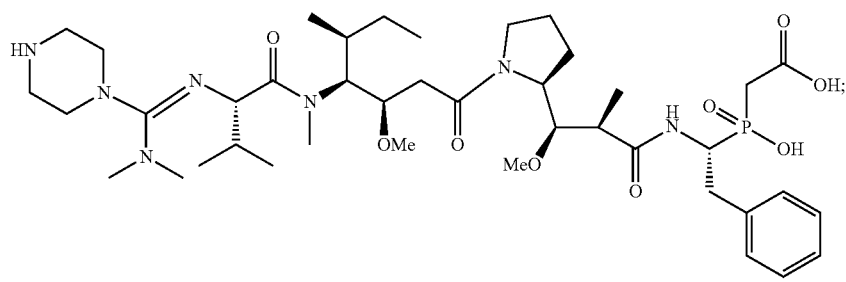
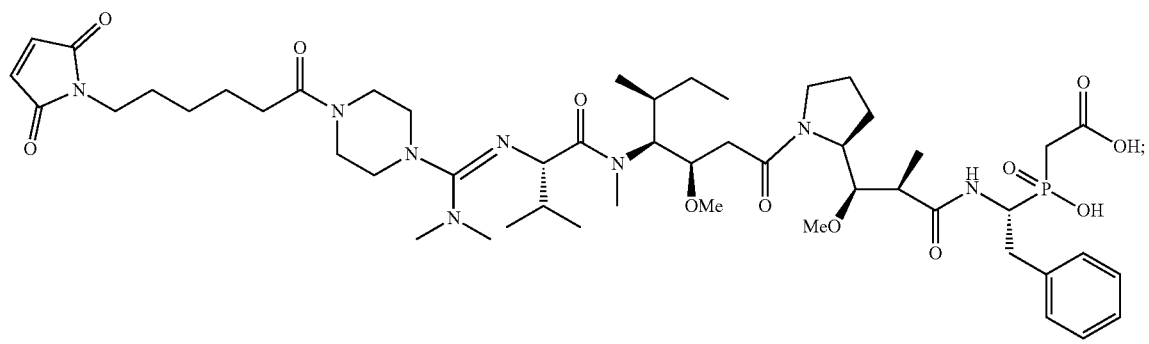
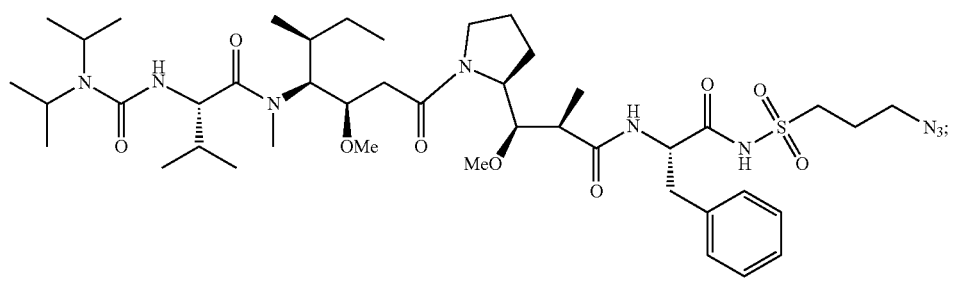

561
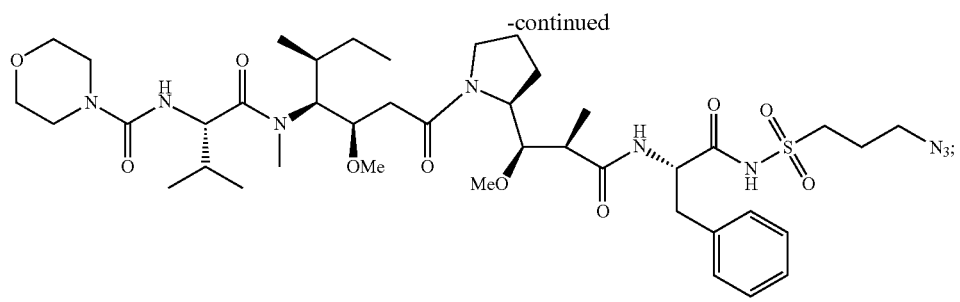
-continued
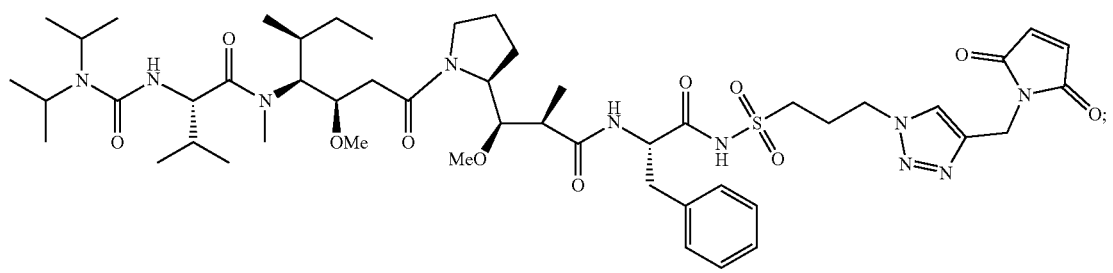
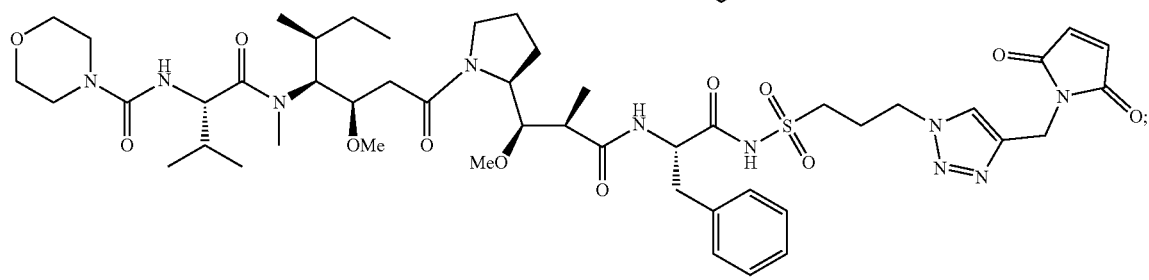
562
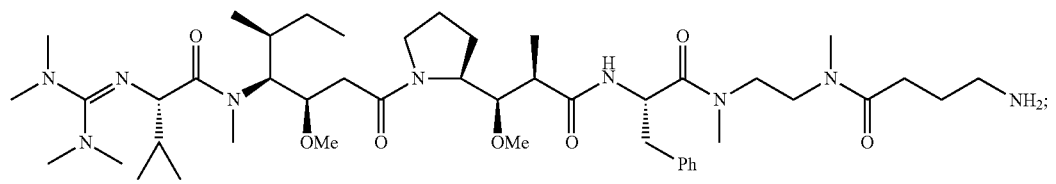
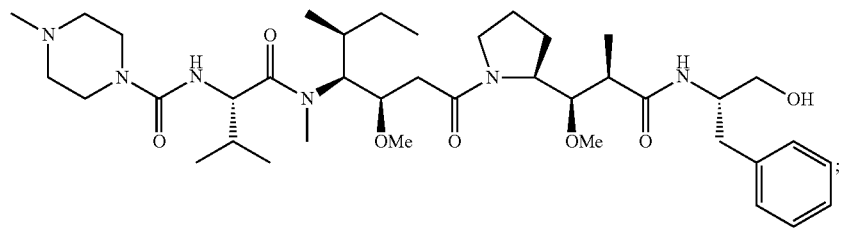
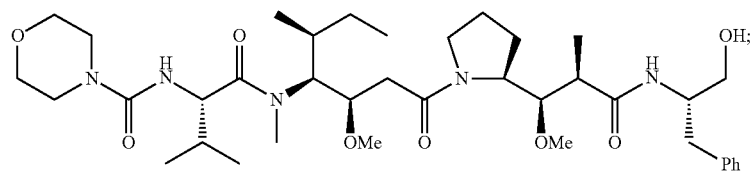
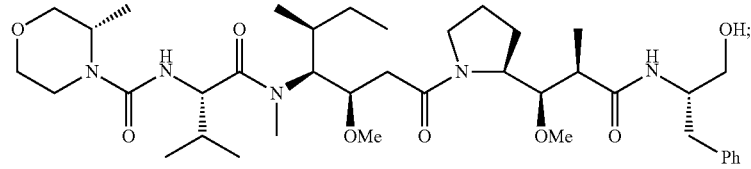

-continued
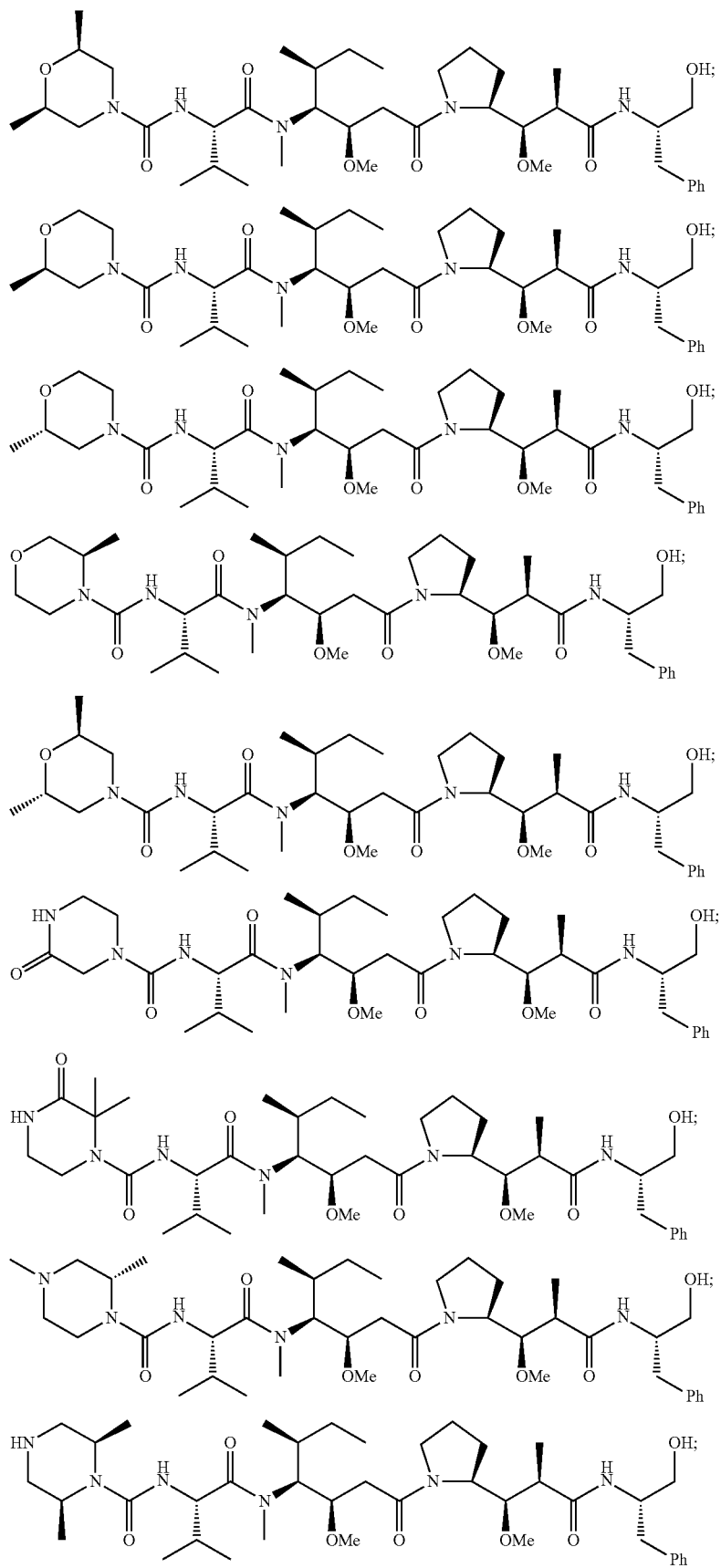

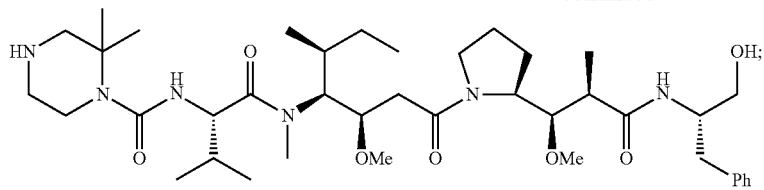
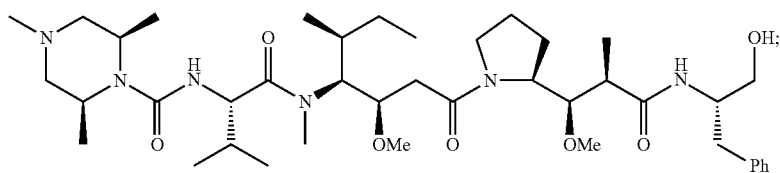
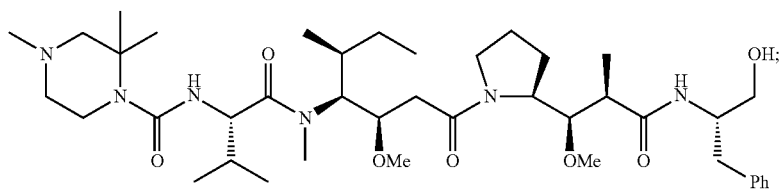
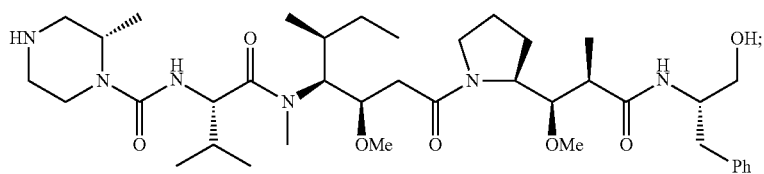
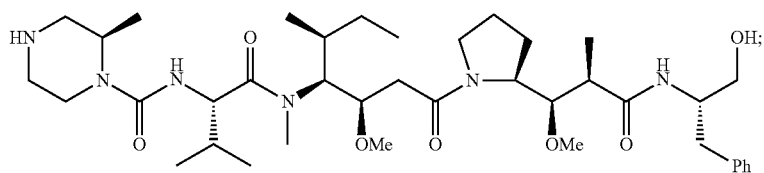
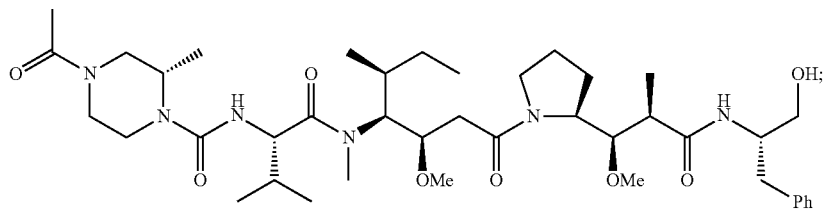
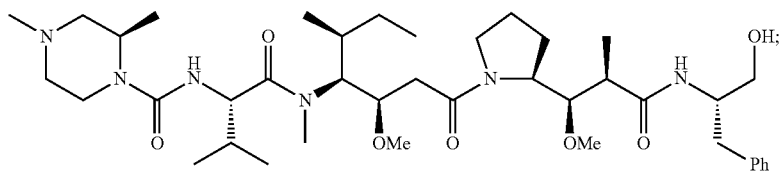
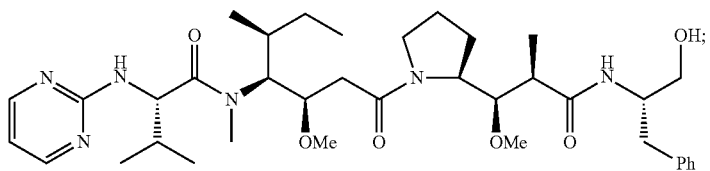

-continued
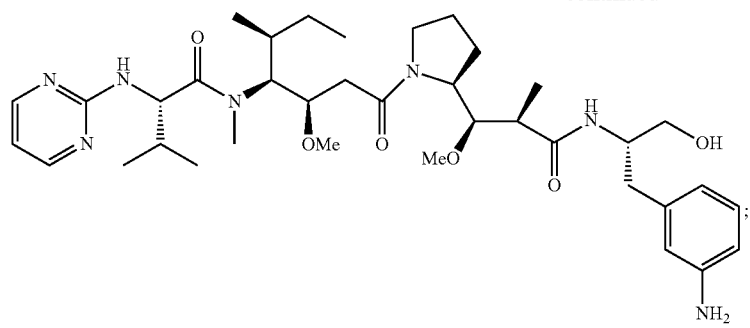
;
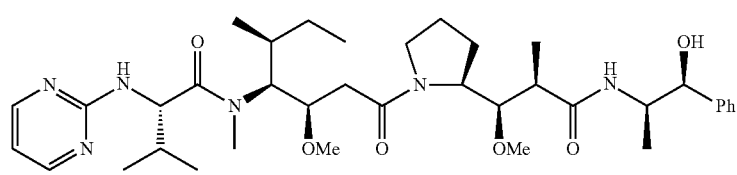
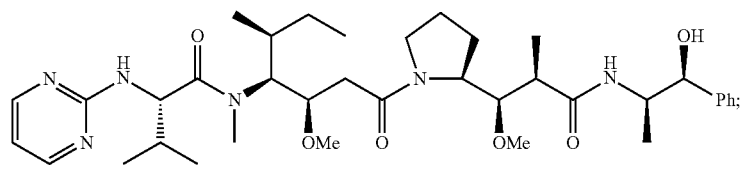
;
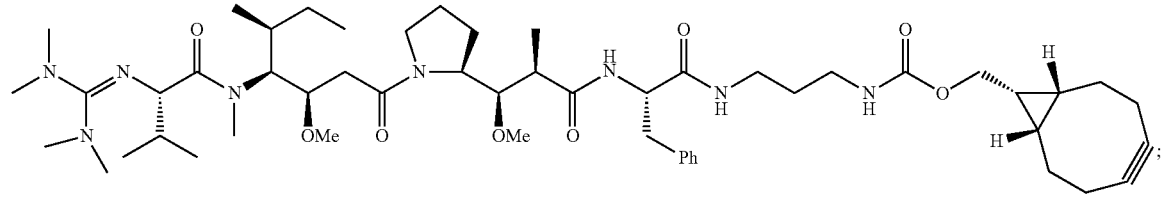
;
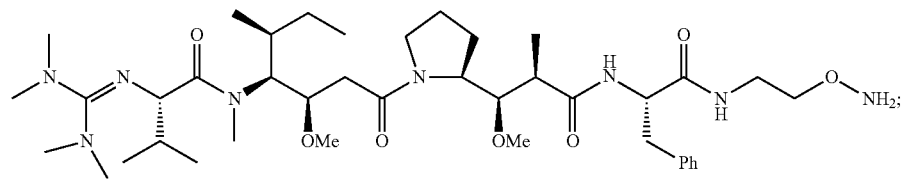
;
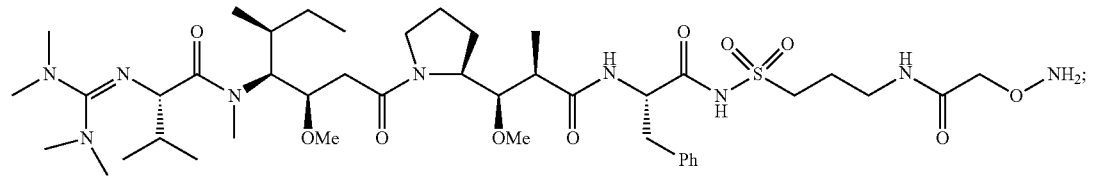
;
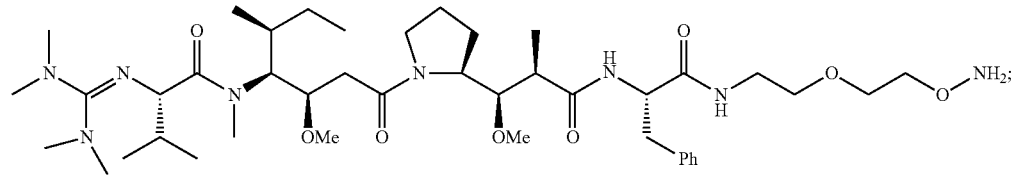
;
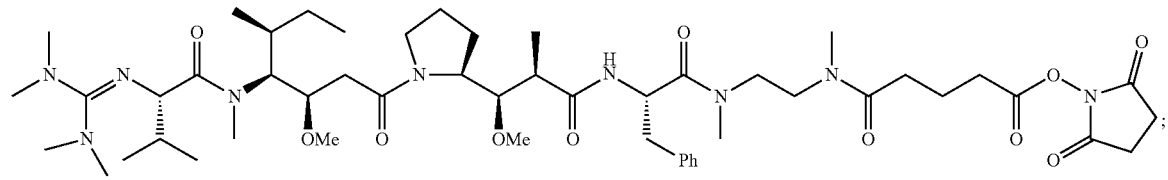
;

-continued
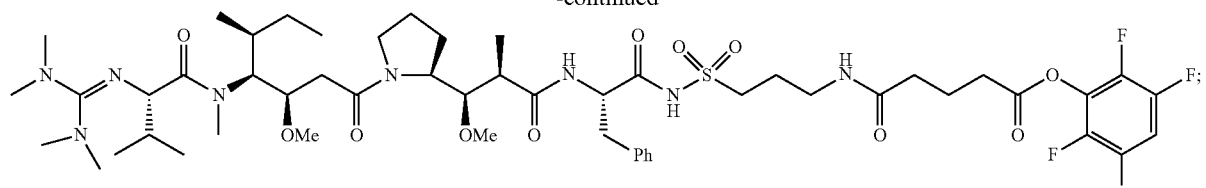
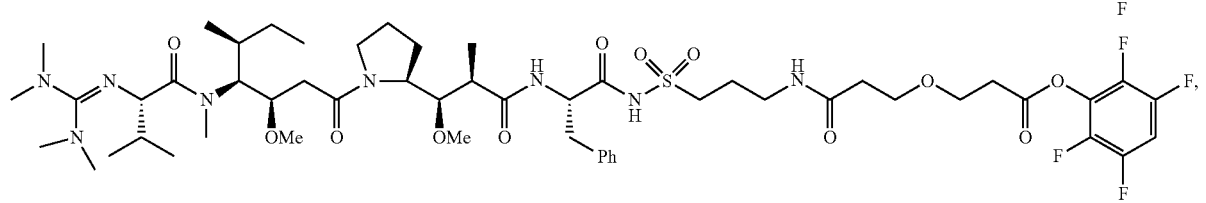
and
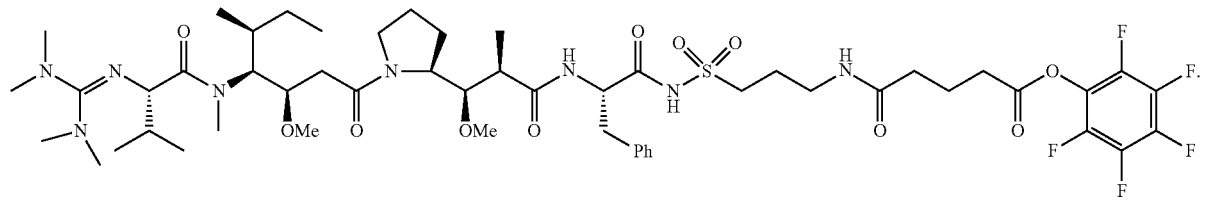
* * * * *